(12) United States Patent
Li et al.

(10) Patent No.: US 9,865,825 B2
(45) Date of Patent: Jan. 9, 2018

(54) EMITTERS BASED ON OCTAHEDRAL METAL COMPLEXES

(71) Applicant: Arizona Board of Regents on behalf of Arizona State University, Scottsdale, AZ (US)

(72) Inventors: Jian Li, Tempe, AZ (US); Guijie Li, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 14/937,136

(22) Filed: Nov. 10, 2015

(65) Prior Publication Data

US 2016/0133861 A1  May 12, 2016

Related U.S. Application Data

(60) Provisional application No. 62/077,443, filed on Nov. 10, 2014.

(51) Int. Cl.
*C07F 15/00* (2006.01)
*H01L 51/50* (2006.01)
(Continued)

(52) U.S. Cl.
CPC ...... *H01L 51/0085* (2013.01); *C07F 15/0033* (2013.01); *C07F 15/0073* (2013.01);
(Continued)

(58) Field of Classification Search
CPC .................................. C07F 15/00; H01L 51/50
(Continued)

(56) References Cited

U.S. PATENT DOCUMENTS 7,026,480 B2    4/2006  Che
7,029,766 B2    4/2006  Huo
(Continued)

FOREIGN PATENT DOCUMENTS

JP    2002105055 A1    4/2002
JP    2003342284 A1    12/2003
(Continued)

OTHER PUBLICATIONS

V. Thamilarasan et al., "Green-emitting phosphorescent iridium(III) complex: Structural, photophysical and electrochemical properties," Inorganica Chimica Acta, vol. 408, 2013, pp. 240-245.
(Continued)

*Primary Examiner* — Charanjit Aulakh
(74) *Attorney, Agent, or Firm* — Fish & Richardson P.C.

(57) ABSTRACT

Iridium, rhodium, and platinum complexes suitable for use as phosphorescent emitters or as delayed fluorescent and phosphorescent emitters having the following structures:

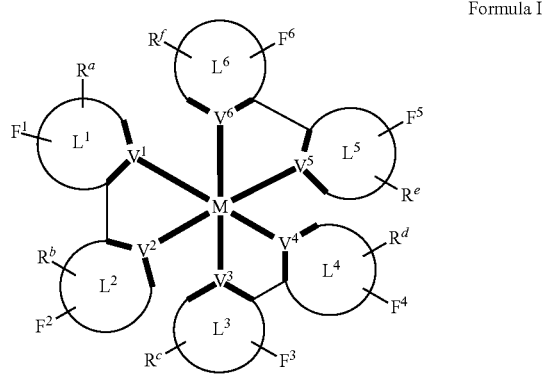

Formula I

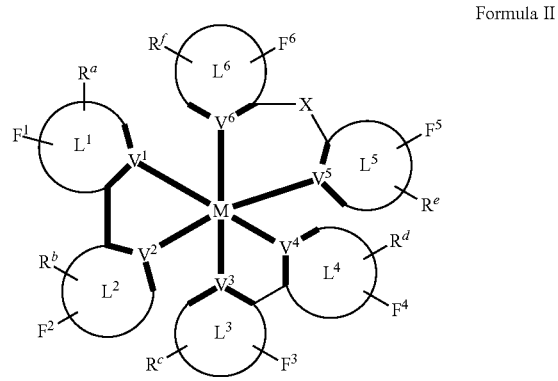

Formula II

Formula III (Continued)

-continued

Formula IV

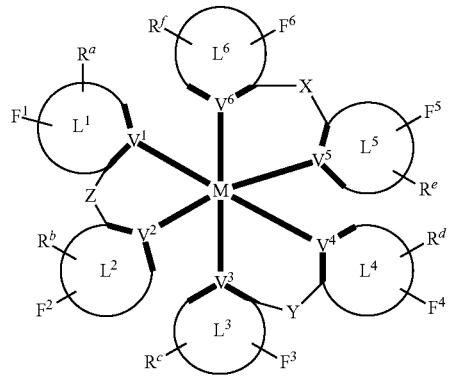

Formula V

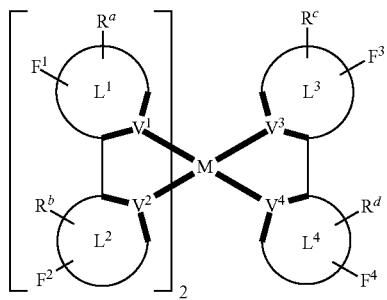

Formula VI

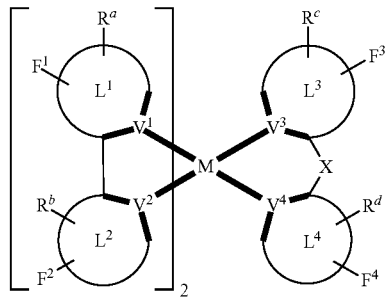

Formula VII

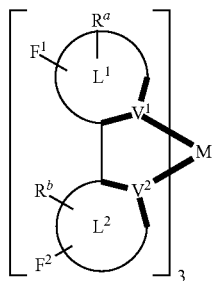

Formula VIII

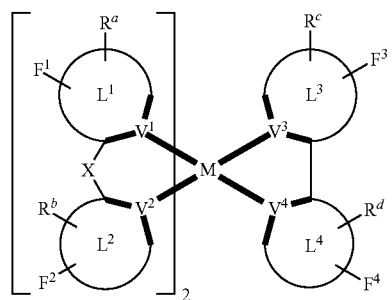

-continued

Formula IX

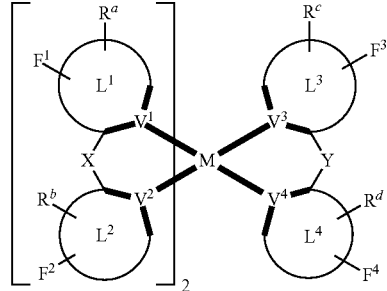

Formula X

16 Claims, 7 Drawing Sheets

(51) Int. Cl.
  H01L 51/00 (2006.01)
  C09K 11/06 (2006.01)
  H05B 33/14 (2006.01)
(52) U.S. Cl.
  CPC .......... *C07F 15/0086* (2013.01); *C09K 11/06* (2013.01); *H05B 33/14* (2013.01); *C09K 2211/1007* (2013.01); *C09K 2211/1011* (2013.01); *C09K 2211/1022* (2013.01); *C09K 2211/1029* (2013.01); *C09K 2211/1044* (2013.01); *C09K 2211/1088* (2013.01); *C09K 2211/1092* (2013.01); *C09K 2211/1096* (2013.01); *C09K 2211/185* (2013.01); *H01L 51/5016* (2013.01)
(58) Field of Classification Search
  USPC .............................. 546/2; 313/504; 548/101
  See application file for complete search history.

(56)  References Cited

U.S. PATENT DOCUMENTS

| | | |
|---|---|---|
| 7,064,228 B1 | 6/2006 | Yu |
| 7,166,368 B2 | 1/2007 | Lecloux |
| 7,276,617 B2 | 10/2007 | Sotoyama |
| 8,389,725 B2 | 3/2013 | Li |
| 8,617,723 B2 | 12/2013 | Stoessel |
| 9,221,857 B2 | 12/2015 | Li |
| 9,598,449 B2 | 3/2017 | Li et al. |
| 9,617,291 B2 | 4/2017 | Li et al. |
| 2001/0019782 A1 | 9/2001 | Igarashi |
| 2002/0189666 A1 | 12/2002 | Forrest |
| 2004/0230061 A1 | 11/2004 | Seo |
| 2006/0024522 A1 | 2/2006 | Thompson |
| 2006/0093854 A1 | 5/2006 | Sotoyama |
| 2006/0094875 A1 | 5/2006 | Itoh |
| 2006/0127696 A1 | 6/2006 | Stossel |

(56) References Cited

U.S. PATENT DOCUMENTS

| | | |
|---|---|---|
| 2006/0182992 A1 | 8/2006 | Nii |
| 2006/0255721 A1 | 11/2006 | Igarashi |
| 2007/0111025 A1 | 5/2007 | Lennartz |
| 2007/0224447 A1 | 9/2007 | Sotoyama |
| 2008/0067925 A1 | 3/2008 | Oshiyama |
| 2008/0269491 A1 | 10/2008 | Jabbour |
| 2010/0141127 A1 | 6/2010 | Xia |
| 2012/0264938 A1 | 10/2012 | Li |
| 2015/0380666 A1* | 12/2015 | Szigethy ............ H01L 51/0087 257/40 |
| 2016/0043331 A1 | 2/2016 | Li |
| 2016/0194344 A1 | 7/2016 | Li |
| 2016/0359125 A1 | 12/2016 | Li |

FOREIGN PATENT DOCUMENTS

| | | |
|---|---|---|
| JP | 2006282965 A1 | 10/2006 |
| JP | 2007031678 A1 | 2/2007 |
| JP | 2006114889 A1 | 12/2008 |
| JP | 2009076509 A1 | 4/2009 |
| WO | WO0070655 A1 | 11/2000 |
| WO | WO2004039781 A1 | 5/2004 |
| WO | WO2004085450 A1 | 10/2004 |
| WO | WO2005075600 A1 | 8/2005 |
| WO | WO2005103195 A1 | 11/2005 |
| WO | WO2005105746 A1 | 11/2005 |
| WO | WO2005113704 A1 | 12/2005 |
| WO | WO2006067074 A1 | 6/2006 |
| WO | WO2006082742 A1 | 8/2006 |
| WO | WO2006100888 A1 | 9/2006 |
| WO | WO2006115301 A1 | 11/2006 |
| WO | WO2009086209 A1 | 7/2009 |
| WO | WO2009111299 A1 | 9/2009 |
| WO | WO2010007098 A1 | 1/2010 |
| WO | WO2010056669 A1 | 5/2010 |
| WO | WO2010093176 A1 | 8/2010 |
| WO | WO2012142387 A1 | 10/2012 |

OTHER PUBLICATIONS

Rui Zhu et al., "Color tuning based on a six-membered chelated iridium (III) complex with aza-aromatic ligand," Chemistry Letters, vol. 34, No. 12, 2005, pp. 1668-1669.
S. A. Willison et al., "A Luminescent Platinum(II) 2,6-Bis(N-pyrazolyl)pyridine Complex", Inorg. Chem. vol. 43, pp. 2548-2555, 2004.
J. M. Longmire et al., "Synthesis and X-ray Crystal Structures of Palladium(II) and Platinum(II) Complexes of the PCP-Type Chiral Tridentate Ligand", Organometallics, vol. 17, pp. 4374-4379, 1998.
V. Adamovich et al., "High efficiency single dopant white electrophosphorescent light emitting diodes", New J. Chem, vol. 26, pp. 1171-1178. 2002.
Del Cano et al., "Near-infrared electroluminescence based on perylenediimide-doped tris(8-quinolinolato) aluminum", Applied Physics Letters, 88, pp. 071117-1-071117-3, 2006.
B. Harrison et al., "Near-infrared electroluminescence from conjugated polymer/lanthanide porphyrin blends", Applied Physics Letter, vol. 79, No. 23, pp. 3770-3772, Dec. 3, 2001.
J. Kido et al., "Organo Lanthanide Metal Complexes for Electroluminescent Materials", Chem. Rev., vol. 102, pp. 2357-2368, 2002.
S. Lamansky et al., "Highly Phosphorescent Bis-Cyclometalated Iridium Complexes: Synthesis, Photophysical Characterization, and Use in Organic Light Emitting Diodes", J. Am. Chem. Soc., vol. 123, pp. 4304-4312, 2001.
S. Lamansky et al., "Synthesis and Characterization of Phosphorescent Cyclometalated Iridium Complexes", Inorg. Chem., vol. 40, pp. 1704-1711, 2001.
X. Li et al., "Synthesis and properties of novel poly(p-phenylenevinylene) copolymers for near-infrared emitting diodes", European Polymer Journal, vol. 41, pp. 2923-2933, 2005.
P. Peumans et al., "Small molecular weight organic thin-film photodetectors and solar cells", Journal of Applied Physics, vol. 93, No. 7, pp. 3693-3723, Apr. 1, 2003.
Rand et al., Organic Double-Heterostructure Photovoltaic Cells Employing Thick Tris (acetylacetonato) ruthenium (III) Exciton-Blocking Layers, Advanced Materials vol. 17, pp. 2714-2718, 2005.
C.W. Tang, "Two-layer organic photovoltaic cell", Appl. Phys. Letters 48 (2), pp. 183-185, 1986).
Vanhelmont et al., "Synthesis, Crystal Structure, High-Resolution Optical Spectroscopy, and Extended Huckel Calculations for [Re(CO)4(thpy)] (thpy-2-(2-Thienyl)pyridinate). Comparison with Related Cyclometalated Complexes", Inorg. Chem., vol. 36, pp. 5512-5517, 1997.
Williams et al., "Organic light-emitting diodes having exclusive near-infrared electrophosphorescence", Applied Physics Letters, vol. 89, pp. 083506 (3 pages), 2006.
Forrest et al., "Measuring the Efficiency of Organic Light-Emitting Devices", Advanced Materials, vol. 15, No. 13, pp. 1043-1048, 2003.
Cardenas et al., "Divergent Behavior of Palladium(II) and Platinum(II) in the Metalation of 1,2-Di(2-pyridyl) benzene," Organometallics 1999, 18, pp. 3337-3341.
Williams et al., "An Alternative Route to Highly Luminescent Platinum(II) Complexes," Inorg. Chem., 2003, 42, pp. 8609-8611.
Sanna et al., "Platinum complexes with N—N—C ligands. Synthesis, electrochemical and spectroscopic characteristics of platinum(II) and relevant electroreduced species," Inorganica Chimica Acta 305, 2000, pp. 189-205.
International Search Report and Written Opinion, PCT/US2008/087847, dated Aug. 6, 2009, 12 pages.
International Search Report and Written Opinion, PCT/US2009/035441, dated Oct. 19, 2009, 14 pages.
Ionkin, A.S. et al.: Synthesis and structural characterization of a series of novel polyaromatic ligands containing pyrene and related biscyclometalated iridium complexes. Organometallics, vol. 25, pp. 1461-1471, 2006.

* cited by examiner

EMITTERS BASED ON OCTAHEDRAL METAL COMPLEXES

CROSS-REFERENCE TO RELATED APPLICATION

This application claims priority to U.S. Provisional Patent Application No. 62/077,443 entitled "EMITTERS BASED ON OCTAHEDRAL METAL COMPLEXES" filed on Nov. 10, 2014, which is hereby incorporated by reference in its entirety.

TECHNICAL FIELD

The present disclosure relates to multidentate iridium, rhodium, and platinum complexes suitable for use as phosphorescent or delayed fluorescent and phosphorescent emitters in display and lighting applications.

BACKGROUND

Compounds capable of absorbing and/or emitting light can be ideally suited for use in a wide variety of optical and electroluminescent devices, including, for example, photo-absorbing devices such as solar- and photo-sensitive devices, organic light emitting diodes (OLEDs), photo-emitting devices, or devices capable of both photo-absorption and emission and as markers for bio-applications. Much research has been devoted to the discovery and optimization of organic and organometallic materials for using in optical and electroluminescent devices. Generally, research in this area aims to accomplish a number of goals, including improvements in absorption and emission efficiency and improvements in the stability of devices, as well as improvements in processing ability.

Despite significant advances in research devoted to optical and electro-optical materials (e.g., red and green phosphorescent organometallic materials are commercially available and have been used as phosphors in organic light emitting diodes (OLEDs), lighting and advanced displays), many currently available materials exhibit a number of disadvantages, including poor processing ability, inefficient emission or absorption, and less than ideal stability, among others.

Good blue emitters are particularly scarce, with one challenge being the stability of the blue devices. The choice of the host materials has an impact on the stability and the efficiency of the devices. The lowest triplet excited state energy of the blue phosphors is very high compared with that of the red and green phosphors, which means that the lowest triplet excited state energy of host materials for the blue devices should be even higher. Thus, one of the problems is that there are limited host materials to be used for the blue devices. Accordingly, a need exists for new materials which exhibit improved performance in optical emitting and absorbing applications.

SUMMARY

The present disclosure relates to iridium, rhodium and platinum complexes suitable for use as emitters in organic light emitting diodes (OLEDs), display and lighting applications.

Disclosed herein are complexes of Formula I, Formula II, Formula III, Formula IV, Formula V, Formula VI, Formula VII, Formula VIII, Formula IX, and Formula X:

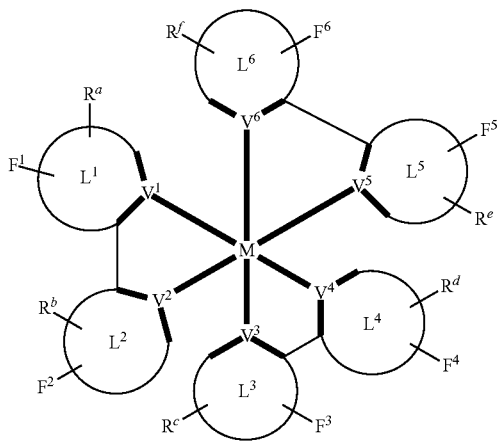

Formula I

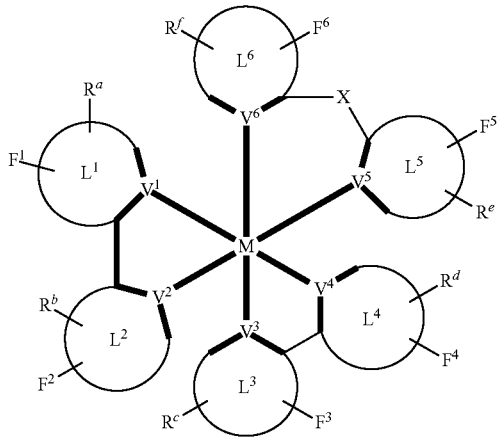

Formula II

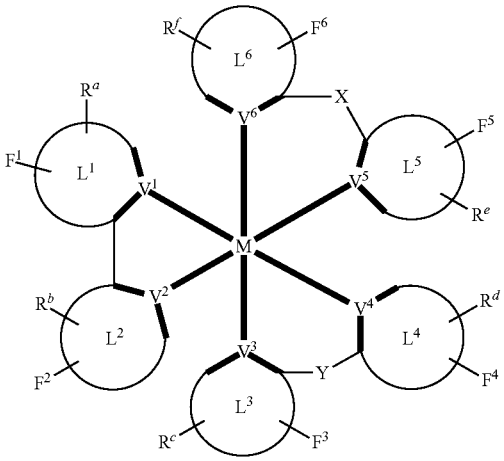

Formula III

Formula IV

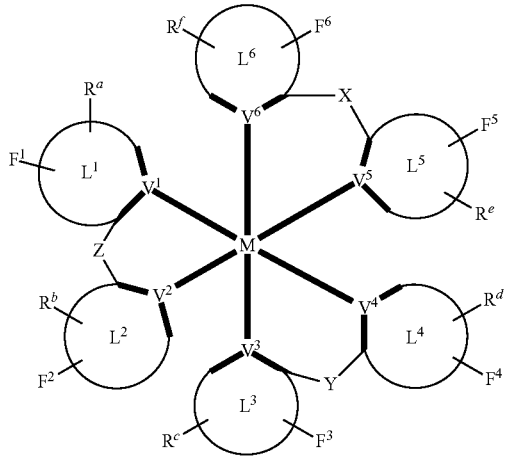

Formula V

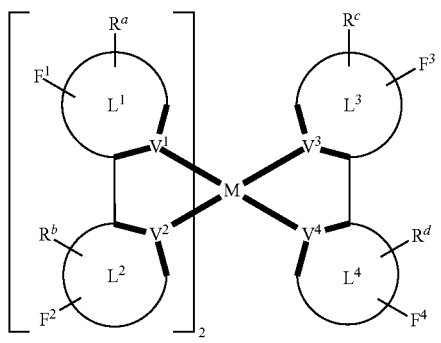

Formula VI

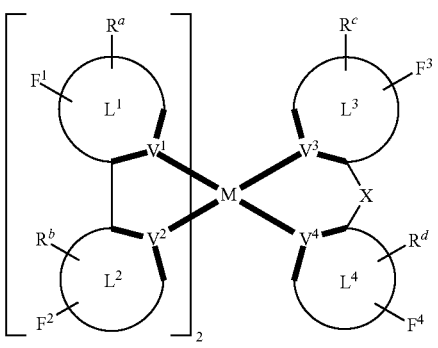

Formula VII

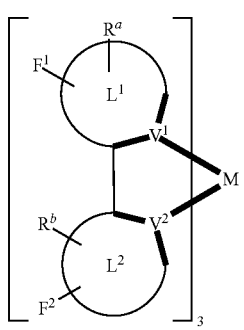

Formula VIII

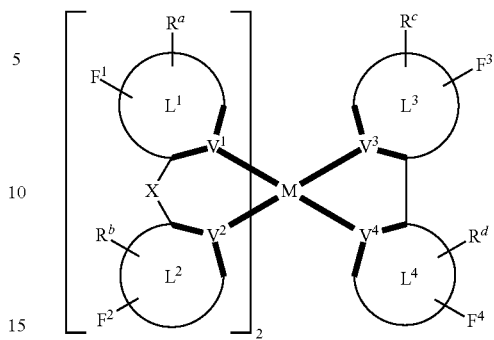

Formula IX

Formula X wherein:

M is Ir(III), Rh(III), or Pt(IV), each of $L^1$, $L^2$, $L^3$, $L^4$, $L^5$, and $L^6$ is independently a substituted or unsubstituted aryl, cycloalkyl, cycloalkenyl, heteroaryl, heterocyclyl, carbene, or N-heterocyclic carbene, dione, cyanogen, or phosphine, each of $V^1$, $V^2$, $V^3$, $V^4$, $V^5$, and $V^6$ is coordinated with M and is independently N, C, P, B, or Si, each of X, Y, and Z is independently $CH_2$, $CR^1R^2$, $C=O$, $CH_2$, $SiR^1R^2$, $GeH_2$, $GeR^1R^2$, NH, $NR^3$, PH, $PR^3$, $R^3P=O$, $AsR^3$, $R^3As=O$, O, S, $S=O$, $SO_2$, Se, $Se=O$, $SeO_2$, BH, $BR^3$, $R^3Bi=O$, BiH, or $BiR^3$, each of $F^1$, $F^2$, $F^3$, $F^4$, $F^5$, and $F^6$ is independently present or absent, wherein at least one of $F^1$, $F^2$, $F^3$, $F^4$, $F^5$, and $F^6$ is present, and each $F^1$, $F^2$, $F^3$, $F^4$, $F^5$, and $F^6$ present is a fluorescent luminophore, each of $R^a$, $R^b$, $R^c$, $R^d$, $R^e$, and $R^f$ is independently present or absent, and if present each of $R^a$, $R^b$, $R^c$, $R^d$, $R^e$ and $R^f$ independently represents mono-, di-, or tri-substitutions, and wherein each of $R^a$, $R^b$, $R^c$, $R^d$, $R^e$ and $R^f$ present is independently deuterium, halogen, hydroxyl, thiol, nitro, cyano, nitrile, isonitrile, sulfinyl, mercapto, sulfo, carboxyl, hydrazino; substituted or unsubstituted aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and each of $R^1$, $R^2$, and $R^3$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

Also disclosed herein are compositions including one or more compounds disclosed herein.

Also disclosed herein are devices, such as OLEDs, including one or more compounds or compositions disclosed herein.

Figure 1:
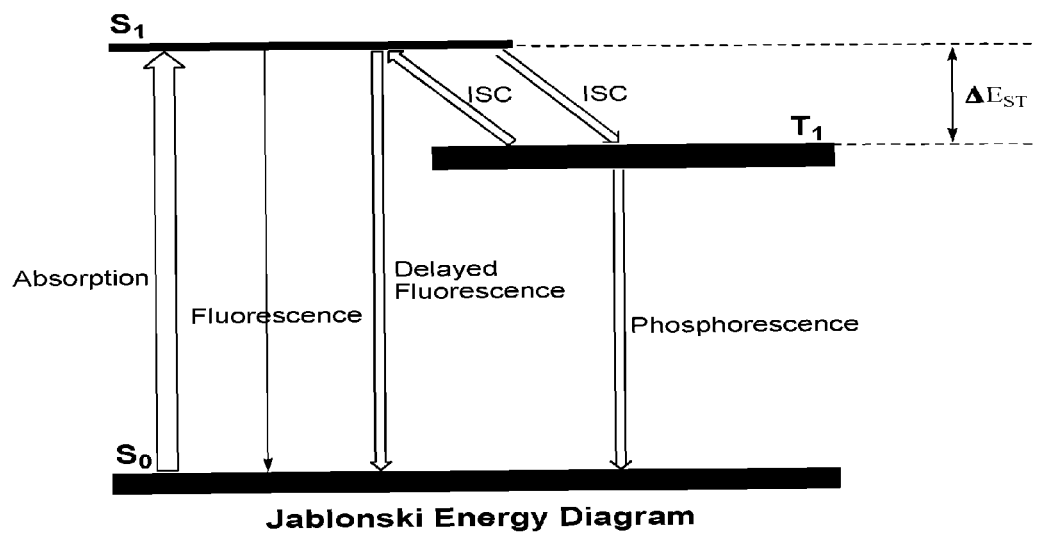
FIG. 1 depicts a Jablonski energy diagram for metal complexes disclosed herein.

Additional aspects will be set forth in the description which follows. Advantages will be realized and attained by means of the elements and combinations particularly pointed out in the claims. It is to be understood that both the foregoing general description and the following detailed description are exemplary and explanatory only and are not restrictive.

DETAILED DESCRIPTION

The present disclosure can be understood more readily by reference to the following detailed description and the Examples included therein.

Before the present compounds, devices, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing, example methods and materials are now described.

As used in the specification and the appended claims, the singular forms "a", "an", and "the" include plural referents unless the context clearly dictates otherwise. Thus, for example, reference to "a component" includes mixtures of two or more components.

As used herein, the terms "optional" and "optionally" mean that the subsequently described event or circumstance can or cannot occur, and that the description includes instances where said event or circumstance occurs and instances where it does not.

Disclosed are the components to be used to prepare the compositions described herein as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions. Thus, if there are a variety of additional steps that can be performed it is understood that each of these additional steps can be performed with any specific embodiment or combination of embodiments of the methods.

As referred to herein, a linking atom or group connects two atoms such as, for example, a N atom and a C atom. A linking group is in one aspect disclosed as X, Y, or Z herein. The linking atom can optionally, if valency permits, have other chemical moieties attached. For example, in one aspect, an oxygen would not have any other chemical groups attached as the valency is satisfied once it is bonded to two atoms (e.g., N or C atoms). In another aspect, when carbon is the linking atom, two additional chemical moieties such as amine, amide, thiol, aryl, heteroaryl, cycloalkyl, and heterocyclyl moieties may be attached to the carbon.

The term "cyclic structure" or the like terms used herein refer to any cyclic chemical structure which includes, but is not limited to, aryl, heteroaryl, cycloalkyl, cycloalkenyl, heterocyclyl, carbene, and N-heterocyclic carbene.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "A," "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula —$(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)$A^1$ or —C(O)O$A^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "polymeric" includes polyalkylene, polyether, polyester, and other groups with repeating units, such as, but not limited to —(CH$_2$O)$_n$—CH$_3$, —(CH$_2$CH$_2$O)$_n$—CH$_3$, —[CH$_2$CH(CH$_3$)]$_n$—CH$_3$, —[CH$_2$CH(COOCH$_3$)]$_n$—CH$_3$, —[CH$_2$CH(COOCH$_2$CH$_3$)]$_n$—CH$_3$, and —[CH$_2$CH(COO$^t$Bu)]$_n$—CH$_3$, where n is an integer (e.g., n>1 or n>2).

The term "halide" as used herein refers to the halogens fluorine, chlorine, bromine, and iodine.

The term "heterocyclyl," as used herein refers to single and multi-cyclic non-aromatic ring systems and "heteroaryl as used herein refers to single and multi-cyclic aromatic ring systems: in which at least one of the ring members is other than carbon. The terms includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

The term "ketone" as used herein is represented by the formula $A^1$C(O)$A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" as used herein is represented by the formula —N$_3$.

The term "nitro" as used herein is represented by the formula —NO$_2$.

The term "nitrile" as used herein is represented by the formula —CN.

The term "silyl" as used herein is represented by the formula —Si$A^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)A$^1$, —S(O)$_2$A$^1$, —OS(O)$_2$A$^1$, or —OS(O)$_2$OA$^1$, where A$^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S═O. The term "sulfonyl" is used herein to refer to the sulfo-oxo group represented by the formula —S(O)$_2$A$^1$, where A$^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula A$^1$S(O)$_2$A$^2$, where A$^1$ and A$^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula A$^1$S(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"R," "R$^1$," "R$^2$," "R$^3$," "R$^n$," where n is an integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Compounds described herein may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

In some aspects, a structure of a compound can be represented by a formula:

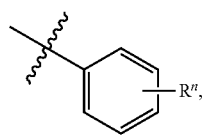

which is understood to be equivalent to a formula:

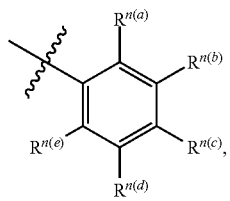

wherein n is typically an integer. That is, R$^n$ is understood to represent five independent substituents, R$^{n(a)}$, R$^{n(b)}$, R$^{n(c)}$, R$^{n(d)}$, R$^{n(e)}$. By "independent substituents," it is meant that each R substituent can be independently defined. For example, if in one instance R$^{n(a)}$ is halogen, then R$^{n(b)}$ is not necessarily halogen in that instance.

Several references to R, R$^1$, R$^2$, R$^3$, R$^4$, R$^5$, R$^6$, etc. are made in chemical structures and moieties disclosed and described herein. Any description of R, R$^1$, R$^2$, R$^3$, R$^4$, R$^5$, R$^6$, etc. in the specification is applicable to any structure or moiety reciting R, R$^1$, R$^2$, R$^3$, R$^4$, R$^5$, R$^6$, etc. respectively.

1. Compounds

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

Excitons decay from singlet excited states to ground state to yield prompt luminescence, which is fluorescence. Excitons decay from triplet excited states to ground state to generate luminescence, which is phosphorescence. Because the strong spin-orbit coupling of the heavy metal atom enhances intersystem crossing (ISC) very efficiently between singlet and triplet excited states, phosphorescent metal complexes, such as platinum complexes, have demonstrated their potential to harvest both the singlet and triplet excitons to achieve 100% internal quantum efficiency. Thus phosphorescent metal complexes are good dopants in the emissive layer of organic light emitting devices (OLEDs). Much achievement has been made in the past decade to lead to the lucrative commercialization of the technology, for example, OLEDs have been used in advanced displays in smart phones, televisions, and digital cameras.

However, to date, blue electroluminescent devices remain the most challenging area of this technology, due at least in part to instability of the blue devices. It is generally understood that the choice of host materials is a factor in the stability of the blue devices. But the lowest triplet excited state (T$_1$) energy of the blue phosphors is high, which generally means that the lowest triplet excited state (T$_1$) energy of host materials for the blue devices should be even higher. This leads to difficulty in the development of the host materials for the blue devices.

This disclosure provides a materials design route by introducing fluorescent luminophore(s) to the ligand of the metal complexes. Thereby chemical structures of the fluorescent luminophores and the ligands may be modified, and also the metal may be changed to adjust the singlet states energy and the triplet states energy of the metal complexes, which all may affect the optical properties of the complexes, for example, emission and absorption spectra. Accordingly, the energy gap ($\Delta E_{ST}$) between the lowest triplet excited state ($T_1$) and the lowest singlet excited state ($S_1$) may be also adjusted. When the $\Delta E_{ST}$ becomes small enough, intersystem crossing (ISC) from the lowest triplet excited state ($T_1$) to the lowest singlet excited state ($S_1$) may occur efficiently, such that the excitons undergo non-radiative relaxation via ISC from $T_1$ to $S_1$, then relax from $S_1$ to $S_0$, which leads to delayed fluorescence, as depicted in the Jablonski Energy Diagram in FIG. 1. Through this pathway, higher energy excitons may be obtained from lower excited state (from $T_1 \rightarrow S_1$), which means more host materials may be available for the dopants. This approach offers a solution to problems associated with blue devices.

The metal complexes described herein can be tailored or tuned to a specific application that requires a particular emission or absorption characteristic. The optical properties of the metal complexes in this disclosure can be tuned by varying the structure of the ligand surrounding the metal center or varying the structure of fluorescent luminophore(s) on the ligands. For example, the metal complexes having a ligand with electron donating substituents or electron withdrawing substituents can generally exhibit different optical properties, including emission and absorption spectra. The color of the metal complexes can be tuned by modifying the conjugated groups on the fluorescent luminophores and ligands.

The emission of such complexes can be tuned (e.g., from the ultraviolet to near-infrared), by, for example, modifying the ligand or fluorescent luminophore structure. A fluorescent luminophore is a group of atoms in an organic molecule, which can absorb energy to generate singlet excited state(s), and the singlet exciton(s) produced decay rapidly to yield prompt luminescence. In another aspect, the complexes provide emission over a majority of the visible spectrum. In one example, the complexes described herein emit light over a range of from about 400 nm to about 700 nm. In another aspect, the complexes have improved stability and efficiency over traditional emission complexes. In yet another aspect, the complexes are suitable for luminescent labels in, for example, bio-applications, anti-cancer agents, emitters in organic light emitting diodes (OLED), or a combination thereof. In another aspect, the complexes described herein are suitable for light emitting devices, such as, for example, compact fluorescent lamps (CFL), light emitting diodes (LED), incandescent lamps, and combinations thereof.

Disclosed herein are compounds or compound complexes comprising iridium, rhodium and platinum compounds. The terms compound, compound complex, and complex are used interchangeably herein. In one aspect, the compounds disclosed herein have a neutral charge.

The compounds disclosed herein can exhibit desirable properties and have emission and/or absorption spectra that can be tuned via the selection of appropriate ligands. In another aspect, any one or more of the compounds, structures, or portions thereof, specifically recited herein may be excluded.

The compounds disclosed herein are suited for use in a wide variety of optical and electro-optical devices, including, but not limited to, photo-absorbing devices such as solar- and photo-sensitive devices, organic light emitting diodes (OLEDs), photo-emitting devices, or devices capable of both photo-absorption and emission and as markers for bio-applications.

As briefly described above, the disclosed compounds are iridium, rhodium, and platinum complexes. In one aspect, the compounds disclosed herein can be used as host materials for OLED applications, such as full color displays.

The compounds disclosed herein are useful in a variety of applications. As light emitting materials, the compounds can be useful in organic light emitting diodes (OLEDs), luminescent devices and displays, and other light emitting devices.

In another aspect, the compounds can provide improved efficiency and/or operational lifetimes in lighting devices, such as, for example, organic light emitting devices, as compared to conventional materials.

Compounds described herein can be made using a variety of methods, including, but not limited to those recited in the examples.

In one aspect, the compounds disclosed herein are delayed fluorescent emitters. In another aspect, the compounds disclosed herein are phosphorescent emitters. In yet another aspect, the compounds disclosed herein are delayed fluorescent emitters and phosphorescent emitters.

Disclosed herein are complexes of Formula I, Formula II, Formula III, Formula IV, Formula V, Formula VI, Formula VII, Formula VIII, Formula IX, and Formula X:

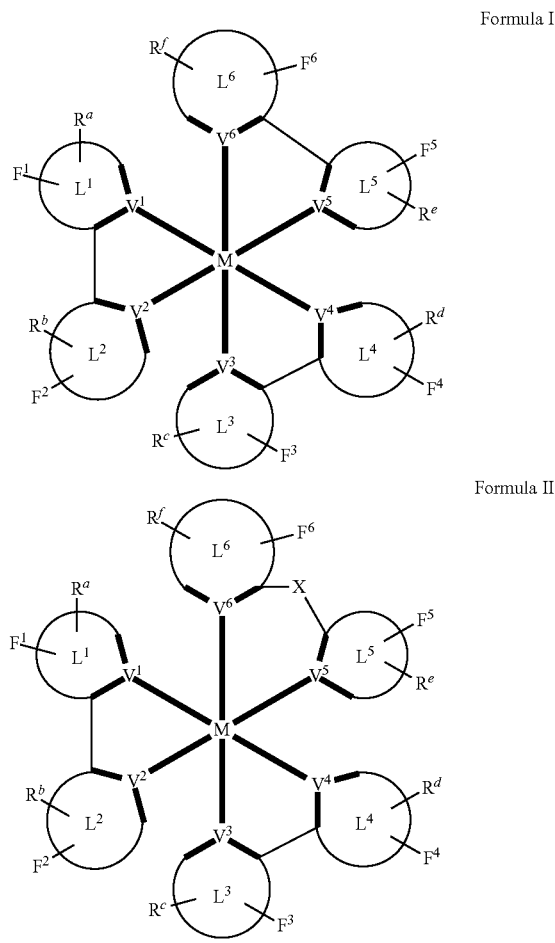

-continued

Formula III
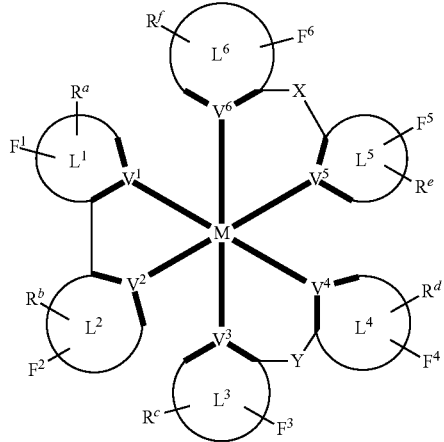

Formula IV
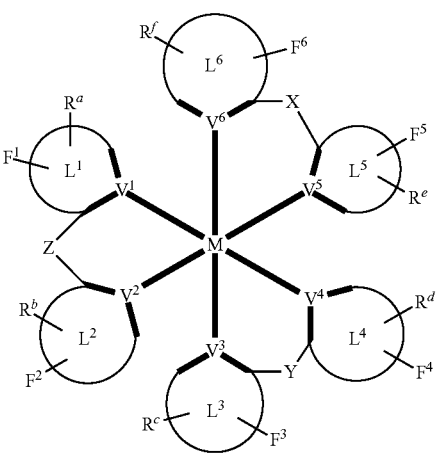

Formula V
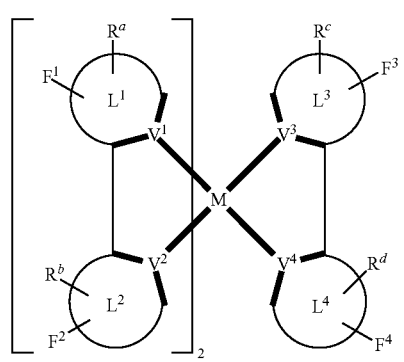

Formula VI
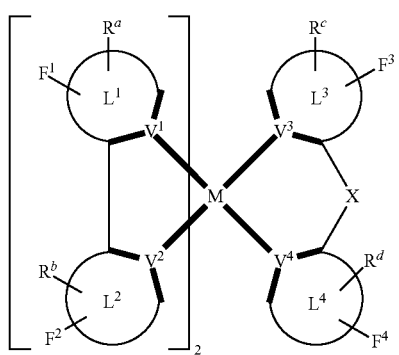

Formula VII
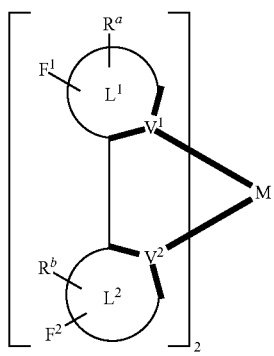

Formula VIII
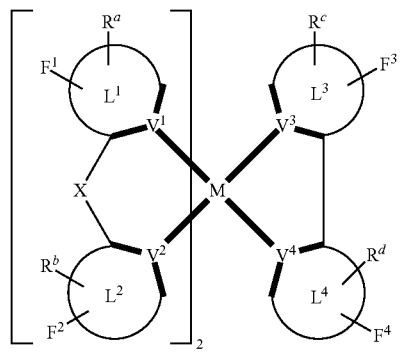

Formula IX
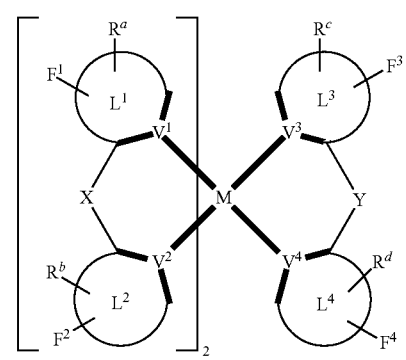

Formula X
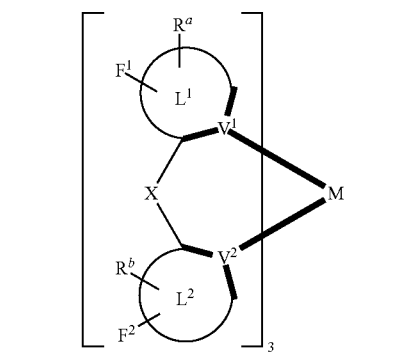

wherein:
M is Ir(III), Rh(III), or Pt(IV),
each of $L^1$, $L^2$, $L^3$, $L^4$, $L^5$ and $L^6$ is independently a substituted or unsubstituted aryl, cycloalkyl, cycloalkenyl, heteroaryl, heterocyclyl, carbene, or N-heterocyclic carbene, dione, cyanogen, or phosphine,
each of $V^1$, $V^2$, $V^3$, $V^4$, $V^5$, and $V^6$ is coordinated with M and is independently N, C, P, B, or Si, each of X, Y, and Z is independently CH$_2$, CR$^1$R$^2$, C=O, CH$_2$, SiR$^1$R$^2$, GeH$_2$, GeR$^1$R$^2$, NH, NR$^3$, PH, PR$^3$, R$^3$P=O, AsR$^3$, R$^3$As=O, O, S, S=O, SO$_2$, Se, Se=O, SeO$_2$, BH, BR$^3$, R$^3$Bi=O, BiH, or BiR$^3$, each of F$^1$, F$^2$, F$^3$, F$^4$, F$^5$, and F$^6$ is independently present or absent, wherein at least one of F$^1$, F$^2$, F$^3$, F$^4$, F$^5$, and F$^6$ is present, and each F$^1$, F$^2$, F$^3$, F$^4$, F$^5$, and F$^6$ present is a fluorescent luminophore, each of R$^a$, R$^b$, R$^c$, R$^d$, R$^e$, and R$^f$ is independently present or absent, and if present each of R$^a$, R$^b$, R$^c$, R$^d$, R$^e$, and R$^f$ independently represents mono-, di-, or tri-substitutions, and wherein each of R$^a$, R$^b$, R$^c$, R$^d$, R$^e$ and R$^f$ present is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and each of R$^1$, R$^2$, and R$^3$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

For Formulas I-X as described herein, groups may be defined as described below.

A. M Groups

In one aspect, M is Ir(III).

In another aspect, M is Rh(III).

In yet another aspect, M is Pt(IV).

B. V Groups

In one aspect, each of V$^1$, V$^2$, V$^3$, V$^4$, V$^5$, and V$^6$ is coordinated with M and is independently N, C, P, B, or Si.

In another aspect, each of V$^1$, V$^2$, V$^3$, V$^4$, V$^5$, and V$^6$ is independently N or C.

In yet another aspect, each of V$^1$, V$^2$, V$^3$, V$^4$, V$^5$, and V$^6$ is independently P or B.

In yet another aspect, each of V$^1$, V$^2$, V$^3$, V$^4$, V$^5$, and V$^6$ is Si.

C. Linking Groups

In one aspect, each of X, Y, and Z is independently present or absent, and each X, Y, and Z present is independently CH$_2$, CR$^1$R$^2$, C=O, CH$_2$, SiR$^1$R$^2$, GeH$_2$, GeR$^1$R$^2$, NH, NR$^3$, PH, PR$^3$, R$^3$P=O, AsR$^3$, R$^3$As=O, O, S, S=O, SO$_2$, Se, Se=O, SeO$_2$, BH, BR$^3$, R$^3$Bi=O, BiH, or BiR$^3$.

In another aspect, each of X, Y, and Z, if present, is independently O, S, or CH$_2$.

D. L Groups

In one aspect, L$^1$ is aryl, cycloalkyl, cycloalkenyl, heteroaryl, heterocyclyl, carbene, or N-heterocyclic carbene. In one example, L$^1$ is aryl, cycloalkyl, cycloalkenyl, heteroaryl, or N-heterocyclyl. In another example, L$^1$ is aryl or heteroaryl. In yet another example, L$^1$ is aryl.

In one aspect, L$^2$ is aryl, cycloalkyl, cycloalkenyl, heteroaryl, heterocyclyl, carbene, or N-heterocyclic carbene. In one example, L$^2$ is aryl, cycloalkyl, cycloalkenyl, heteroaryl, or N-heterocyclyl. In another example, L$^2$ is aryl or heteroaryl. In yet another example, L$^2$ is aryl.

In one aspect, L$^3$ is aryl, cycloalkyl, cycloalkenyl, heteroaryl, heterocyclyl, carbene, or N-heterocyclic carbene. In one example, L$^3$ is aryl, cycloalkyl, cycloalkenyl, heteroaryl, or heterocyclyl. In another example, L$^3$ is aryl or heteroaryl. In yet another example, L$^3$ is aryl.

In one aspect, L$^4$ is aryl, cycloalkyl, cycloalkenyl, heteroaryl, heterocyclyl, carbene, or N-heterocyclic carbene. In one example, L$^4$ is aryl, cycloalkyl, cycloalkenyl, heteroaryl, or heterocyclyl. In another example, L$^4$ is aryl or heteroaryl. In yet another example, L$^4$ is aryl.

In one aspect, L$^5$ is aryl, cycloalkyl, cycloalkenyl, heteroaryl, heterocyclyl, carbene, or N-heterocyclic carbene. In one example, L$^5$ is aryl, cycloalkyl, cycloalkenyl, heteroaryl, or heterocyclyl. In another example, L$^5$ is aryl or heteroaryl. In yet another example, L$^5$ is aryl.

In one aspect, L$^6$ is aryl, cycloalkyl, cycloalkenyl, heteroaryl, heterocyclyl, carbene, or N-heterocyclic carbene. In one example, L$^6$ is aryl, cycloalkyl, cycloalkenyl, heteroaryl, or heterocyclyl. In another example, L$^6$ is aryl or heteroaryl. In yet another example, L$^6$ is heteroaryl. In yet another example, L$^6$ is heterocyclyl.

It is understood that V$^n$ can be a part of L$^n$, where n=1 to 6, and is intended to be included the descriptions of L$^n$ above.

In one aspect, for any of the formulas disclosed herein, each of

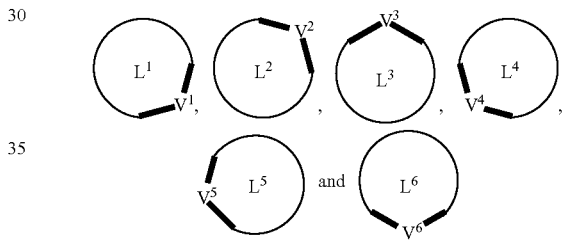

is independently one following structures:

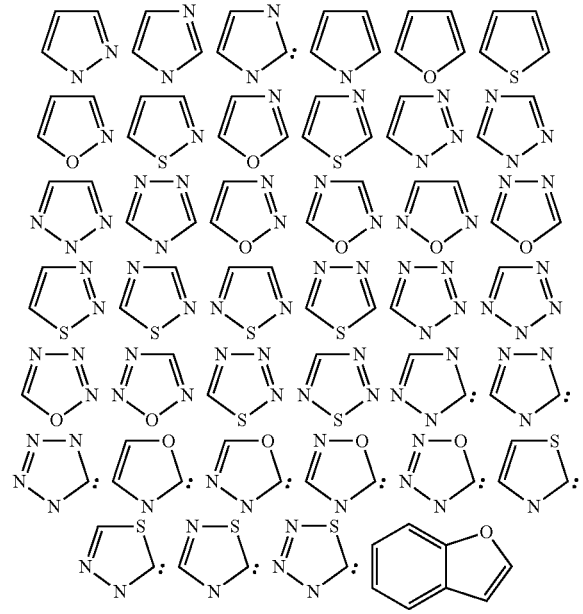

-continued
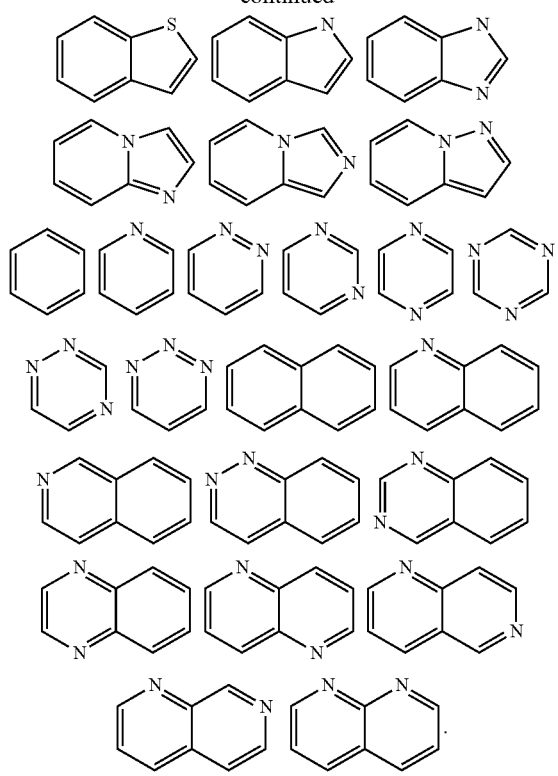
It is understood that one or more of $R^a$, $R^b$, $R^c$, $R^d$, $R^e$, and $R^f$ as described herein can be bonded to one of the above structures as permitted by valency.
In one aspect,
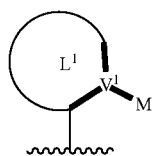
has the structure
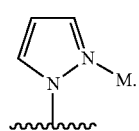
In one aspect, for any of the formulas illustrated in this disclosure, each of
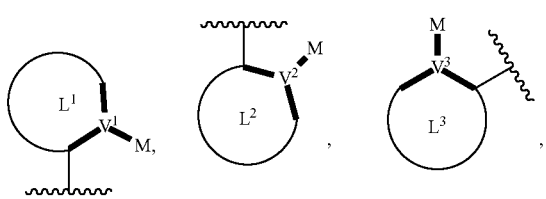
-continued
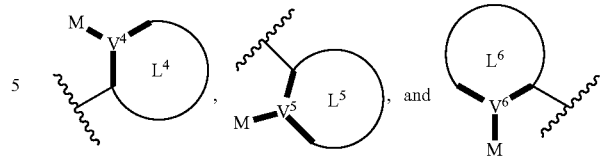
is independently one of following structures:
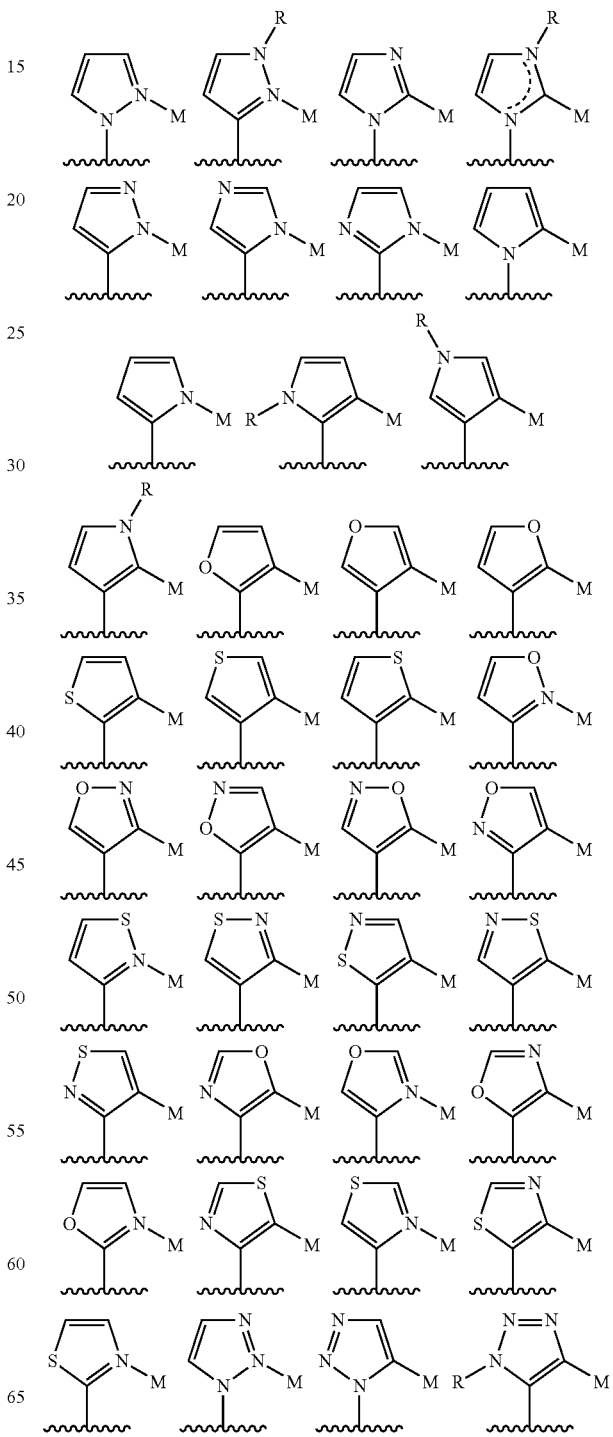

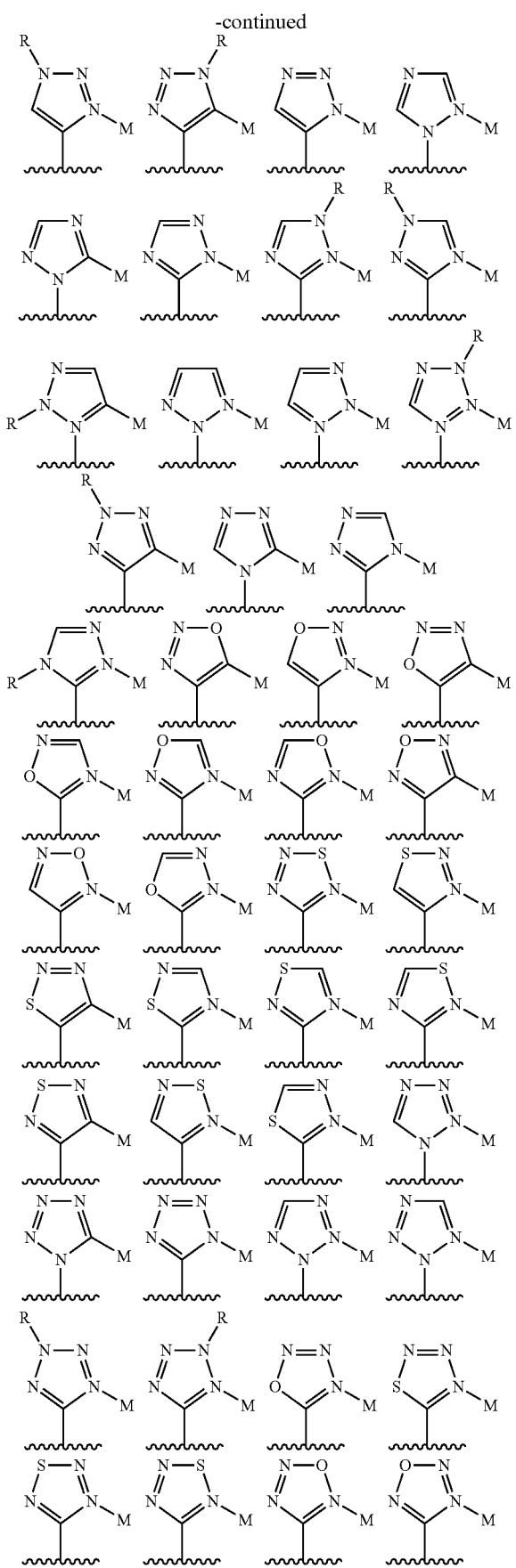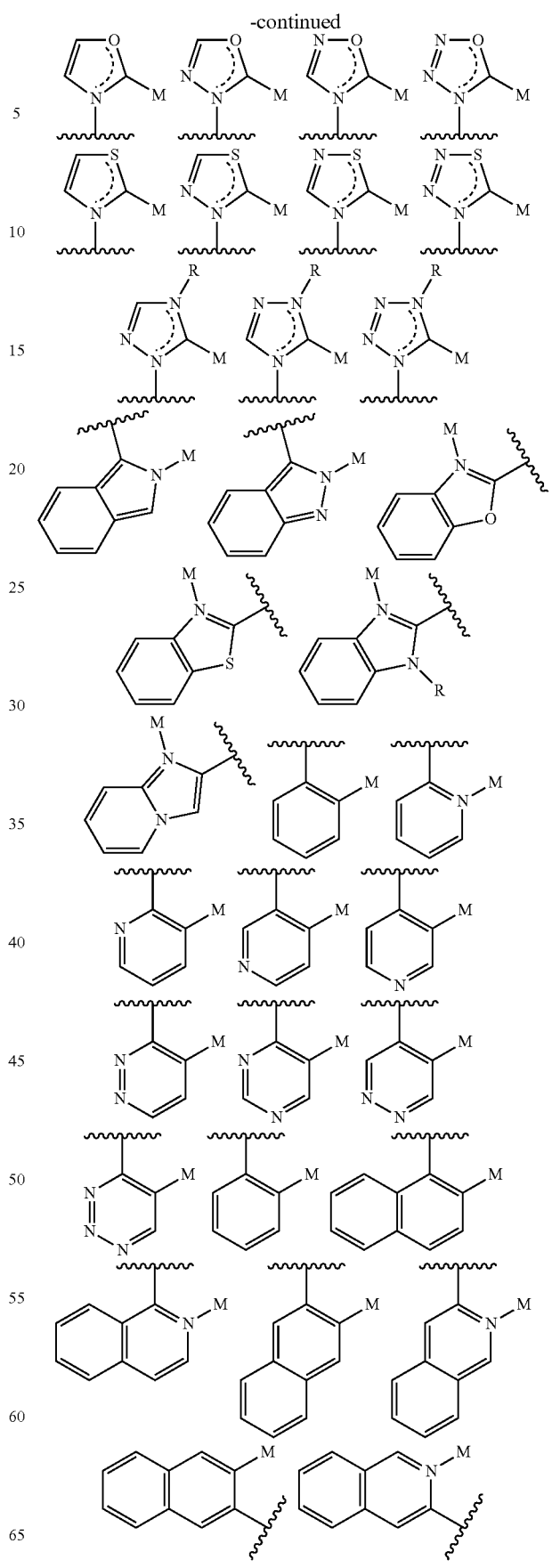

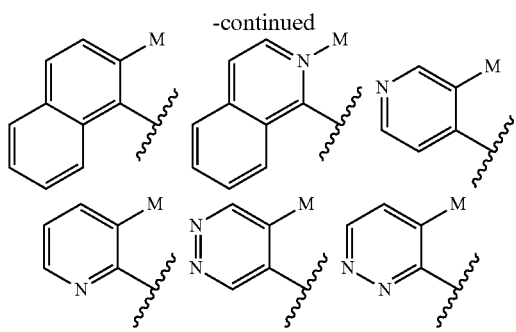

wherein R is hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

E. Fluorescent Luminophore Groups

In one aspect, at least one of $F^1$, $F^2$, $F^3$, $F^4$, $F^5$, and $F^6$ is present. In one example, $F^1$ is present, and $F^2$, $F^3$, $F^4$, $F^5$, and $F^6$ are absent.

In one aspect, each of $F^1$, $F^2$, $F^3$, $F^4$, $F^5$, and $F^6$ present is independently selected from aromatic hydrocarbons and their derivatives, polyphenyl hydrocarbons, hydrocarbons with condensed aromatic nuclei, naphthalene, anthracene, phenanthrene, chrysene, pyrene, triphenylene, perylene, acenapthene, tetracene, pentacene, tetraphene, coronene, fluorene, biphenyl, p-terphenyl, o-diphenylbenzene, m-diphenylbenzene, p-quaterphenyl, benzo[a]tetracene, benzo[k]tetraphene, indeno[1,2,3-cd]fluoranthene, tetrabenzo[de,hi,op,st]pentacene, arylethylene, arylacetylene and their derivatives, diarylethylenes, diarylpolyenes, diaryl-substituted vinylbenzenes, distyrylbenzenes, trivinylbenzenes, arylacetylenes, stilbene, and functional substitution products of stilbene.

In another aspect, each $F^1$, $F^2$, $F^3$, $F^4$, $F^5$, and $F^6$ present is independently selected from substituted or unsubstituted five-, six- or seven-membered heterocyclic compounds, furan, thiophene, pyrrole and their derivatives, aryl-substituted oxazoles, 1,3,4-oxadiazoles, 1,3,4-thiadiazoles, aryl-substituted 2-pyrazolines and pyrazoles, benzazoles, 2H-benzotriazole and its substitution products, heterocycles with one, two or three nitrogen atoms, oxygen-containing heterocycles, coumarins and their derivatives, miscellaneous dyes, acridine dyes, xanthene dyes, oxazines, and thiazines.

In yet another aspect, for any of the formulas disclosed herein, each $F^1$, $F^2$, $F^3$, $F^4$, $F^5$, and $F^6$ present may independently have one of the following structures:

1. Aromatic Hydrocarbons and their Derivatives

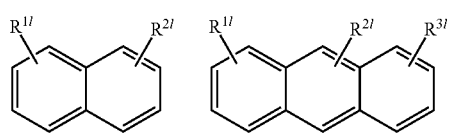

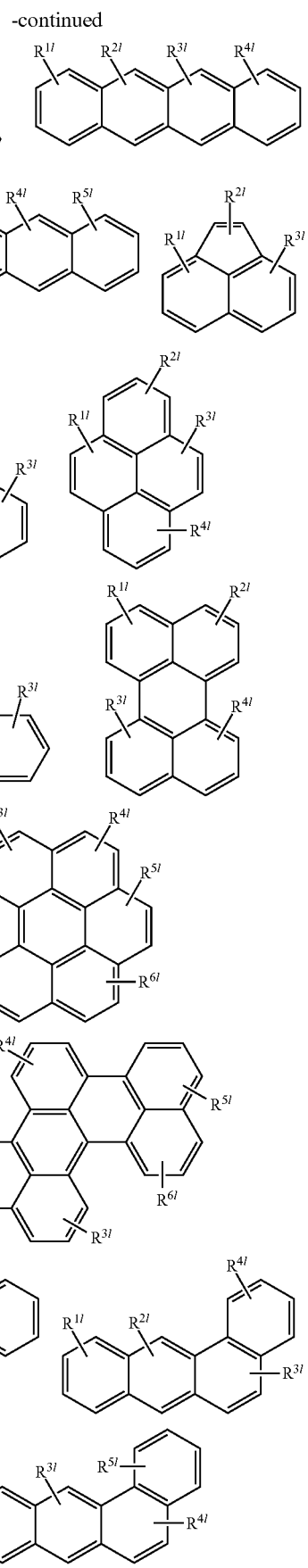

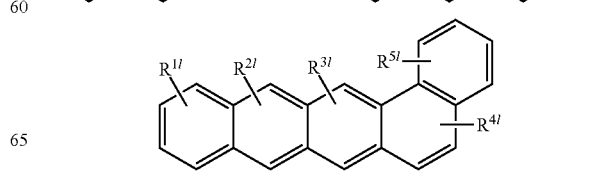

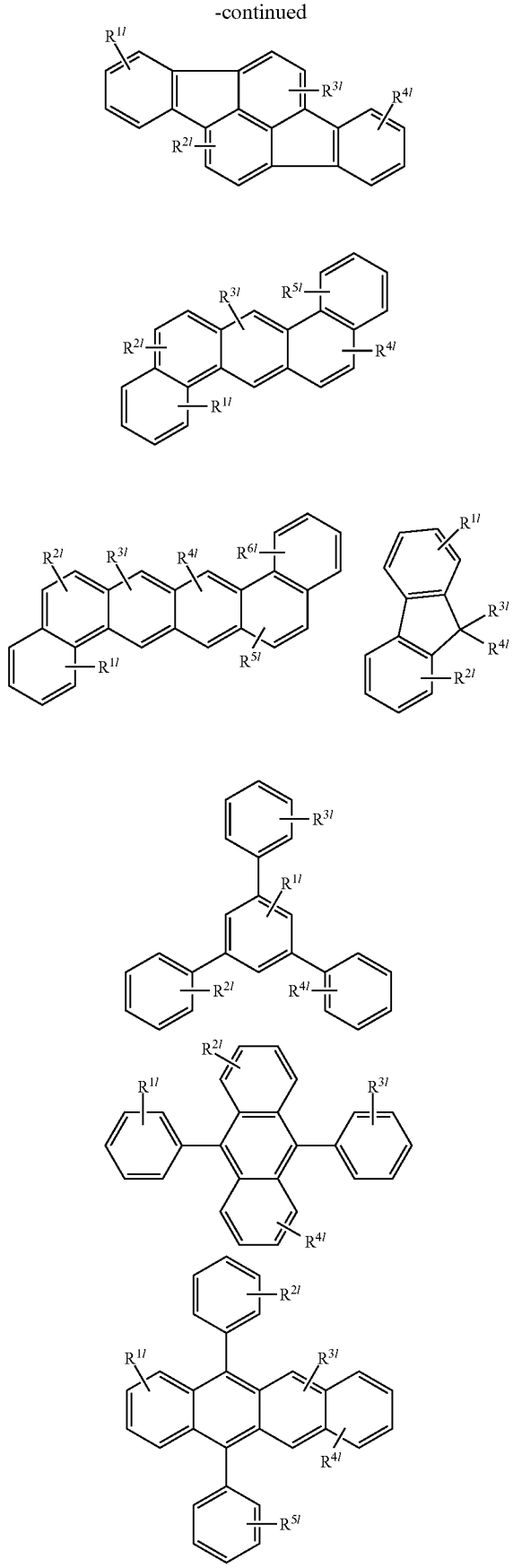
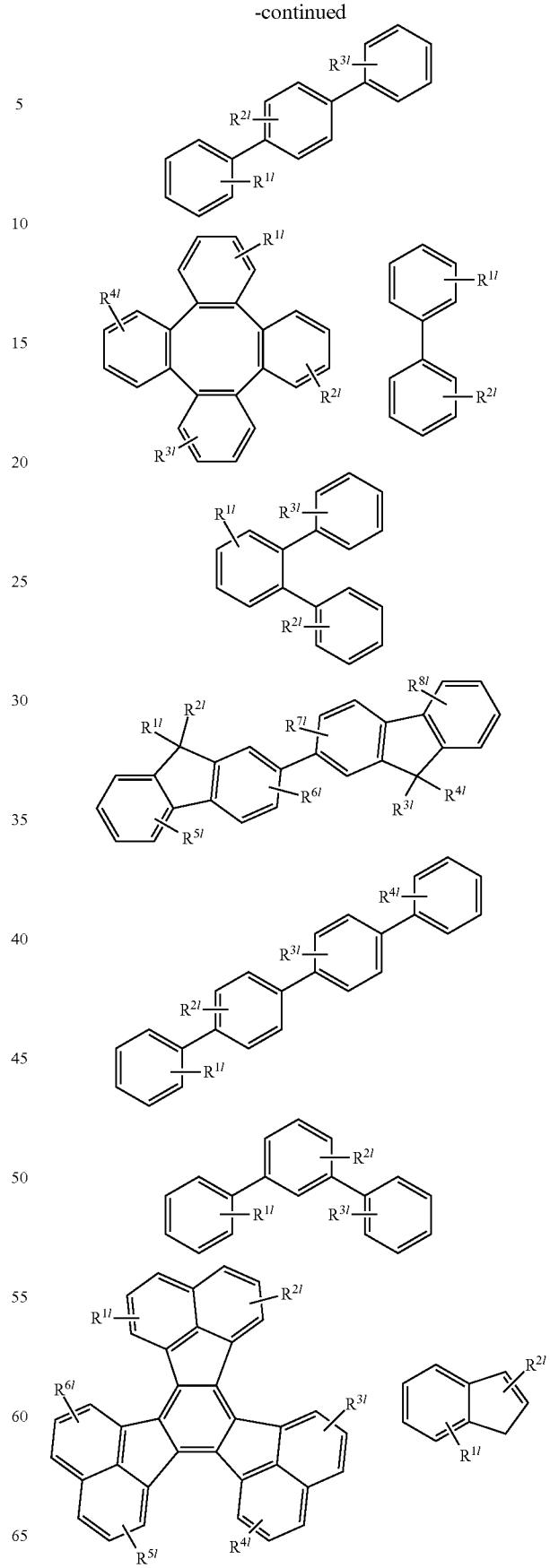

-continued
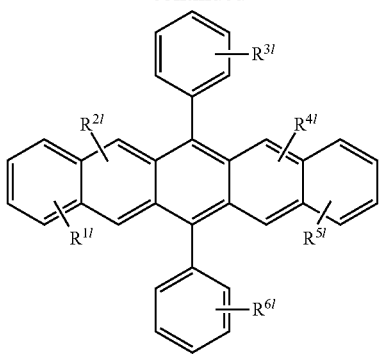
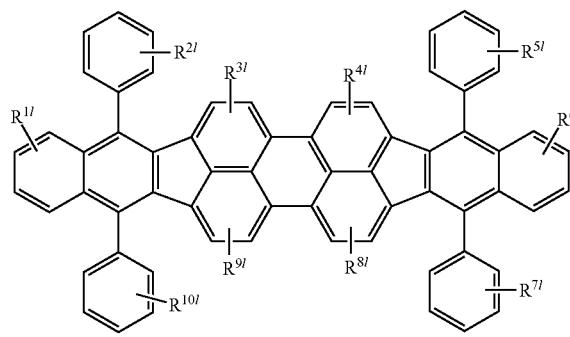
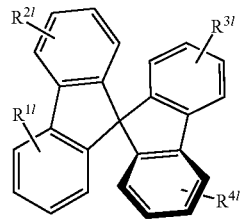
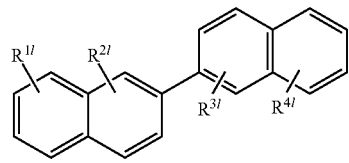
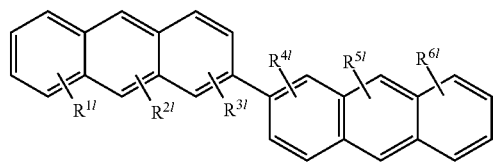
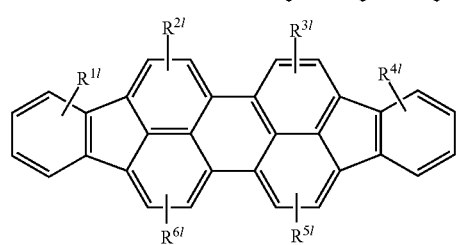
-continued
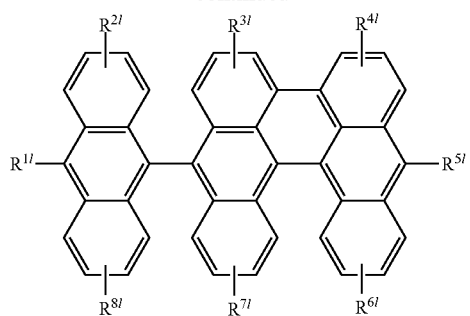
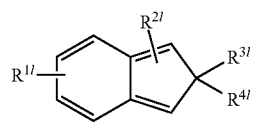
2. Arylethylene, Arylacetylene and their Derivatives
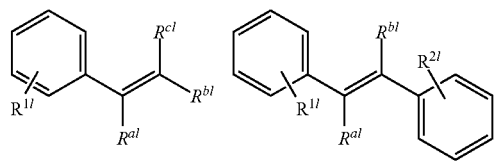
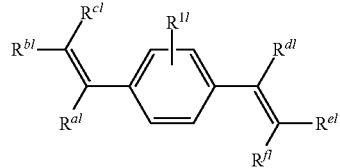
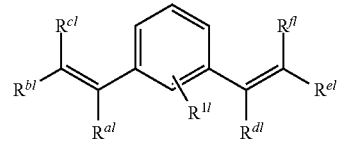
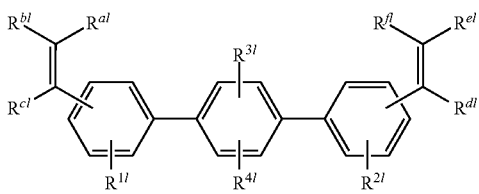
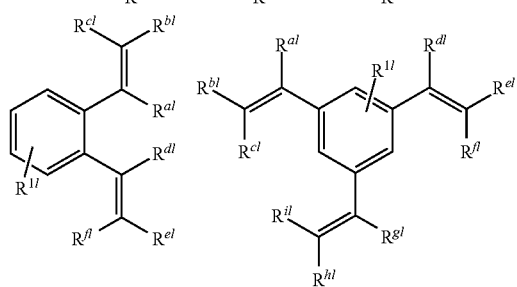

-continued
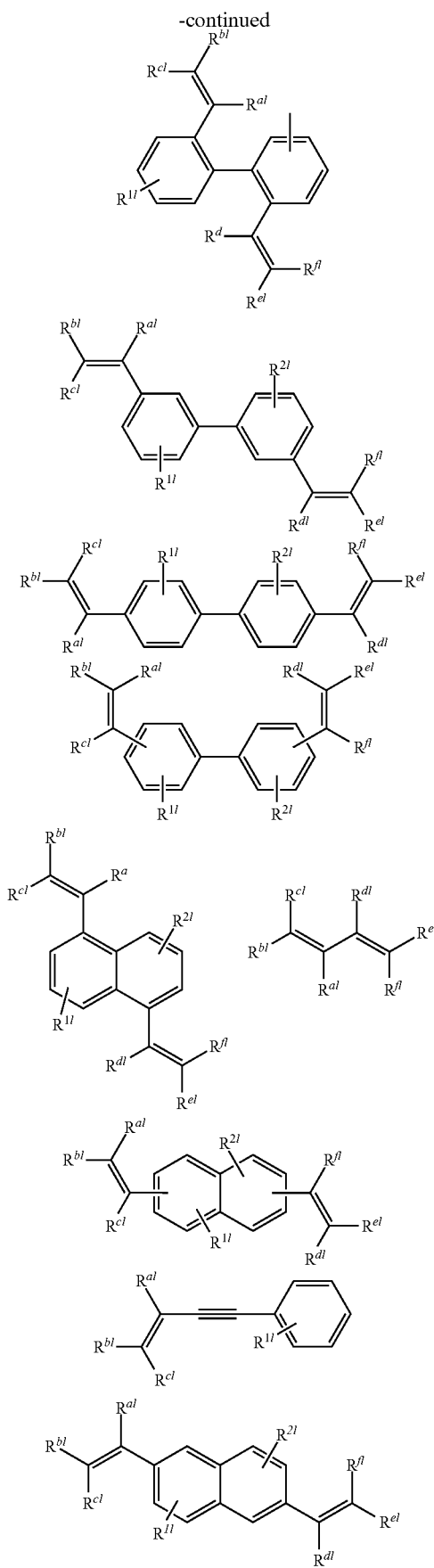
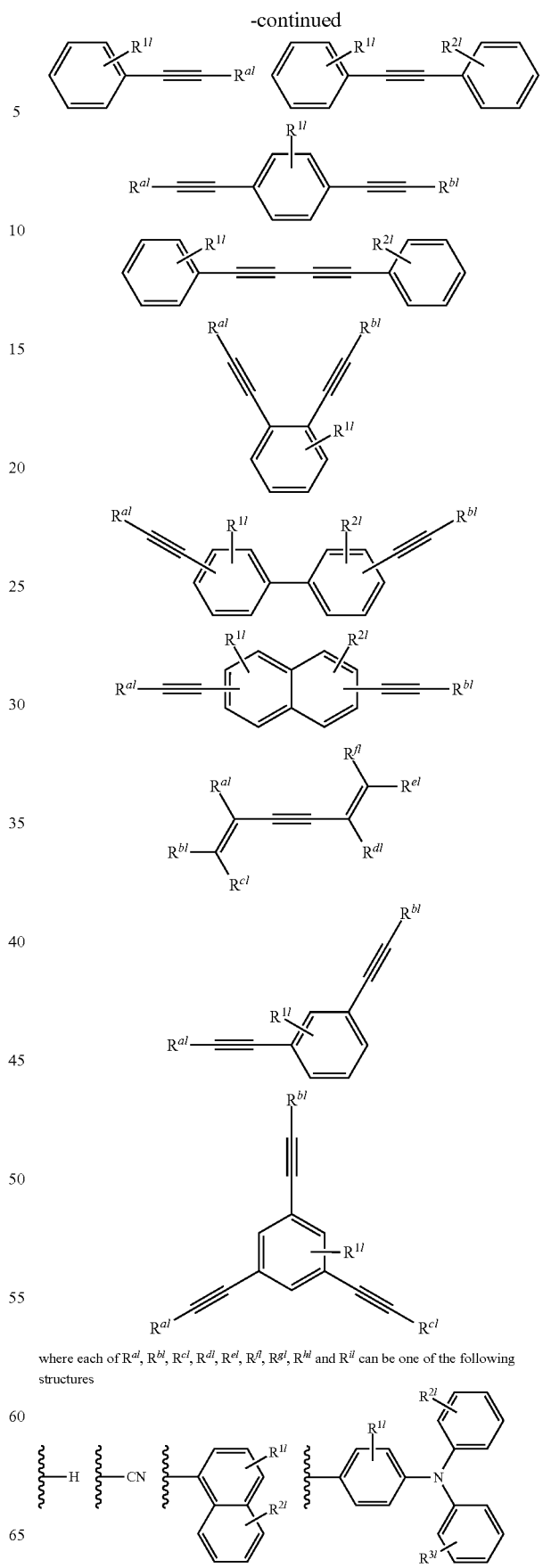
where each of $R^{al}$, $R^{bl}$, $R^{cl}$, $R^{dl}$, $R^{el}$, $R^{fl}$, $R^{gl}$, $R^{hl}$ and $R^{il}$ can be one of the following structures
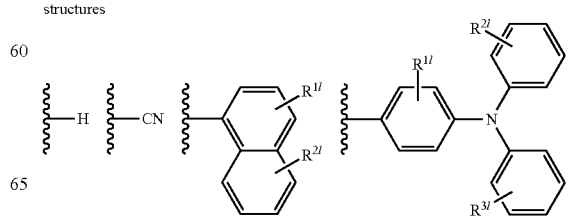

-continued
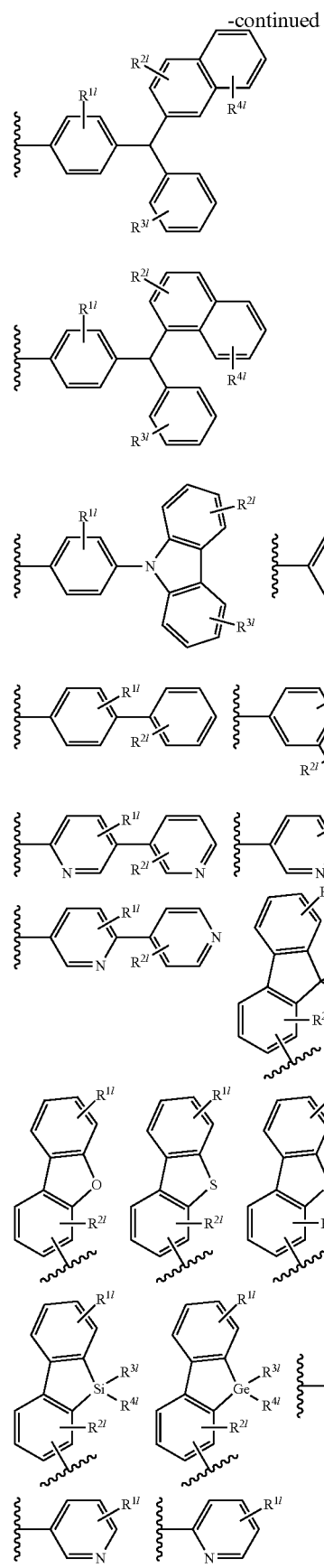
3. Heterocyclic Compounds and their Derivatives
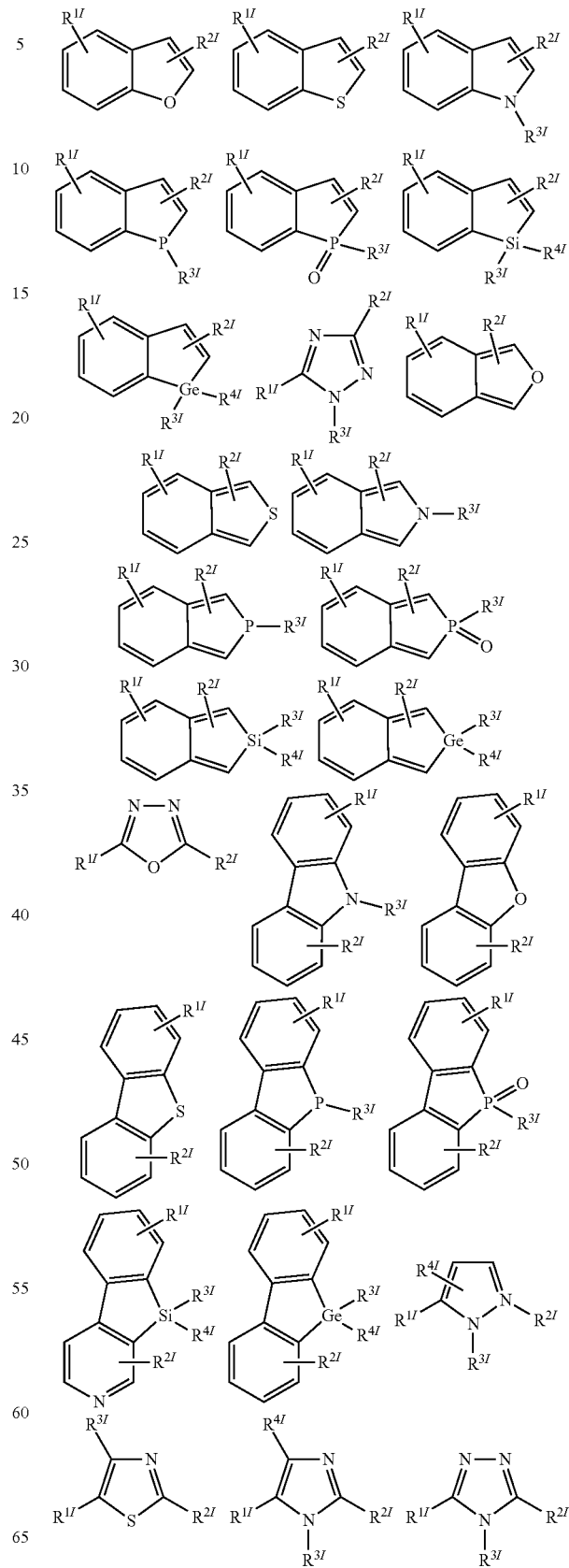

-continued
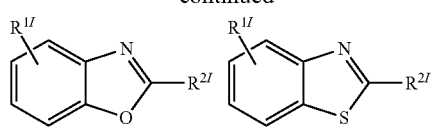
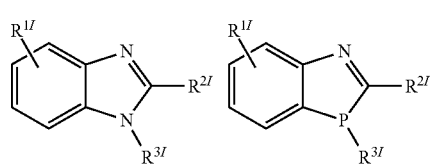
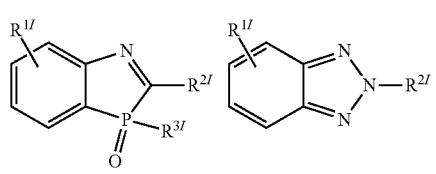
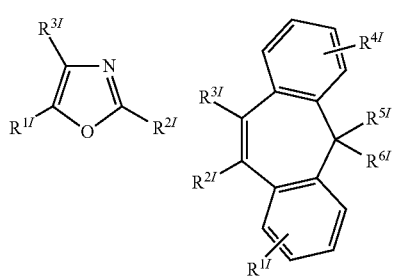
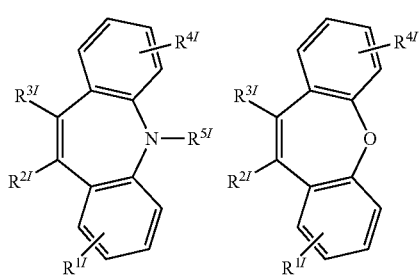
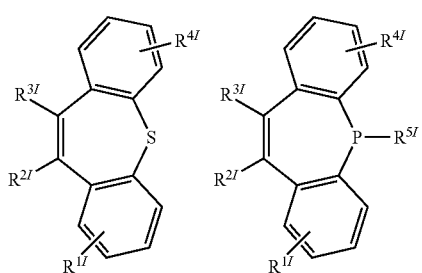
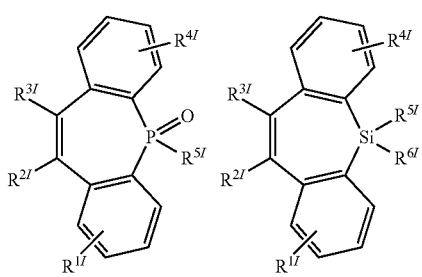
-continued
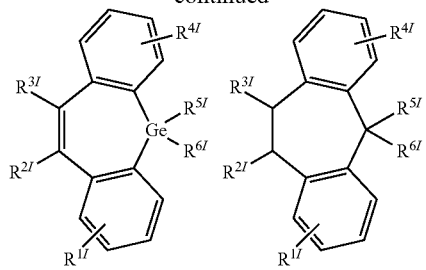
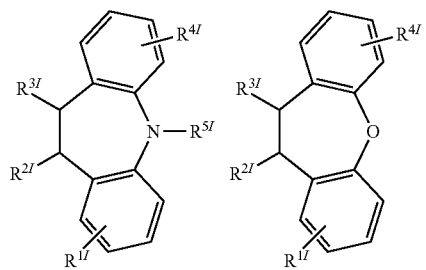
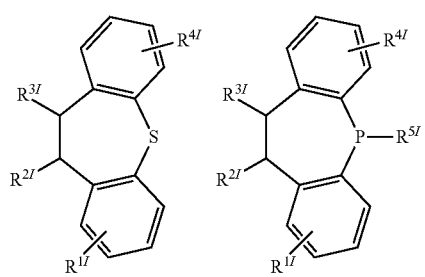
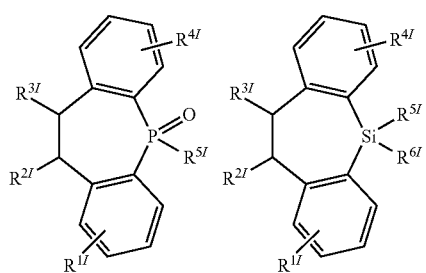
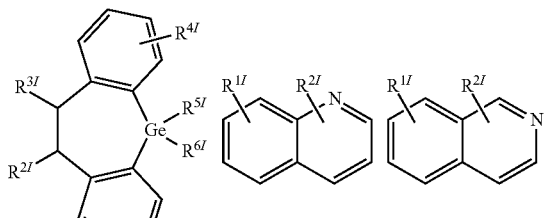
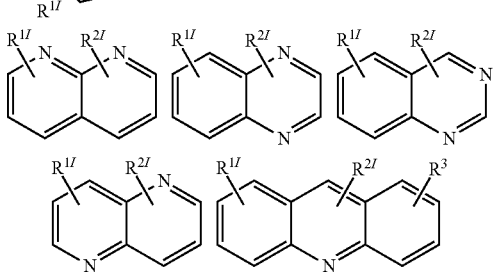

-continued
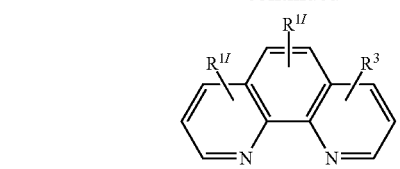
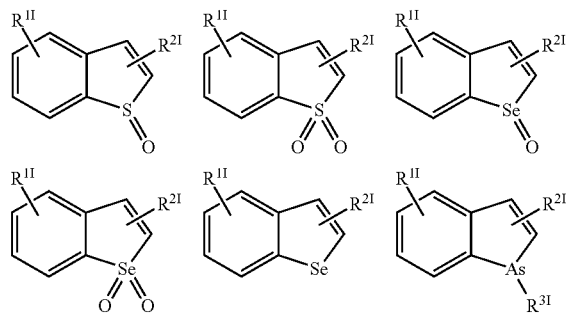
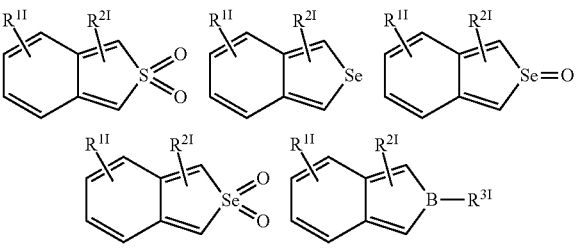
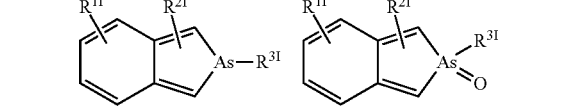
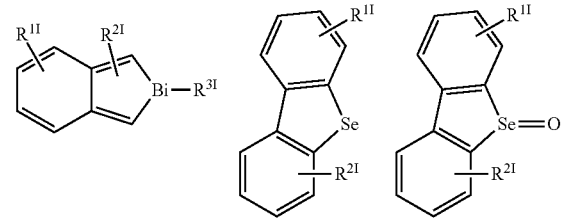
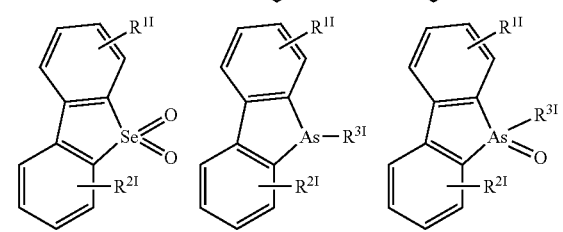
-continued
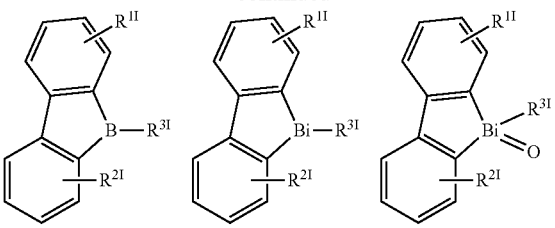
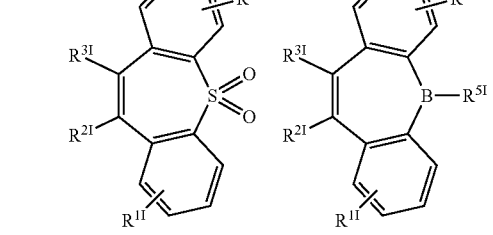
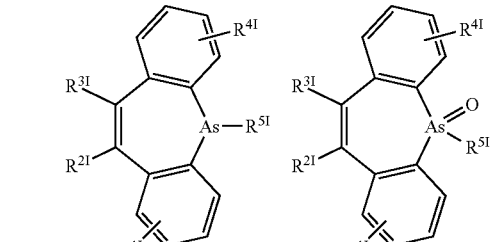
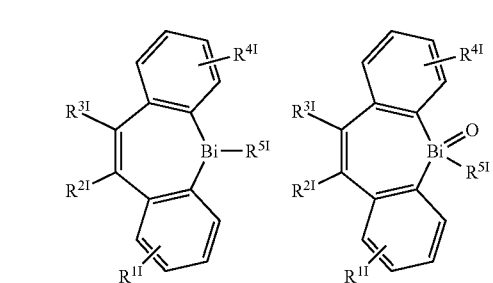

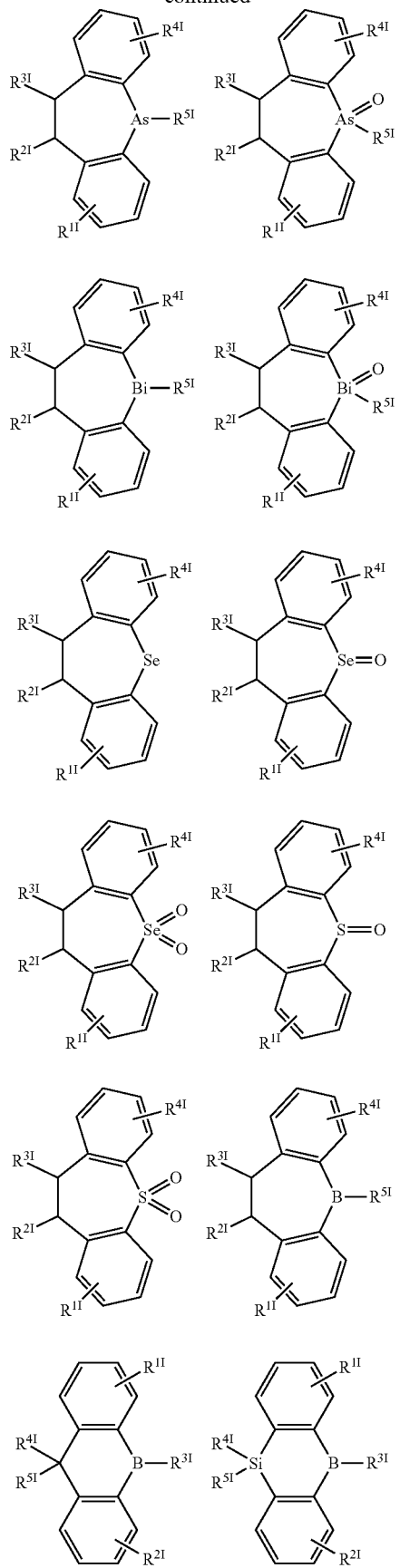
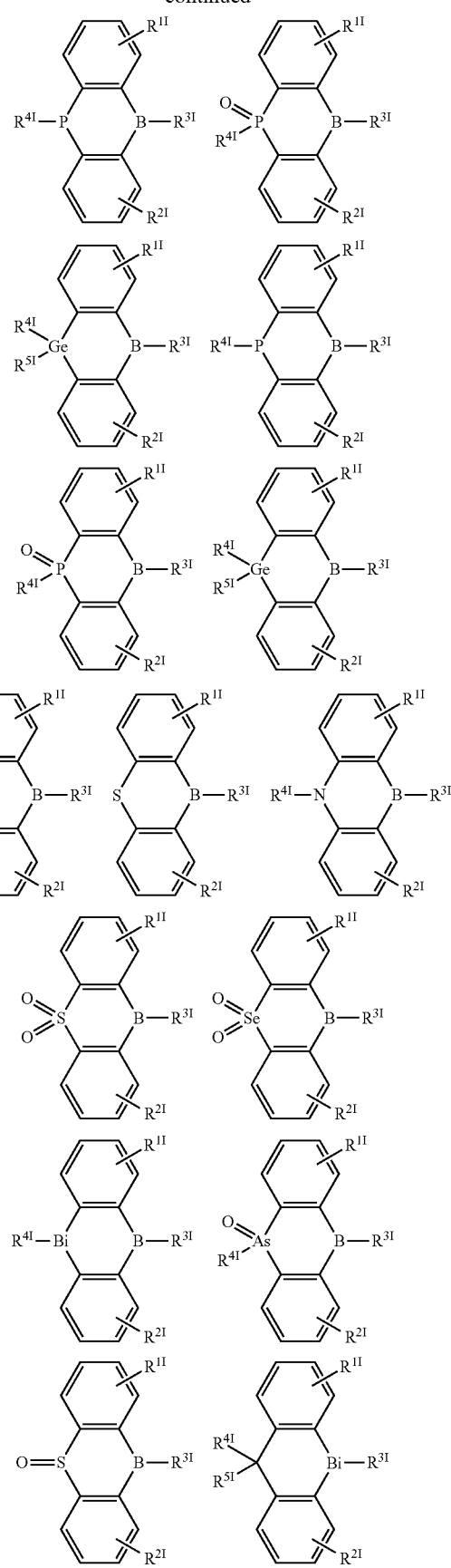

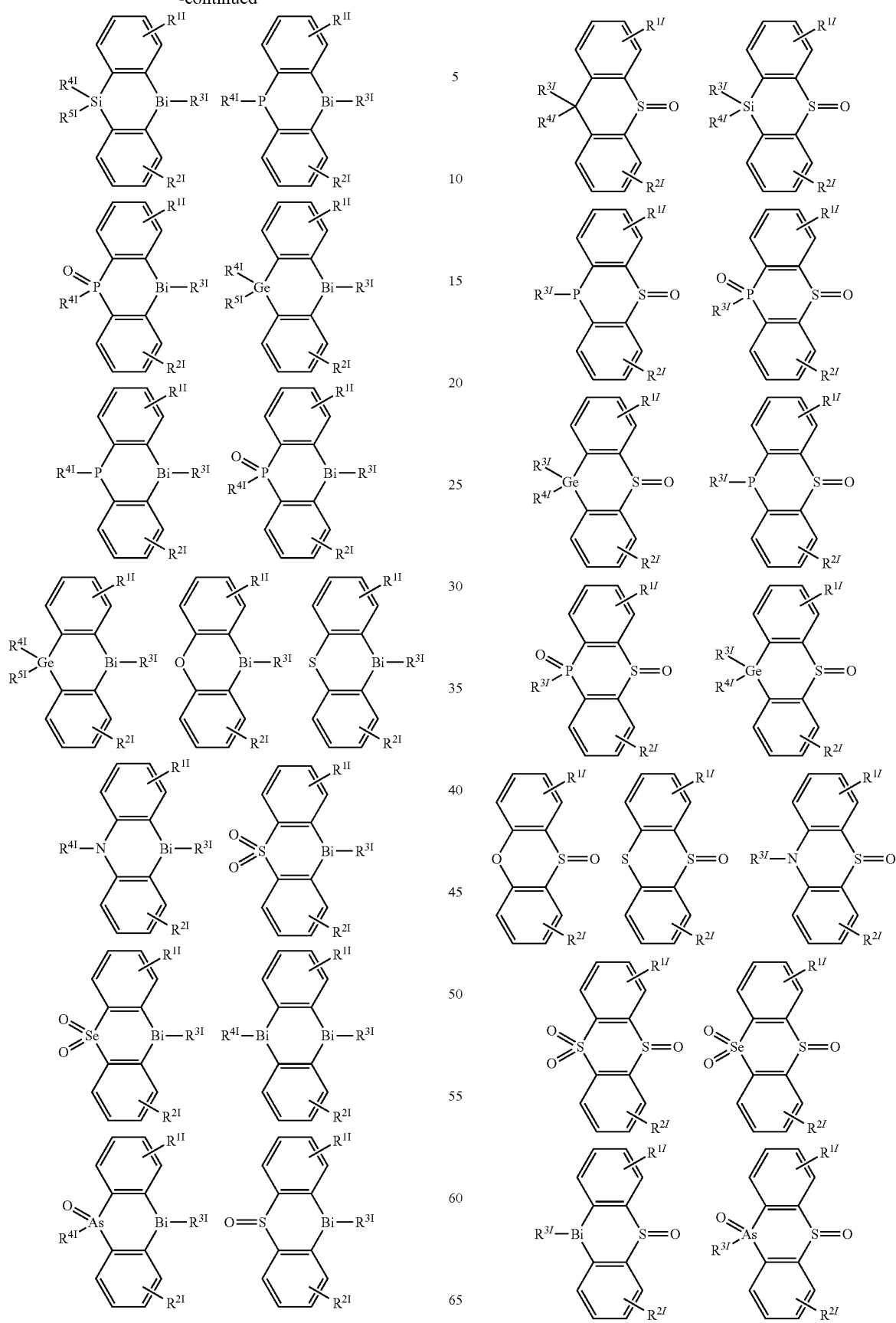

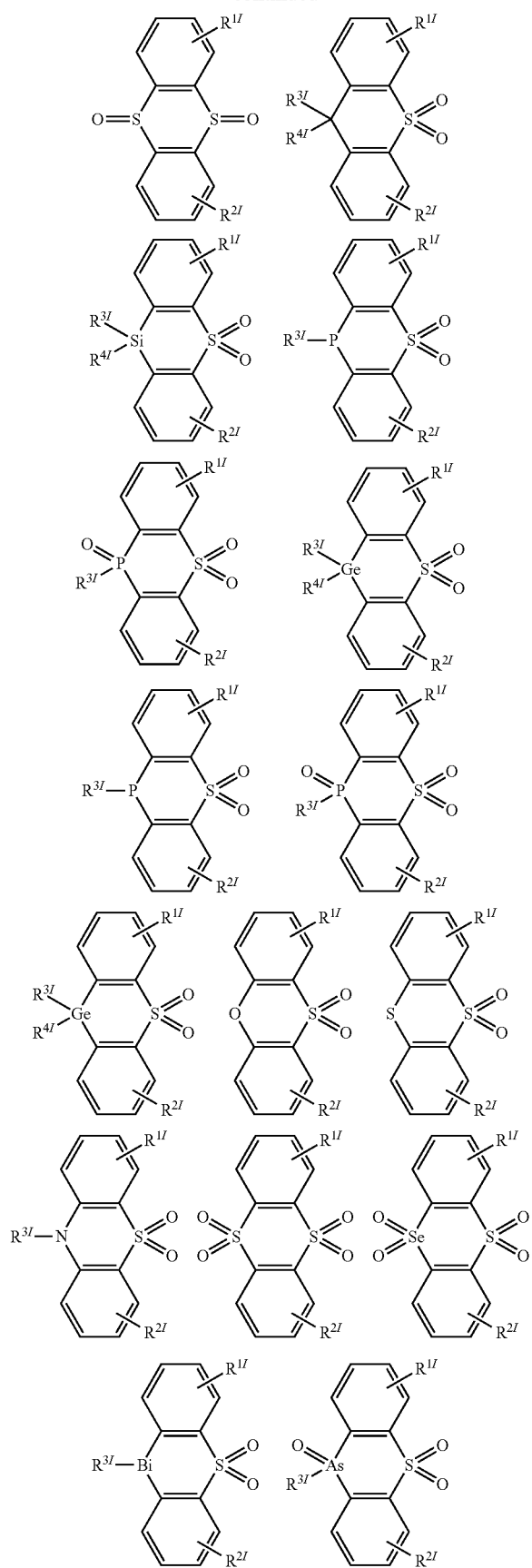
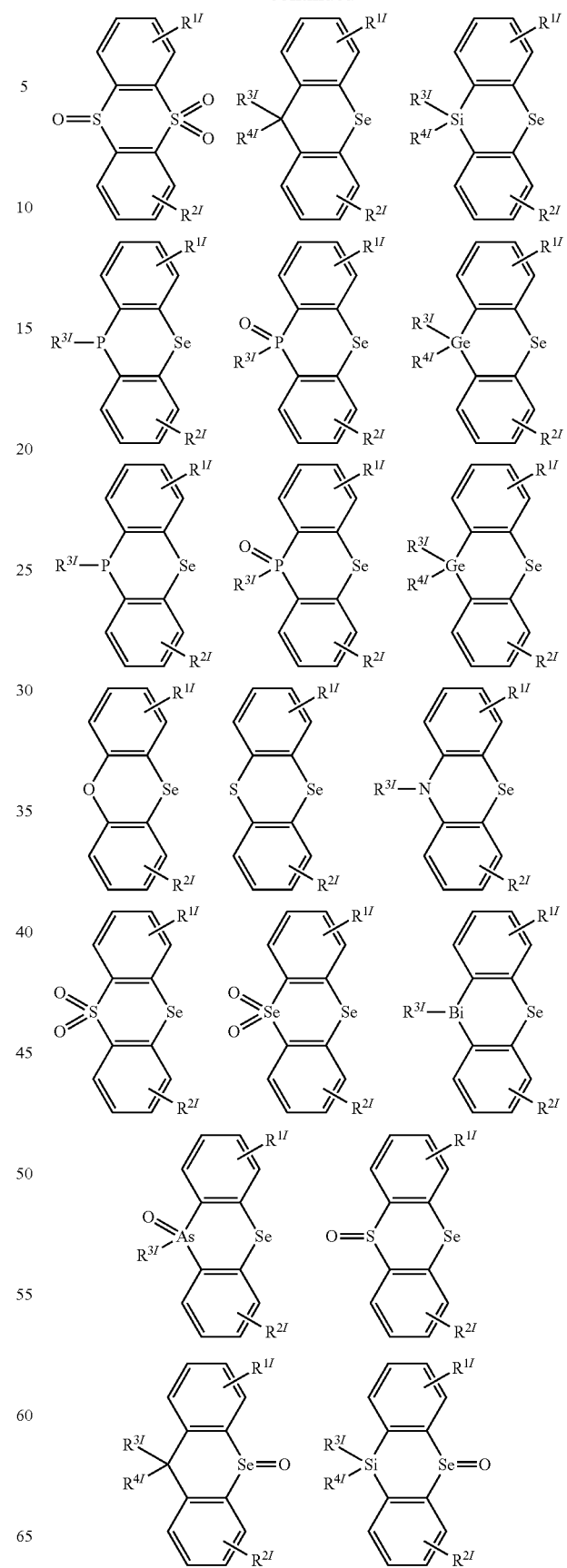

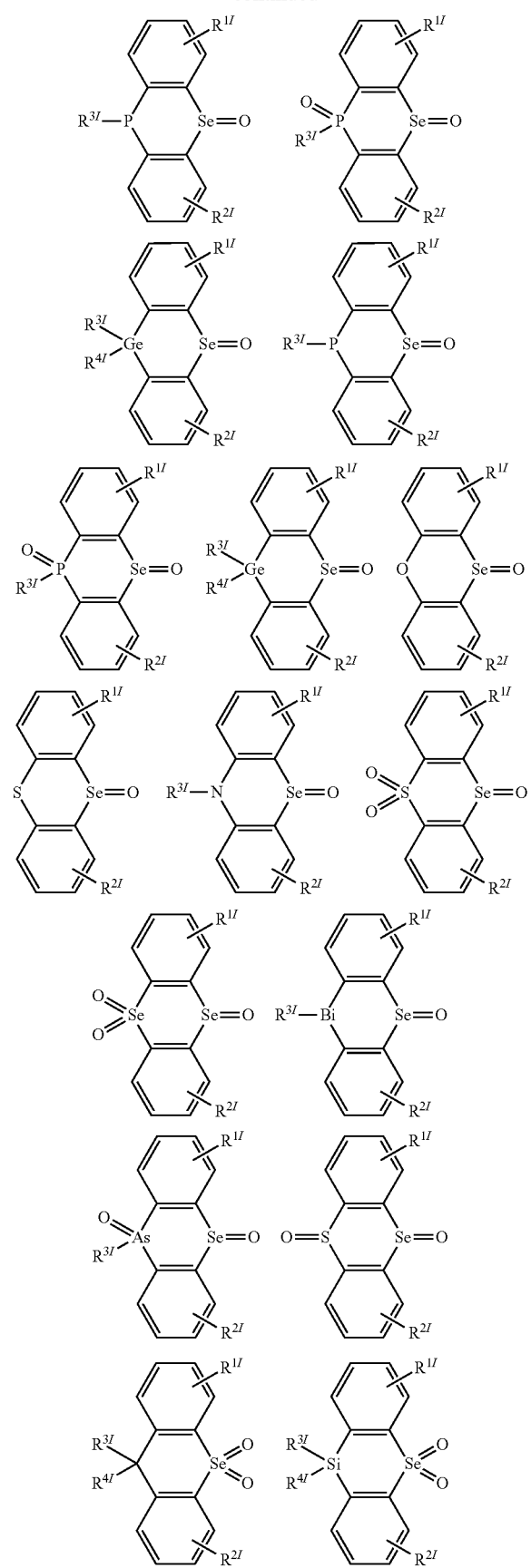
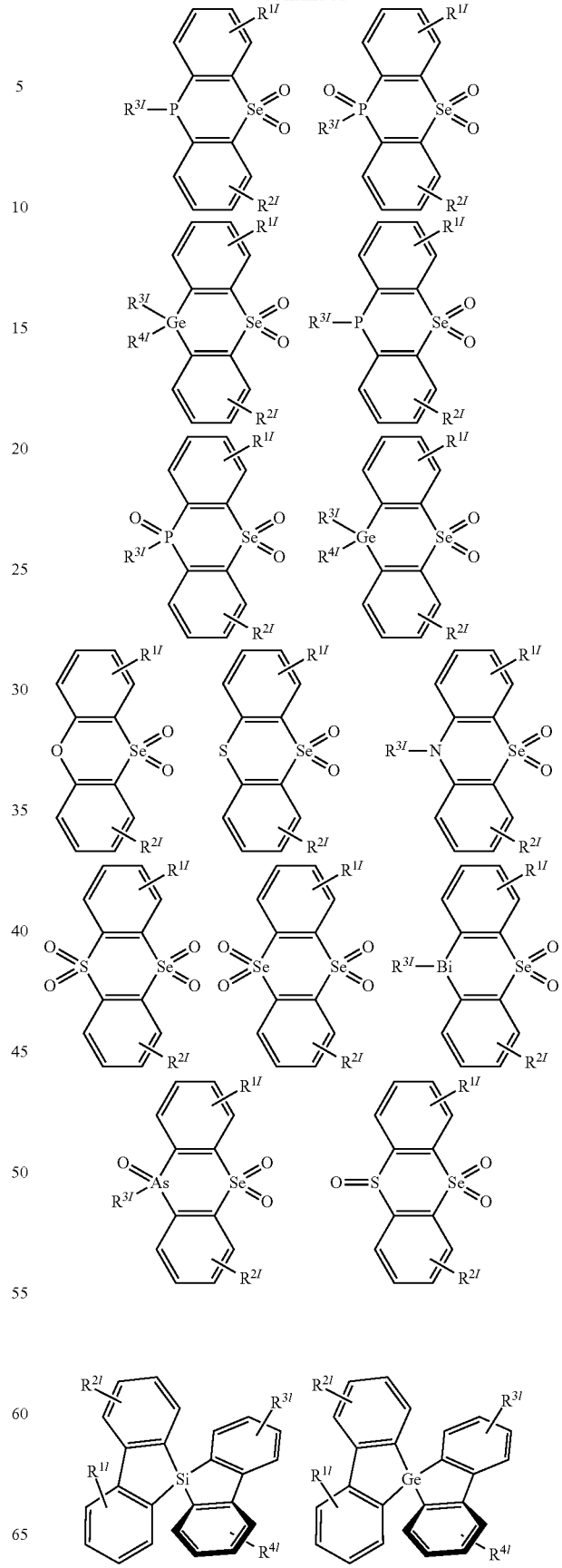

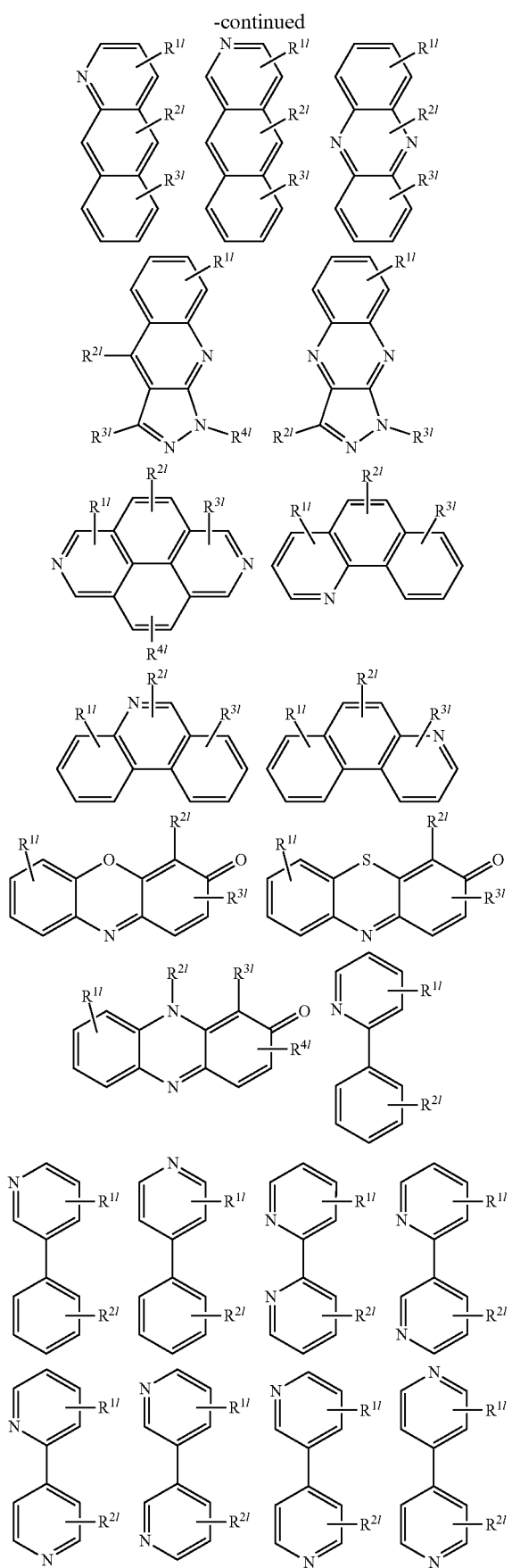
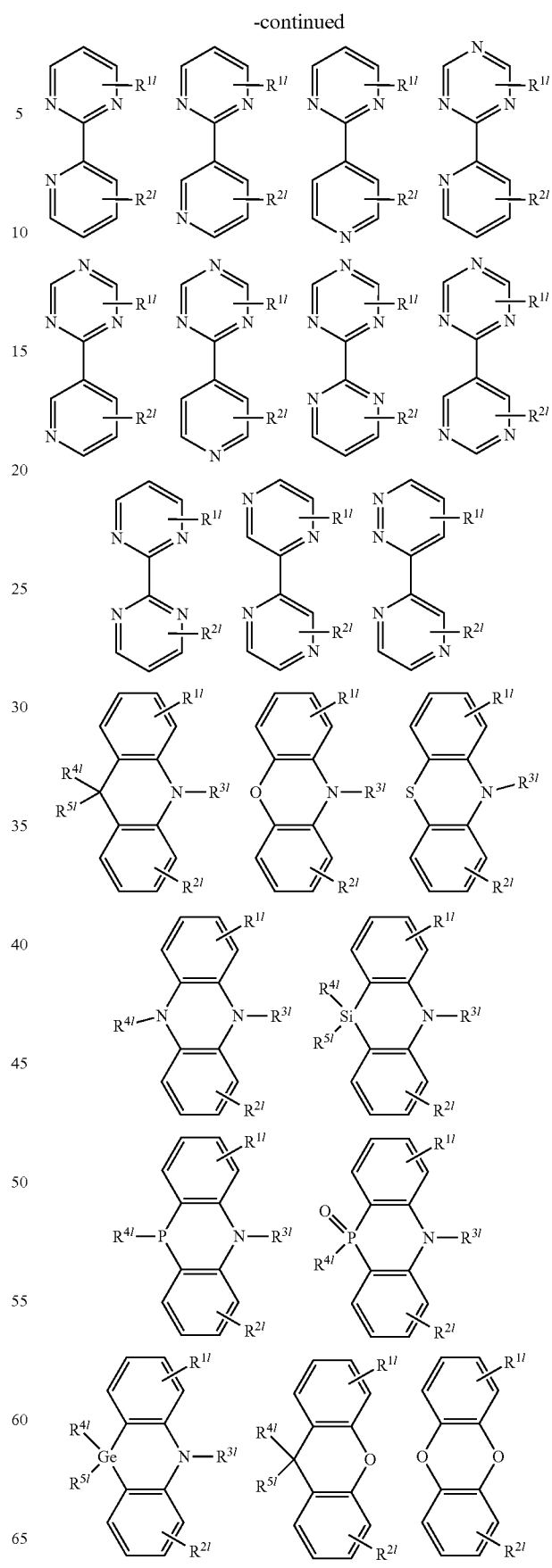

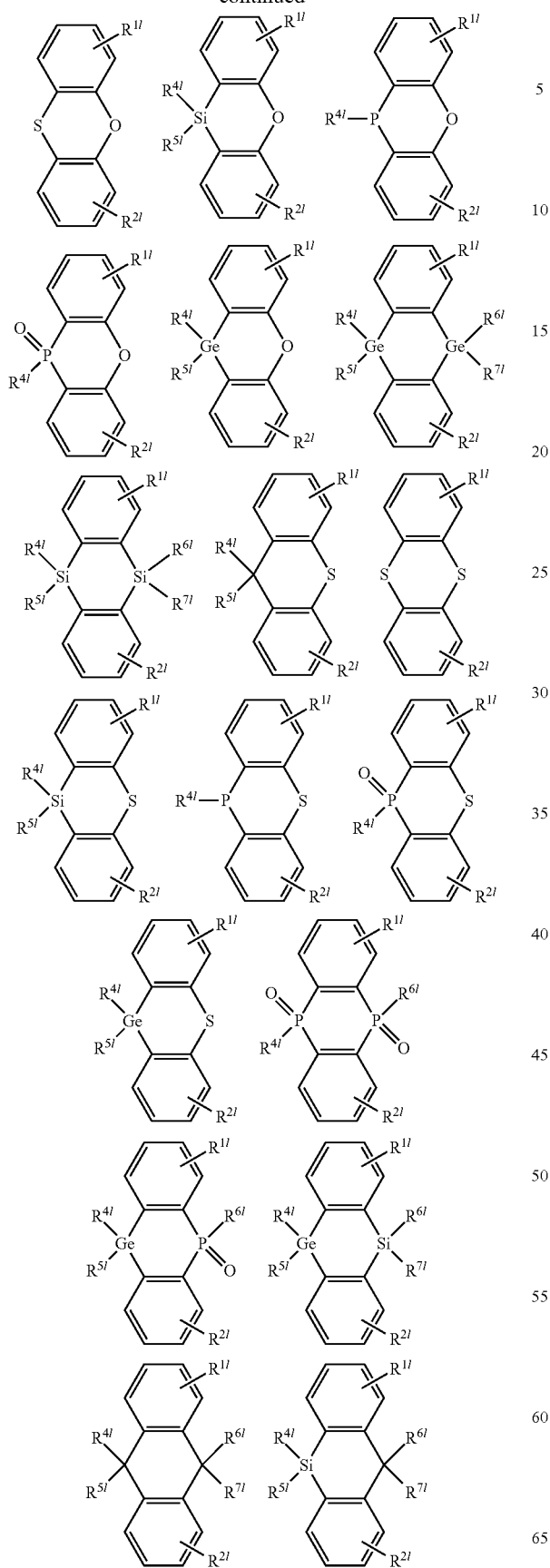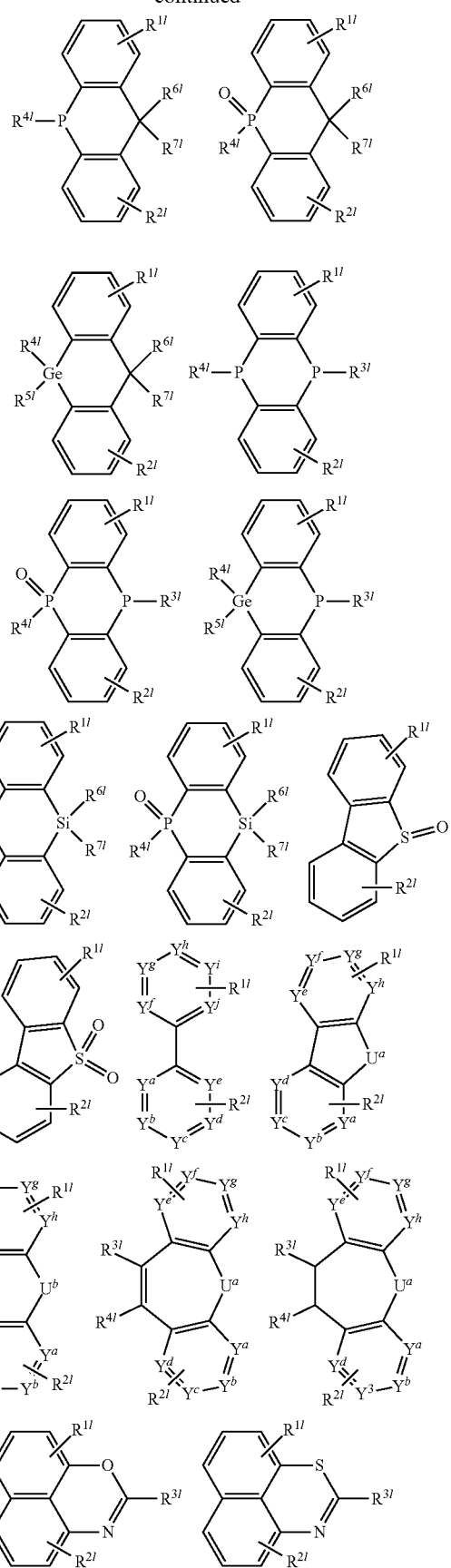

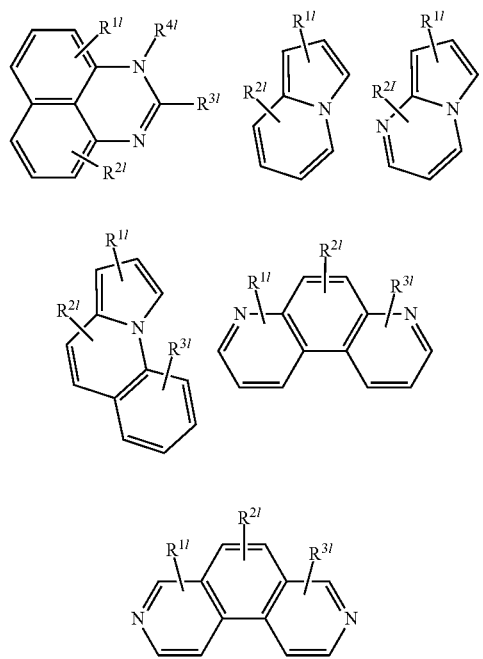
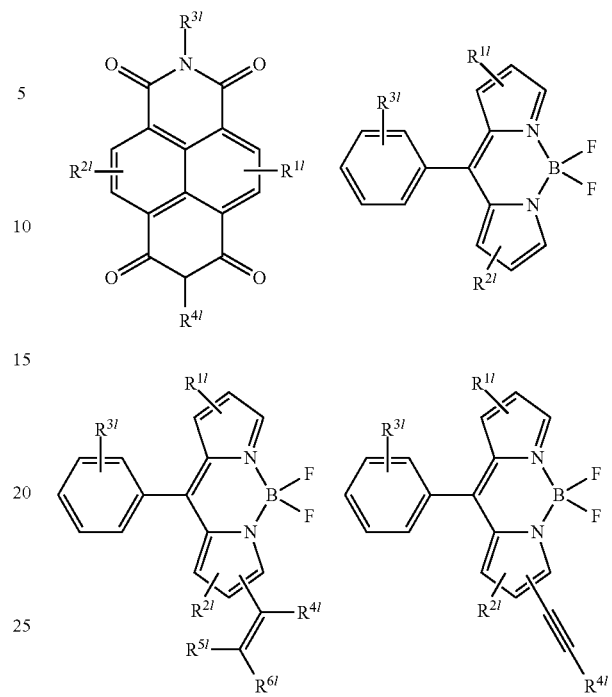
4. Other Fluorescent Luminophors
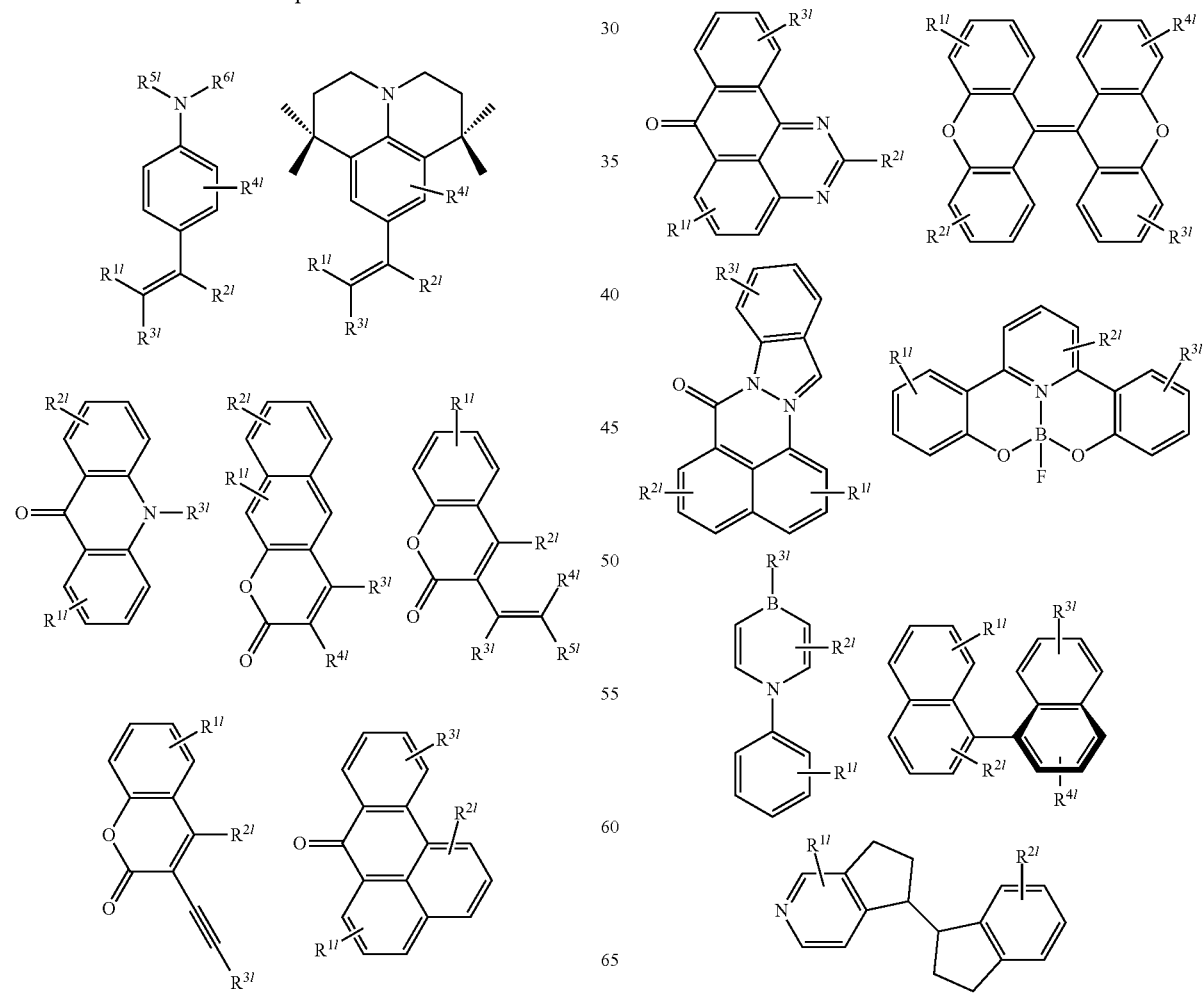

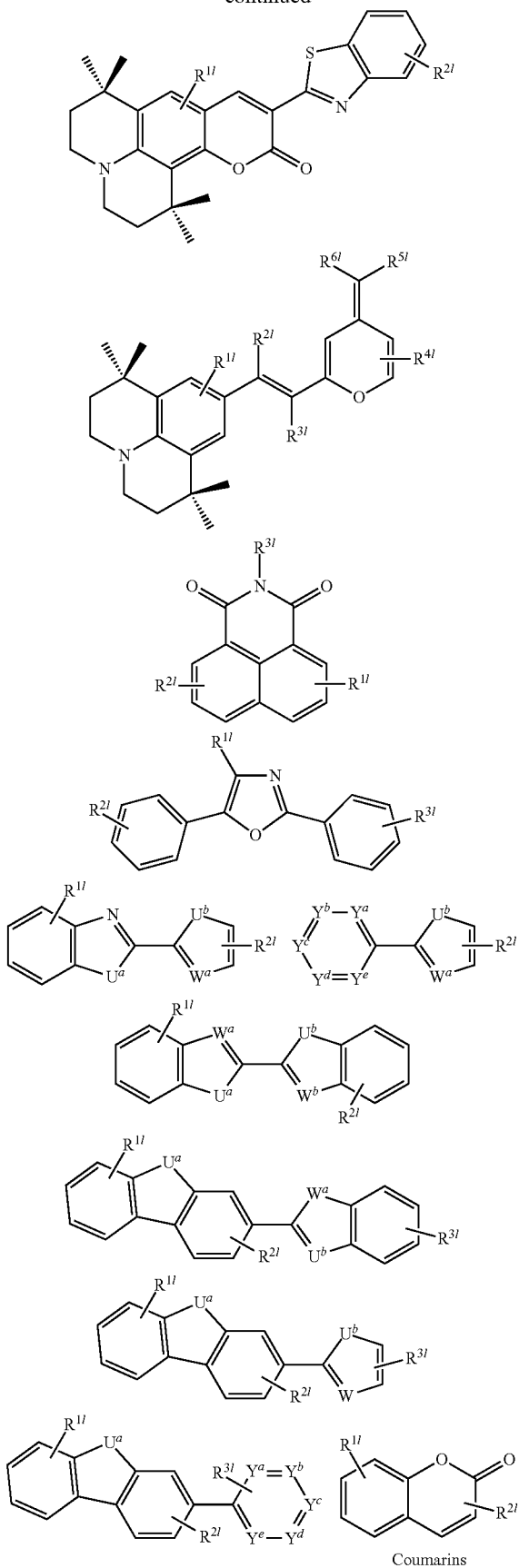

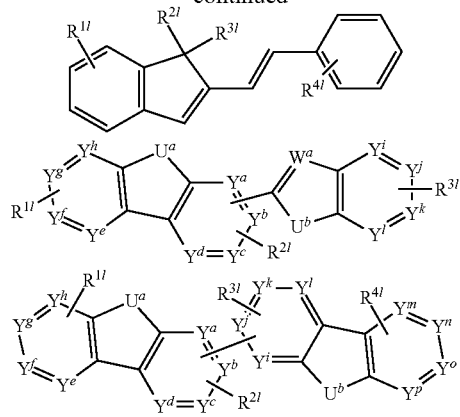

wherein:

each of $R^{11}$, $R^{21}$, $R^{31}$, $R^{41}$, $R^{51}$, $R^{61}$, $R^{71}$, and $R^{81}$ is independently a mono-, di-, or tri-substitution, and if present each of $R^{11}$, $R^{21}$, $R^{31}$, $R^{41}$, $R^{51}$, $R^{61}$, $R^{71}$, and $R^{81}$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, substituted or unsubstituted alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, each of $Y^a$, $Y^b$, $Y^c$, $Y^d$, $Y^e$, $Y^f$, $Y^g$, $Y^h$, $Y^i$, $Y^j$, $Y^k$, $Y^l$, $Y^m$, $Y^n$, $Y^o$, and $Y^p$ is independently C, N, or B, each of $U^a$, $U^b$, and $U^c$ is independently $CH_2$, $CR^1R^2$, C=O, $CH_2$, $SiR^1R^2$, $GeH_2$, $GeR^1R^2$, NH, $NR^3$, PH, $PR^3$, $R^3P$=O, $AsR^3$, $R^3As$=O, O, S, S=O, $SO_2$, Se, Se=O, $SeO_2$, BH, $BR^3$, $R^3Bi$=O, BiH, or $BiR^3$, and each of W, $W^a$, $W^b$, and $W^c$ is independently CH, $CR^1$, $SiR^1$, GeH, $GeR^1$, N, P, B, Bi, or Bi=O.

In one aspect, $F^1$ is covalently bonded to $L^1$ directly. In one aspect $F^2$ is covalently bonded to $L^2$ directly. In one aspect, $F^3$ is covalently bonded to $L^3$ directly. In one aspect, $F^4$ is covalently bonded to $L^4$ directly. In one aspect, $F^5$ is covalently bonded to $L^5$ directly. In one aspect, $F^6$ is covalently bonded to $L^6$ directly.

In another aspect, fluorescent luminophore $F^1$ is covalently bonded to $L^1$ by a linking atom or linking group. In another aspect, $F^2$ is covalently bonded to $L^2$ by a linking atom or linking group. In another aspect, $F^3$ is covalently bonded to $L^3$ by a linking atom or linking group. In another aspect, $F^4$ is covalently bonded to $L^4$ by a linking atom or linking group. In another aspect, $F^5$ is covalently bonded to $L^5$ by a linking atom or linking group. In another aspect, $F^6$ is covalently bonded to $L^6$ by a linking atom or linking group.

F. Linking Atoms or Linking Groups

In some cases, each linking atom or linking group in the structures disclosed herein is independently one of the atoms or groups depicted below:

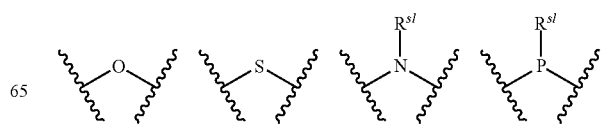

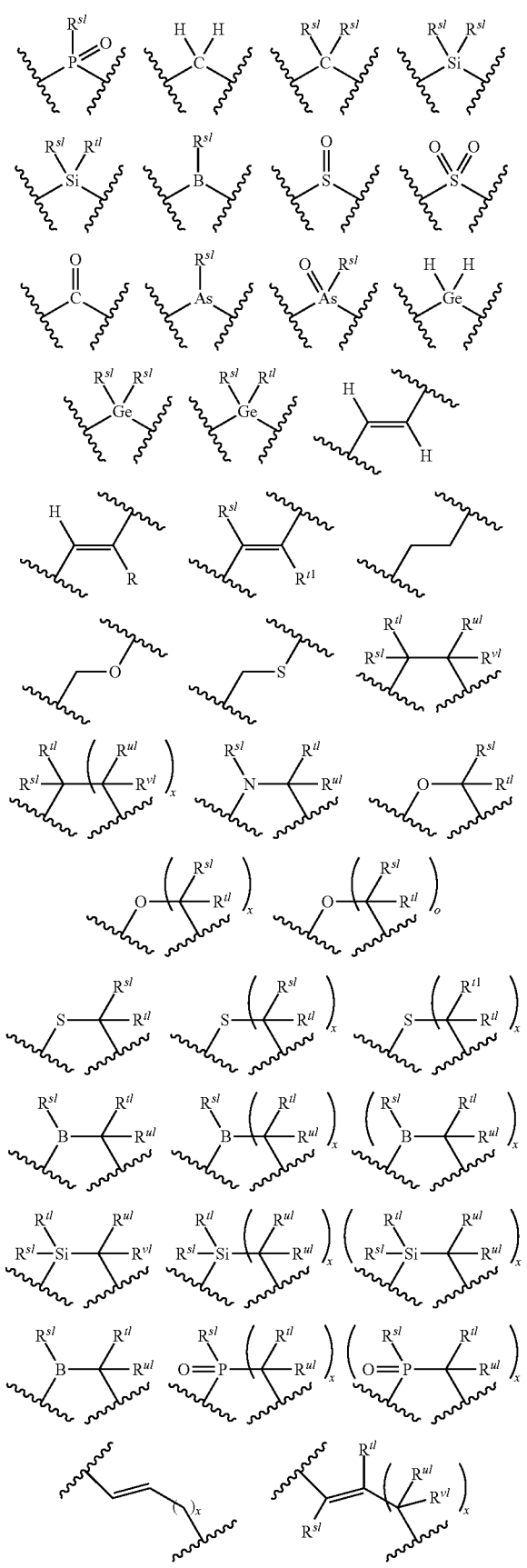
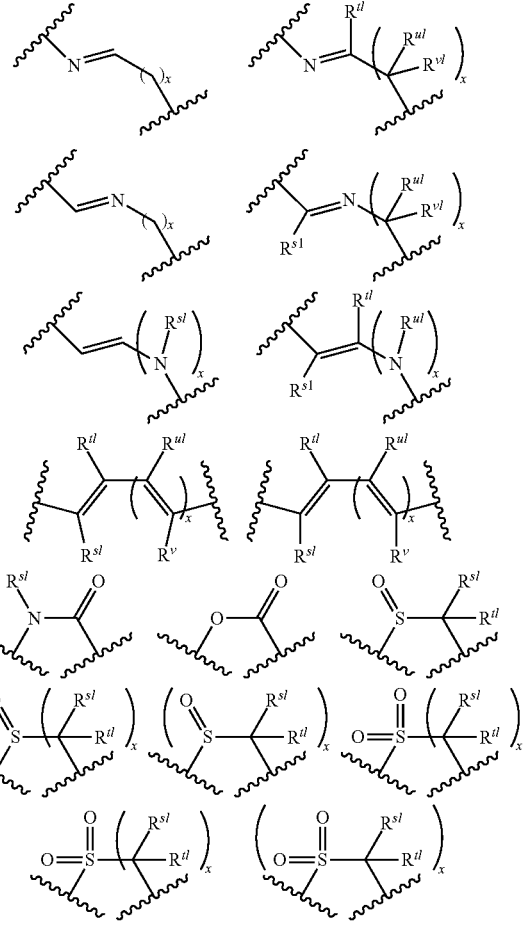

wherein x is from 1 to 10, wherein each of $R^{sl}$, $R^{tl}$, $R^{ul}$, and $R^{vl}$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, or polymeric, or any conjugate or combination thereof. In other cases, a linking atom or linking group in the structures disclosed herein includes other structures or portions thereof not specifically recited herein, and the present disclosure is not intended to be limited to those structures or portions thereof specifically recited.

In one aspect, a linking atom and linking group recited above is covalently bonded to any atom of a fluorescent luminophore $F^1$, $F^2$, $F^3$, $F^4$, $F^5$, and $F^6$ if present and if valency permits. In one example, if $F^1$ is

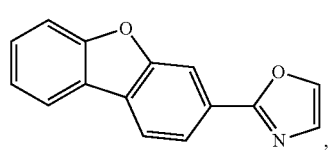
,

-continued

F¹ can be

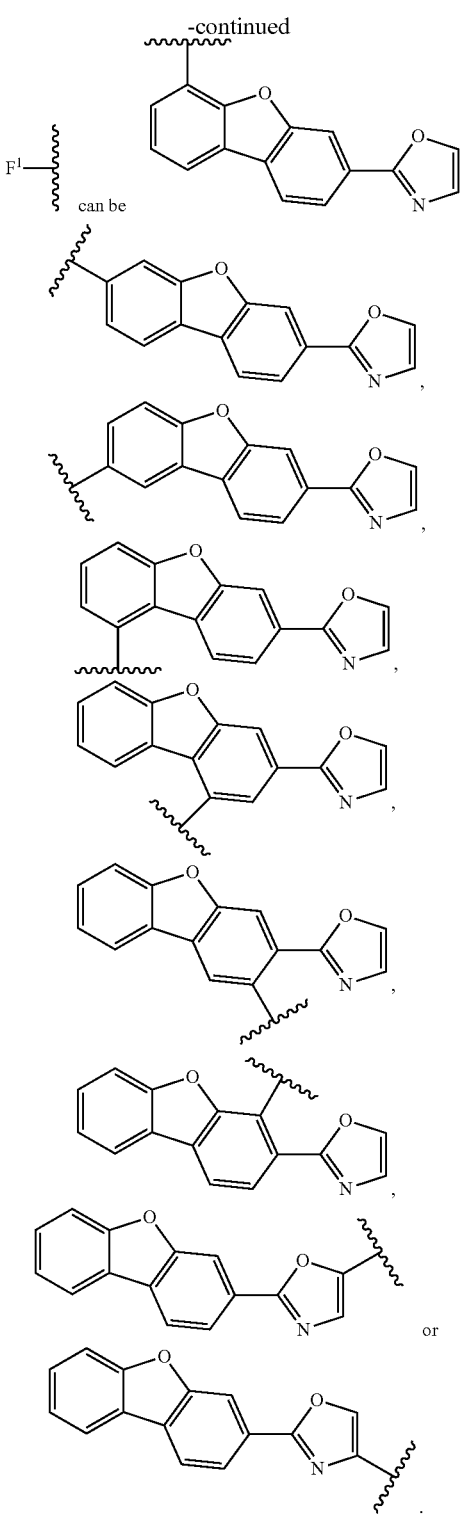

G. R Groups

In one aspect, at least one $R^a$ is present. In another aspect, $R^a$ is absent.

In one aspect, $R^a$ is a mono-substitution. In another aspect, $R^a$ is a di-substitution. In yet another aspect, $R^a$ is a tri-substitution.

In one aspect, $R^a$ is connected to at least $L^1$. In another aspect, $R^b$ is connected to at least $L^2$. In yet another aspect, $R^c$ is connected to at least $L^3$. In one aspect, $R^d$ is connected to at least $L^4$. In one aspect, $R^e$ is connected to at least $L^5$. In one aspect, $R^f$ is connected to at least $L^6$.

In one aspect, $R^a$ is a di-substitution and the $R^a$'s are linked together. When the $R^a$'s are linked together the resulting structure can be a cyclic structure that includes a portion of the five-membered cyclic structure as described herein. For example, a cyclic structure can be formed when the di-substitution is of $L^1$ and $L^2$ and the $R^a$'s are linked together. A cyclic structure can also be formed when the di-substitution is of $L^3$ and $L^4$ and the $R^a$'s are linked together. A cyclic structure can also be formed when the di-substitution is of $L^5$ and $L^6$ and the $R^a$'s are linked together.

In one aspect, each $R^a$, if present, is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and two or more of $R^a$ are optionally linked together. In one aspect, at least one $R^a$ is halogen, hydroxyl, substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl; or any conjugate or combination thereof, and two or more of $R^a$ are optionally linked together.

In one aspect, at least one $R^b$ is present. In another aspect, $R^b$ is absent.

In one aspect, $R^b$ is a mono-substitution. In another aspect, $R^b$ is a di-substitution. In yet another aspect, $R^b$ is a tri-substitution.

In one aspect, each $R^b$, if present, is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and two or more of $R^b$ are optionally linked together. In one aspect, at least one $R^b$ is halogen, hydroxyl; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl; or any conjugate or combination thereof, and two or more of $R^b$ are optionally linked together.

In one aspect, at least one $R^c$ is present. In another aspect, $R^c$ is absent.

In one aspect, $R^c$ is a mono-substitution. In another aspect, $R^c$ is a di-substitution. In yet another aspect, $R^c$ is a tri-substitution.

In one aspect, each $R^c$, if present, is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and two or more of $R^c$ are optionally linked together. In one aspect, at least one $R^c$ is halogen, hydroxyl; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl; or any conjugate or combination thereof, and two or more of $R^c$ are optionally linked together.

In one aspect, at least one $R^d$ is present. In another aspect, $R^d$ is absent.

In one aspect, $R^d$ is a mono-substitution. In another aspect, $R^d$ is a di-substitution. In yet another aspect, $R^d$ is a tri-substitution.

In one aspect, each $R^d$, if present, is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, substituted silyl, polymeric, or any conjugate or combination thereof, and two or more of $R^d$ are optionally linked together.

In one aspect, at least one $R^f$ is present. In another aspect, $R^f$ is absent.

In one aspect, $R^f$ is a mono-substitution. In another aspect, $R^f$ is a di-substitution. In yet another aspect, $R^f$ is a tri-substitution.

In one aspect, each $R^f$, if present, is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and two or more of $R^f$ are optionally linked together.

In one aspect, at least one $R^f$ is present. In another aspect, $R^f$ is absent.

In one aspect, $R^f$ is a mono-substitution. In another aspect, $R^f$ is a di-substitution. In yet another aspect, $R^f$ is a tri-substitution.

In one aspect, each $R^f$, if present, is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and two or more of $R^f$ are optionally linked together.

In one aspect, each of R, $R^1$, $R^2$, $R^3$, and $R^4$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In another aspect, each of R, $R^1$, $R^2$, $R^3$, and $R^4$ is independently hydrogen, halogen, hydroxyl, thiol, nitro, cyano; substituted or unsubstituted: aryl, cycloalkyl, cycloalkenyl, heterocyclyl, heteroaryl, alkyl, alkenyl, alkynyl, or amino. In another aspect, each of R, $R^1$, $R^2$, $R^3$, and $R^4$ is independently hydrogen; or substituted or unsubstituted: aryl, cycloalkyl, cycloalkenyl, heterocyclyl, heteroaryl, alkyl, alkenyl, or alkynyl.

H. Exemplary Compounds

In one aspect, Formulas I-X of this disclosure include the following structures. In another aspect, Formulas I-X include other structures or portions thereof not specifically recited herein, and the present disclosure is not intended to be limited to those structures or portions thereof specifically recited.

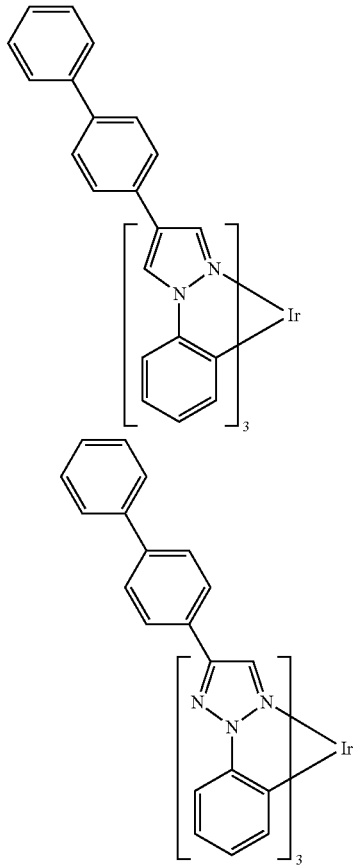

Structures Ir-1

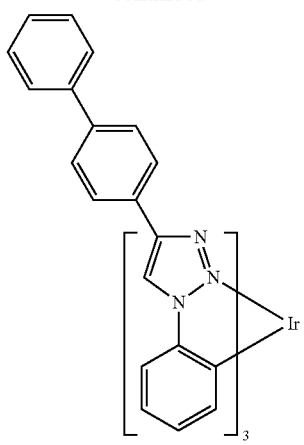
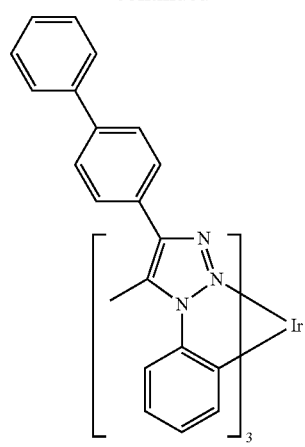
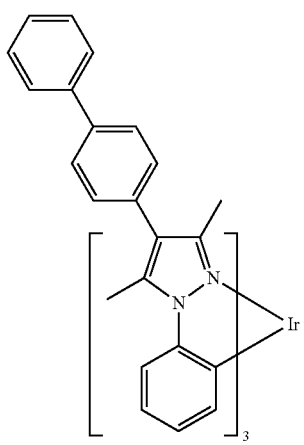
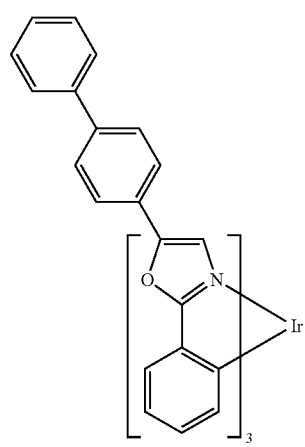
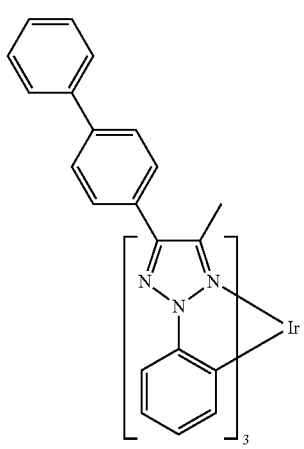
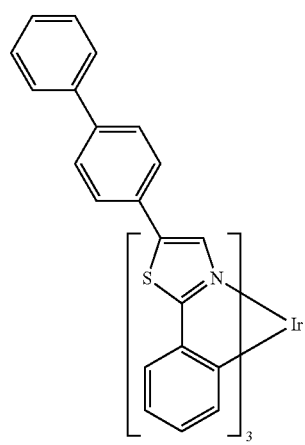

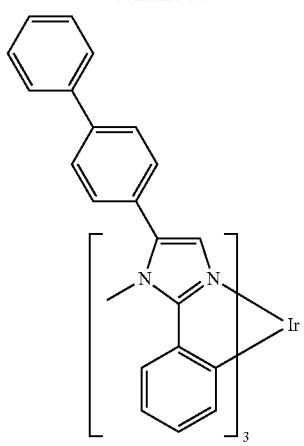
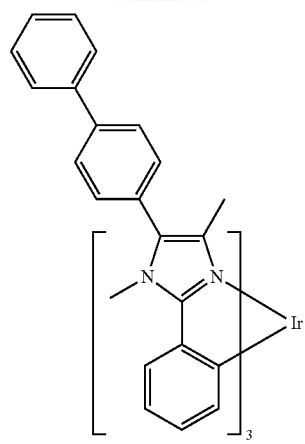
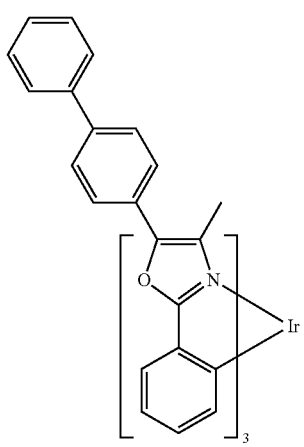
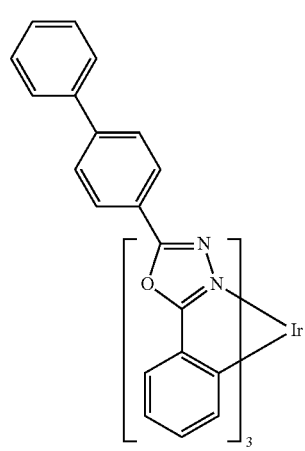
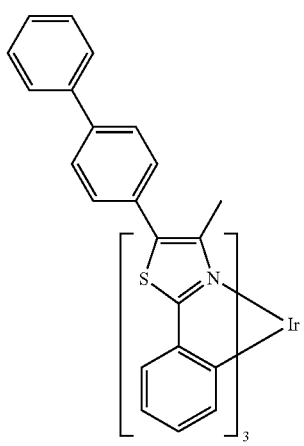
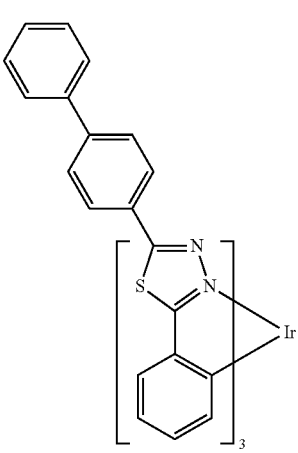

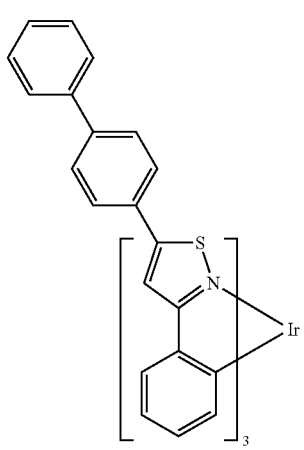
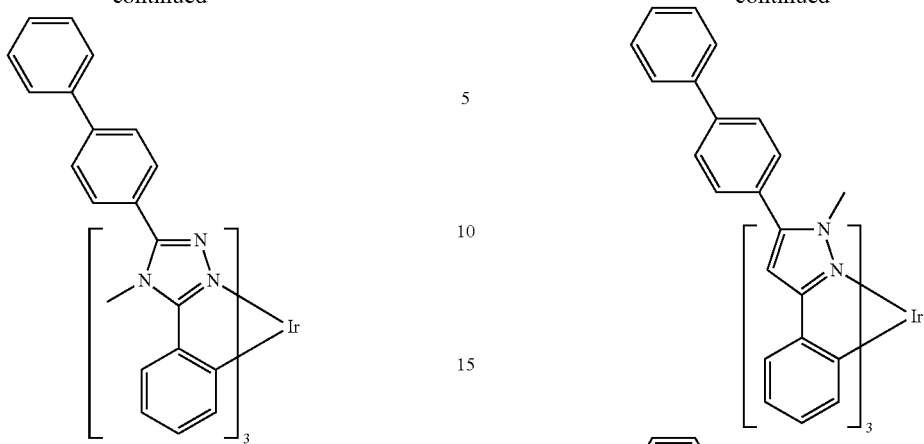
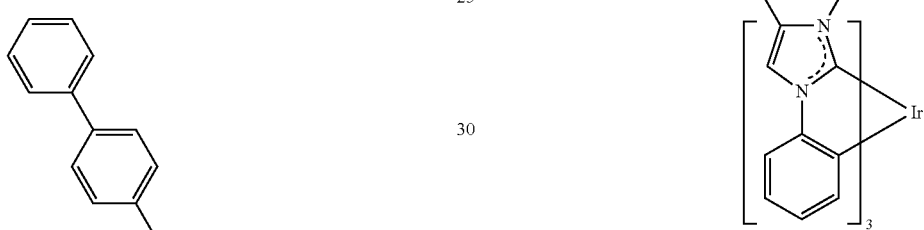
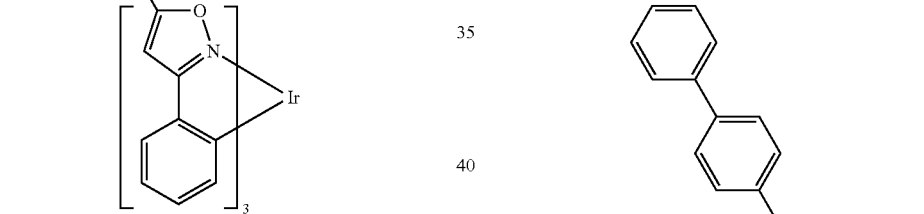
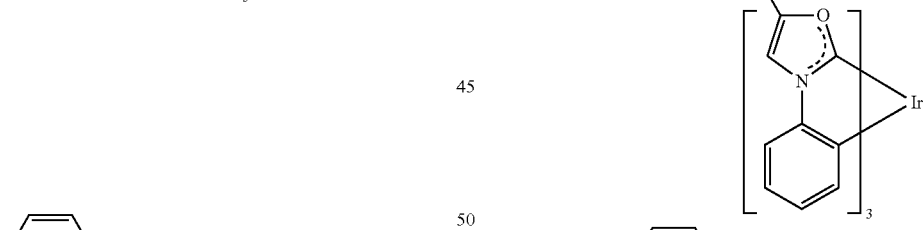
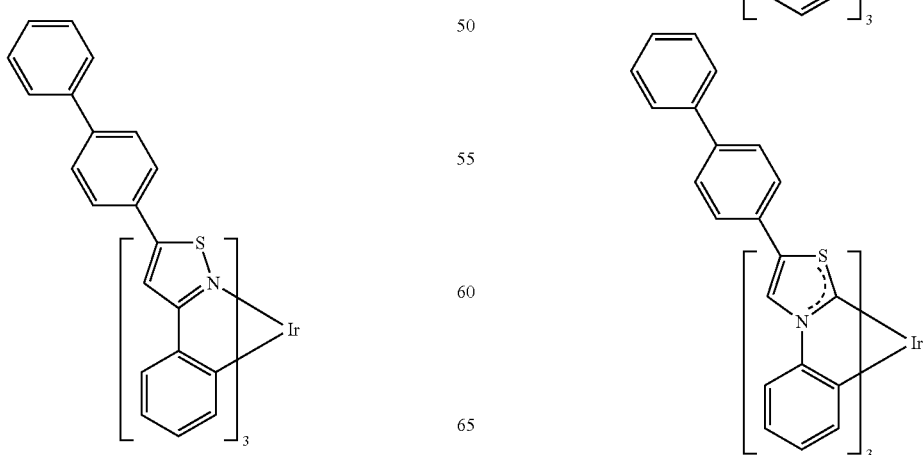

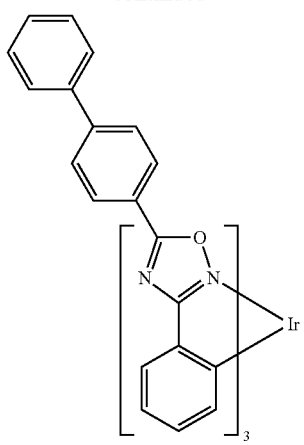
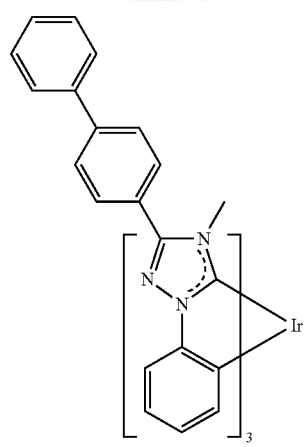
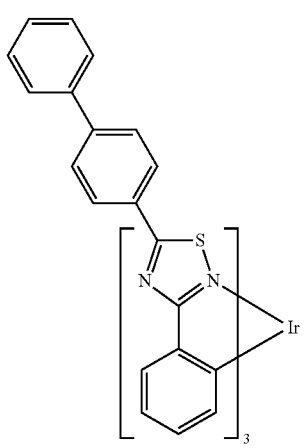
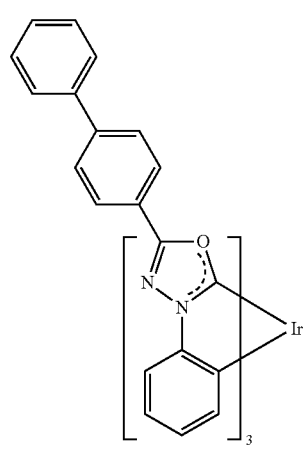
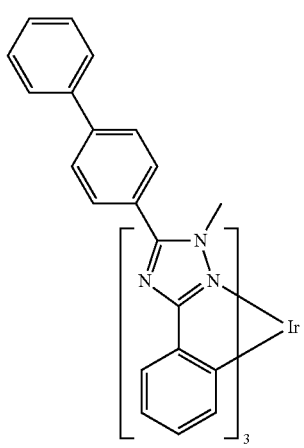
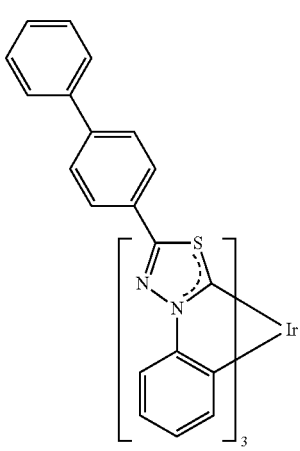

67
-continued
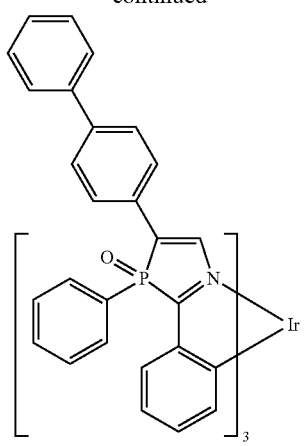
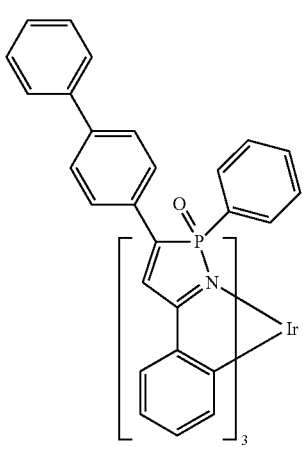
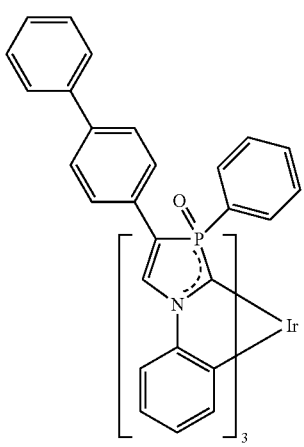
68
-continued
Structures Ir-2
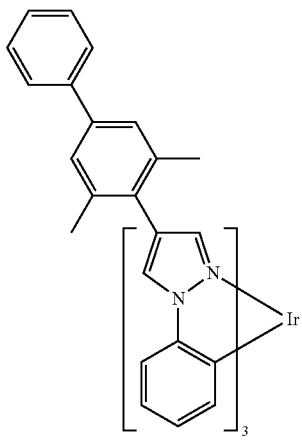
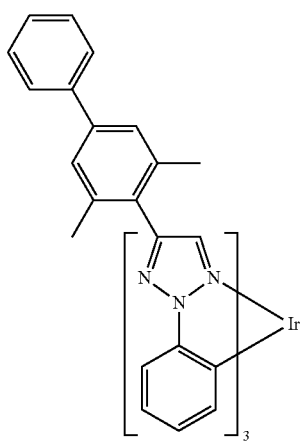
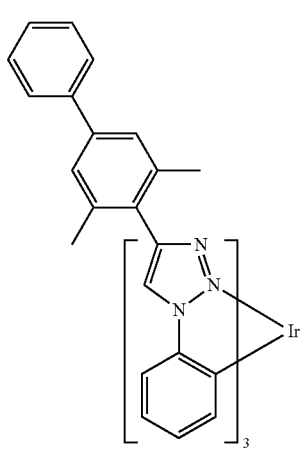

69
-continued
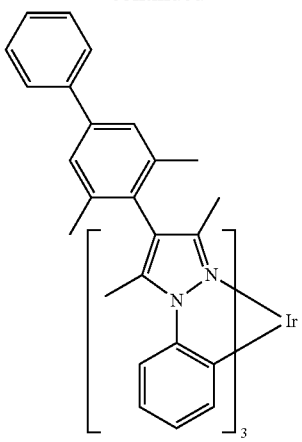
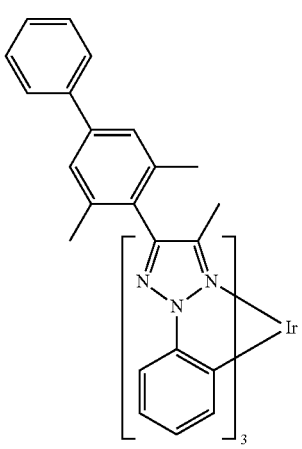
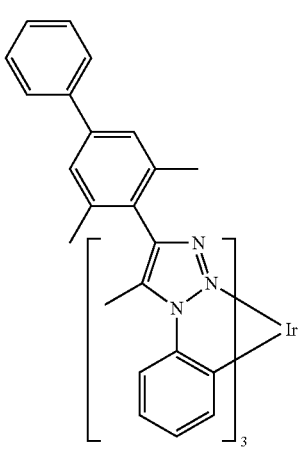
70
-continued
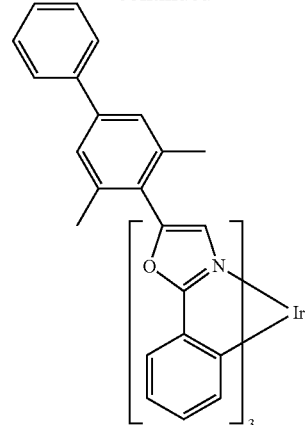

71
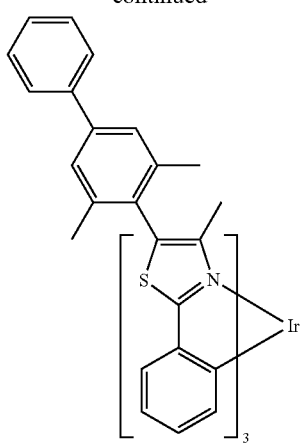
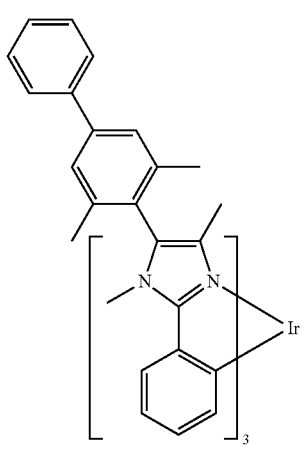
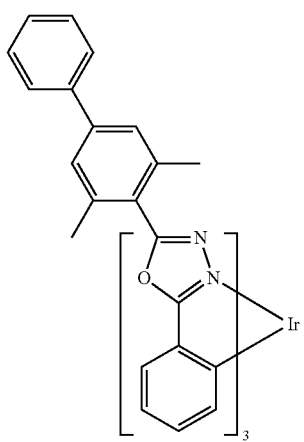
72
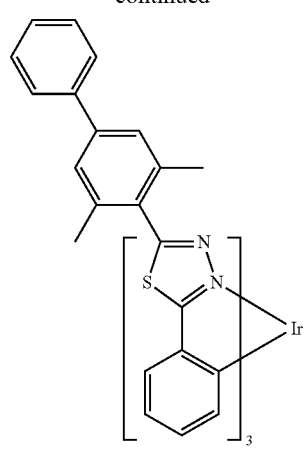
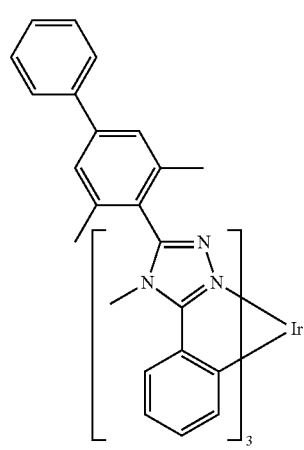
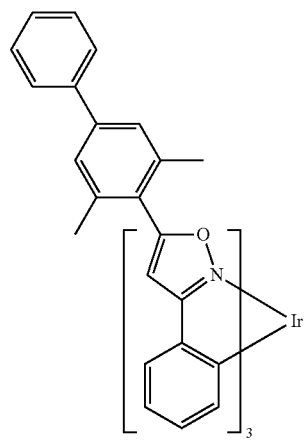

73
-continued
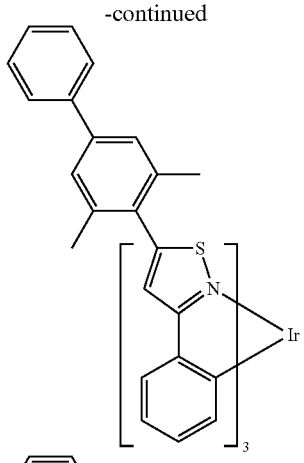
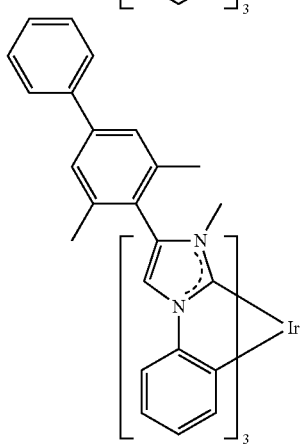
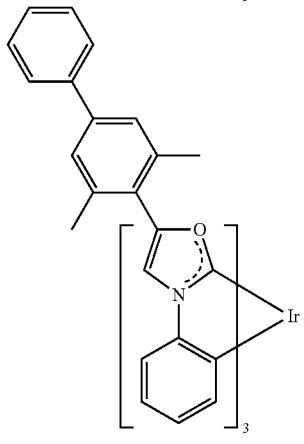
74
-continued

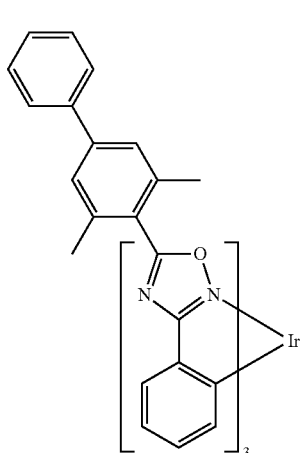

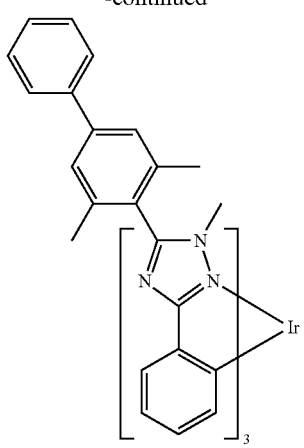
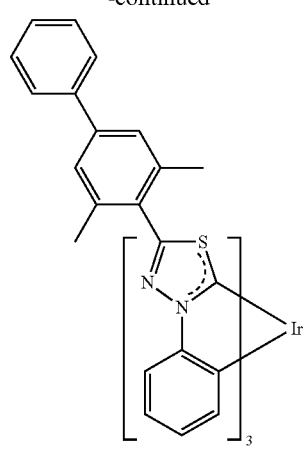
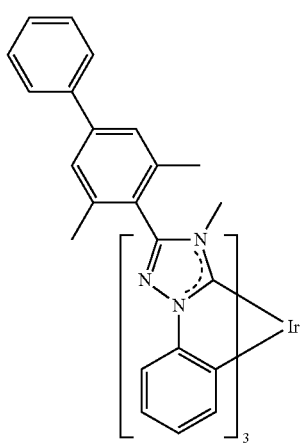
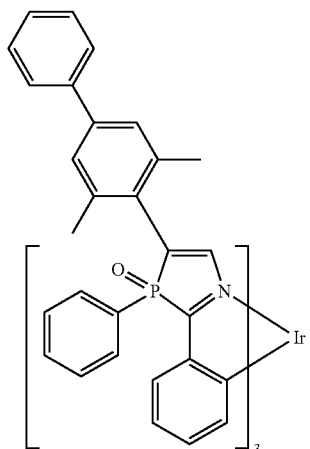
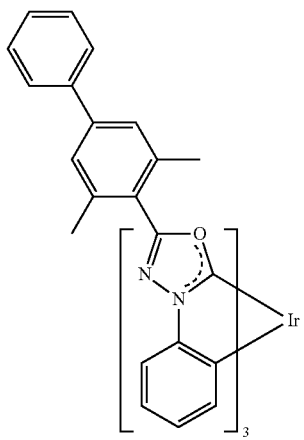
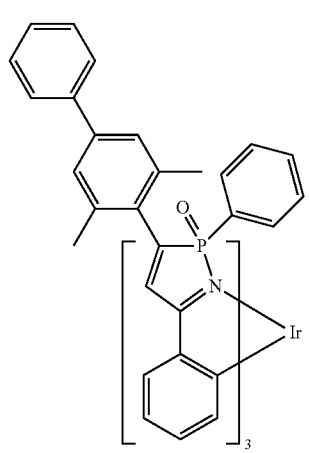

77
-continued
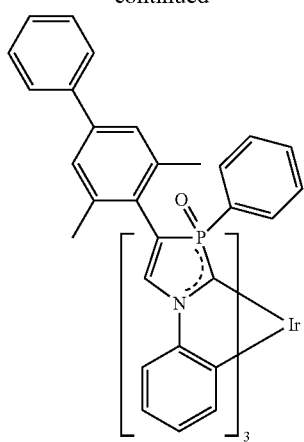
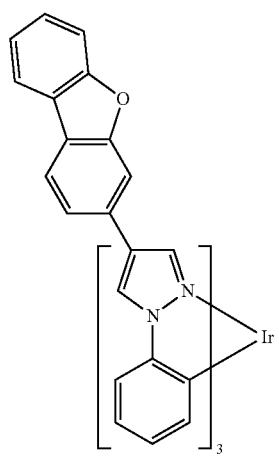
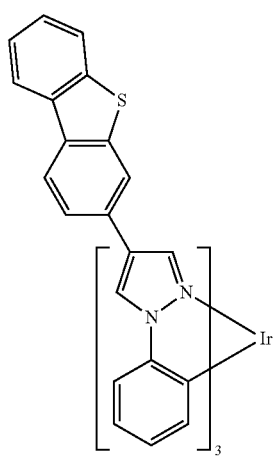
78
-continued
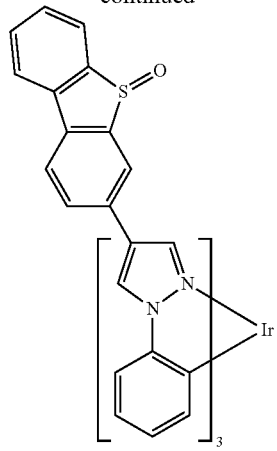
Structures Ir-3
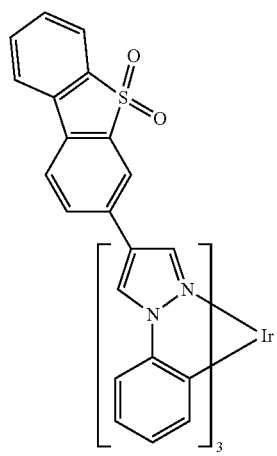
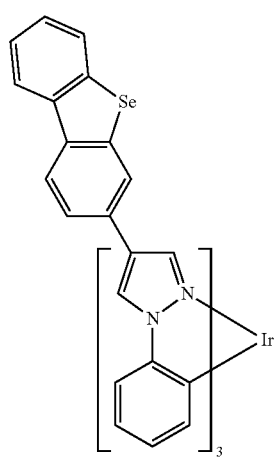

79
-continued
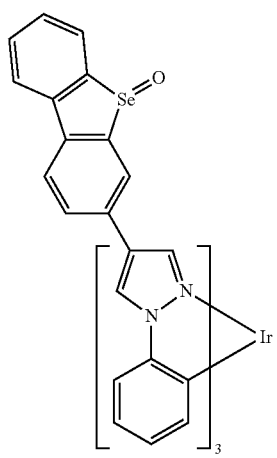
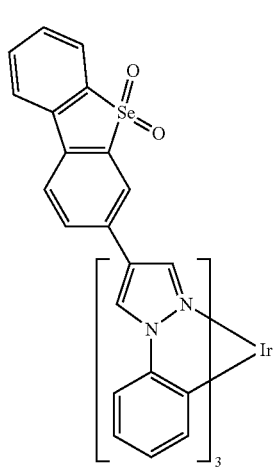
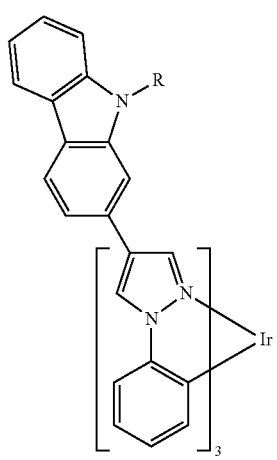
80
-continued
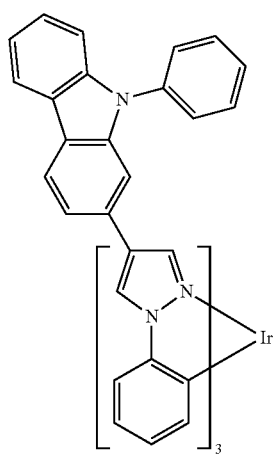
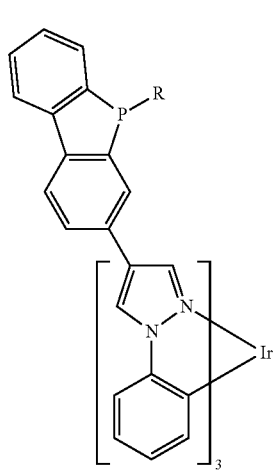
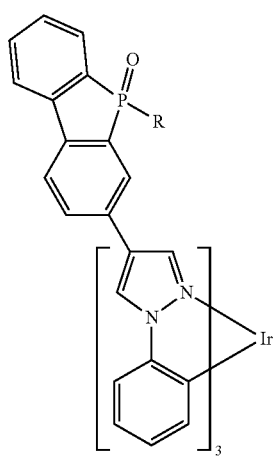

81
-continued
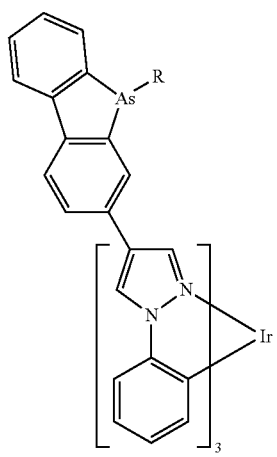
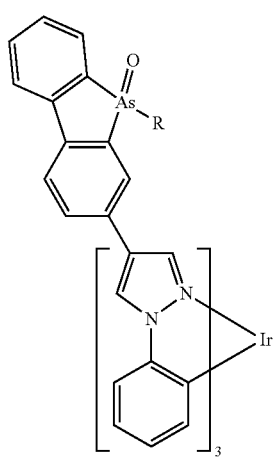
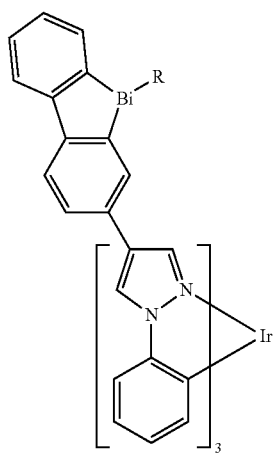
82
-continued
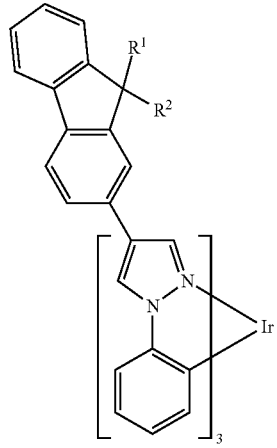
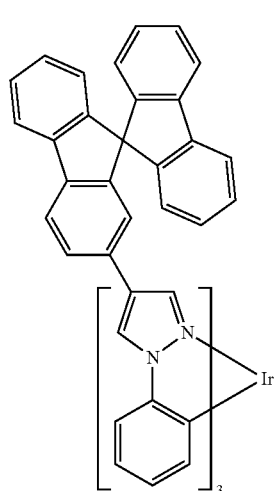
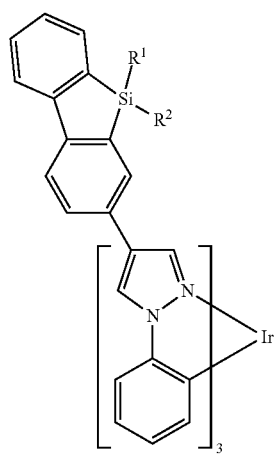

83
-continued
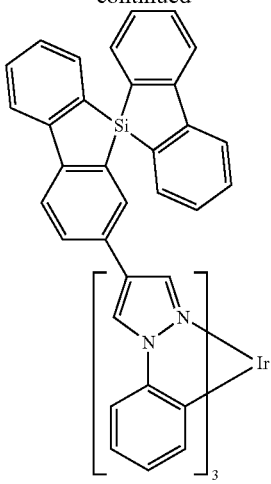
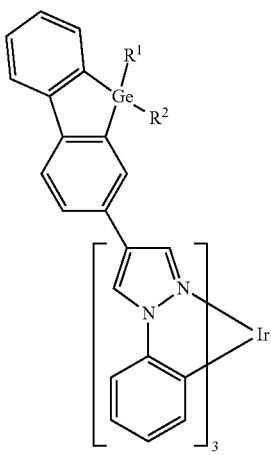
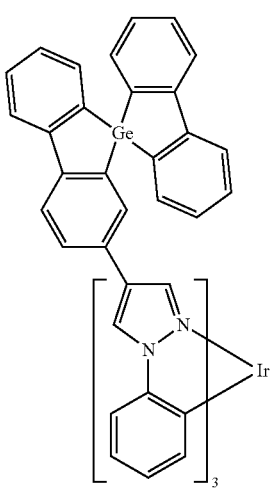
84
-continued
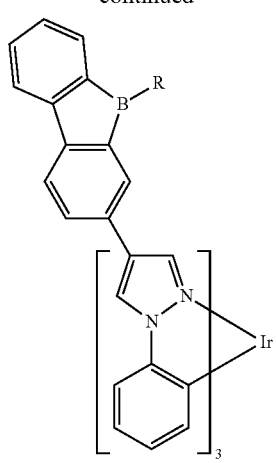
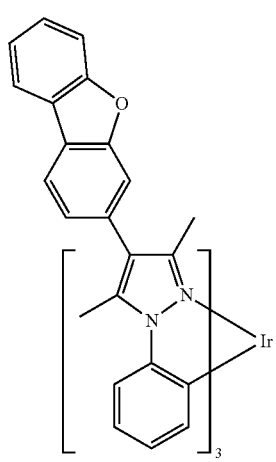
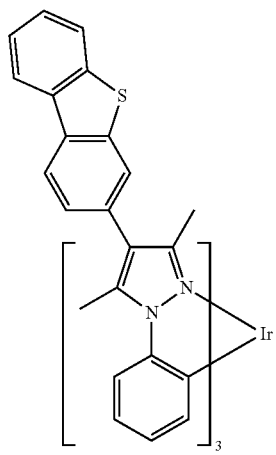

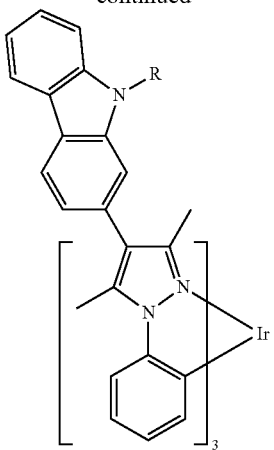
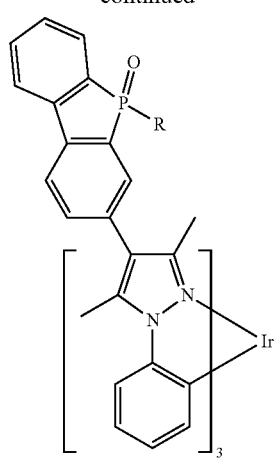
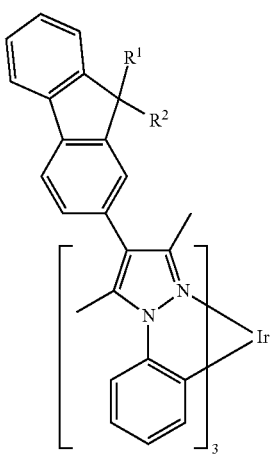
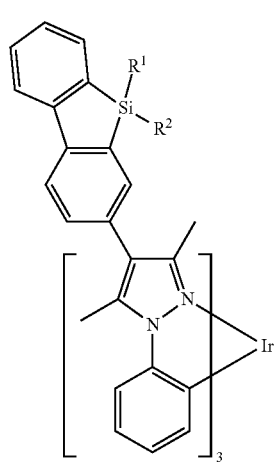
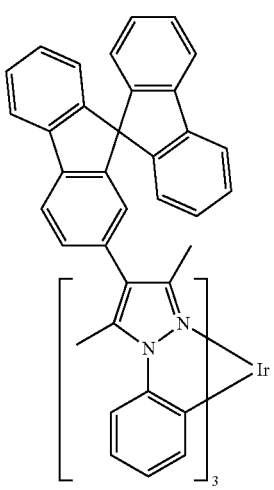
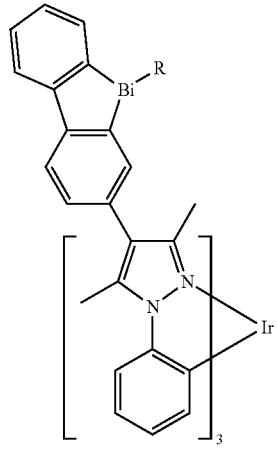

87
-continued
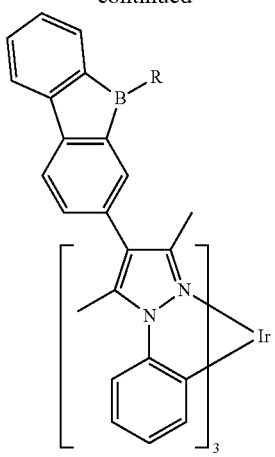
88
-continued
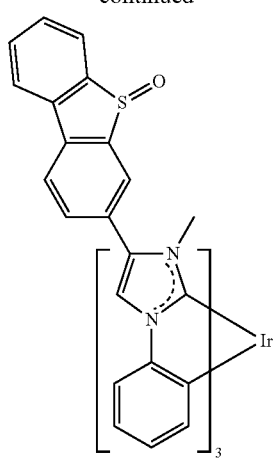
Structures Ir-4
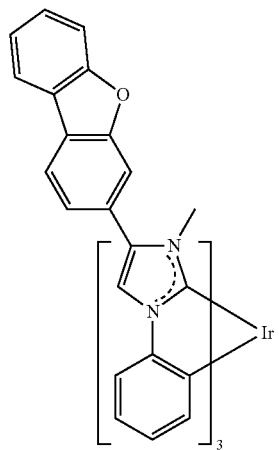
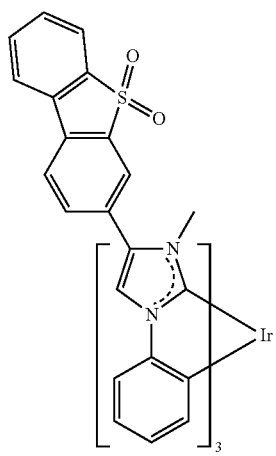
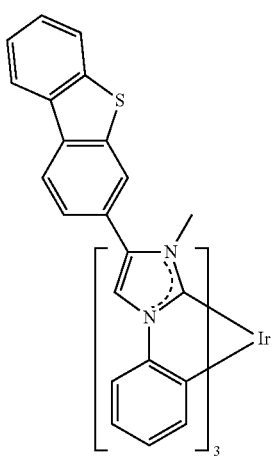
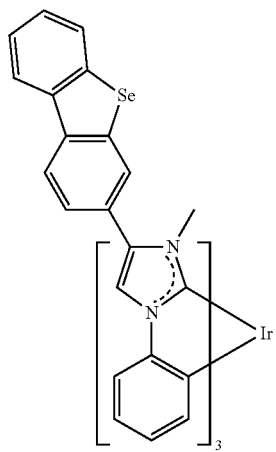

89
-continued
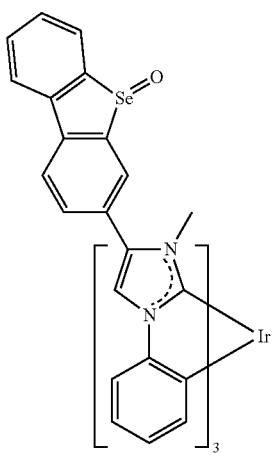
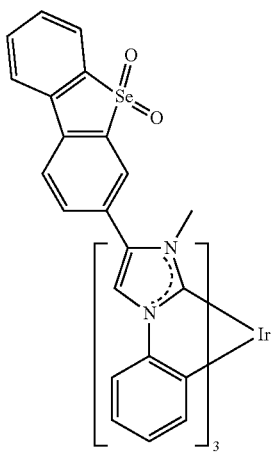
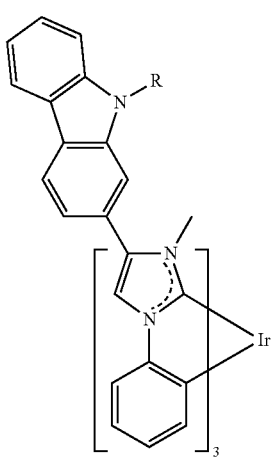
90
-continued
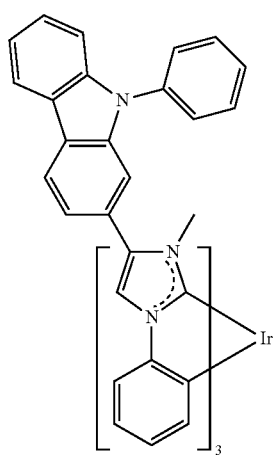
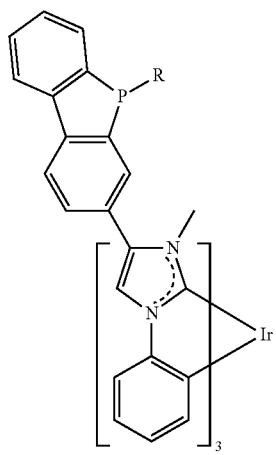
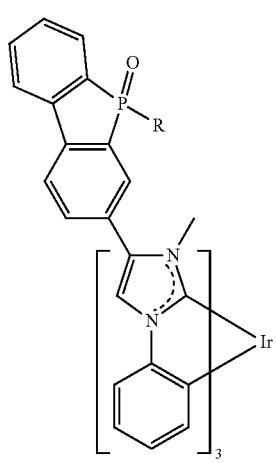

91
-continued
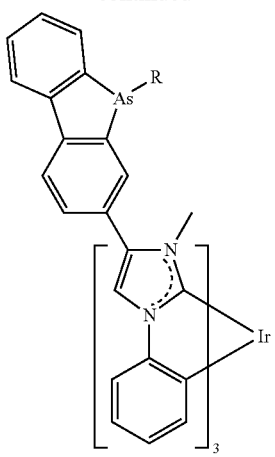
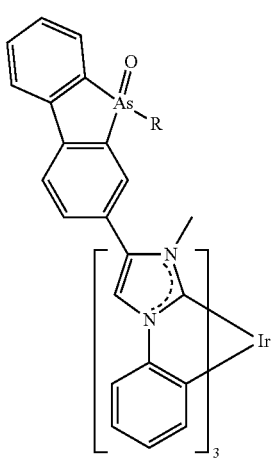
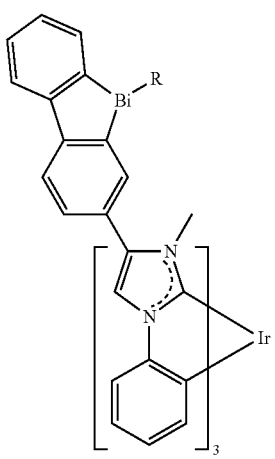
92
-continued
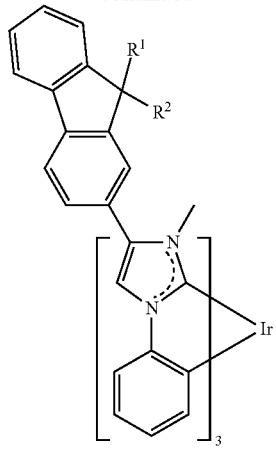
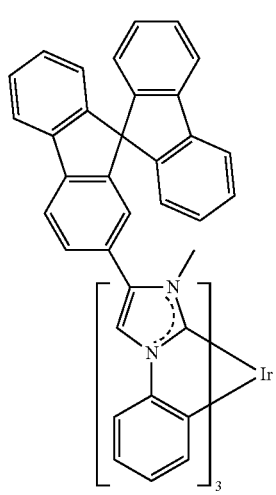
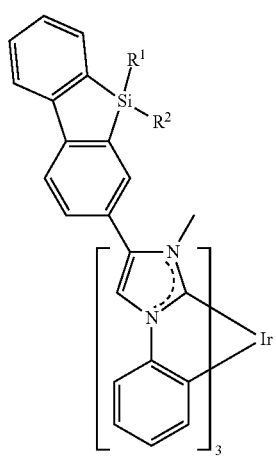

93
-continued
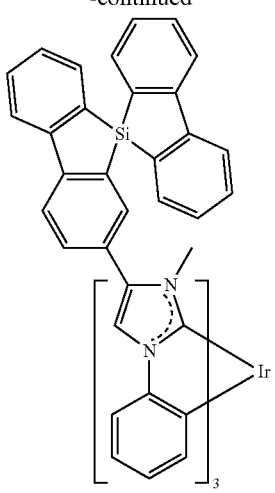
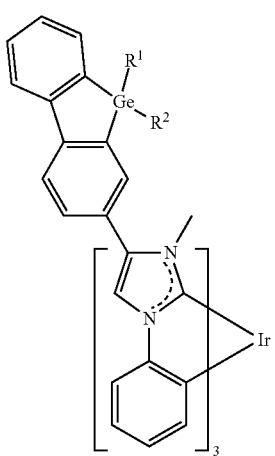
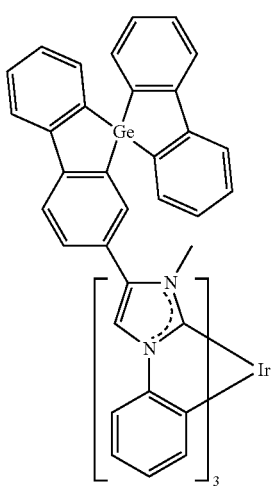
94
-continued
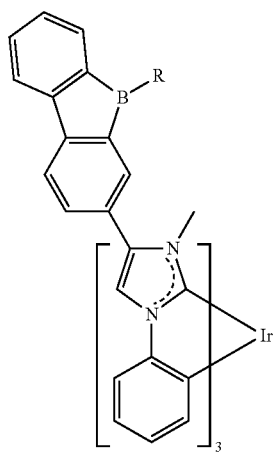
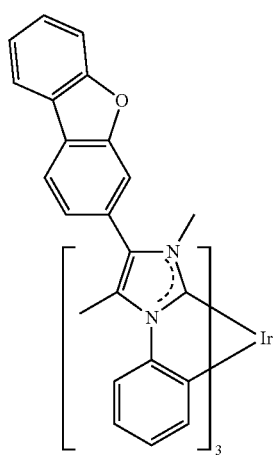
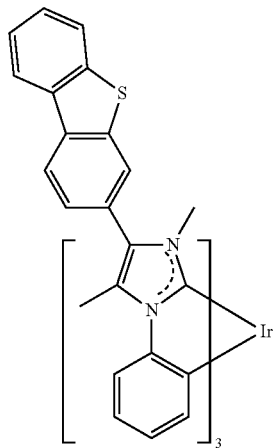

95
-continued
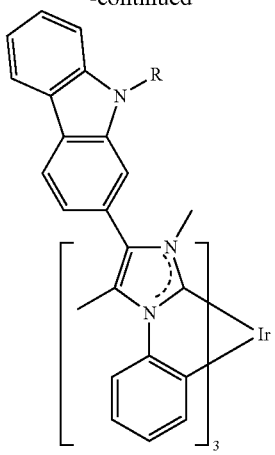
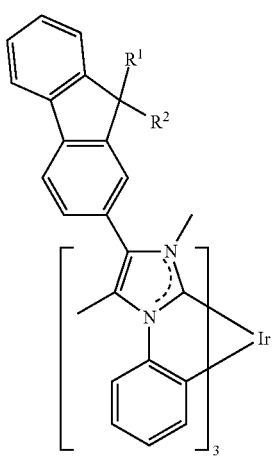
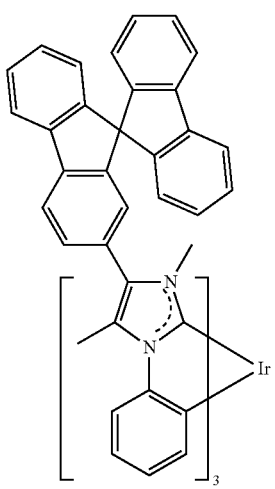
96
-continued
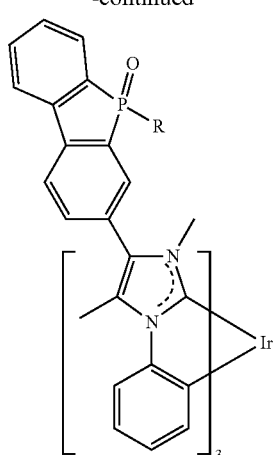
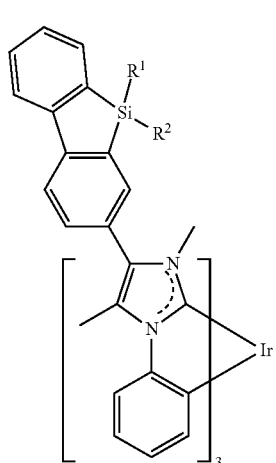
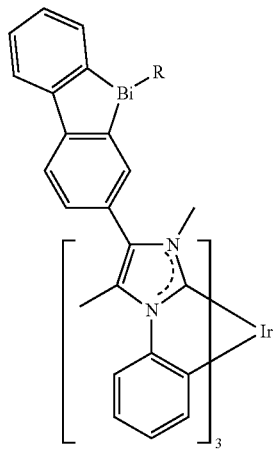

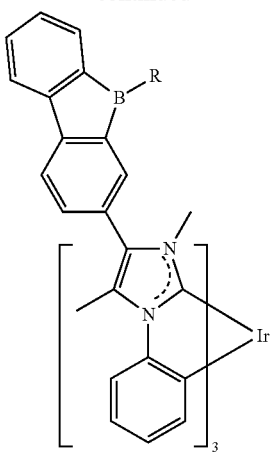
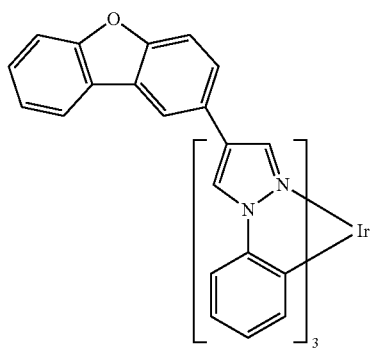
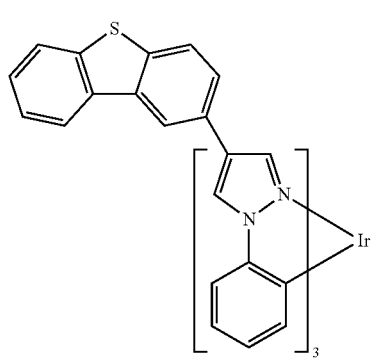
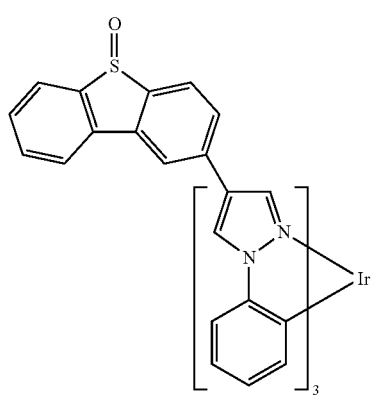
Structures Ir-5
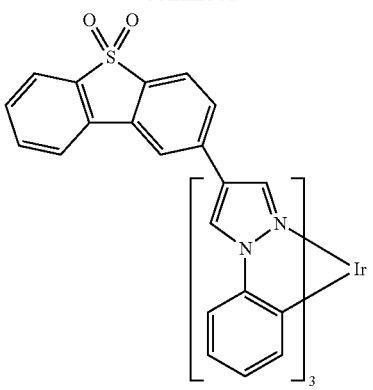
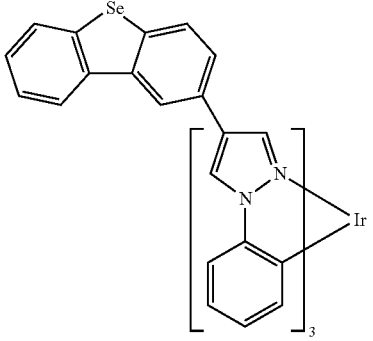
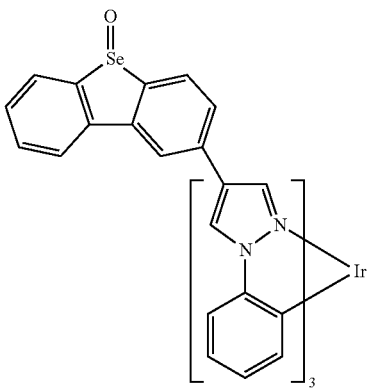
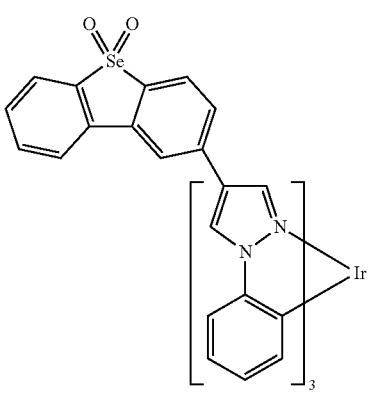

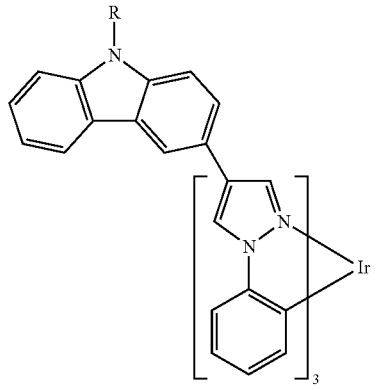
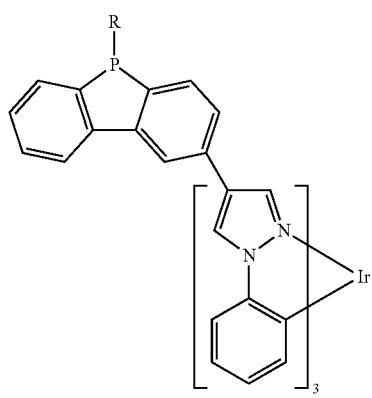
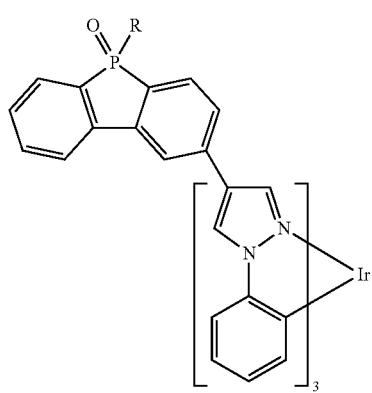
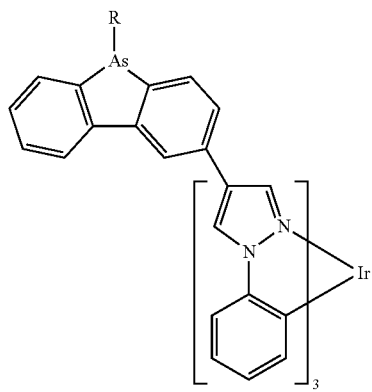
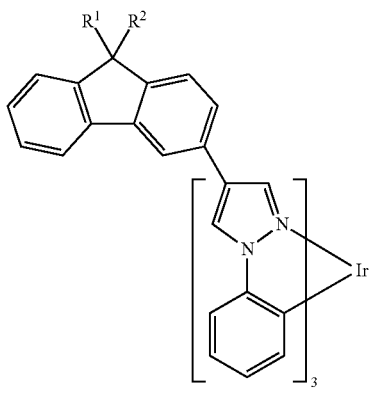
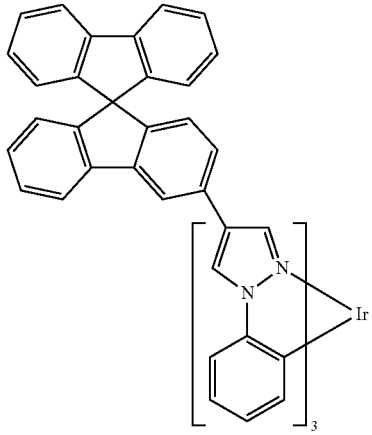
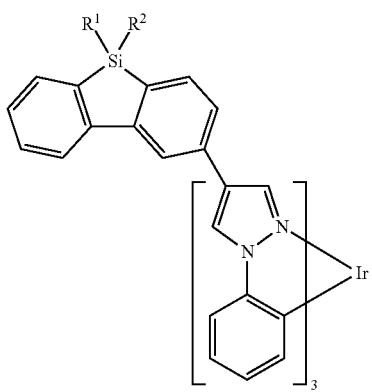

101
-continued
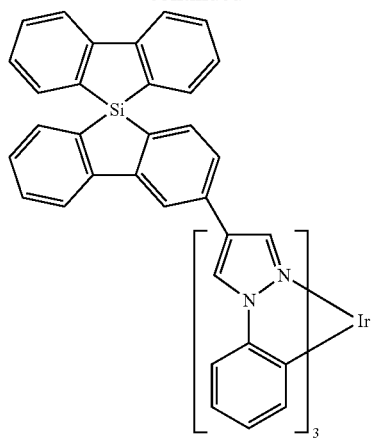
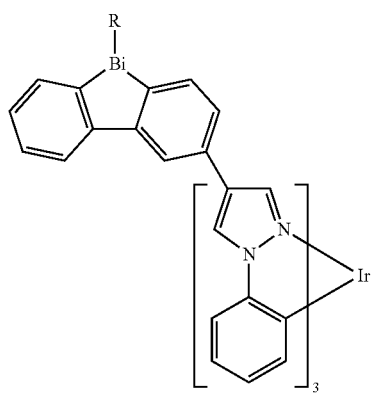
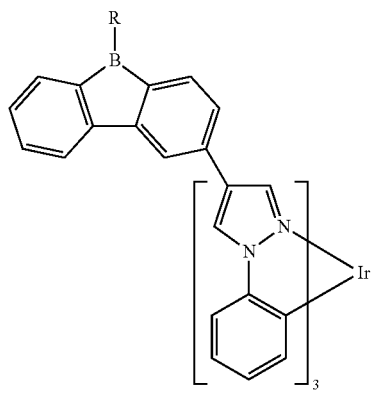
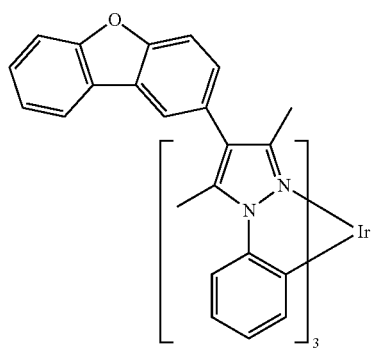
102
-continued
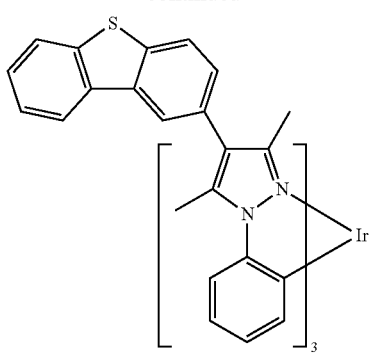
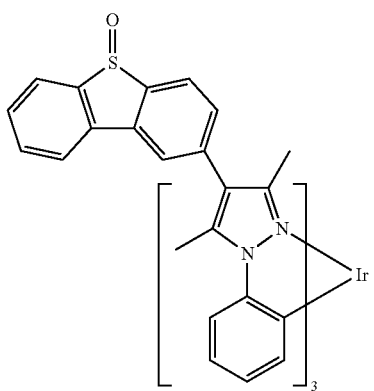
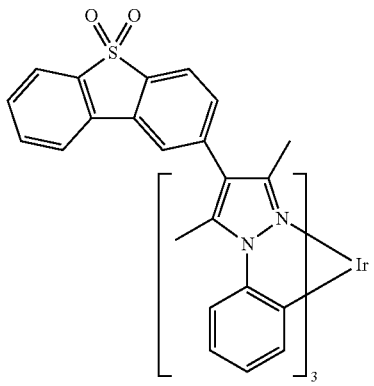
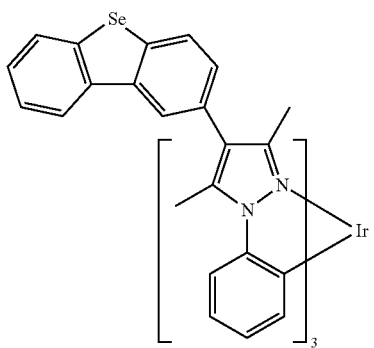

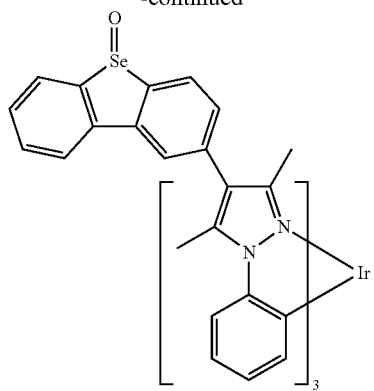
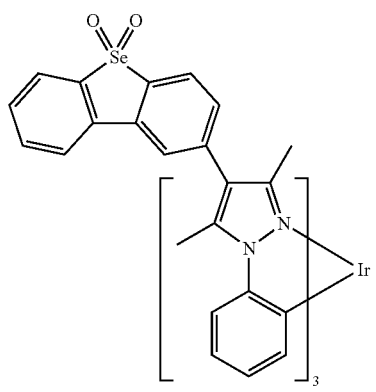
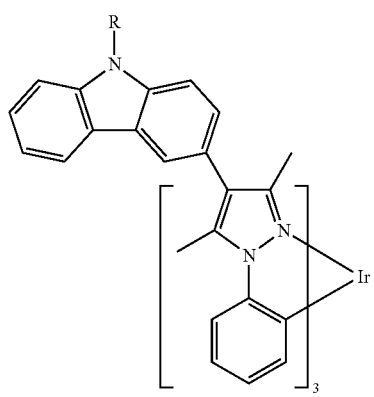
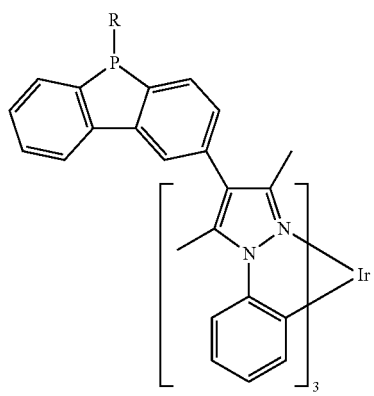
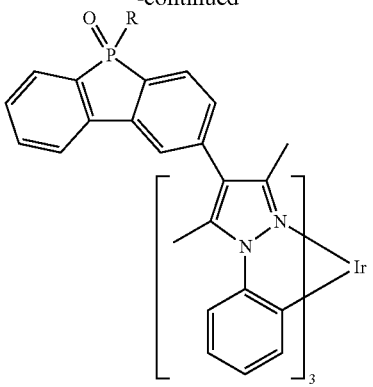
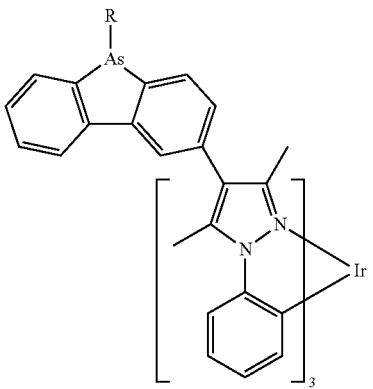
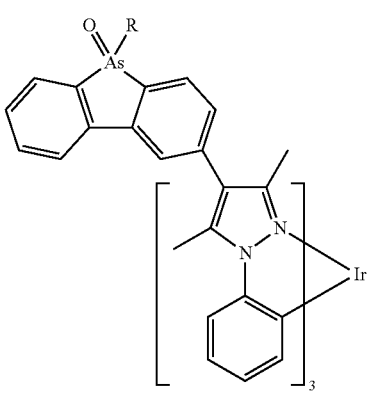
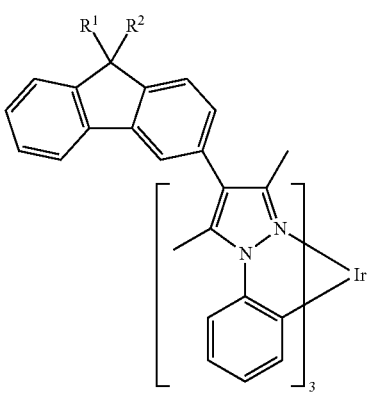

-continued
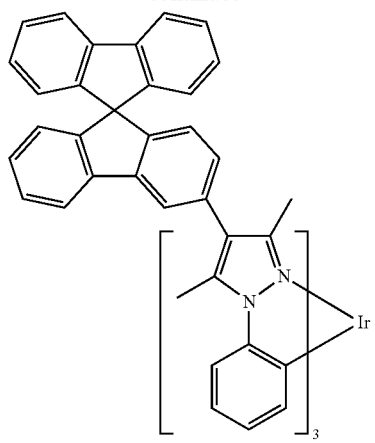
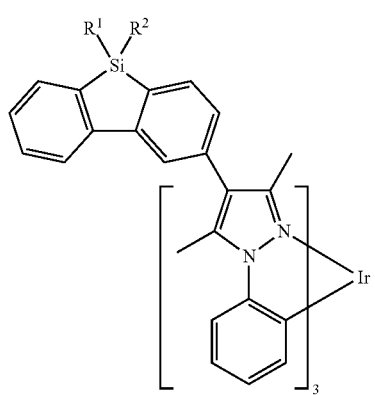
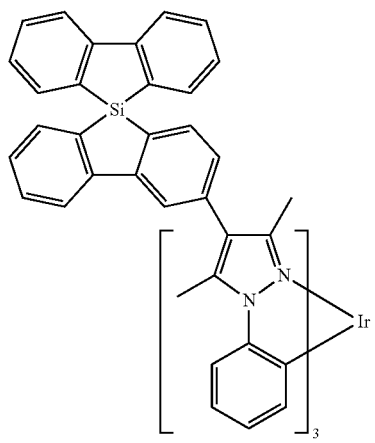
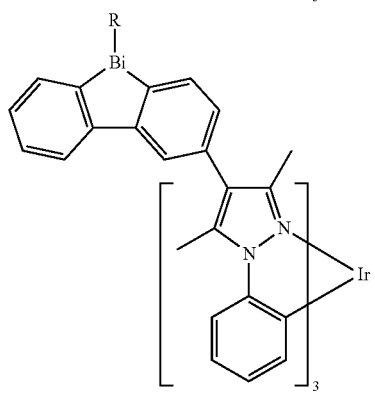
-continued
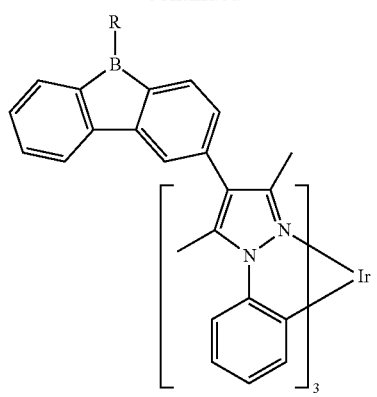
Structures Ir-6
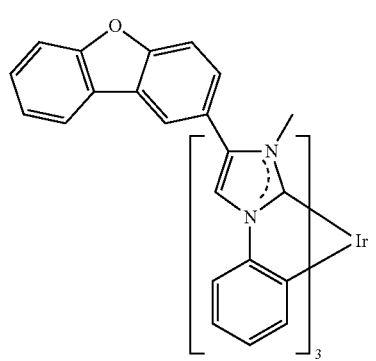
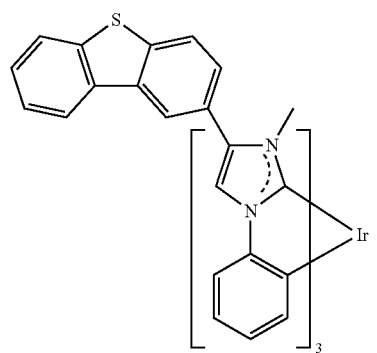
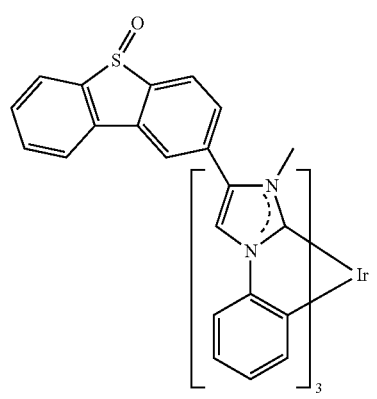

| 107 -continued | 108 -continued |
|---|---|
| 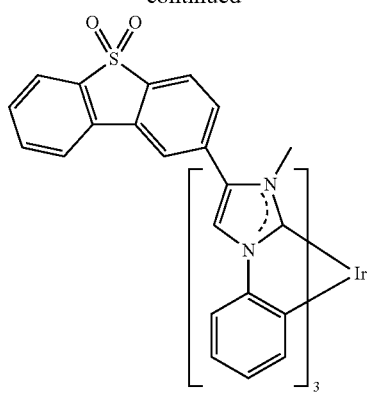 | 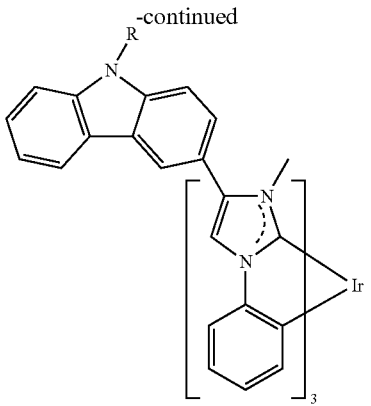 |
| 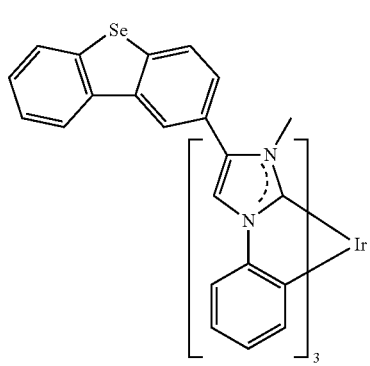 | 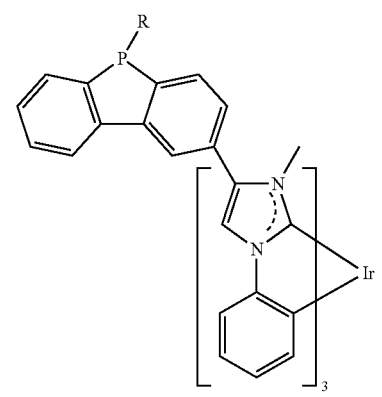 |
| 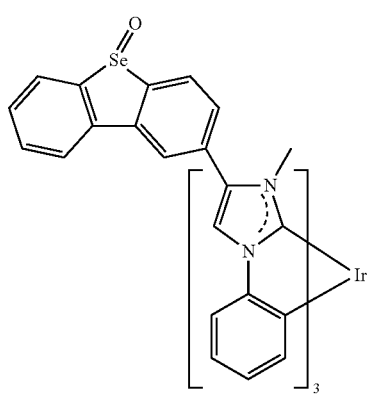 | 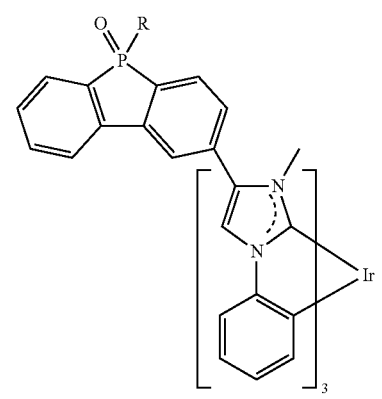 |
| 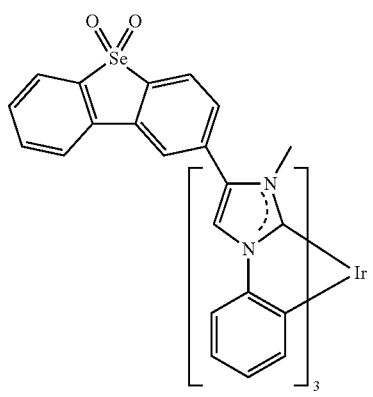 | 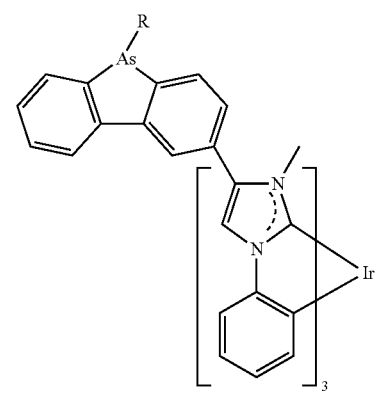 |

109
-continued
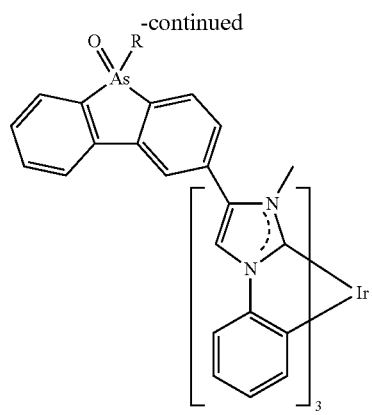
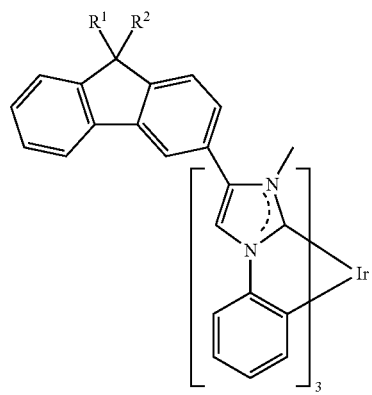
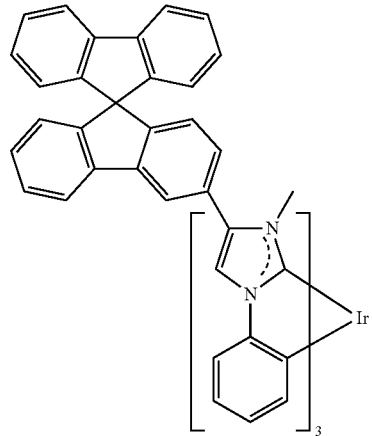
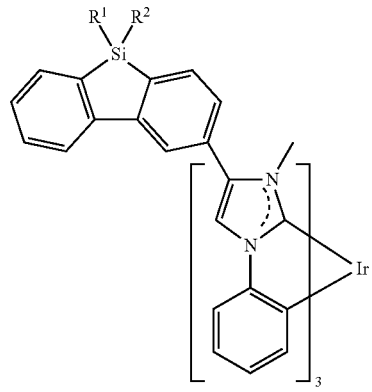
110
-continued
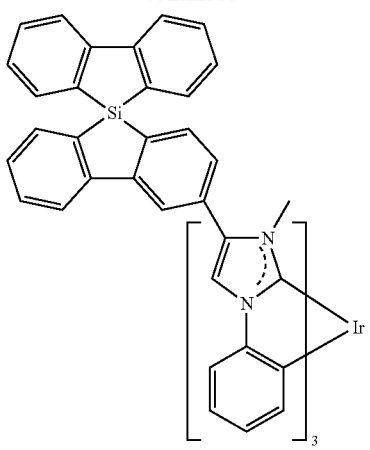
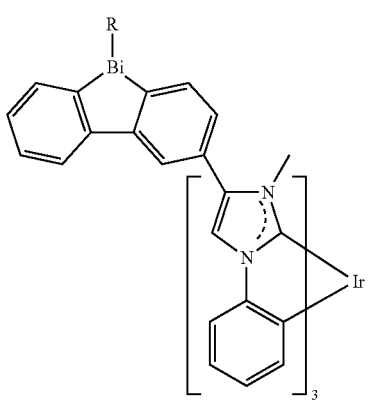
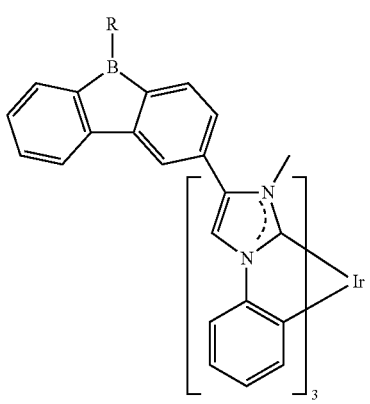
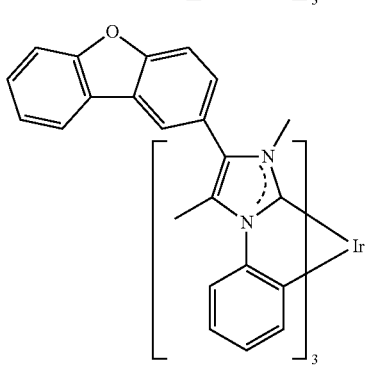

111
-continued
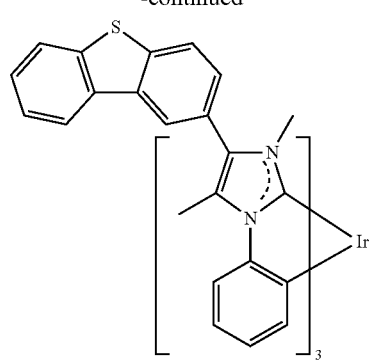
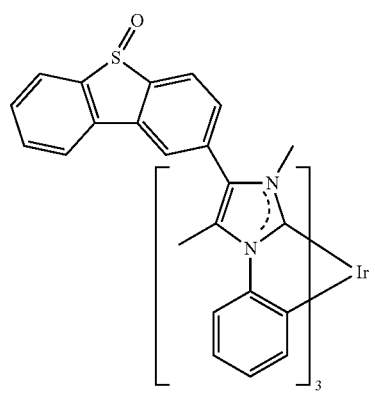
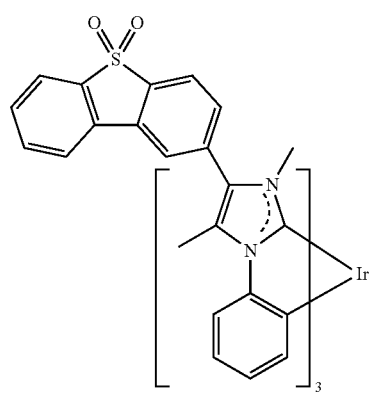
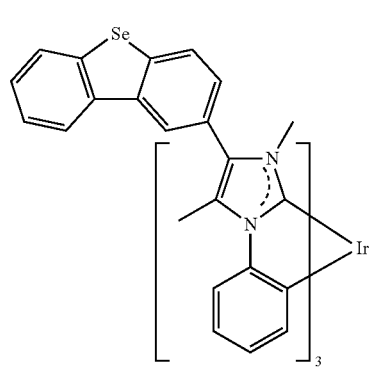
112
-continued
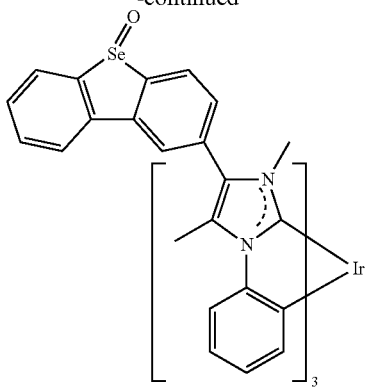
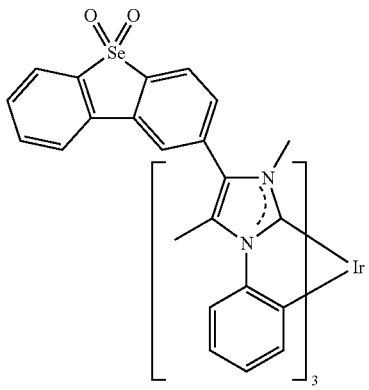
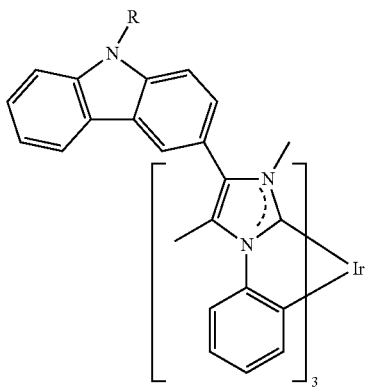
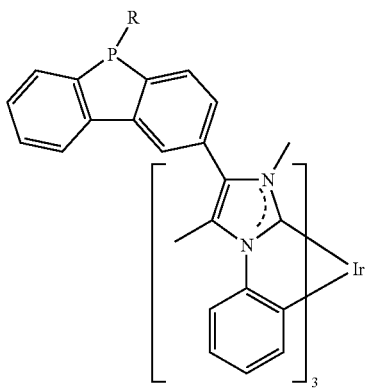

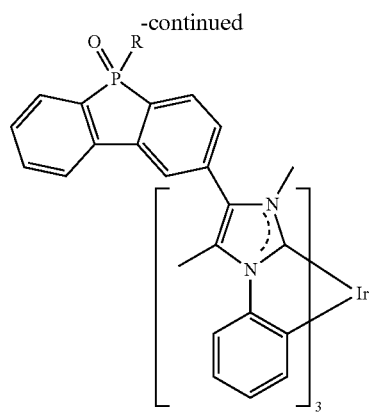
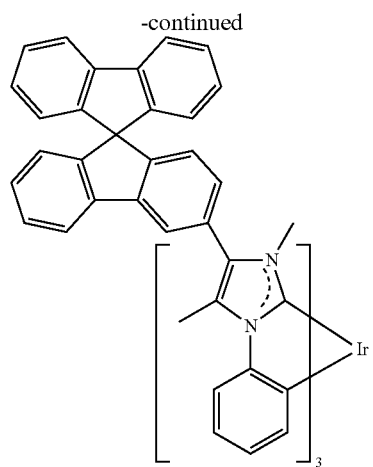
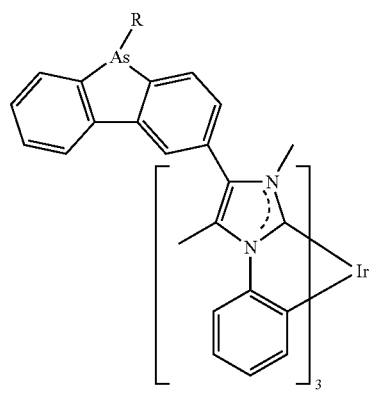
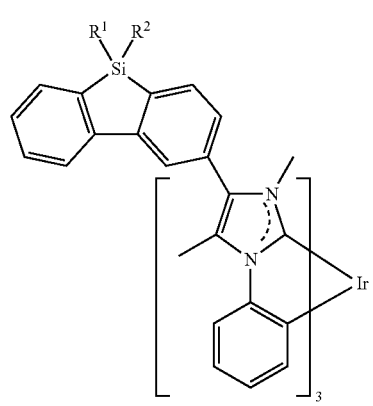
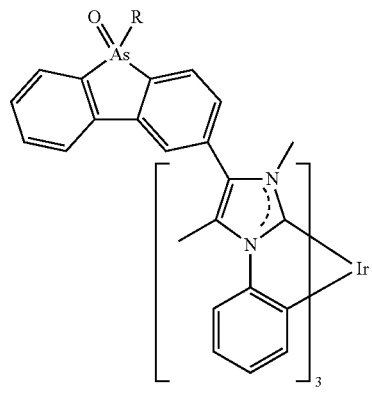
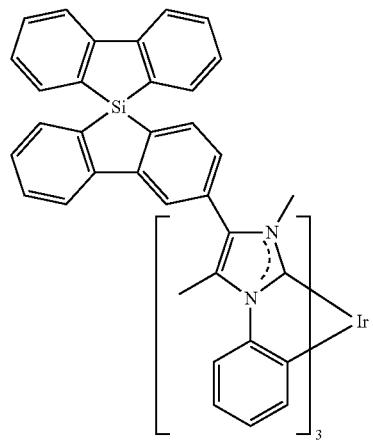
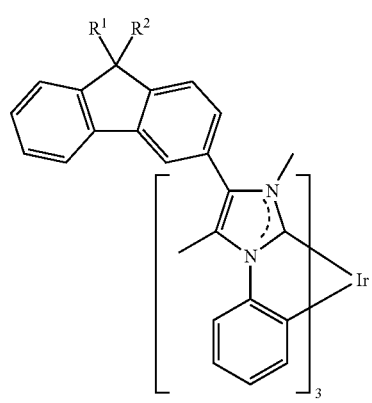
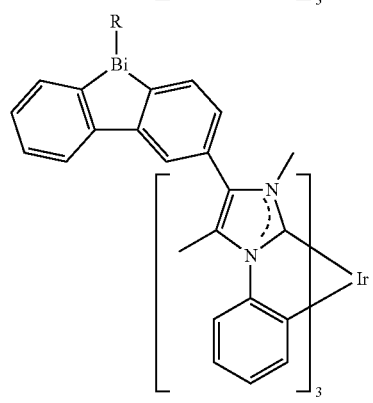

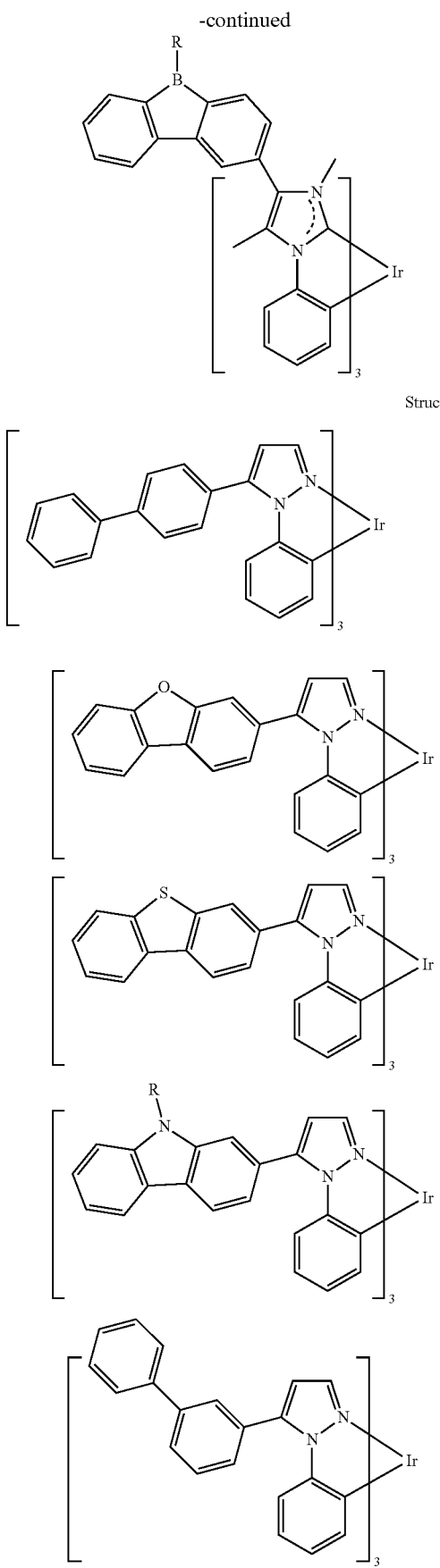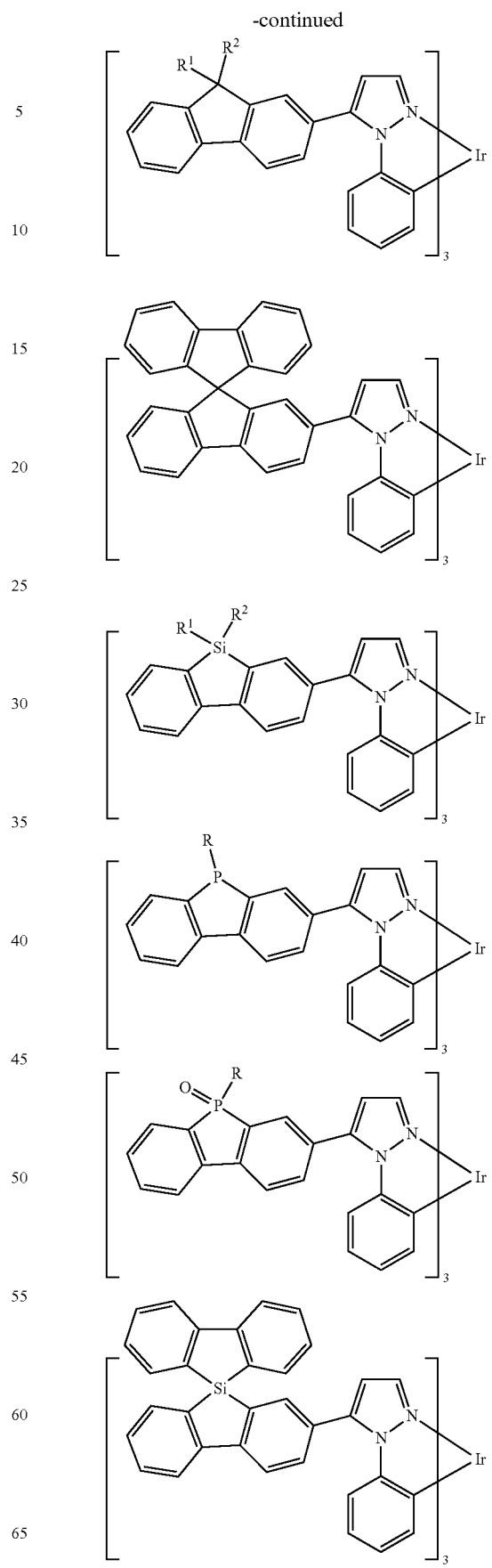

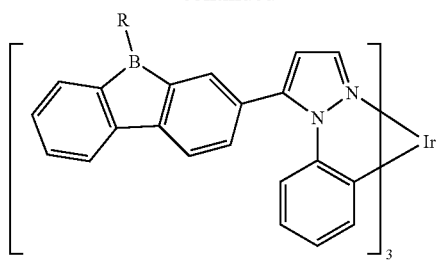
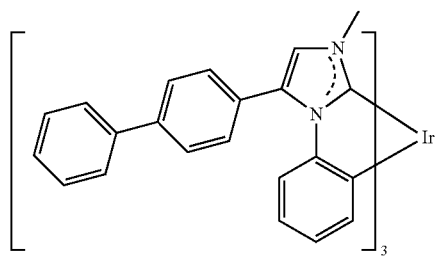
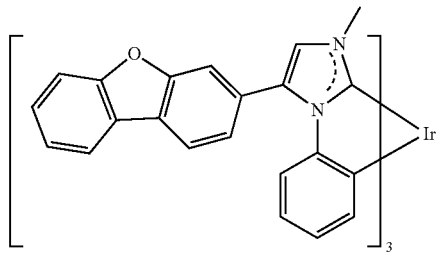
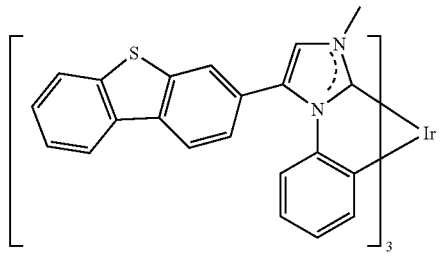
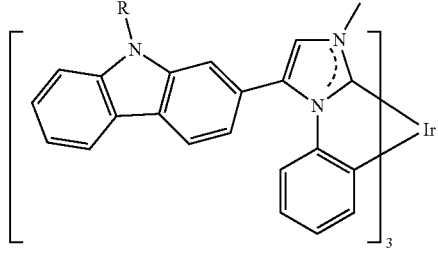
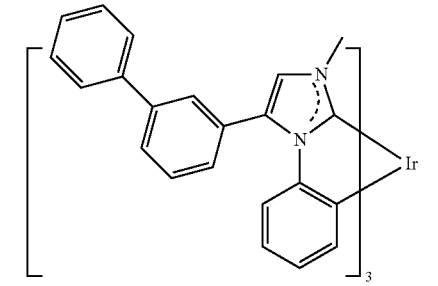
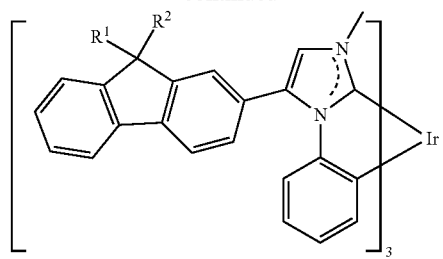
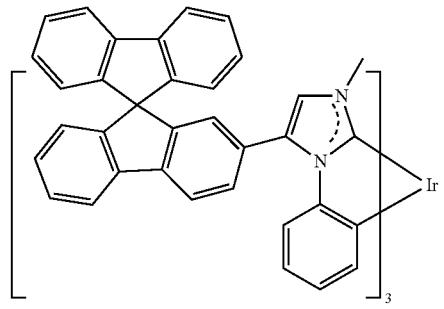
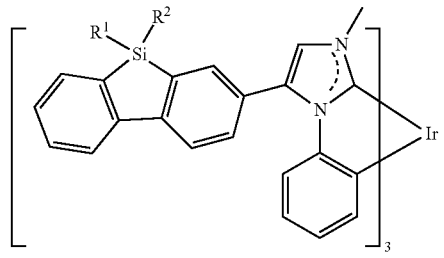
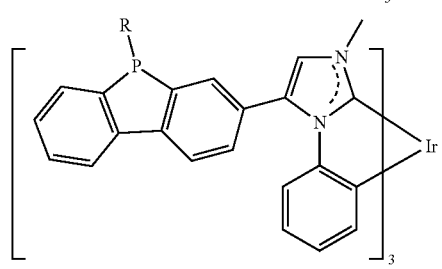
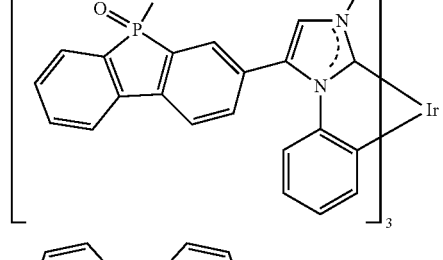
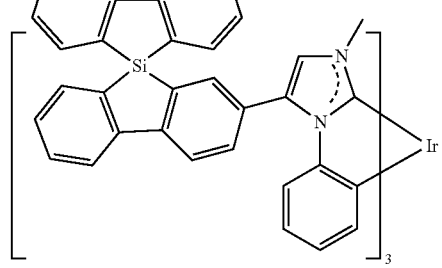

119
-continued
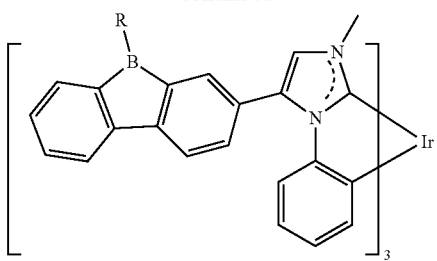
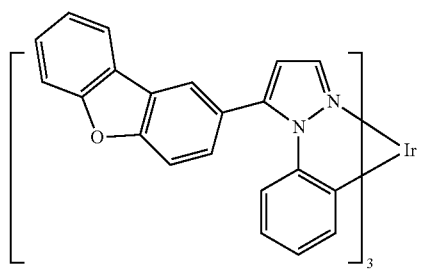
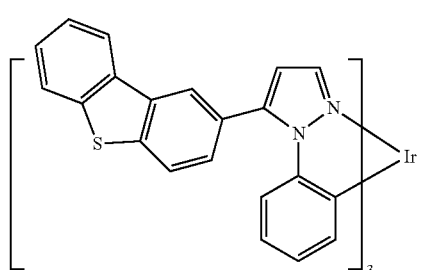
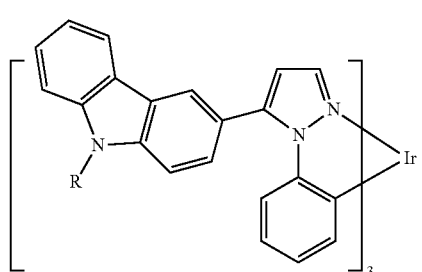
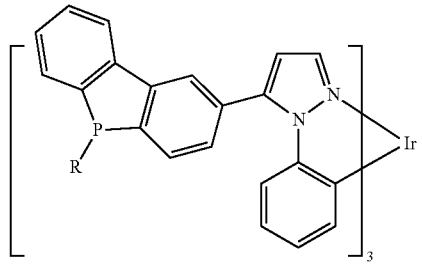
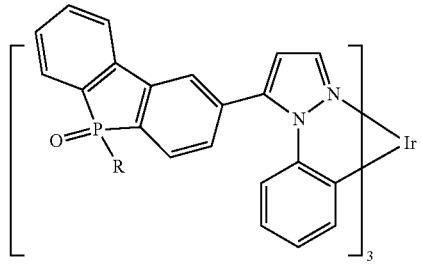
120
-continued
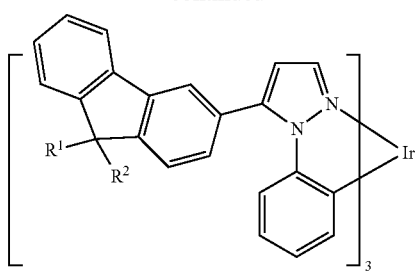
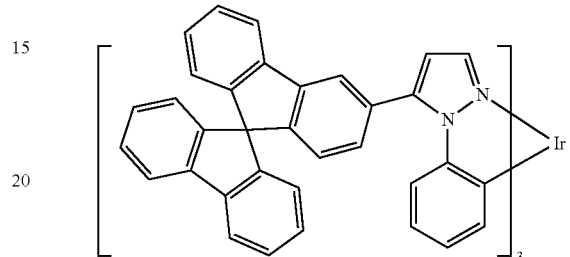
Structures Ir-8
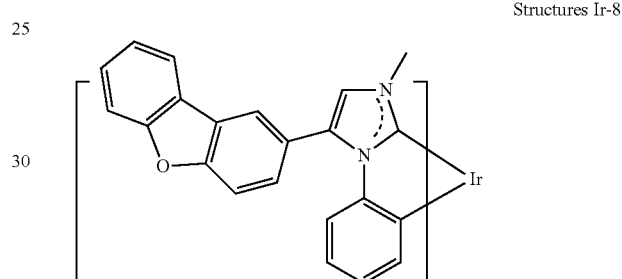
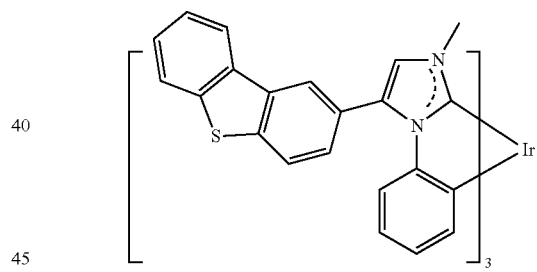
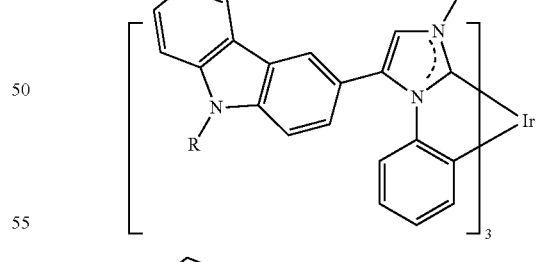
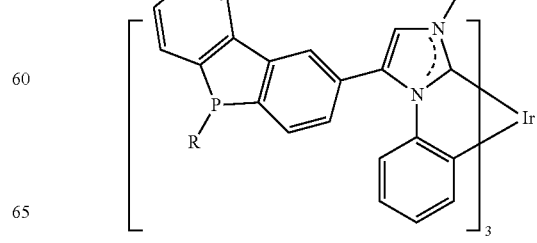

-continued
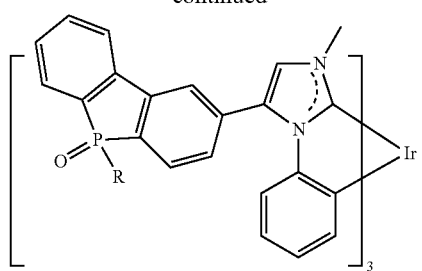
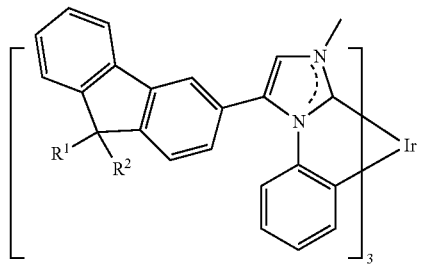
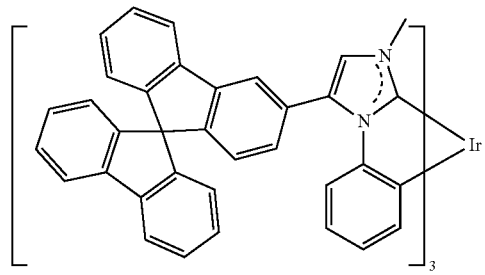
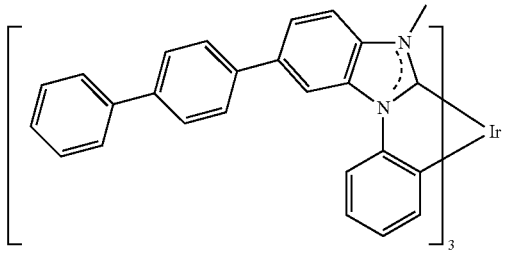
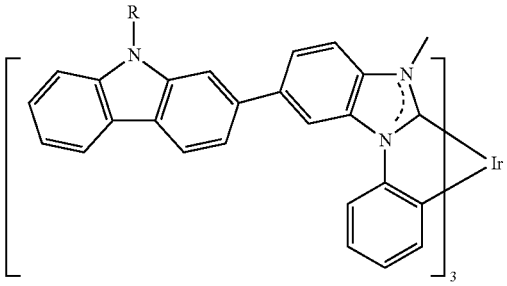
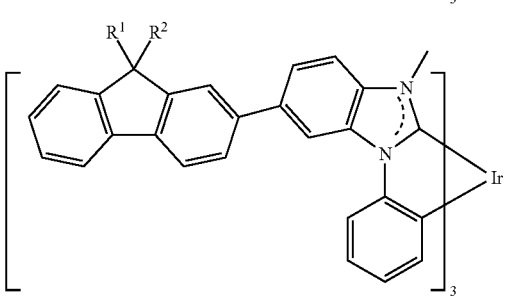
-continued
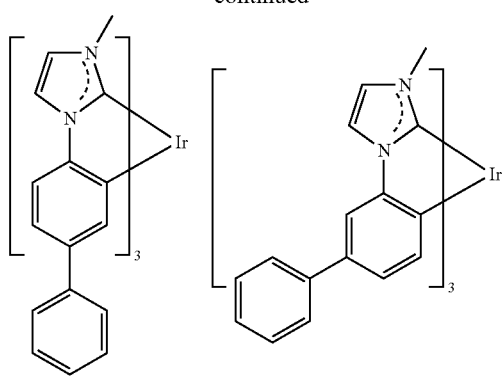
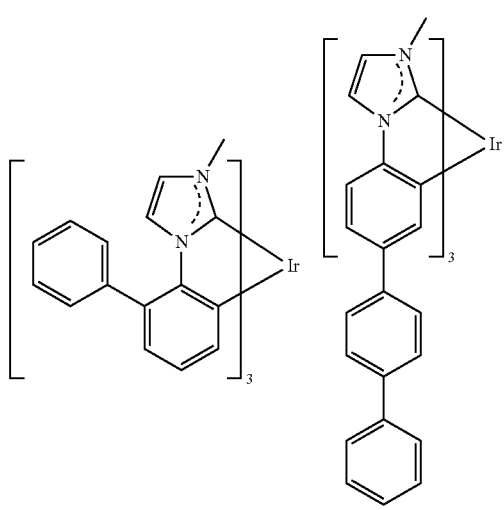
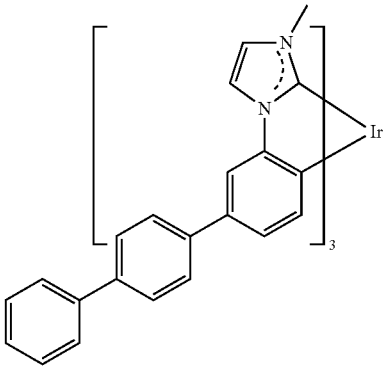
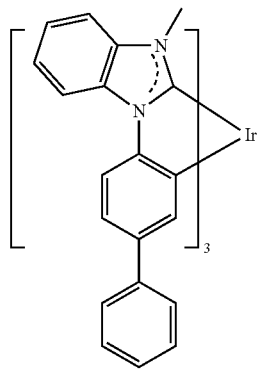

123
-continued
124
-continued
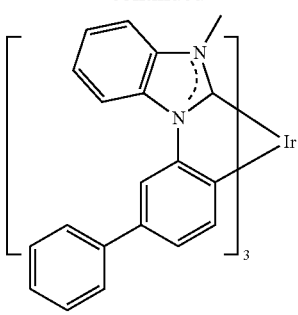
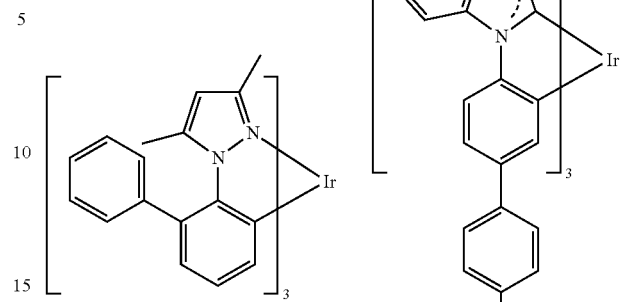
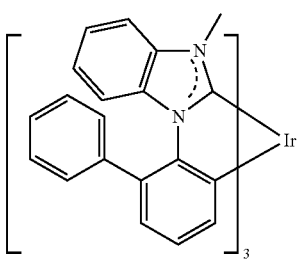
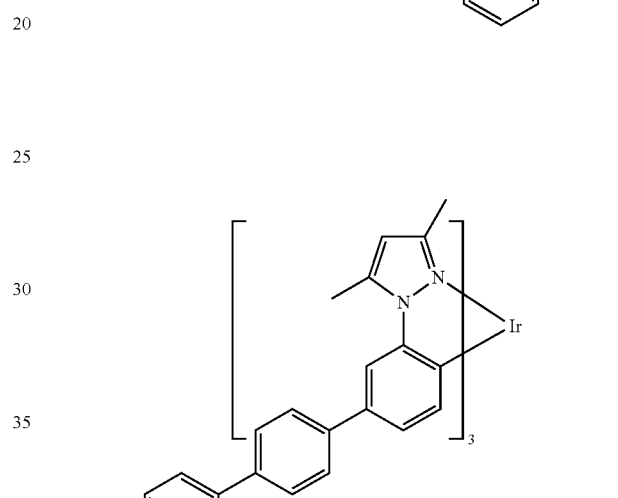
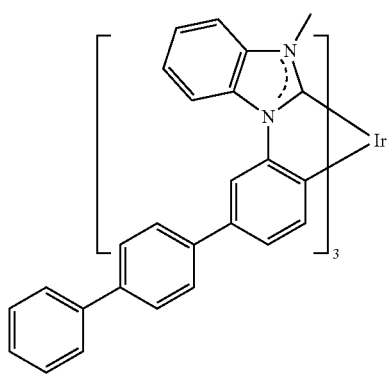
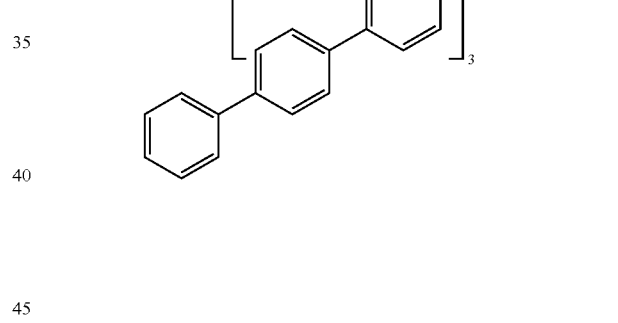
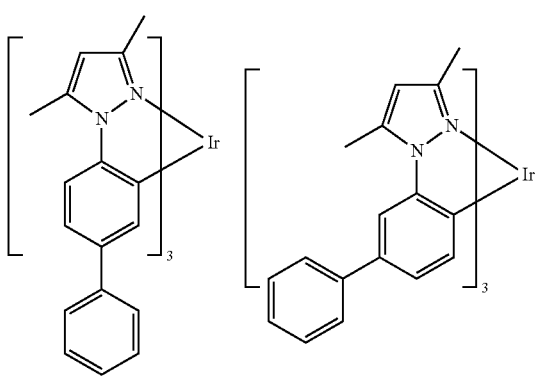
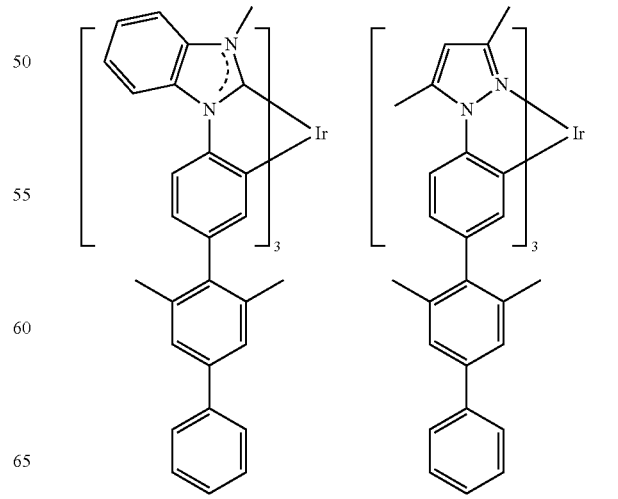

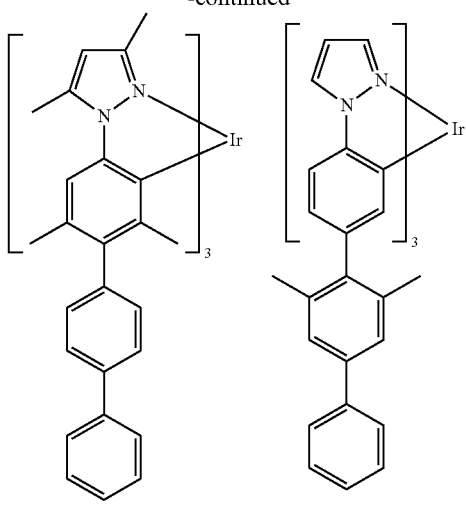
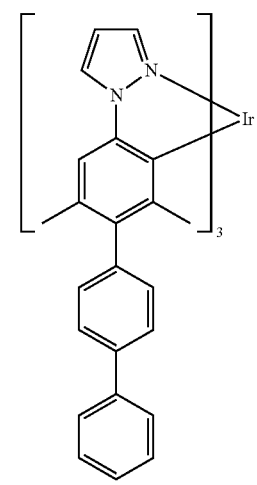
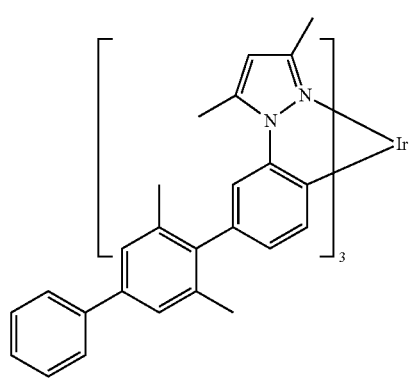
Structures Ir-9
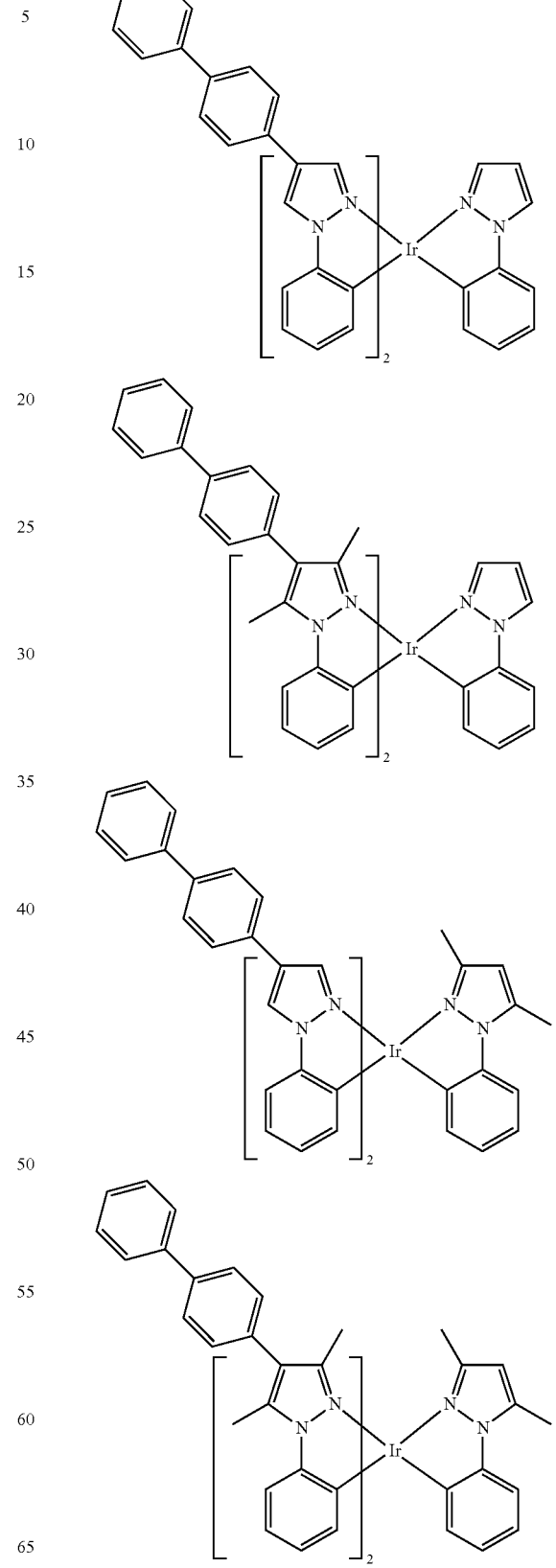

127
-continued
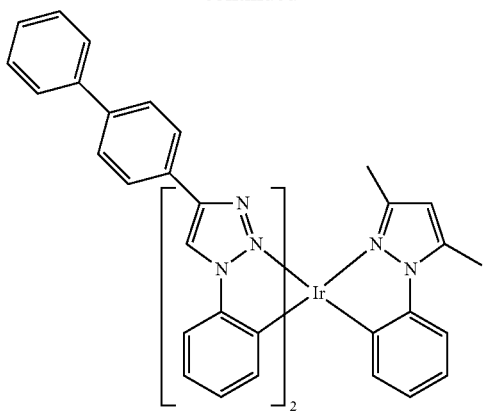
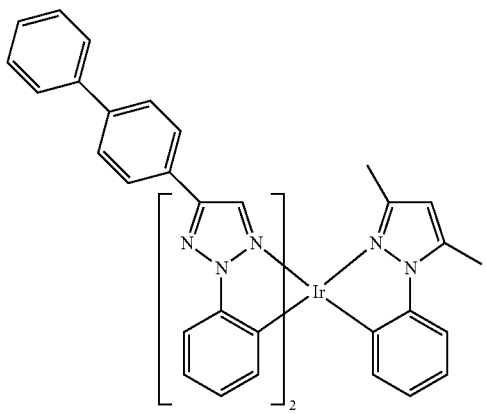
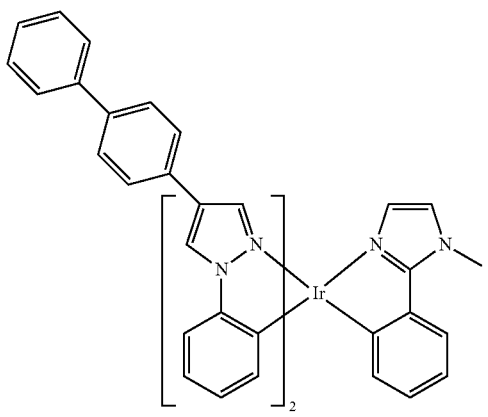
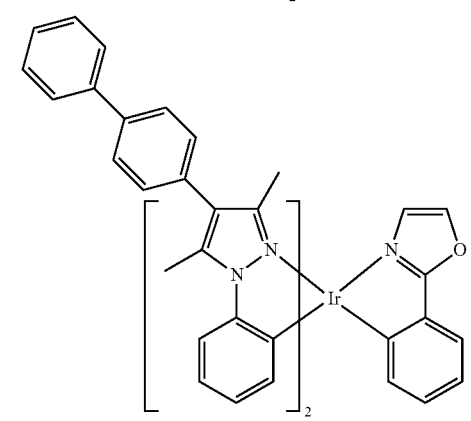
128
-continued
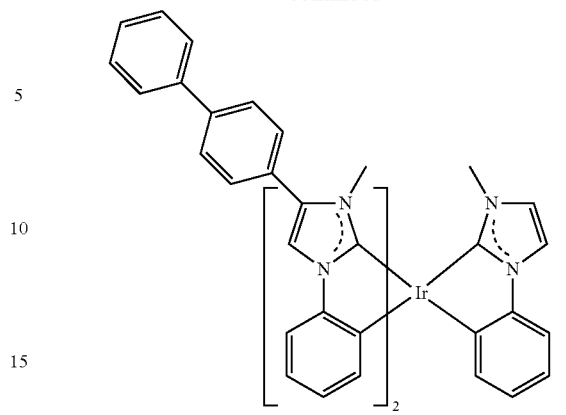
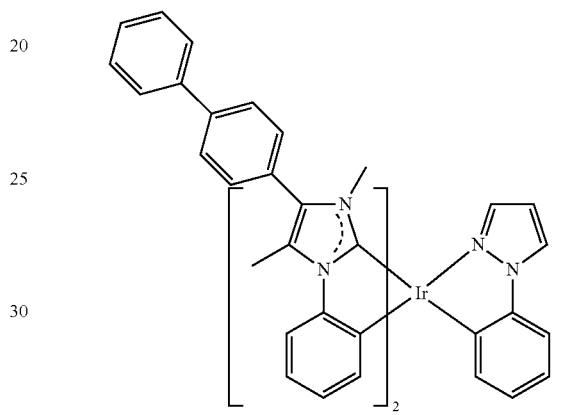

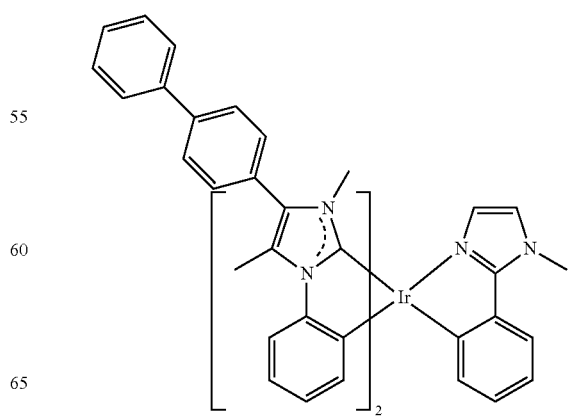

129
-continued
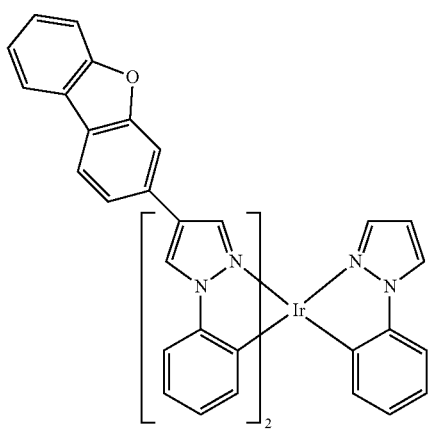
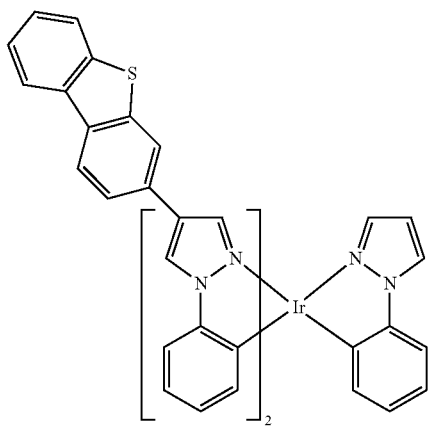
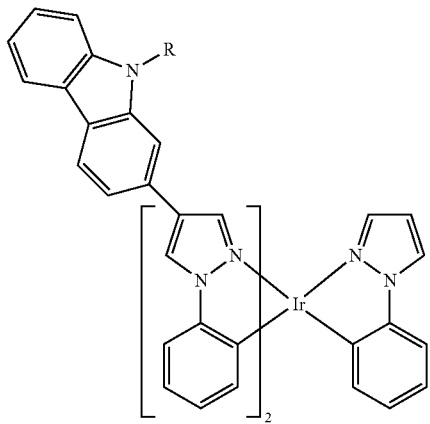
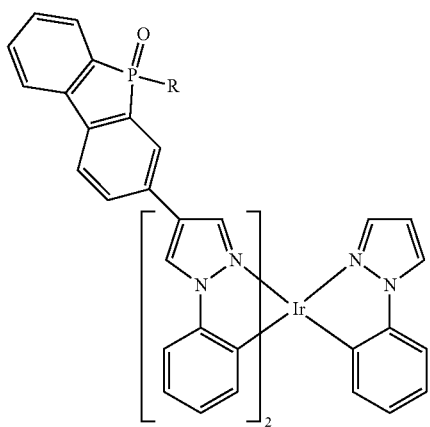
130
-continued
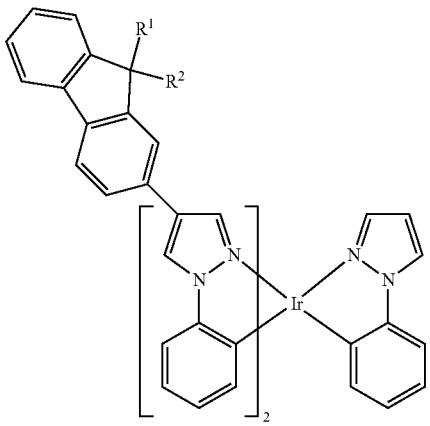
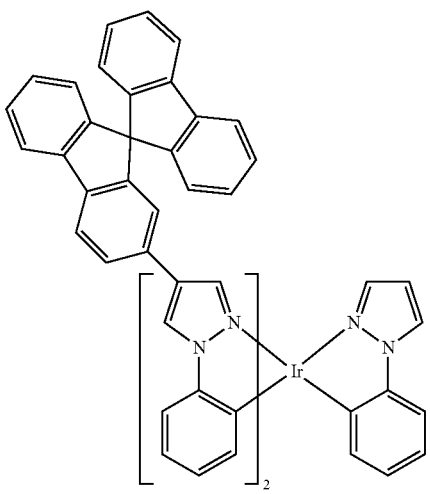
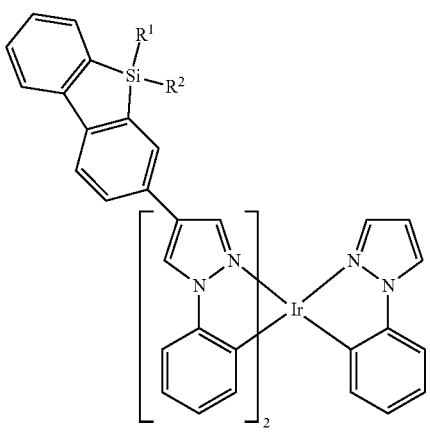

131
-continued
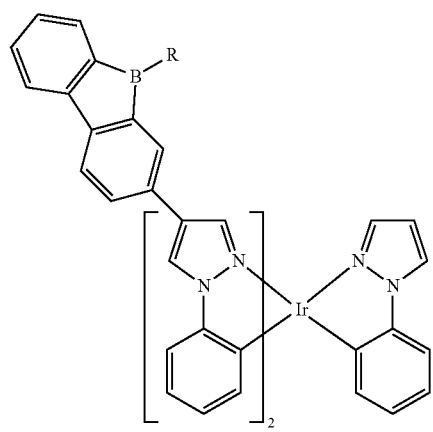
132
-continued
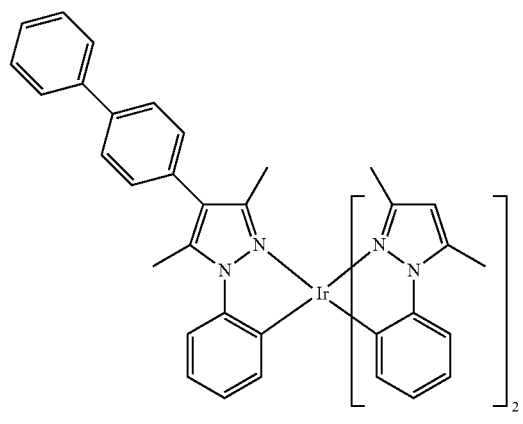
Structures Ir-10
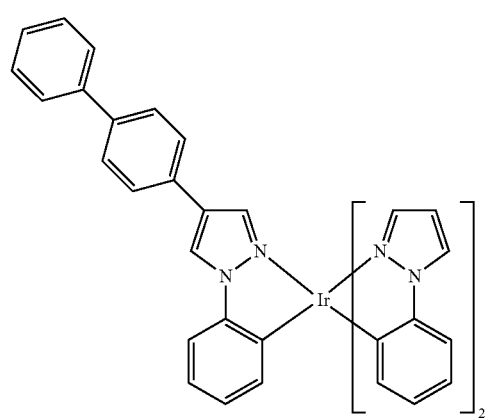
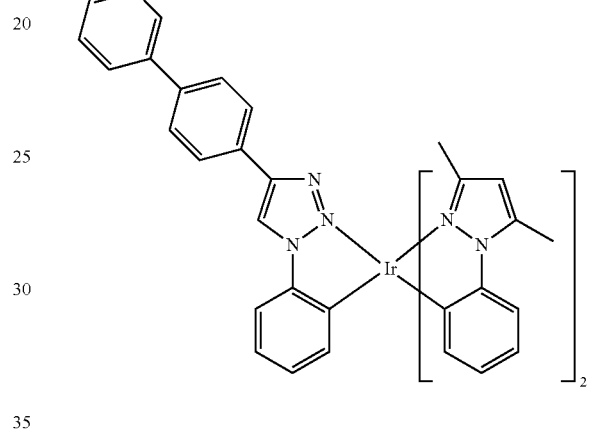
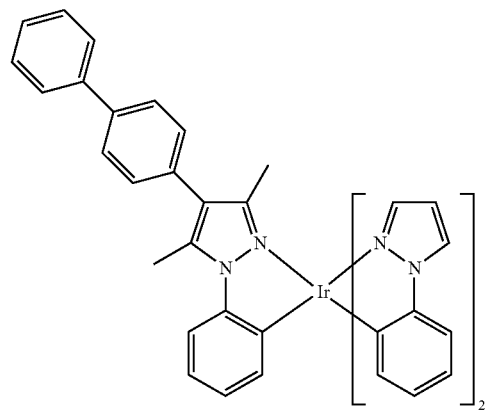
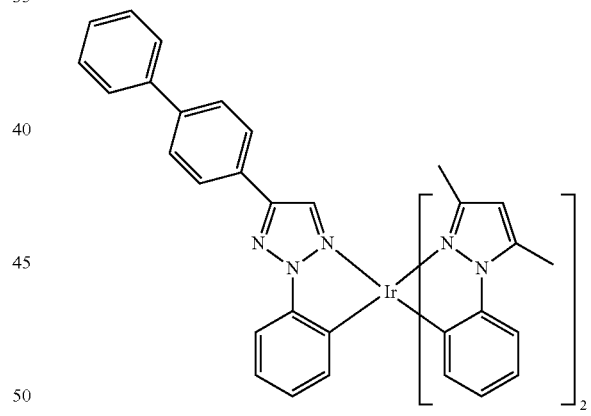
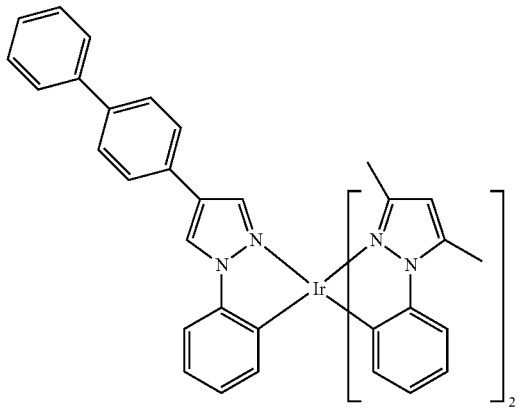
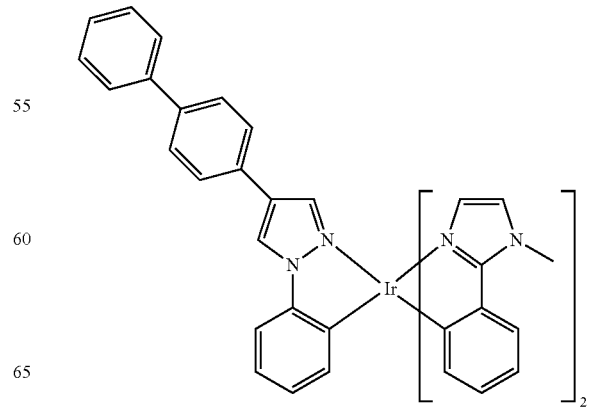

133
-continued
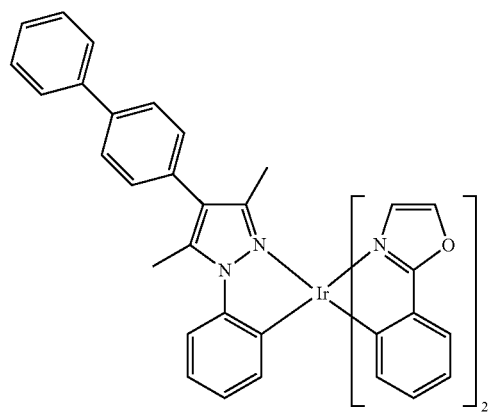
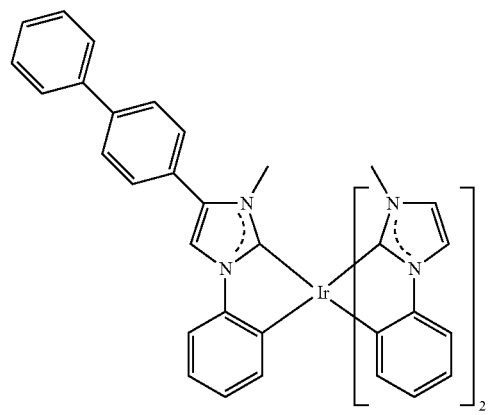
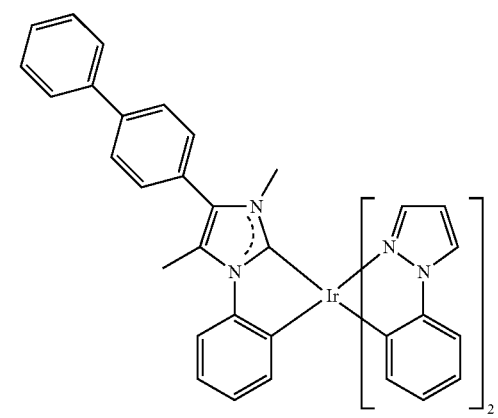
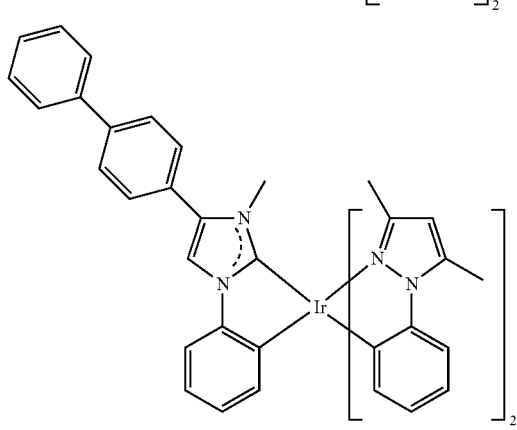
134
-continued
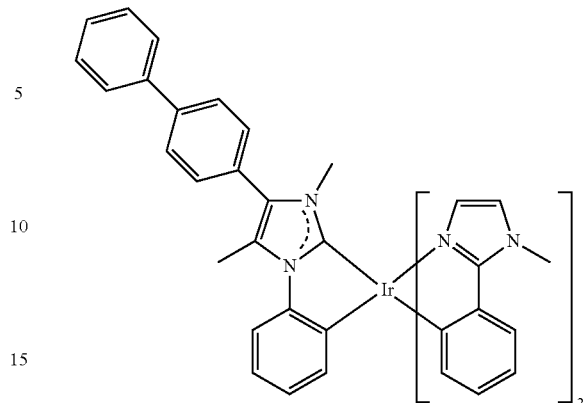
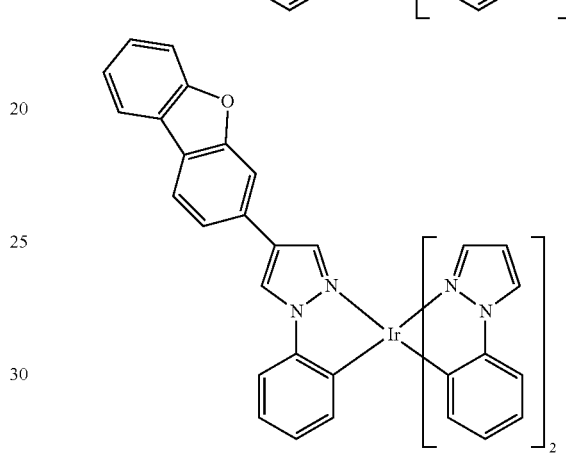
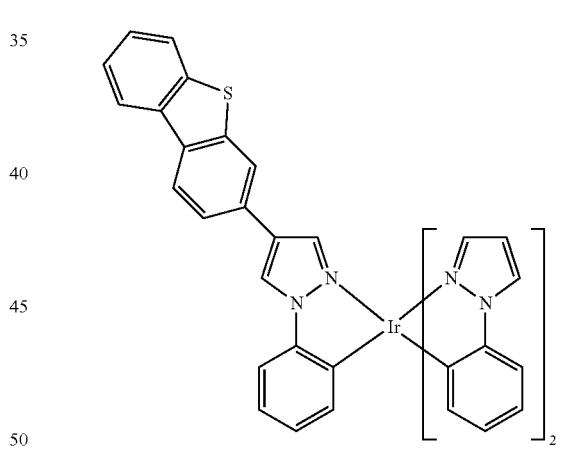
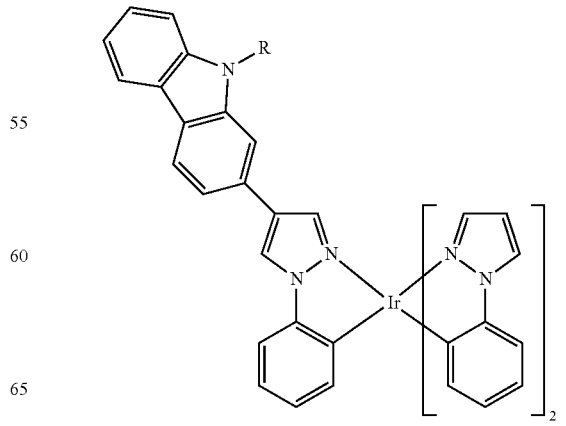

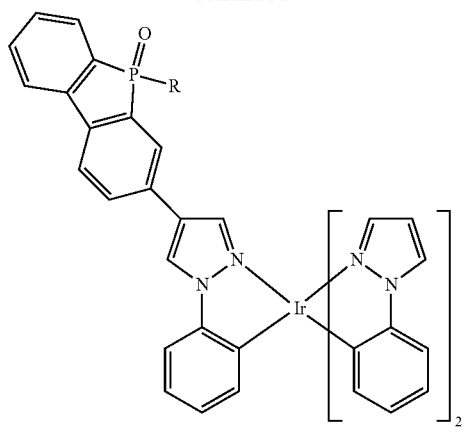
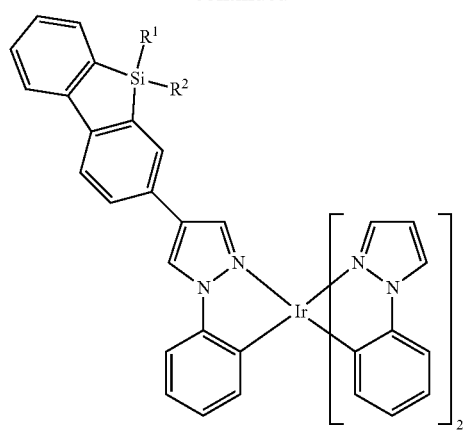
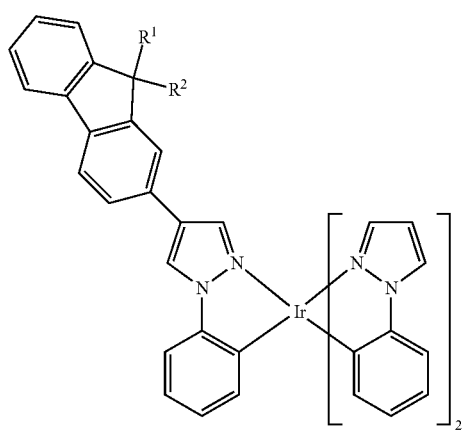
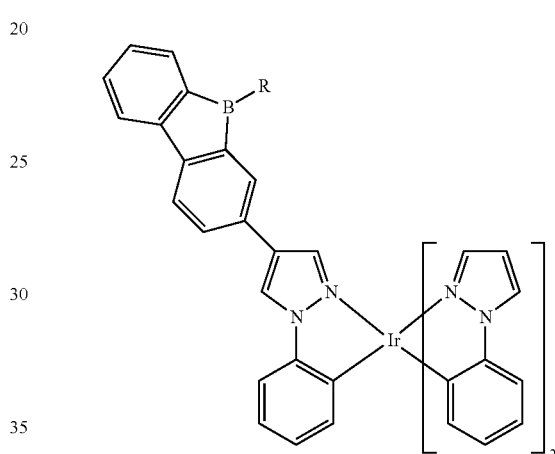
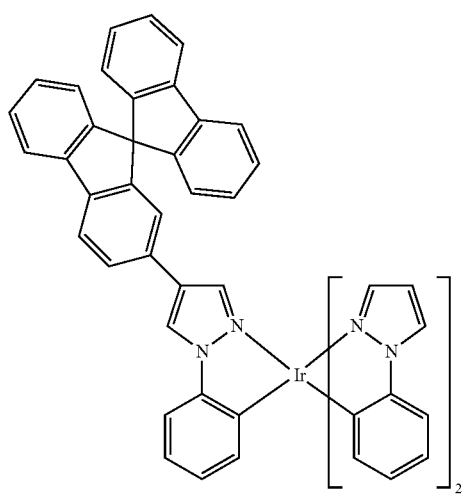
Structures Ir-11
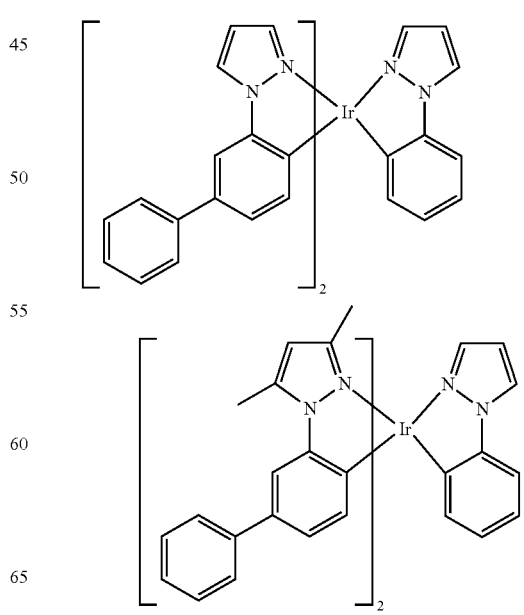

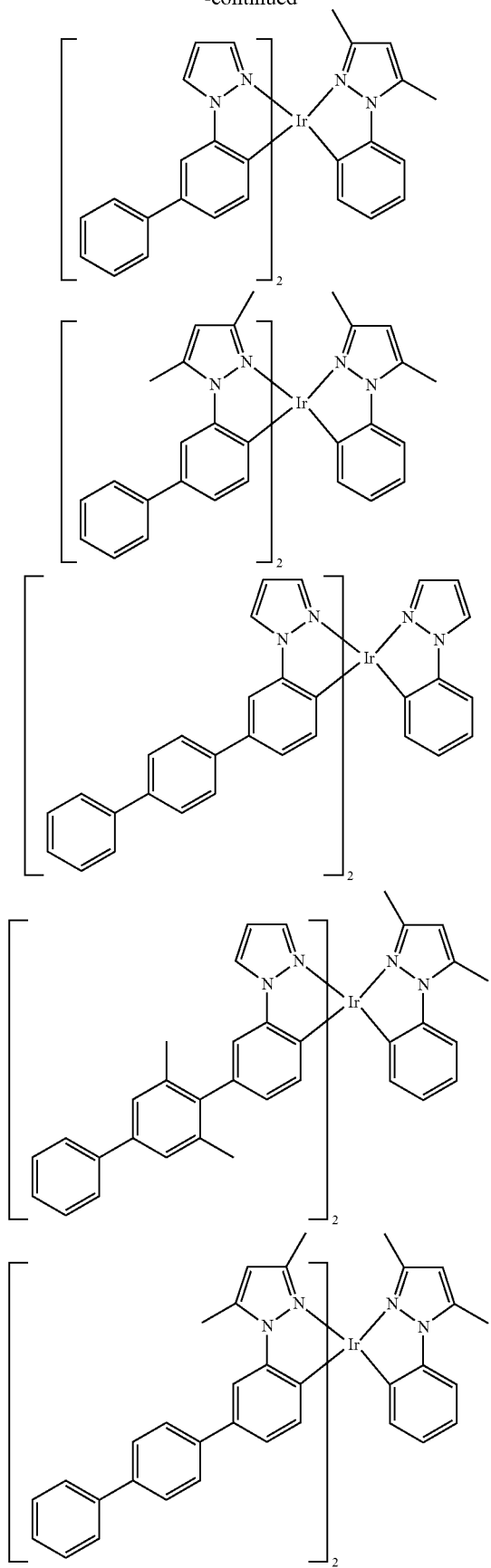
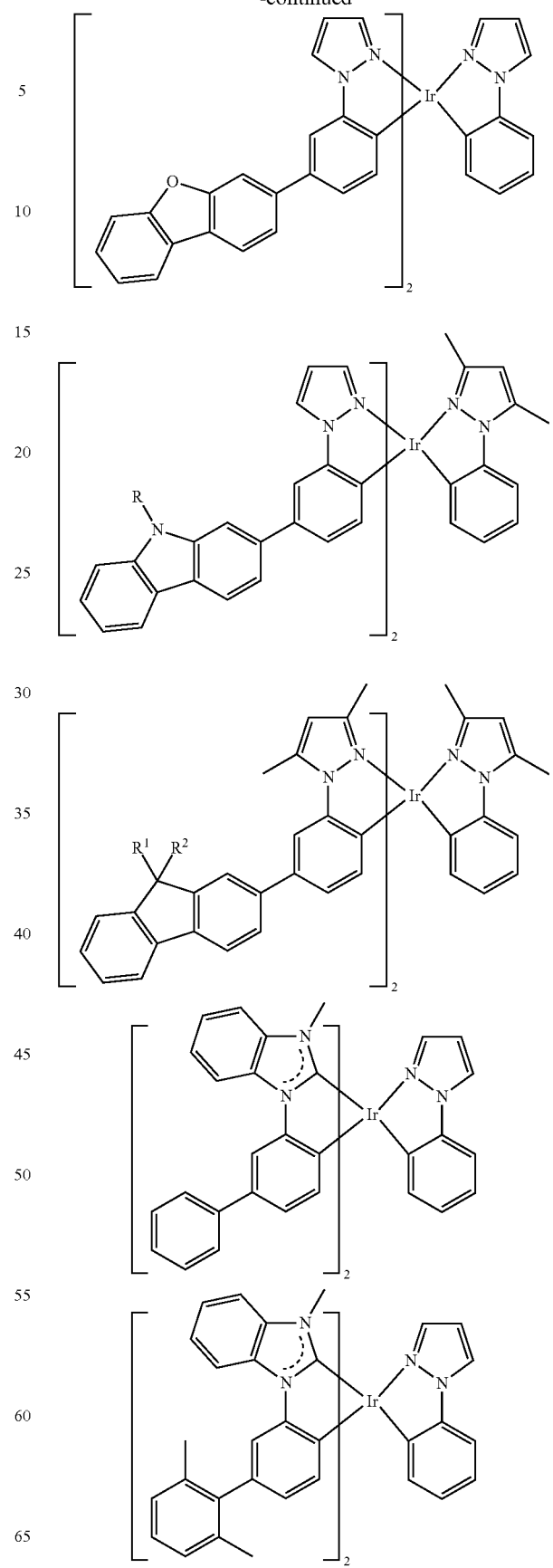

139
-continued
140
-continued
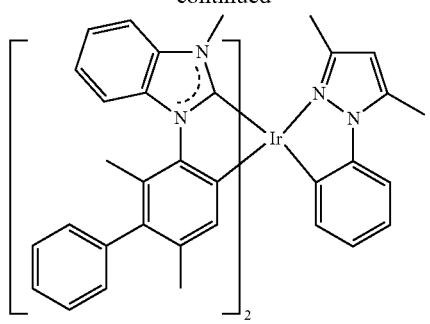
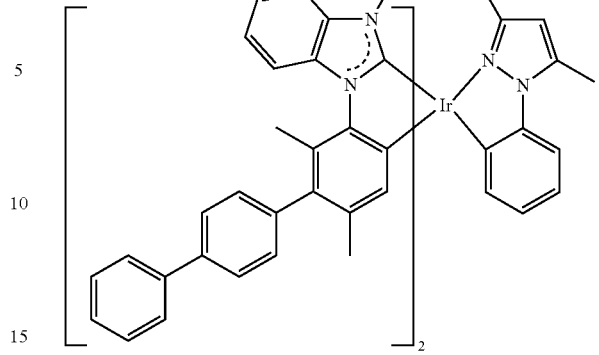
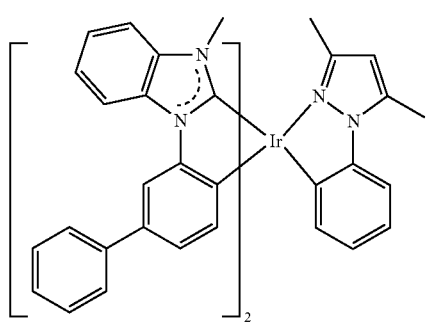
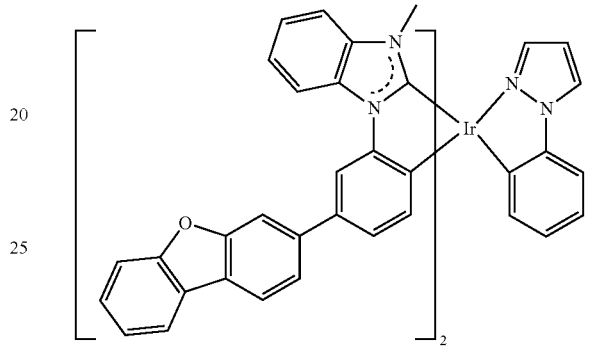
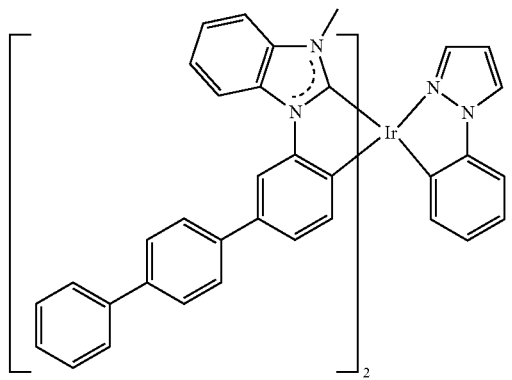
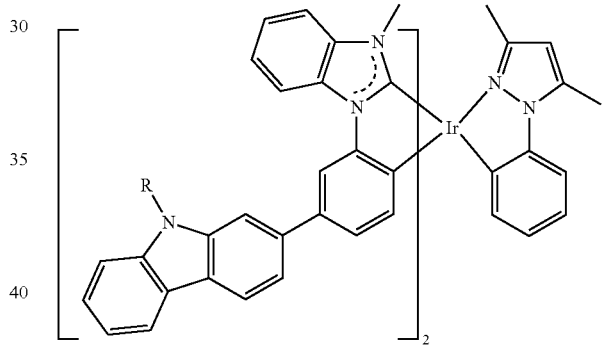
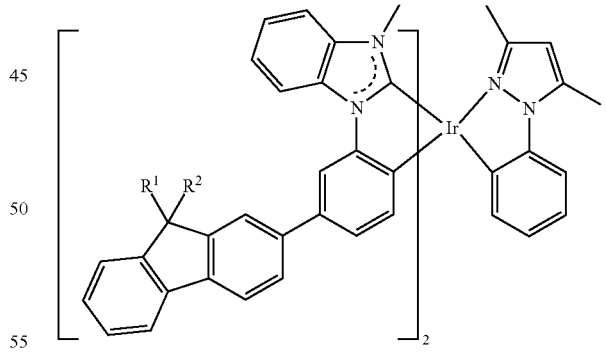
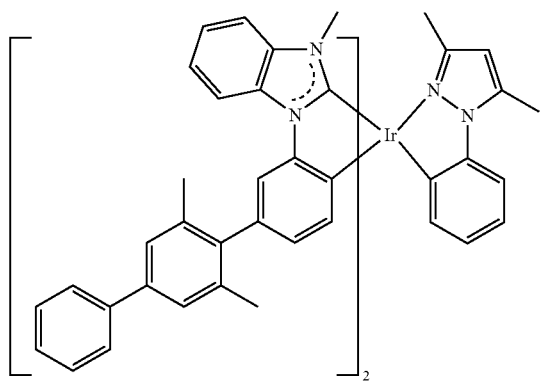
Structures Ir-12
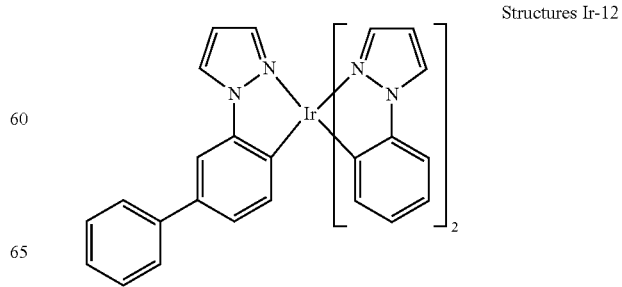

141
-continued
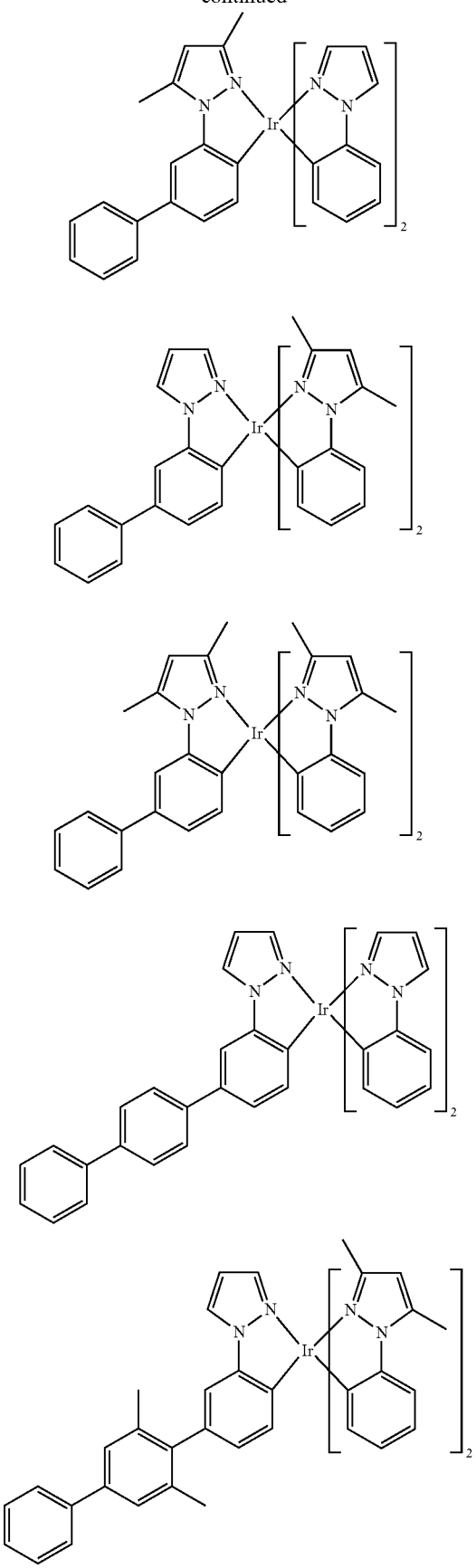
142
-continued
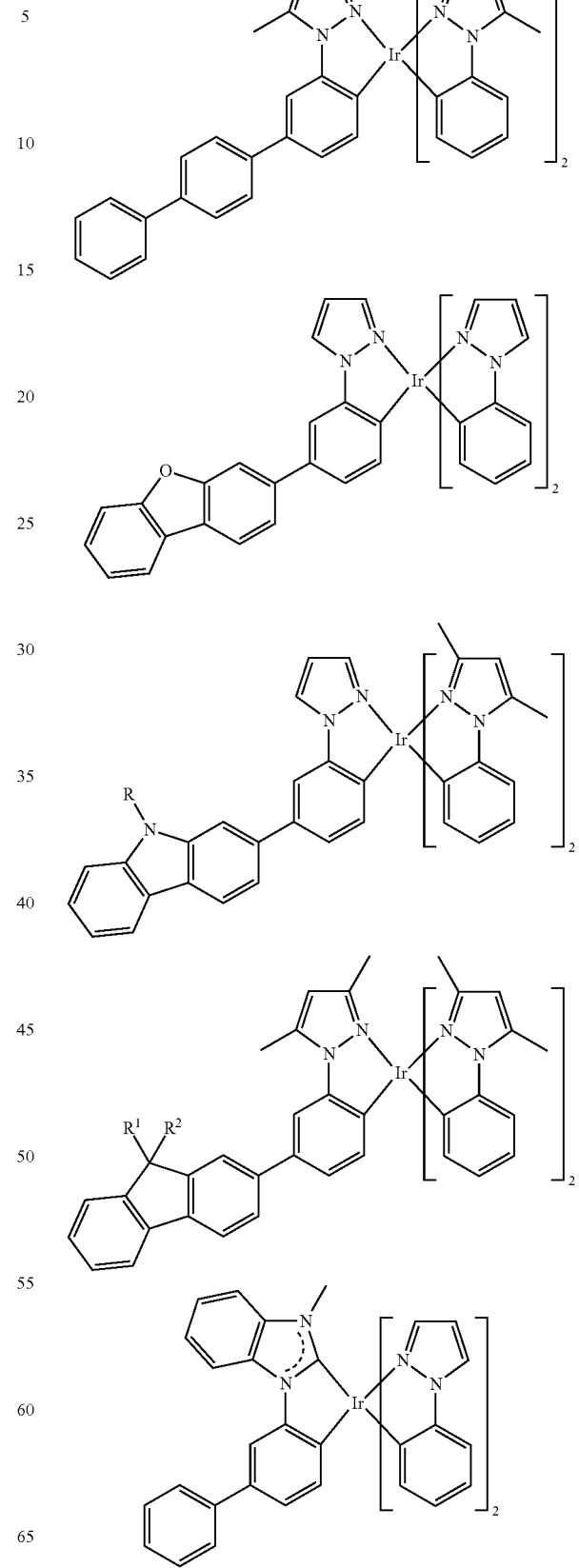

143
-continued
144
-continued
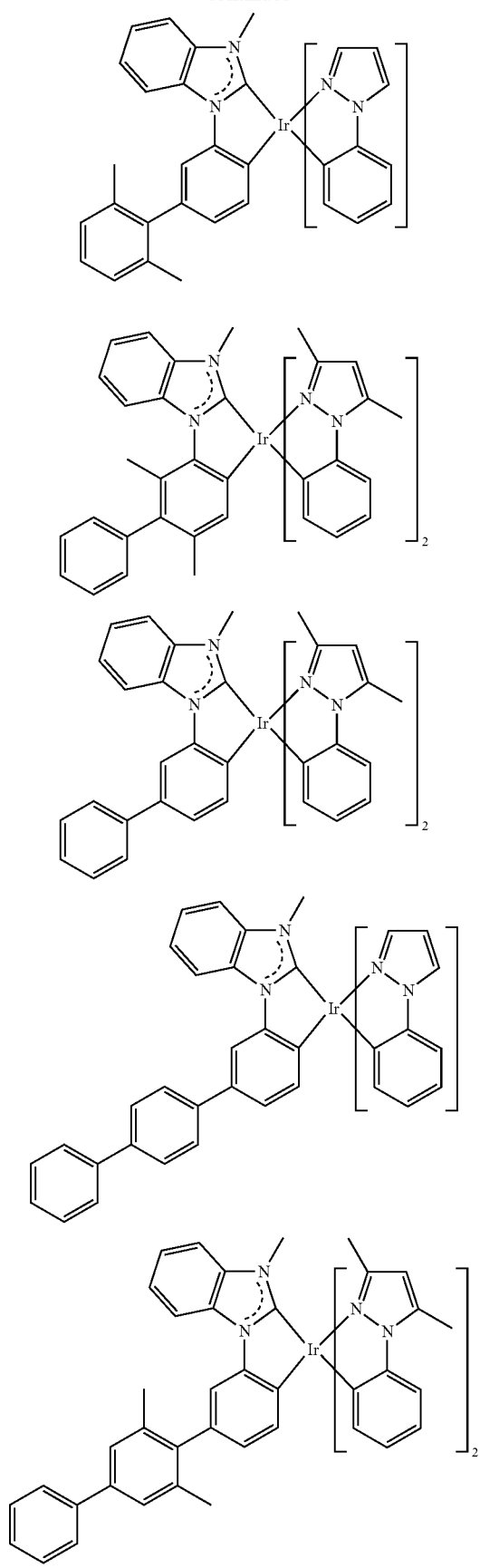
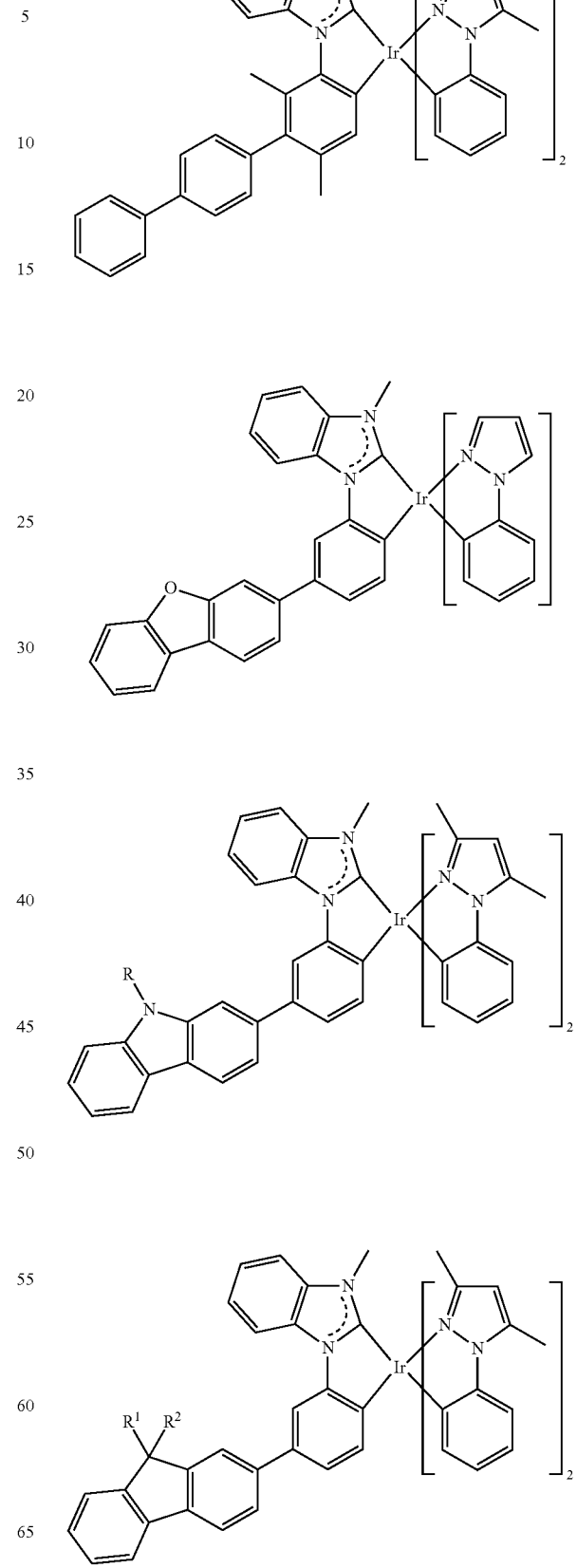

Structures Ir-13
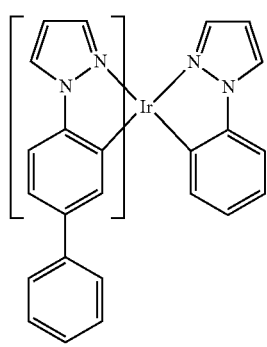
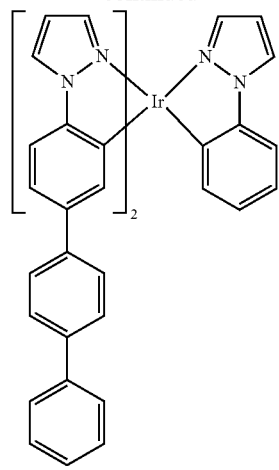
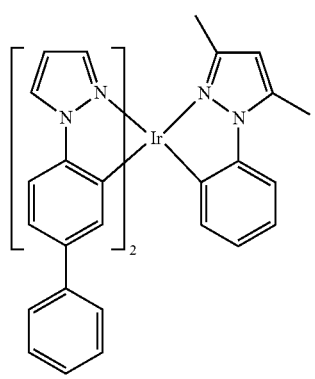
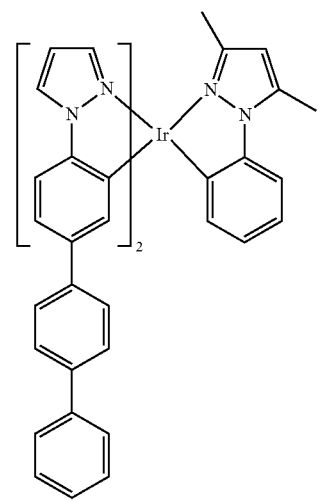
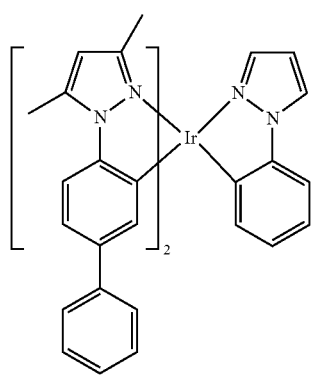
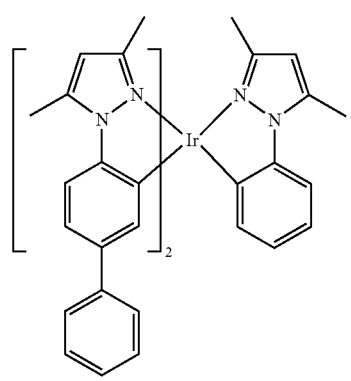
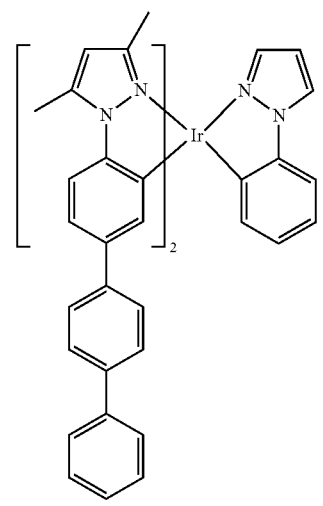

147
-continued
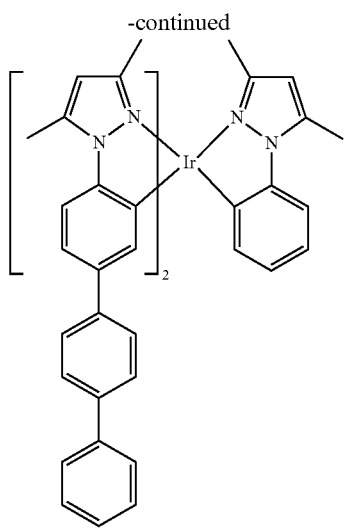
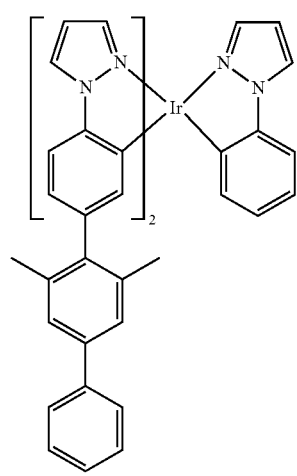
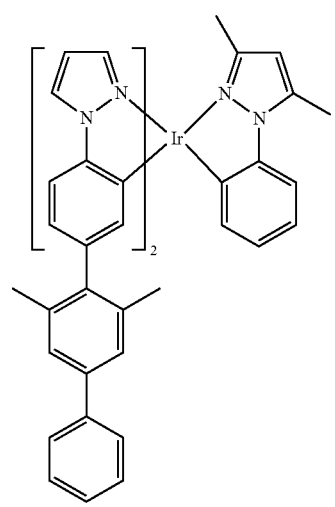
148
-continued
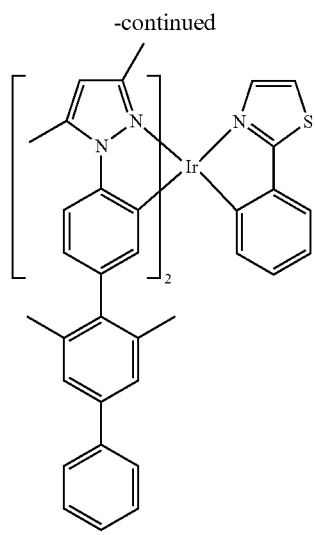
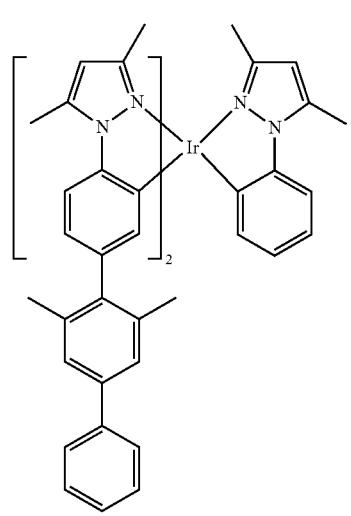
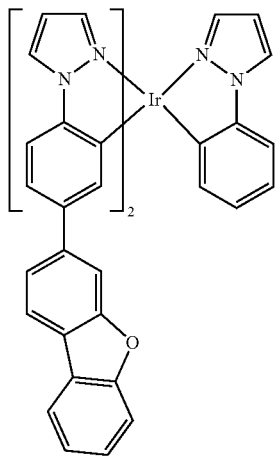

149
-continued
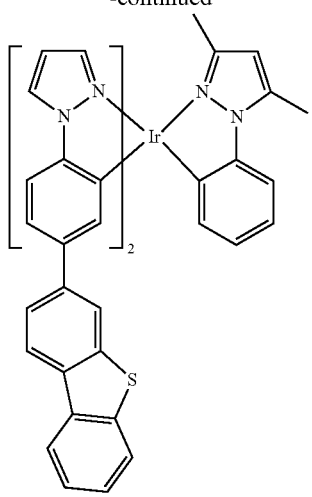
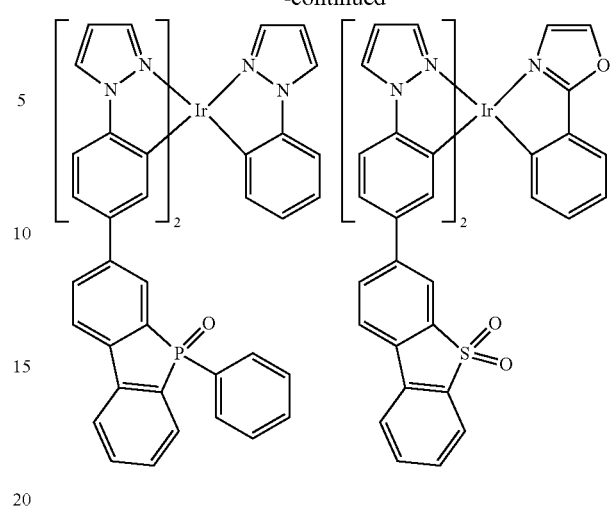
150
-continued
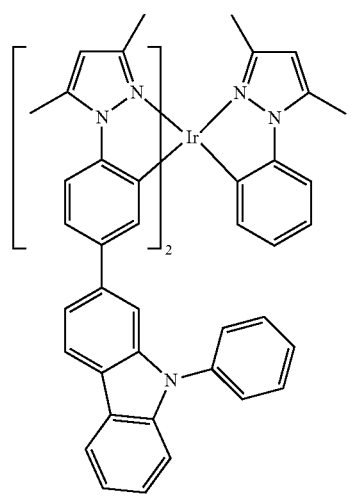
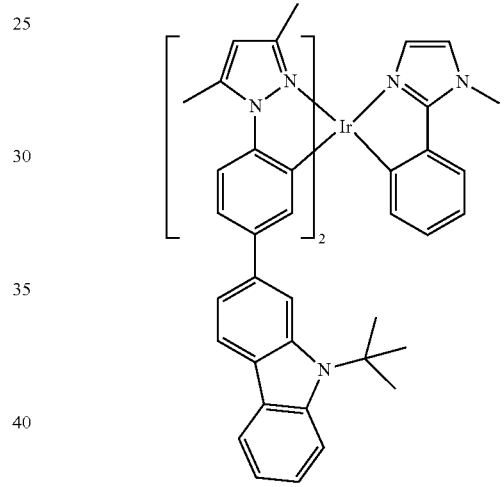
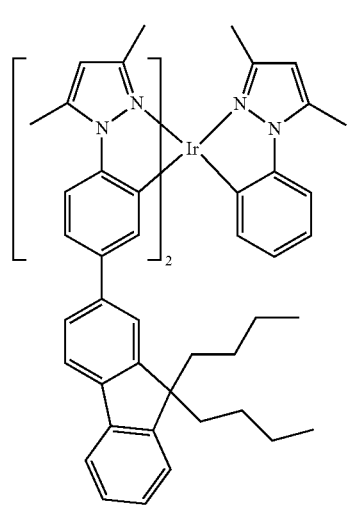
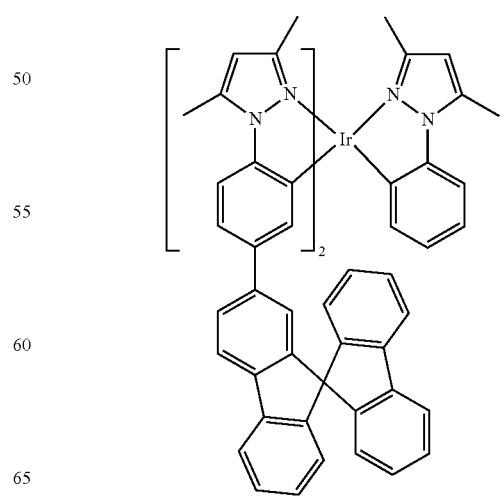

Structures Ir-14
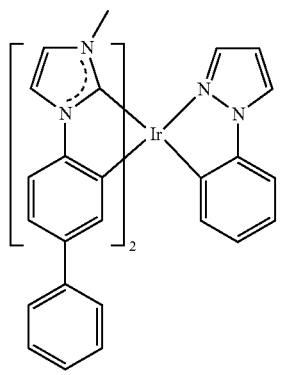
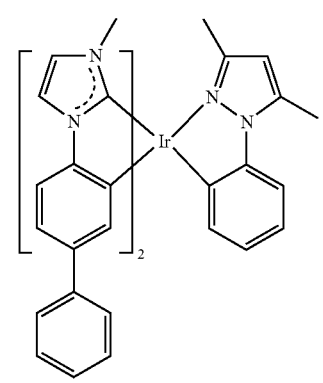
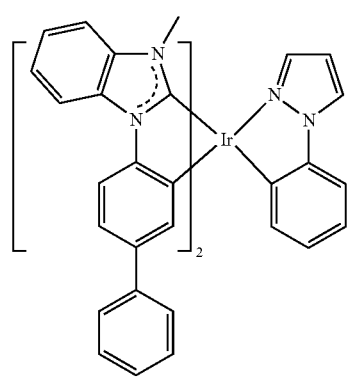
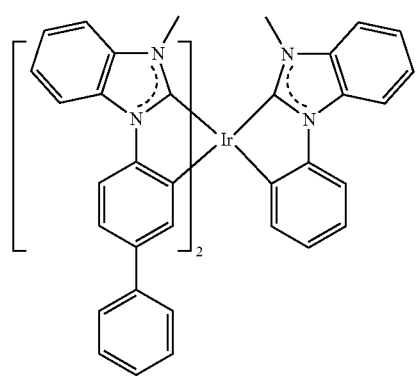
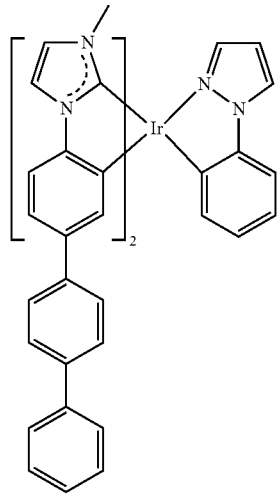
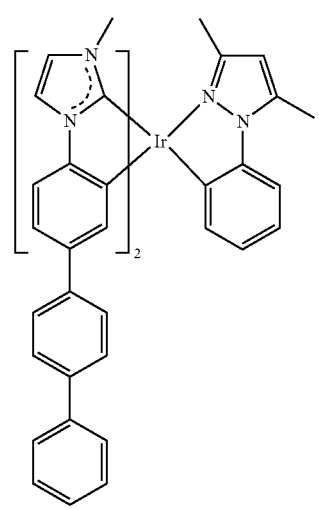
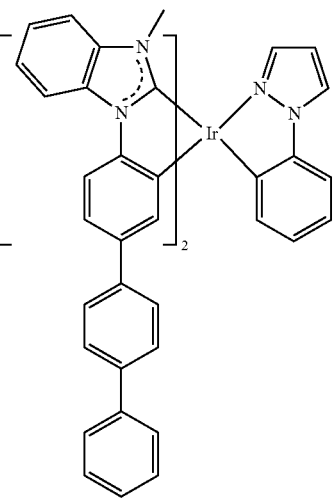

153
-continued
154
-continued
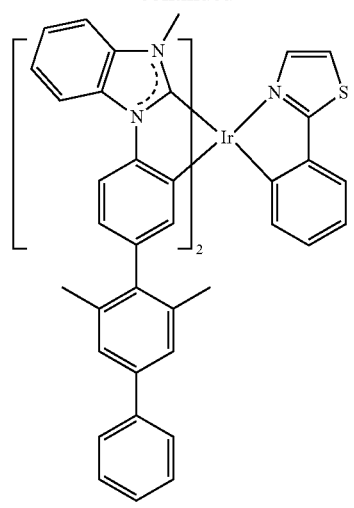
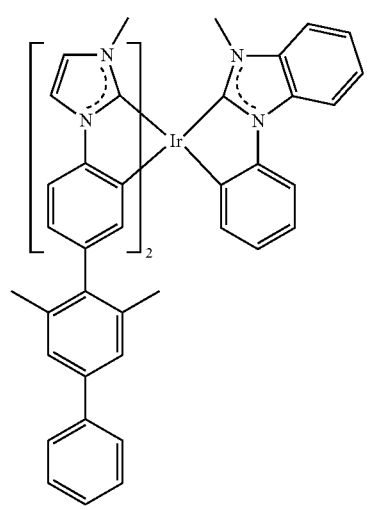
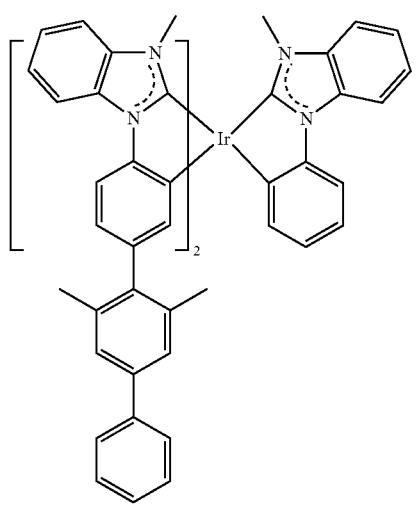
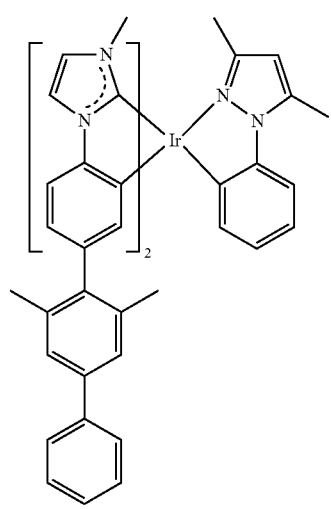
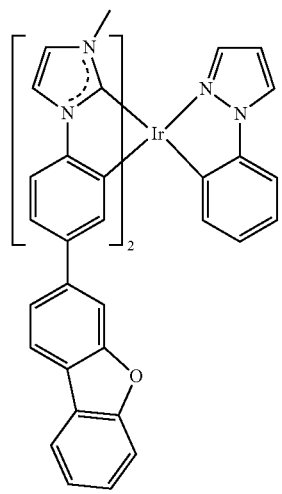

155
-continued
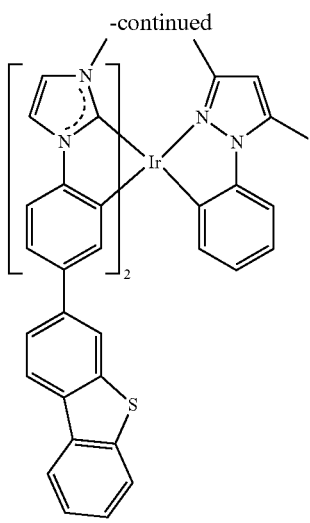
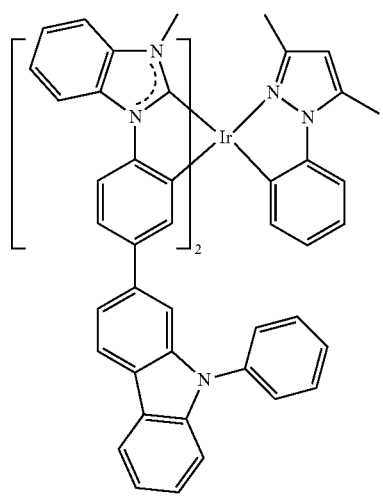
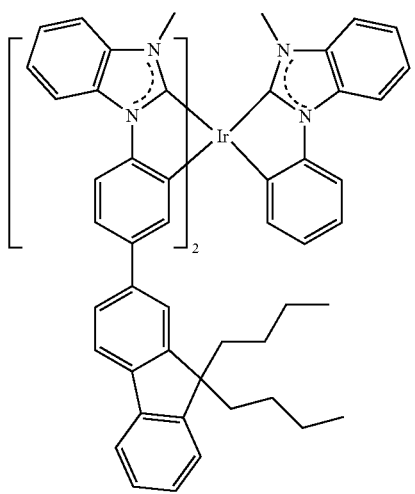
156
-continued
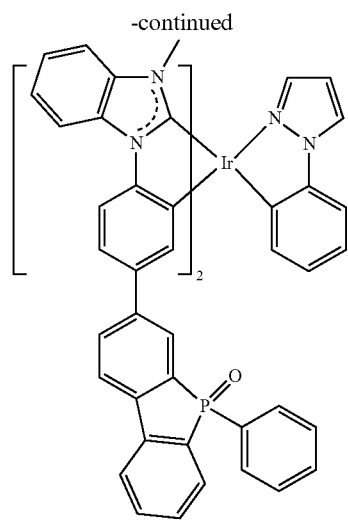
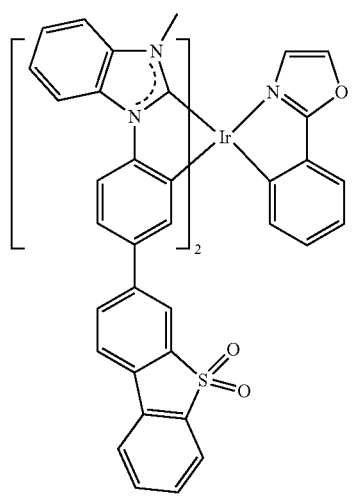
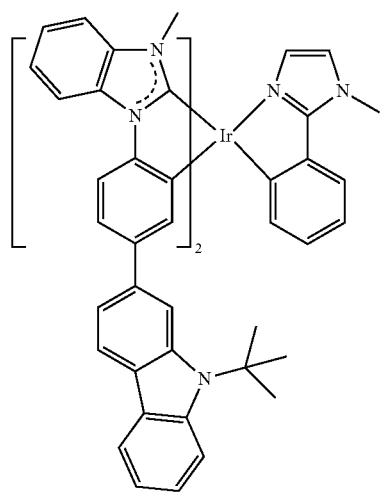

157
-continued
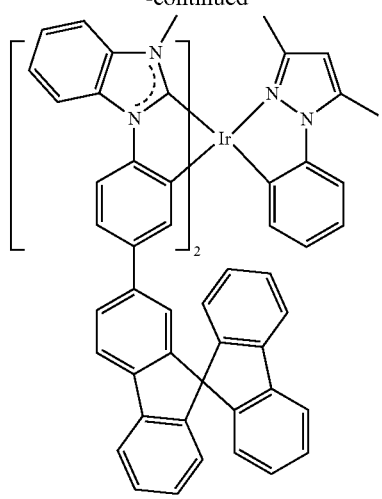
158
-continued
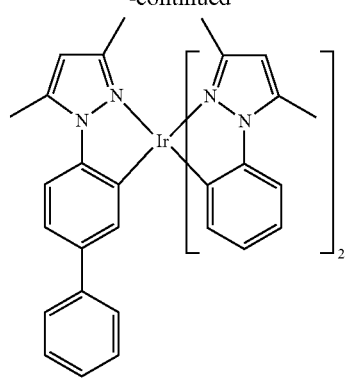
Structures Ir-15
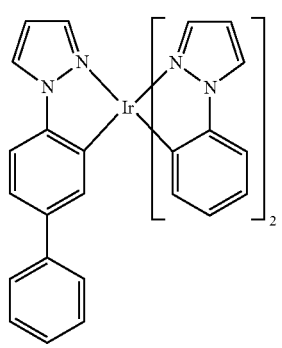
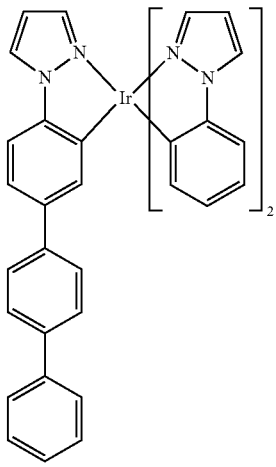
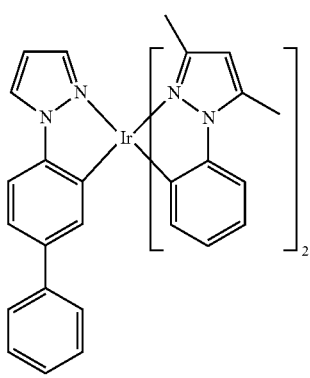
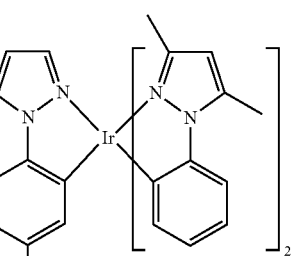
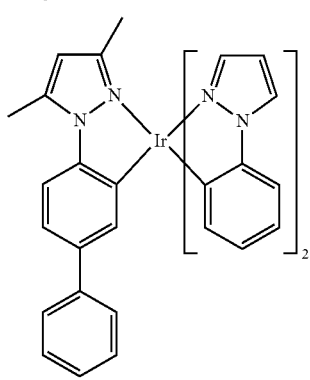

159
-continued
160
-continued
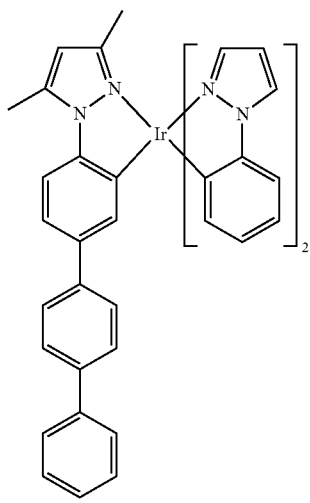
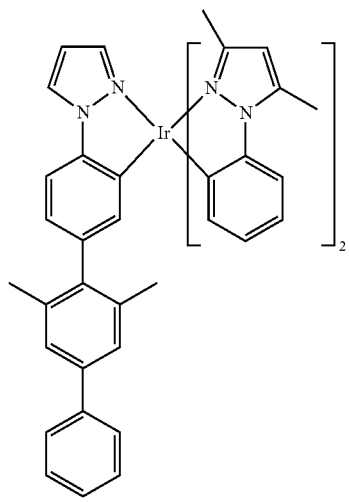
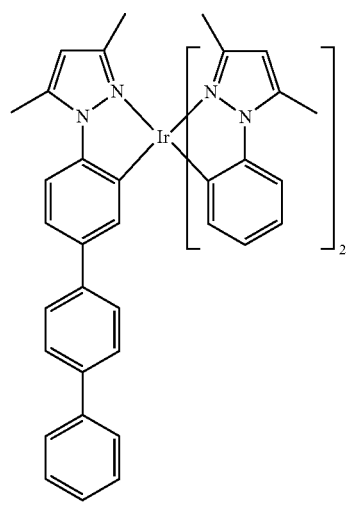
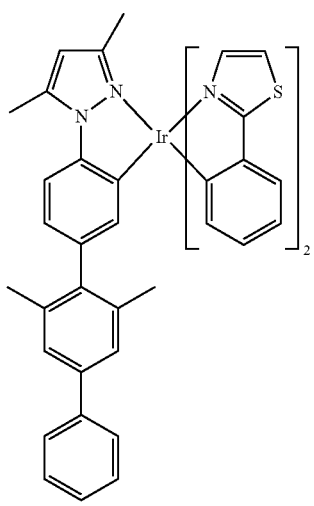
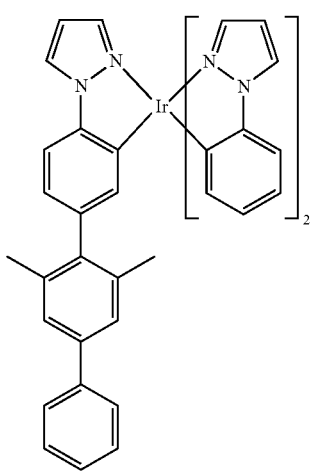
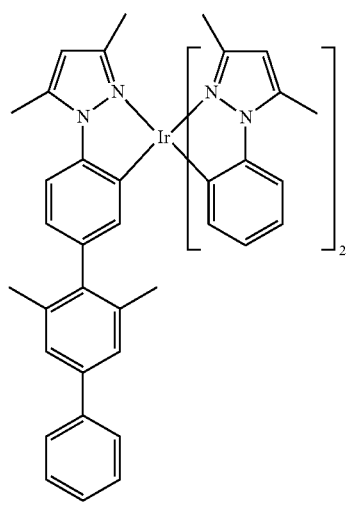

161
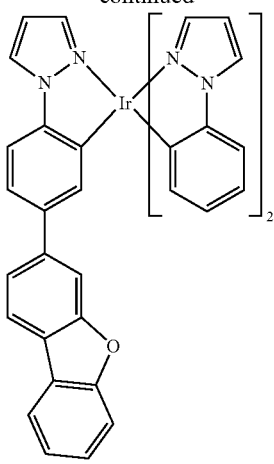
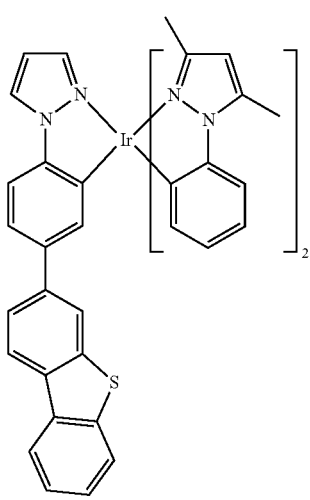
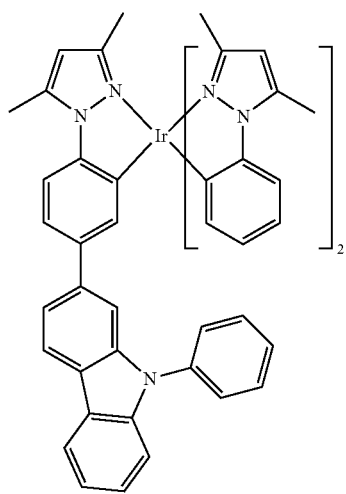
162
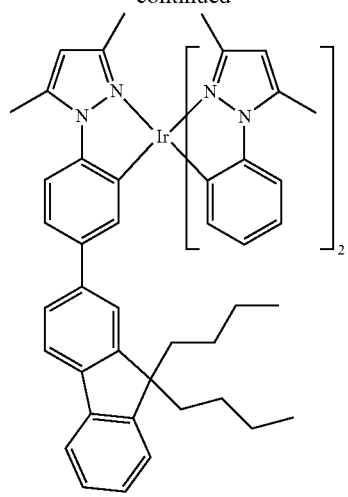
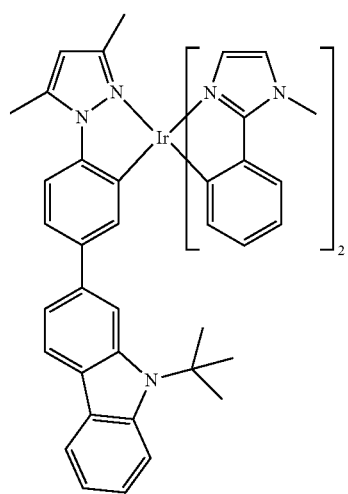

163
-continued
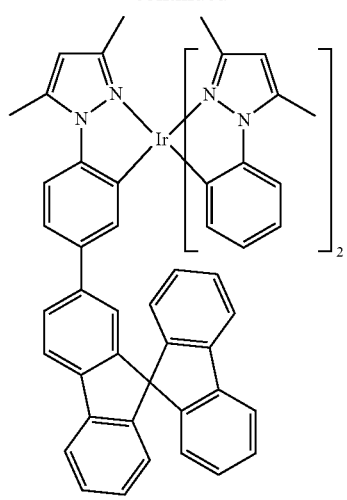
164
-continued
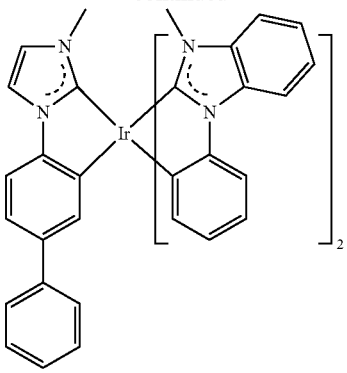
Structures Ir-16
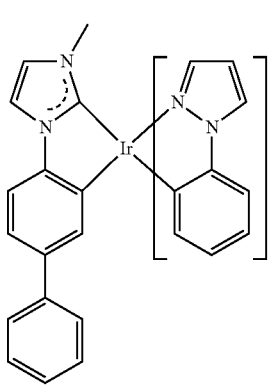
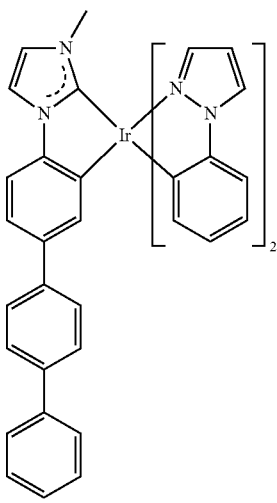
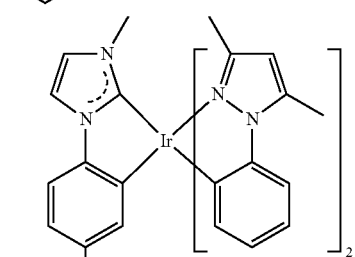
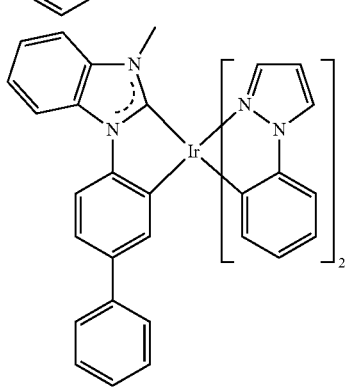
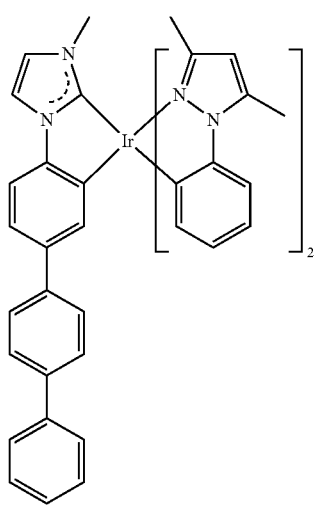

-continued
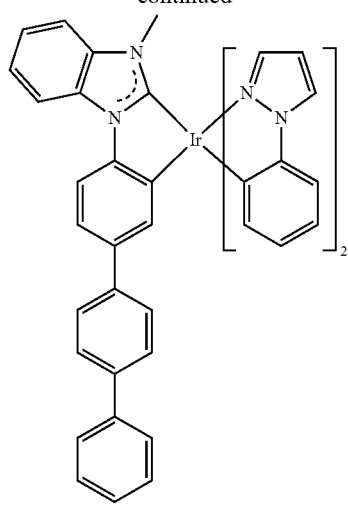
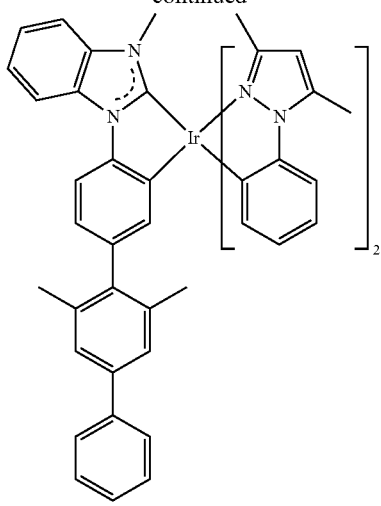
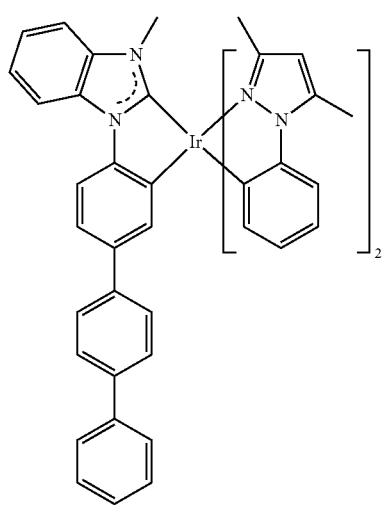
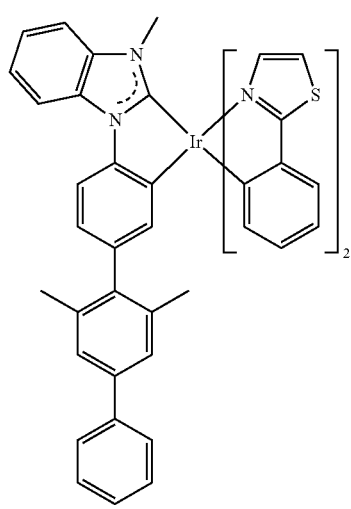
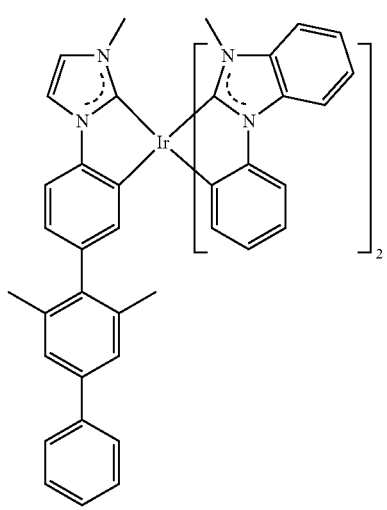
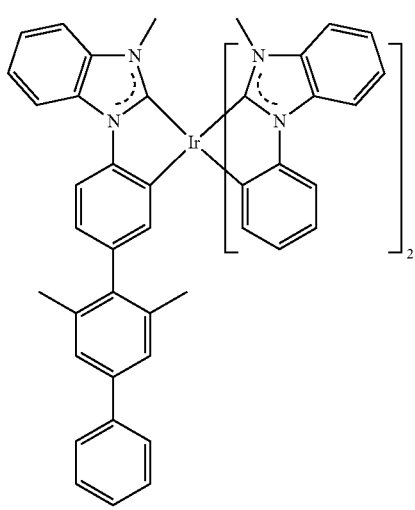

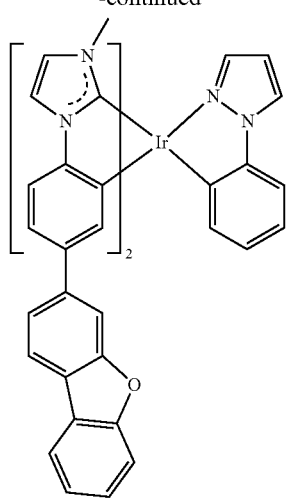
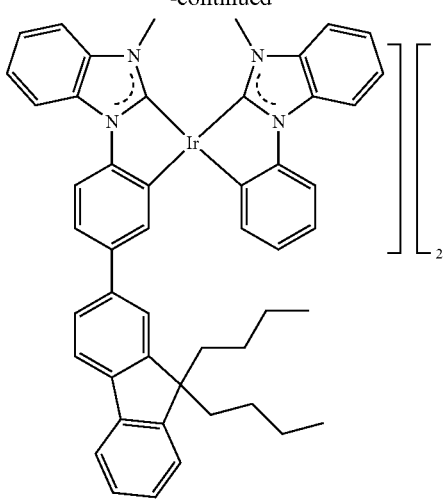
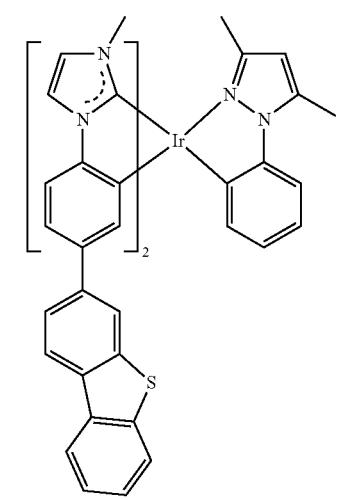
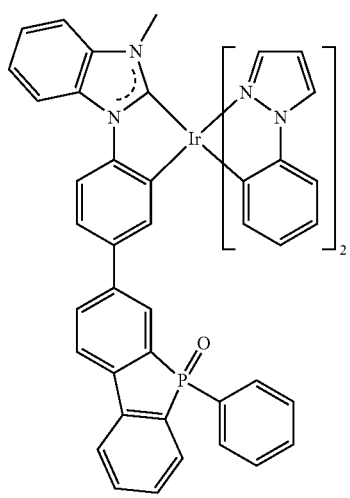
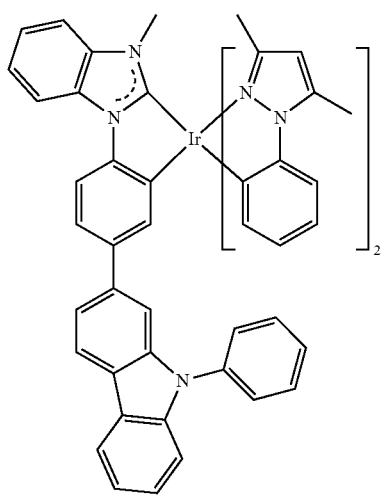
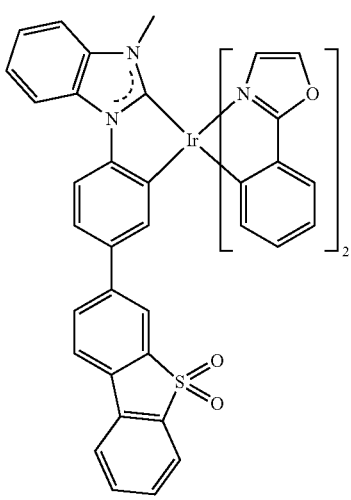

169
-continued
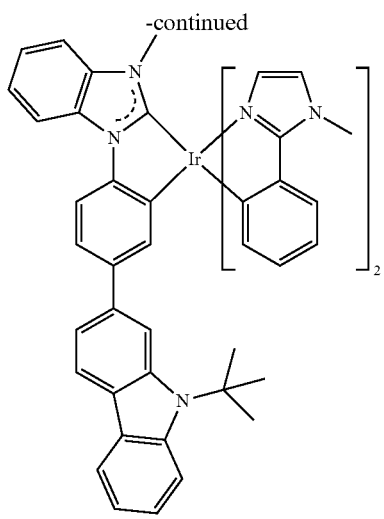
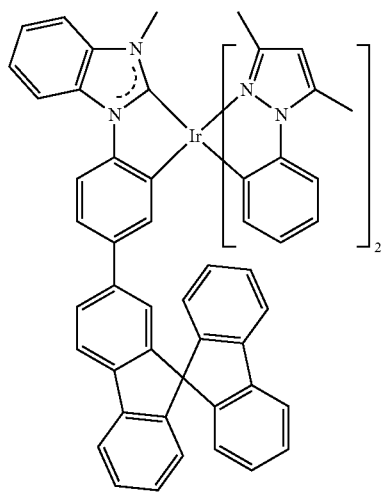
170
-continued
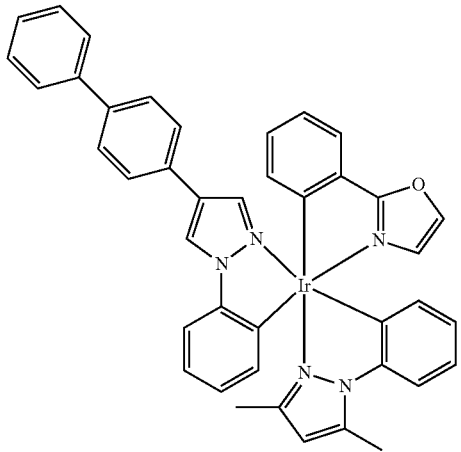
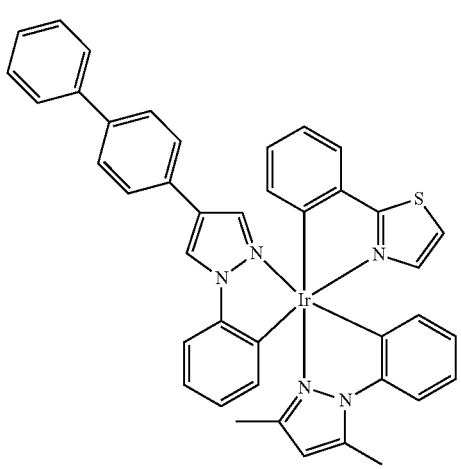
Structures Ir-17
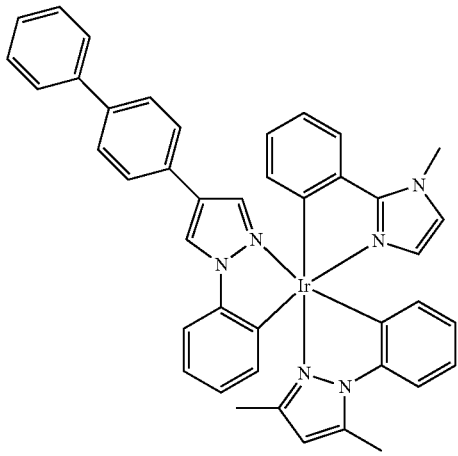
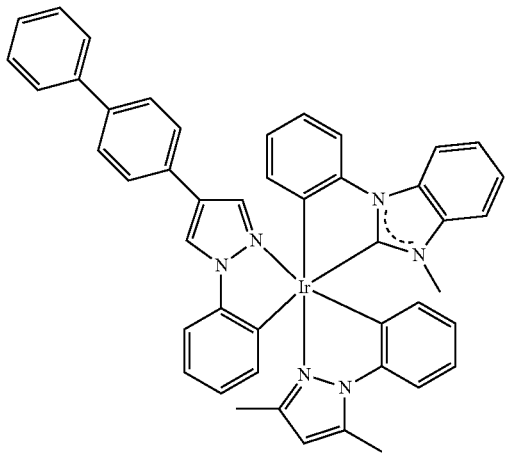

171
-continued
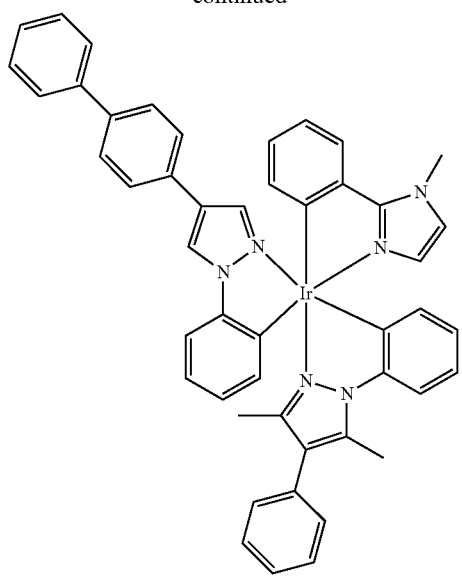
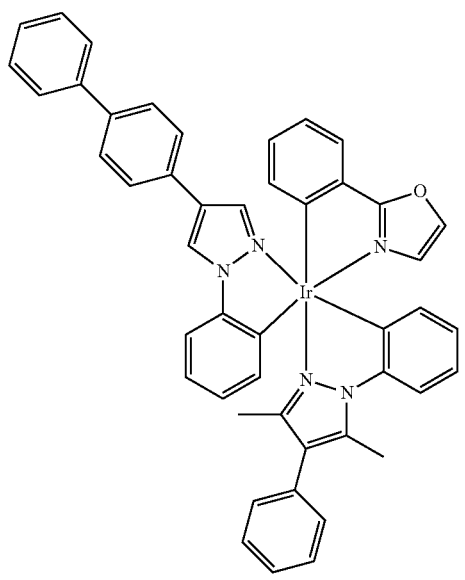
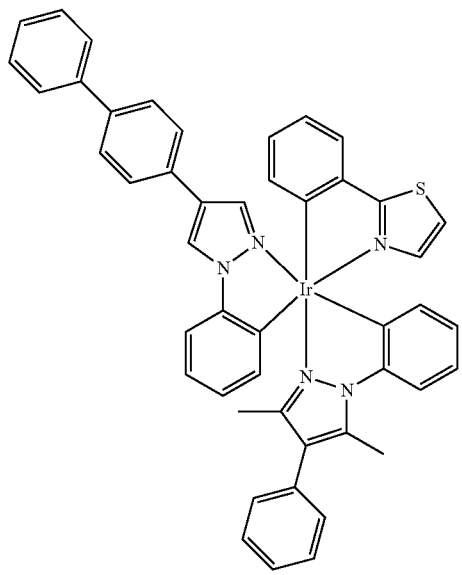
172
-continued
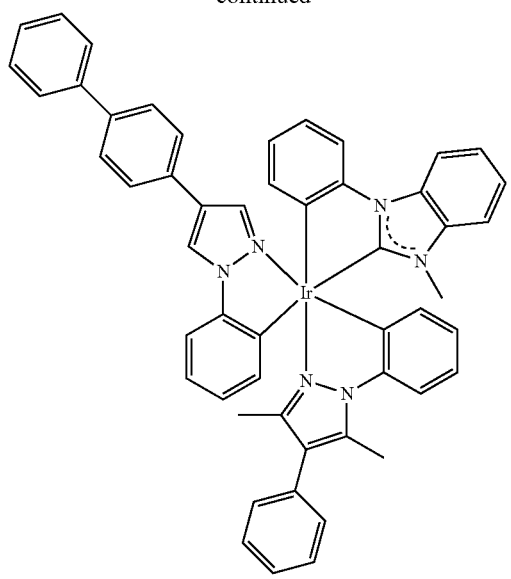
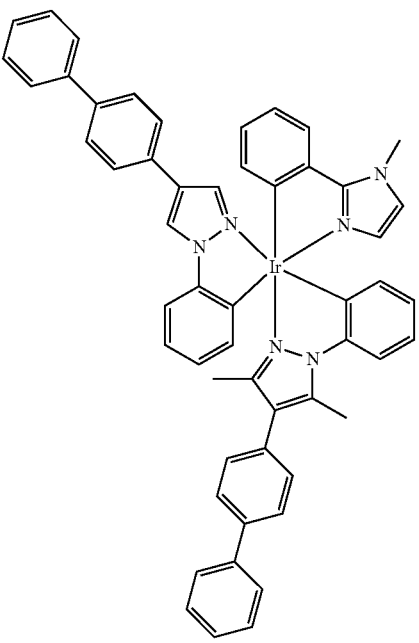

173
-continued
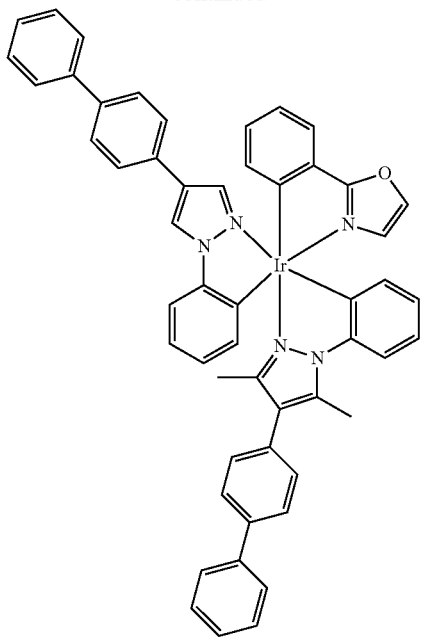
174
-continued
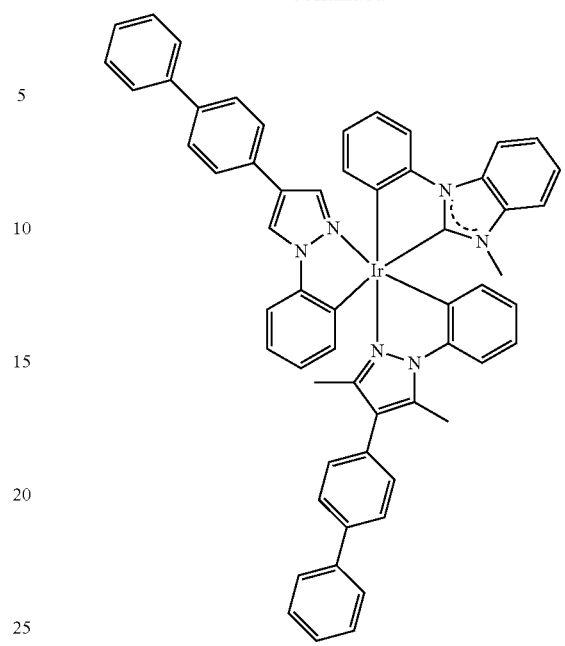
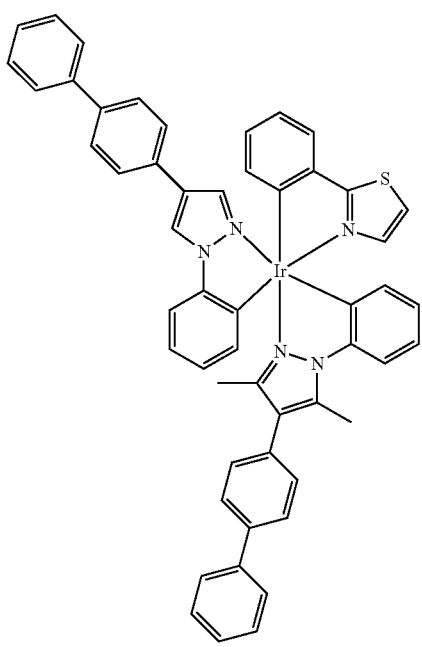
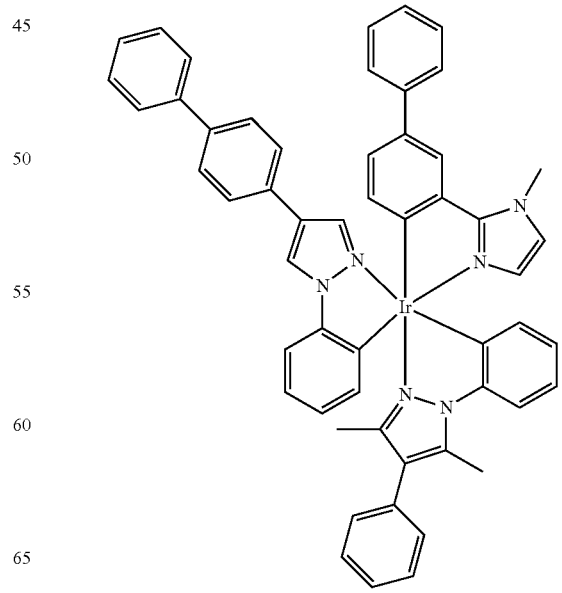

175
-continued
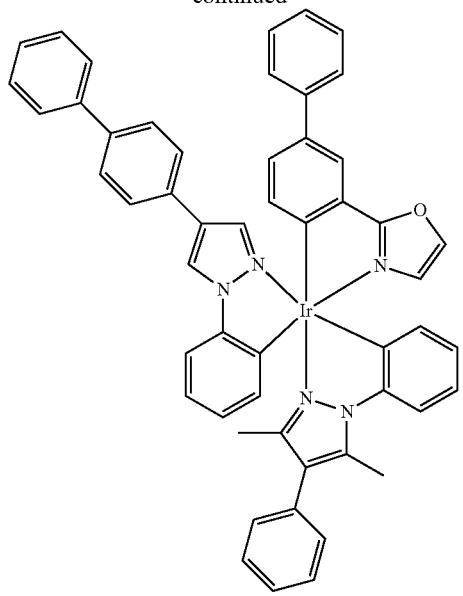
176
-continued
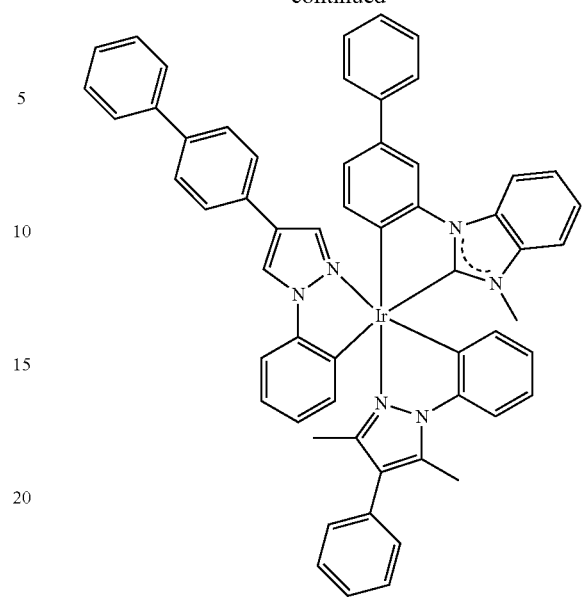
Structures Ir-18
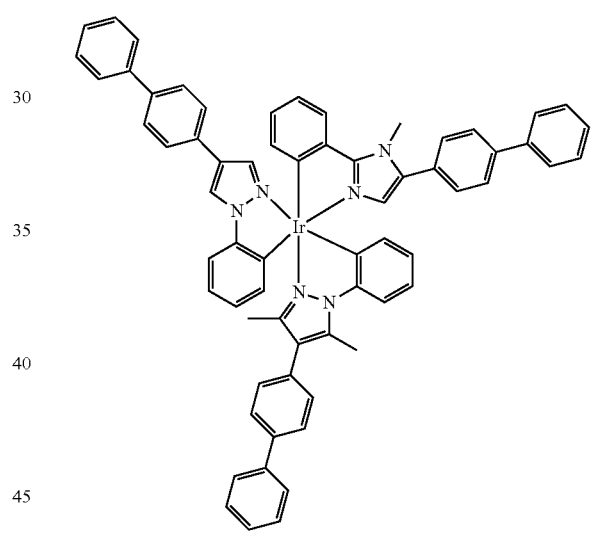
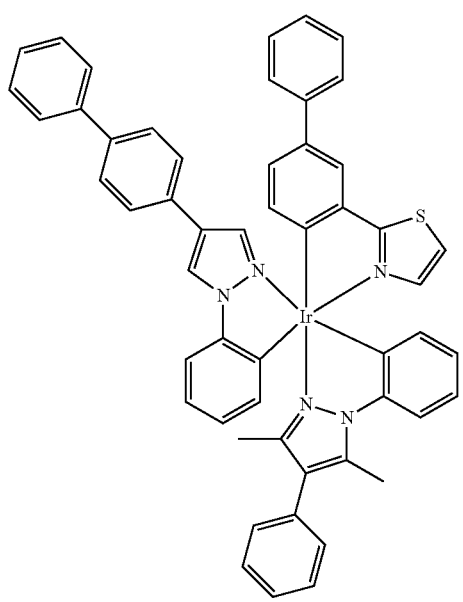
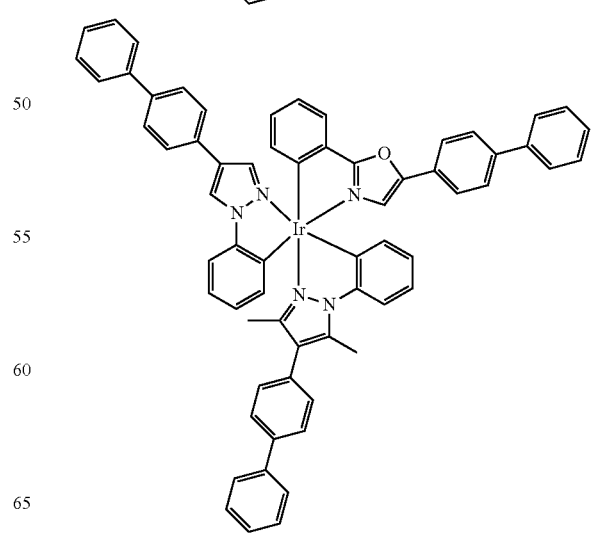

177
-continued
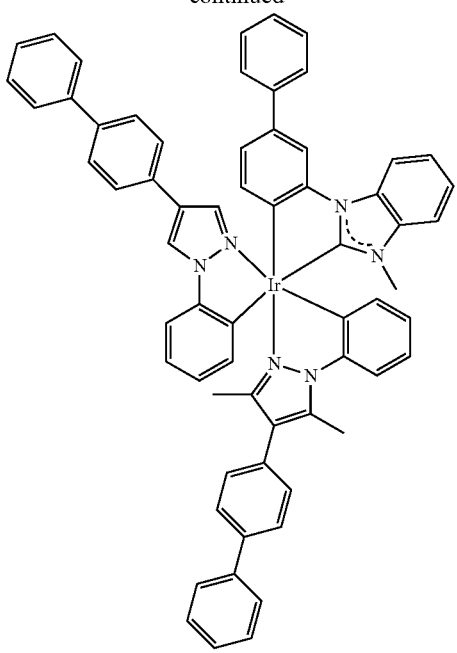
178
-continued
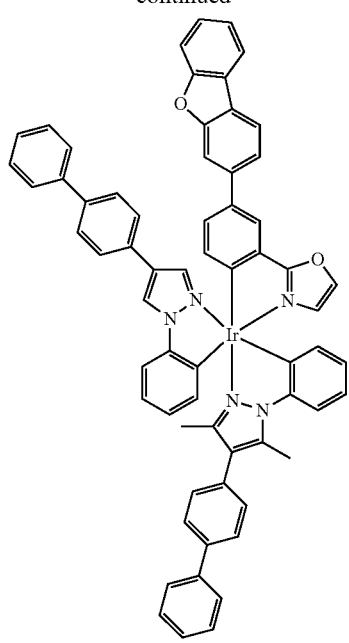
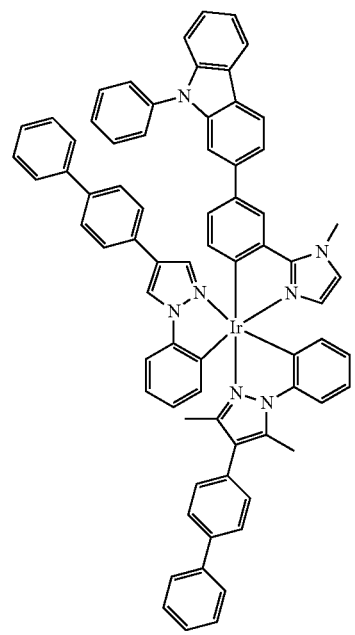
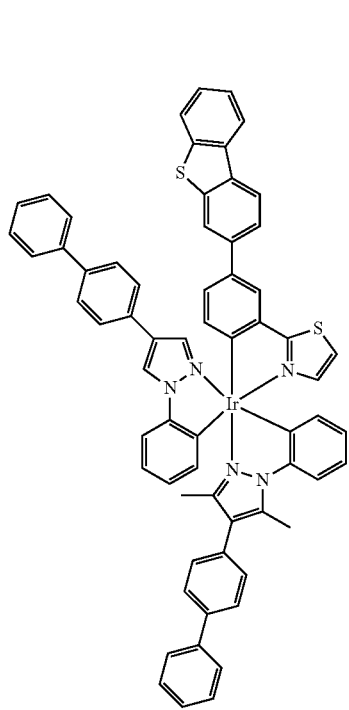

179
-continued
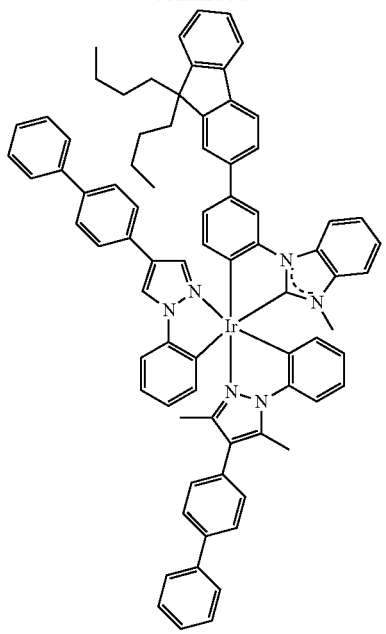
180
-continued
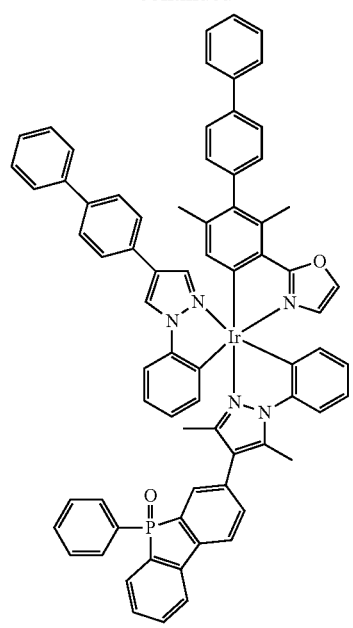
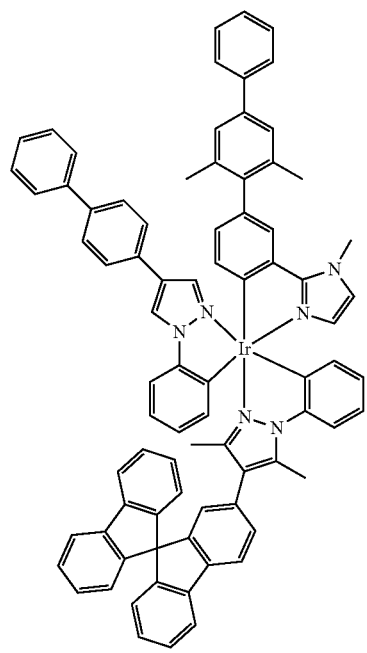
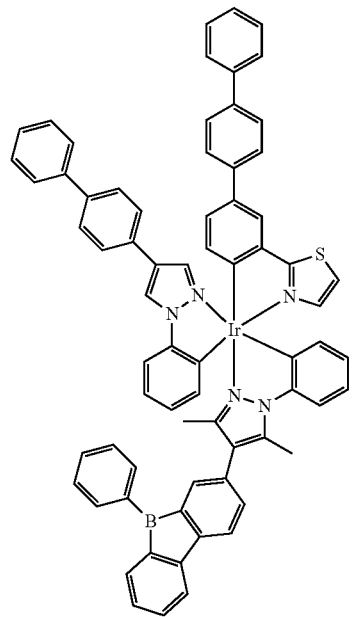

-continued
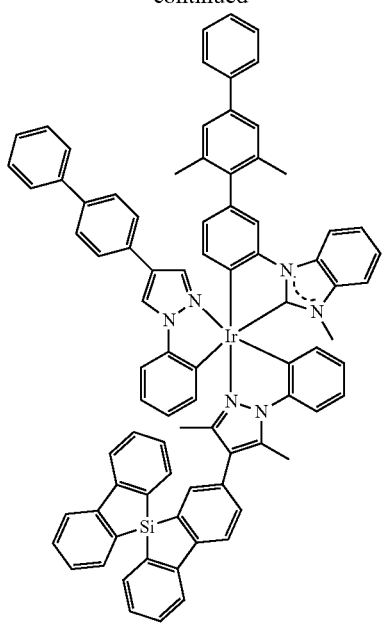
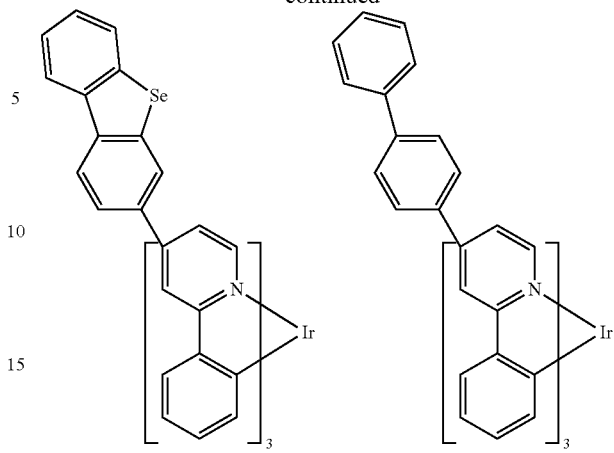
Structures Ir-19
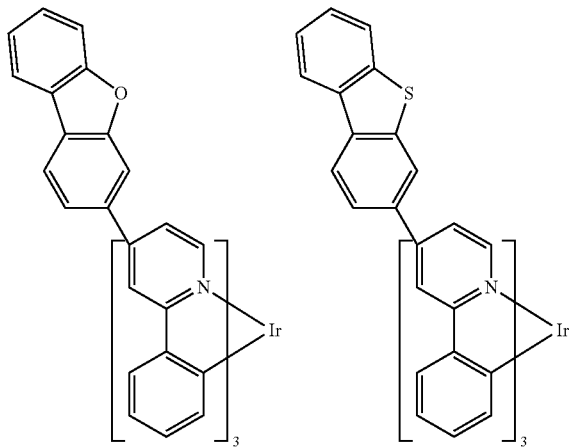
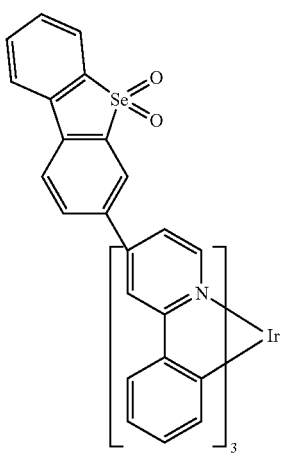
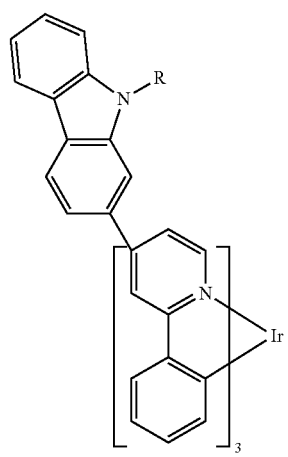
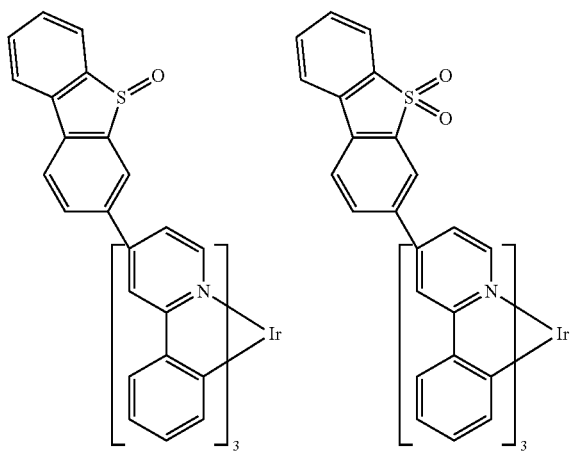
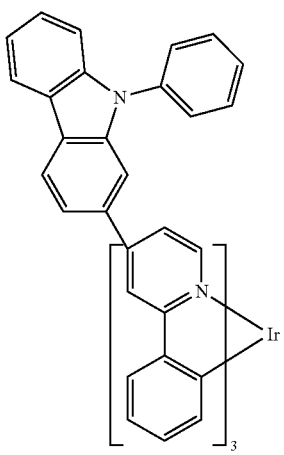
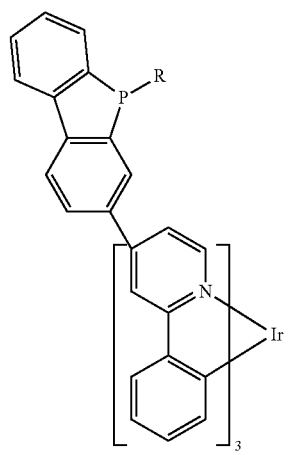

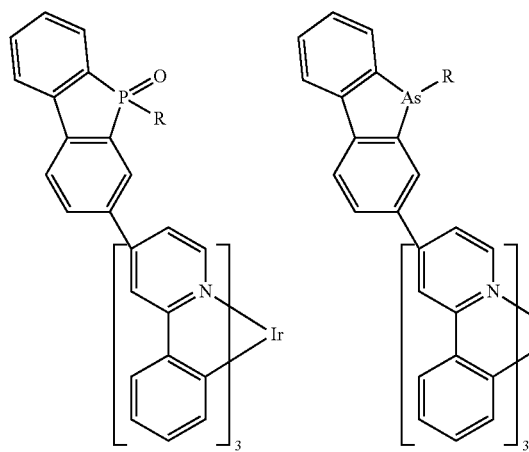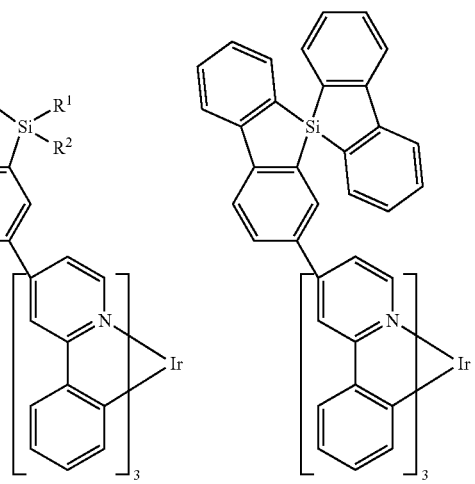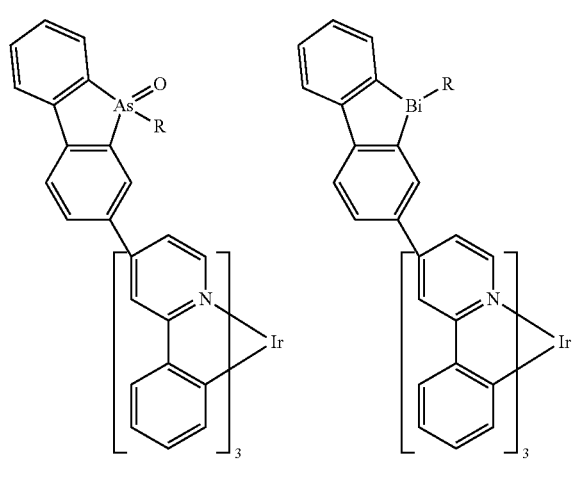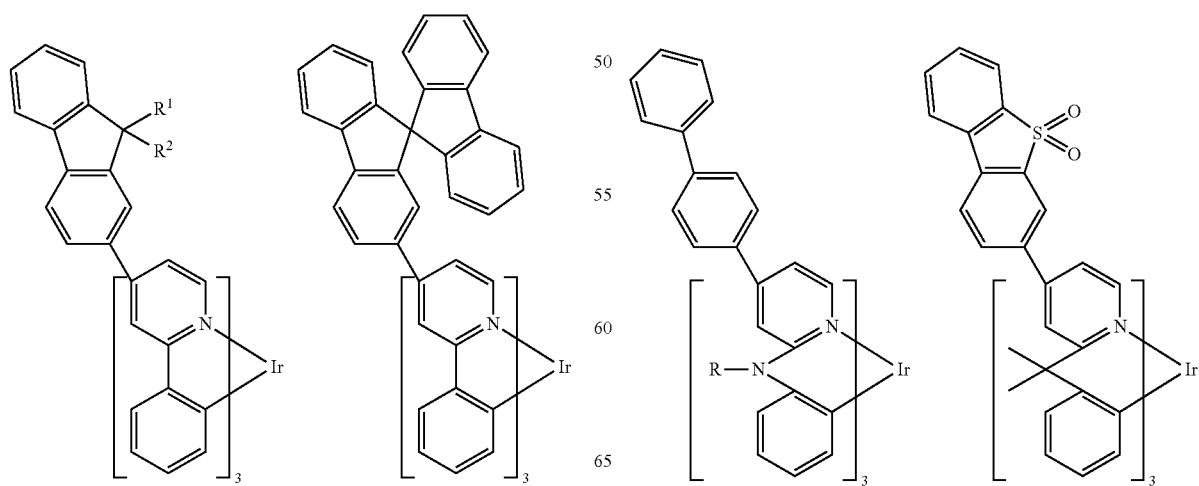

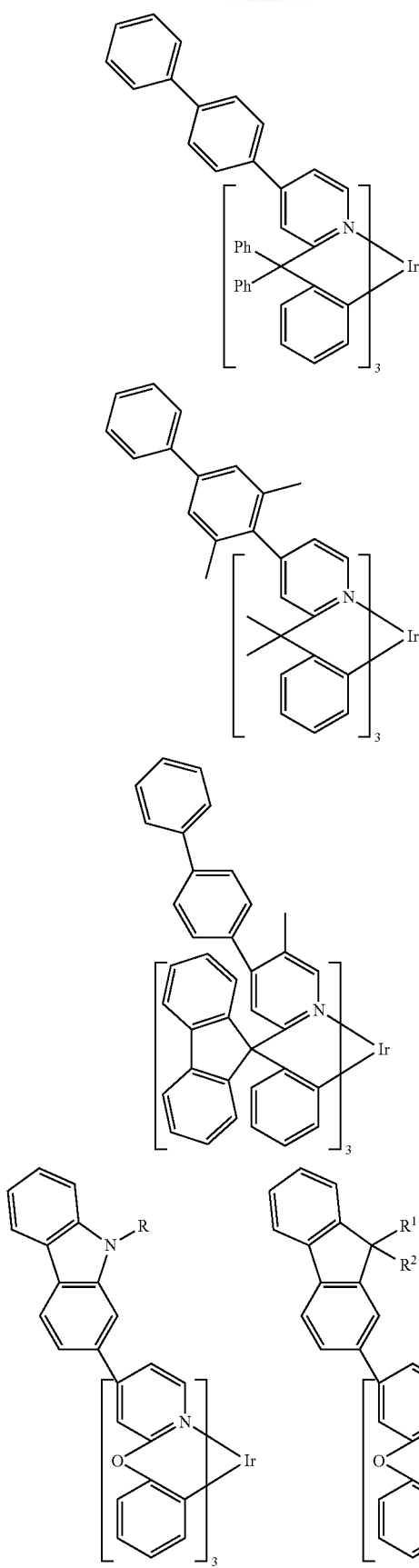
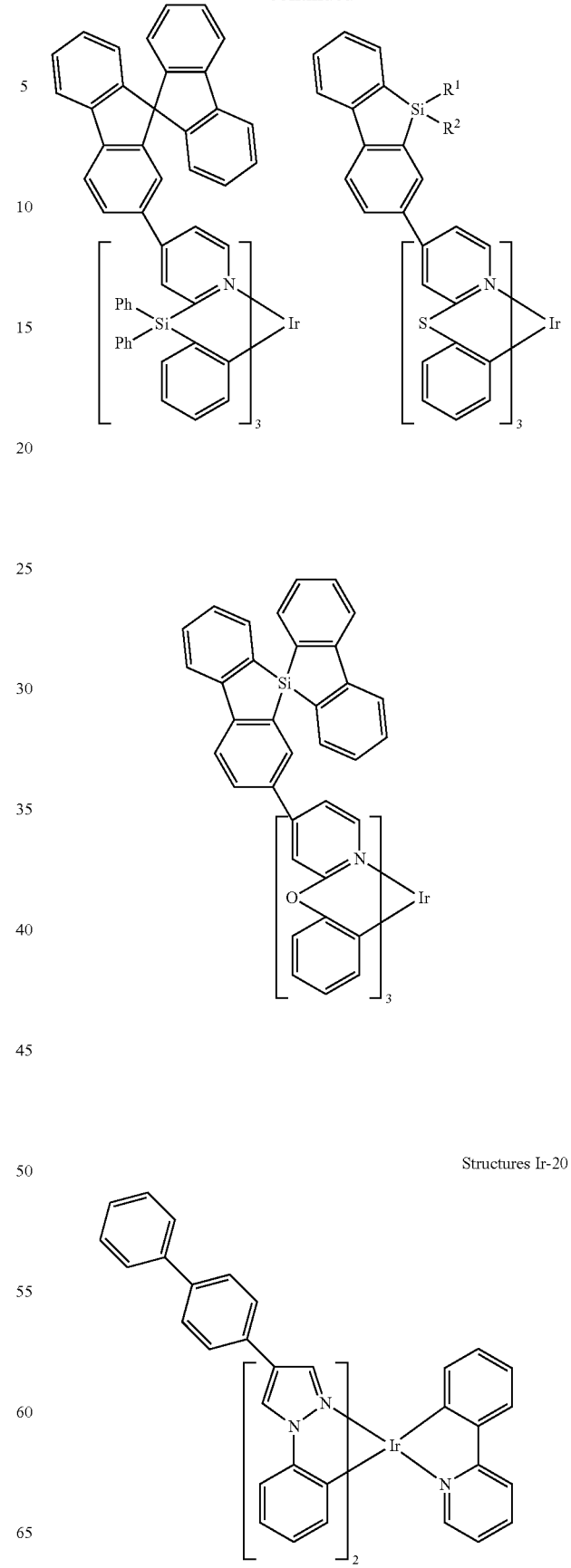
Structures Ir-20

187
-continued
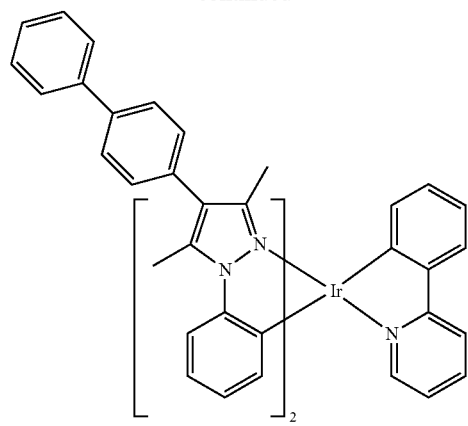
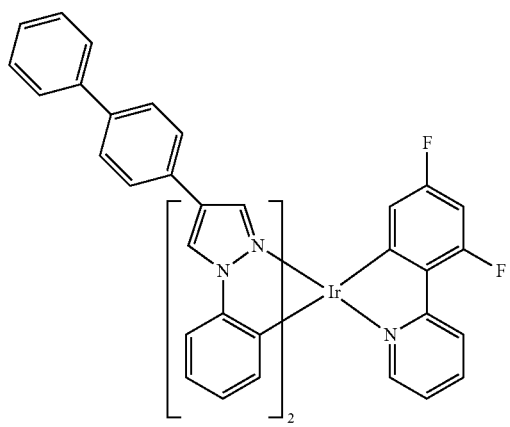
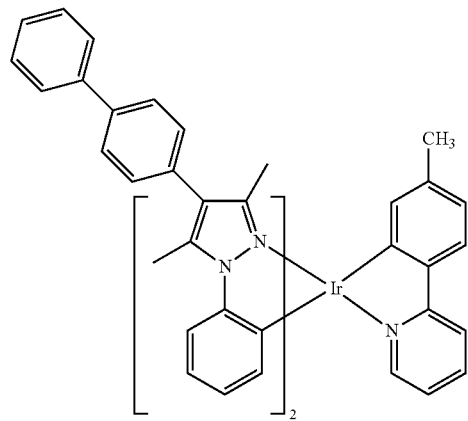
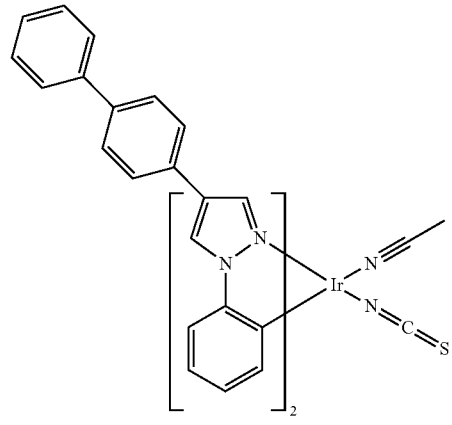
188
-continued
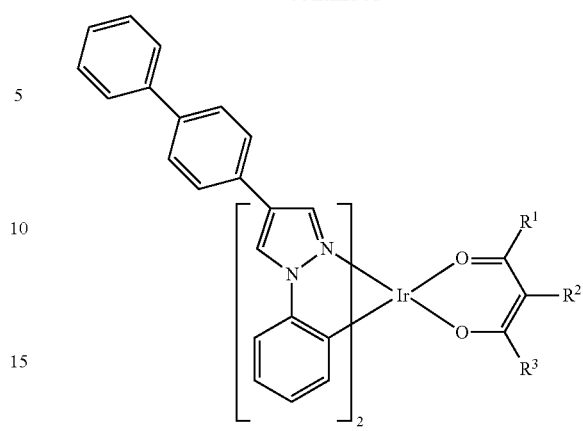
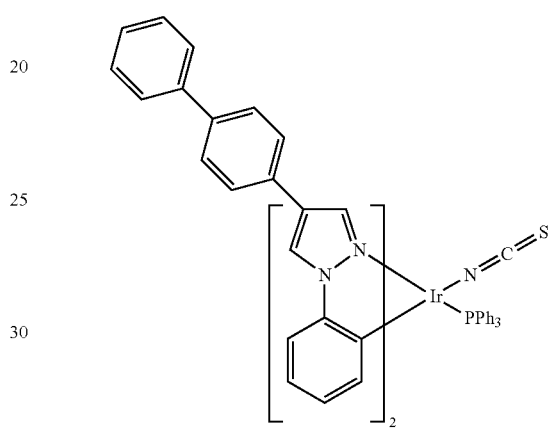
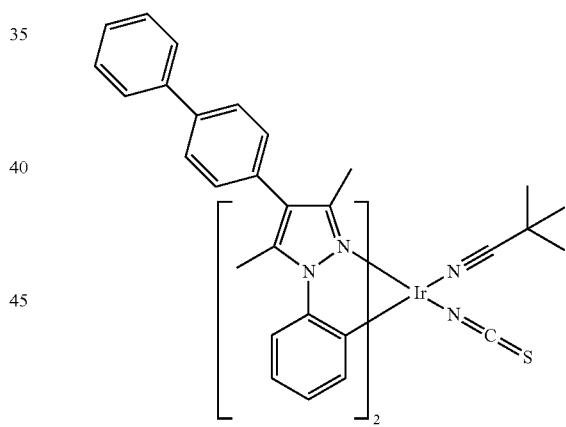
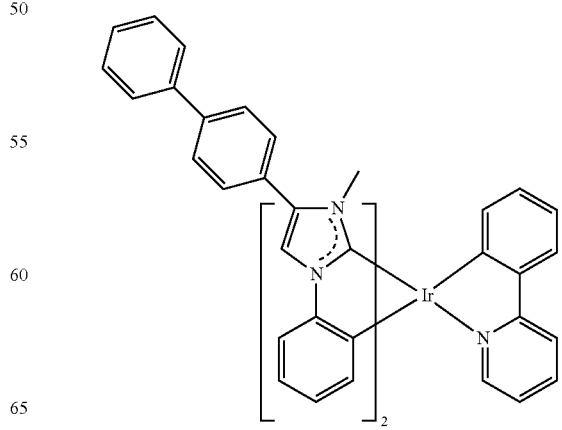

189
-continued
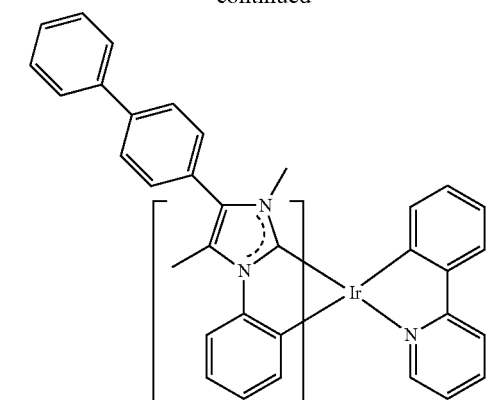
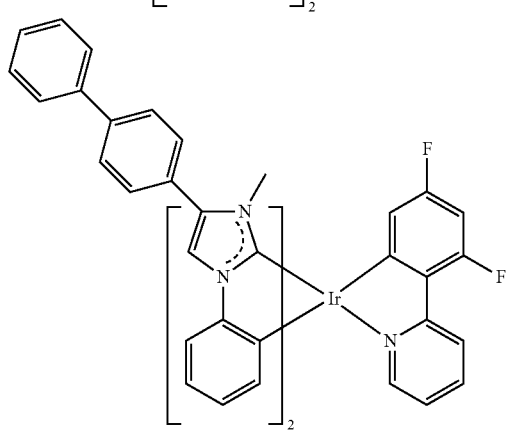
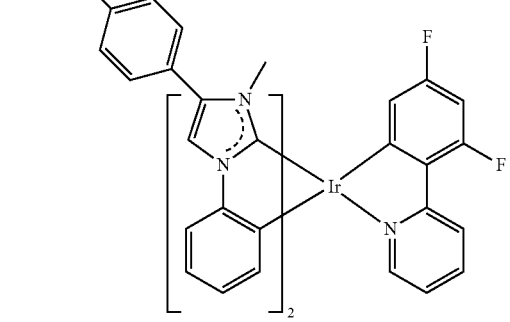
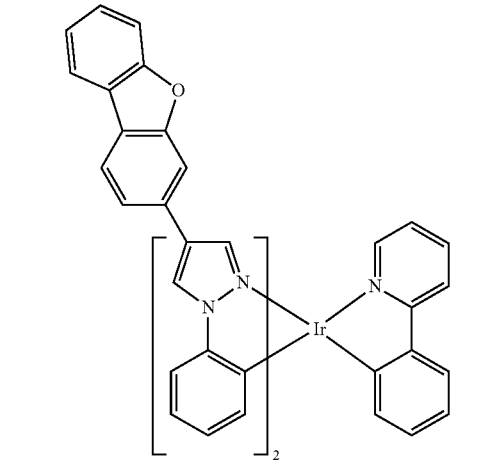
190
-continued
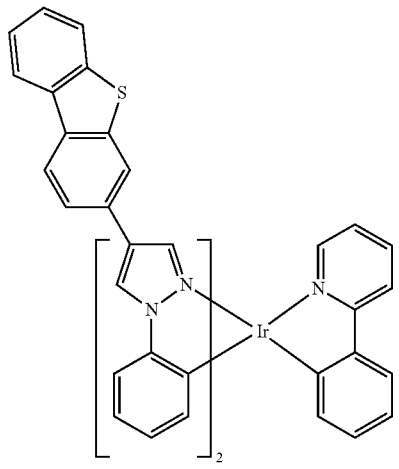
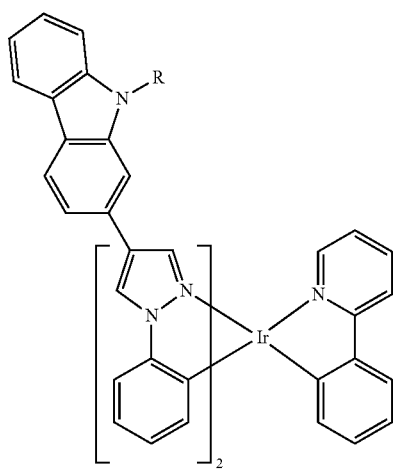
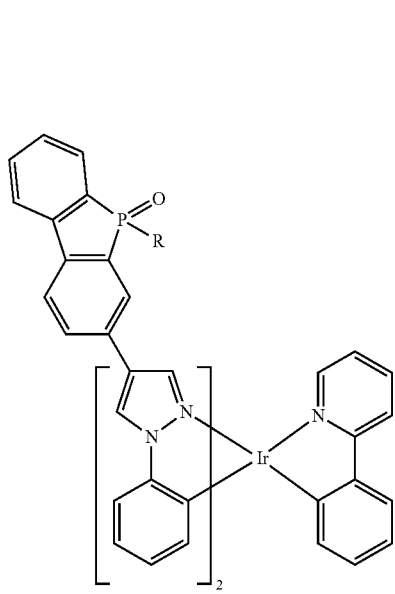

191
-continued
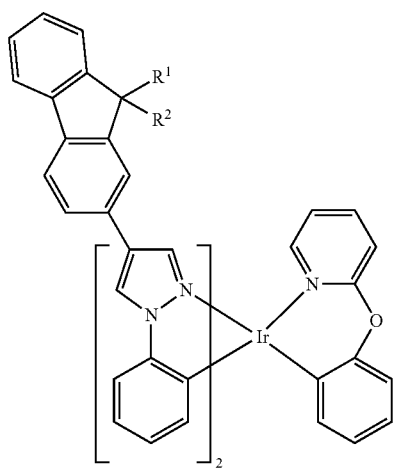
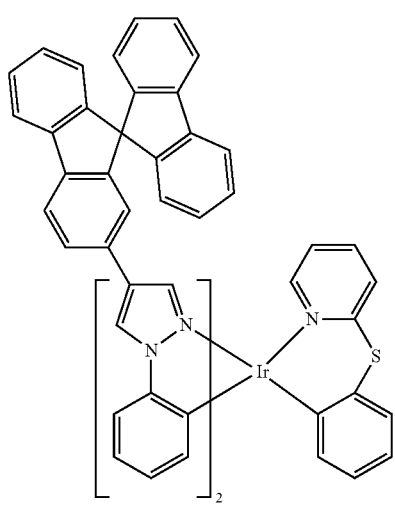
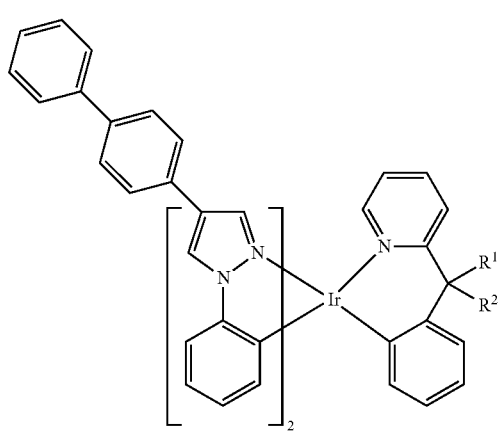
192
-continued
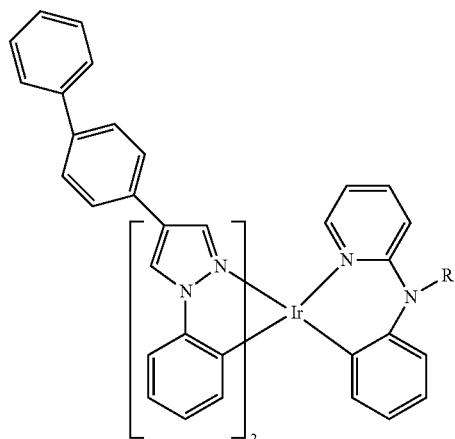
Structures Ir-21
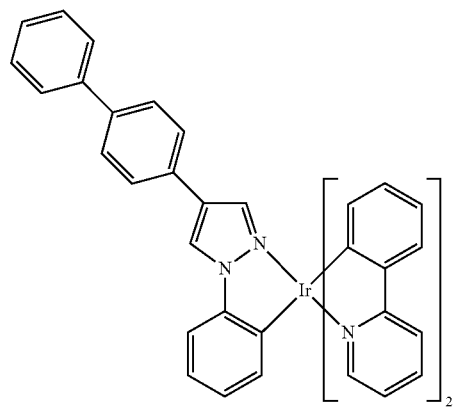
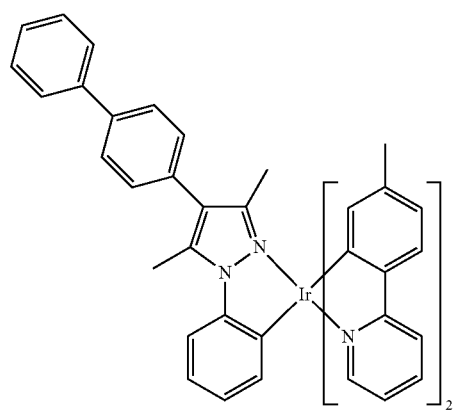

193
-continued
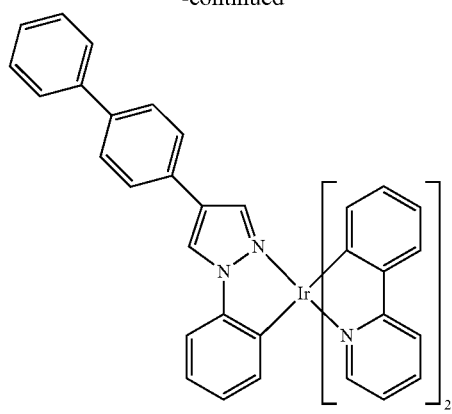
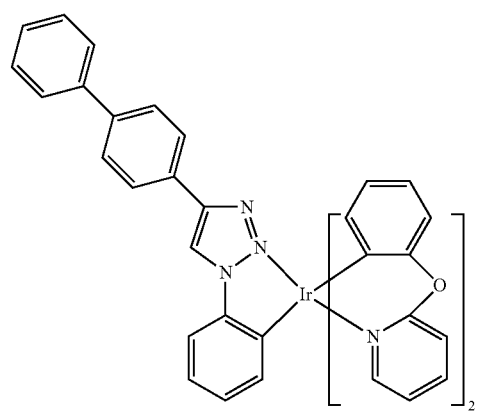
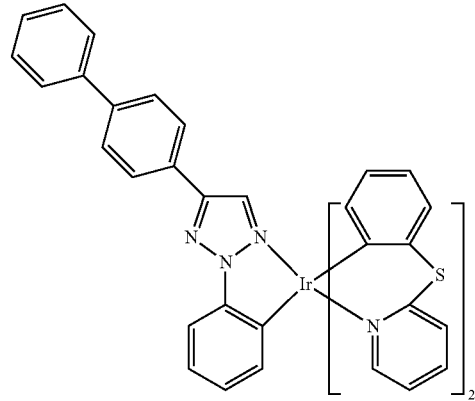
194
-continued
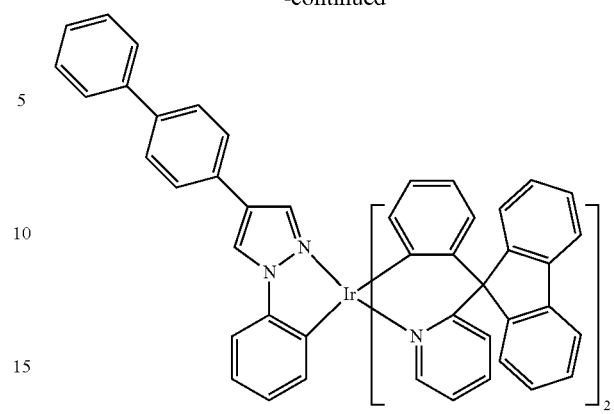
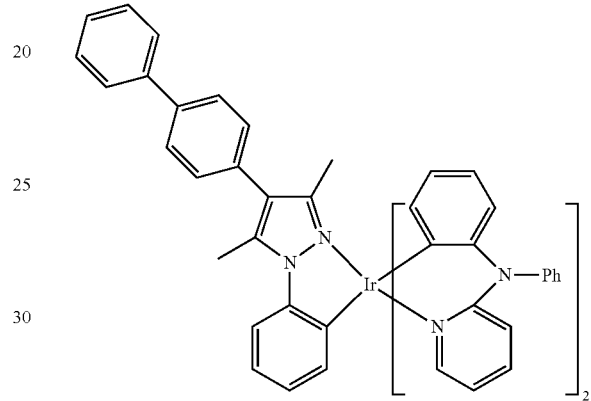
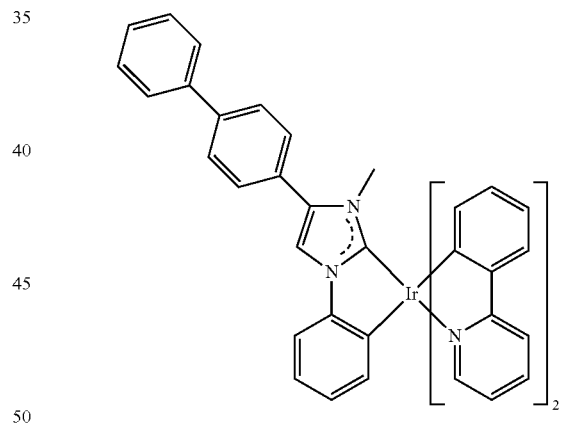
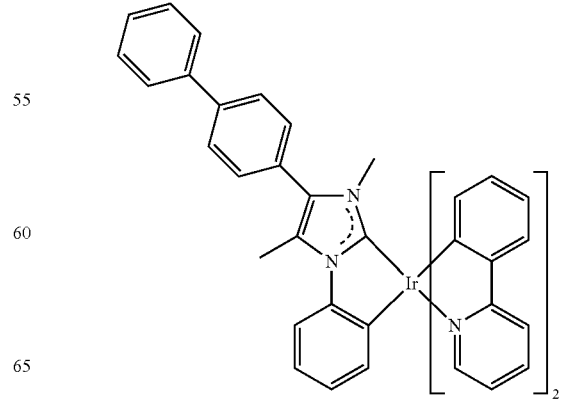

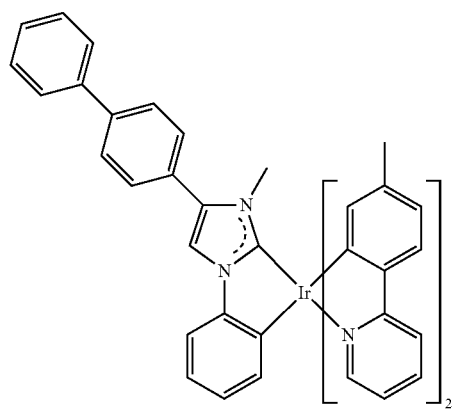
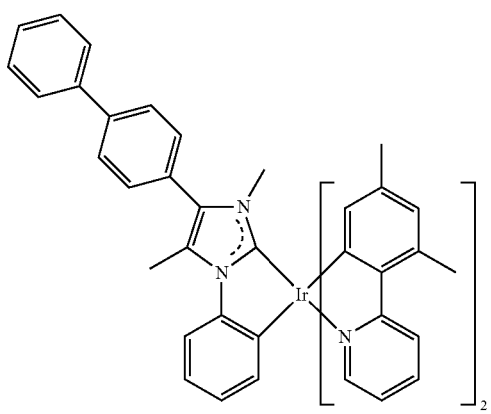
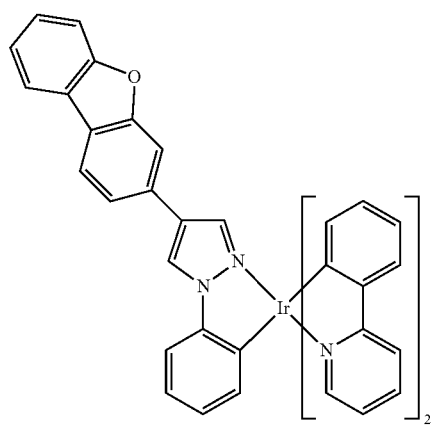
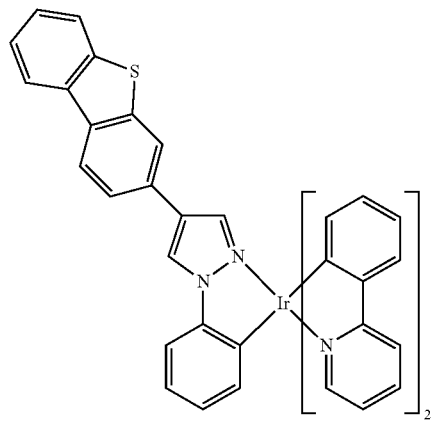
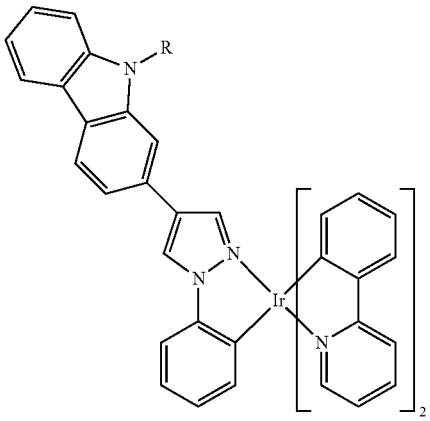

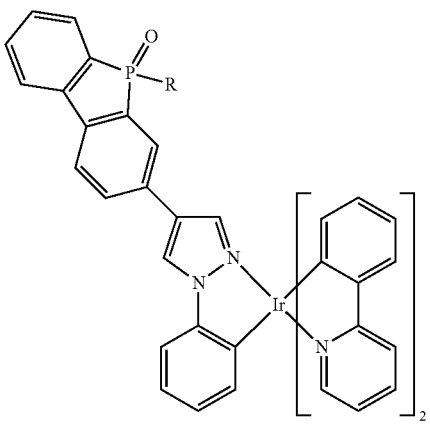
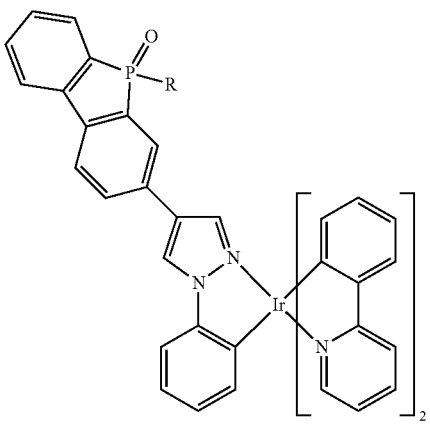

-continued
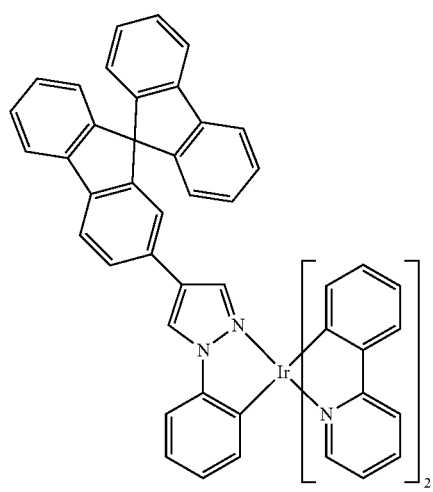
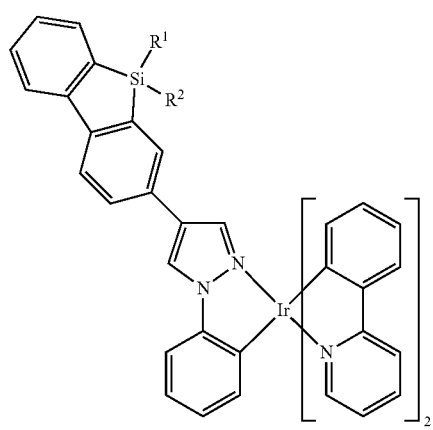
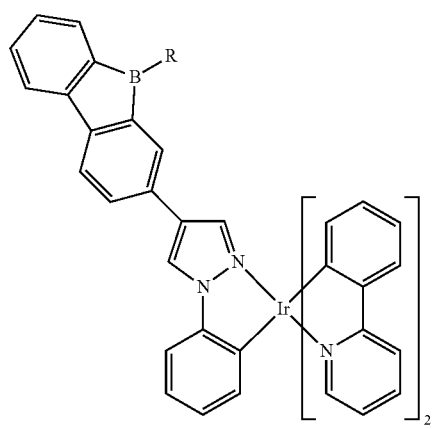
Structures It-22
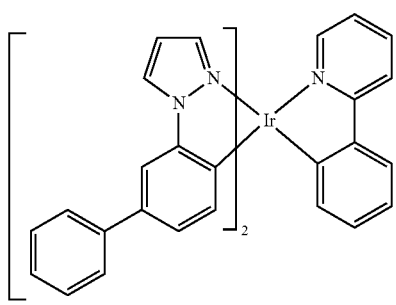
-continued
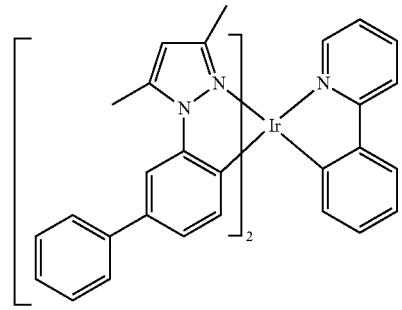
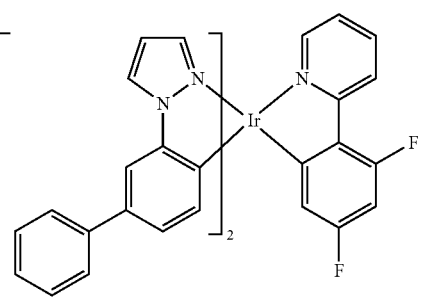
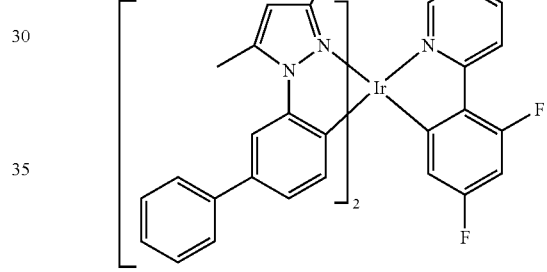
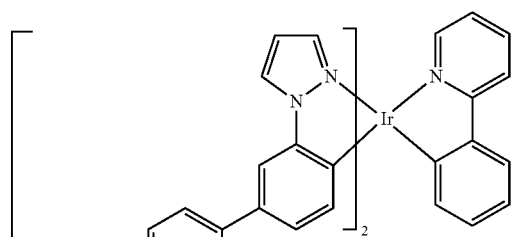
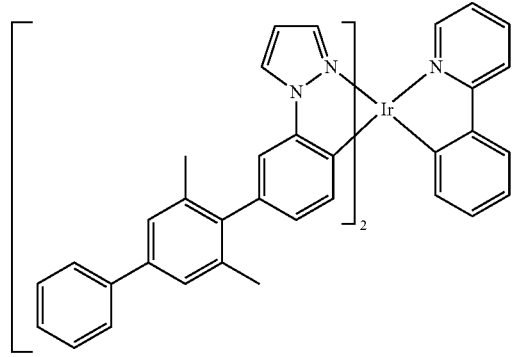

199
-continued
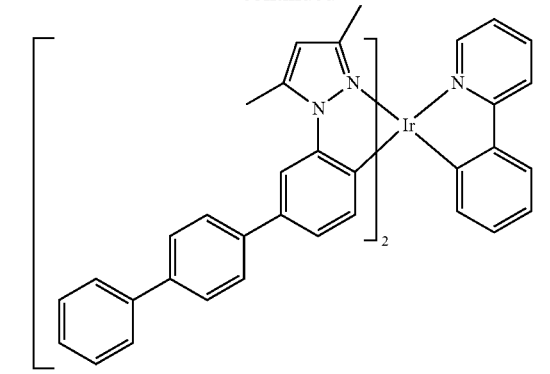
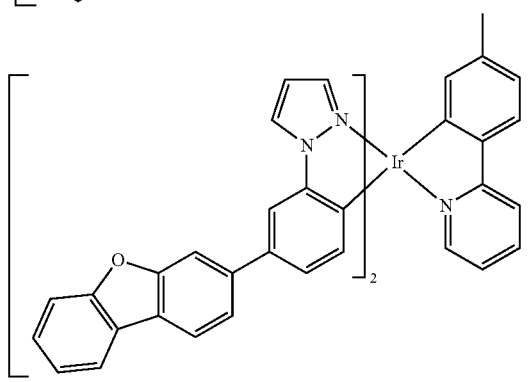
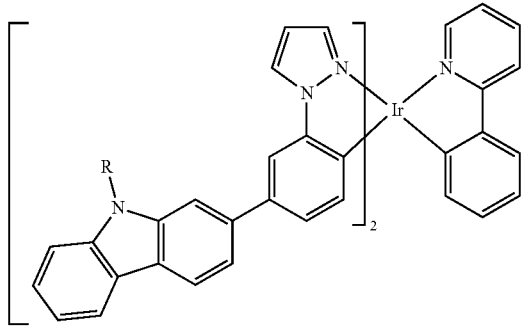
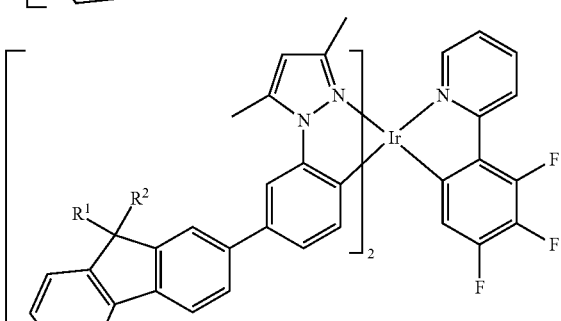
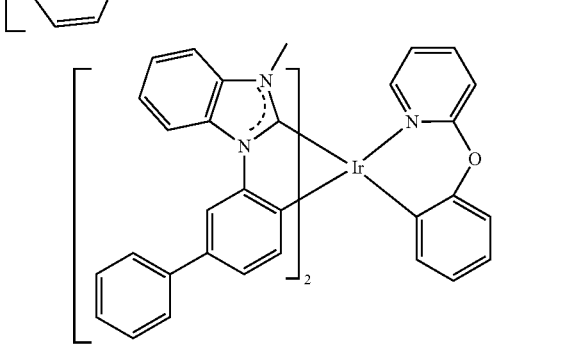
200
-continued
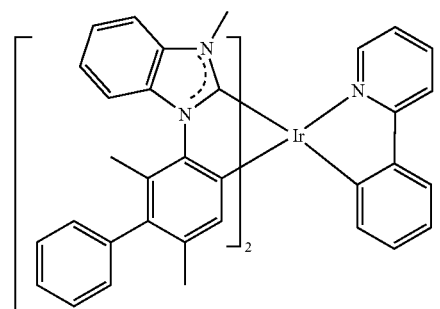
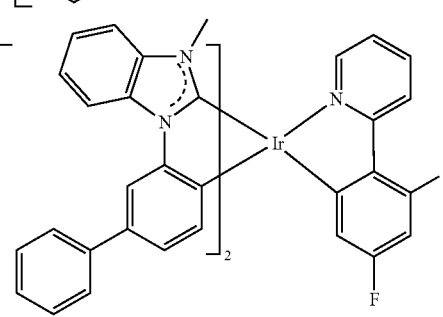
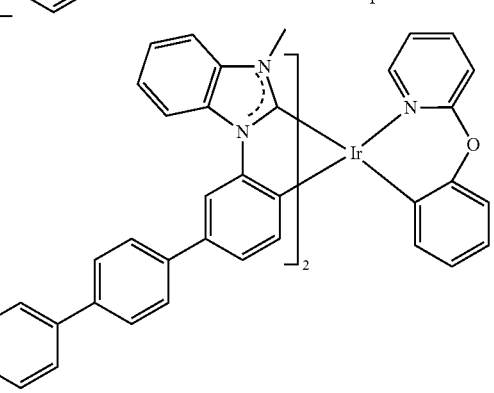
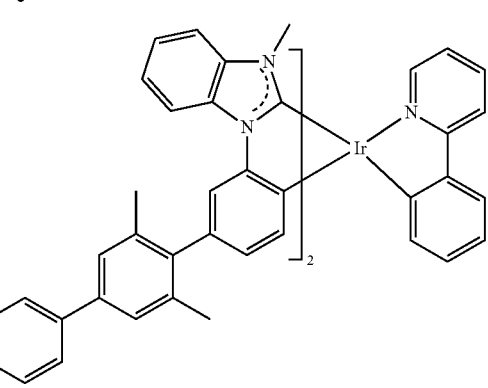

201
-continued
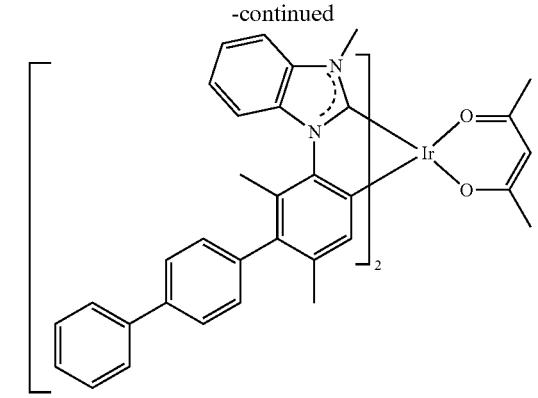
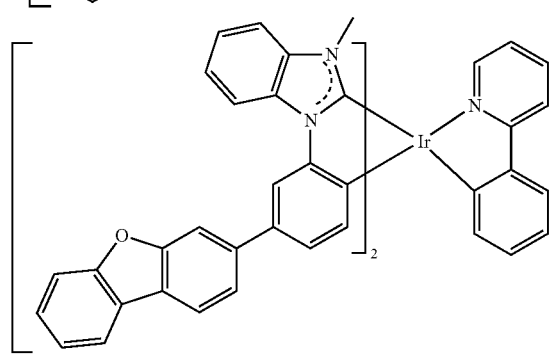
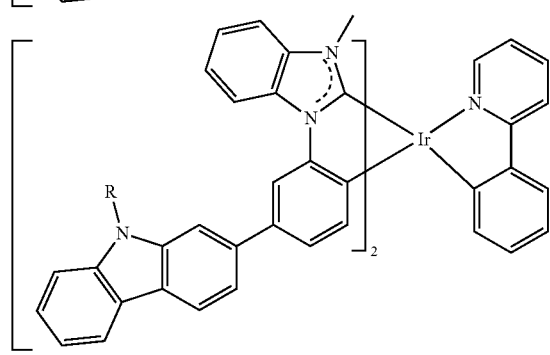
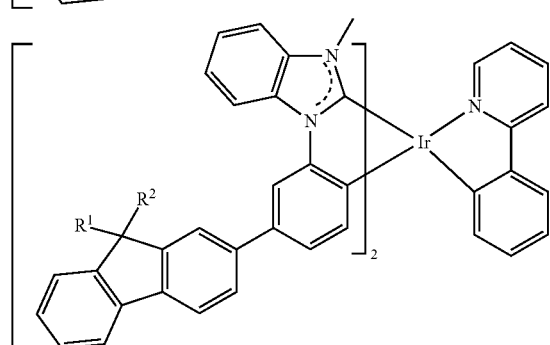
Structures It-23
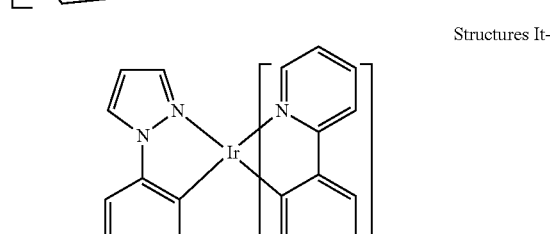
202
-continued
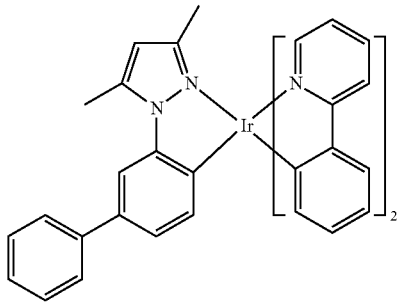
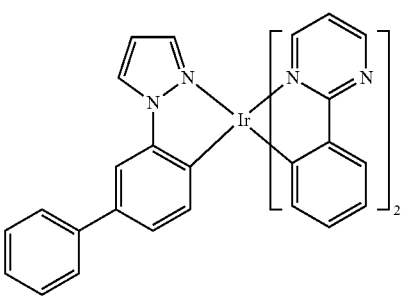
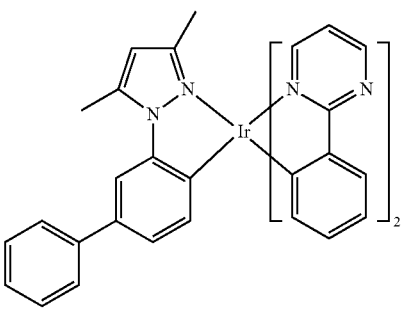
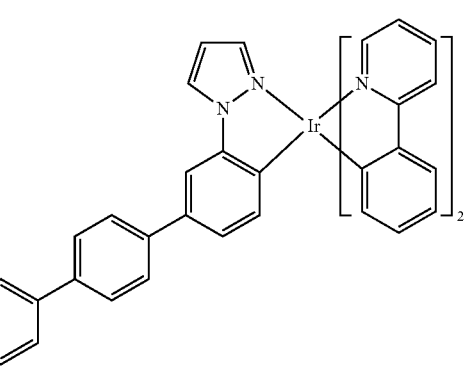
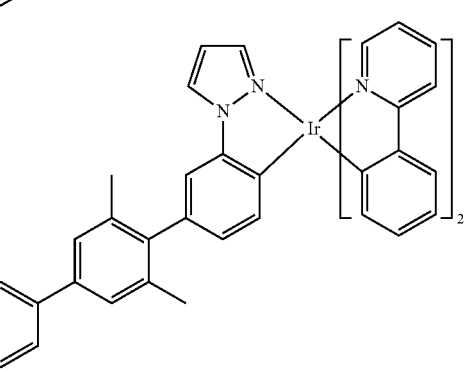

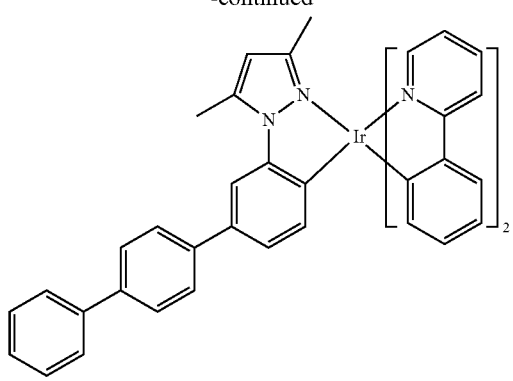
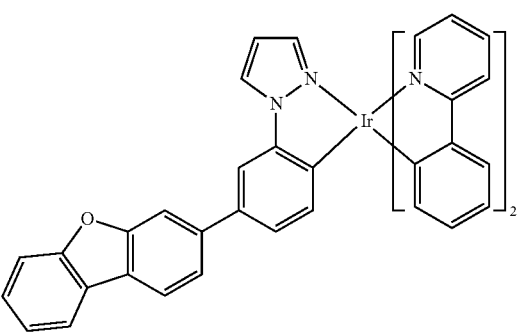
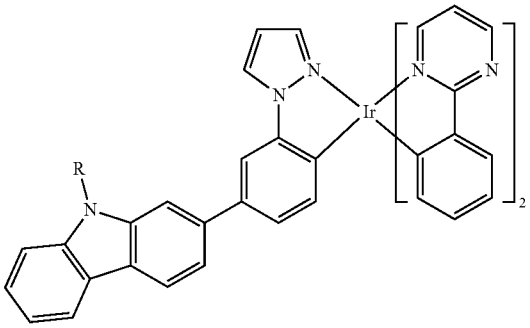
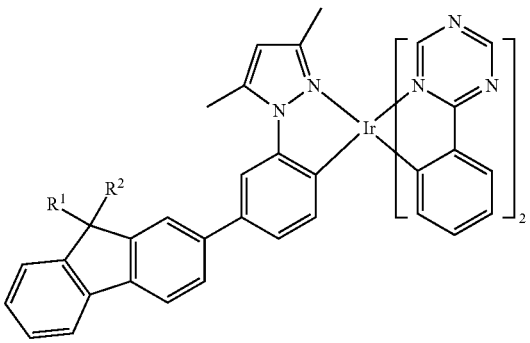
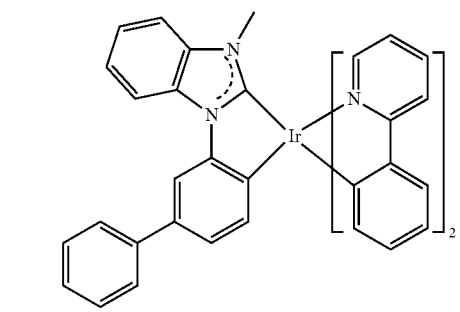
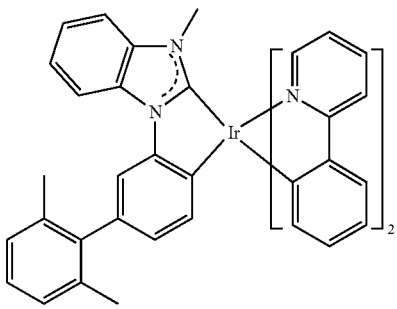
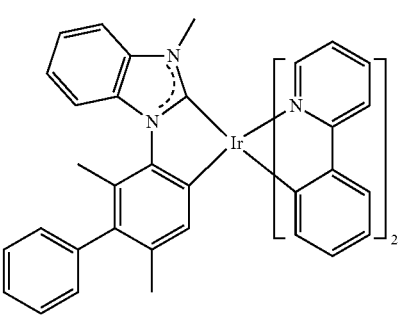
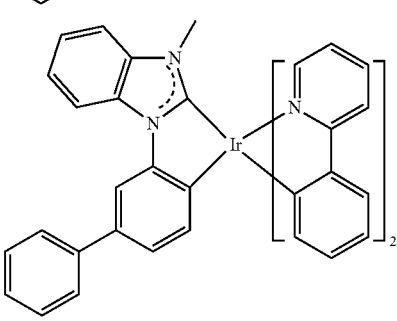
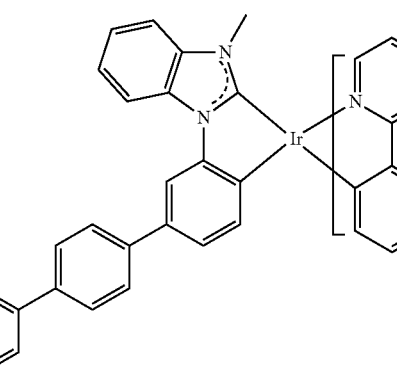
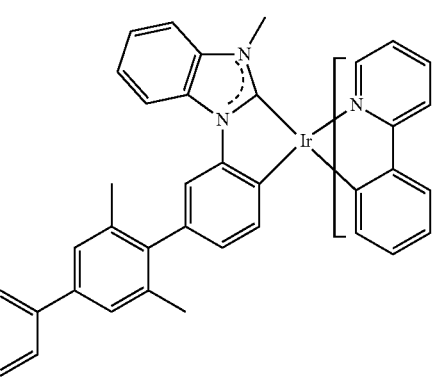

205
-continued
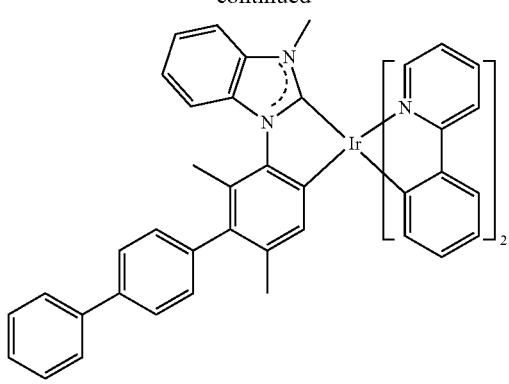
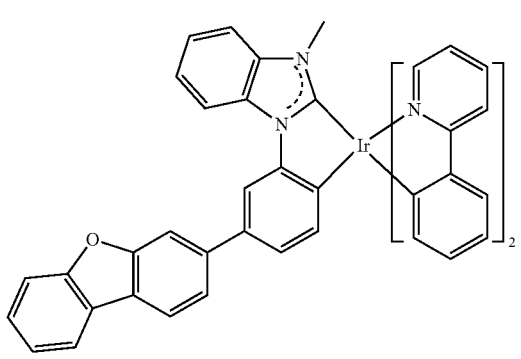
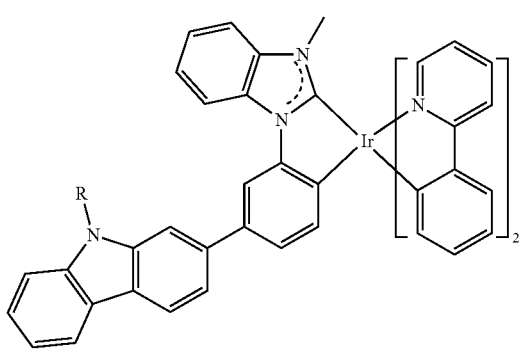
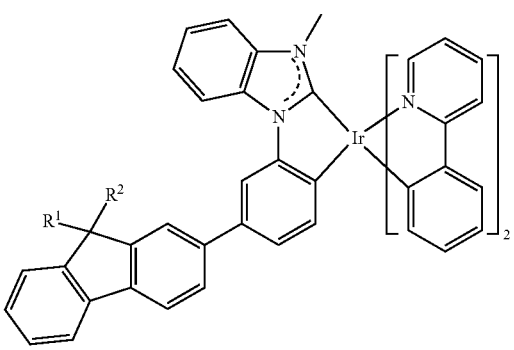
206
-continued
Structures Ir-24
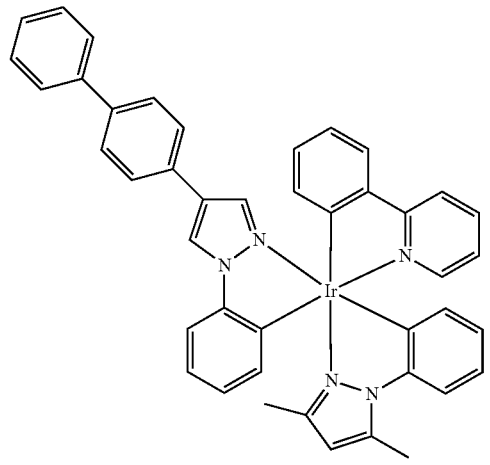
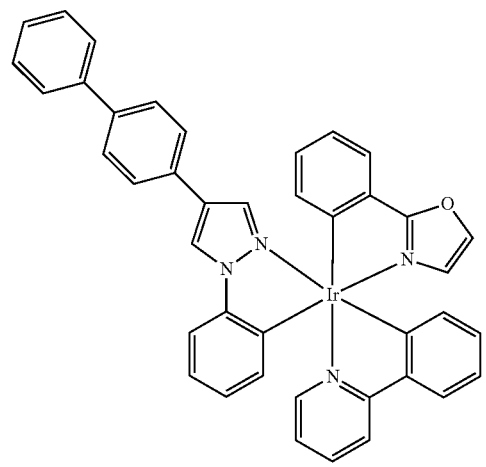
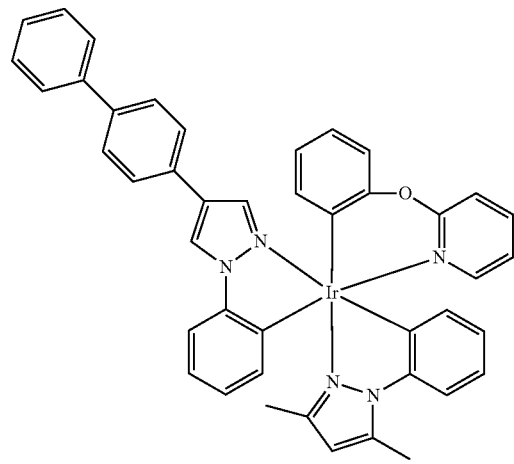

207
-continued
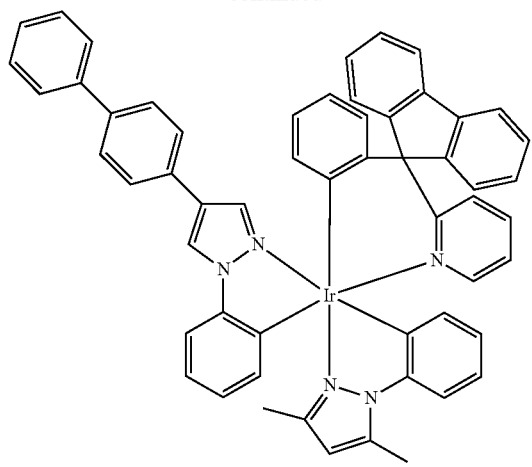
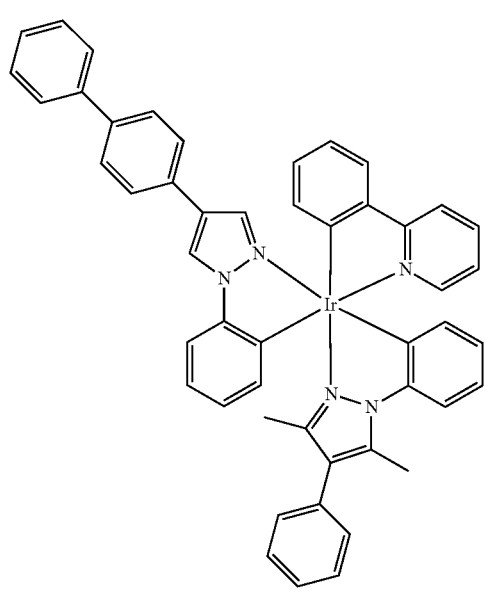
208
-continued
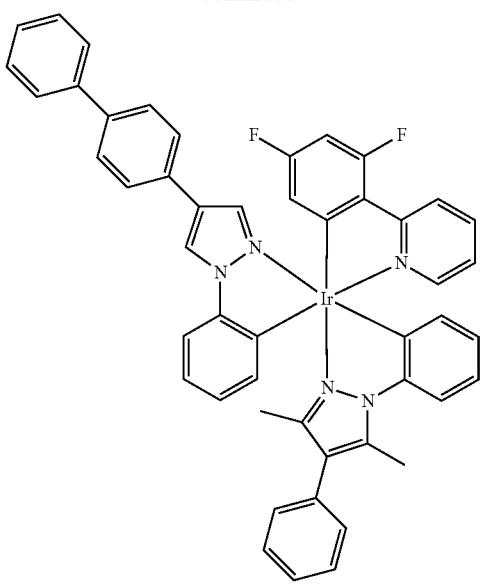
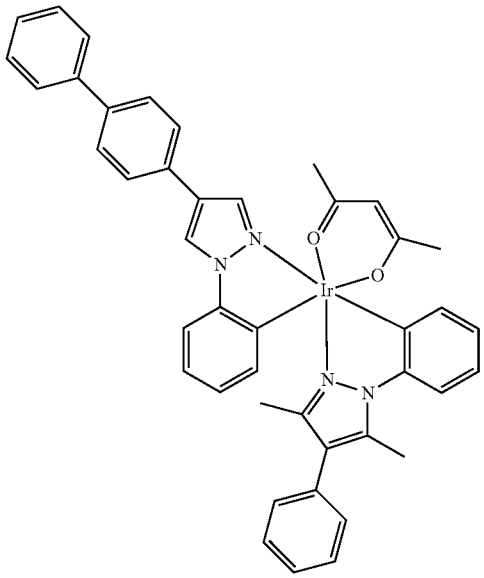

209
-continued
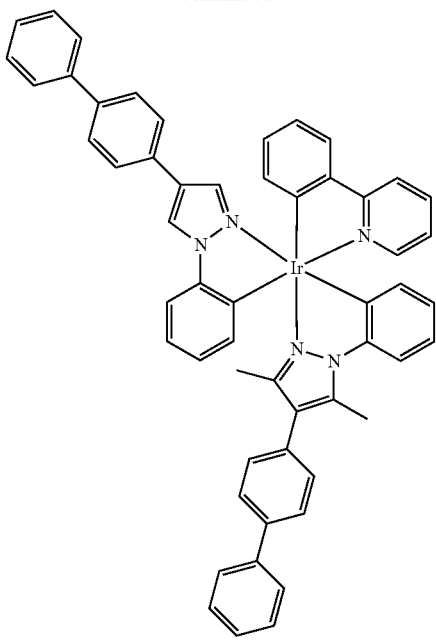
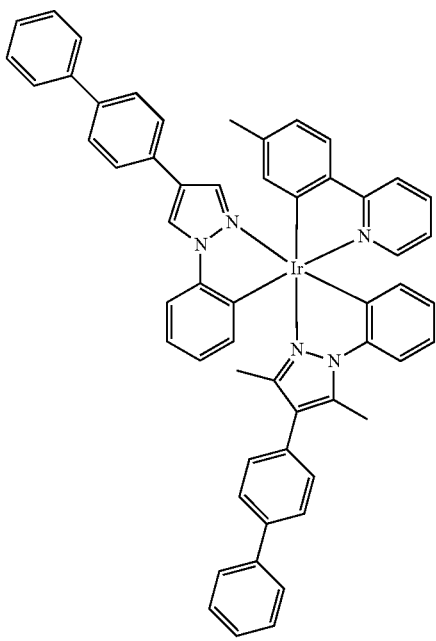
210
-continued
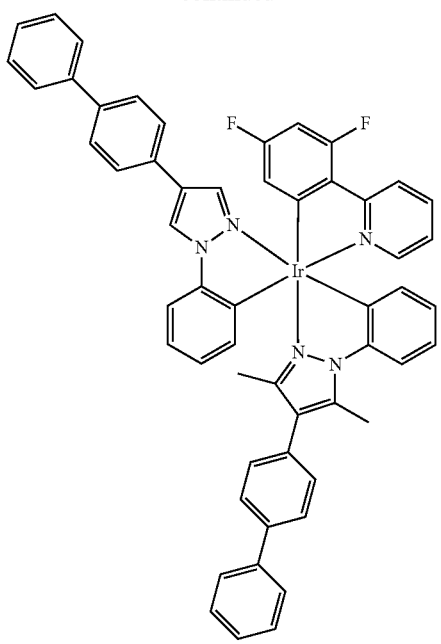
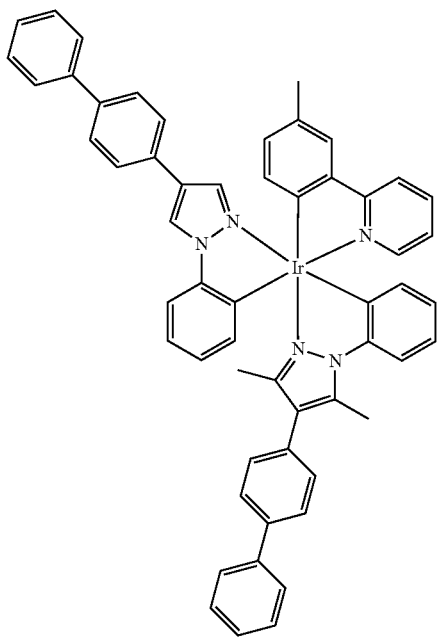

211
-continued
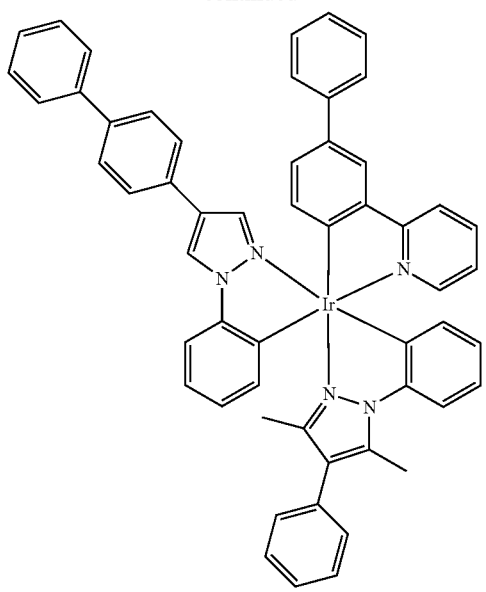
212
-continued
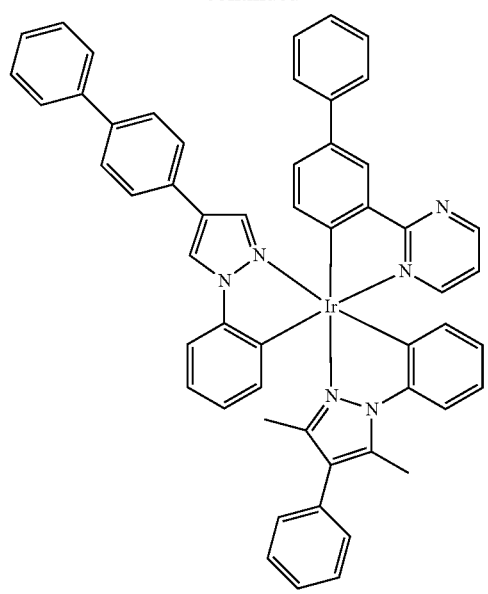
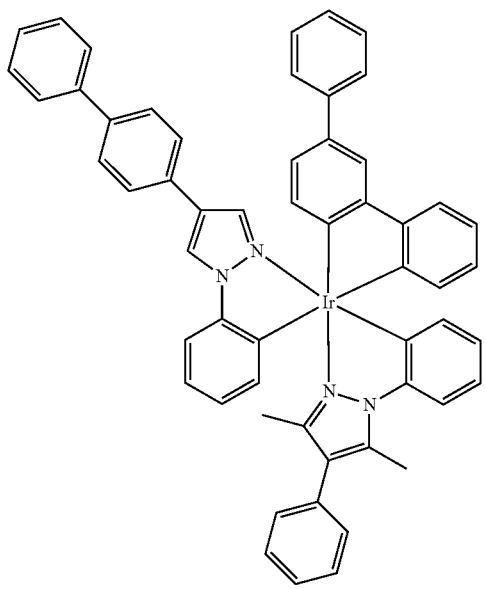
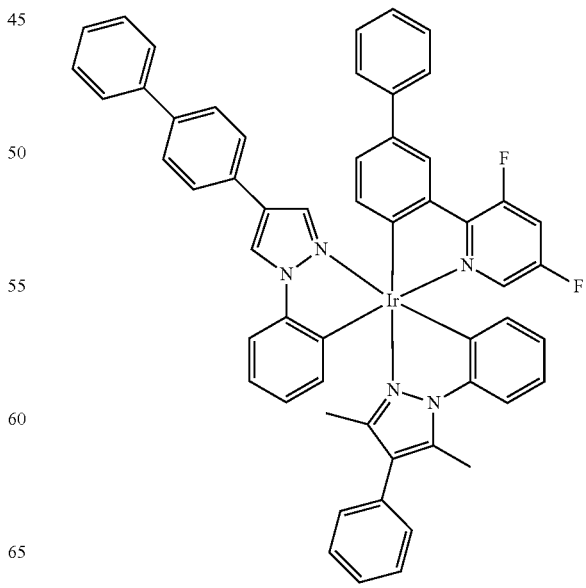

-continued
Structues Ir-25
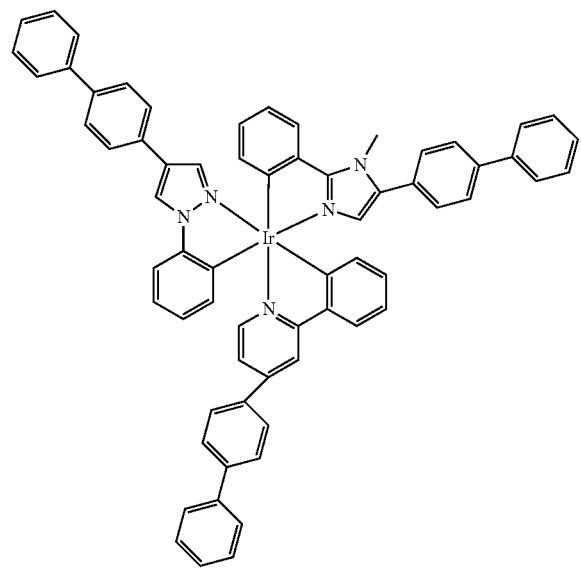
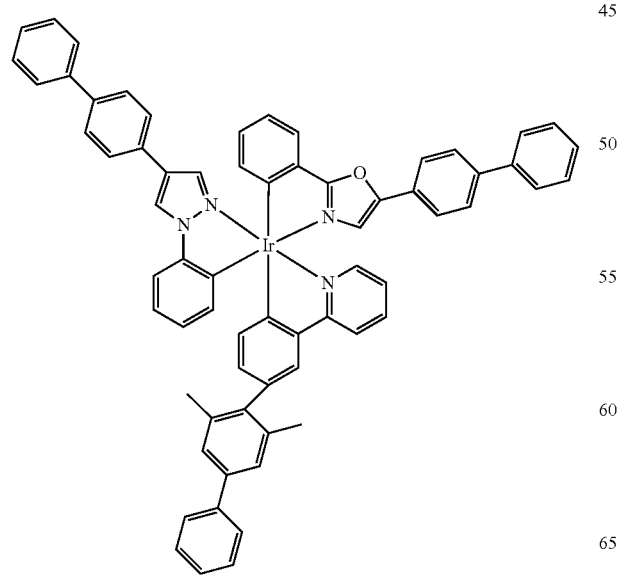
-continued
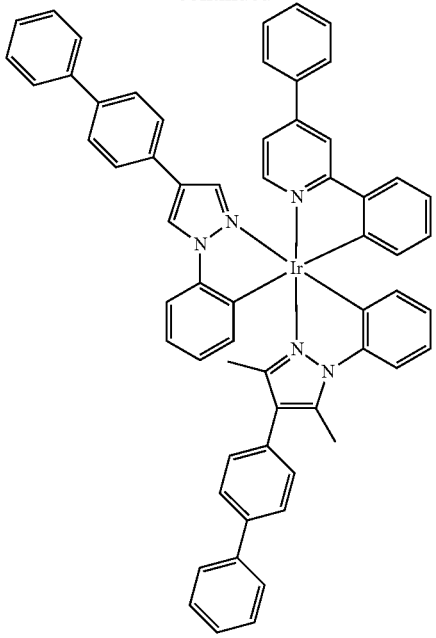
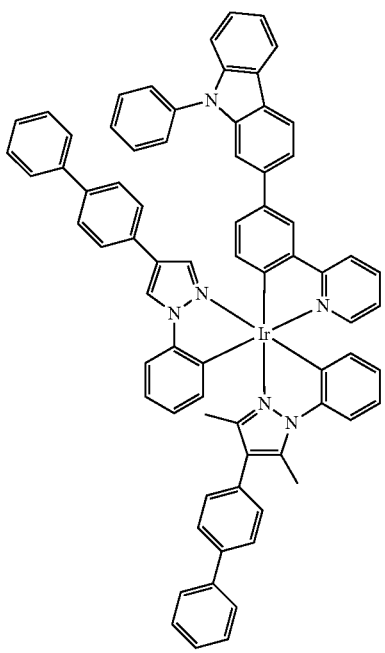

215
-continued
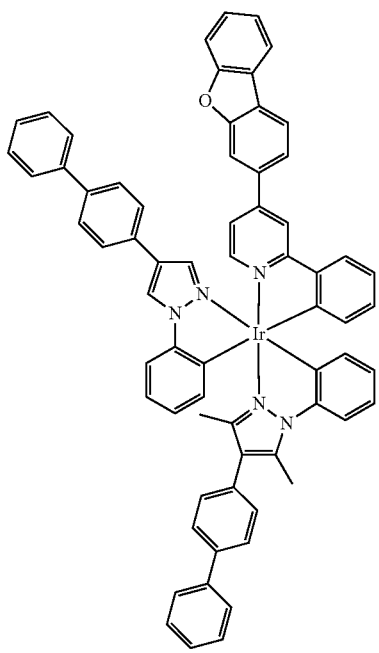
216
-continued
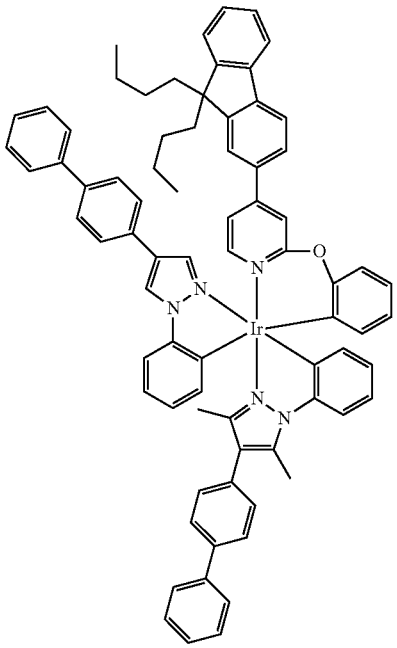
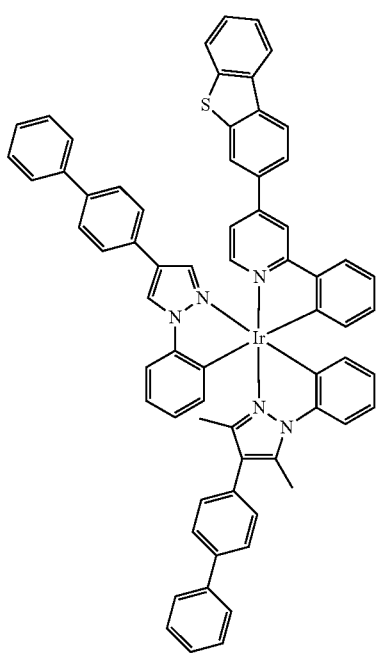
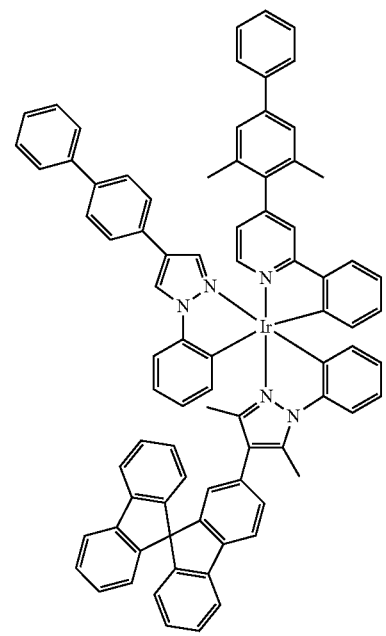

217
-continued
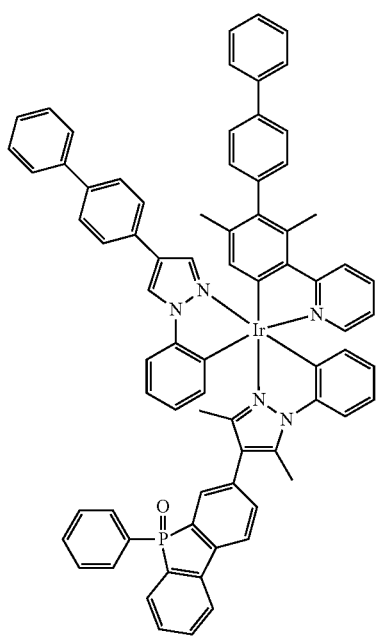
218
-continued
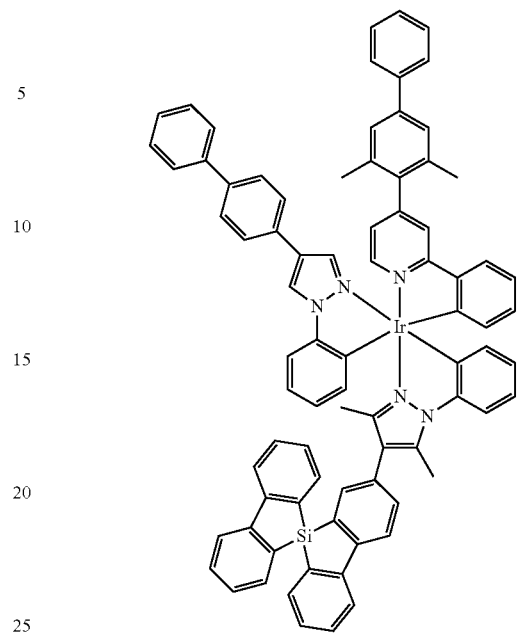
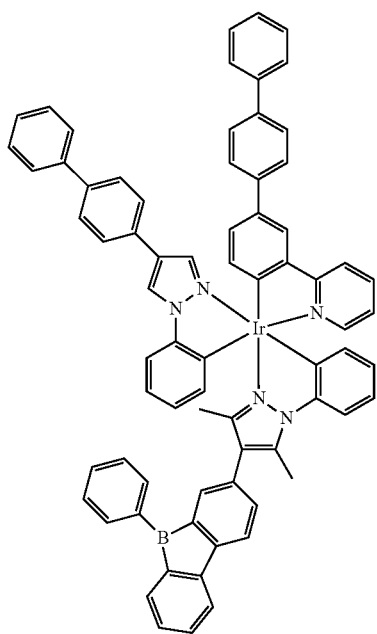
Structure Rh-1
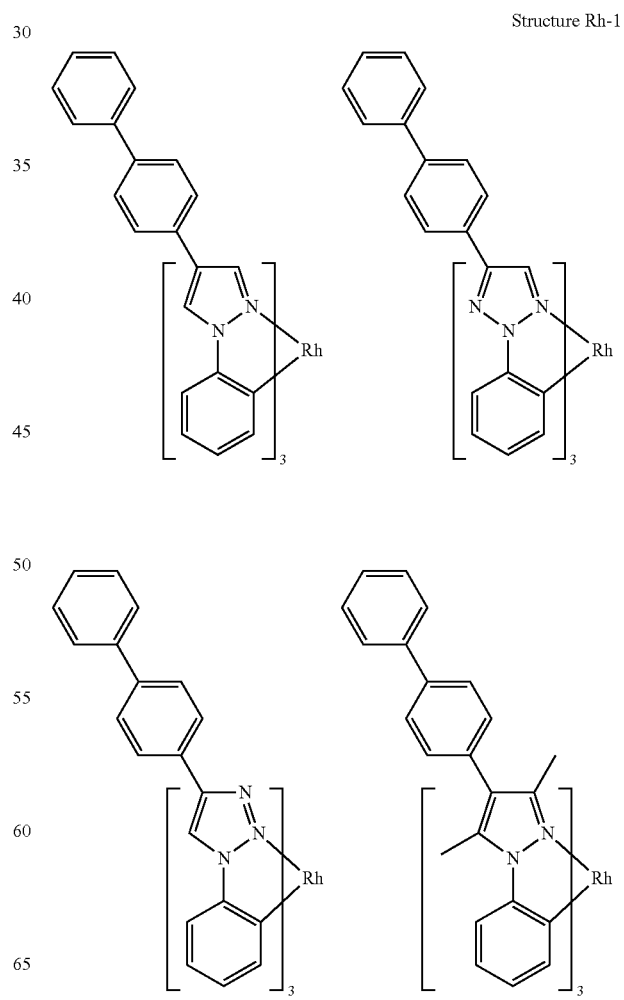

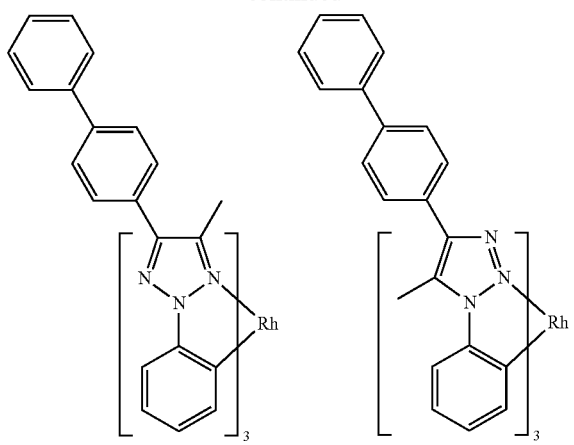
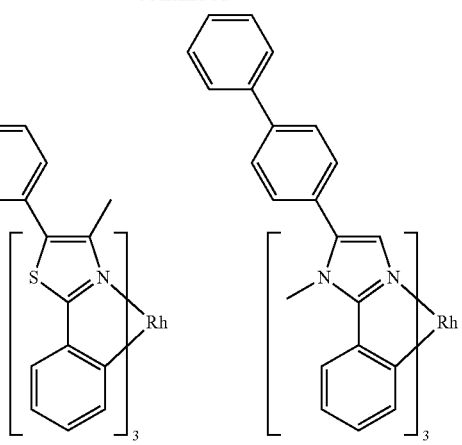
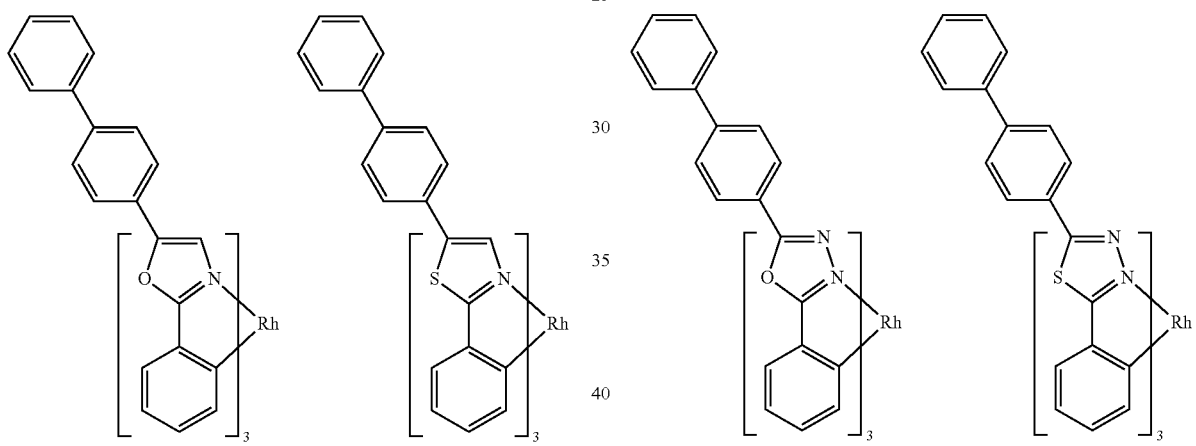
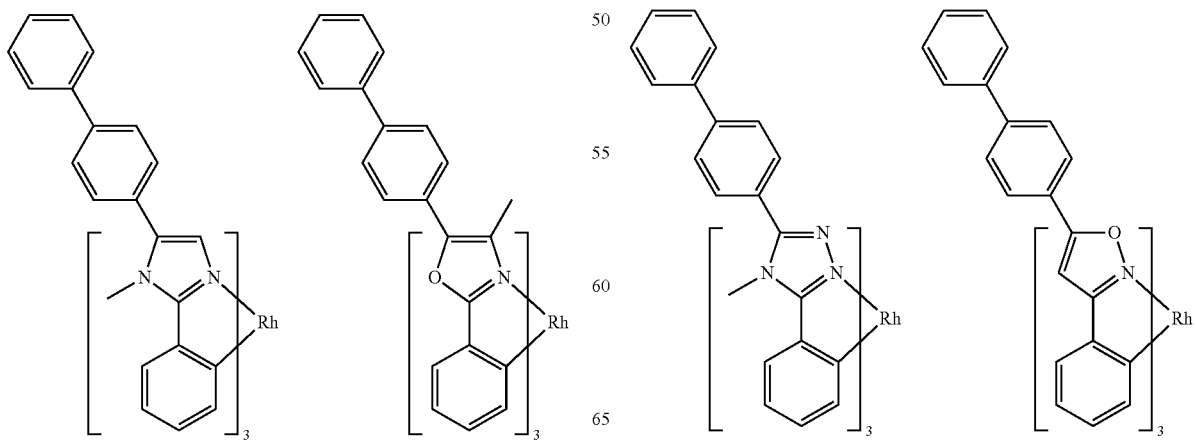

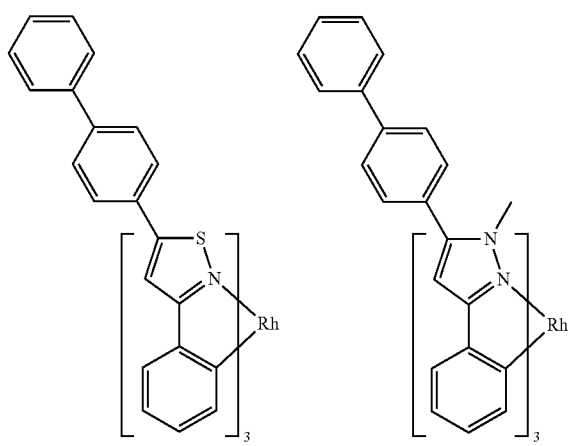
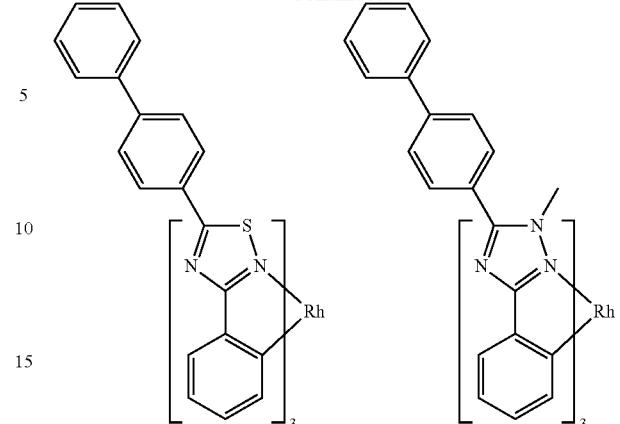
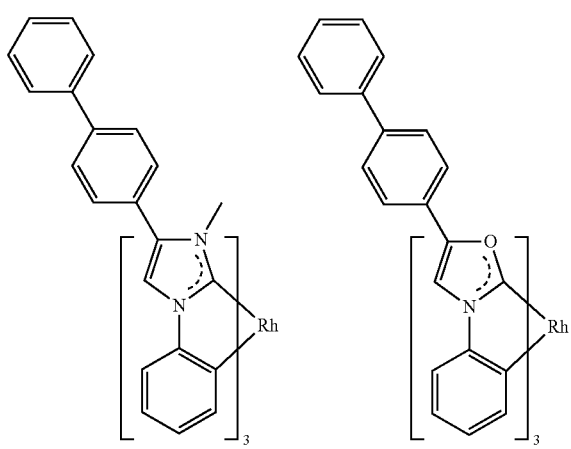
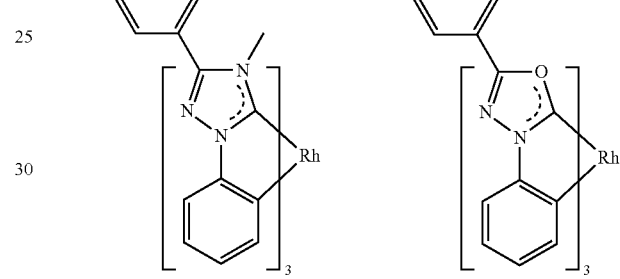
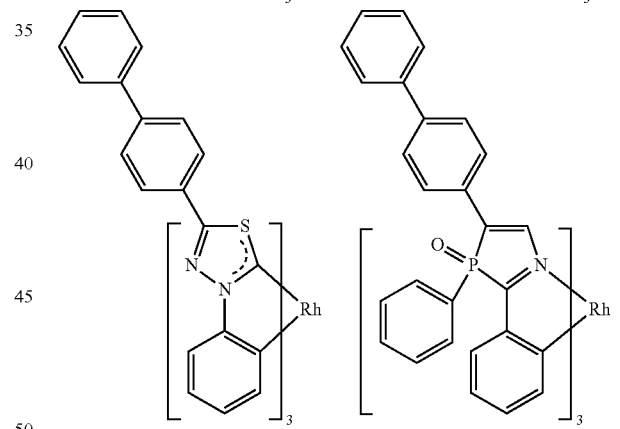
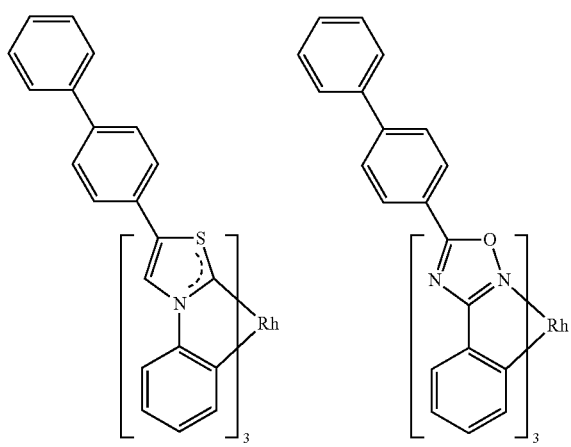
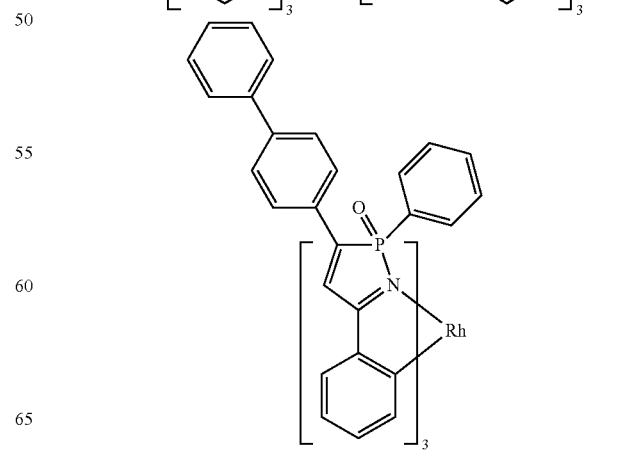

223
-continued
224
-continued
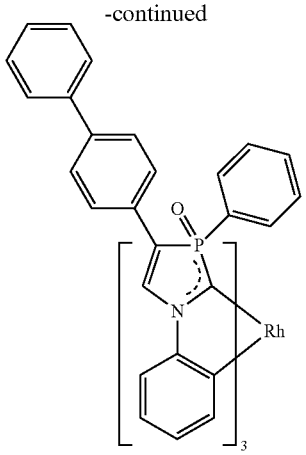
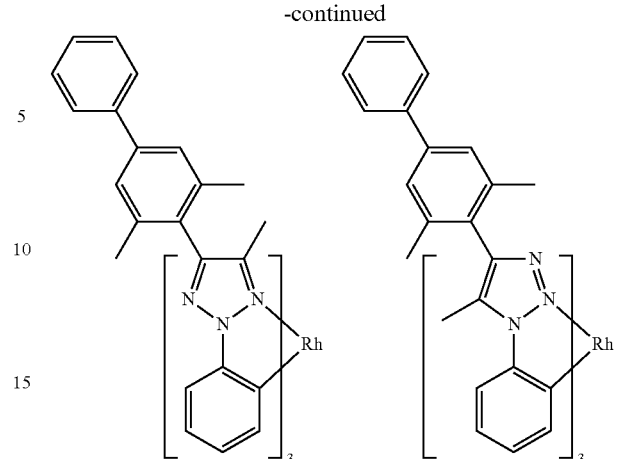
Structure Rh-2

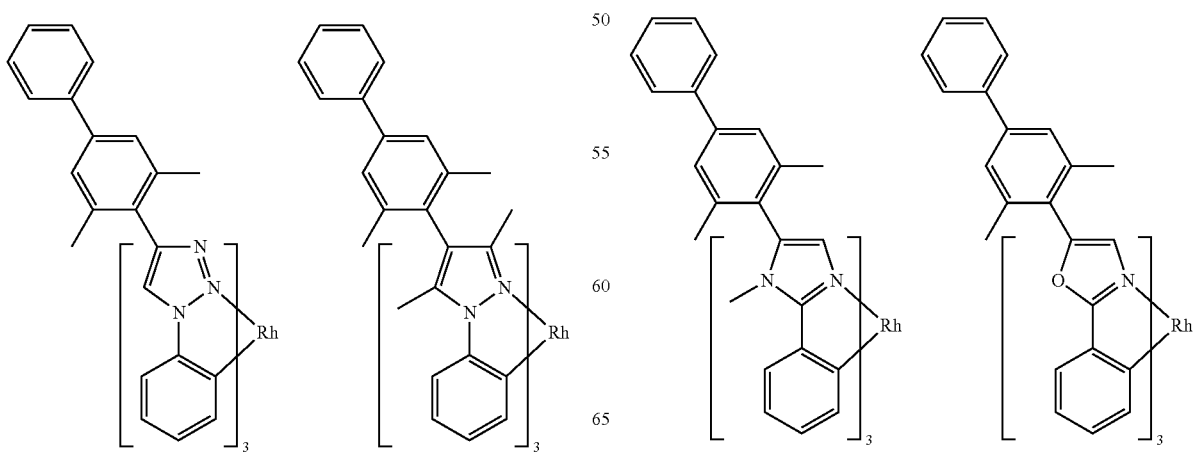

-continued
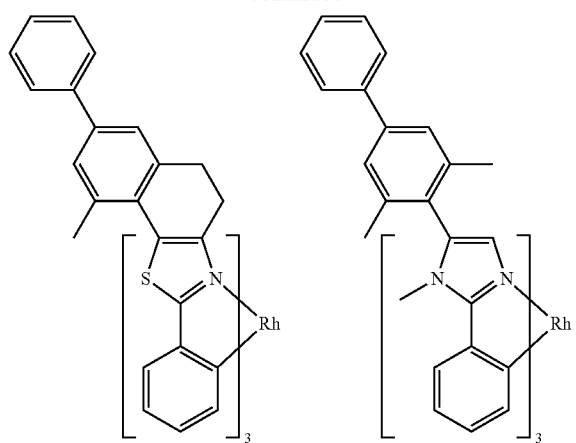
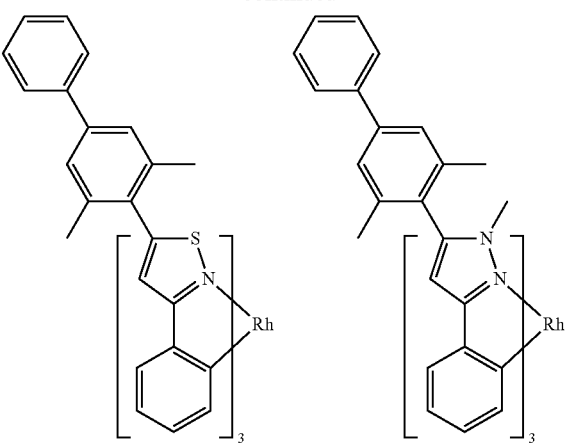
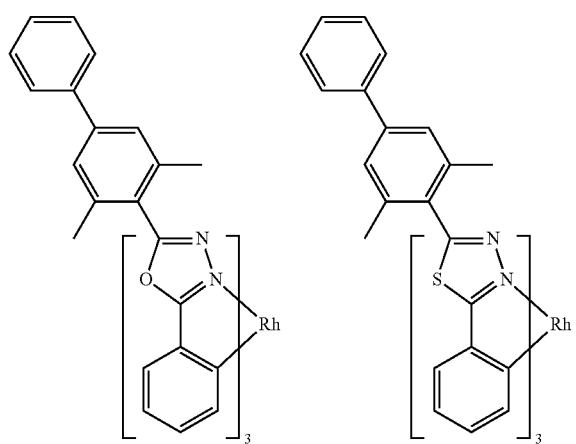
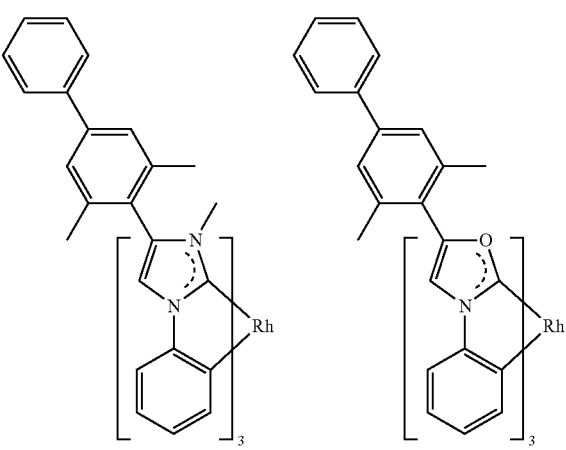
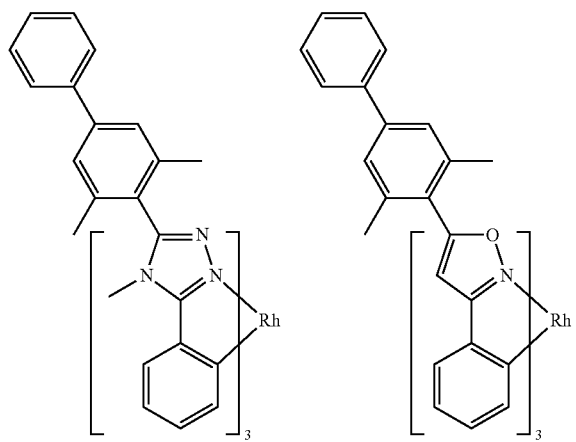
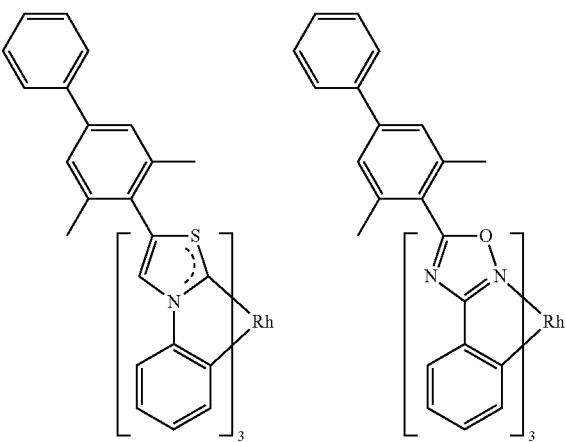

227
-continued
228
-continued
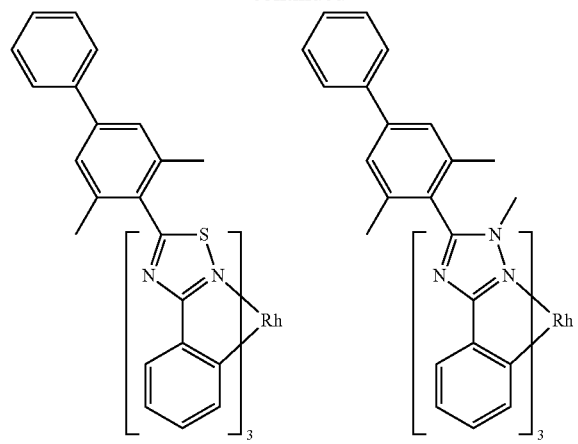
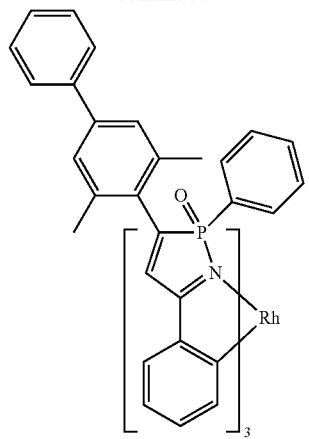
Structures Rh-3
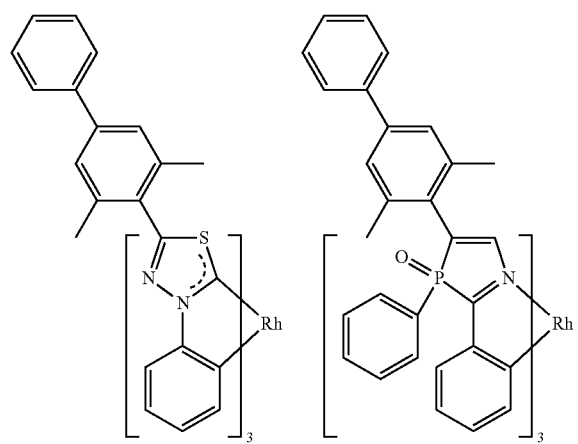
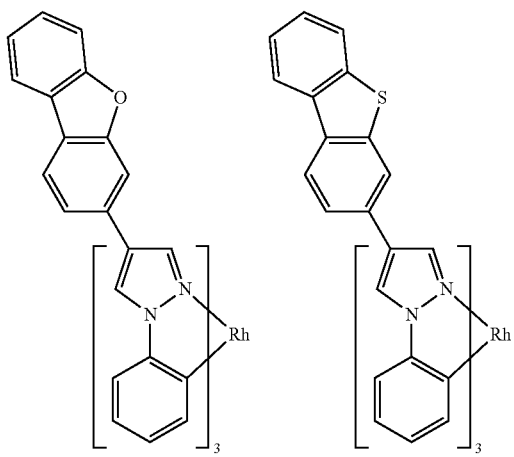

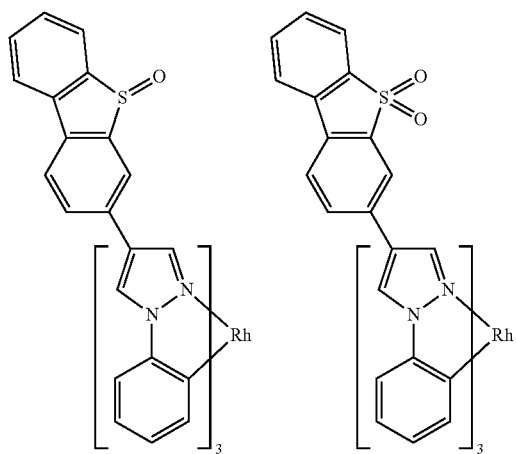
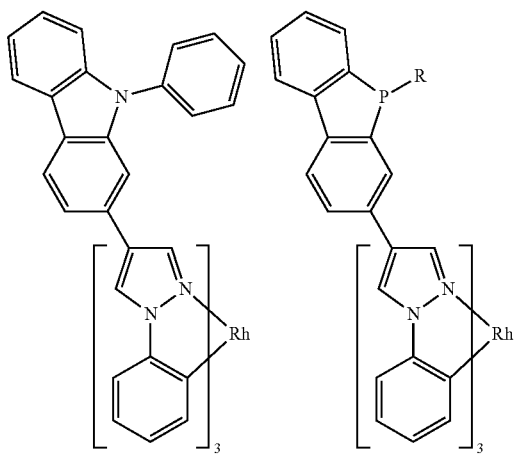
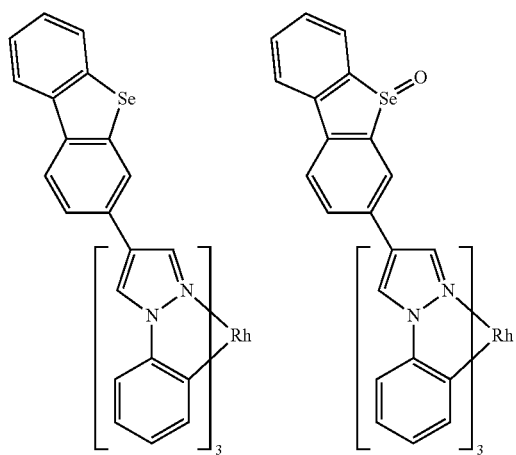
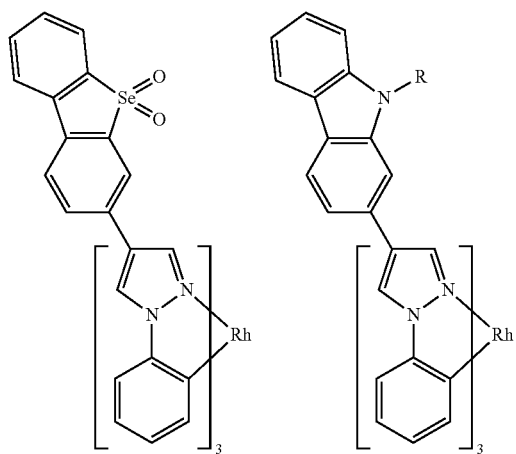
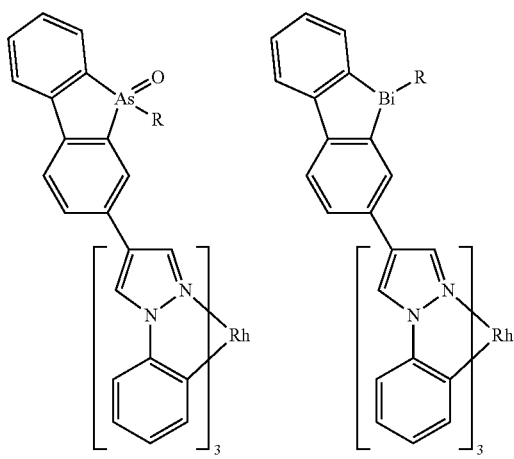

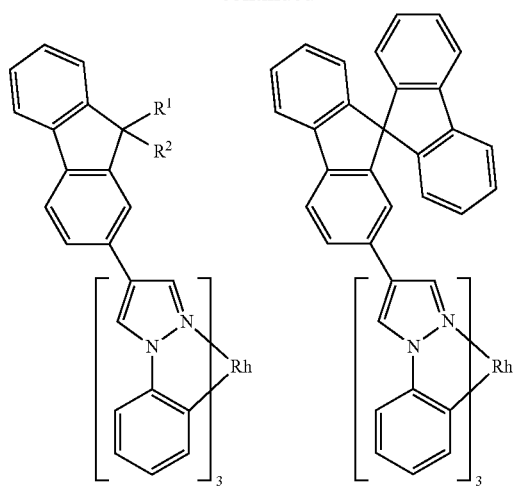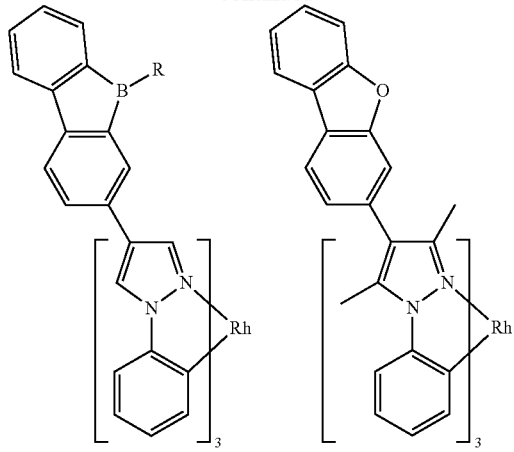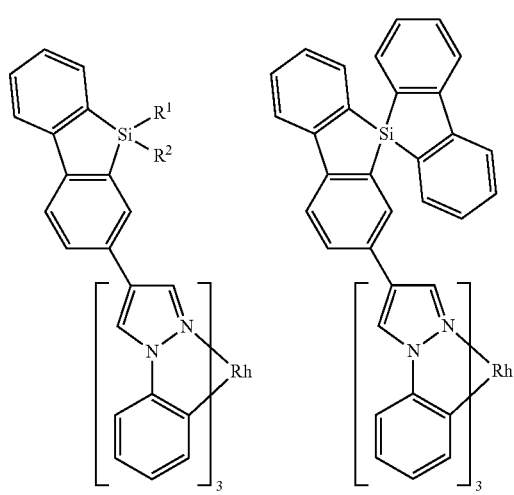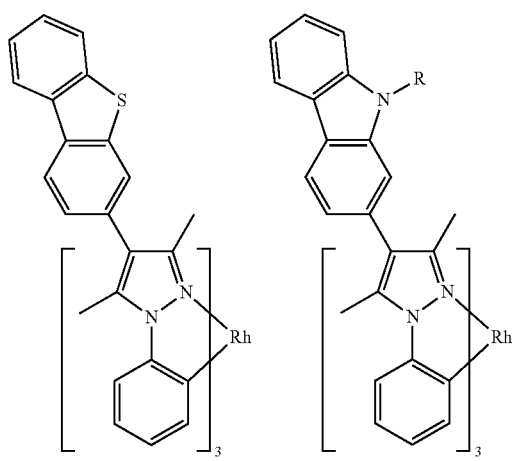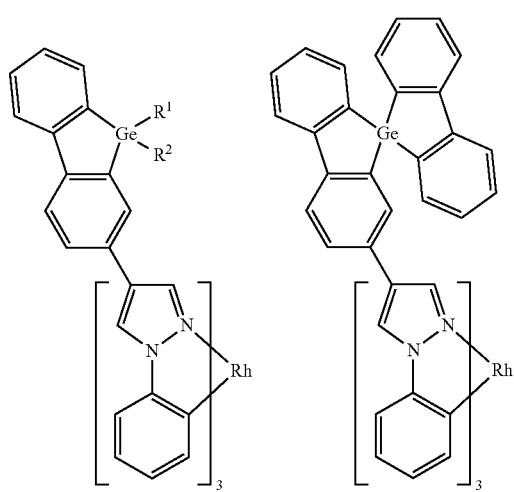

233
-continued
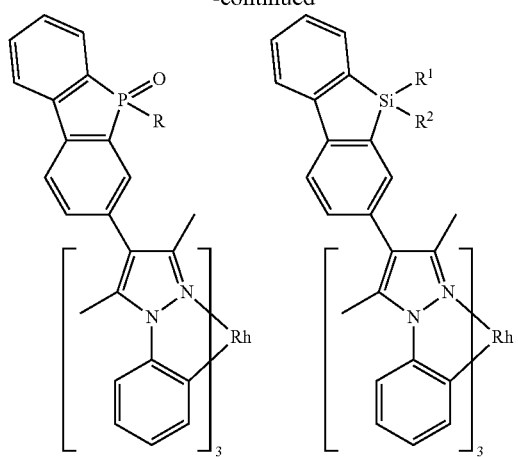
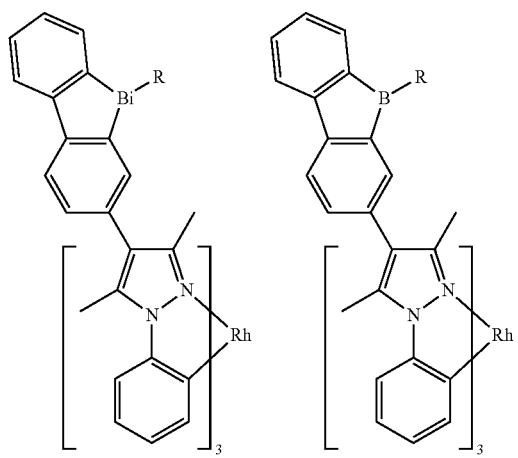
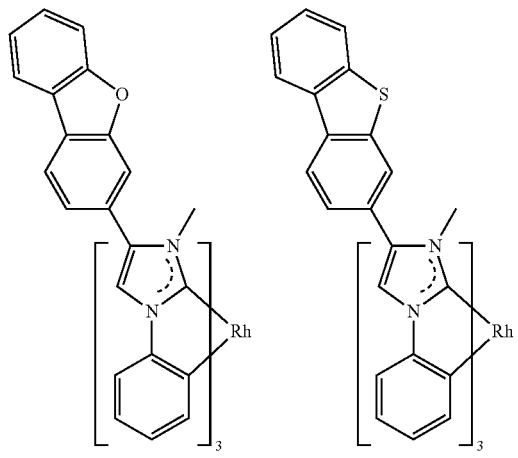
234
-continued
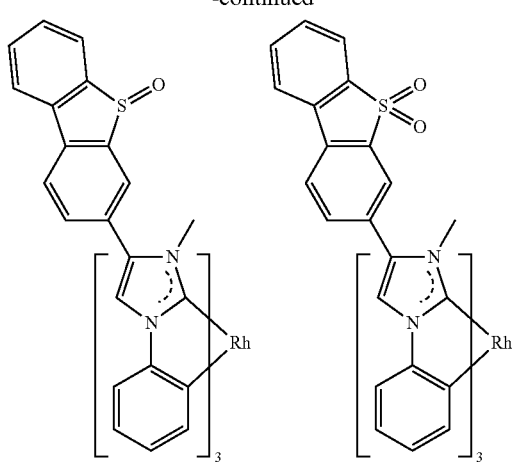
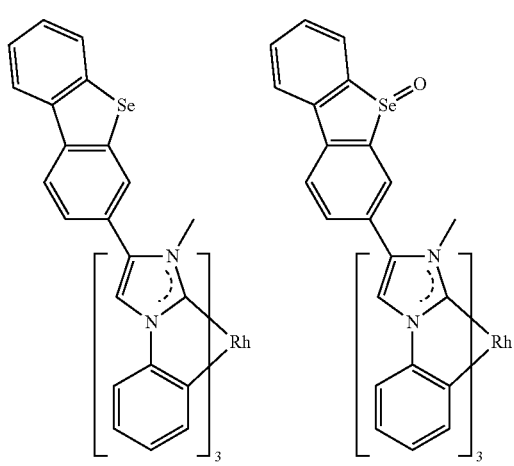
Structures Rh-4
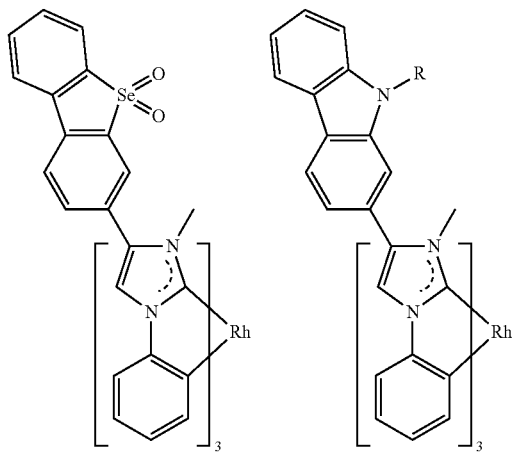

235
-continued
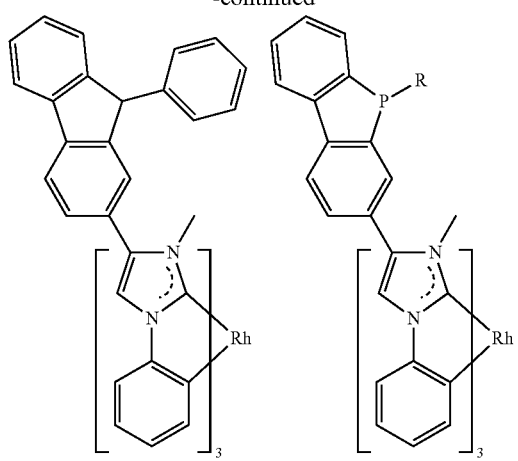
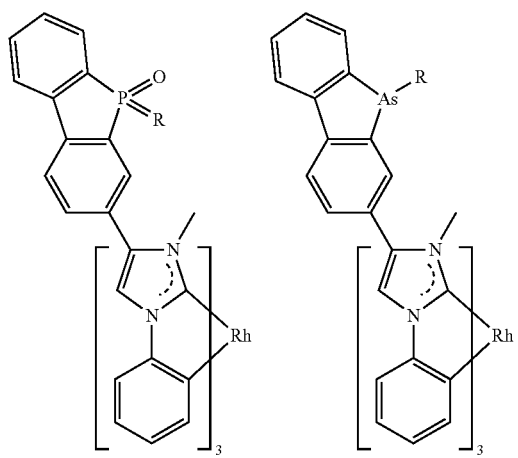
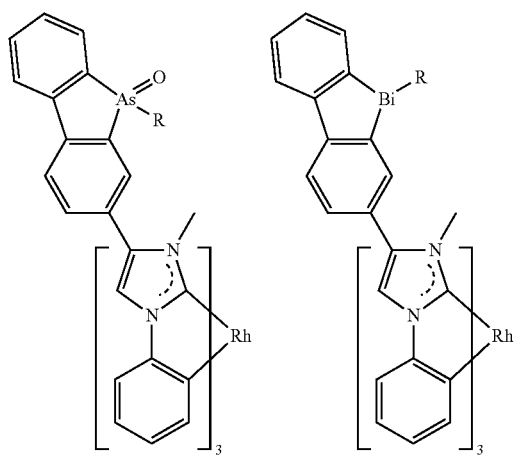
236
-continued
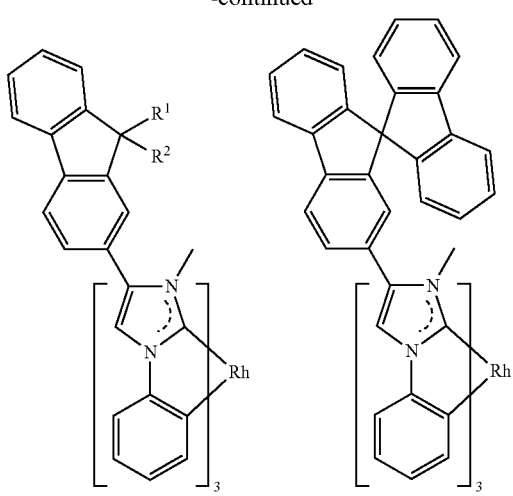
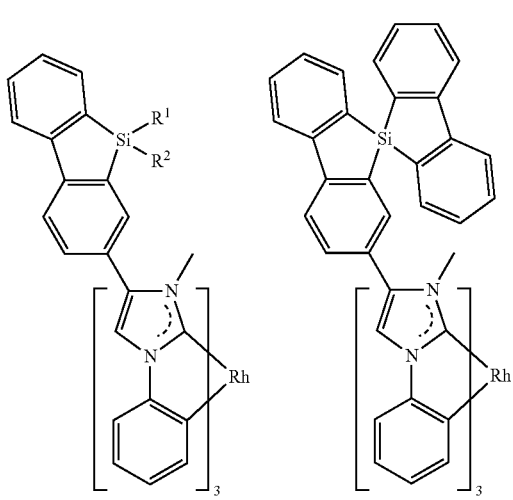
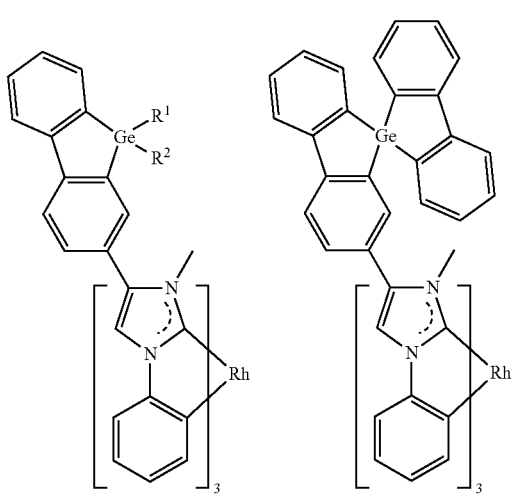

-continued
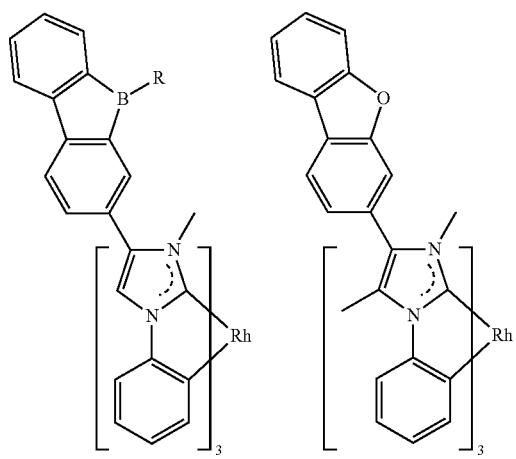
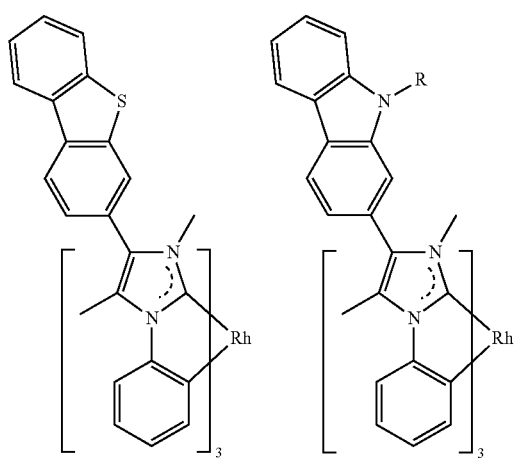
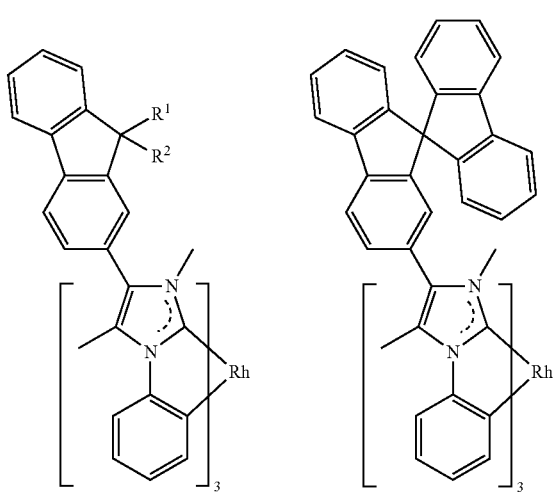
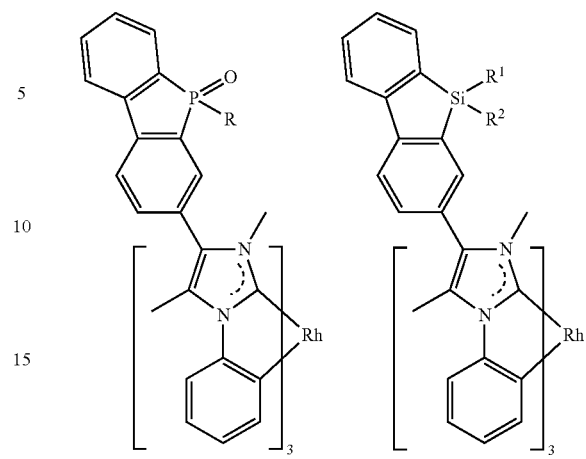
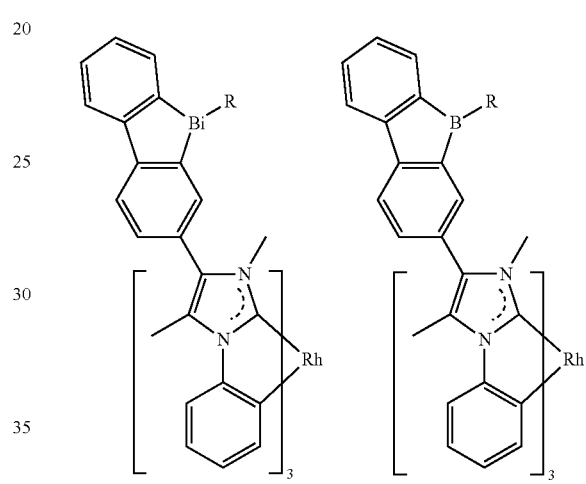
Structures Rh-5
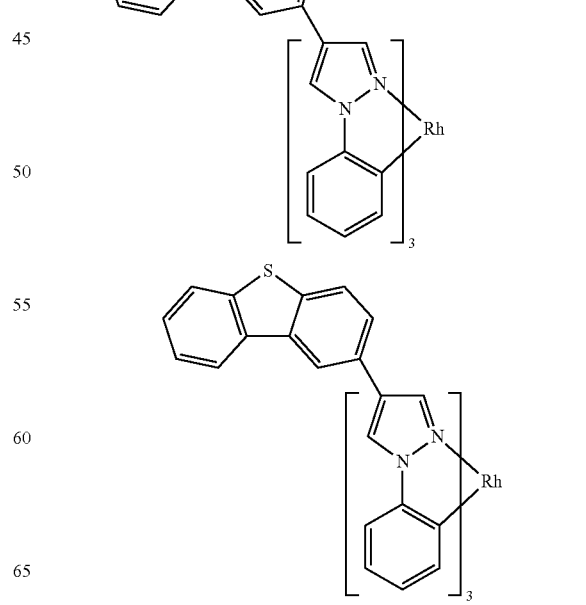

239
-continued
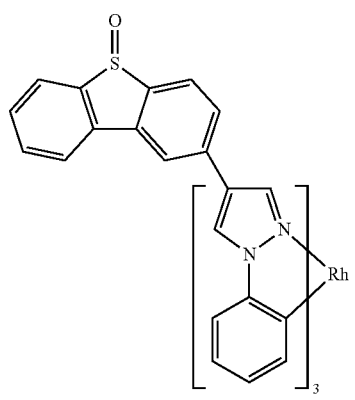
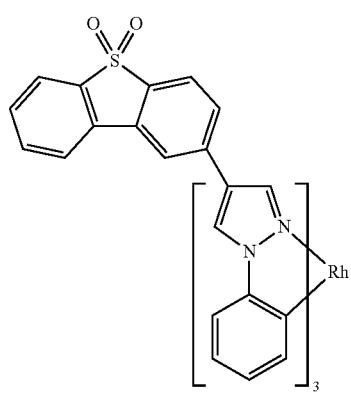
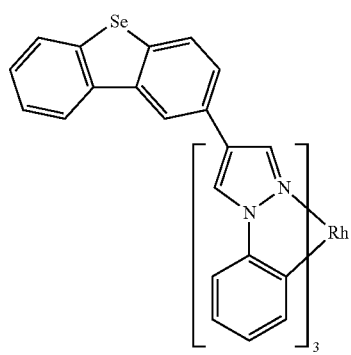
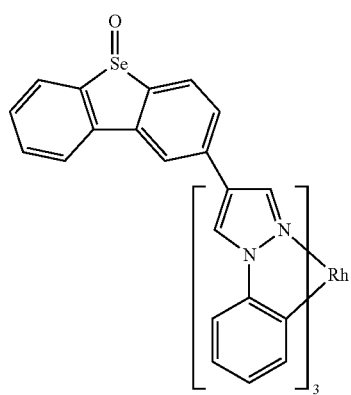
240
-continued
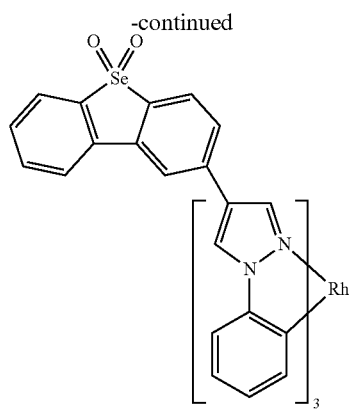
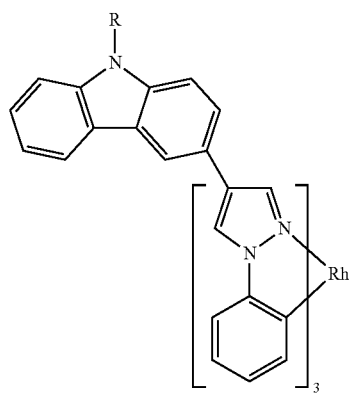
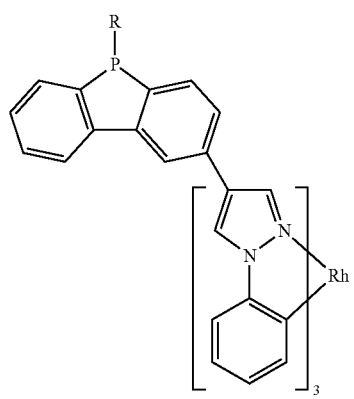
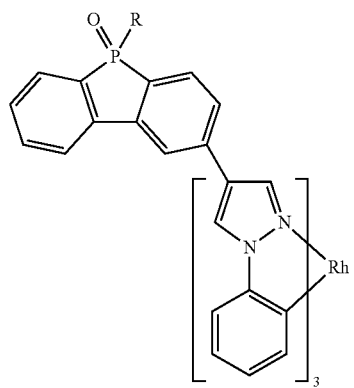

241
-continued

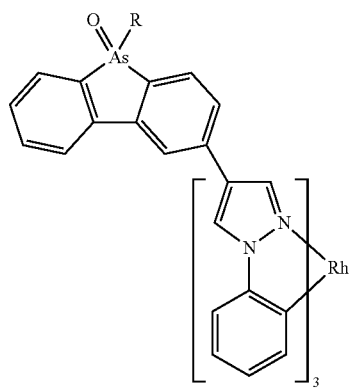
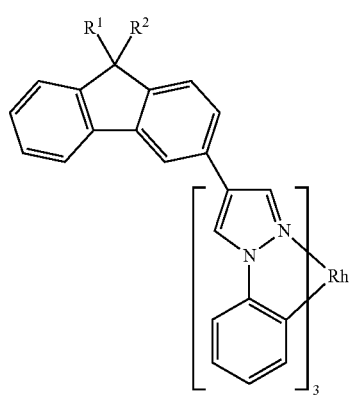
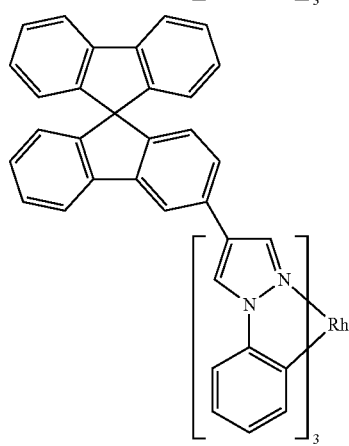
242
-continued
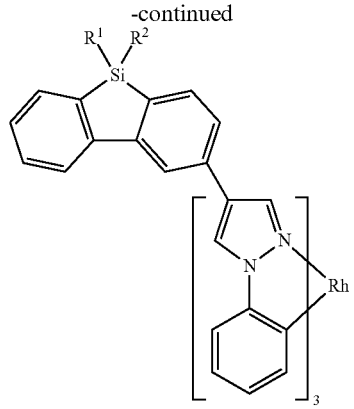
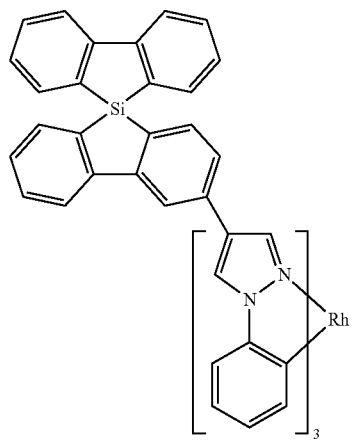
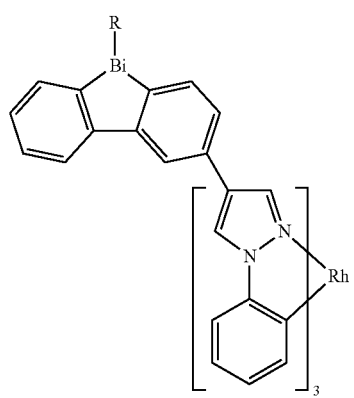
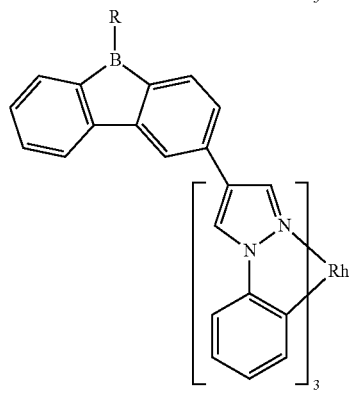

243
-continued
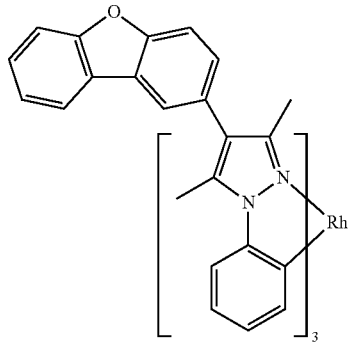
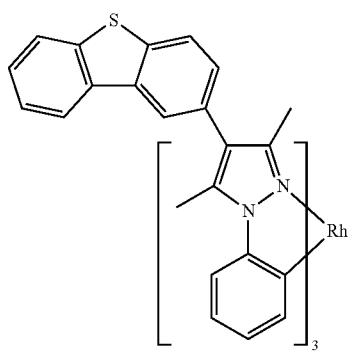
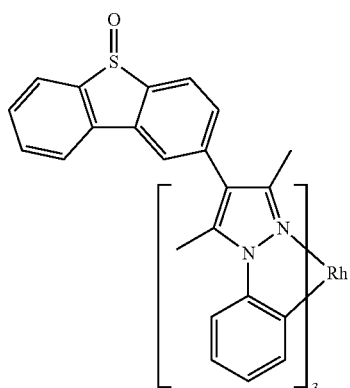
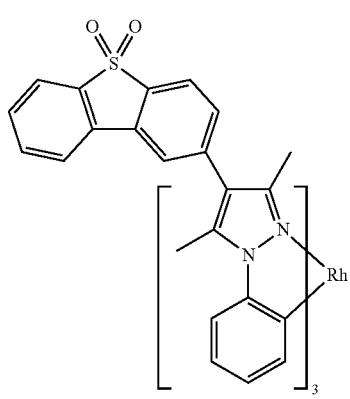
244
-continued
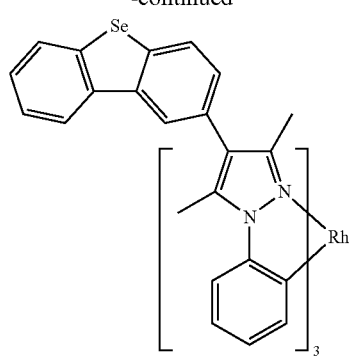
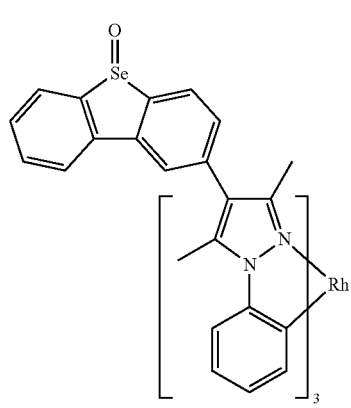
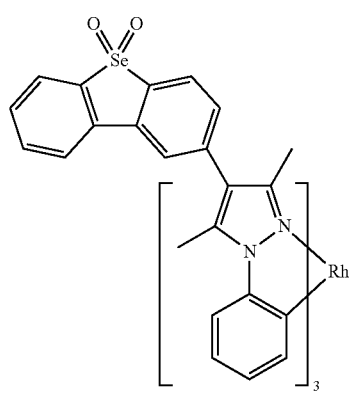
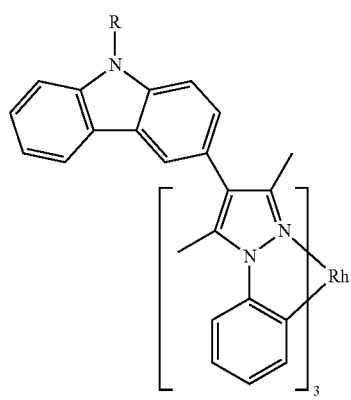

-continued
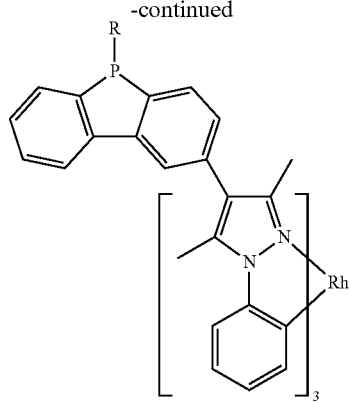
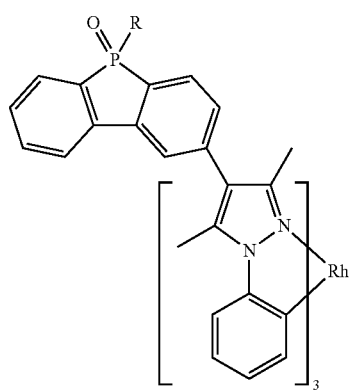
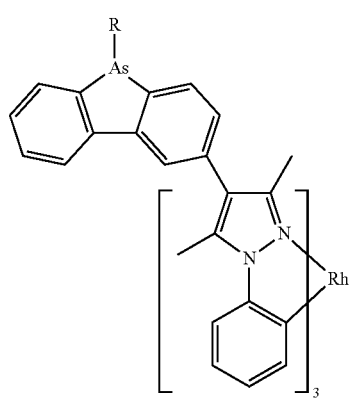
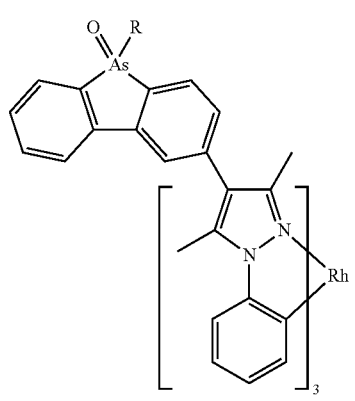
-continued
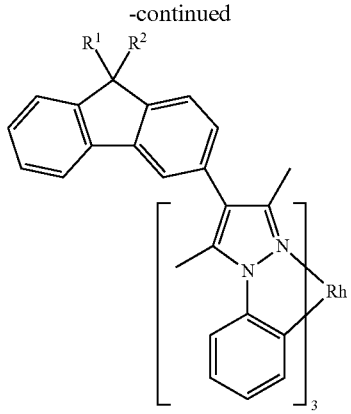
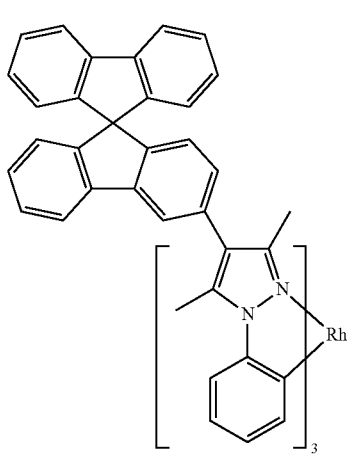
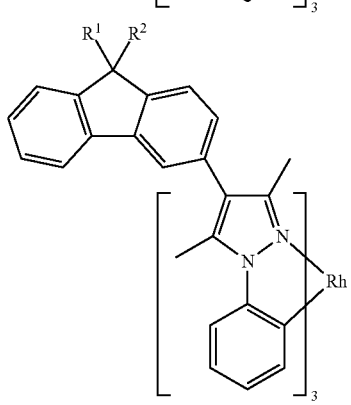
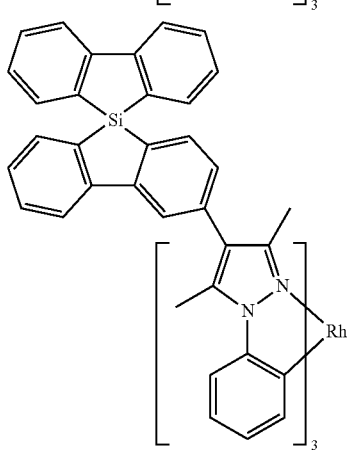

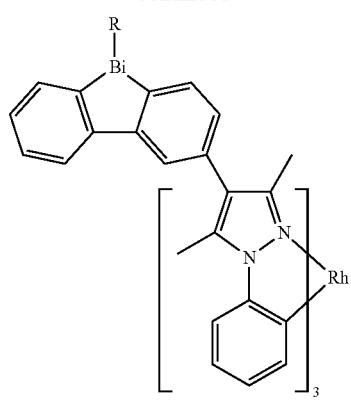
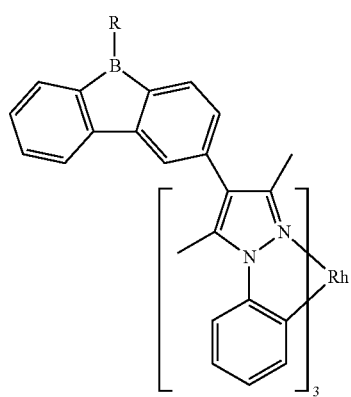
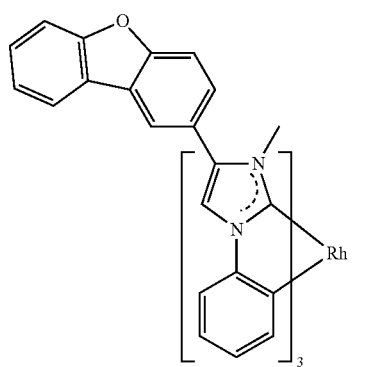
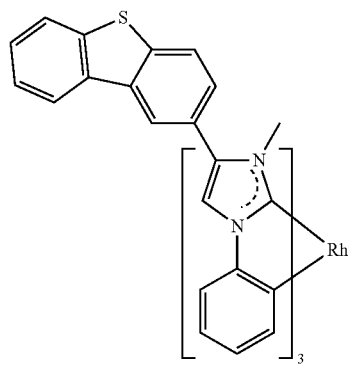
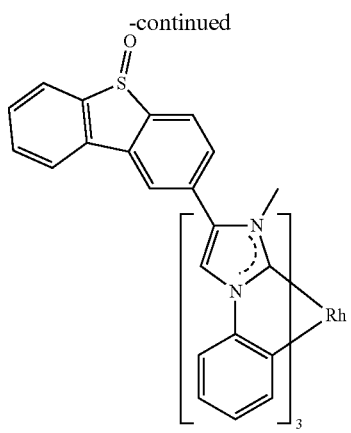
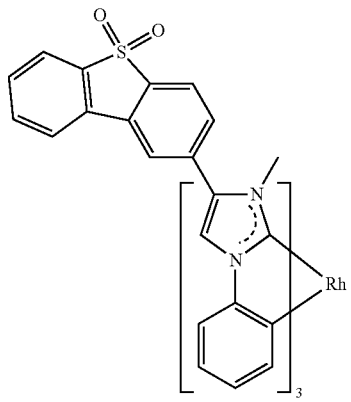
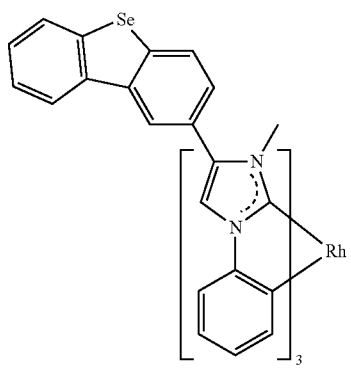
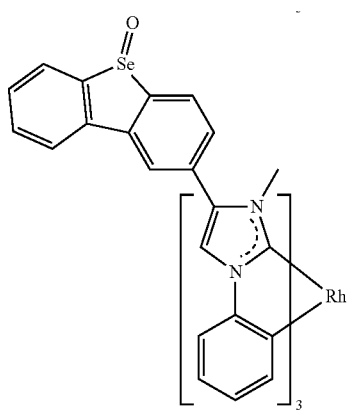
Structures Rh-6

249
-continued
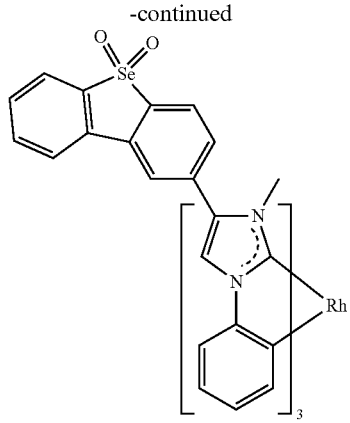
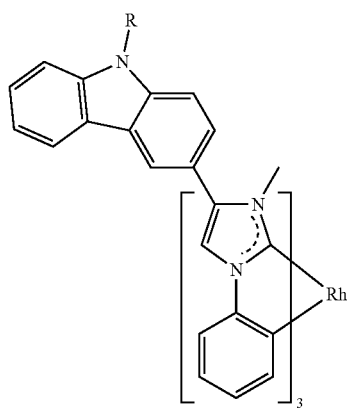
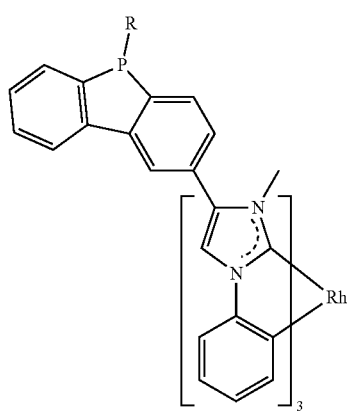
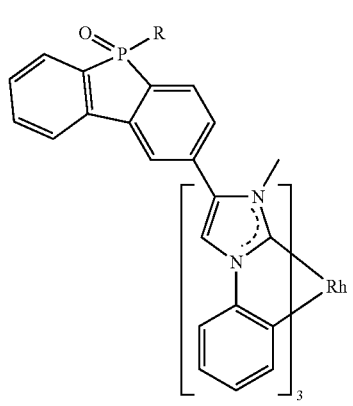
250
-continued
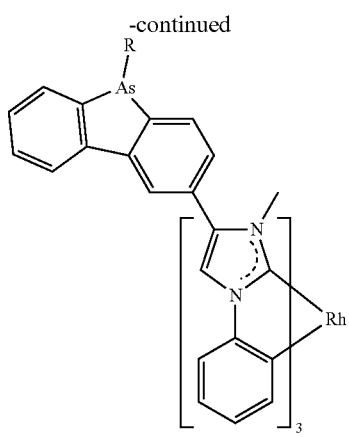

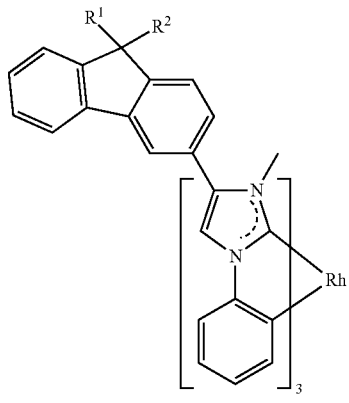
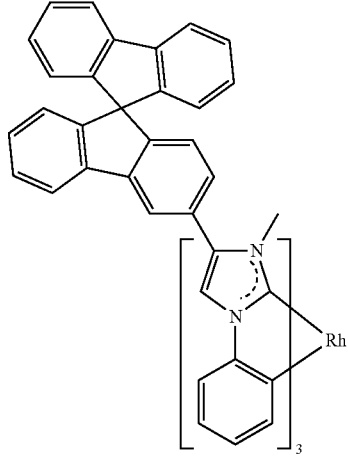

251
-continued
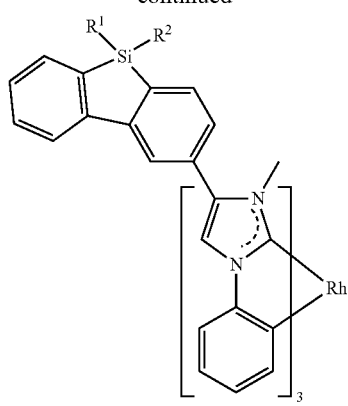
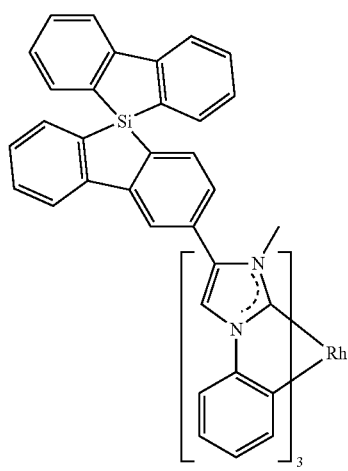
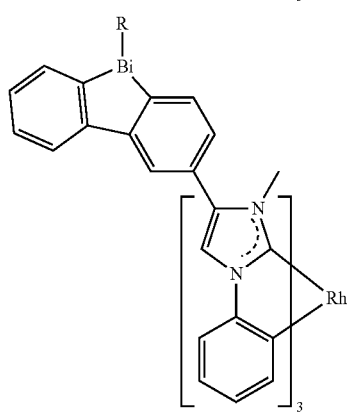
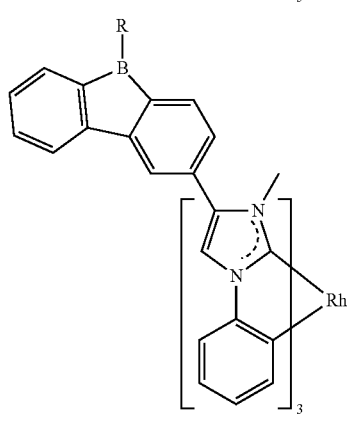
252
-continued
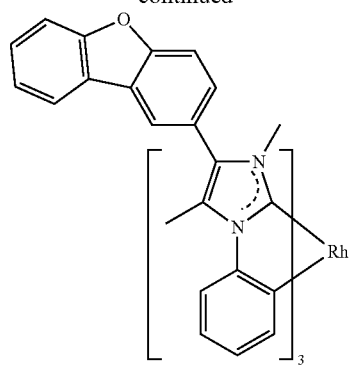
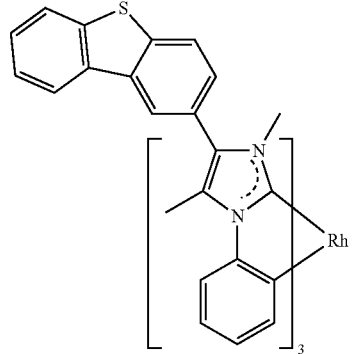
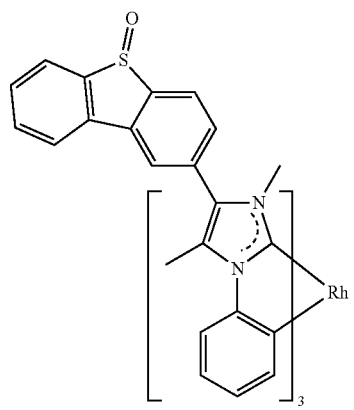
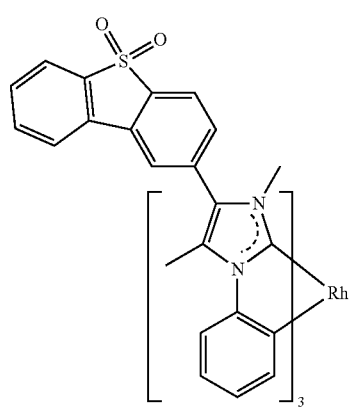

253 -continued
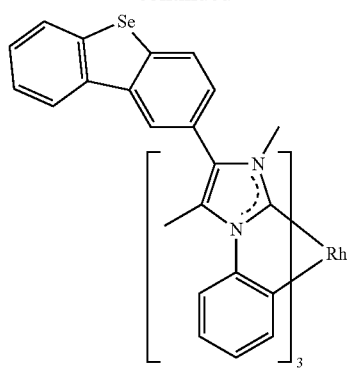
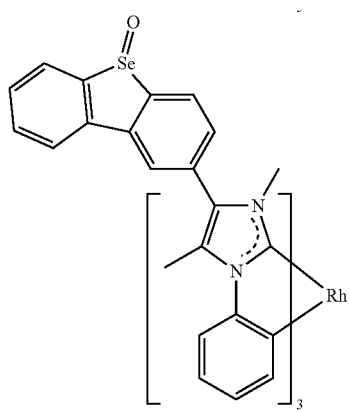
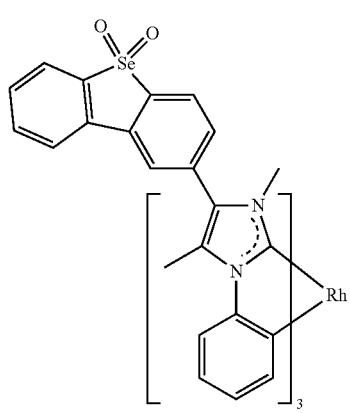
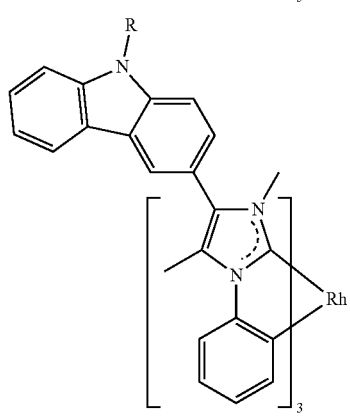
254 -continued
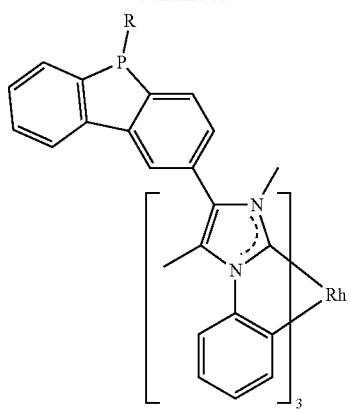
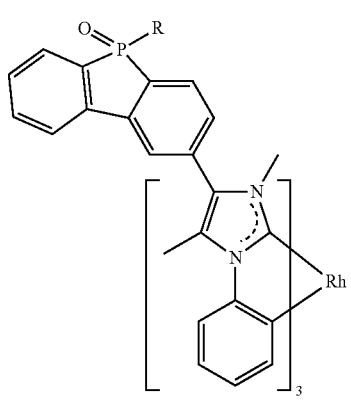
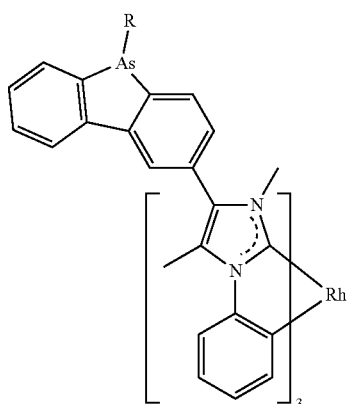
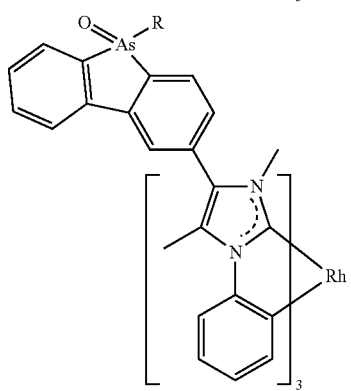

255
-continued
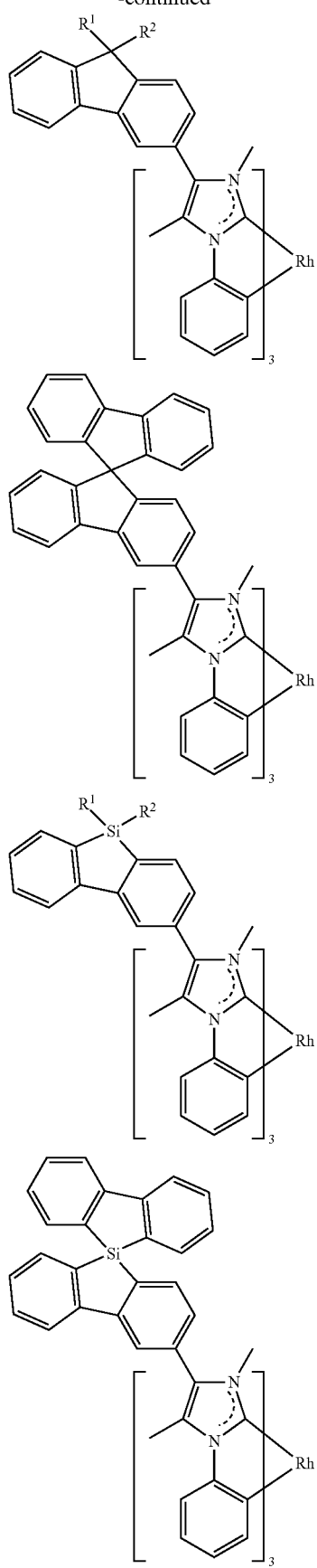
256
-continued
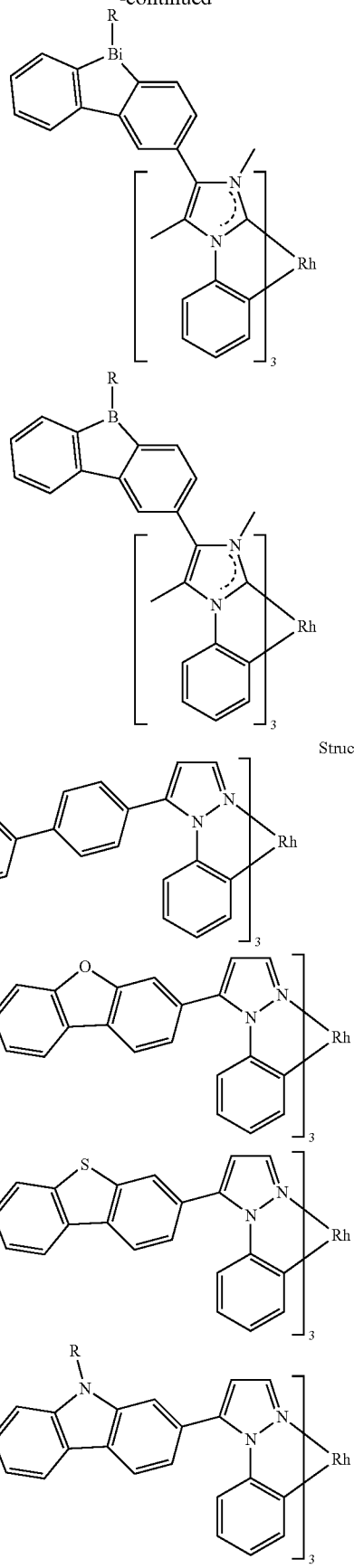
Structures Rh-7

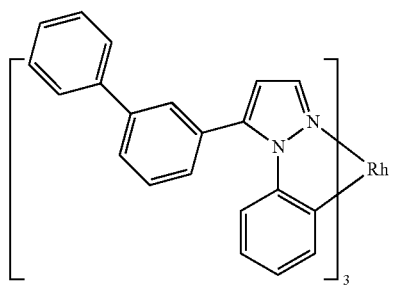
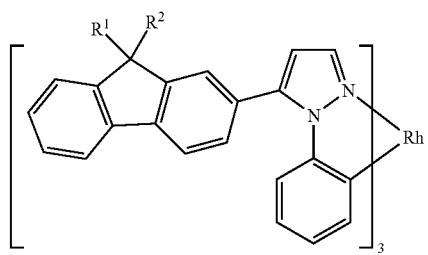
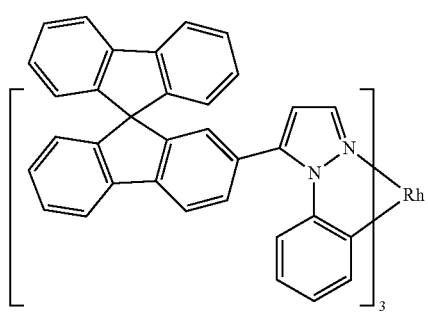
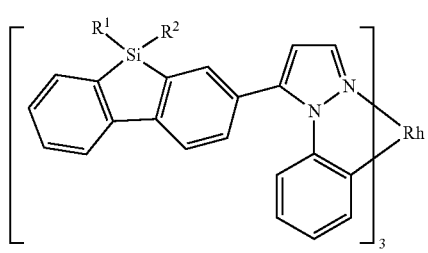
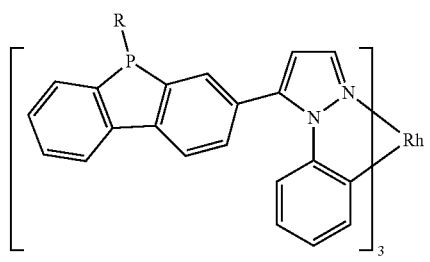
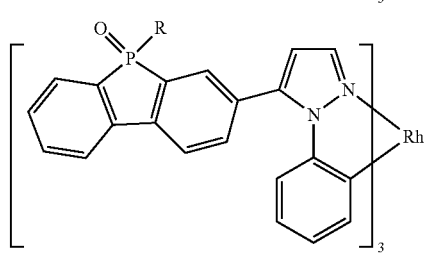
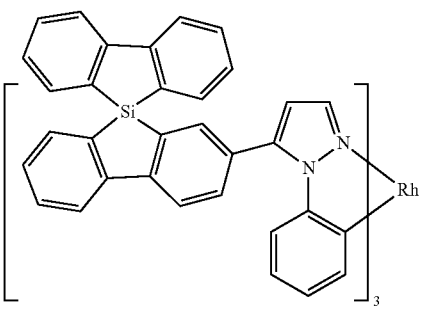
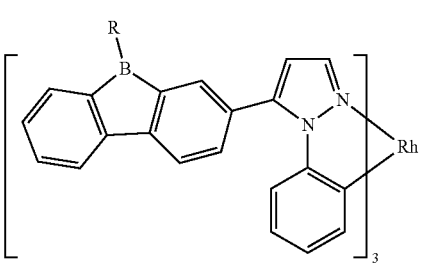
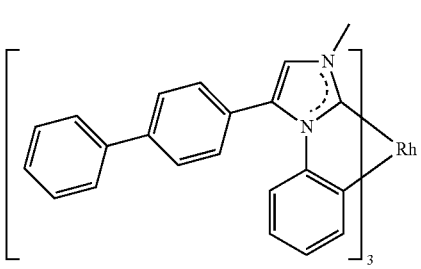
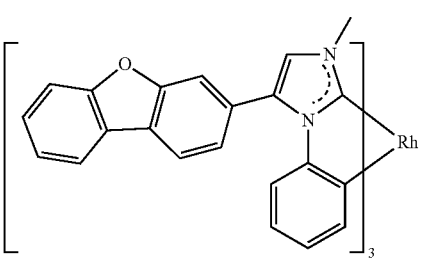
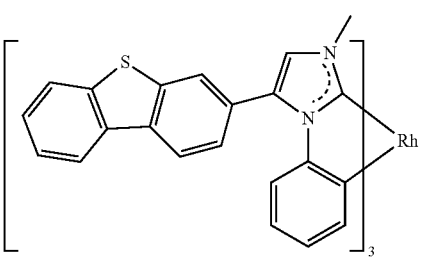
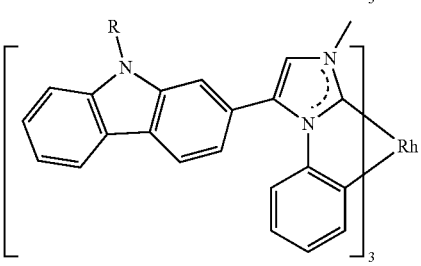

-continued
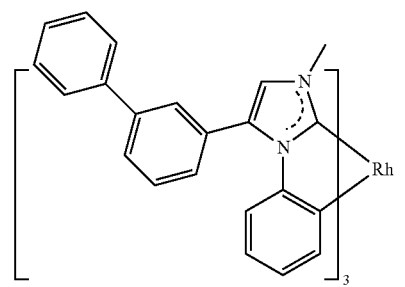
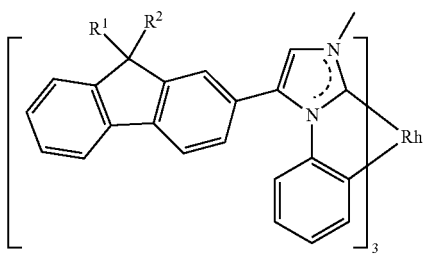
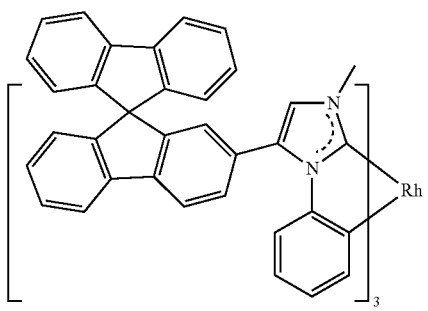
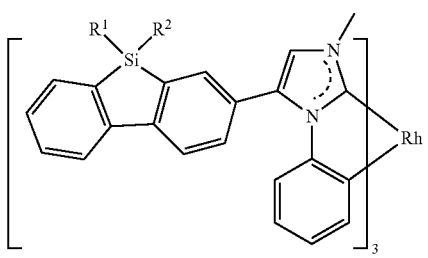
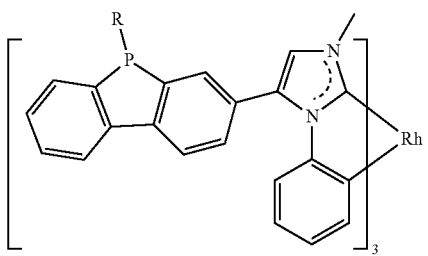
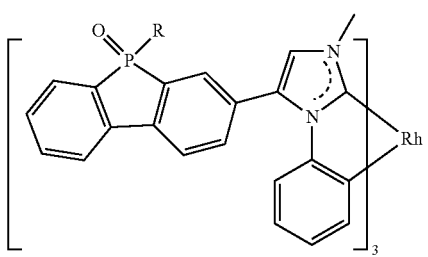
-continued
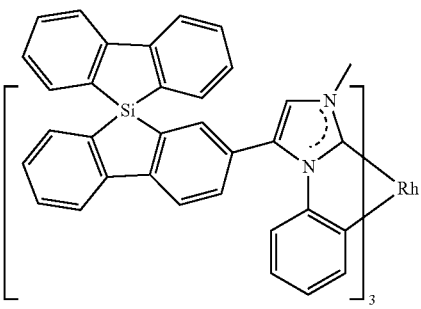
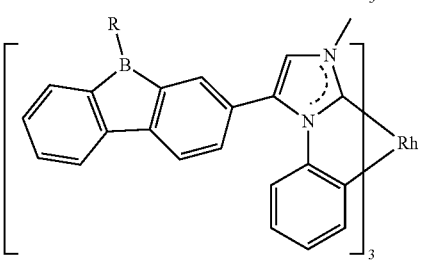
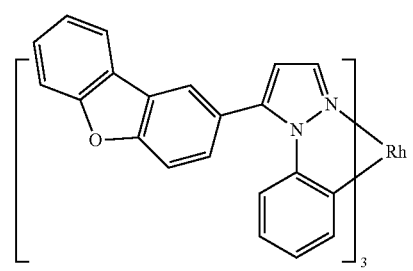
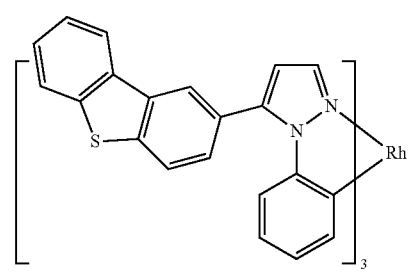
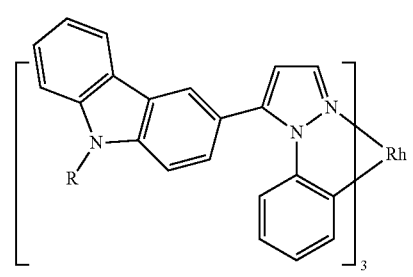
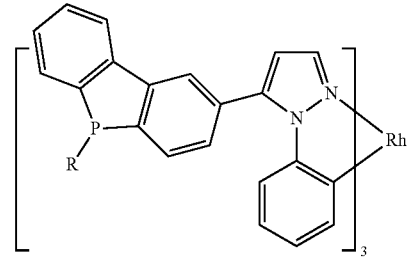

-continued
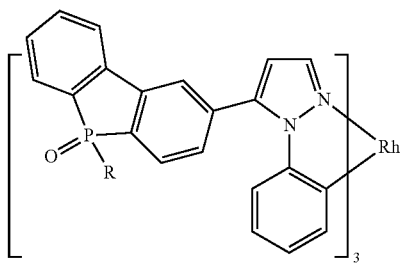
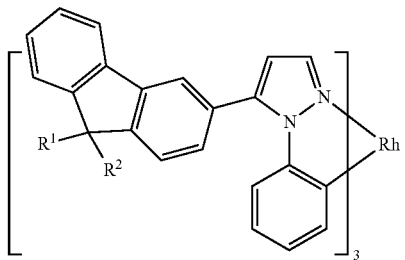
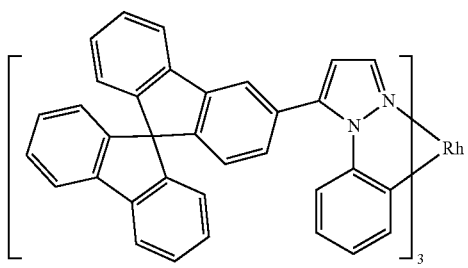
Structures Rh-8
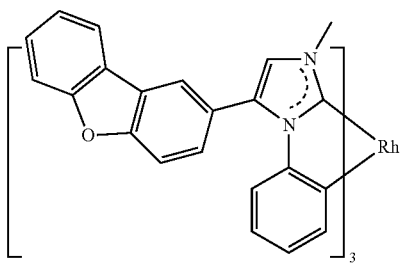
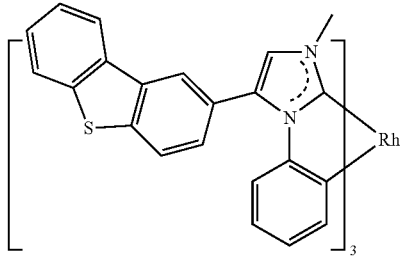
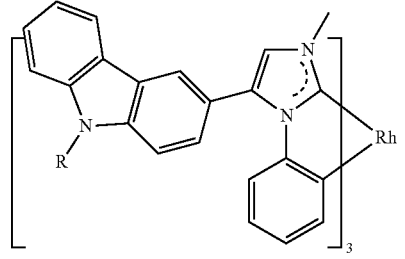
-continued
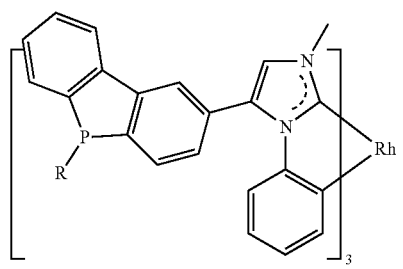
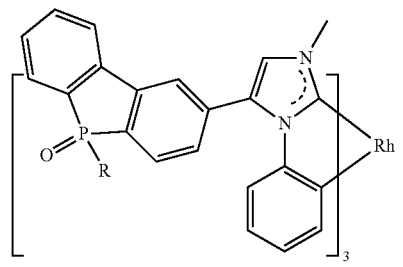
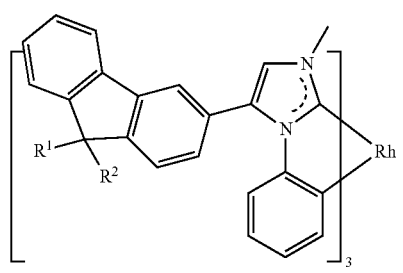
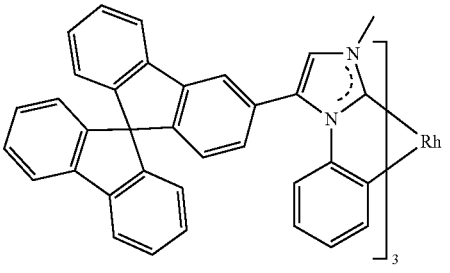
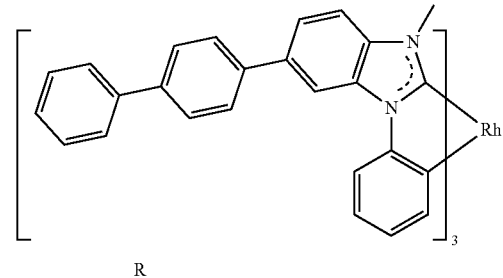
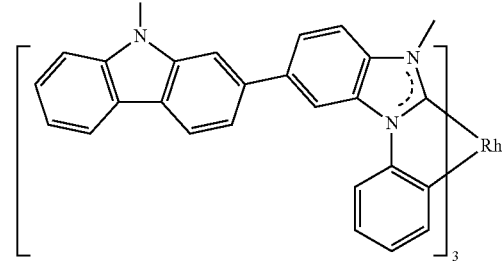

-continued
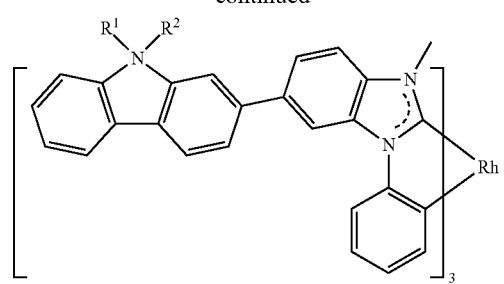
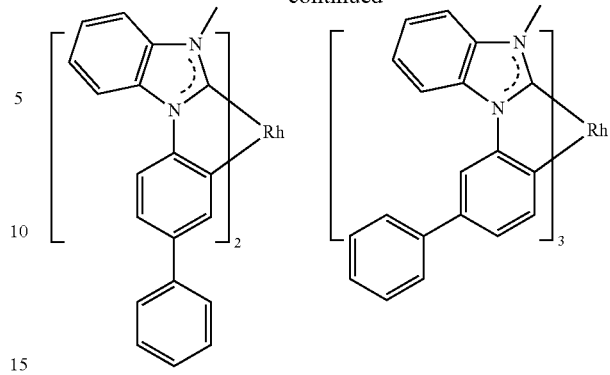
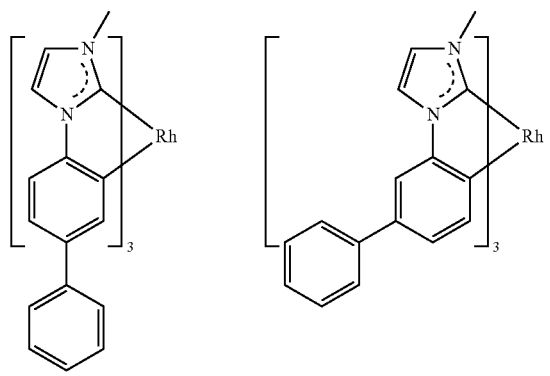
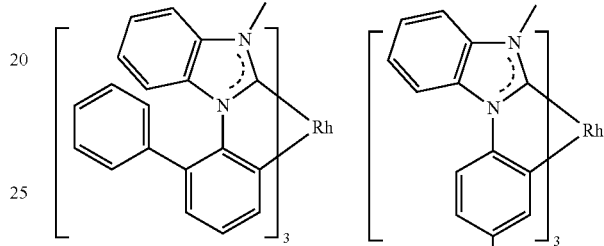
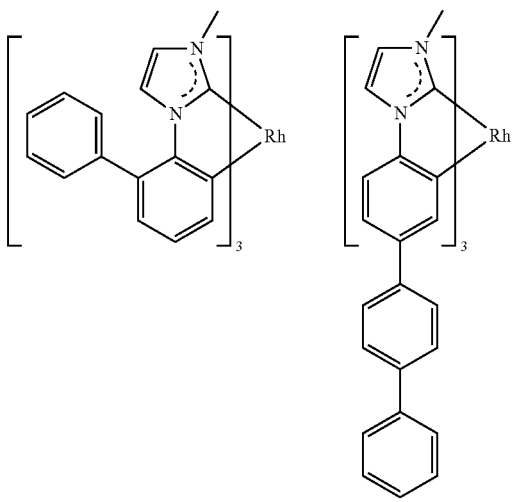
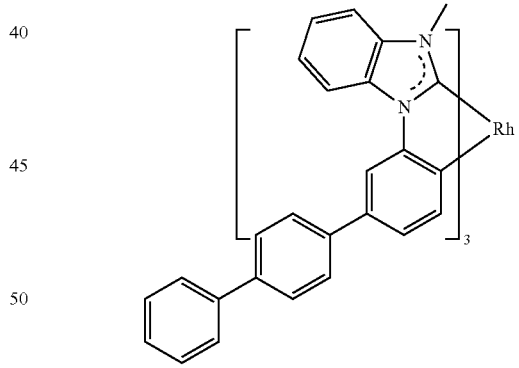
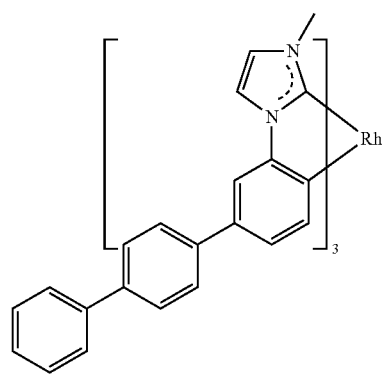
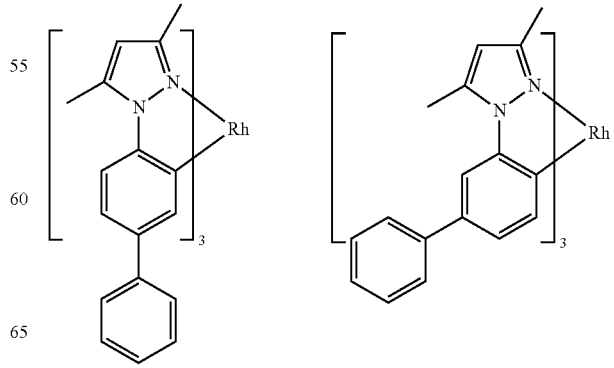

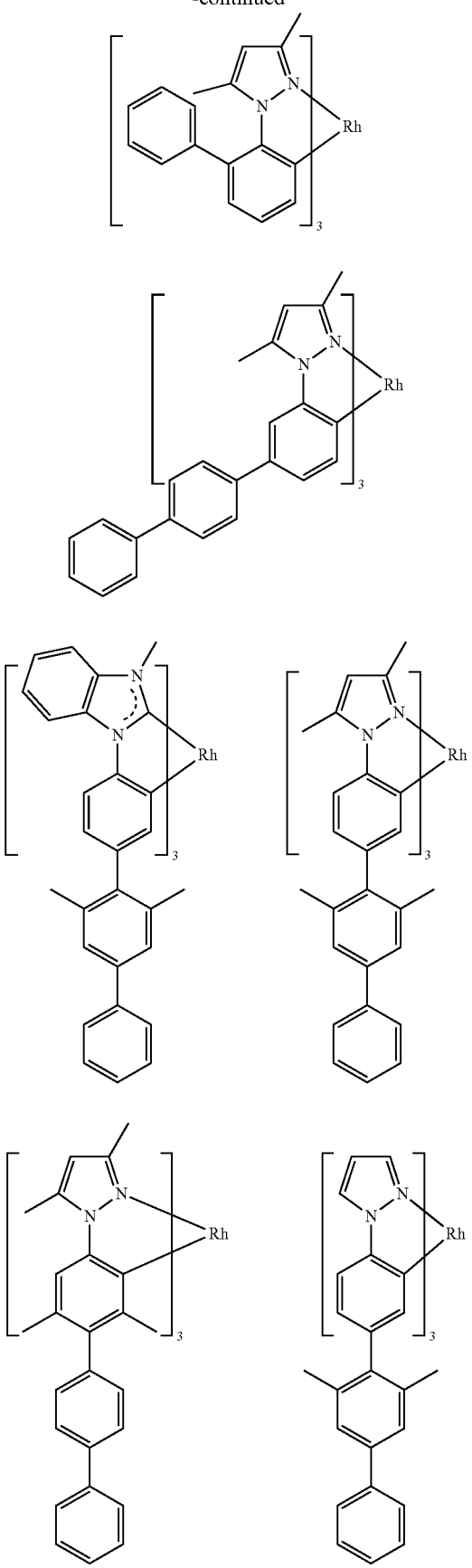
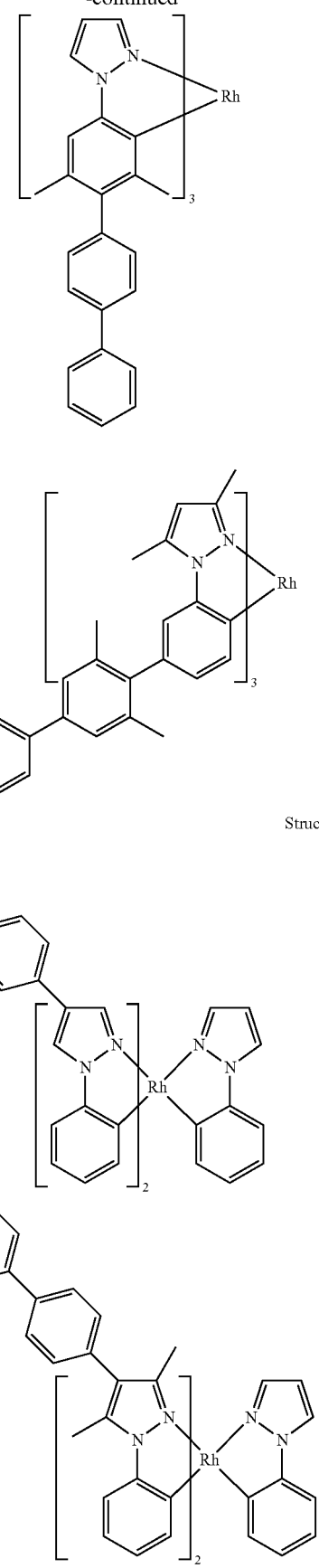
Structures Rh-9

267
-continued
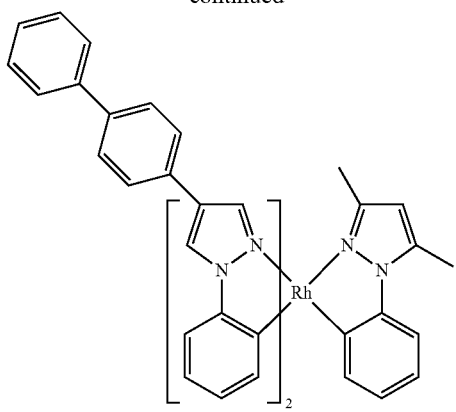
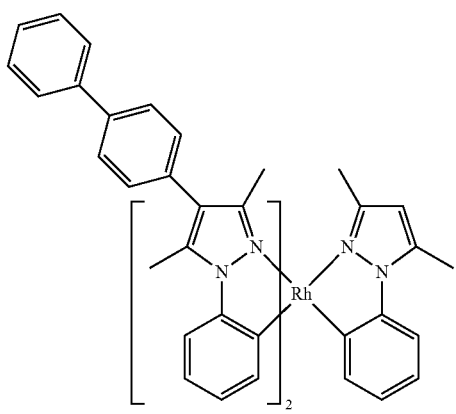
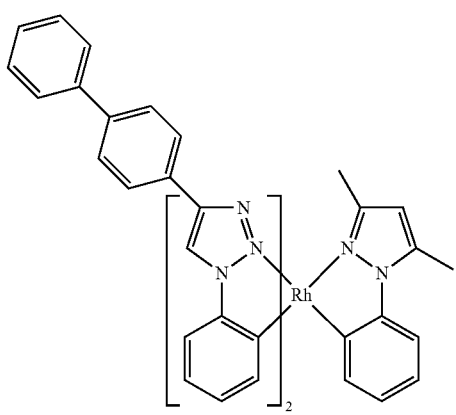
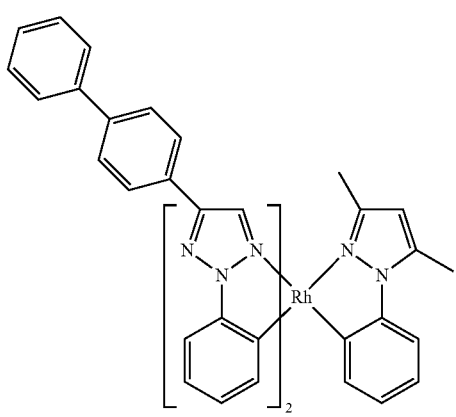
268
-continued
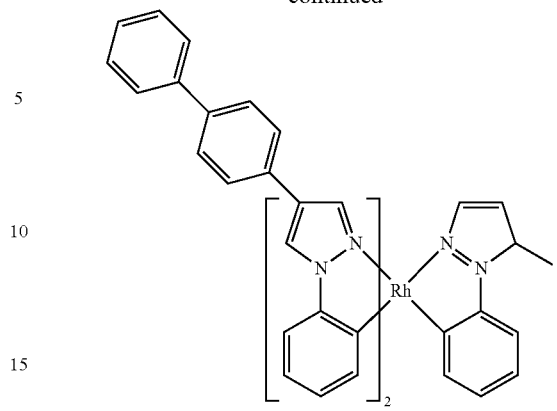
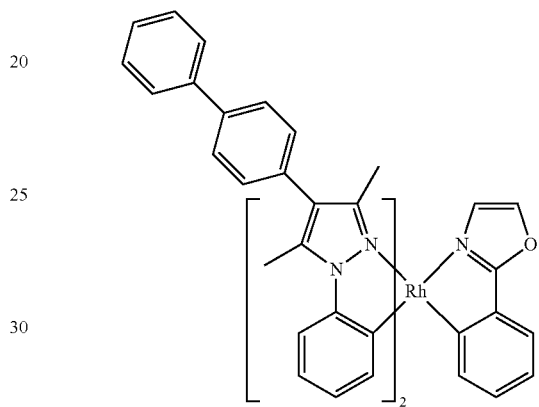
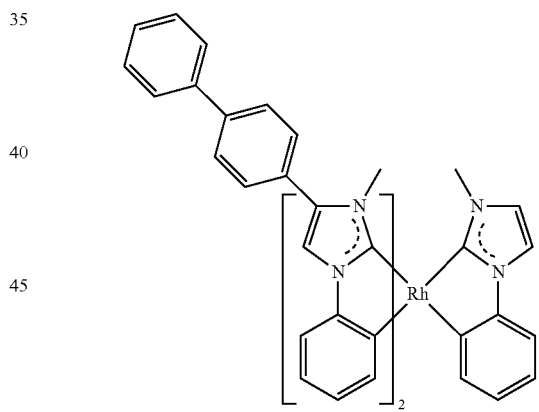
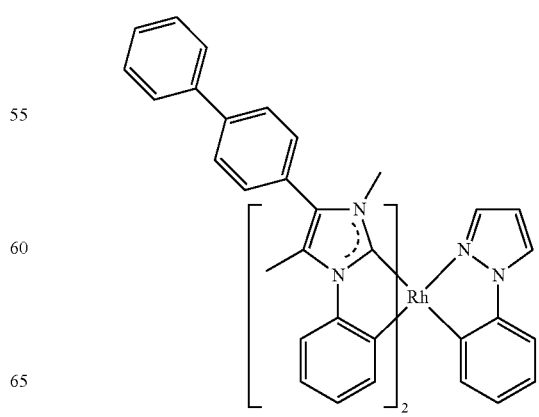

269
-continued
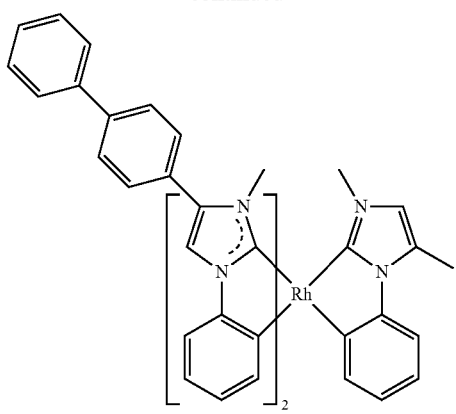
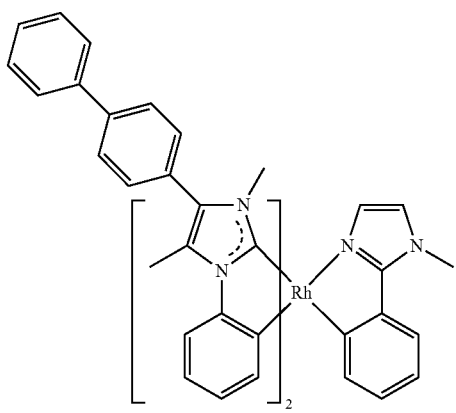
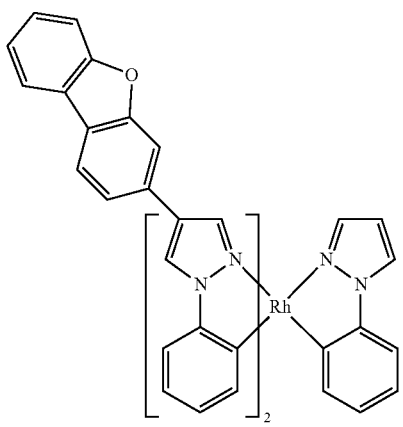
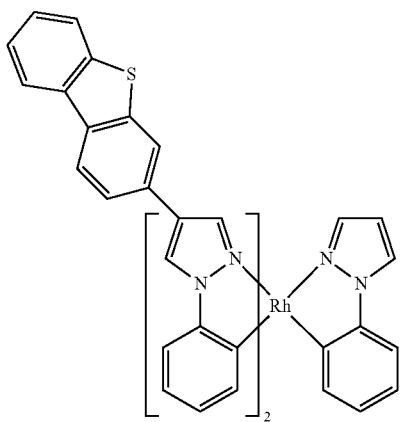
270
-continued
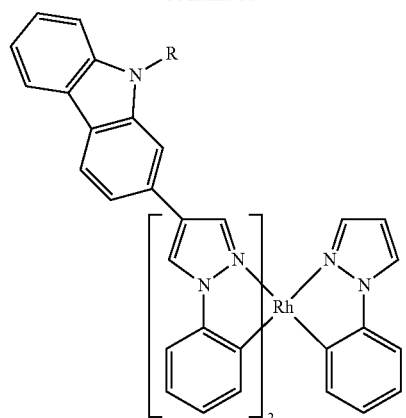
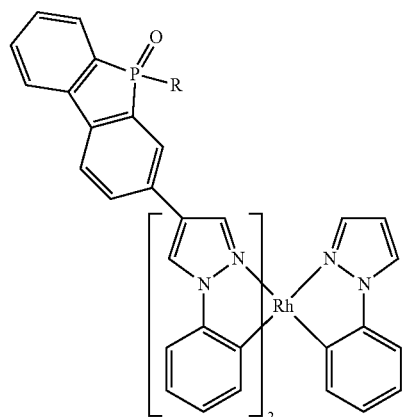
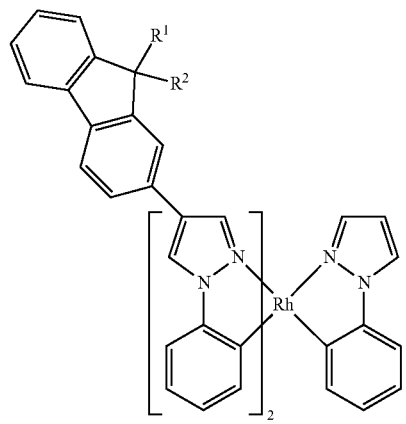

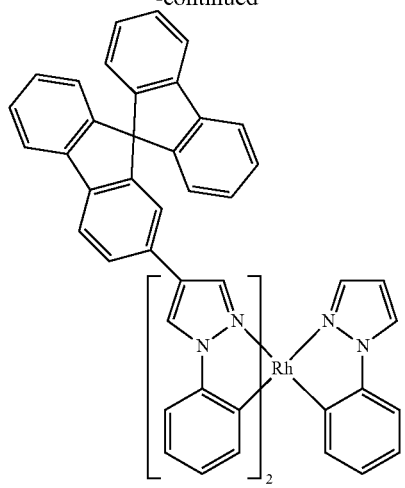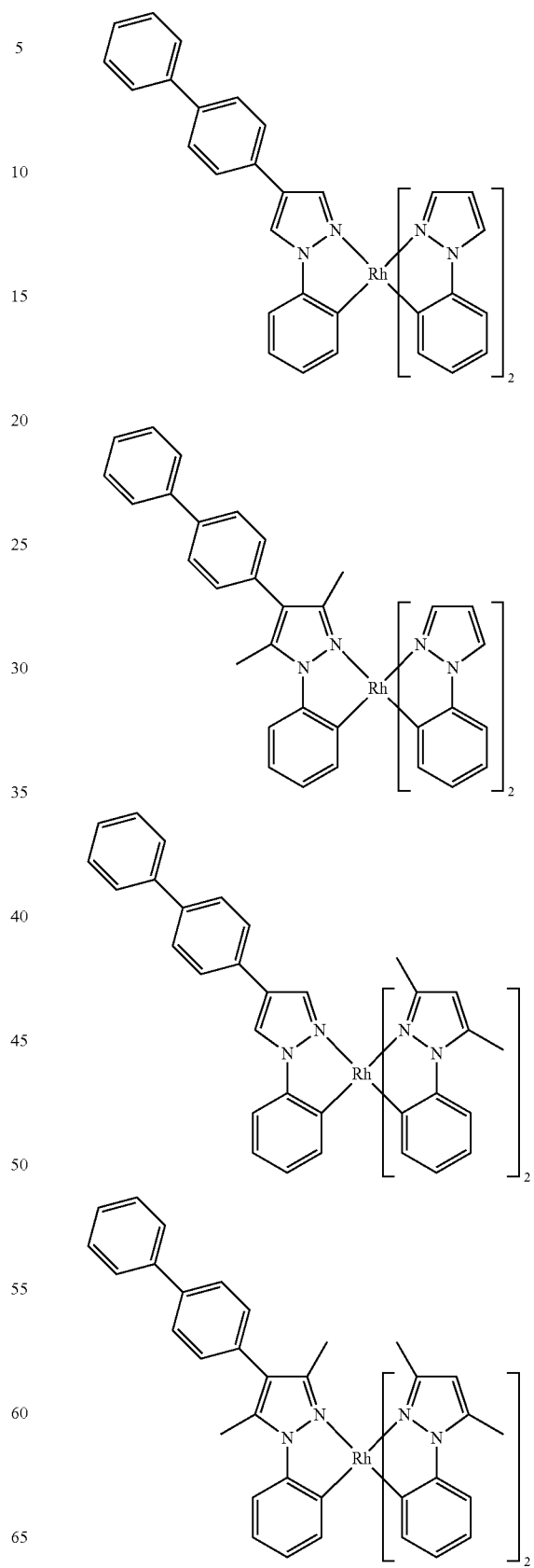
Structures Rh-10

-continued
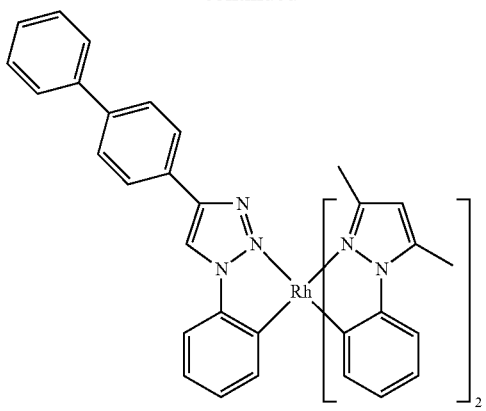
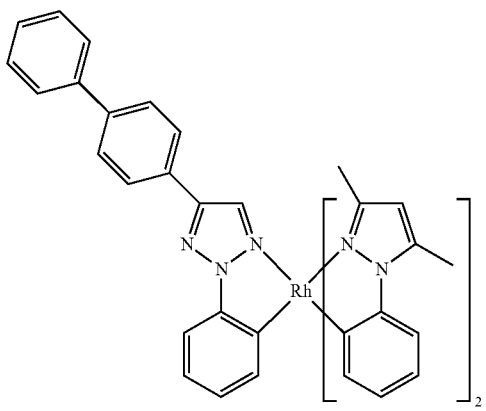
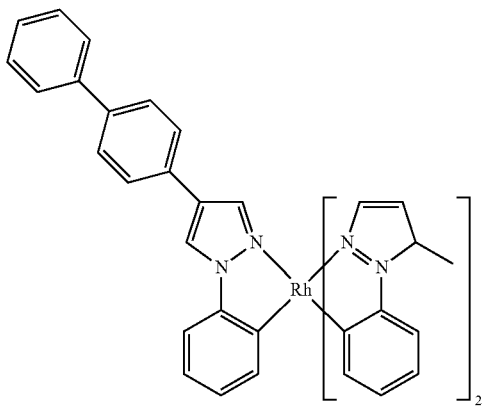
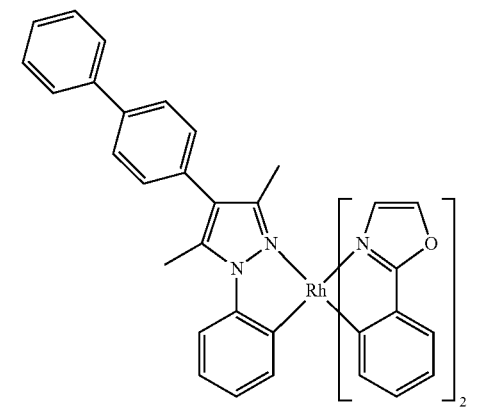
-continued
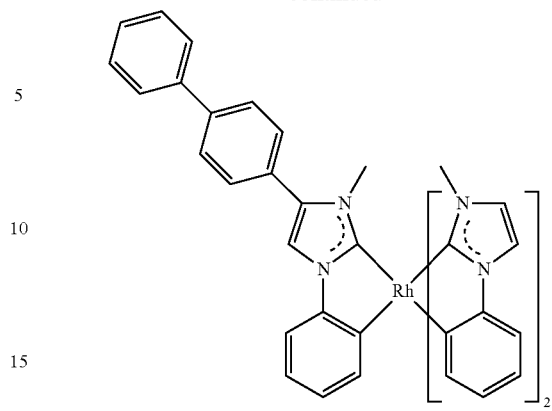
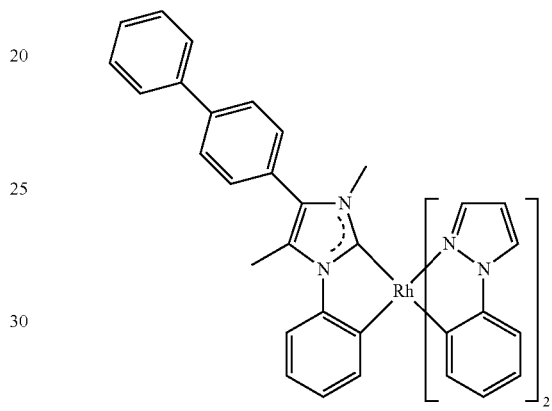

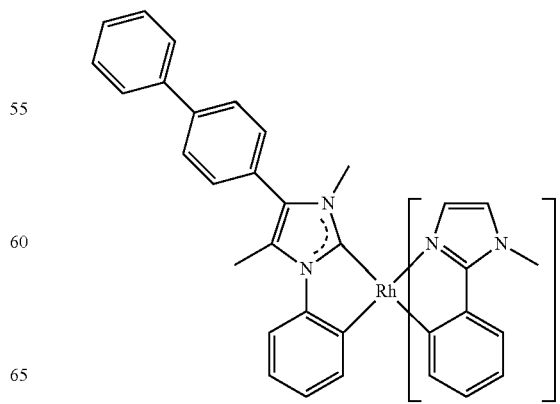

275
-continued
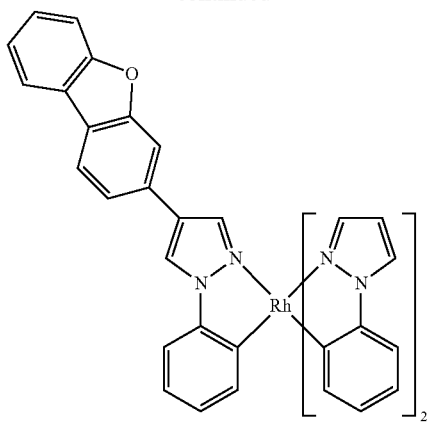
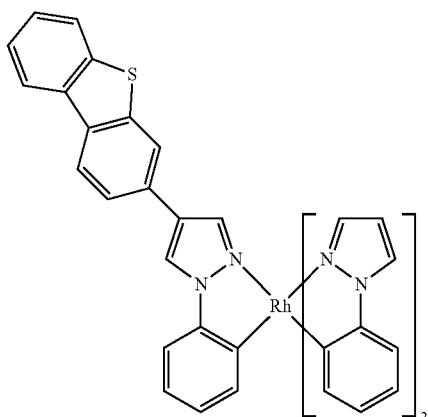
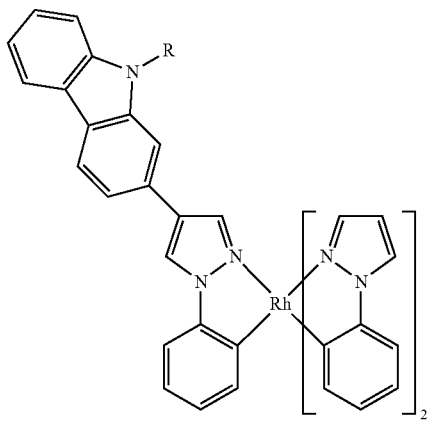
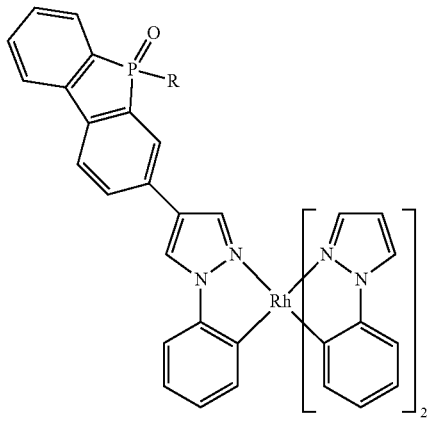
276
-continued
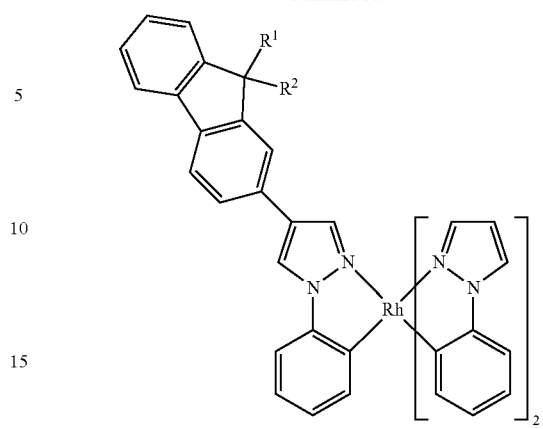
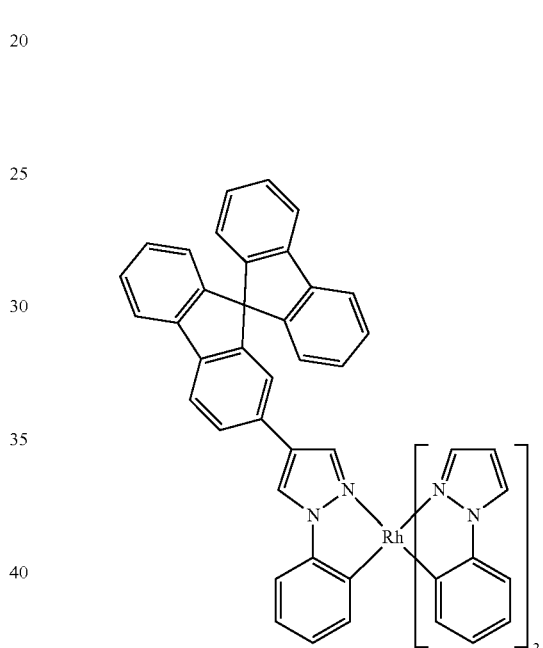
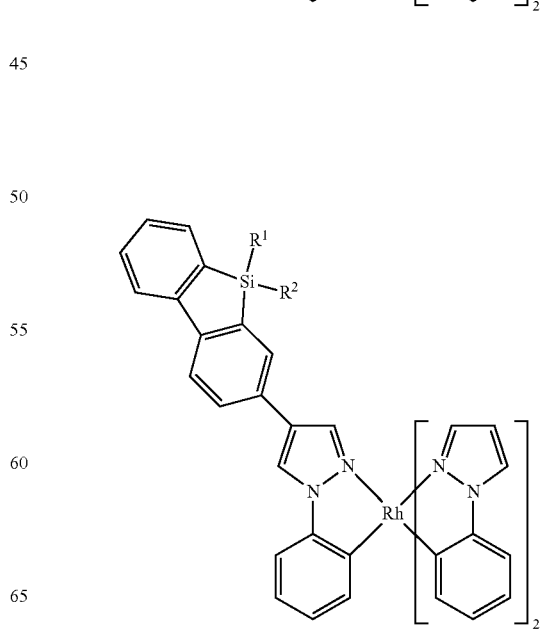

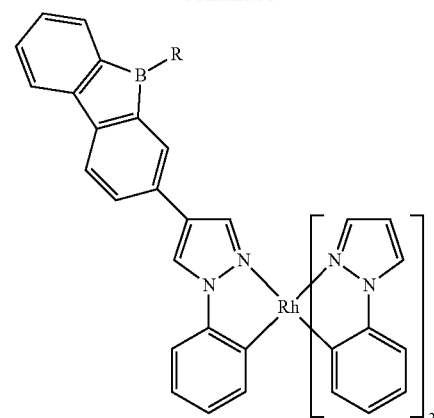
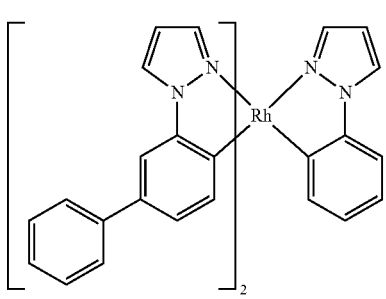
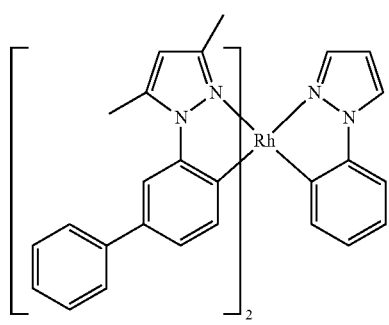
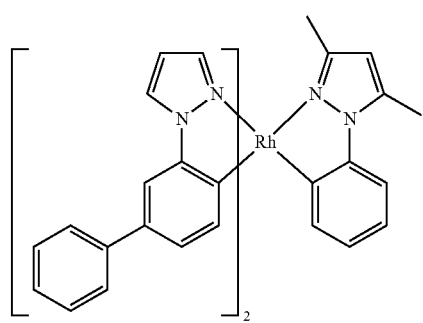
Structures Rh-11
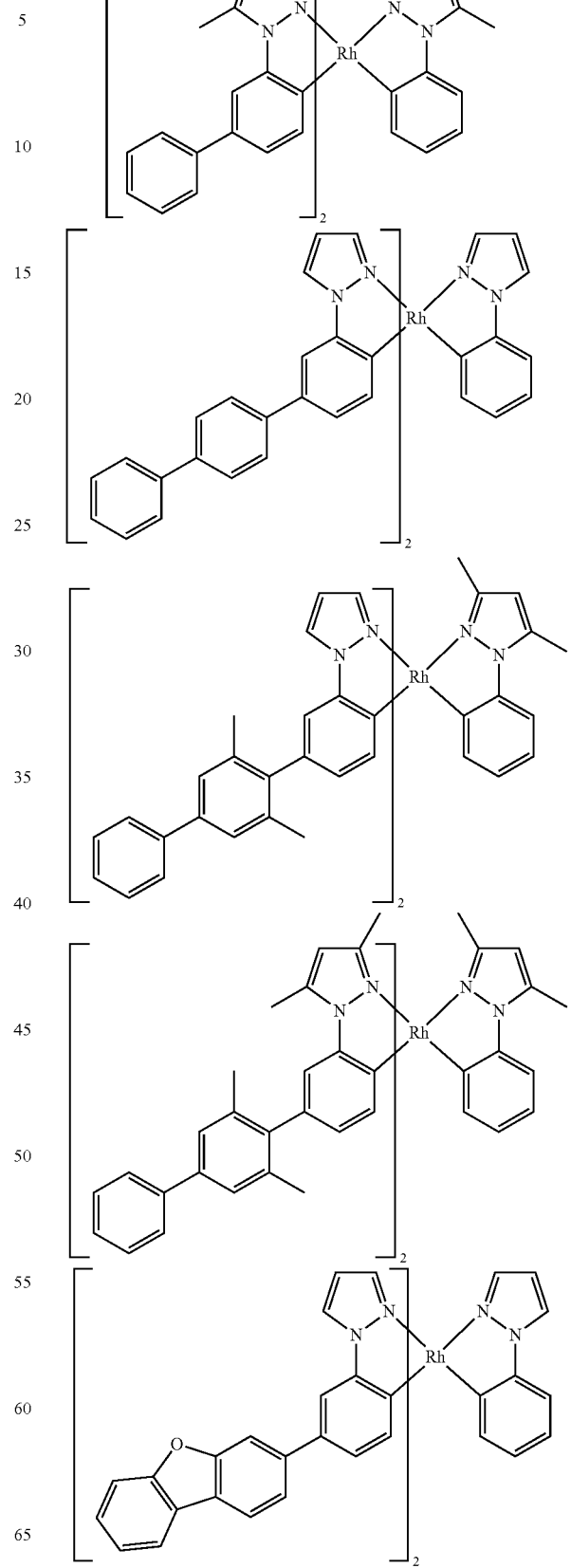

279
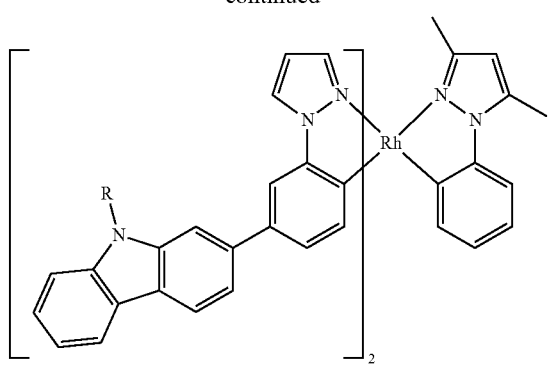
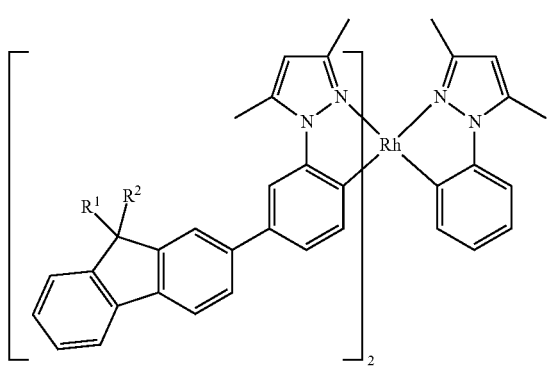
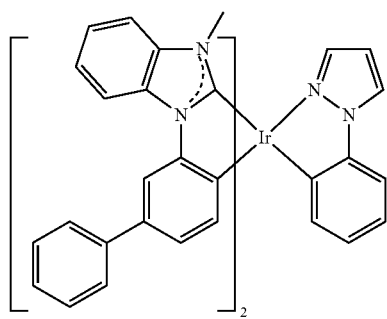
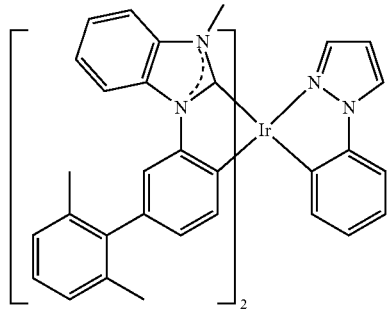
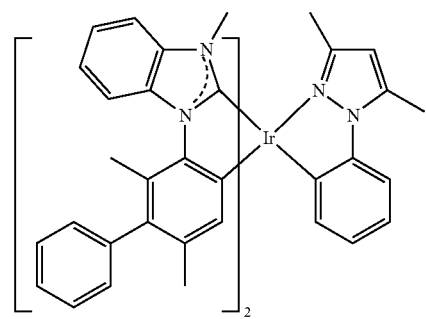
280
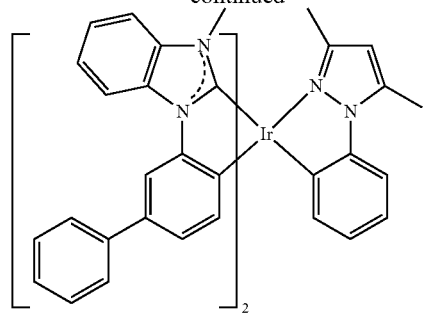
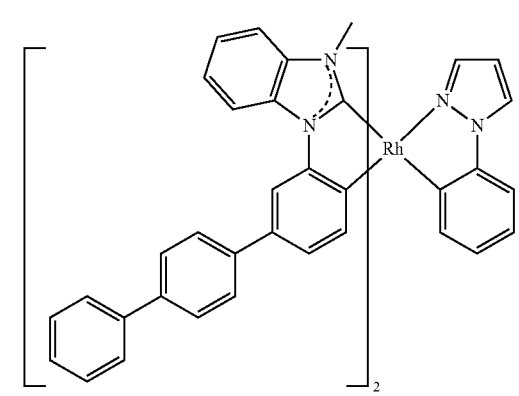
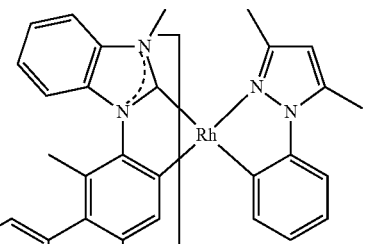

-continued
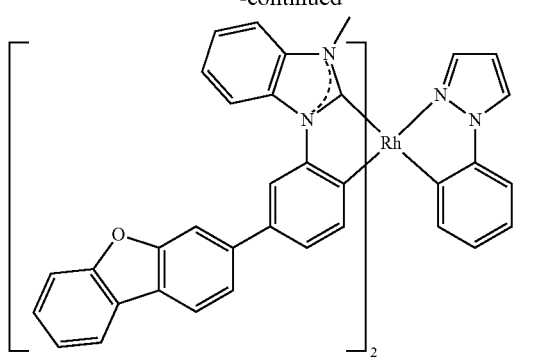
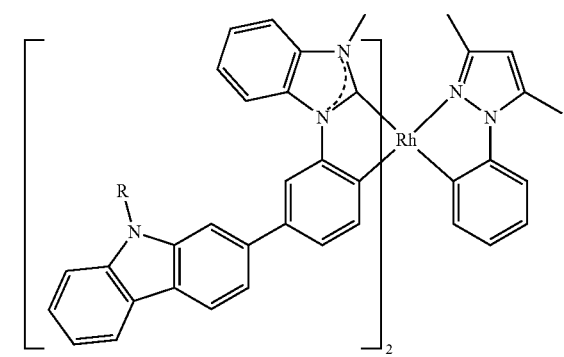
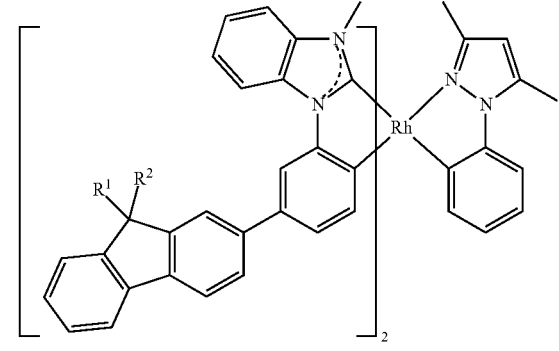
Structures Rh-12
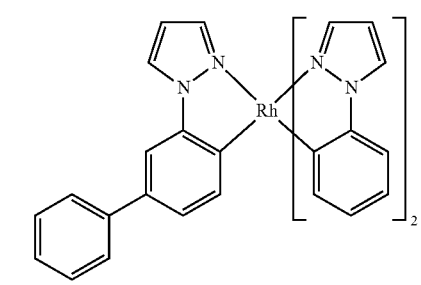
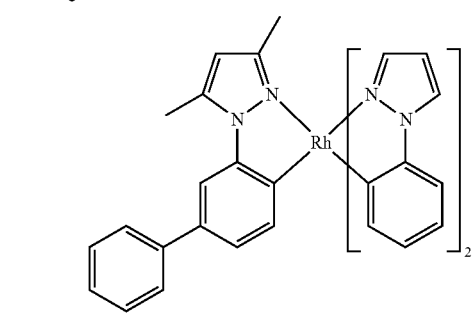
-continued
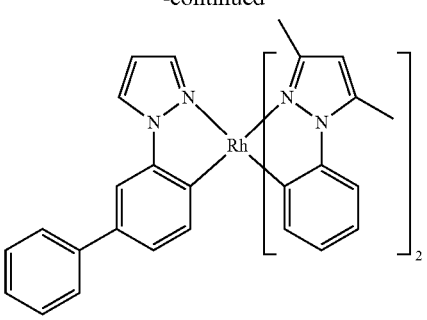
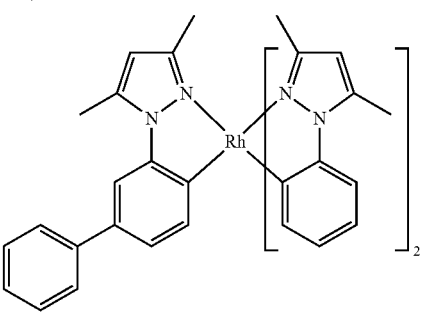
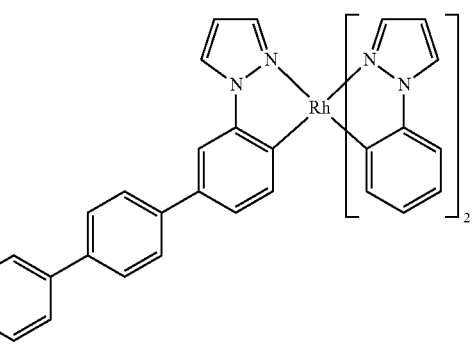
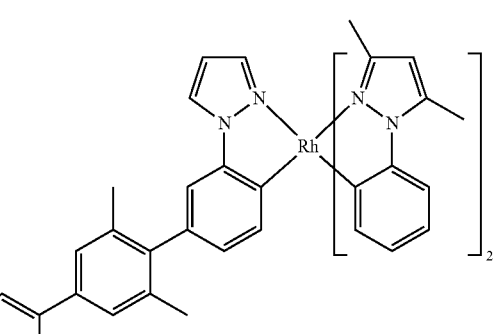
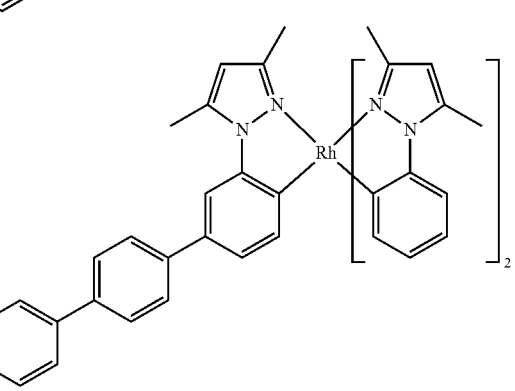

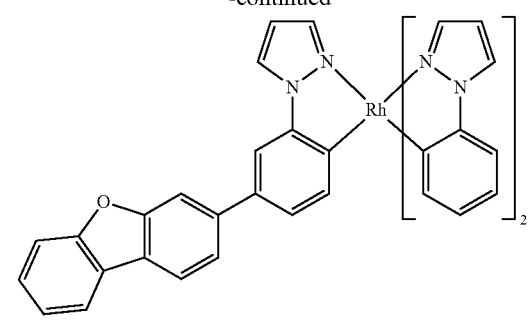
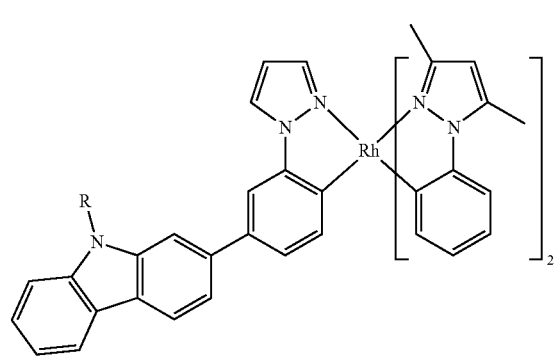
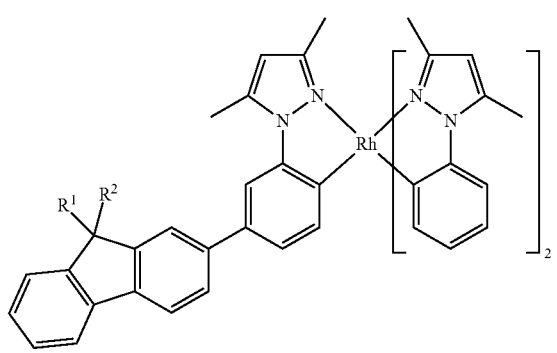
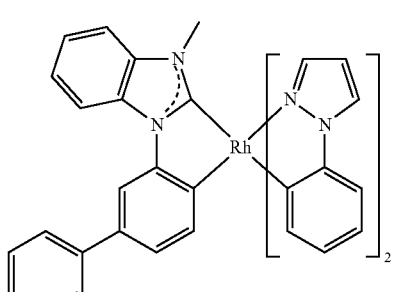
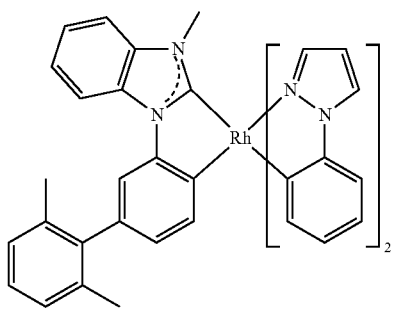
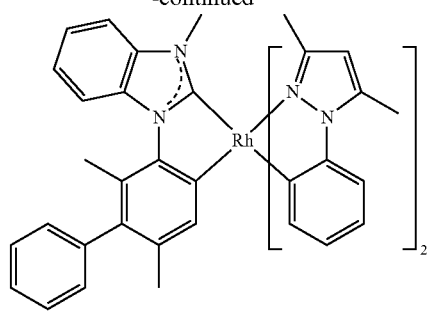
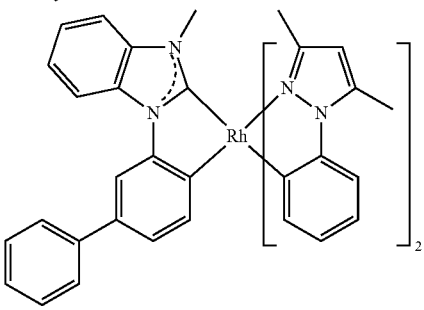
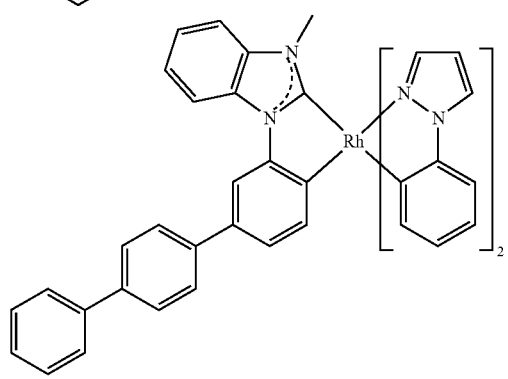
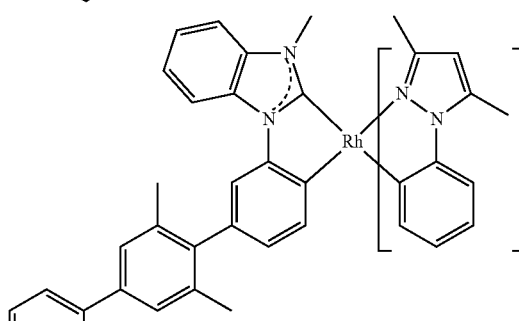
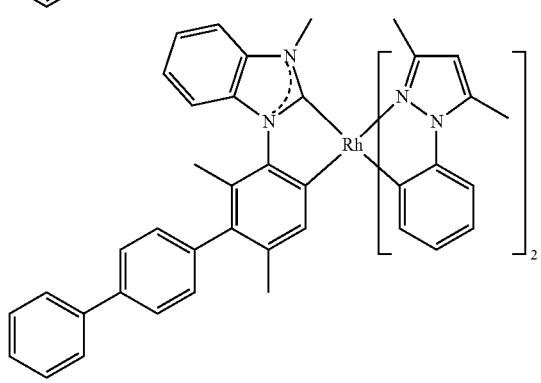

285
-continued
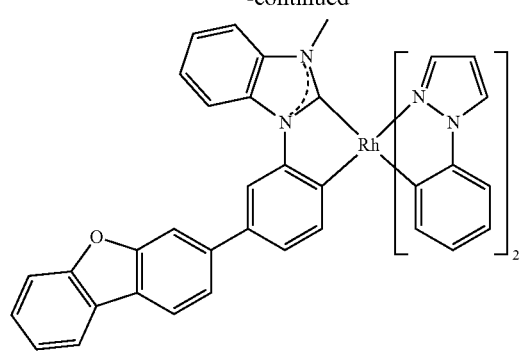
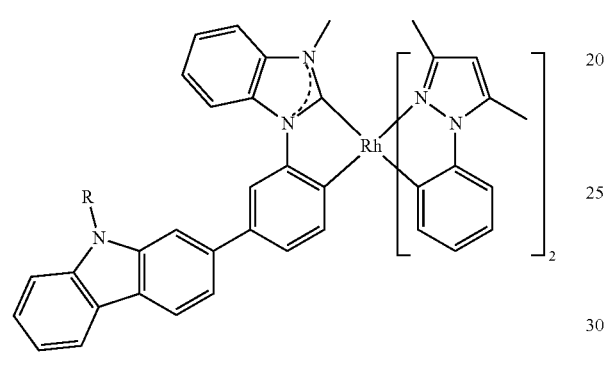
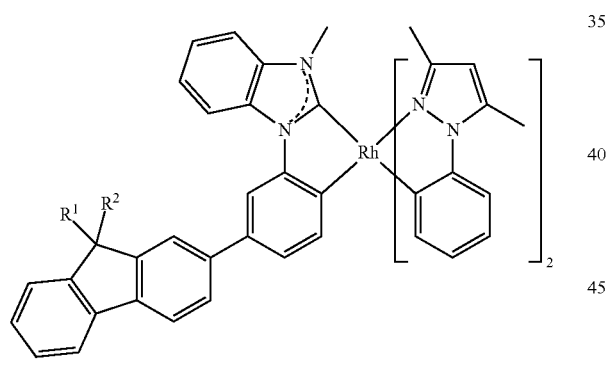
Structures Rh-13
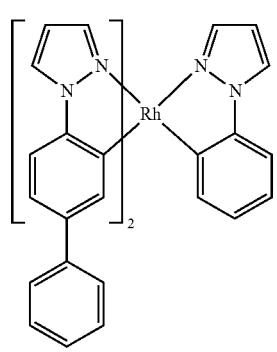
286
-continued
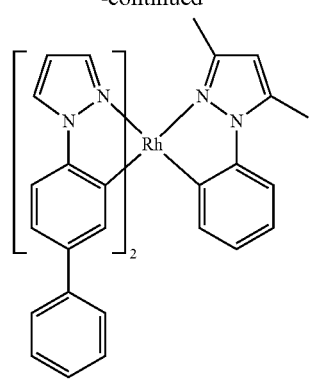
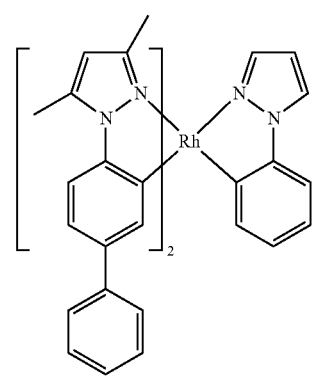
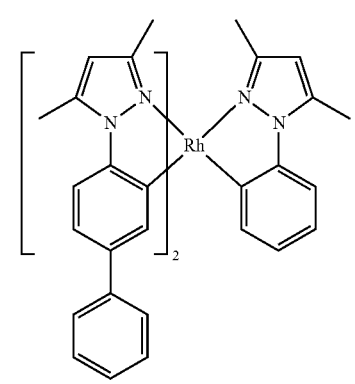
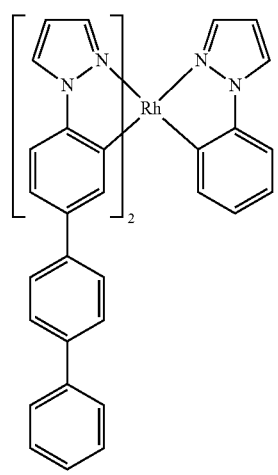

287 -continued
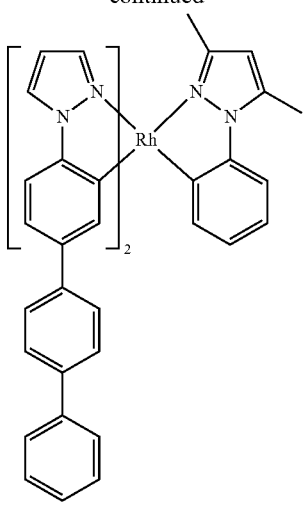
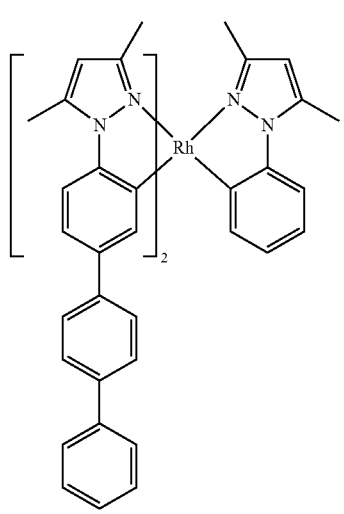
288 -continued
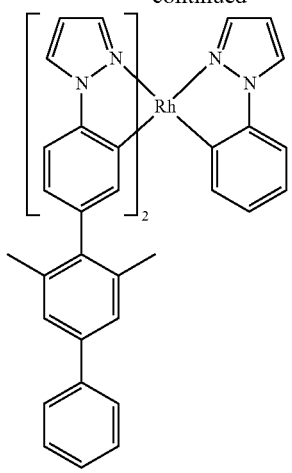
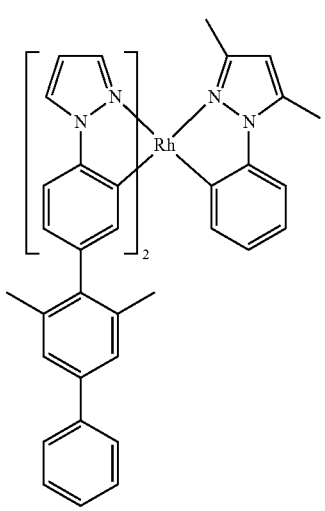
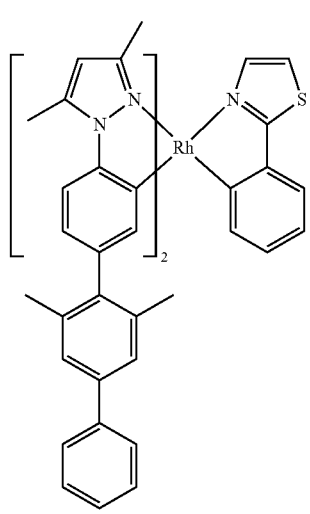

289
-continued
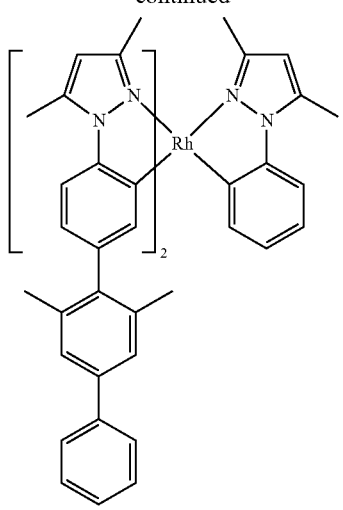
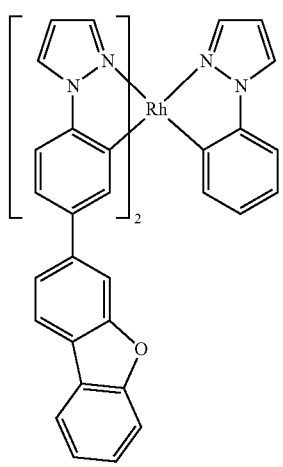
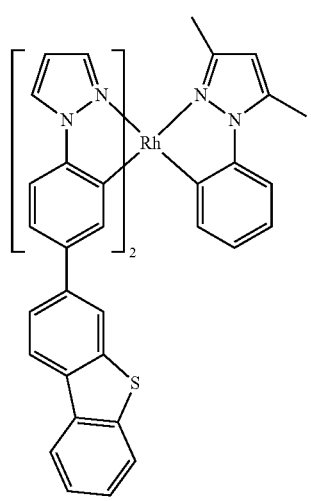
290
-continued
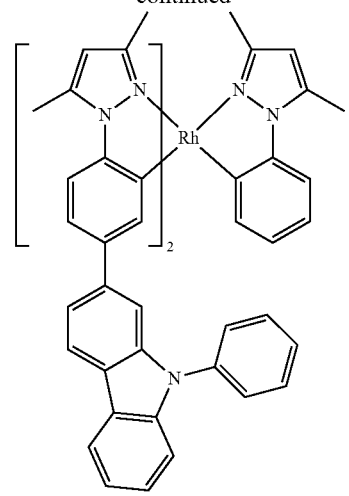
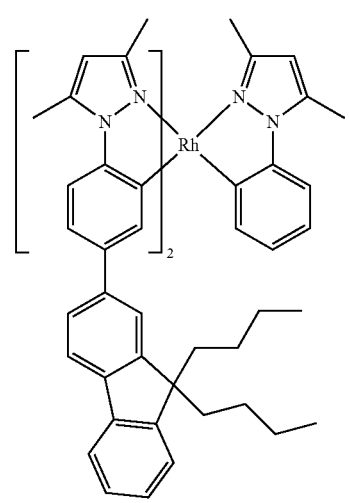
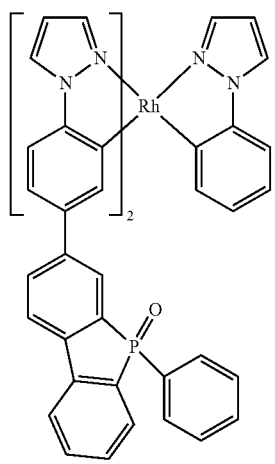

-continued
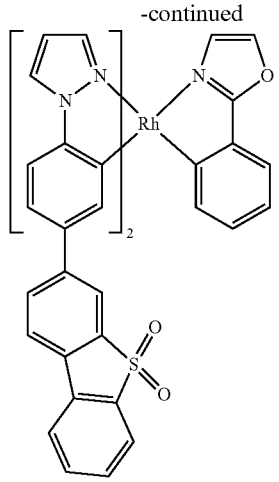
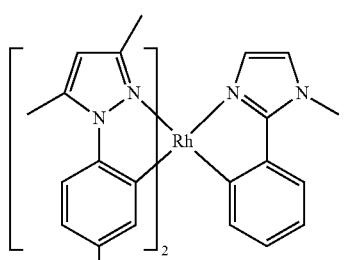
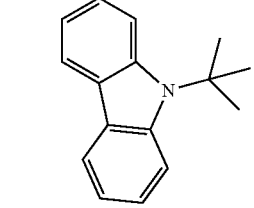
-continued
Structures Rh-14
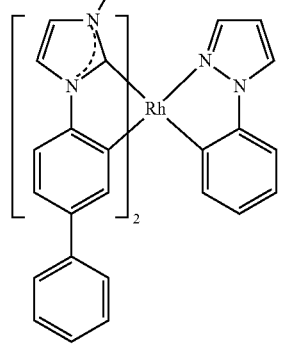
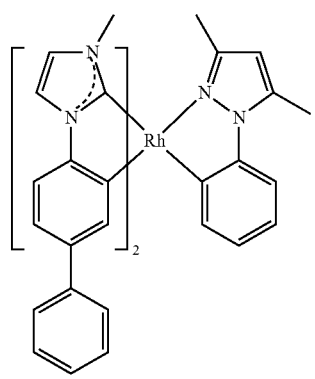
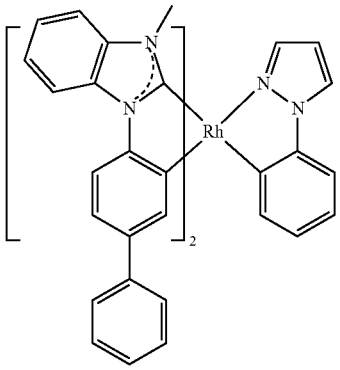
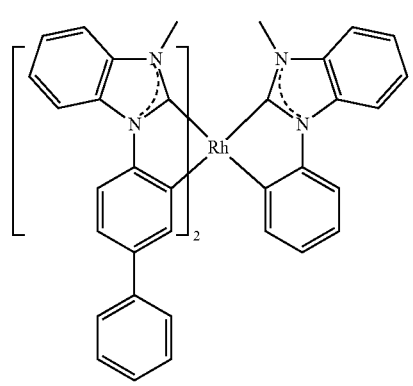
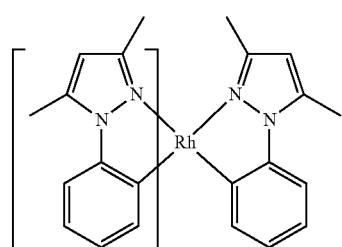
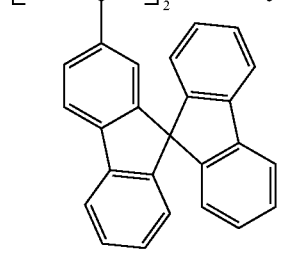

293
-continued
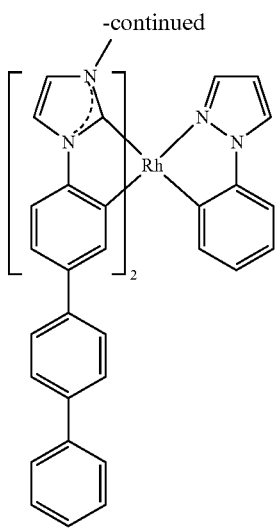
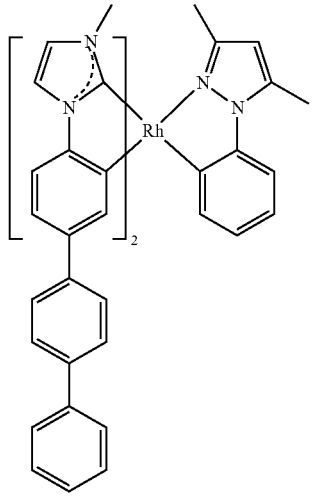
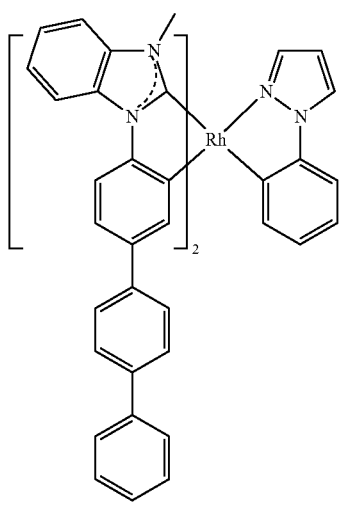
294
-continued
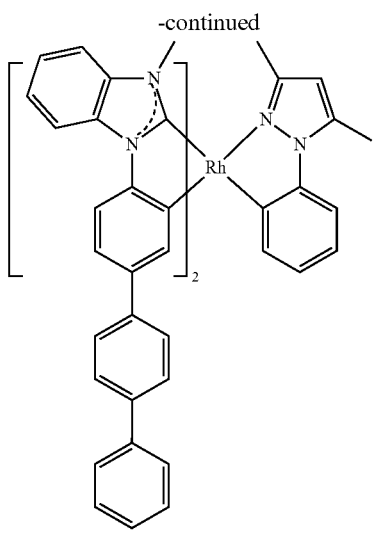
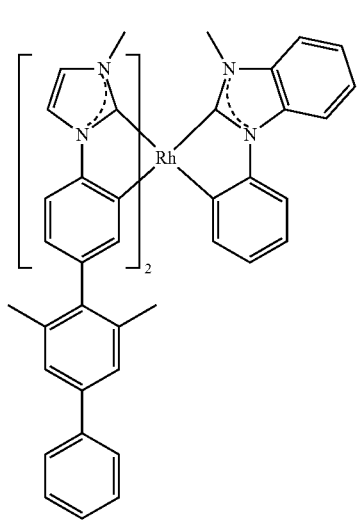
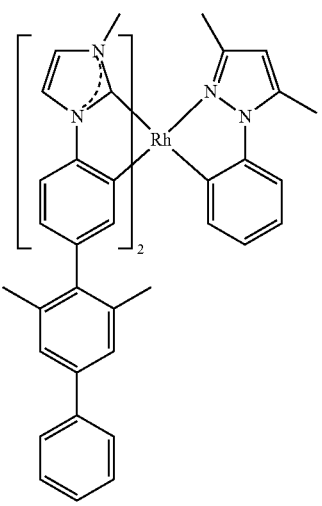

295
-continued
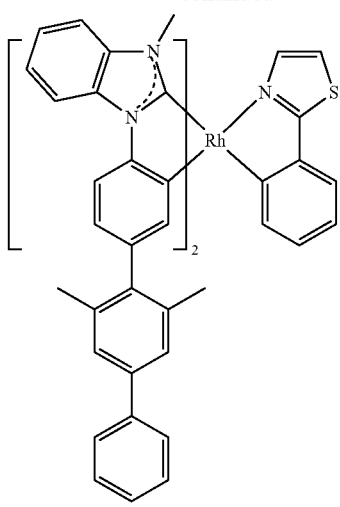
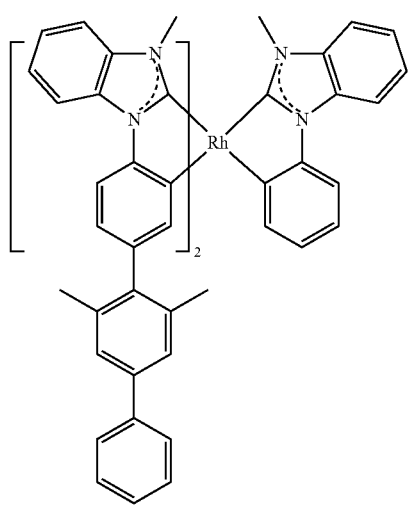
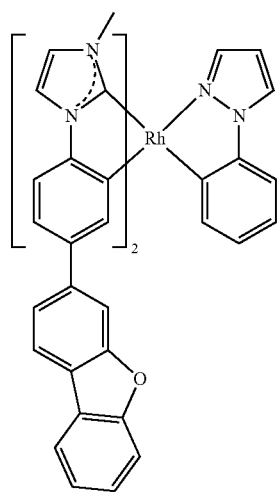
296
-continued
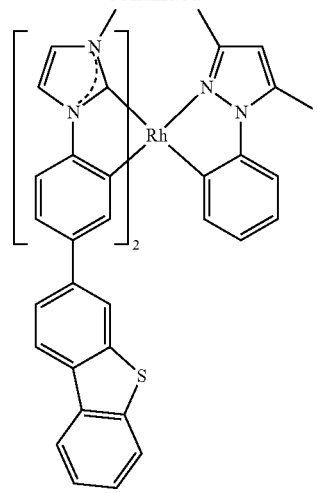
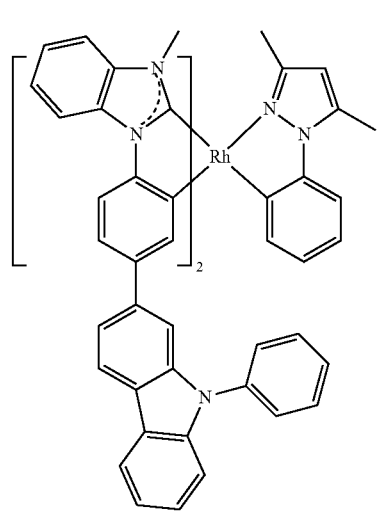
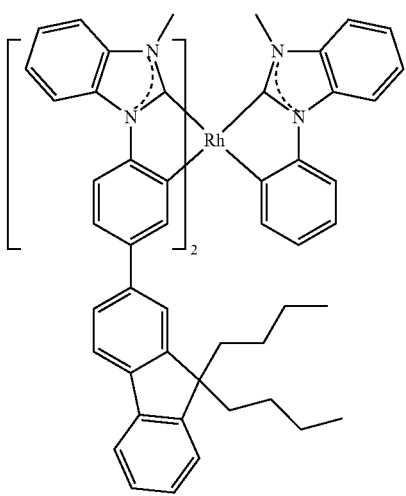

297
-continued
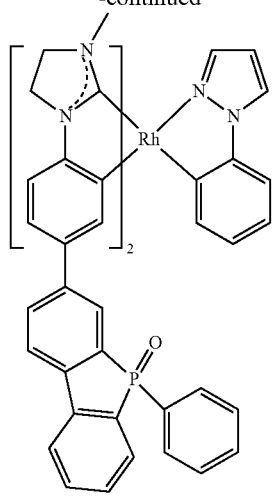
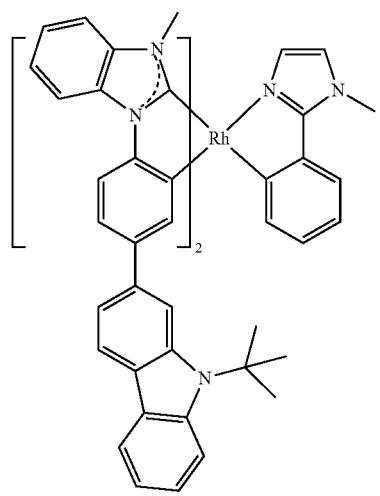
298
-continued
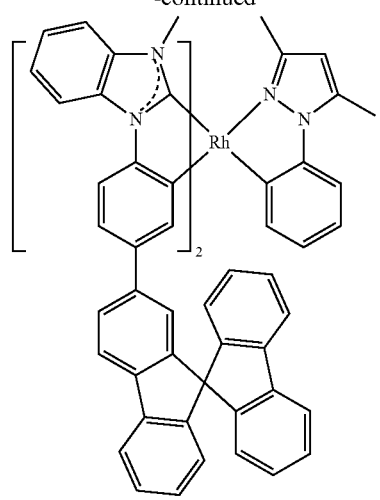
Structures Rh-15
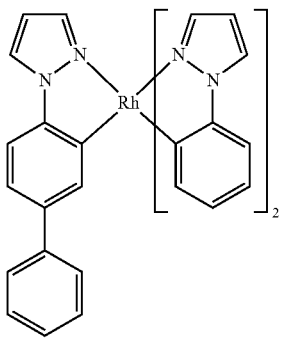
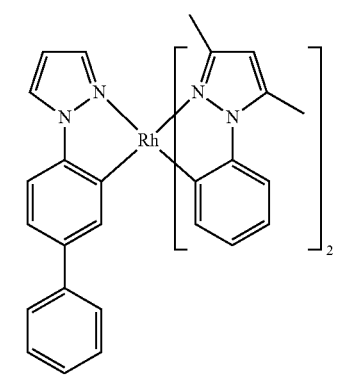
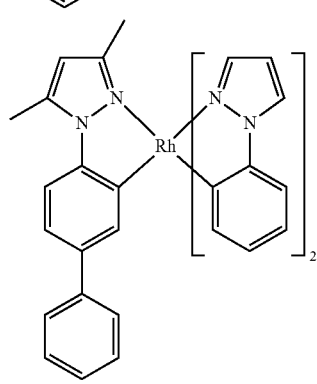

299
-continued
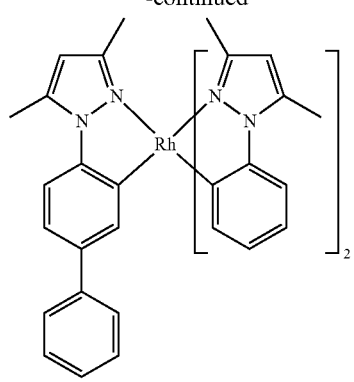
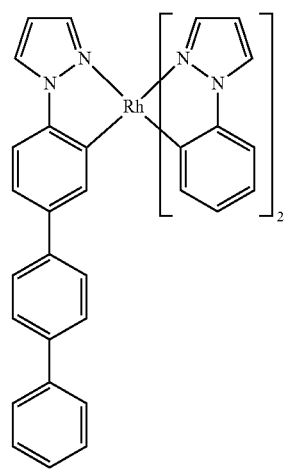
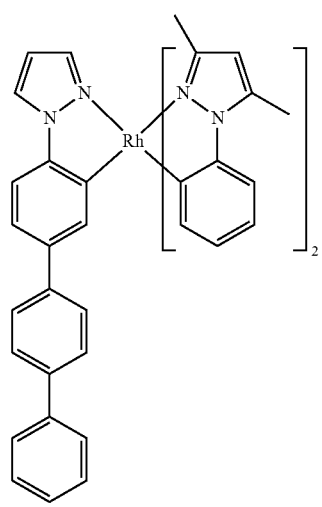
300
-continued
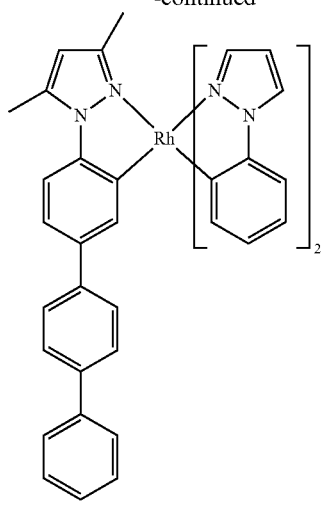
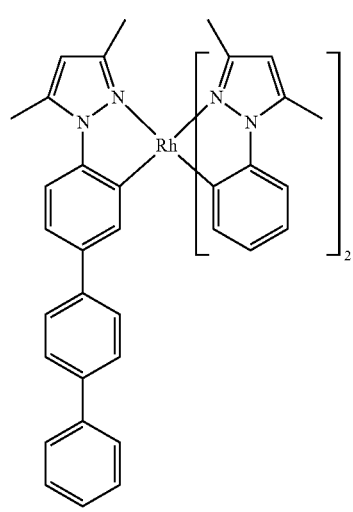
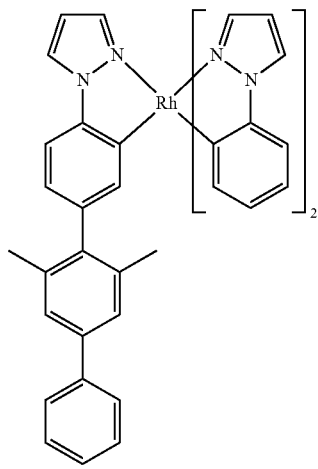

301
-continued
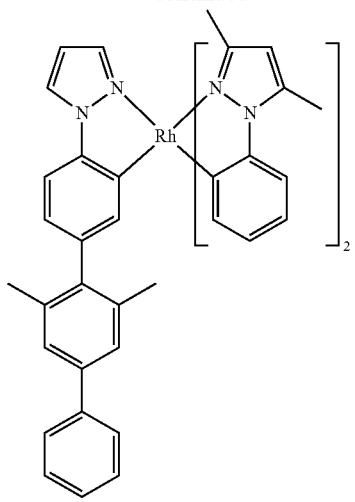
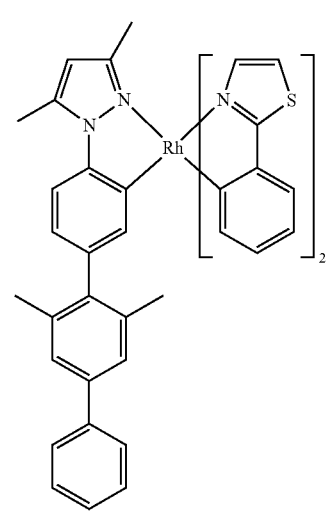
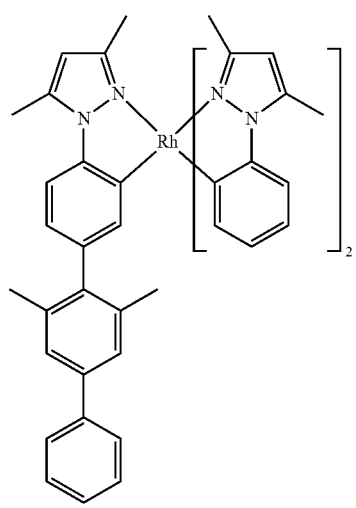
302
-continued
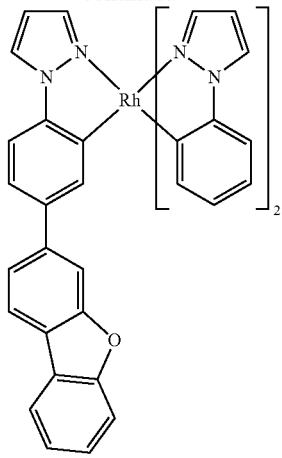
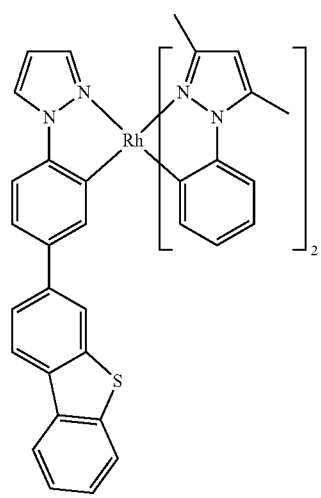
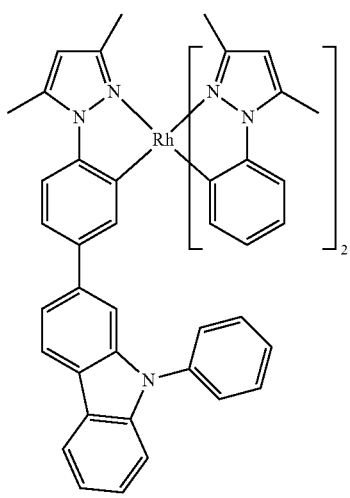

303
-continued
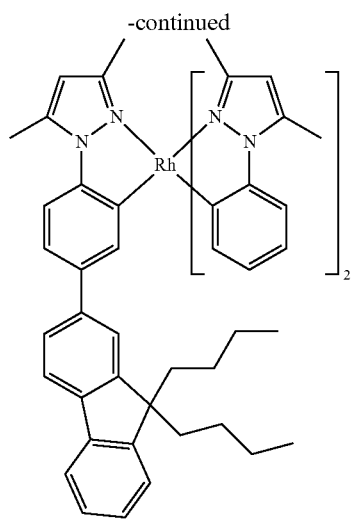
304
-continued
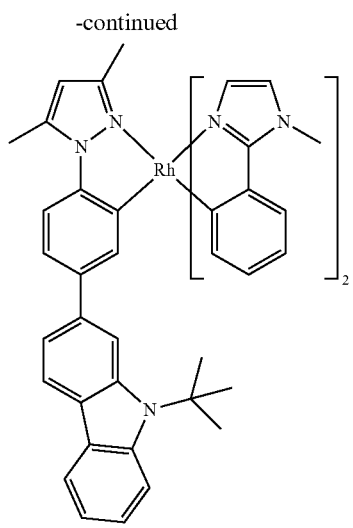
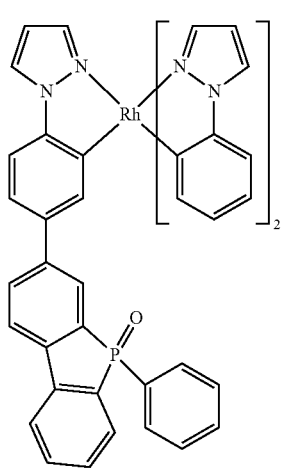
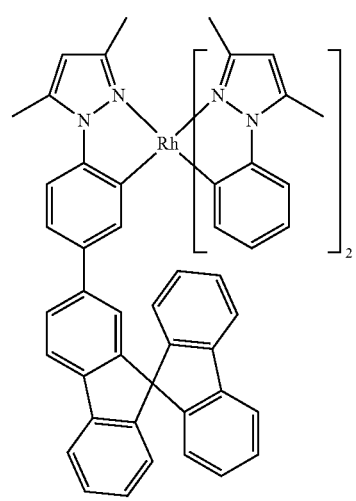
Structures Rh-16
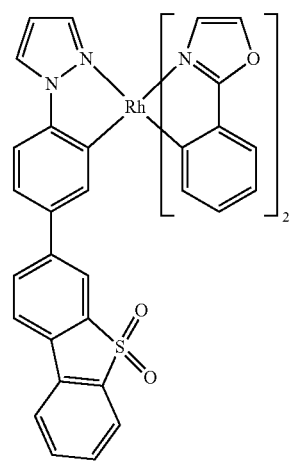

305
-continued
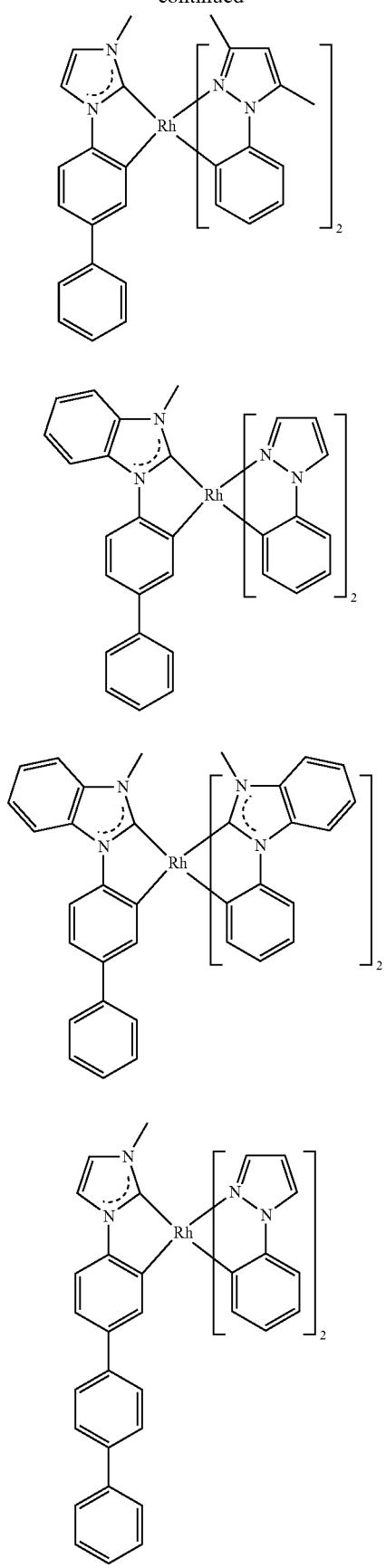
306
-continued
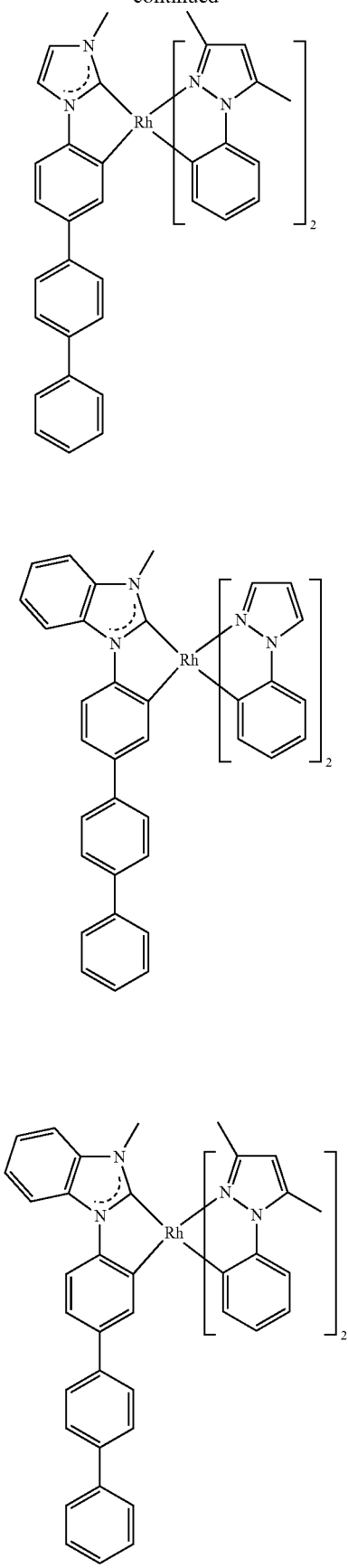

307
-continued
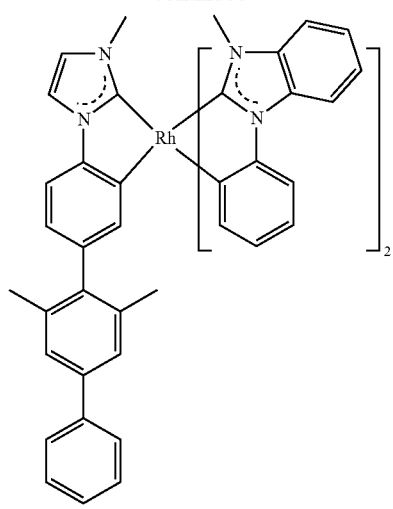
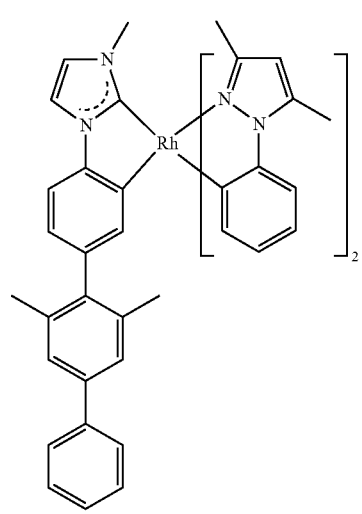
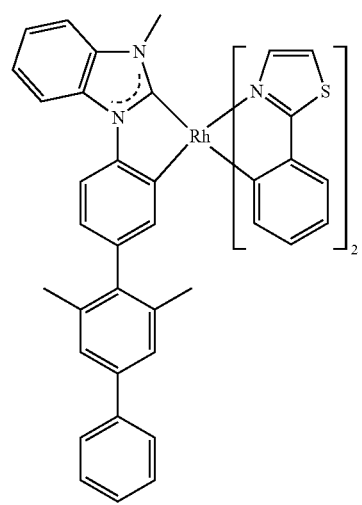
308
-continued
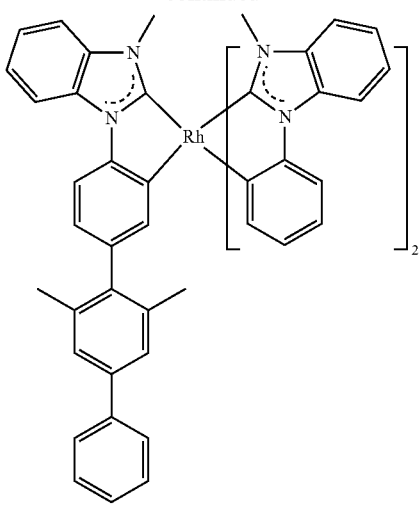
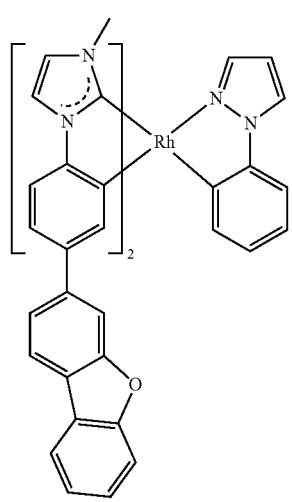
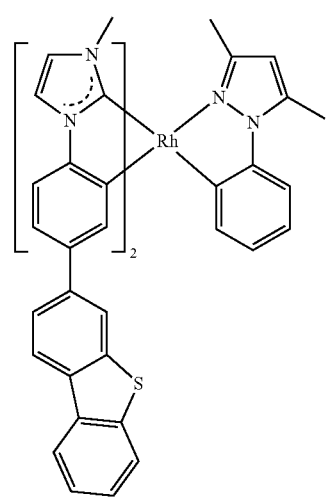

309
-continued
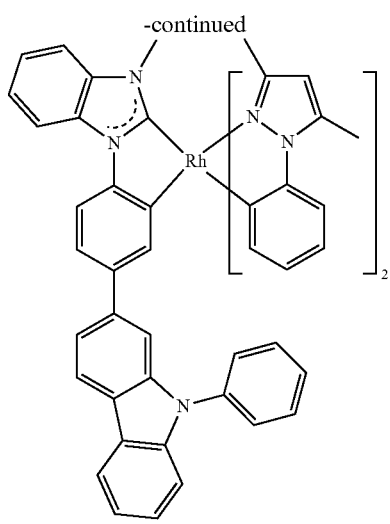
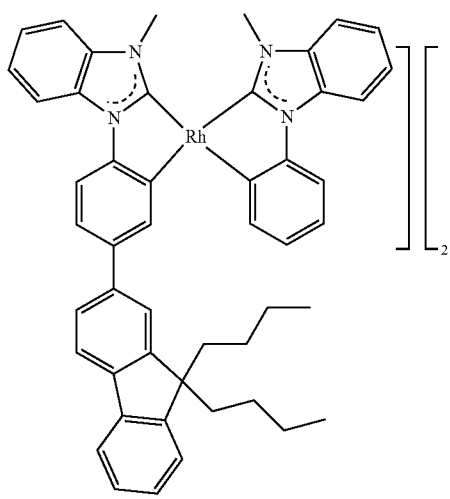
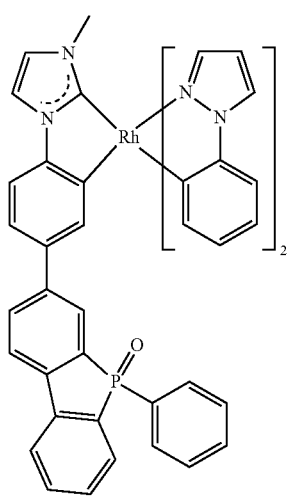
310
-continued
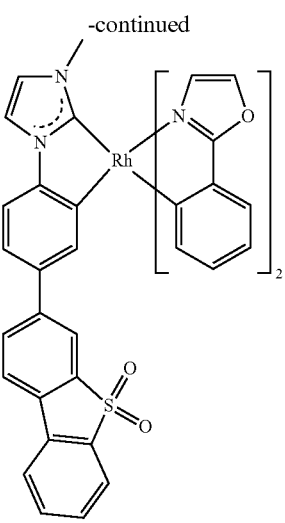
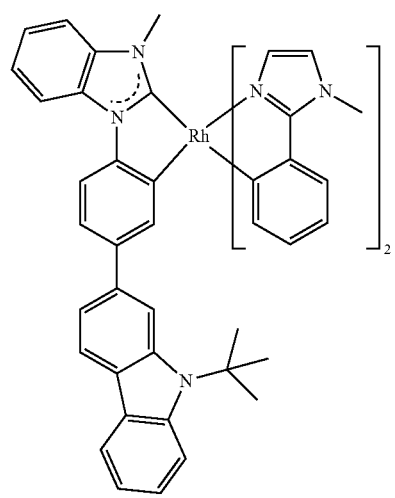
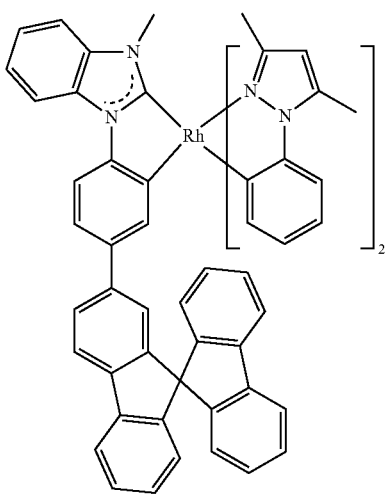

Structures Rh-17
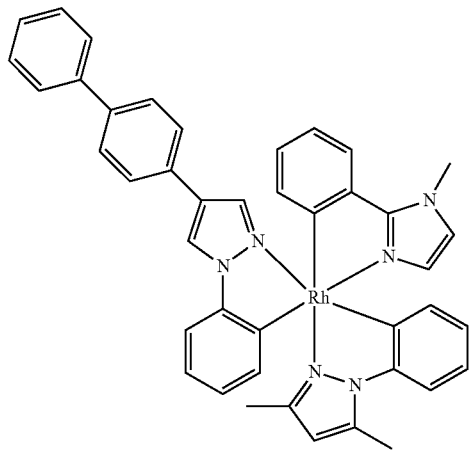
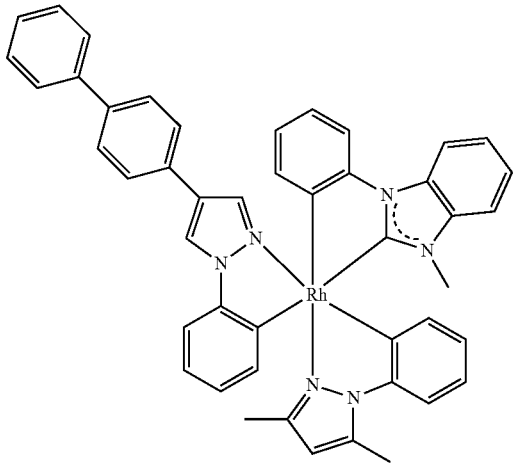
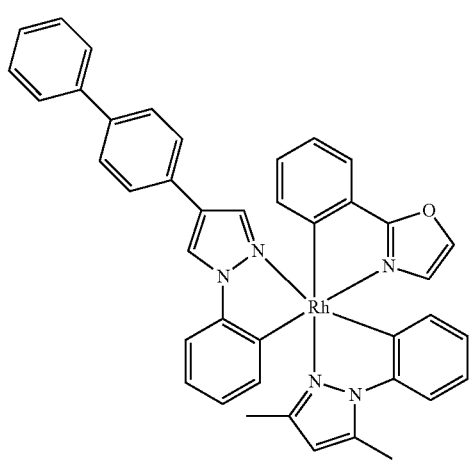
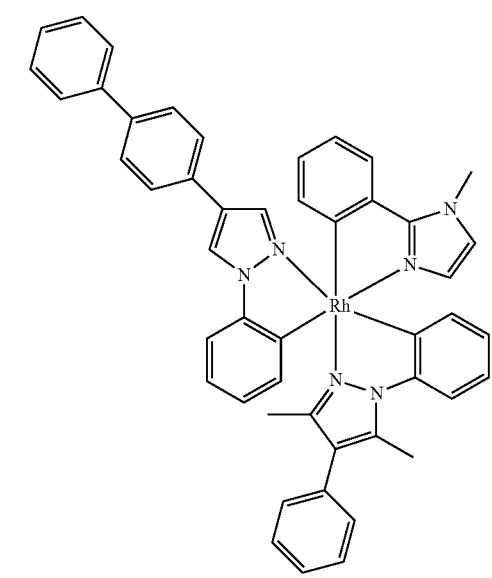
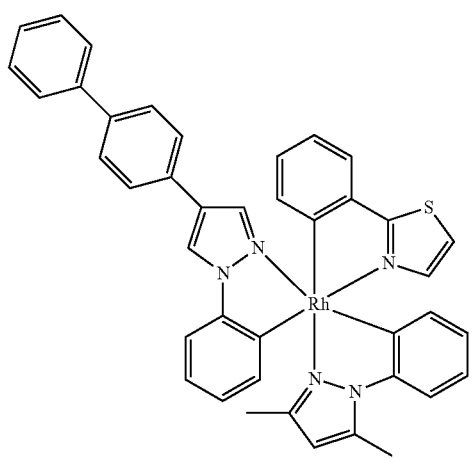
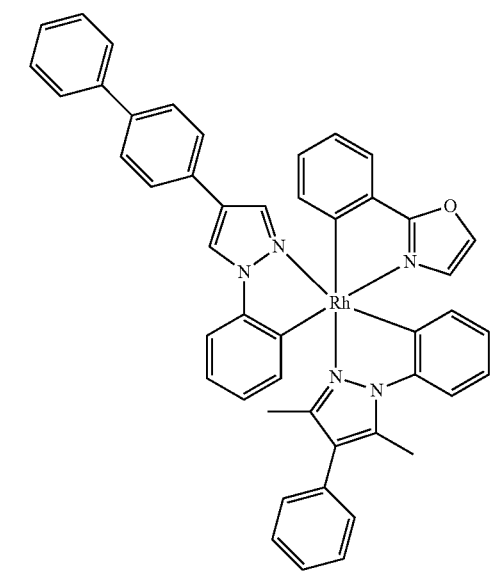

313
-continued
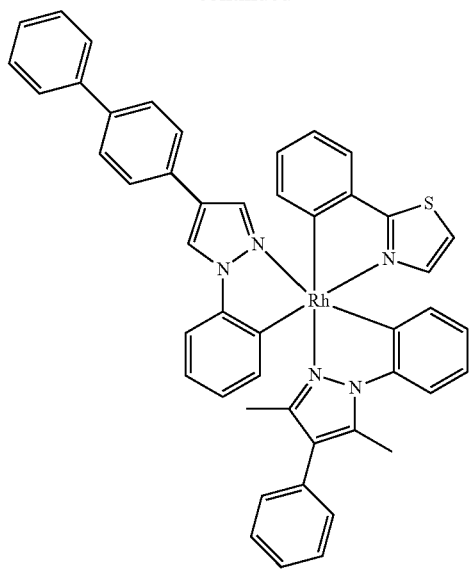
314
-continued
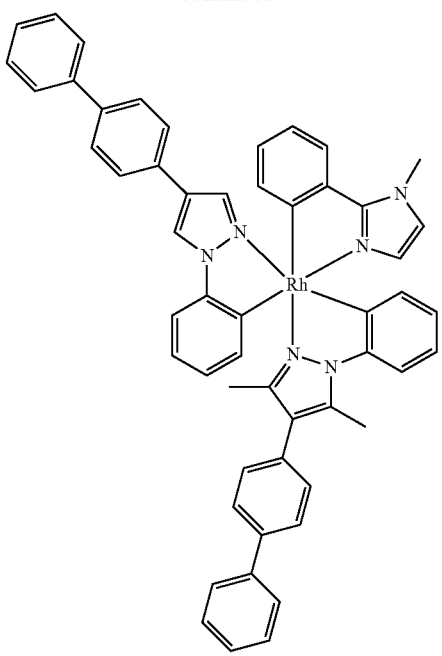
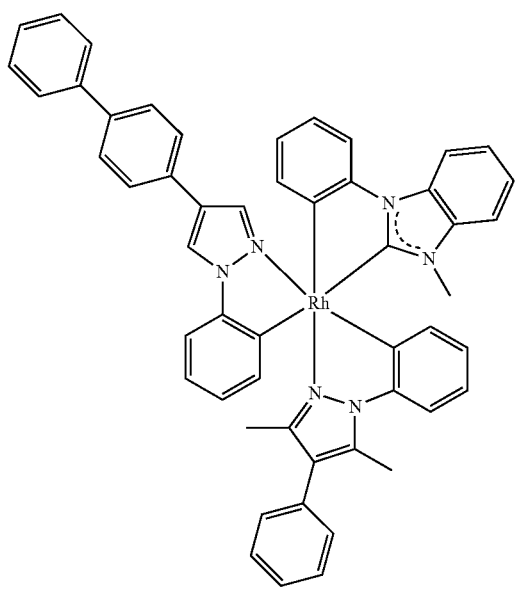

315
-continued
316
-continued
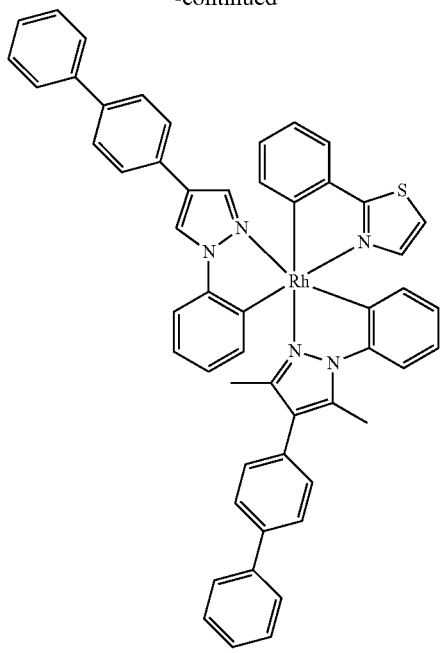
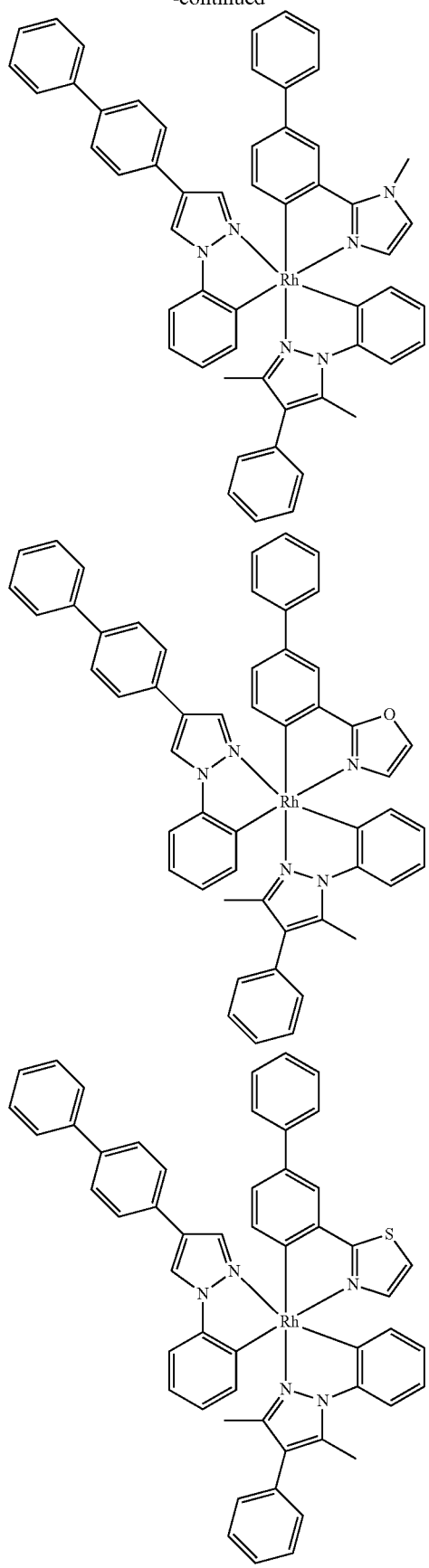
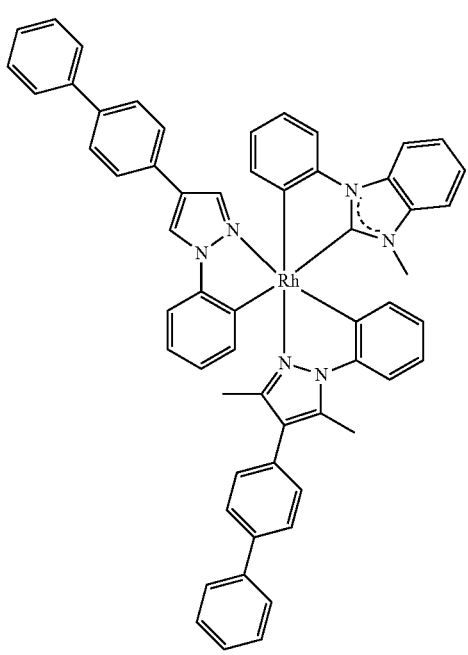

317
-continued
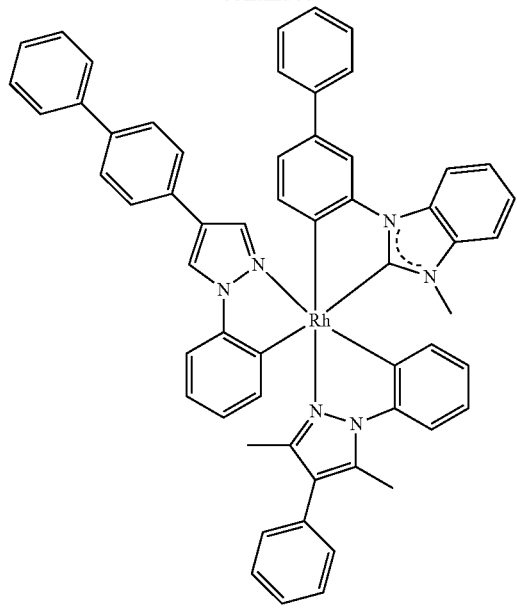
318
-continued
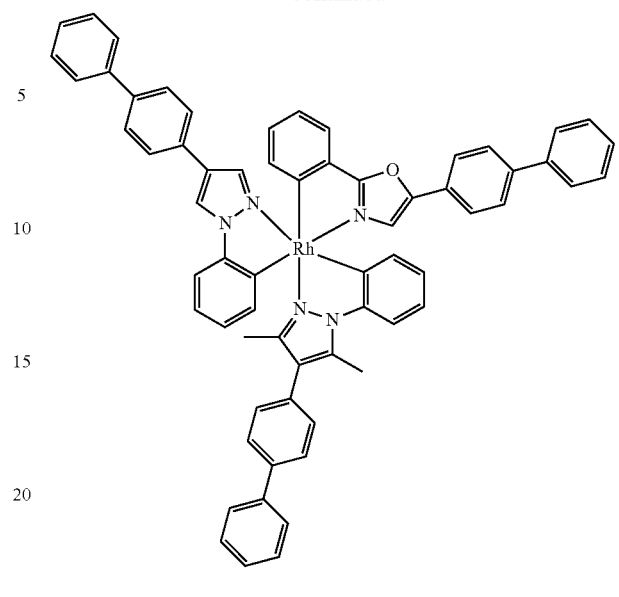
Structures Rh-18
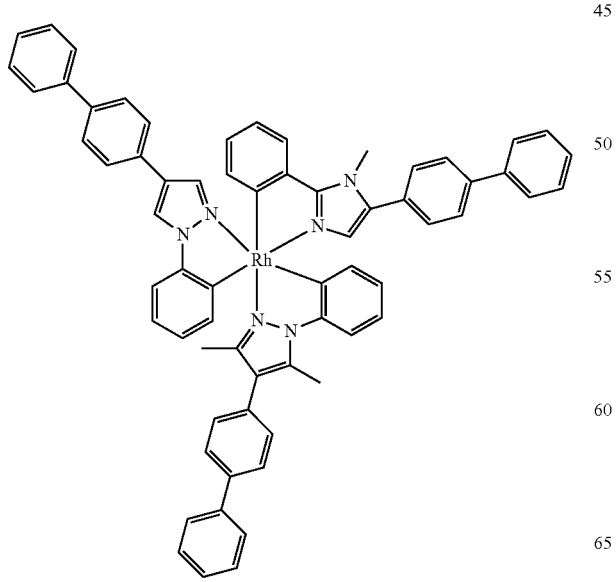
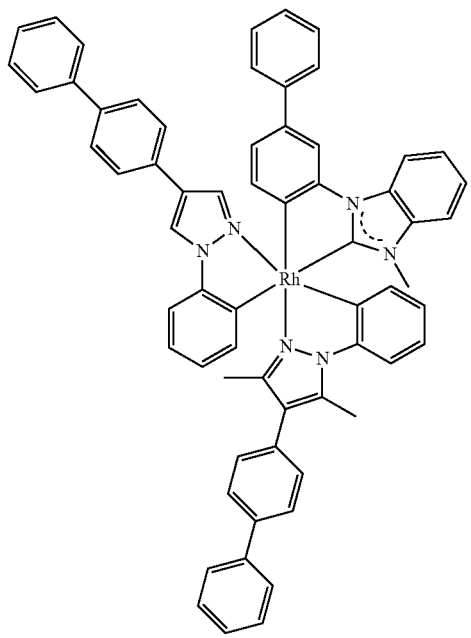

319
-continued
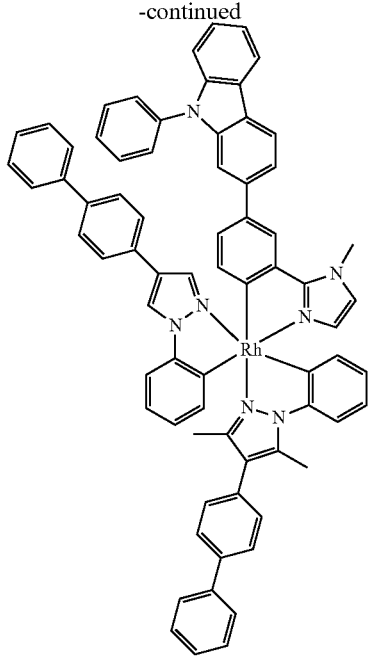
320
-continued
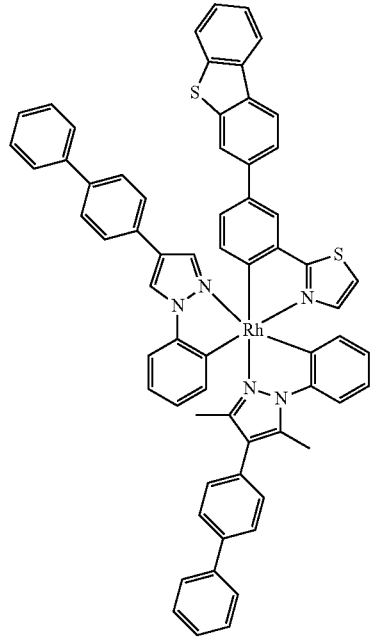
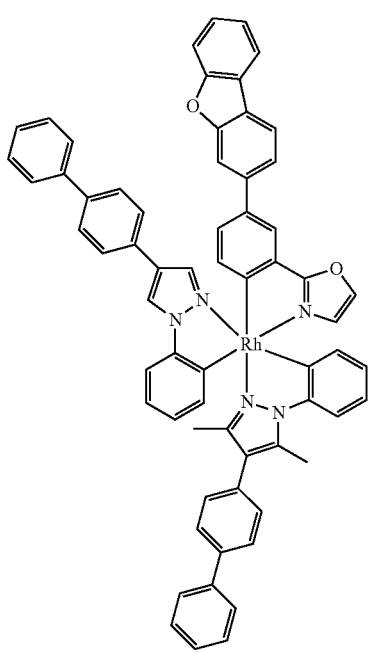
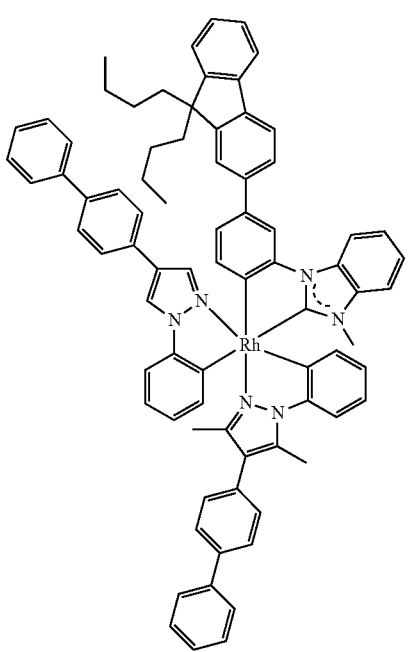

321
-continued
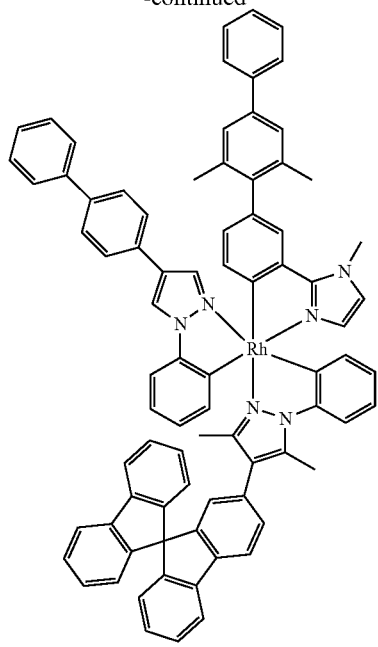
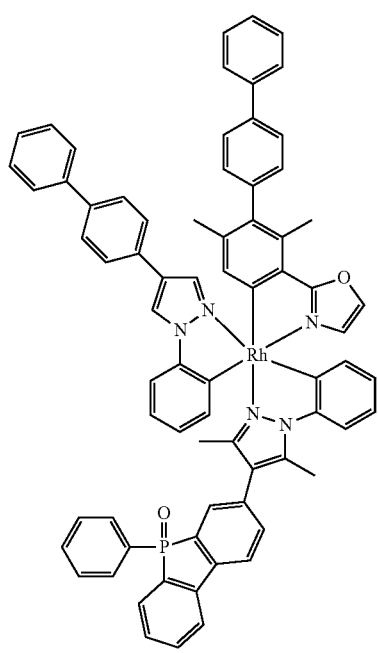
322
-continued
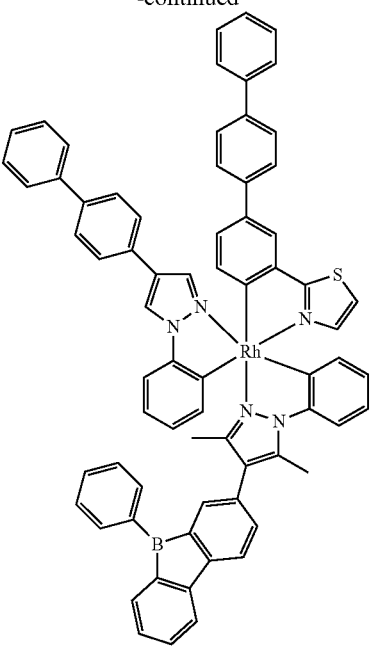
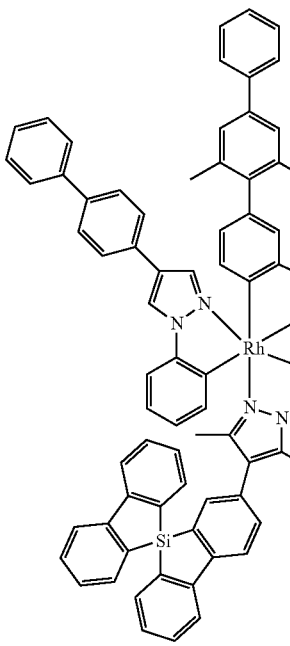
Structures Rh-19
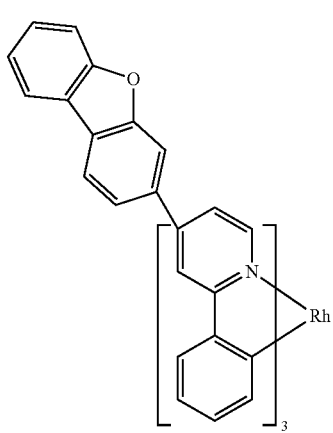

323
-continued
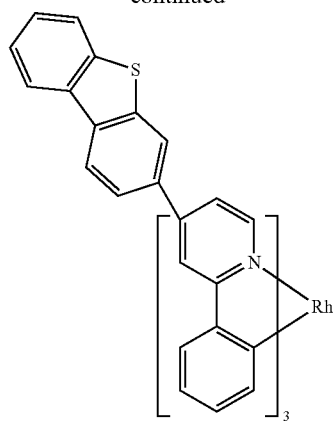
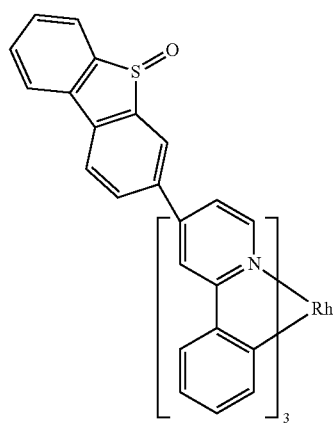
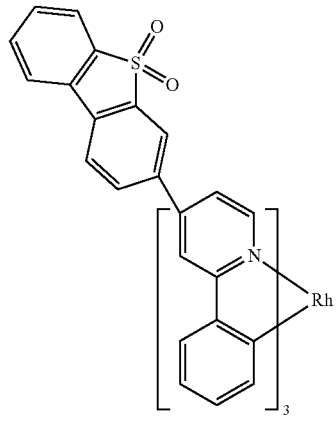
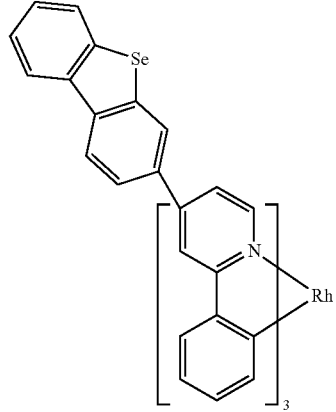
324
-continued
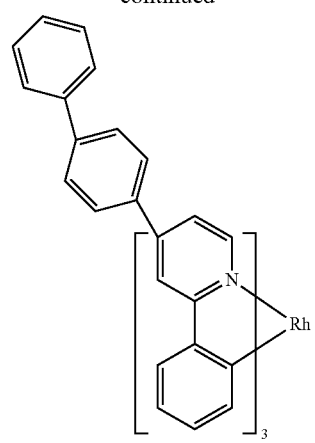
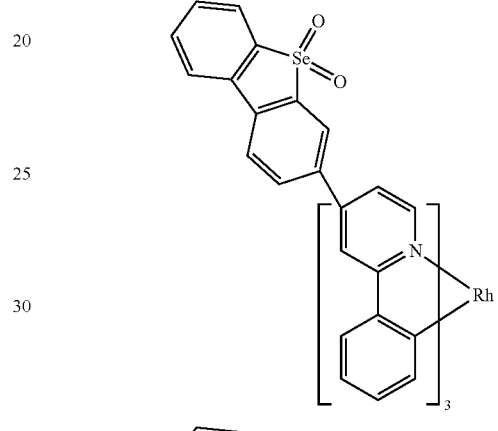
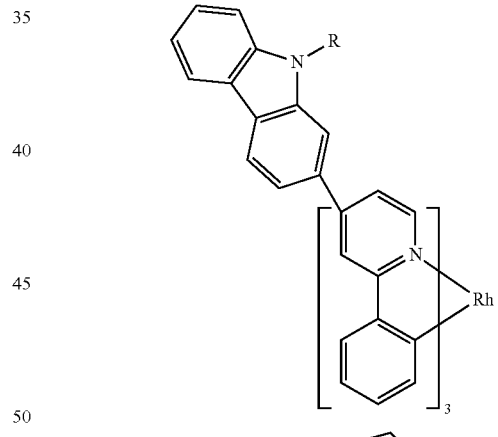
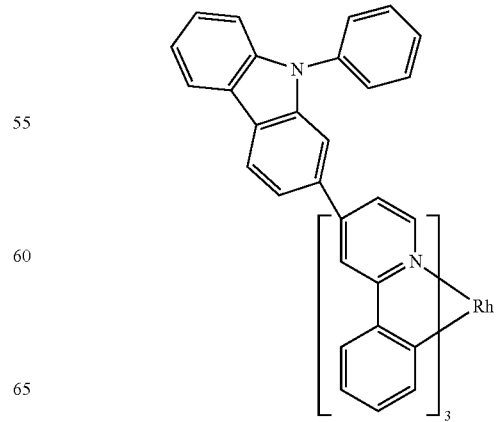

325
-continued
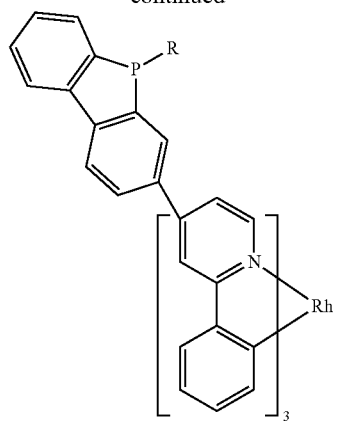
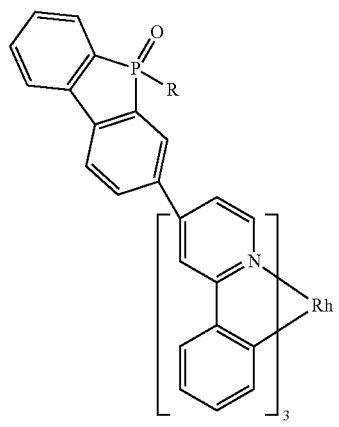
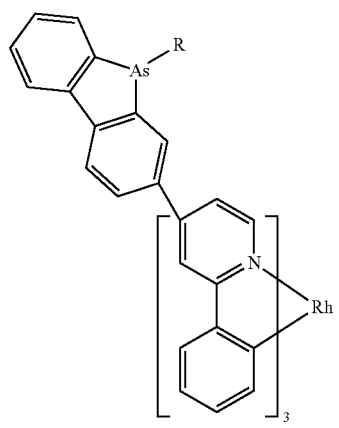
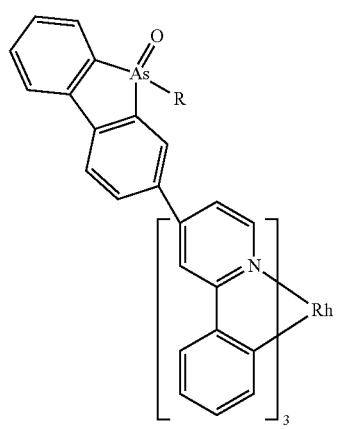
326
-continued
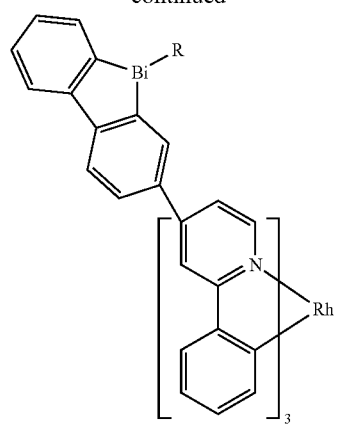
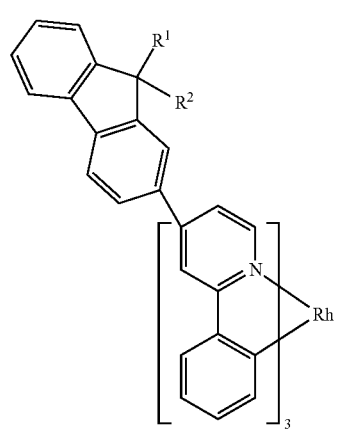
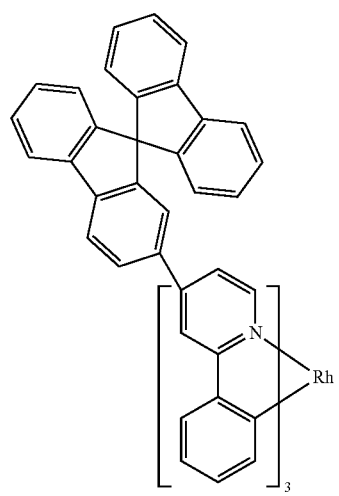

327
-continued
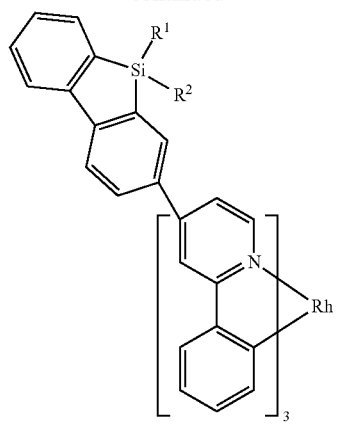
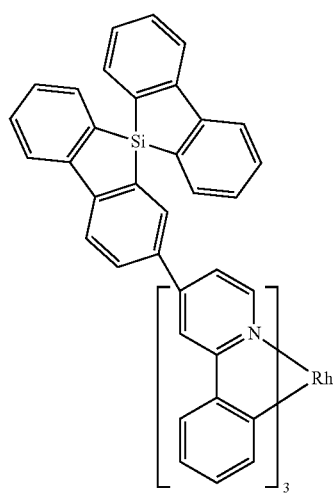
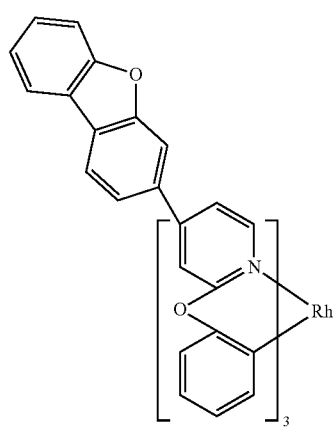
328
-continued
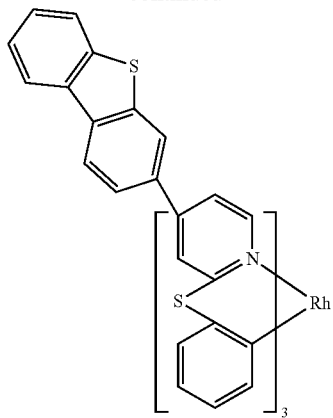
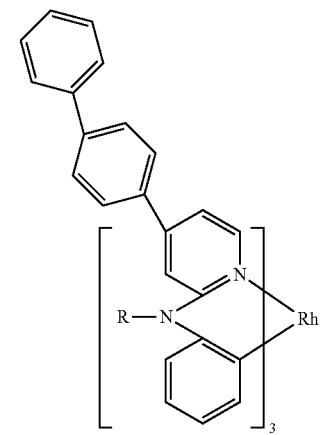
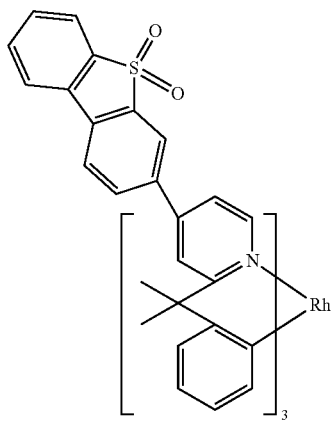
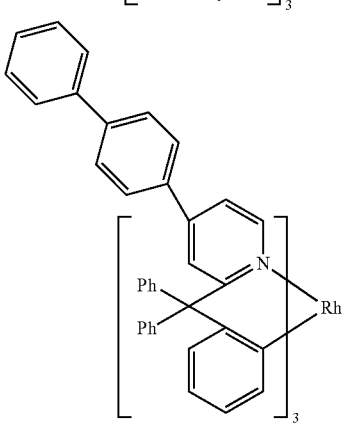

329
-continued
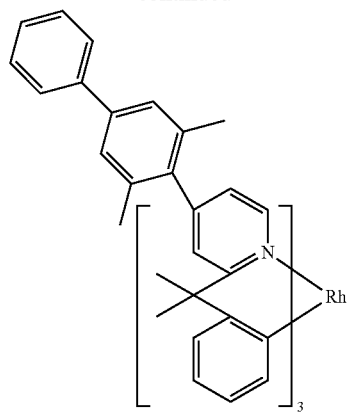
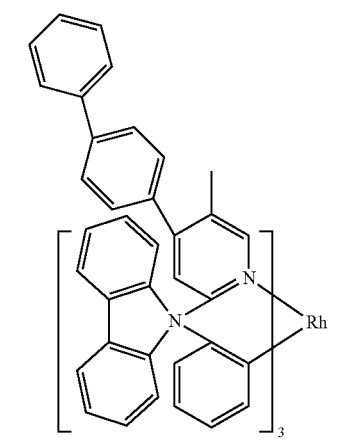
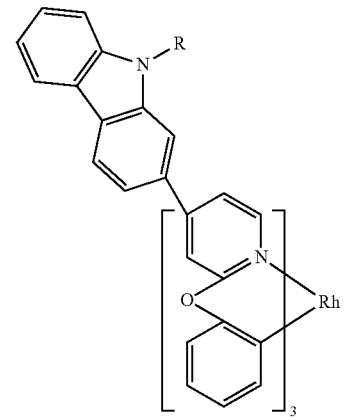
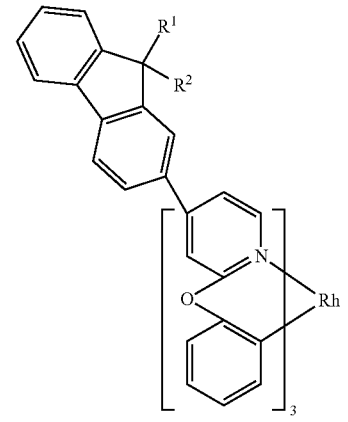
330
-continued
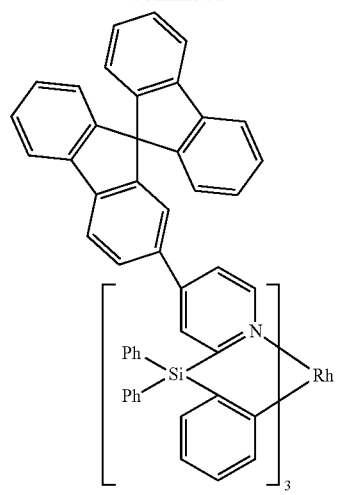
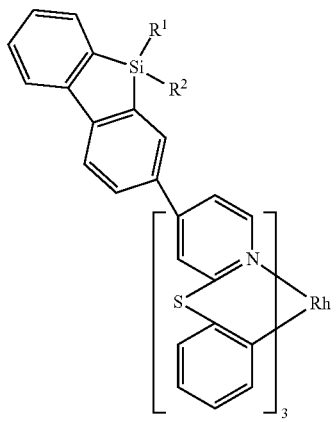
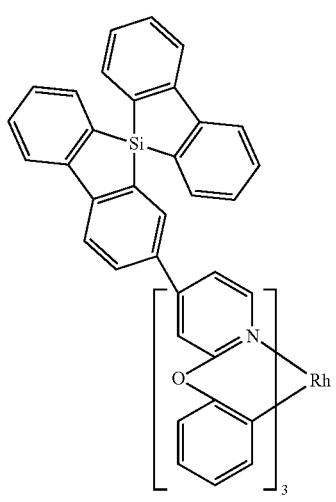

Structures Rh-20
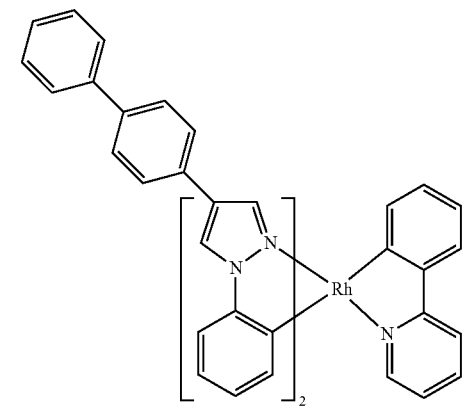
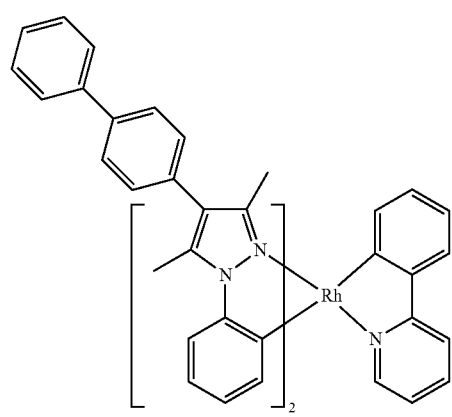
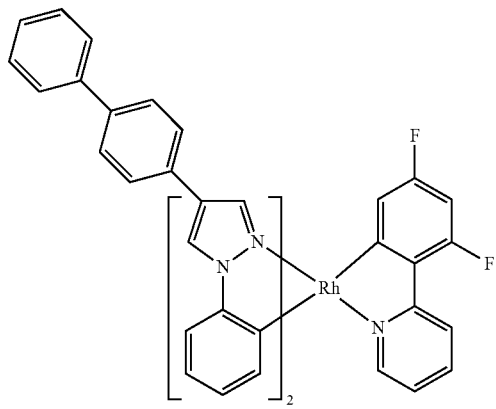
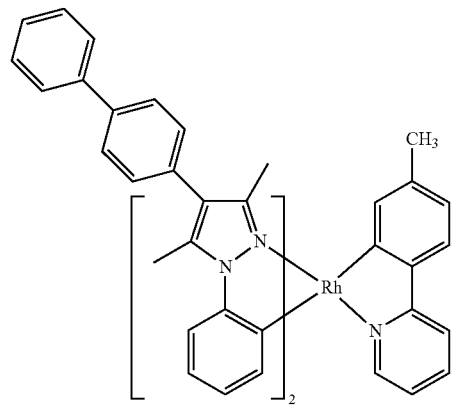
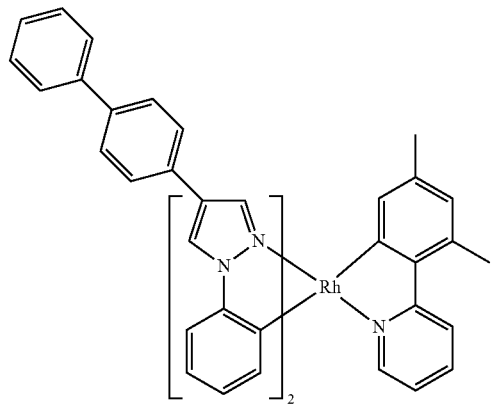
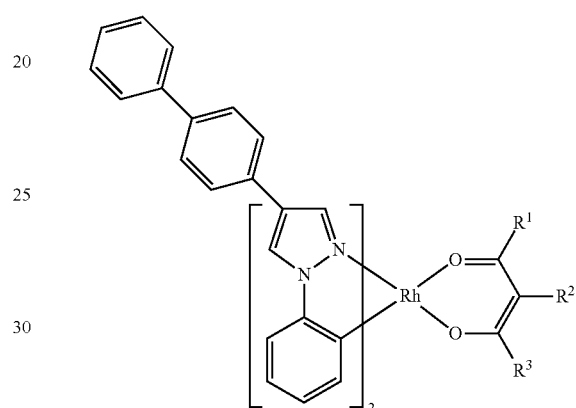
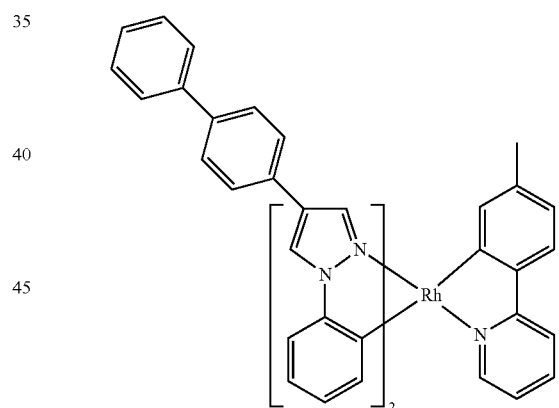
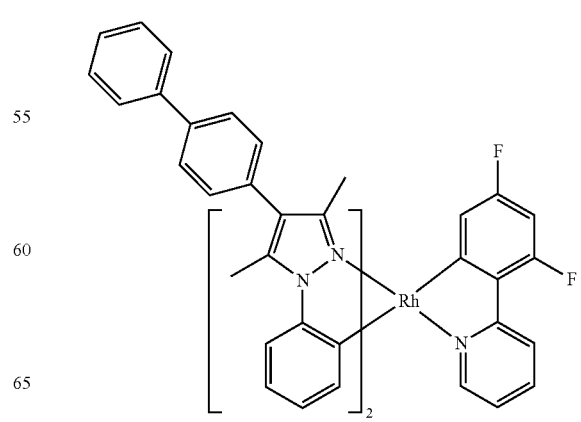

333
-continued
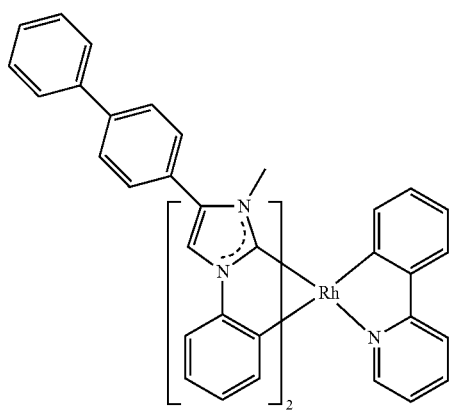
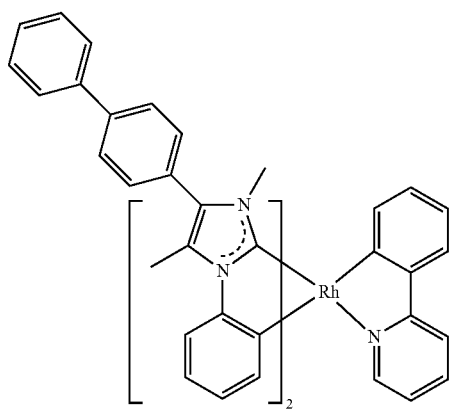
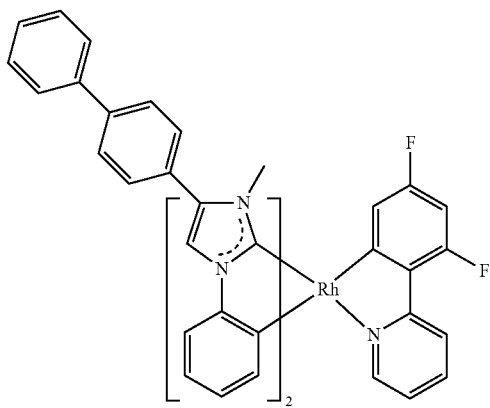
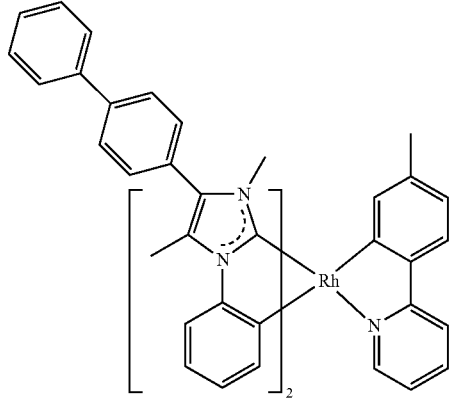
334
-continued
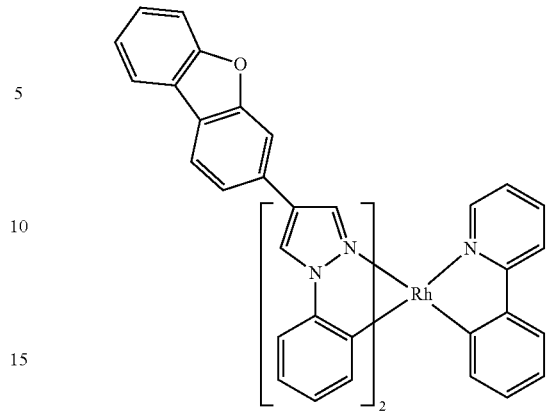
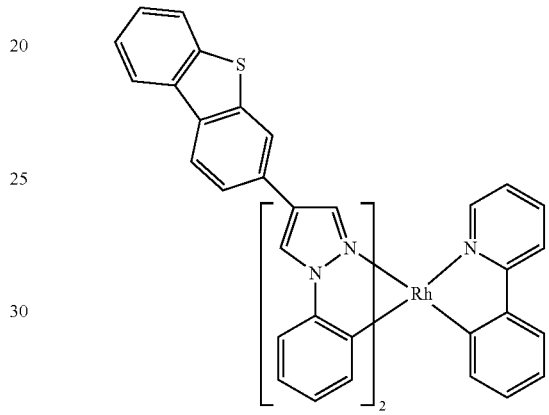
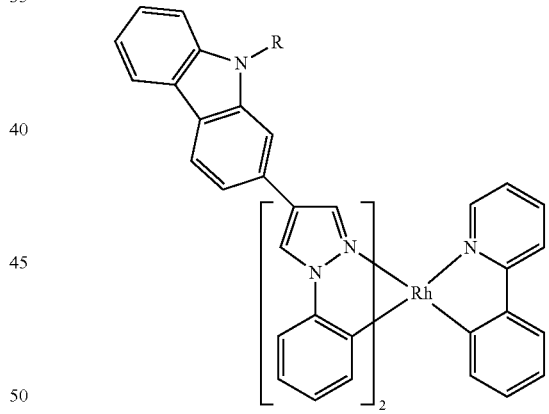
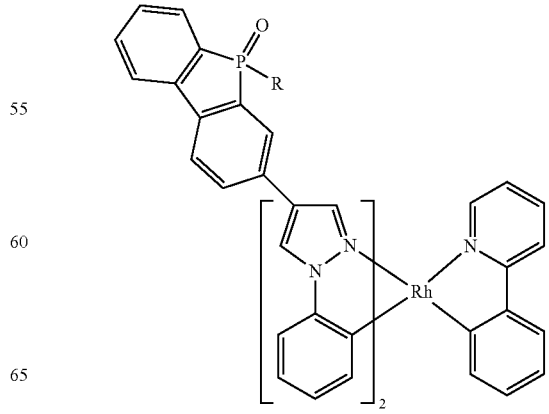

335
-continued
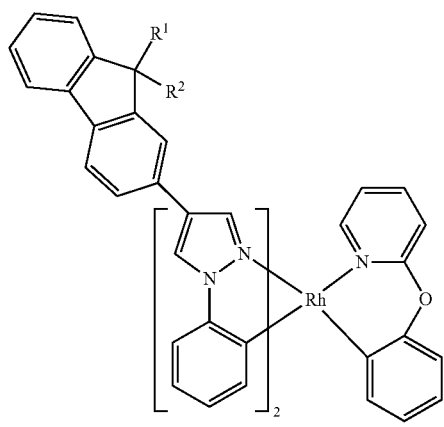
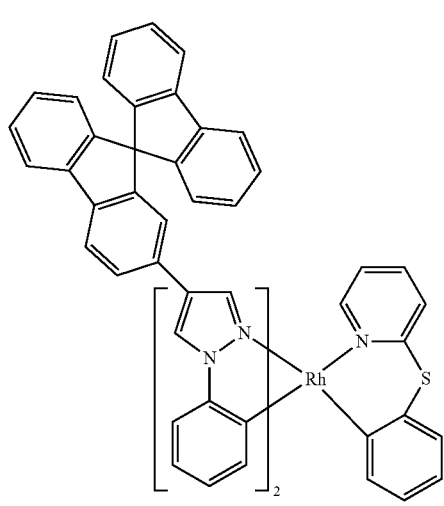
336
-continued
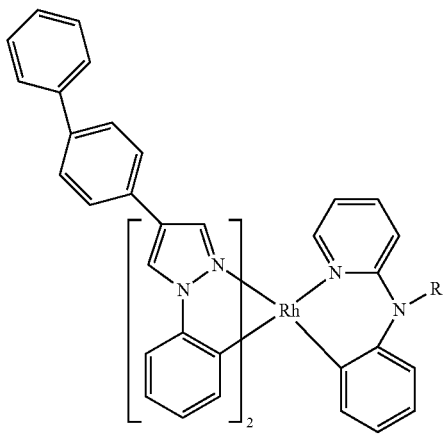
Structures Rh-21
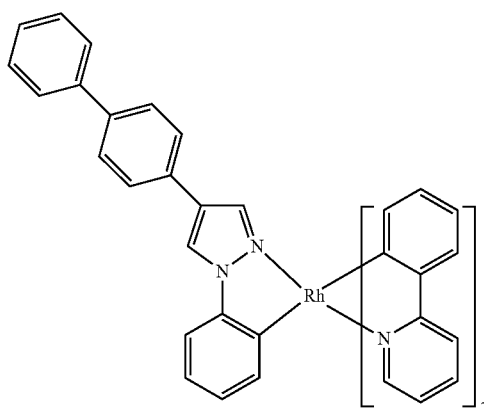
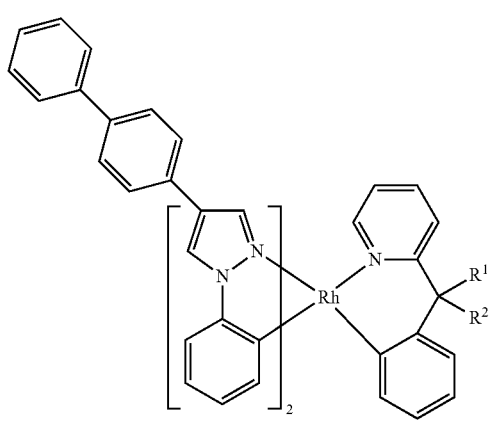
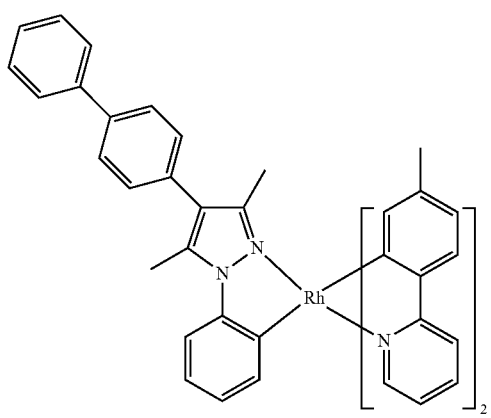

337
-continued
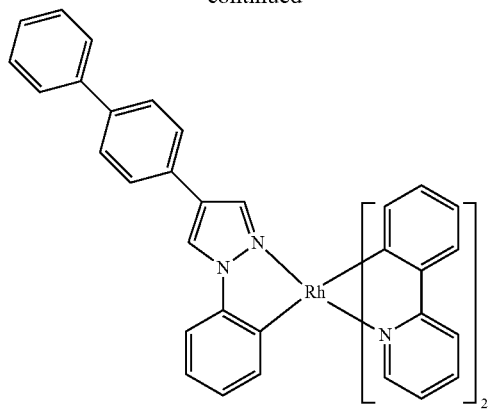
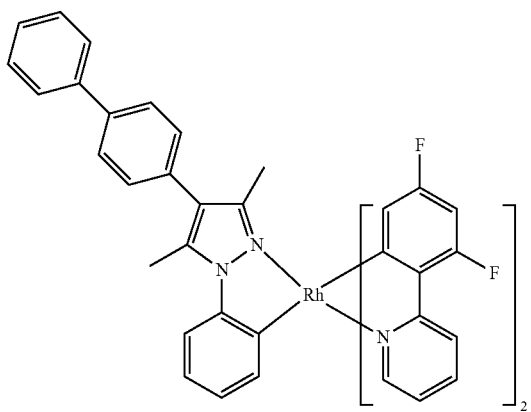
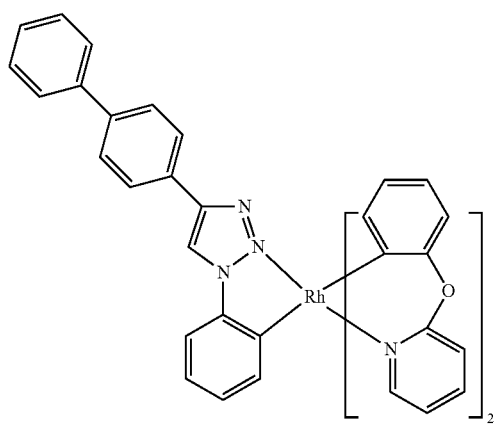
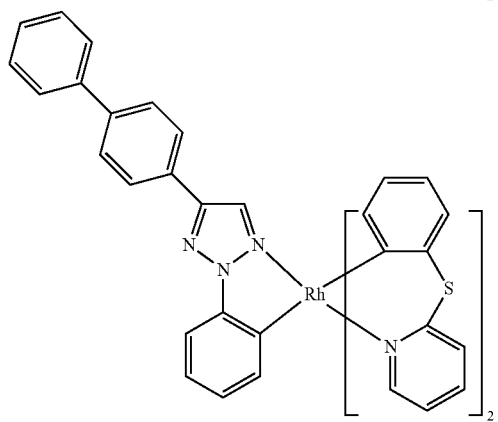
338
-continued
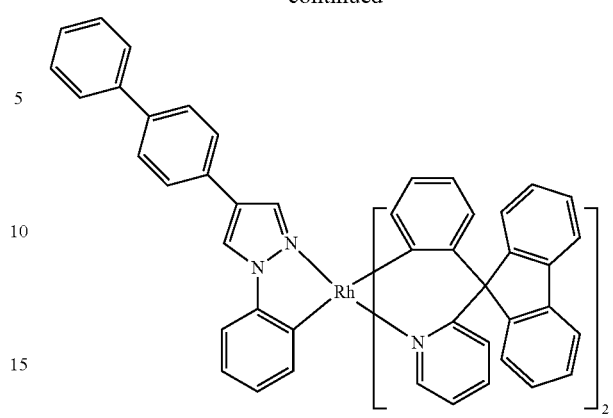
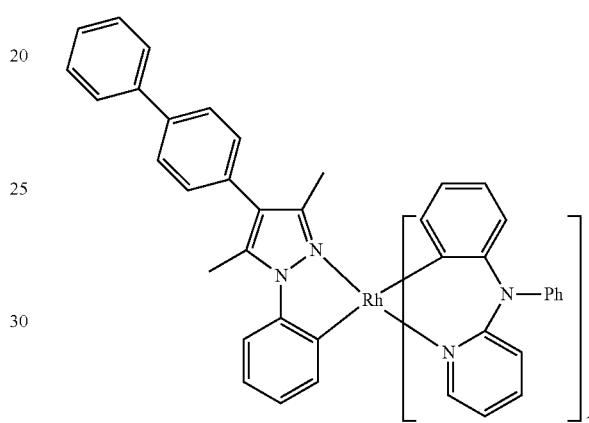
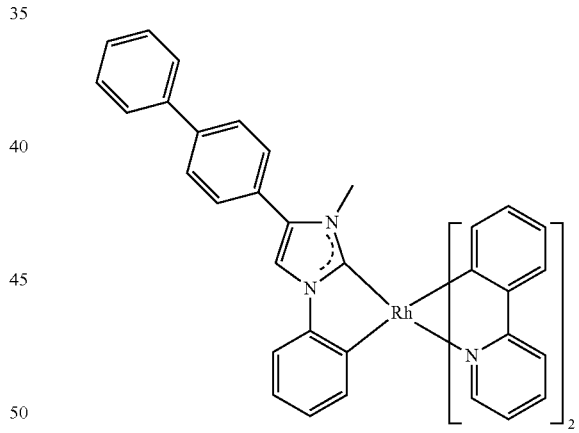
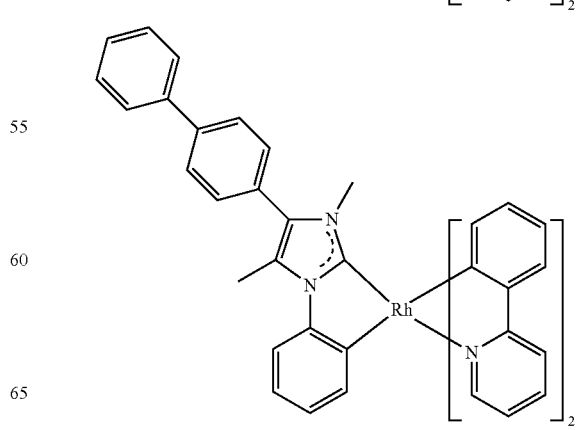

339
-continued
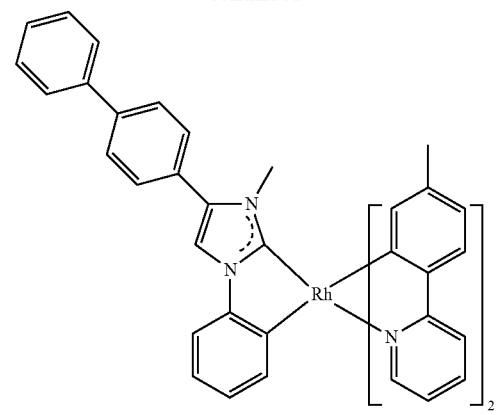
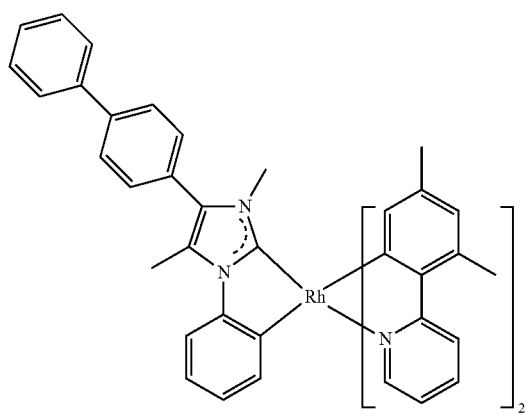
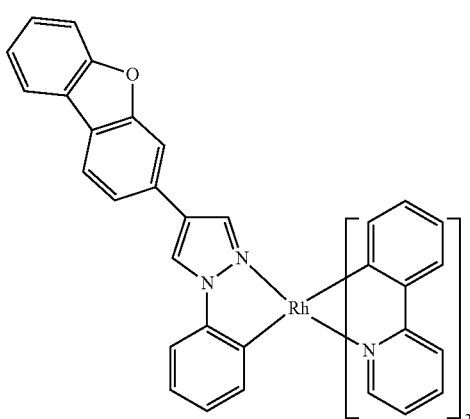
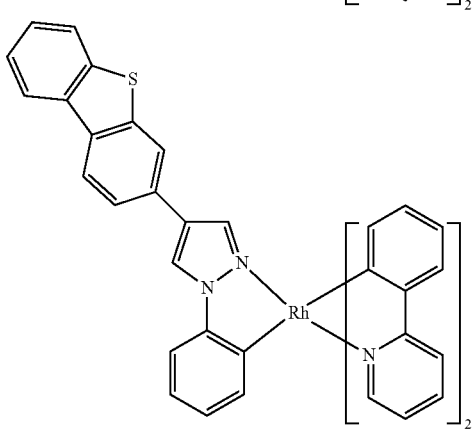
340
-continued
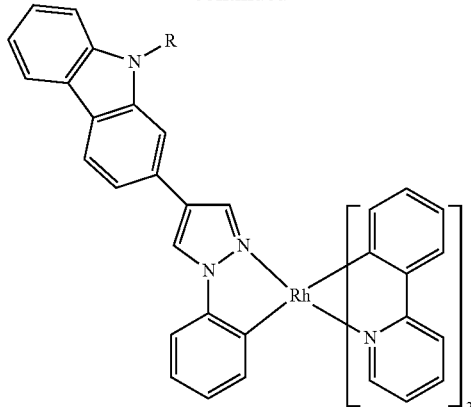
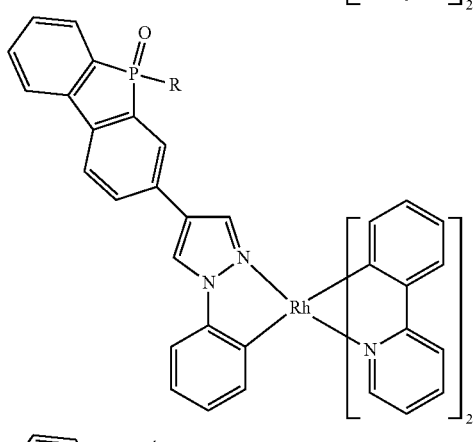
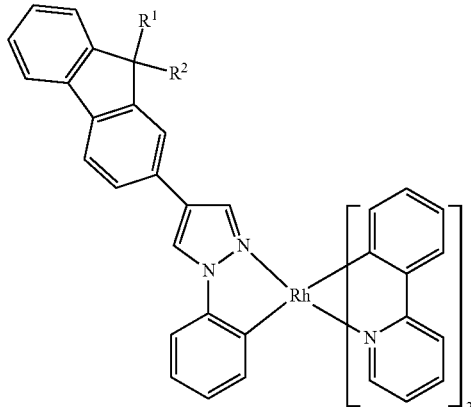
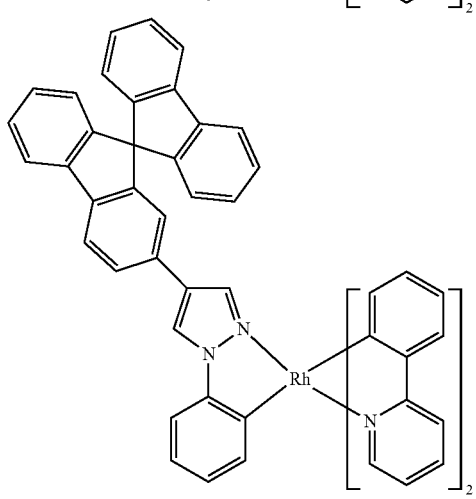

341
-continued
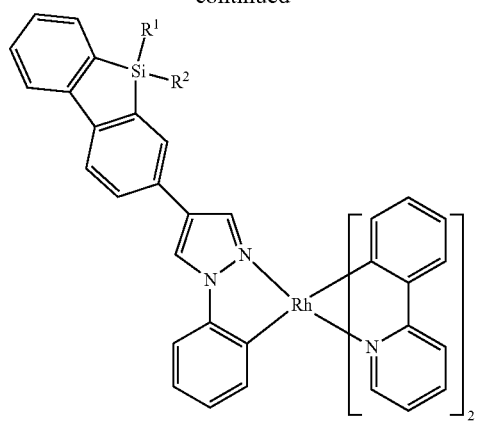
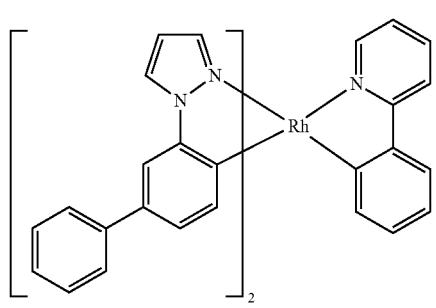
Structures Rh-22
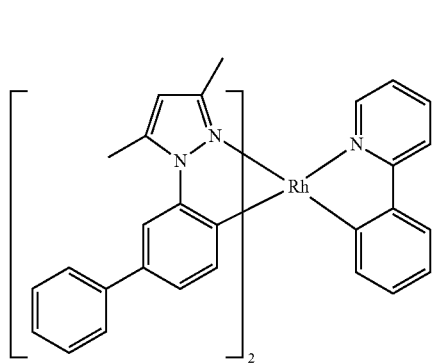
342
-continued
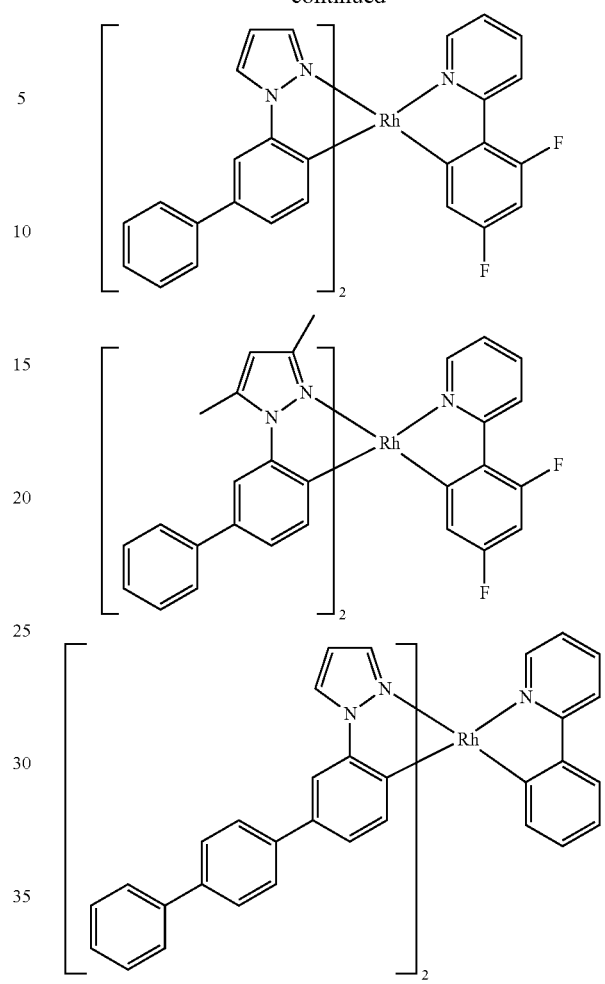
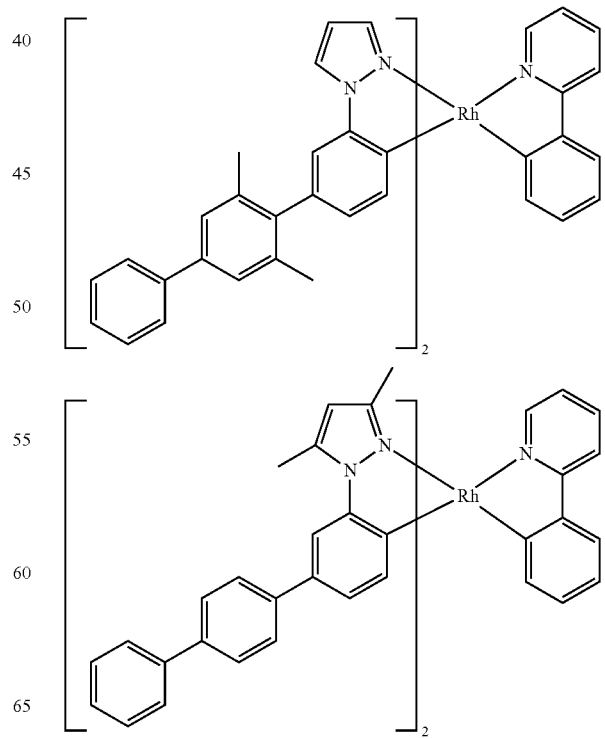

343
-continued
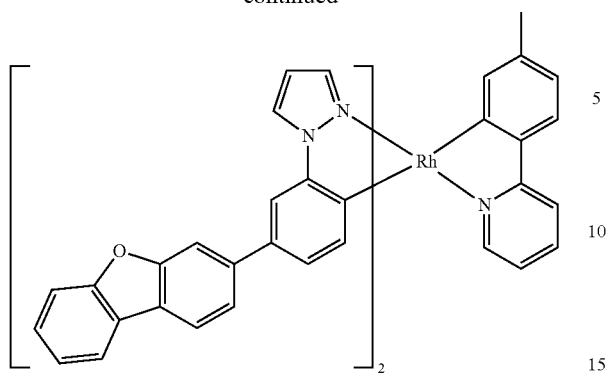
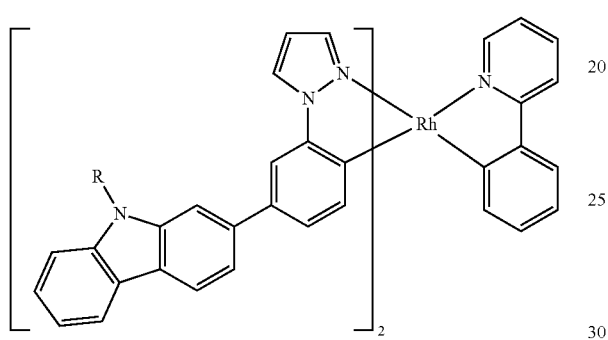
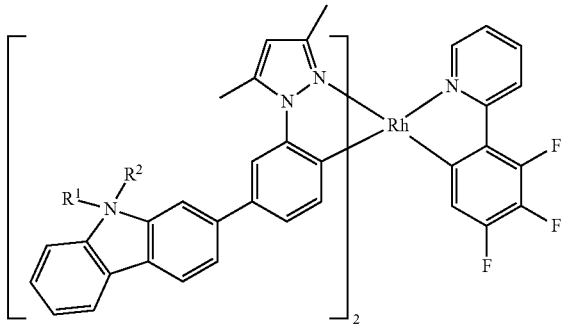
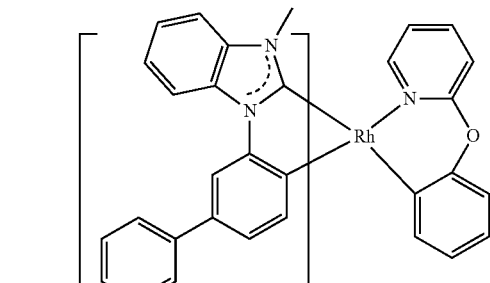
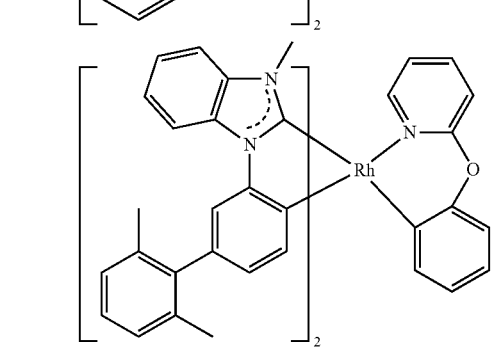
344
-continued
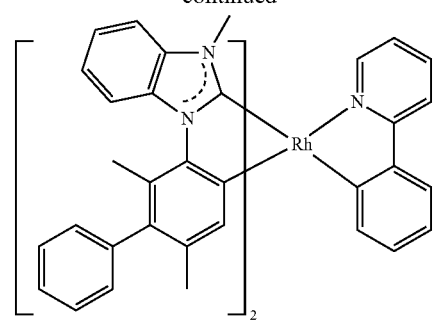
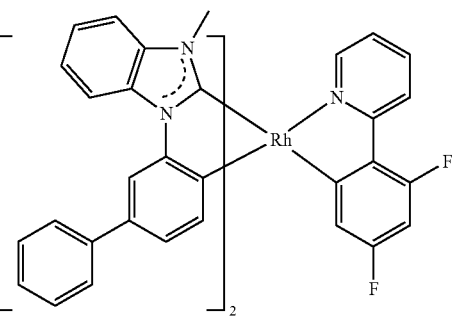
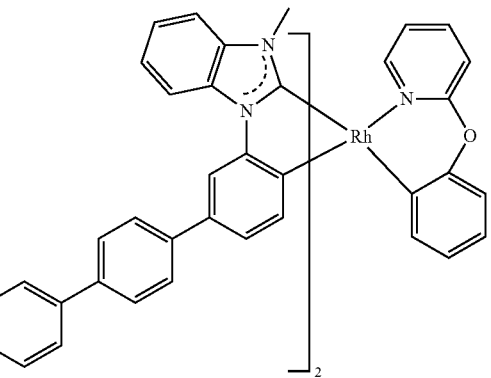
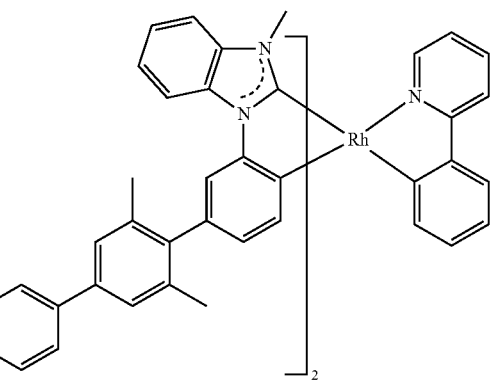

-continued
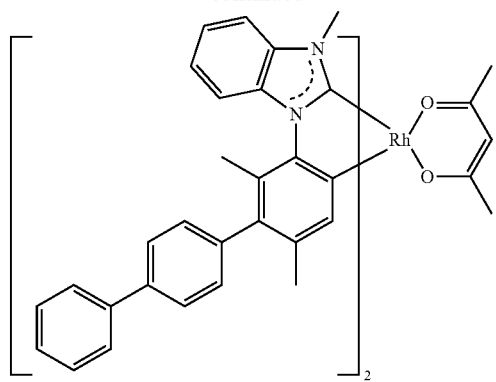
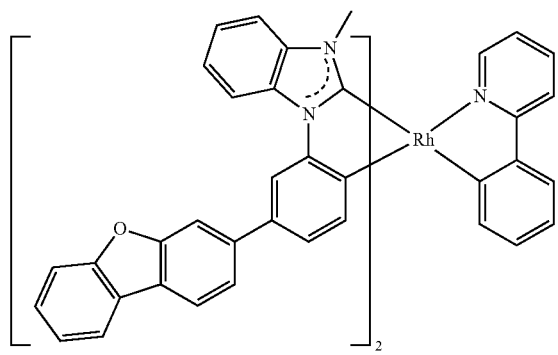
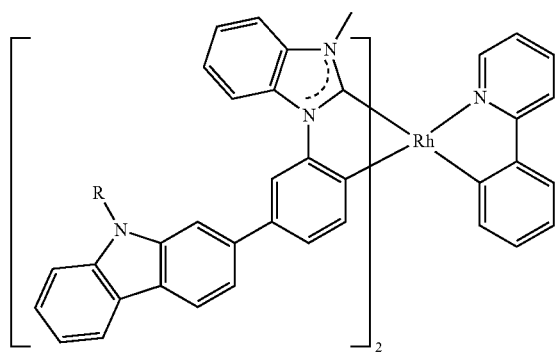
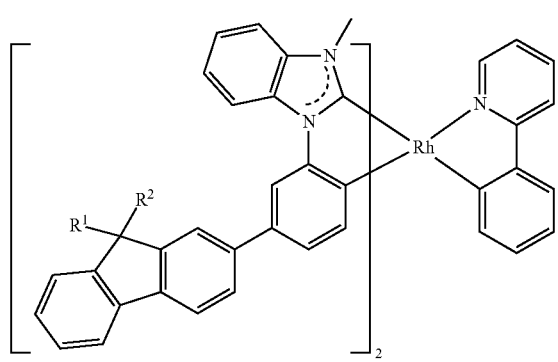
-continued
Structures Rh-23
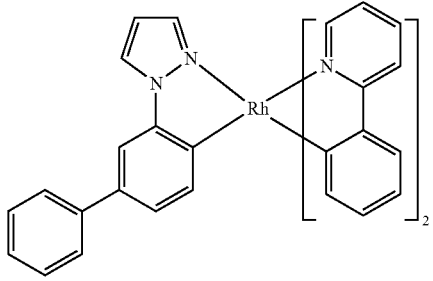
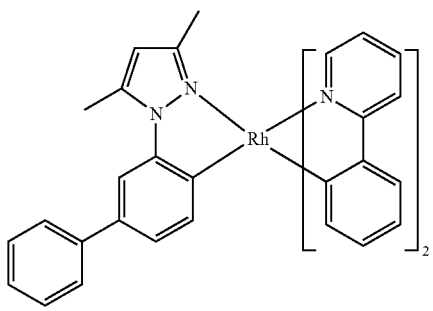
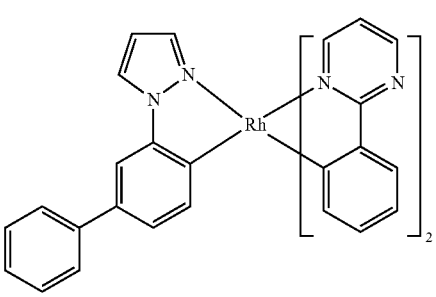
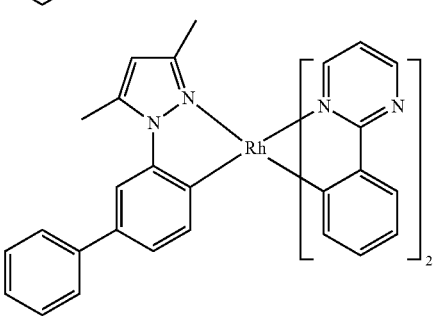
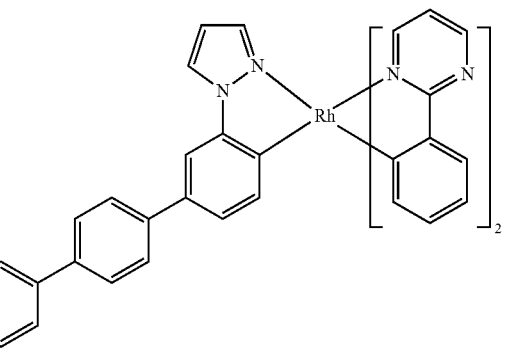

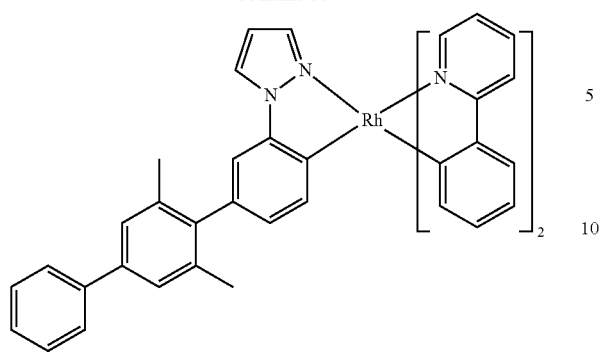
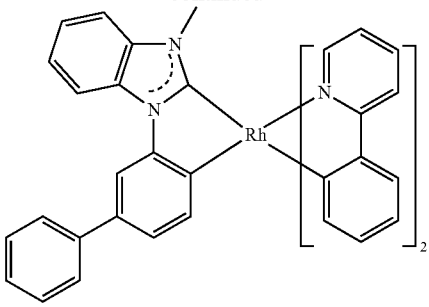
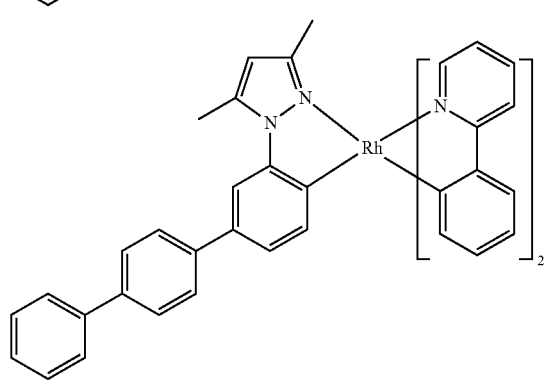
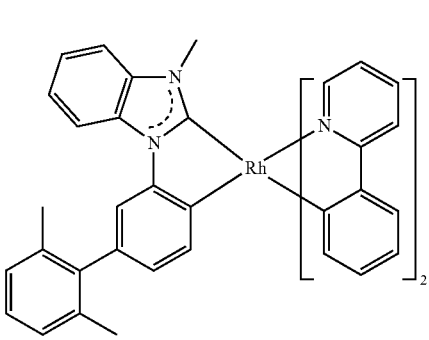
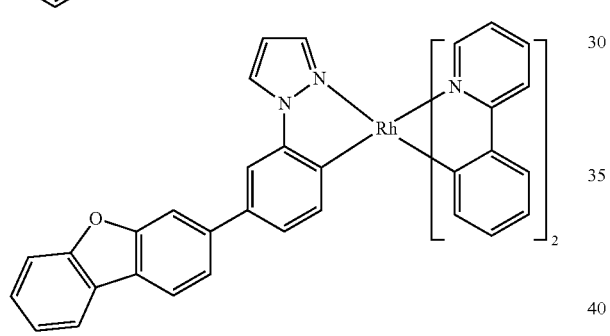
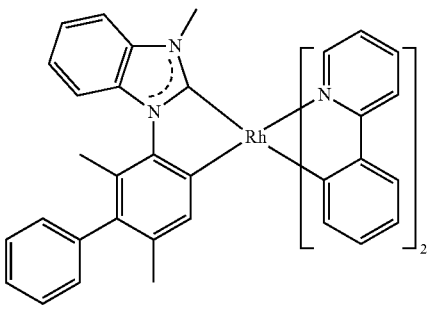
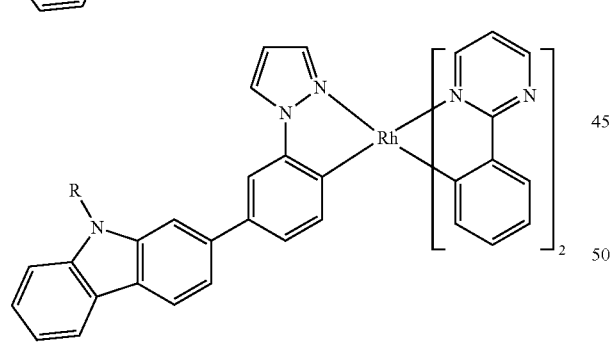
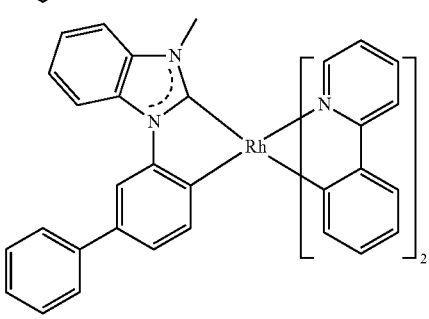
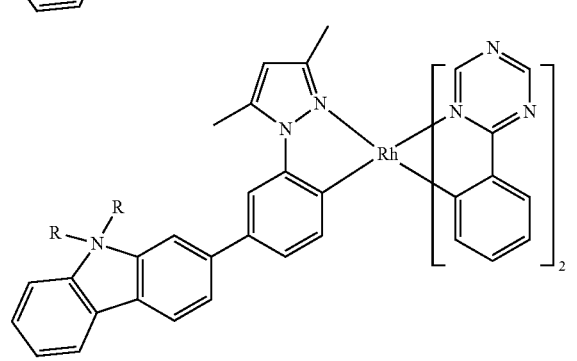
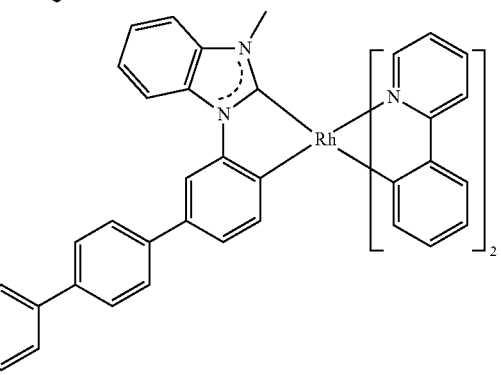

349
-continued
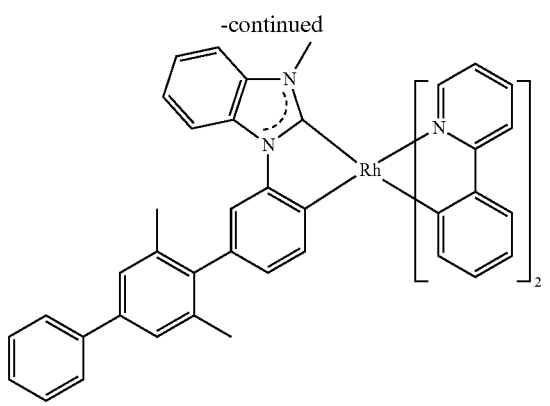
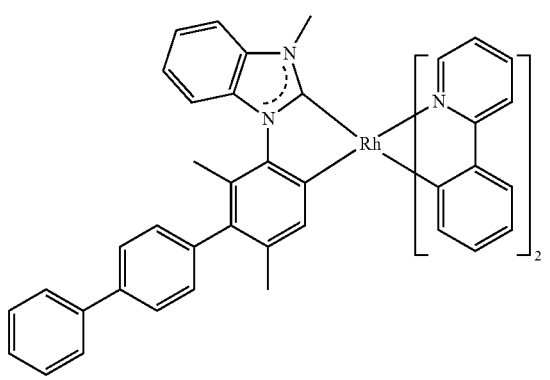
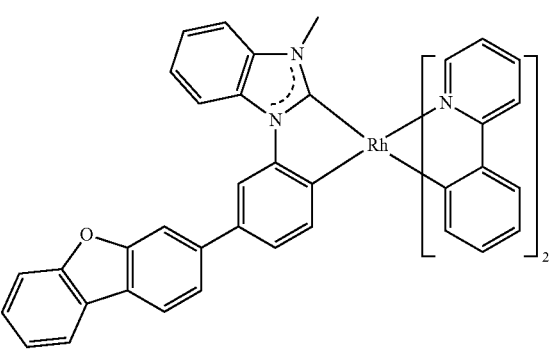
350
-continued
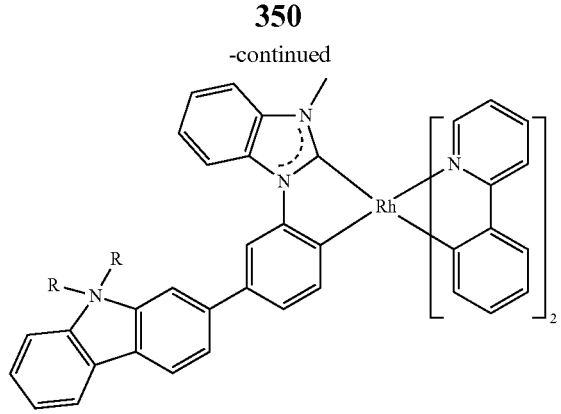
Structures Rh-24
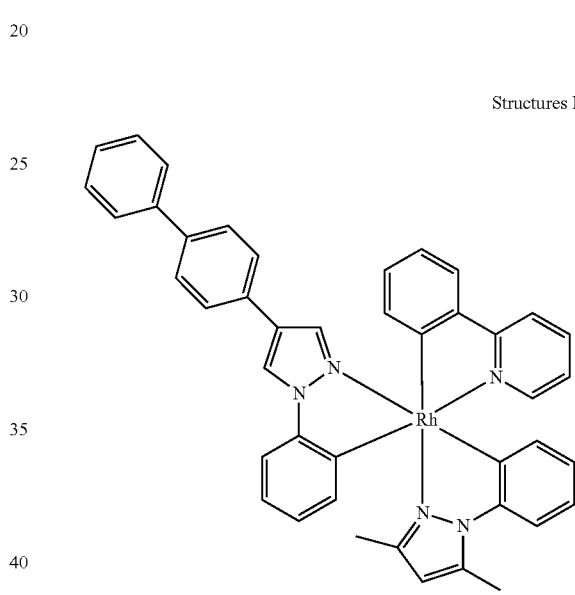
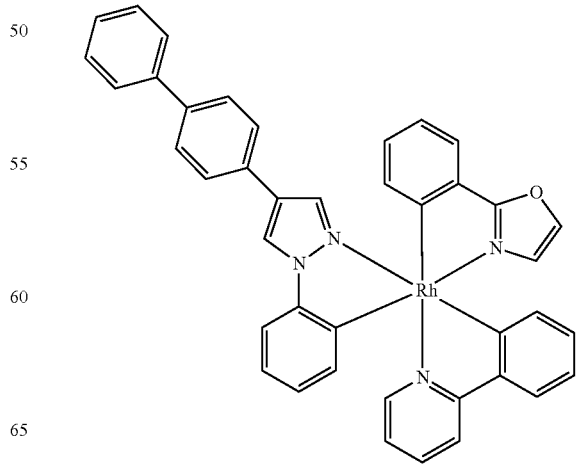

351
-continued
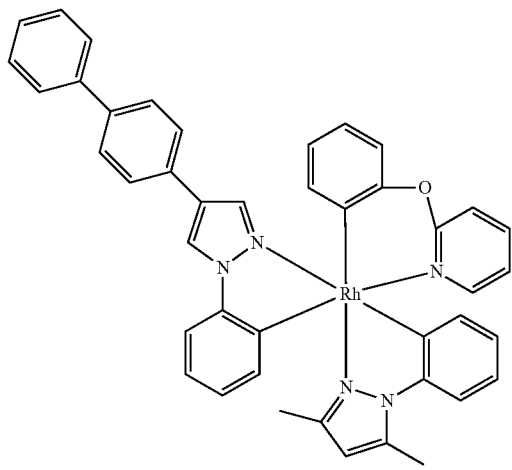
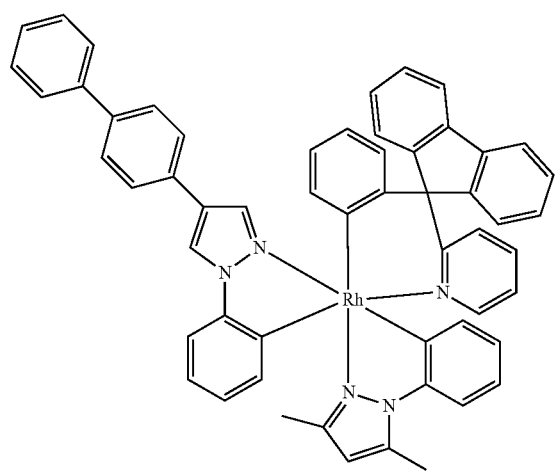
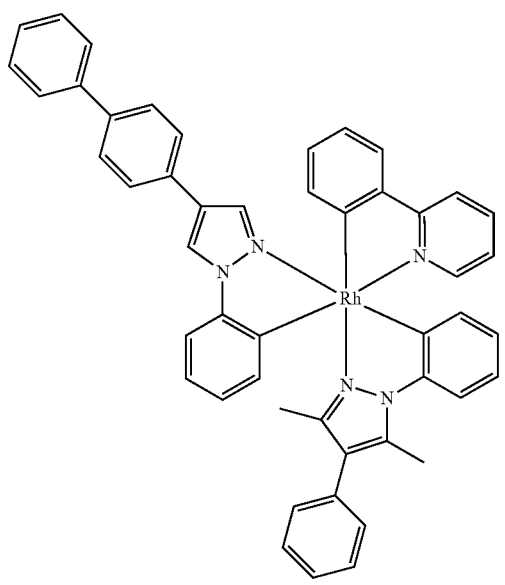
352
-continued
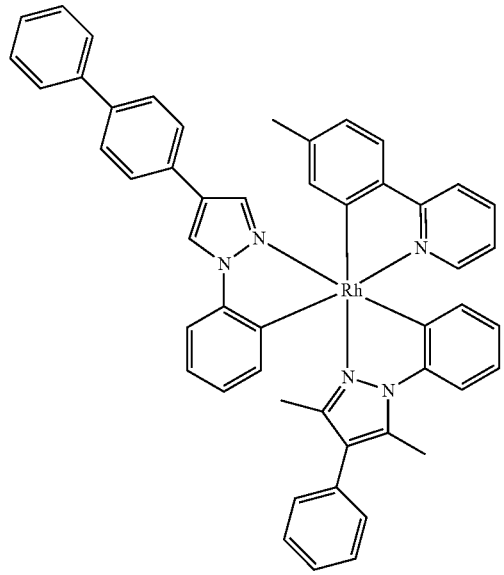
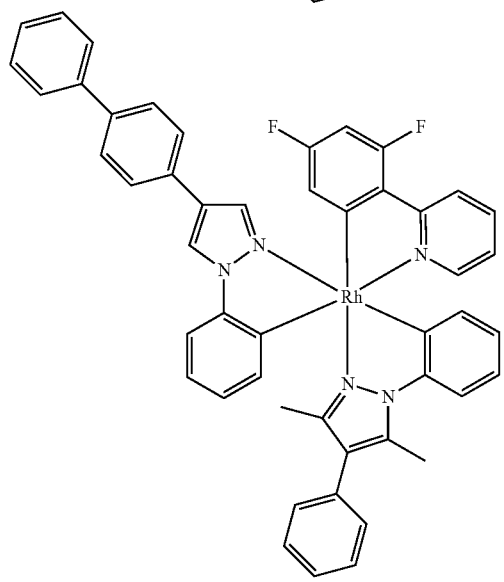

353
-continued
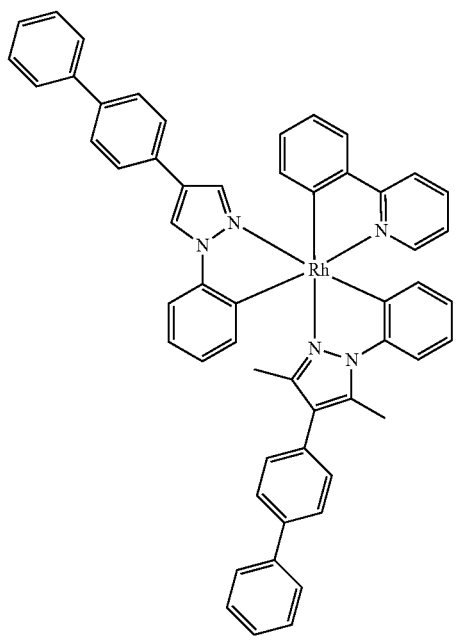
354
-continued
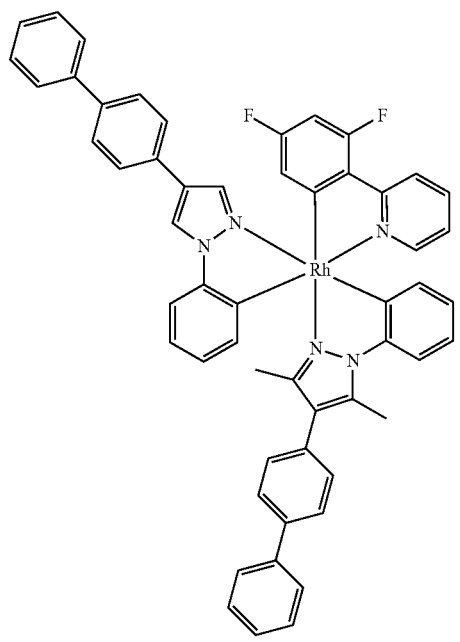
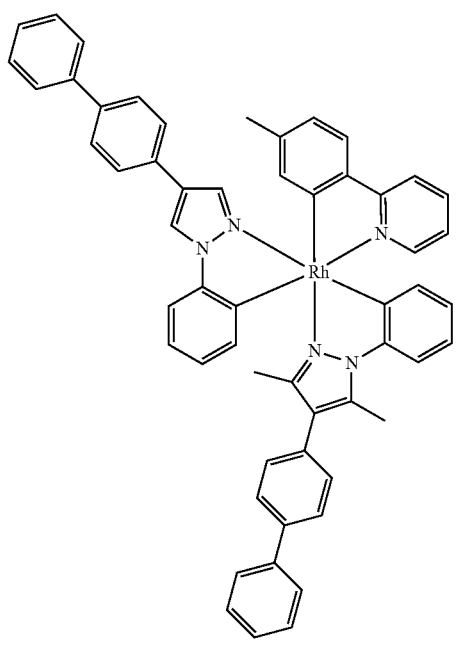
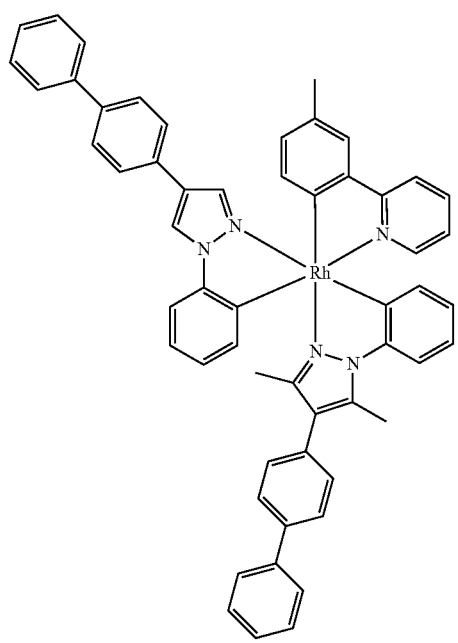

355
-continued
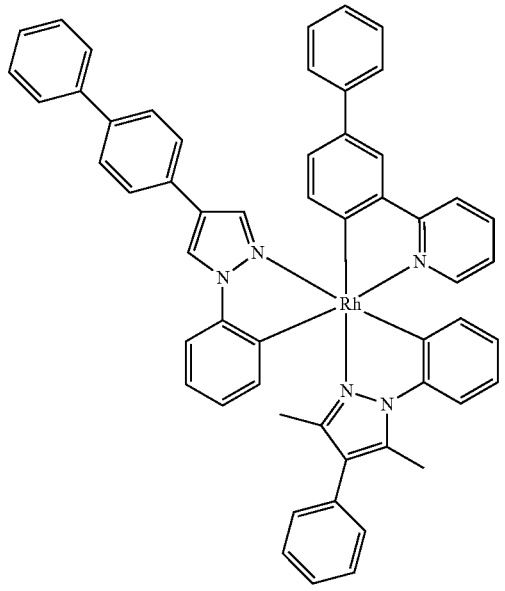
356
-continued
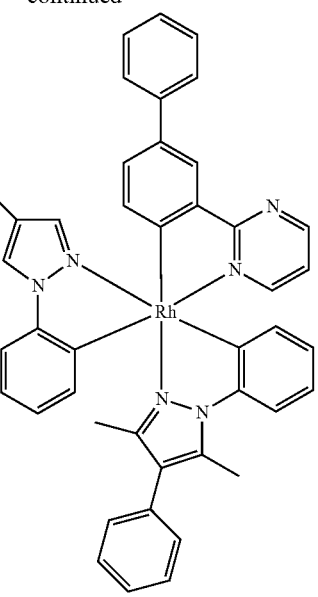
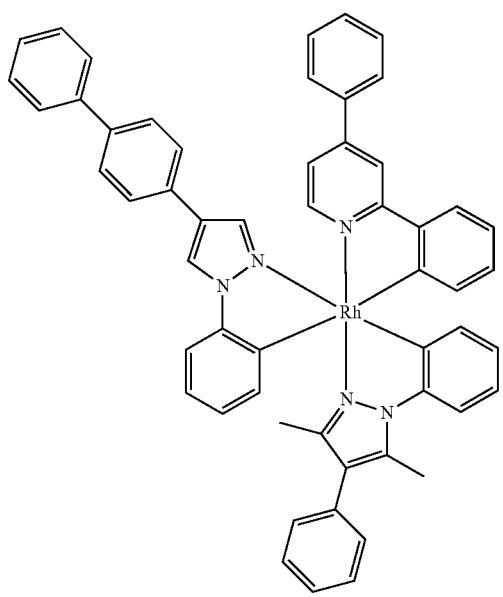
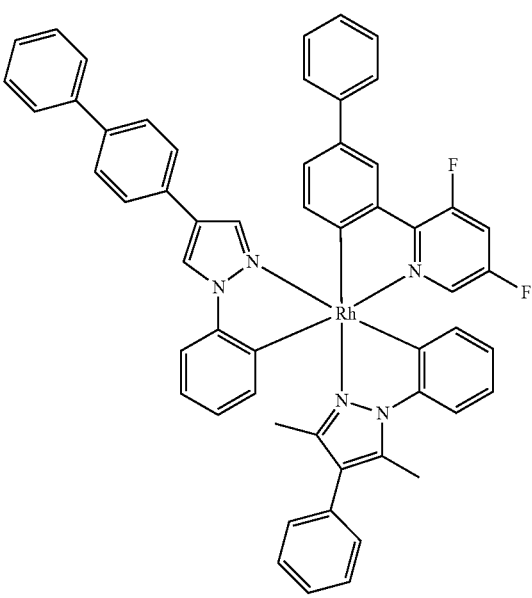

Structures Rh-25
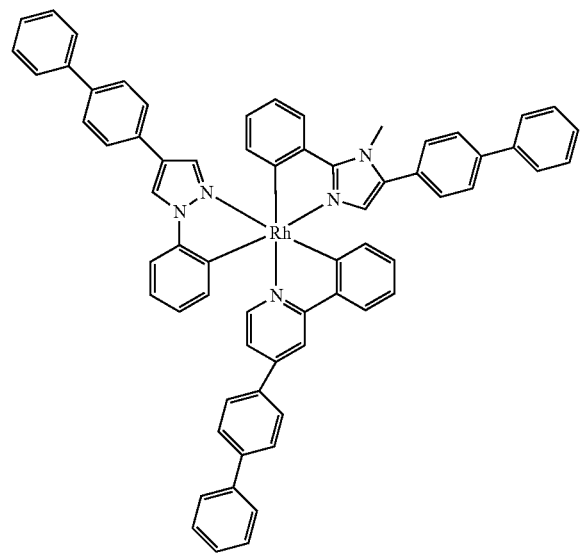
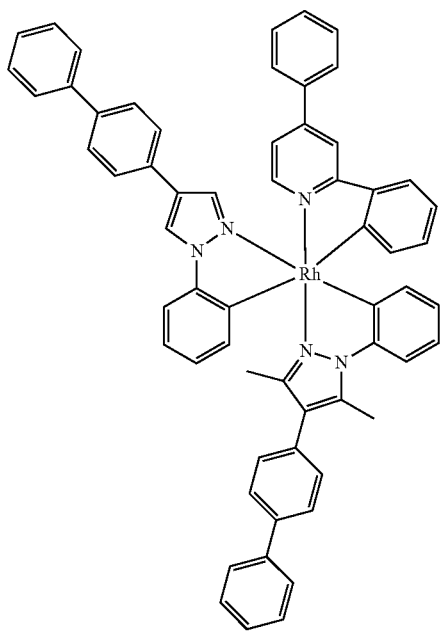
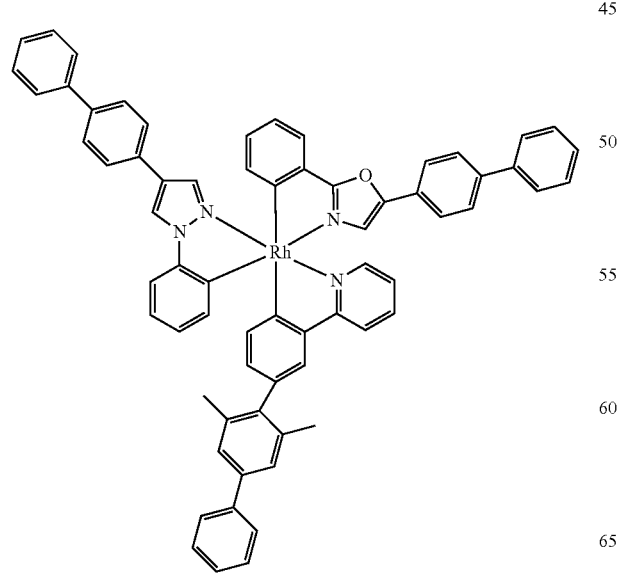
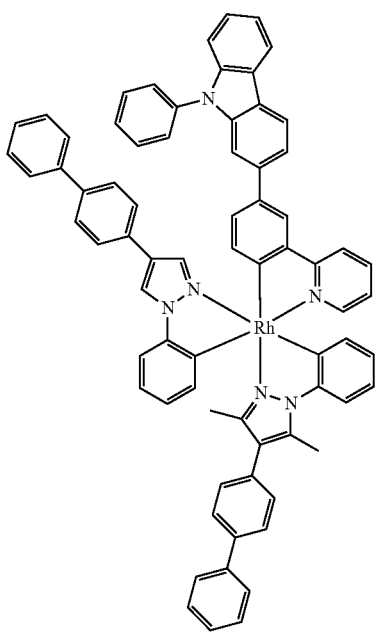

359
-continued
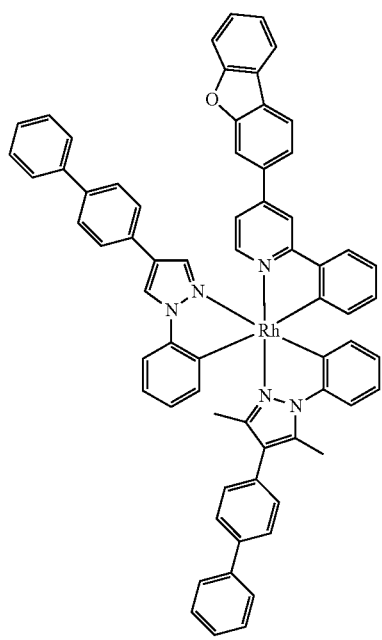
360
-continued
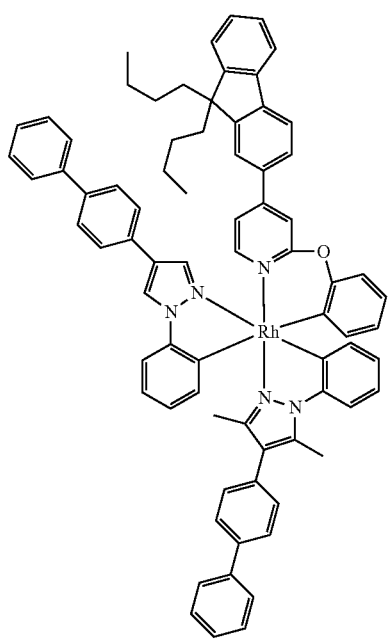
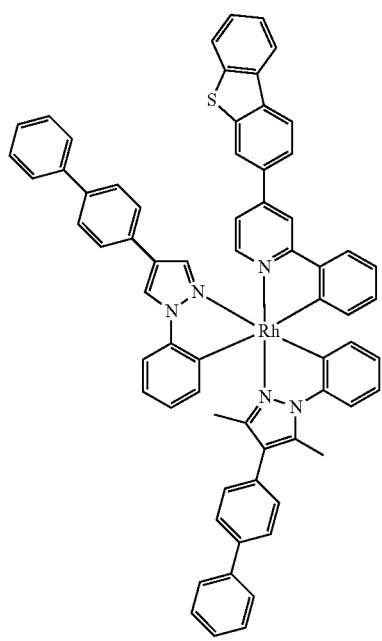
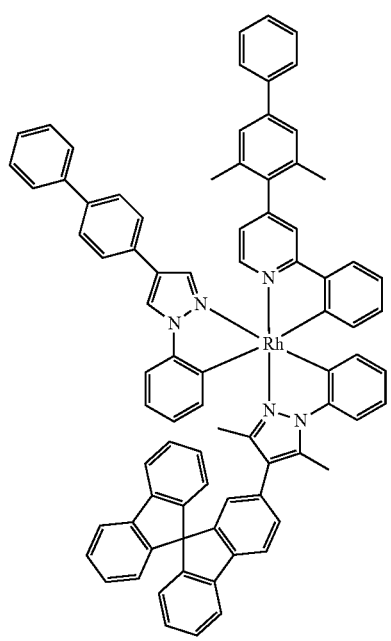

361
-continued
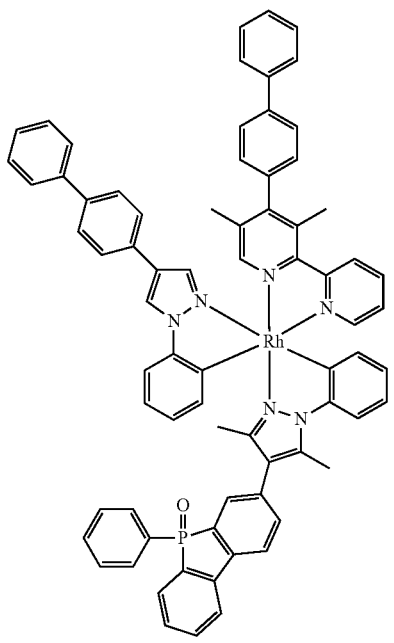
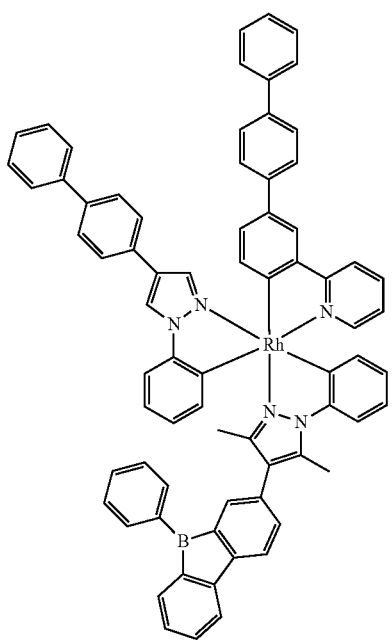
362
-continued
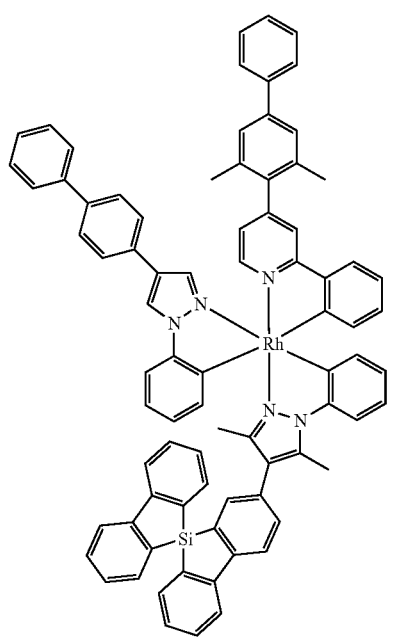
Structures Pt-1
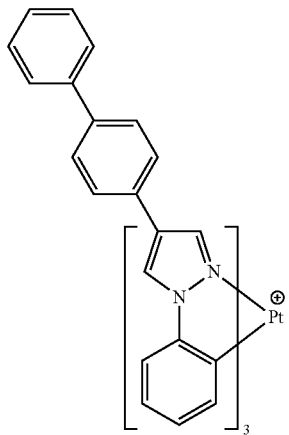
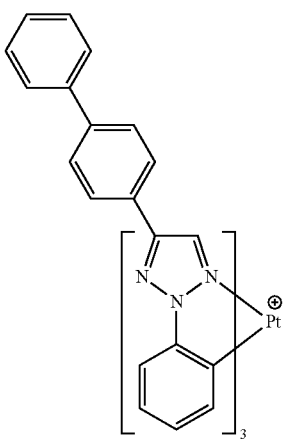

363
-continued
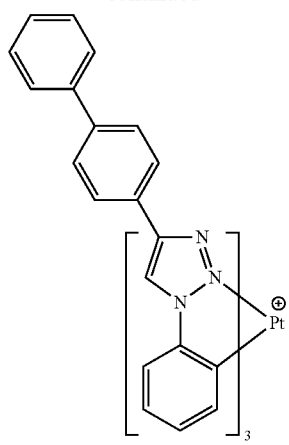
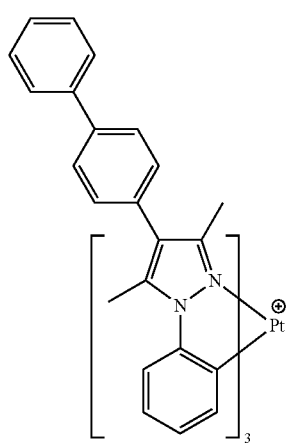
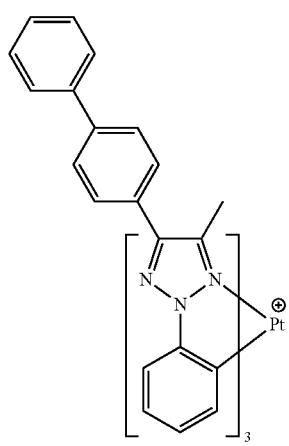
364
-continued
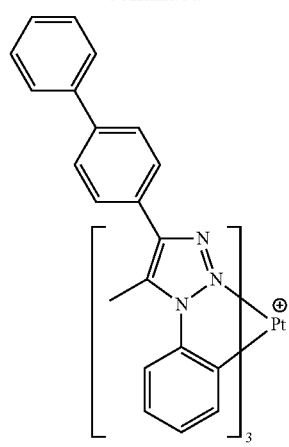
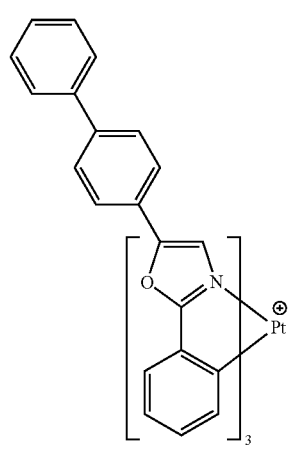
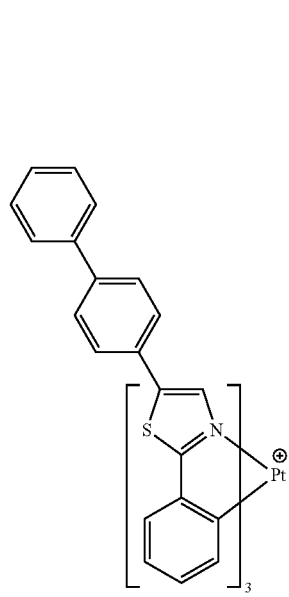

365
-continued
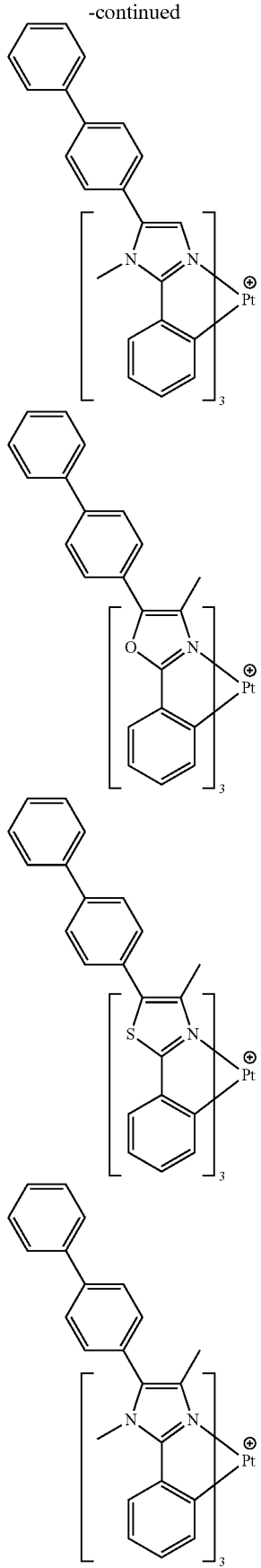
366
-continued
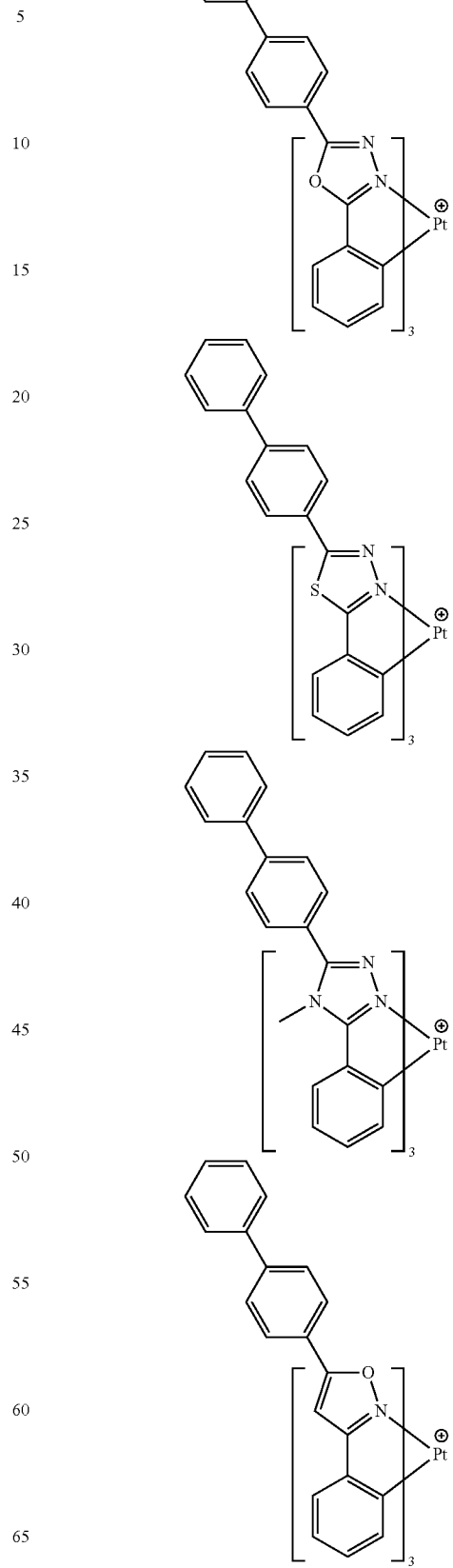

367
-continued
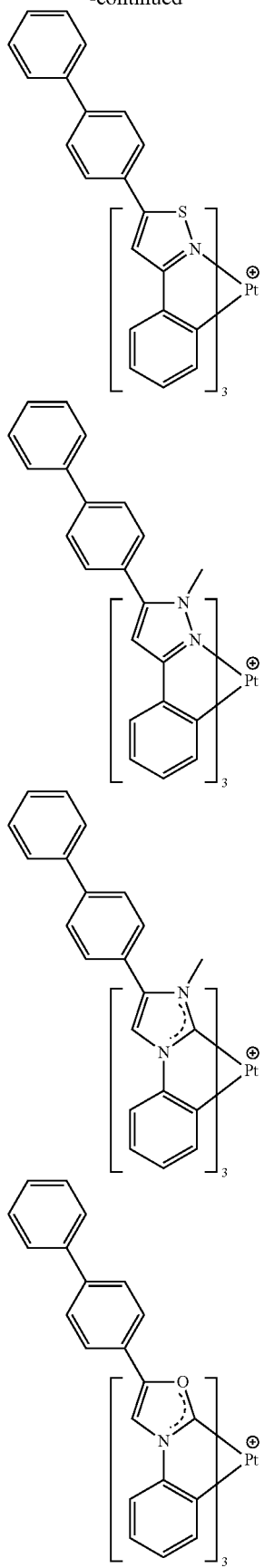
368
-continued
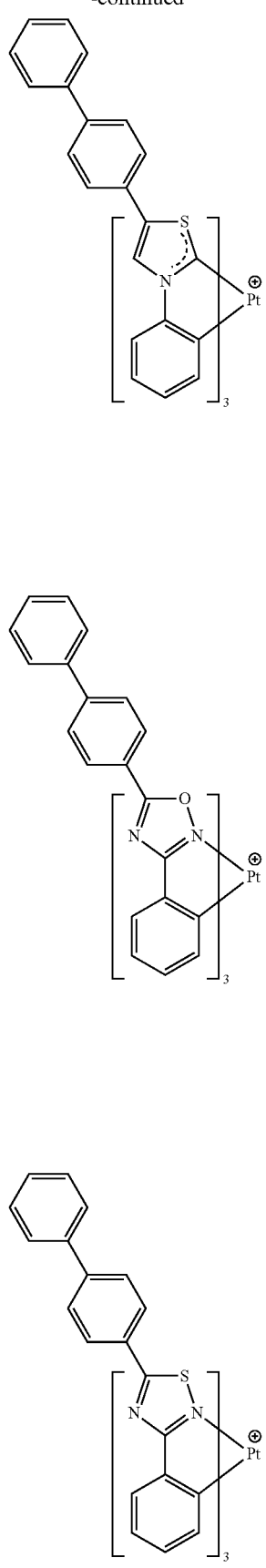

369
-continued
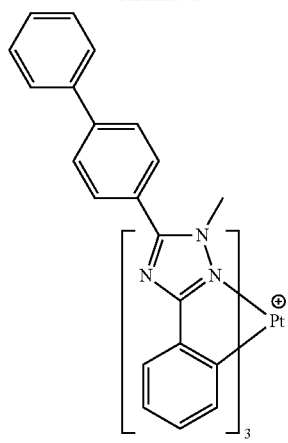
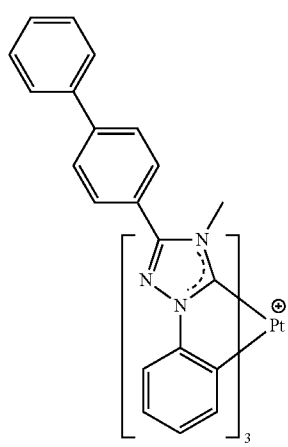
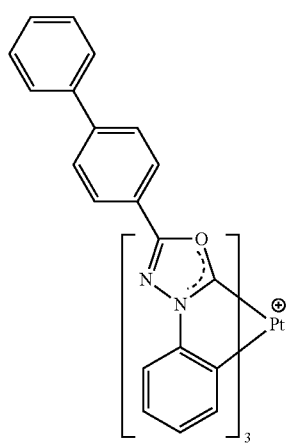
370
-continued
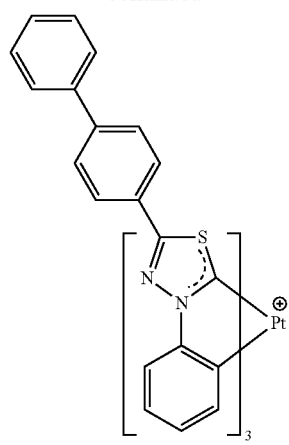
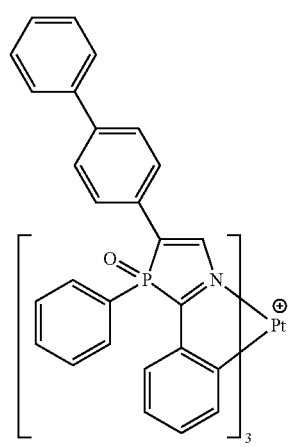
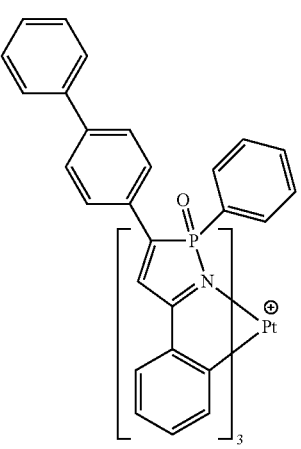

371
-continued
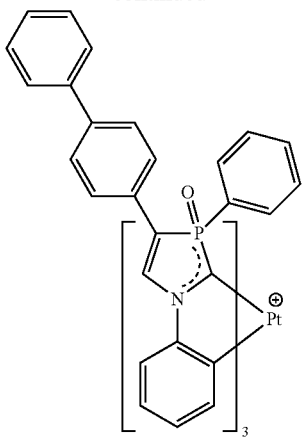
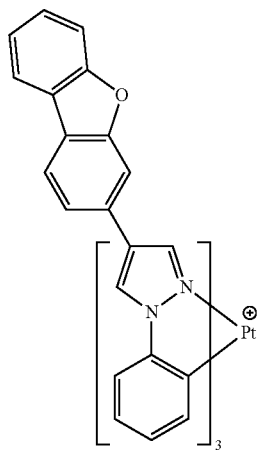
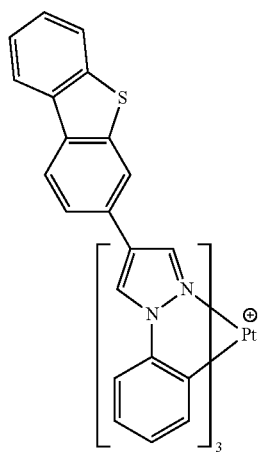
372
-continued
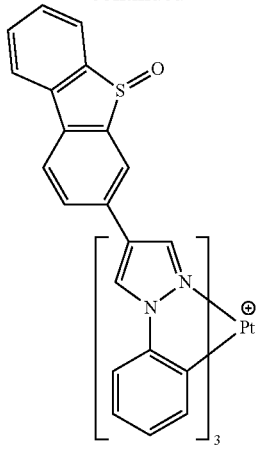
Structures Pt-2
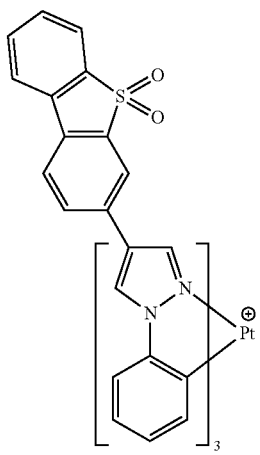
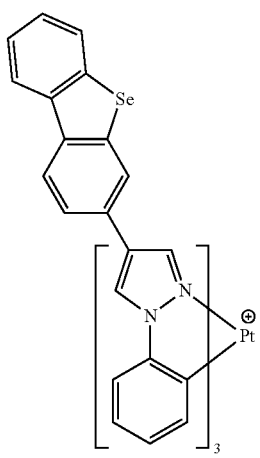

373
-continued
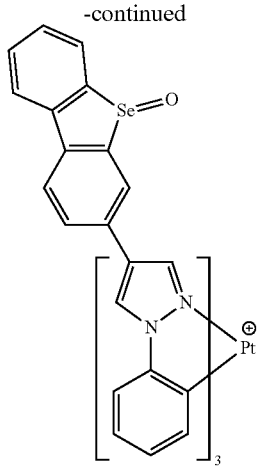
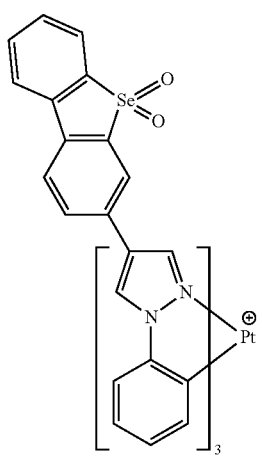
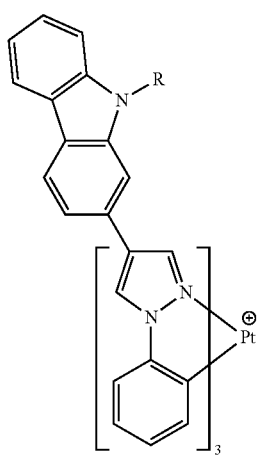
374
-continued
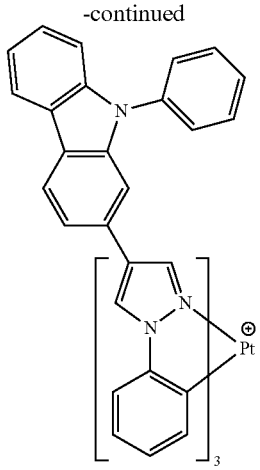
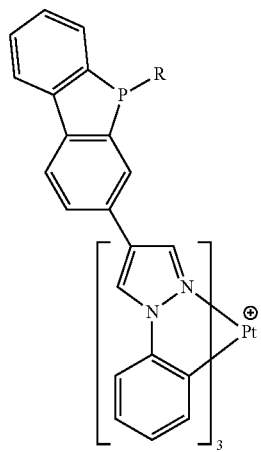
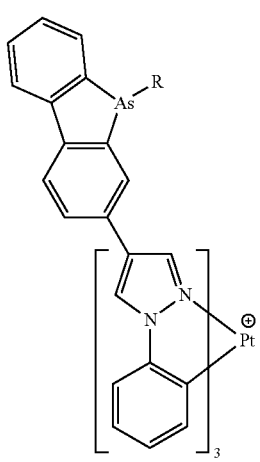

375
-continued
376
-continued
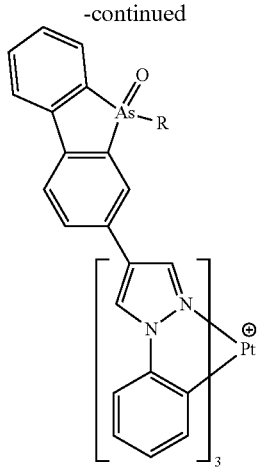
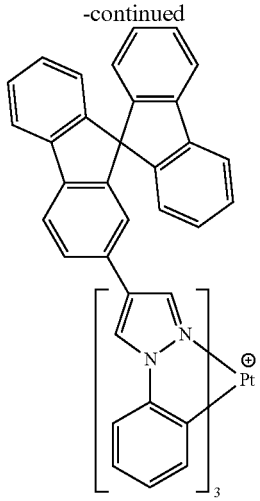
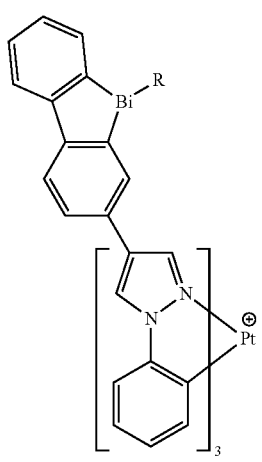
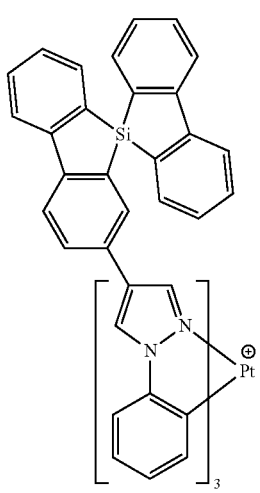
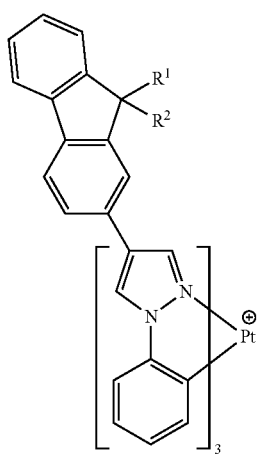

377
-continued
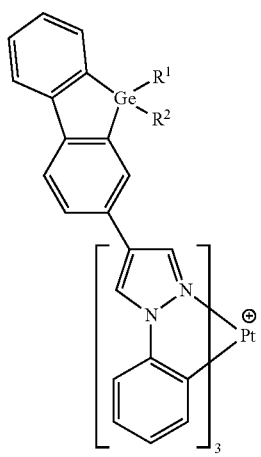
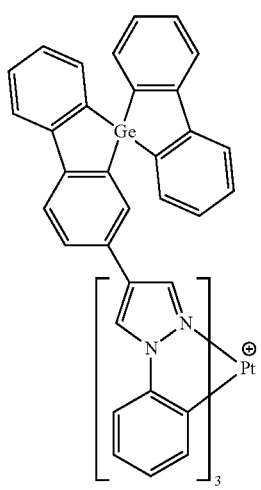
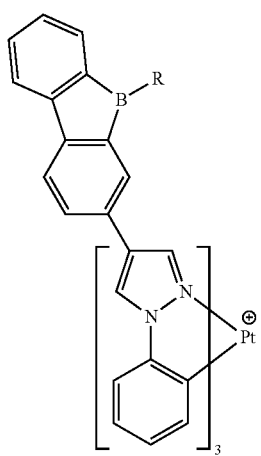
378
-continued
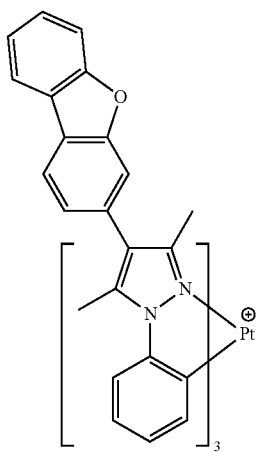
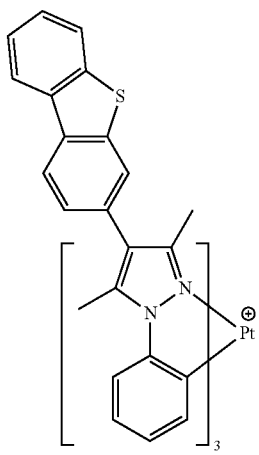
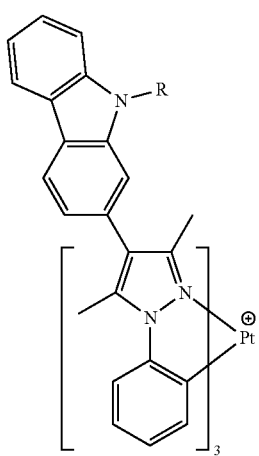

379
-continued
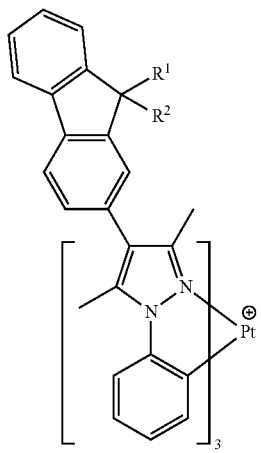
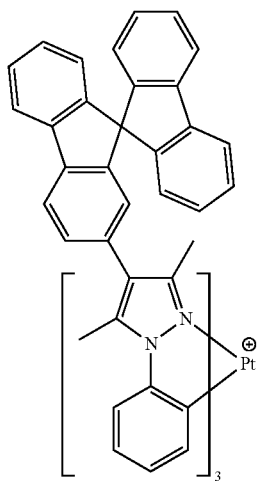
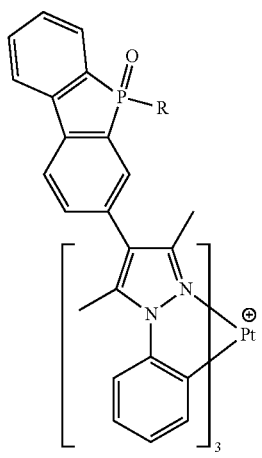
380
-continued
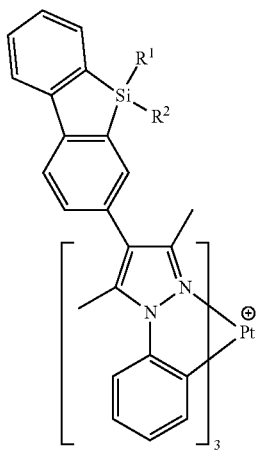
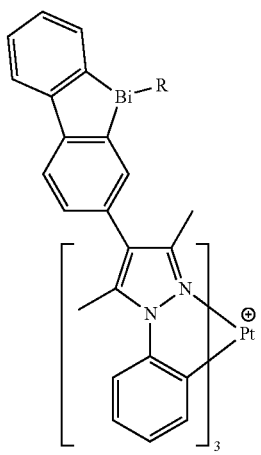
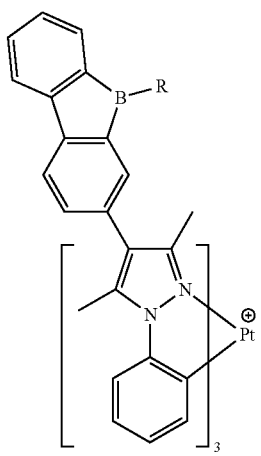

Structures Pt-3
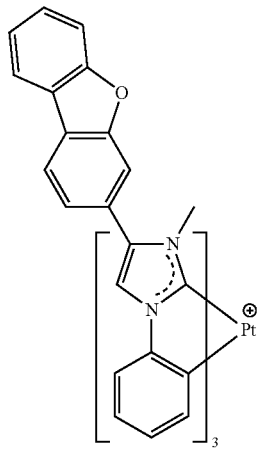
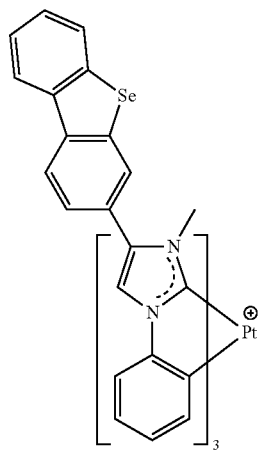
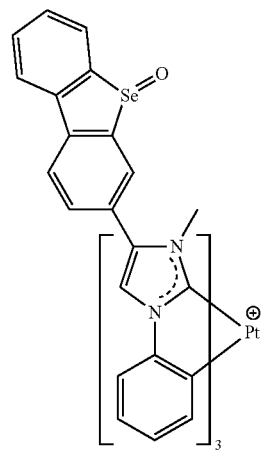
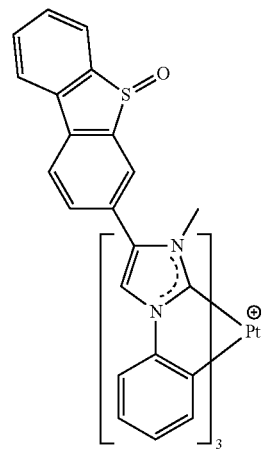
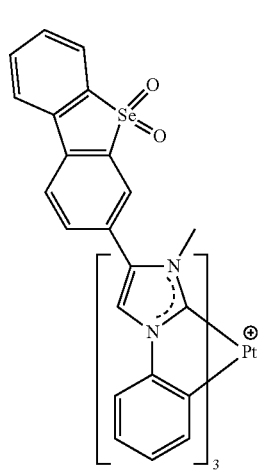
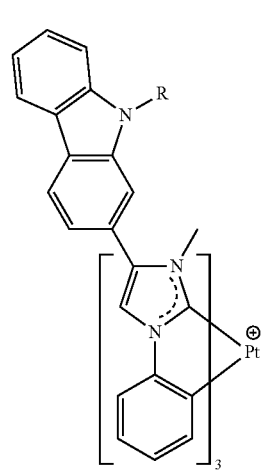
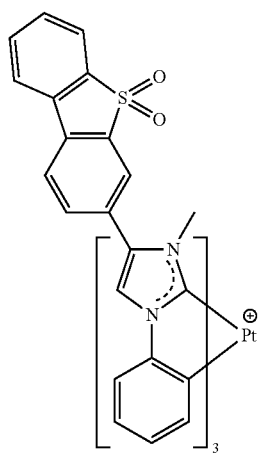
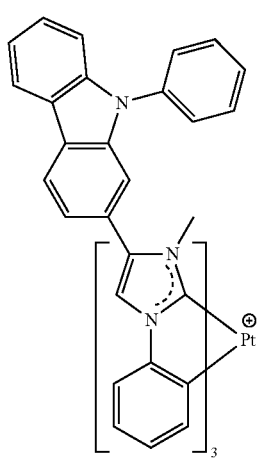
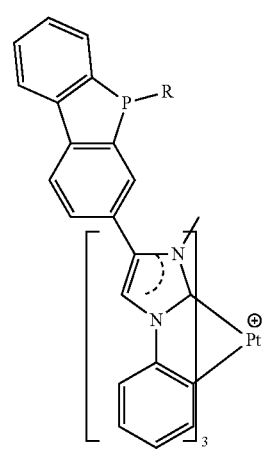

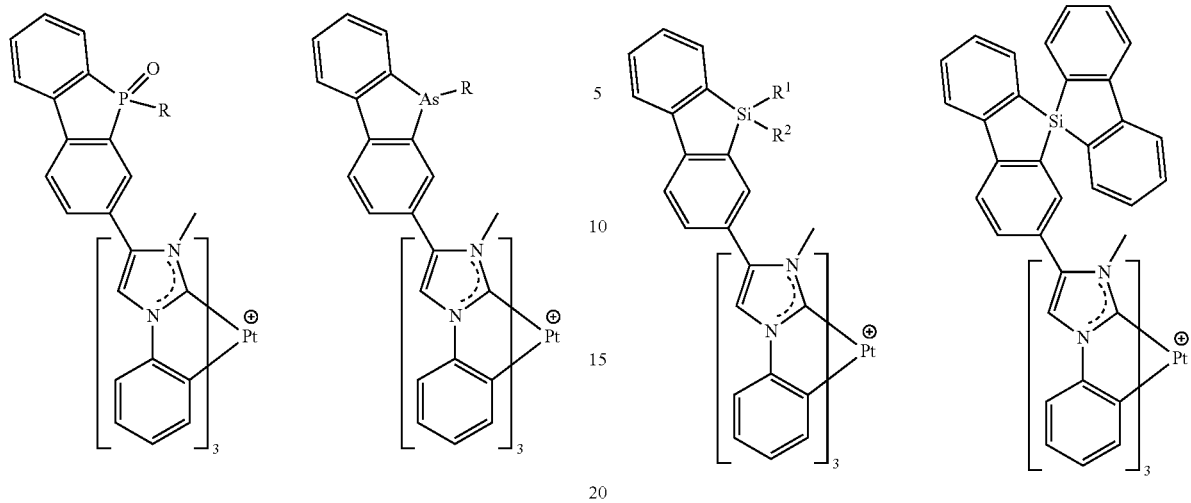
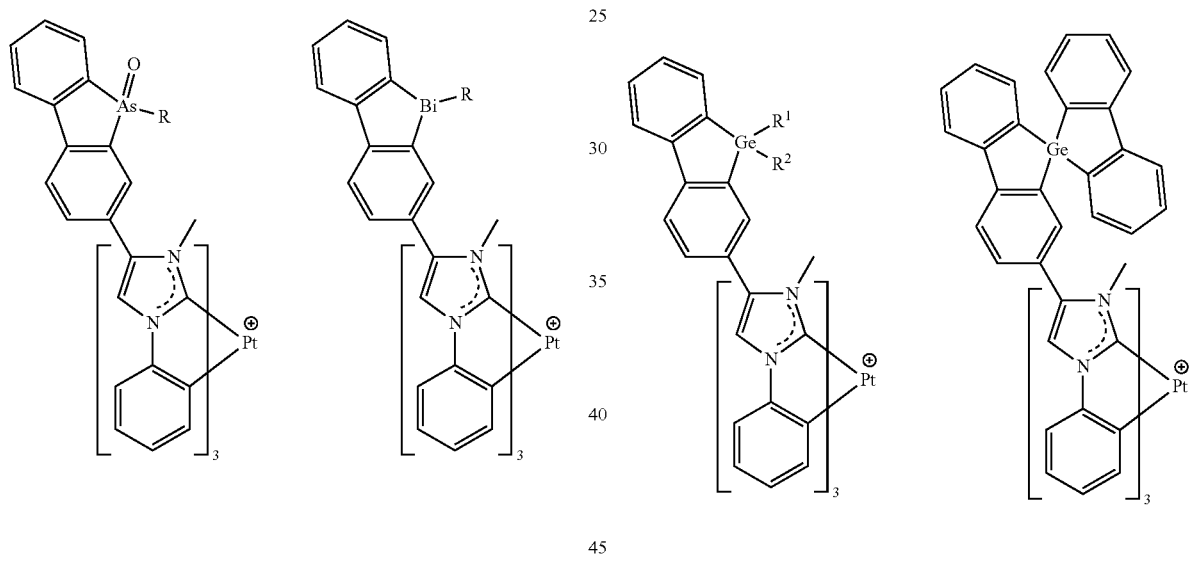
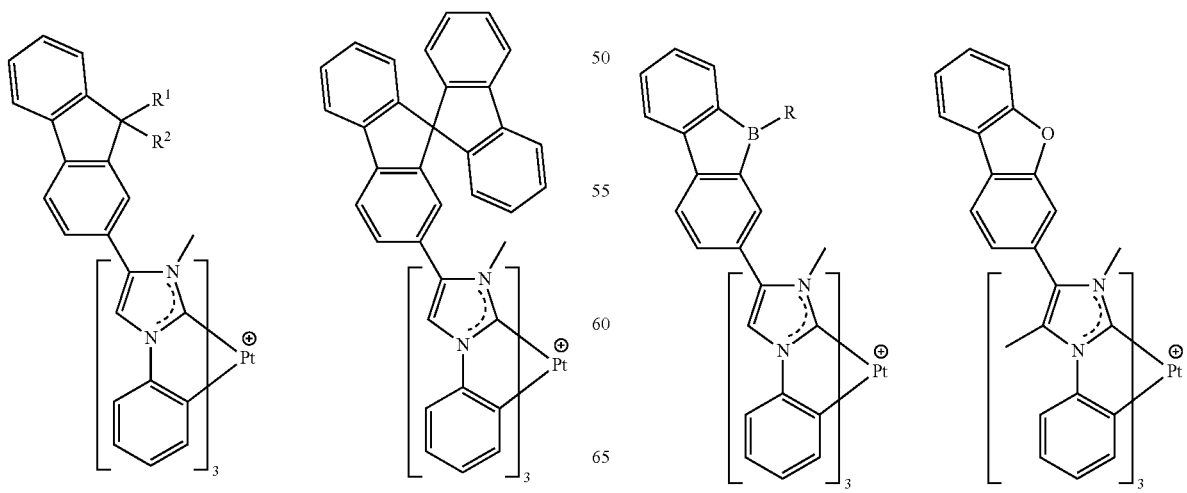

385
-continued
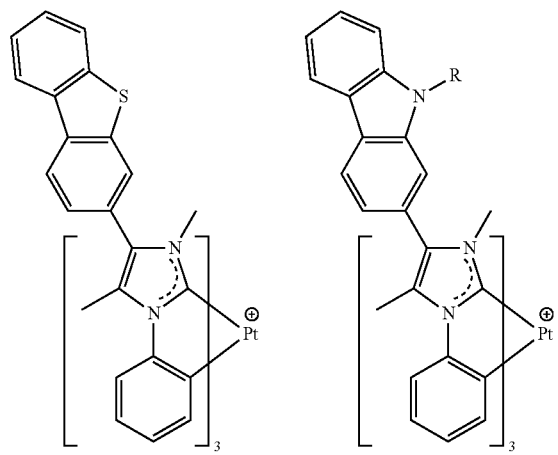
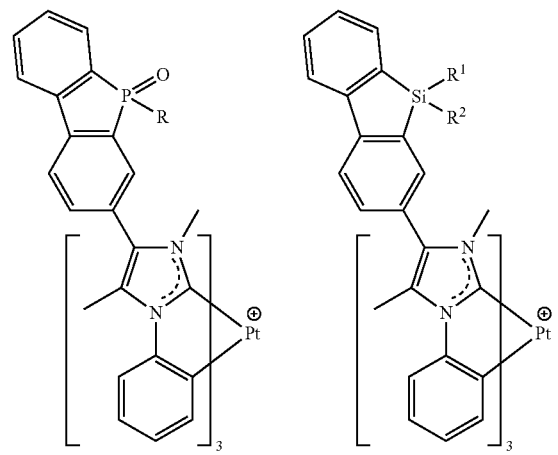
386
-continued
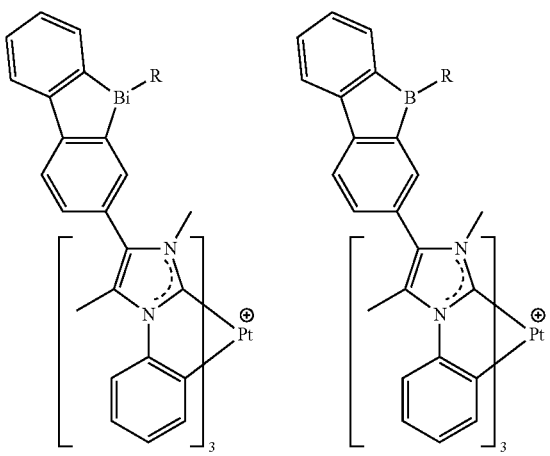
Structures Pt-4
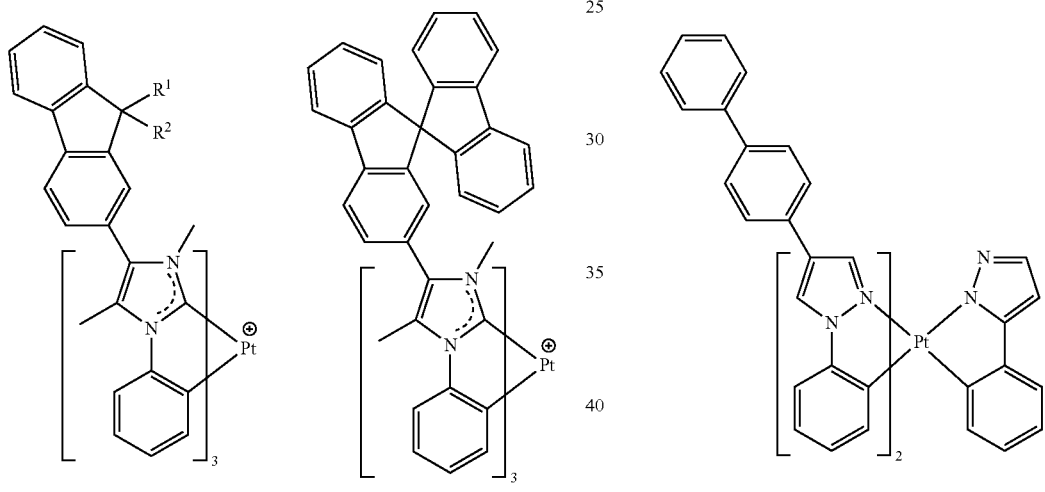

387
-continued
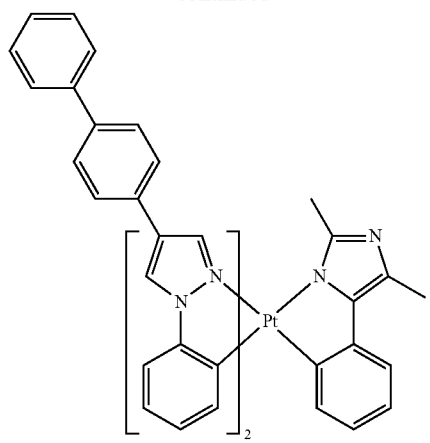
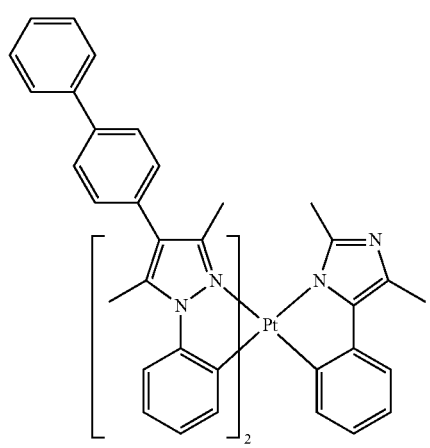
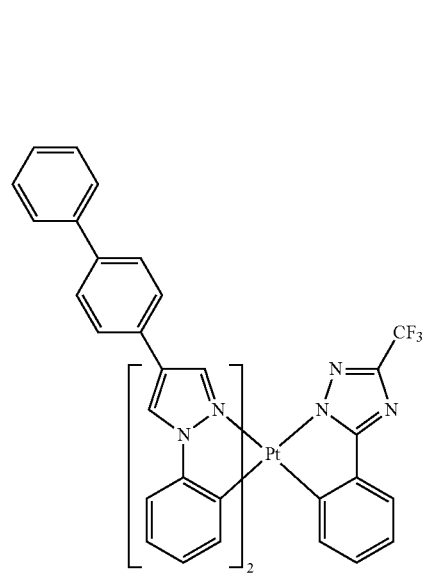
388
-continued
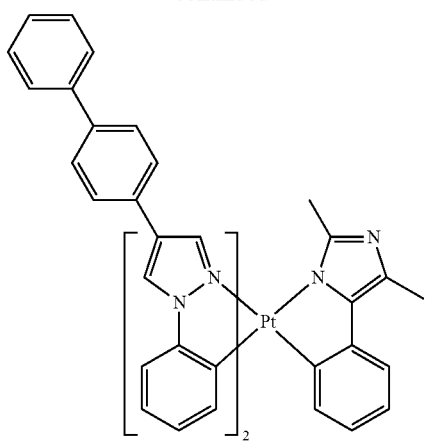
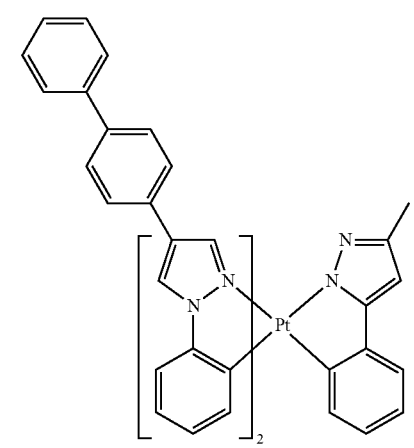
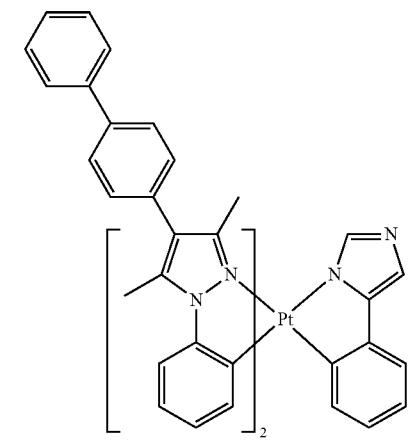

389
-continued
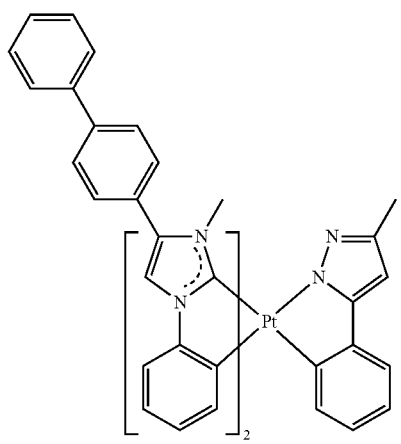
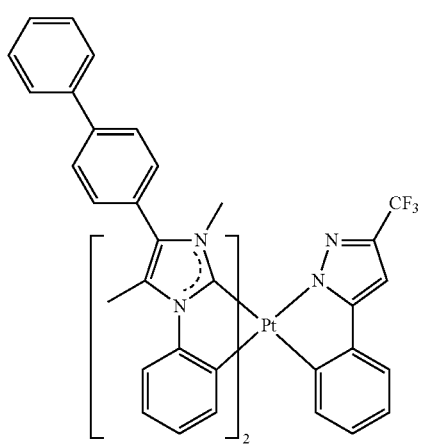
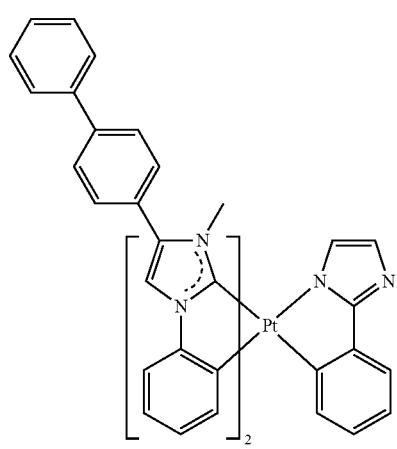
390
-continued
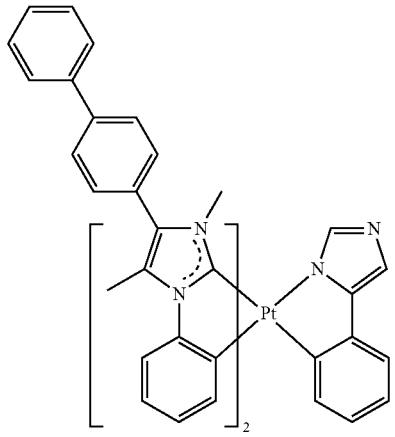
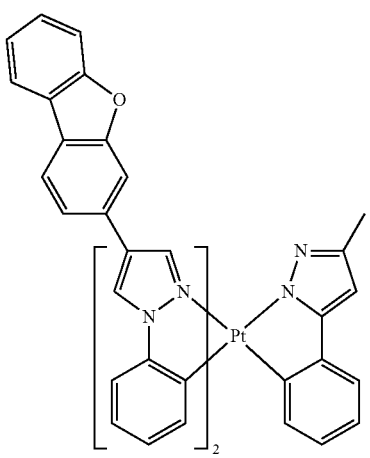
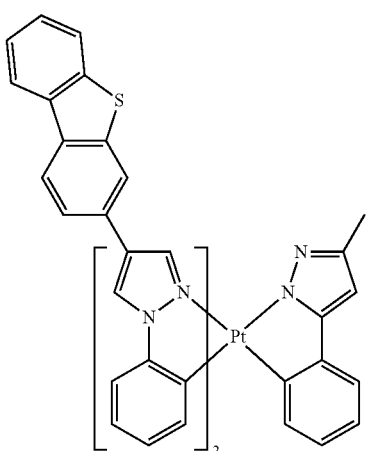

391
-continued
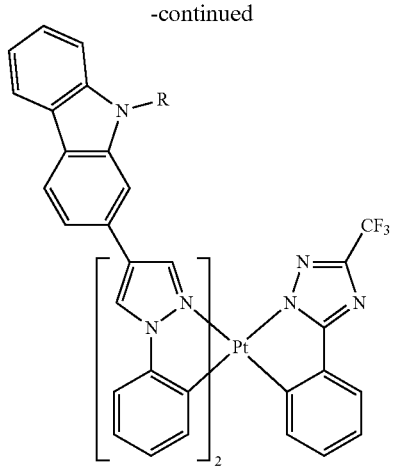
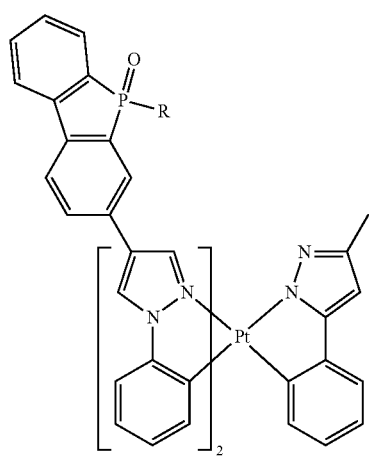
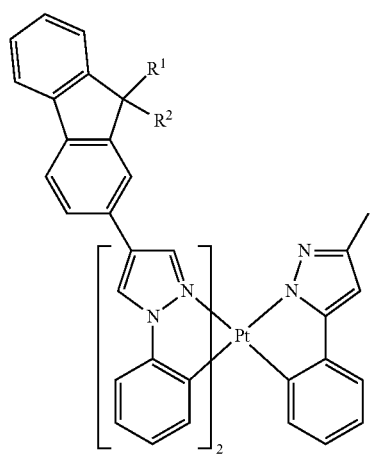
392
-continued
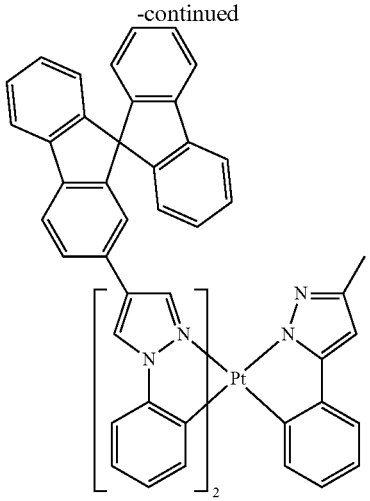
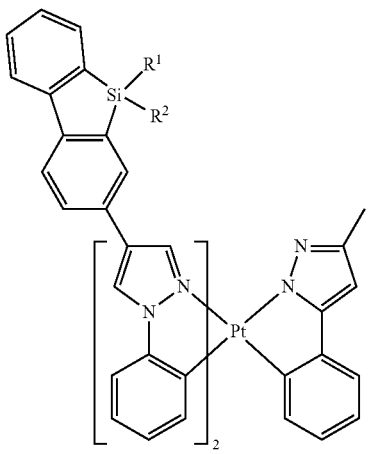
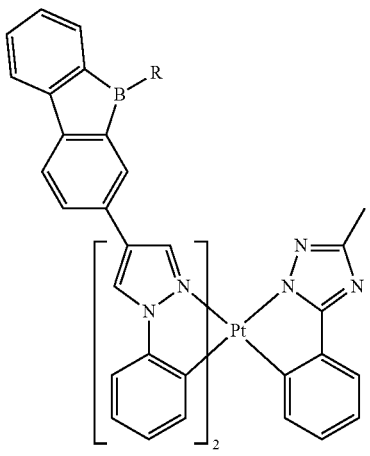

393
-continued
Structures Pt-5
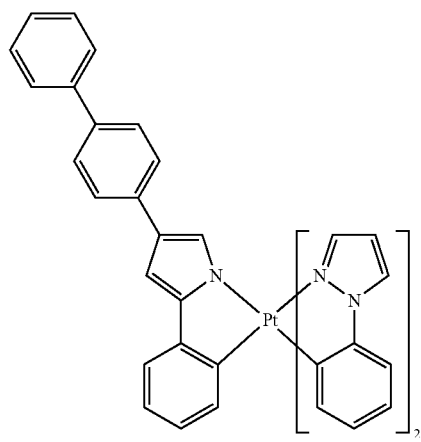
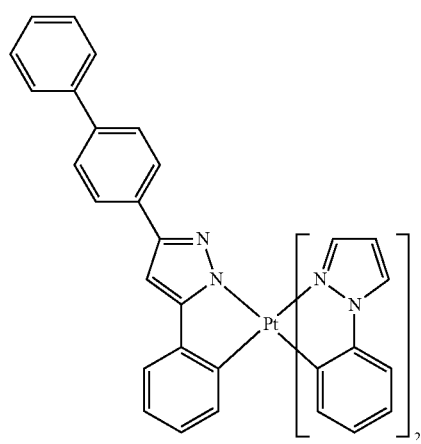
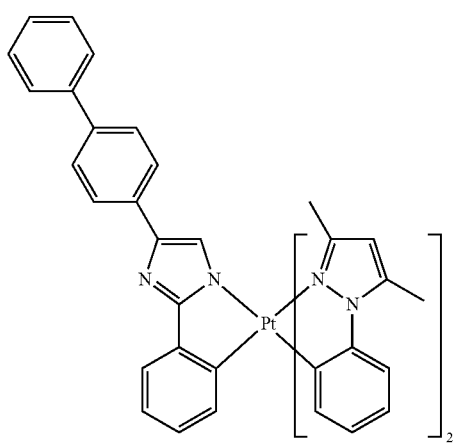
394
-continued
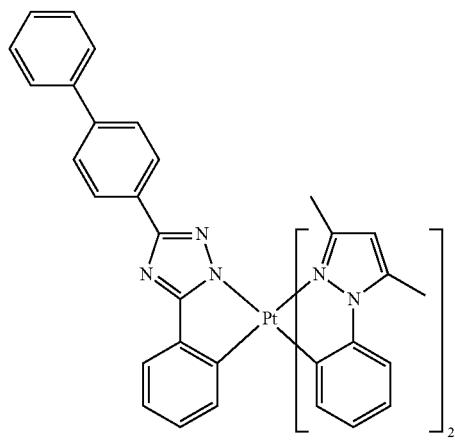
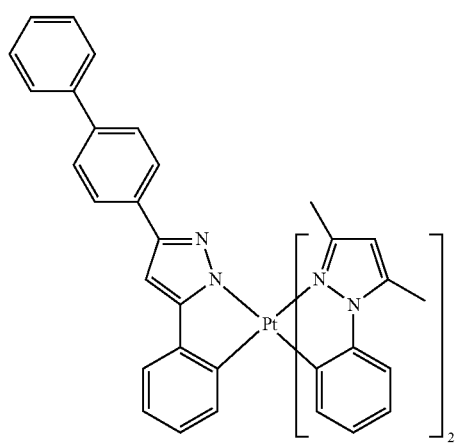
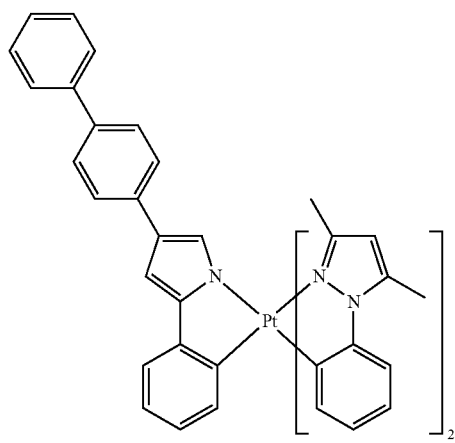

395
-continued
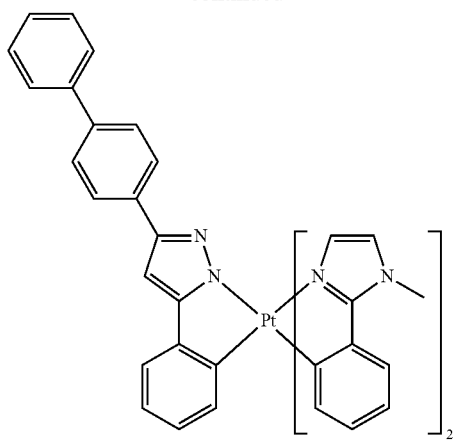
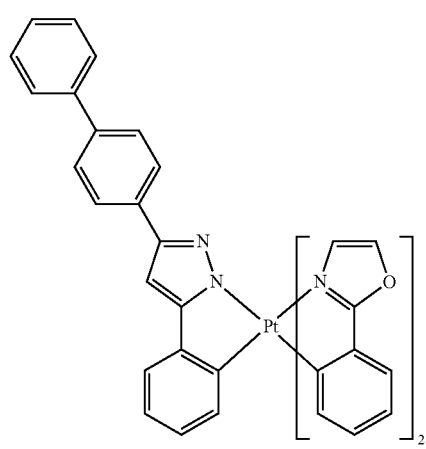
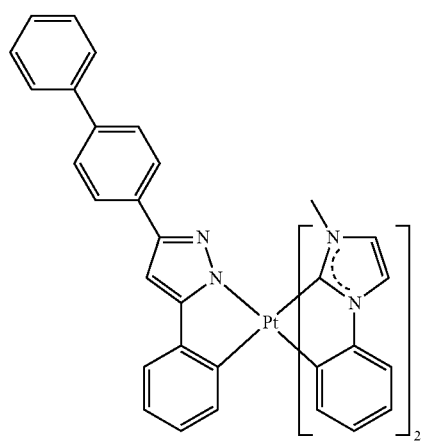
396
-continued
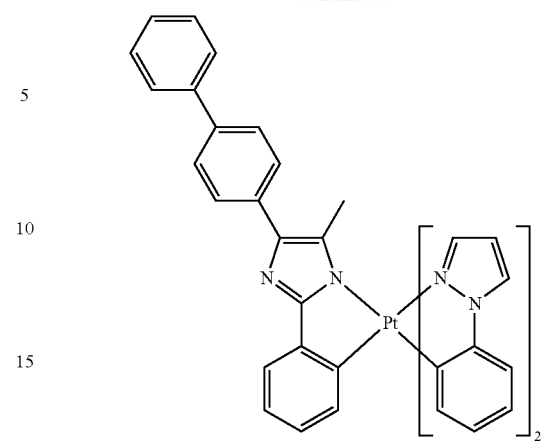
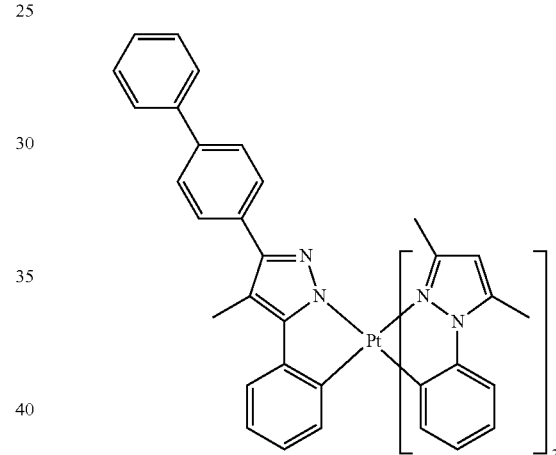
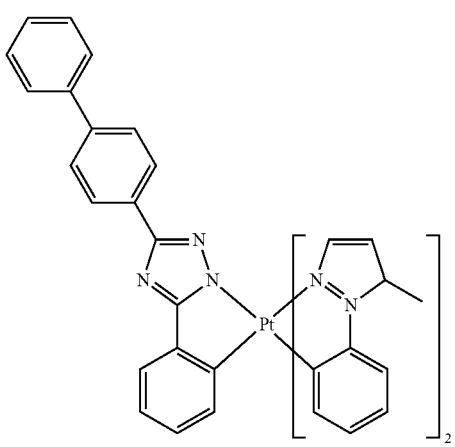

397
-continued
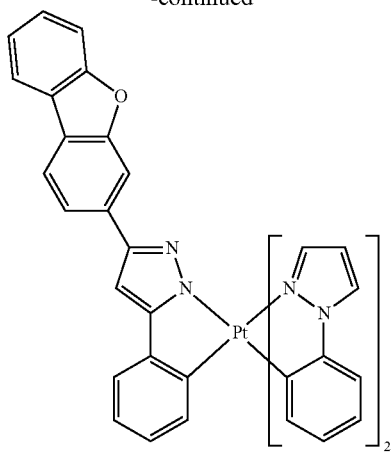
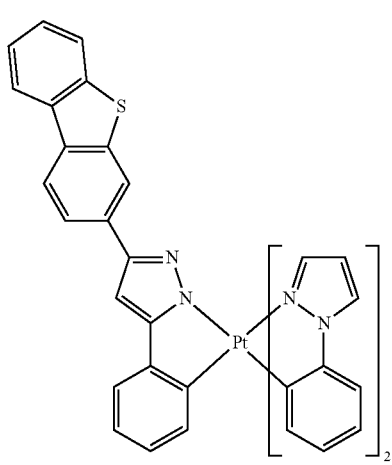
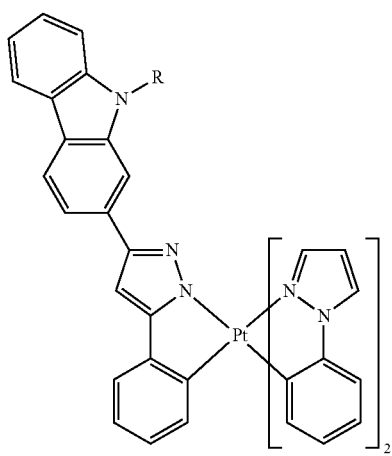
398
-continued
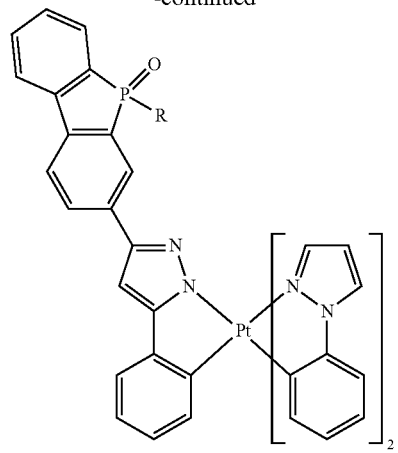
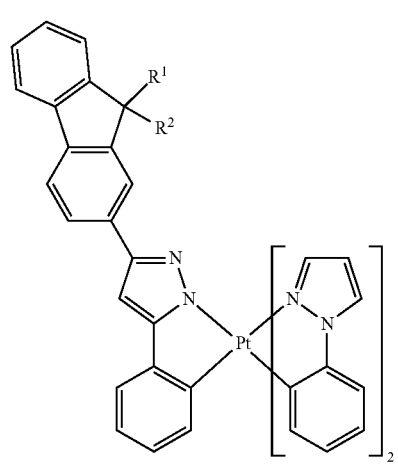
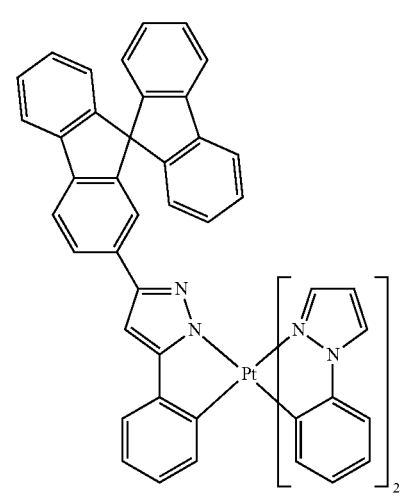

399
-continued
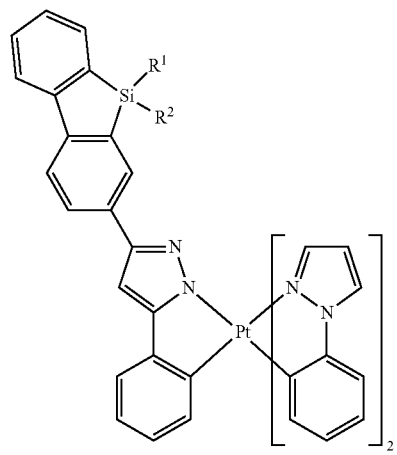
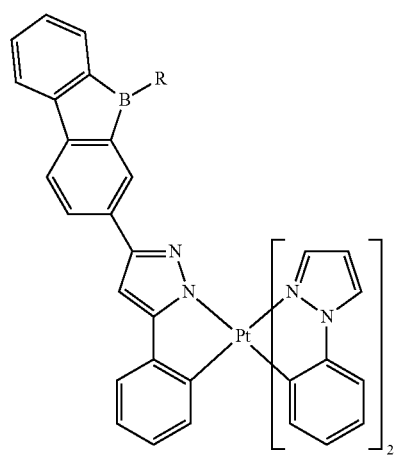
Structures Pt-6
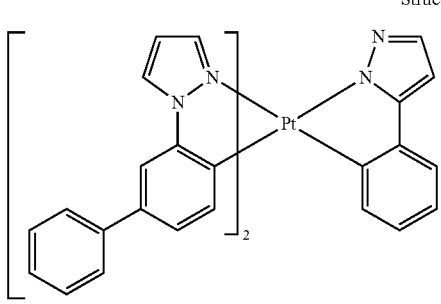
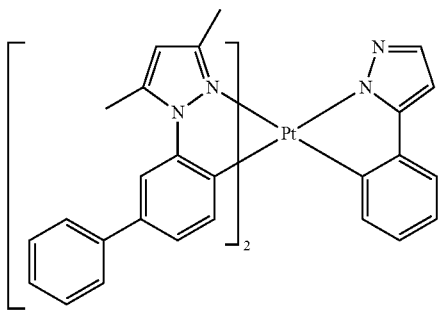
400
-continued
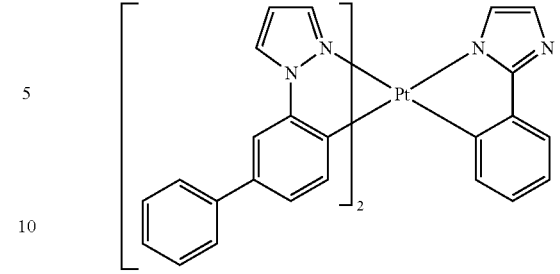
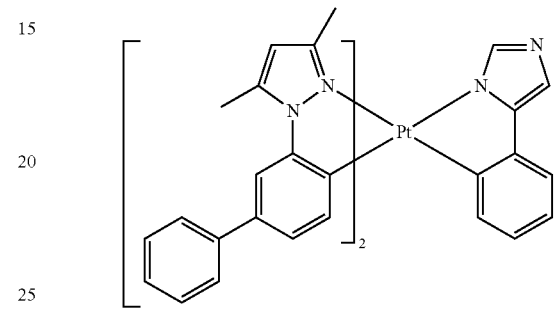
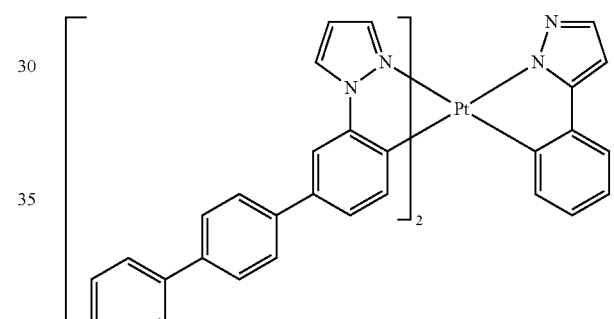
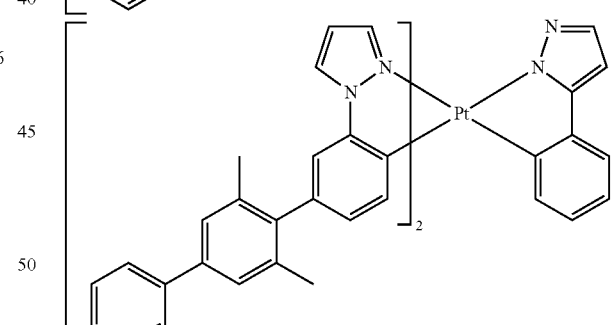
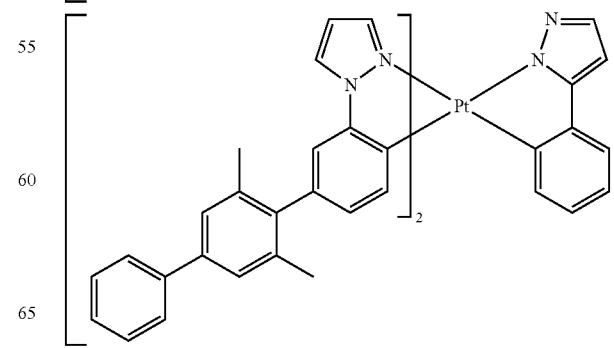

401
-continued
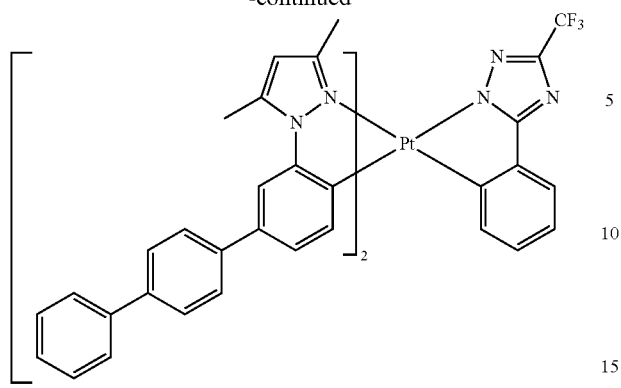
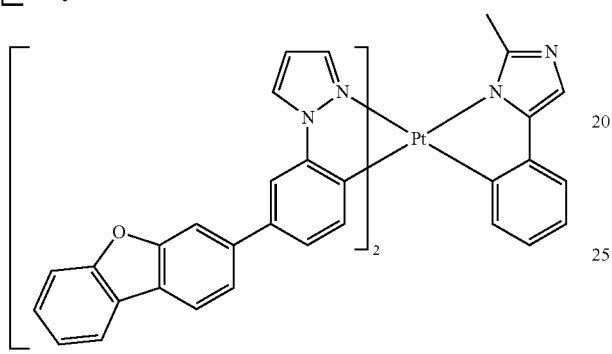
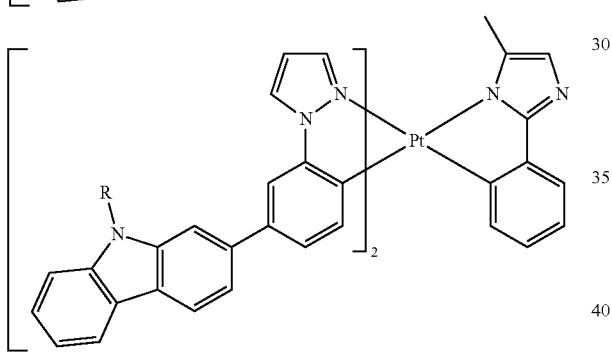
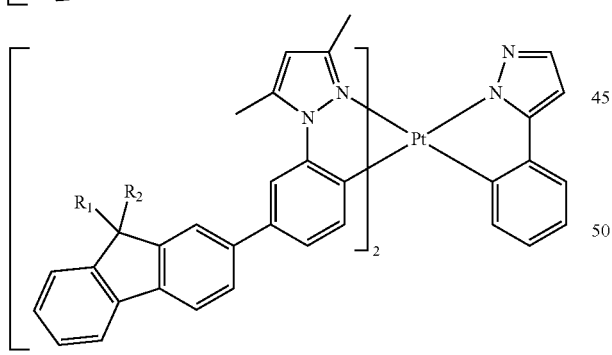
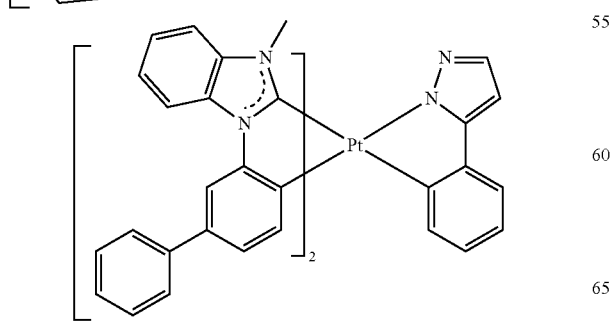
402
-continued
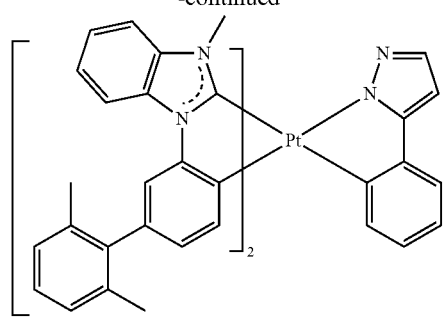
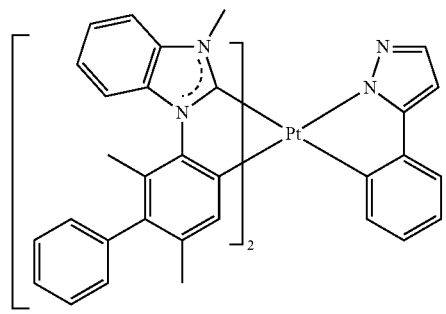
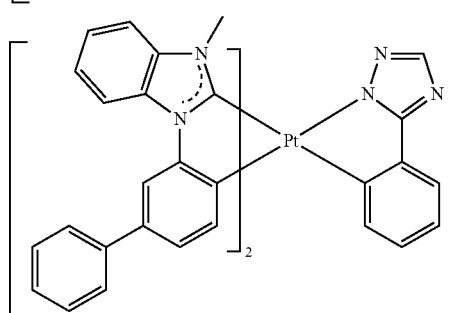
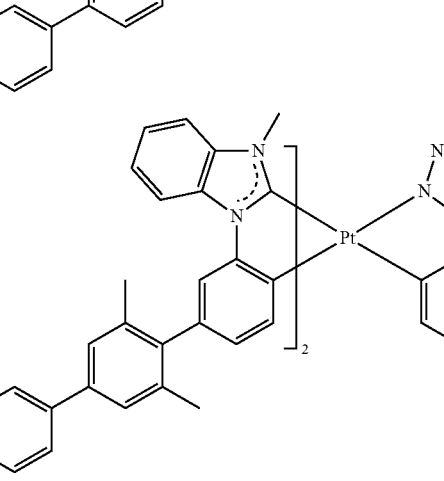

403
-continued
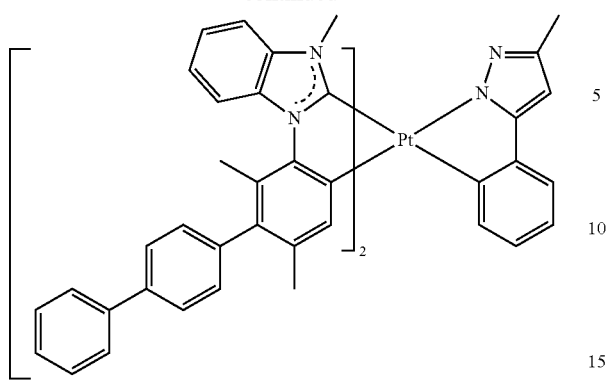
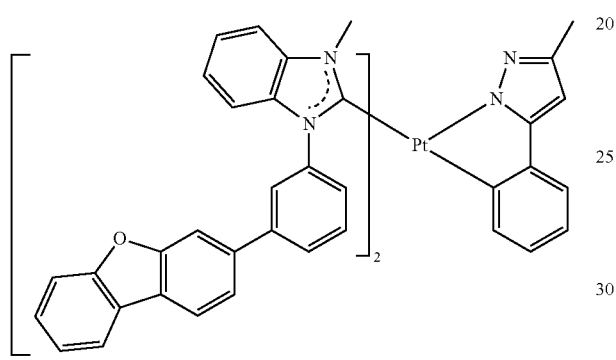
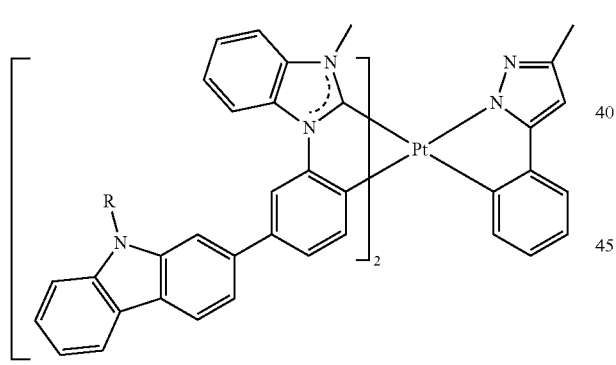
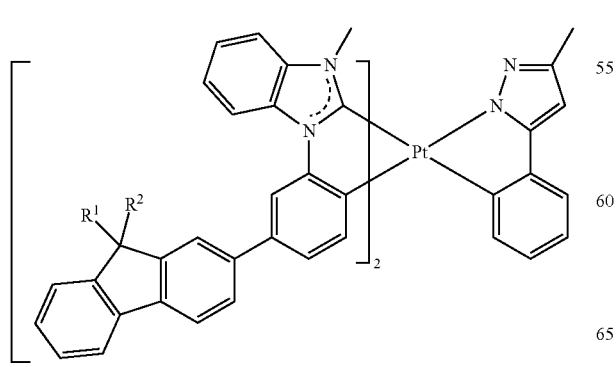
404
-continued
Structures Pt-7
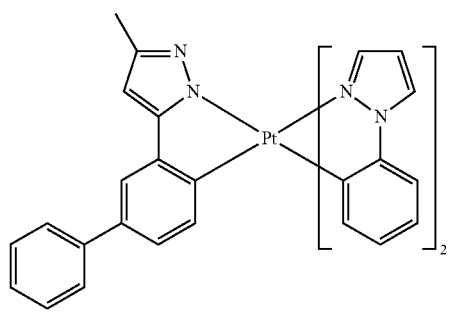
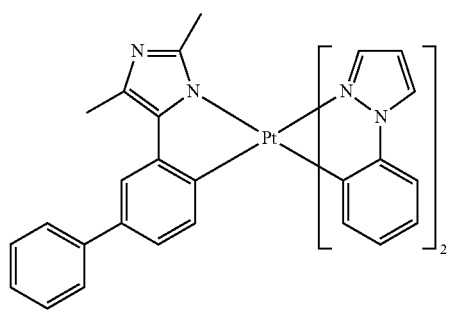
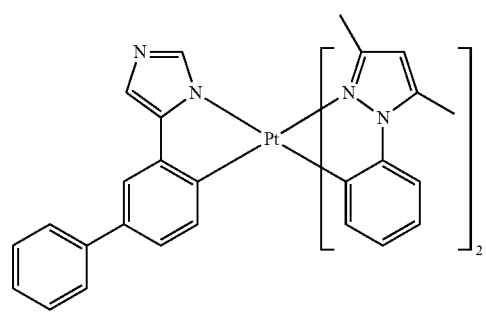
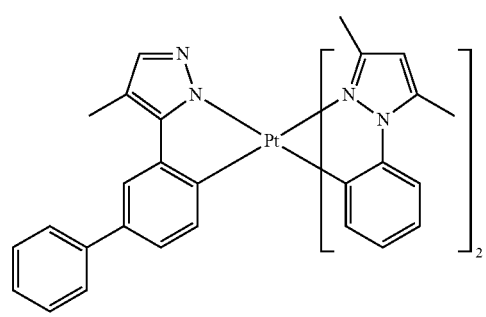
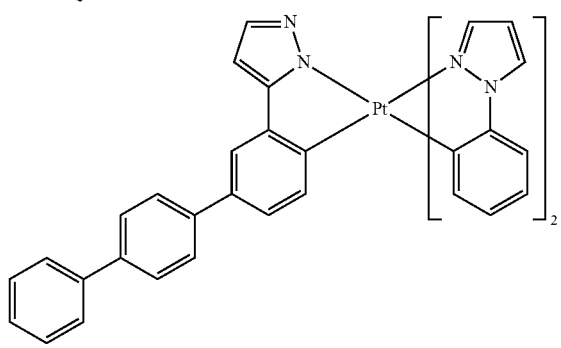

405
-continued
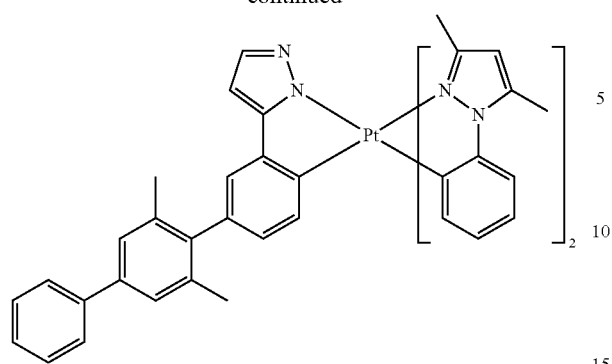
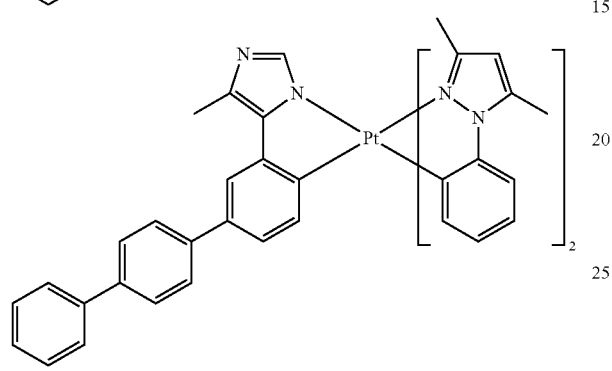
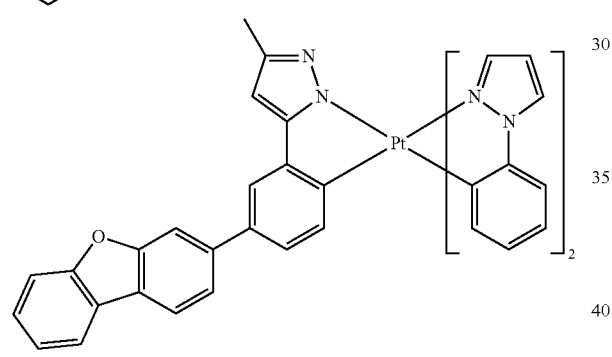
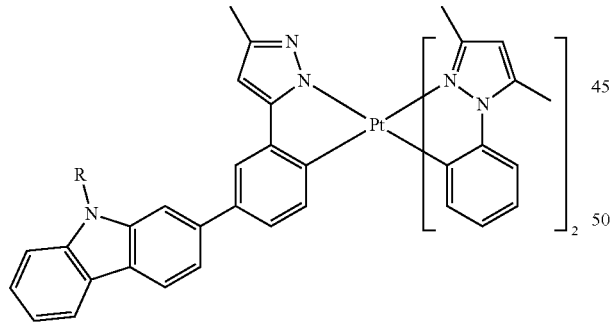
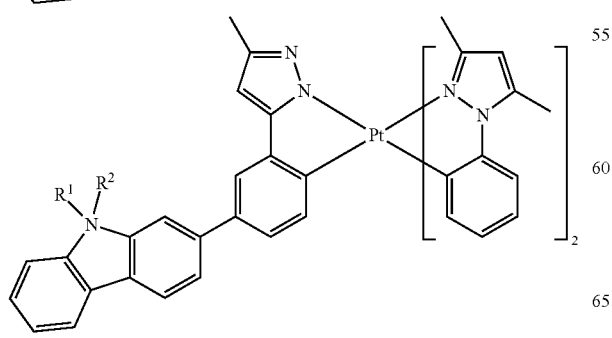
406
-continued
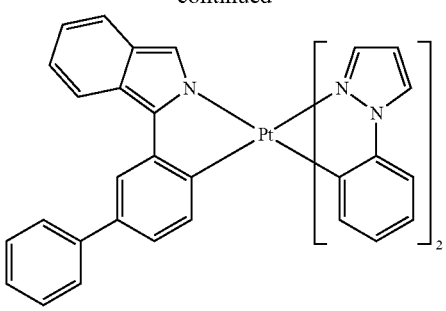
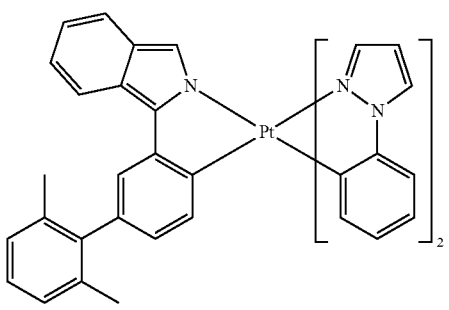
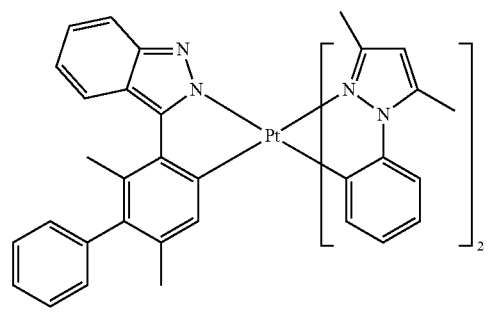
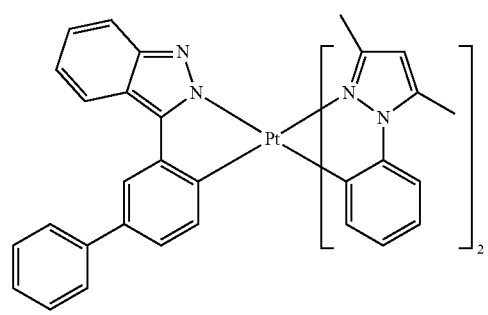
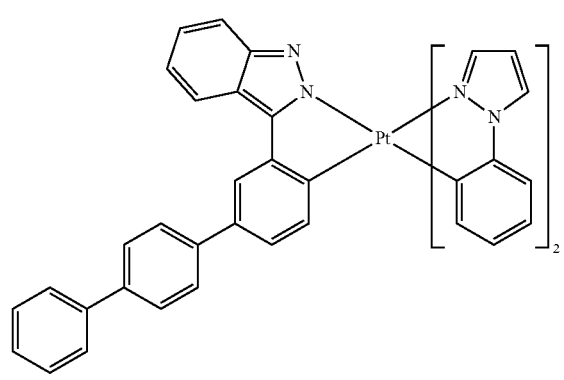

407
-continued
408
-continued
Structures Pt-8
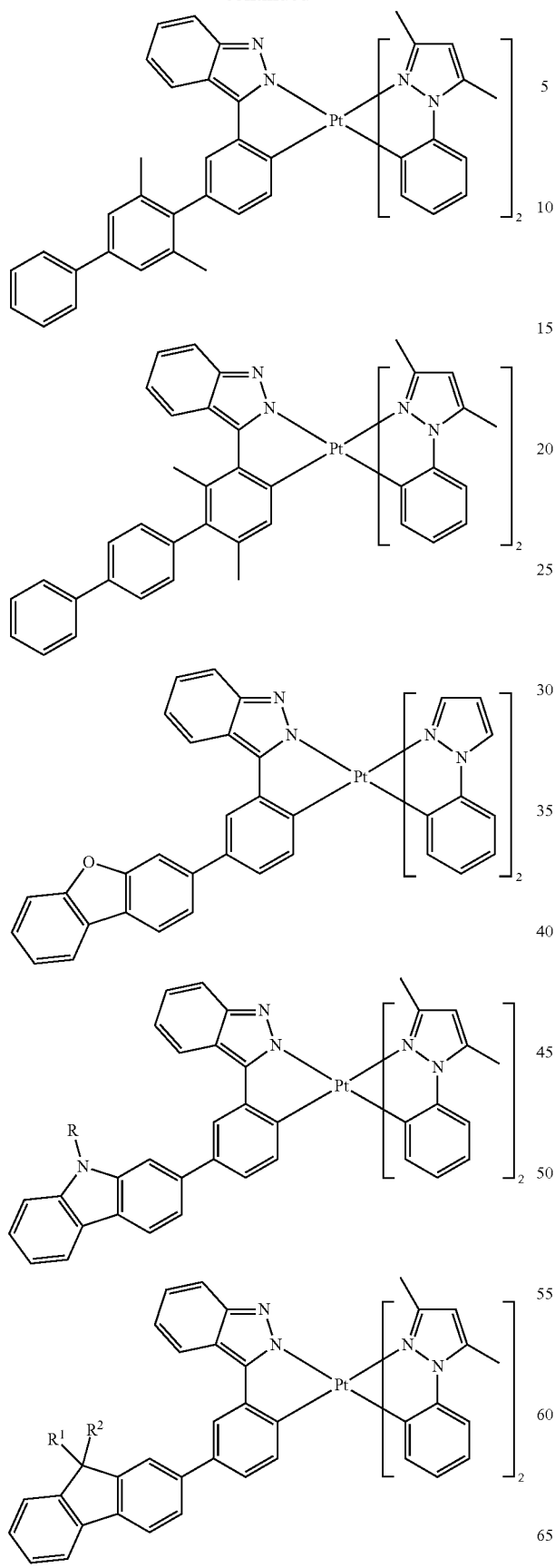
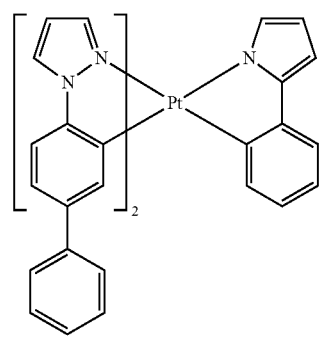

-continued
| 409 | 410 |
|---|---|
| 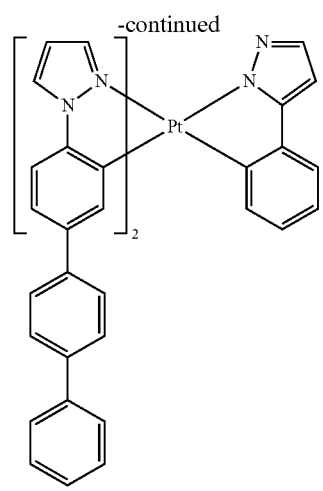 | 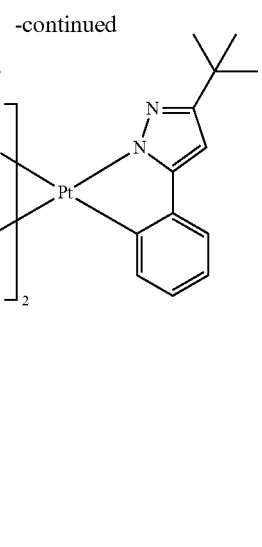 |
| 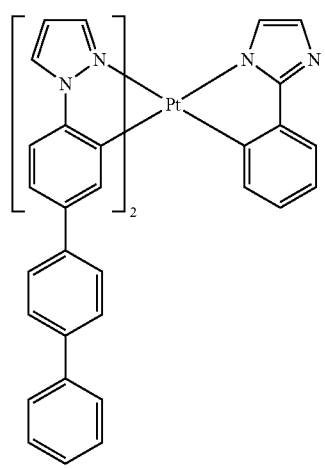 | 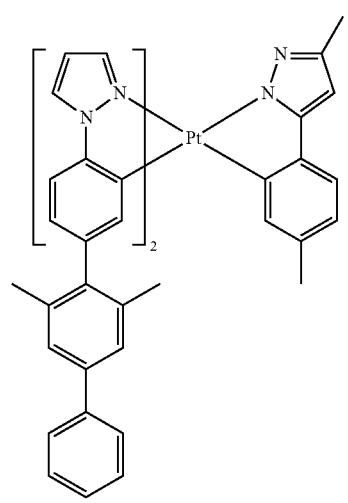 |
| 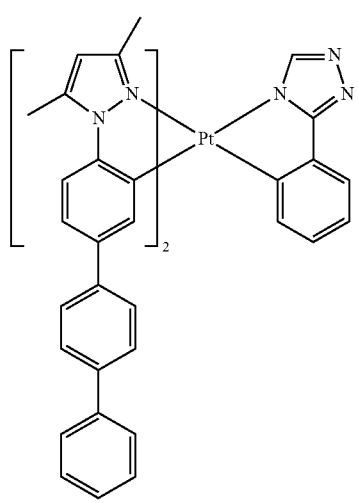 | 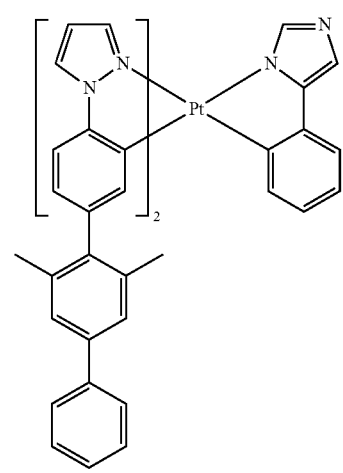 |

411
-continued
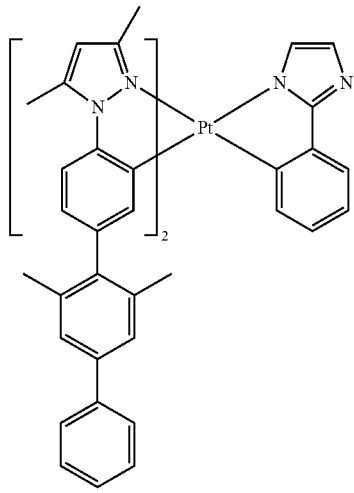
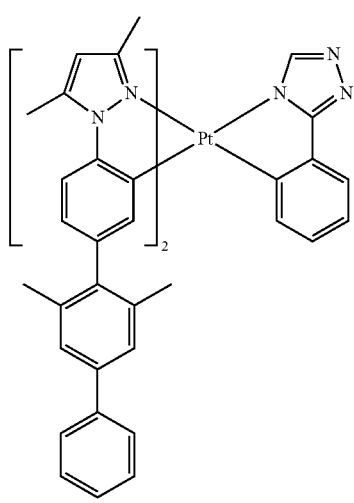
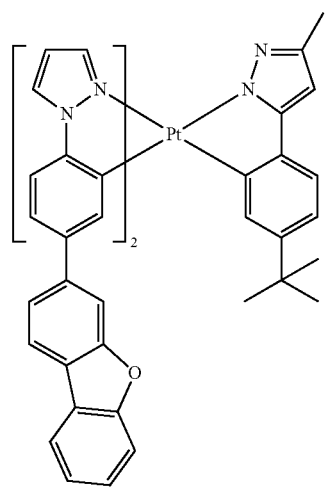
412
-continued
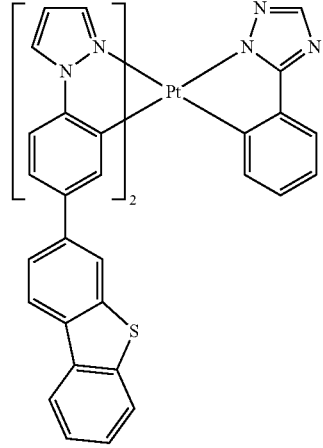
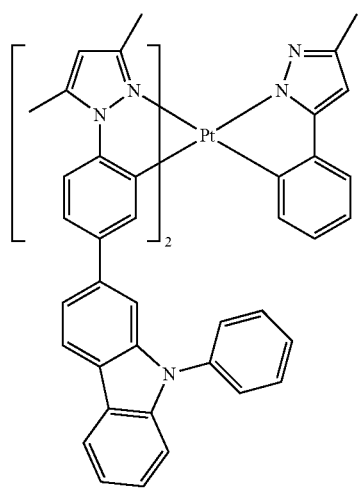
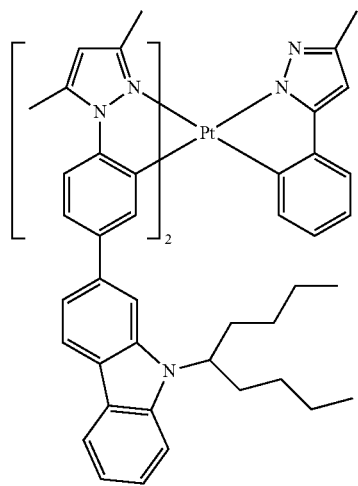

-continued
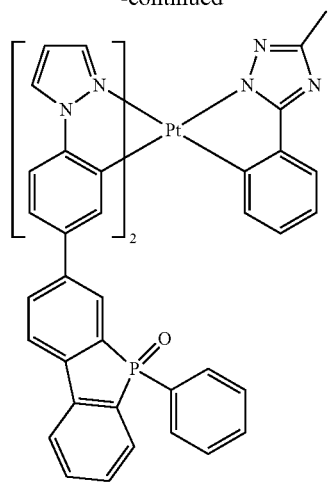
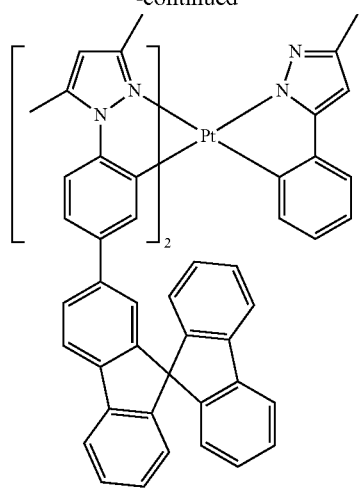
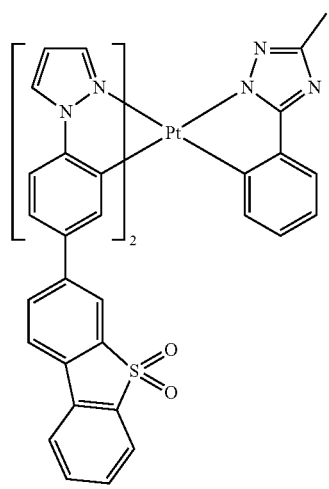
Structures Pt-9
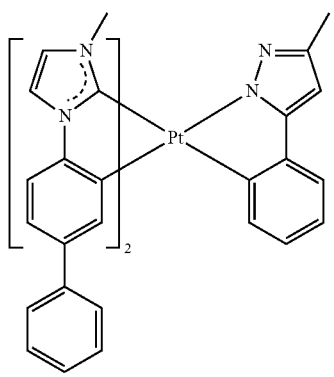
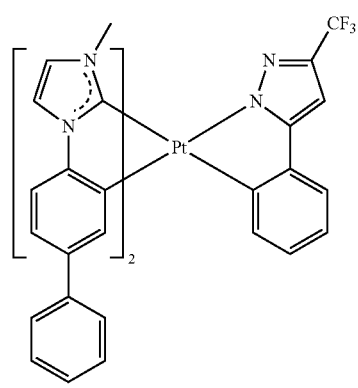
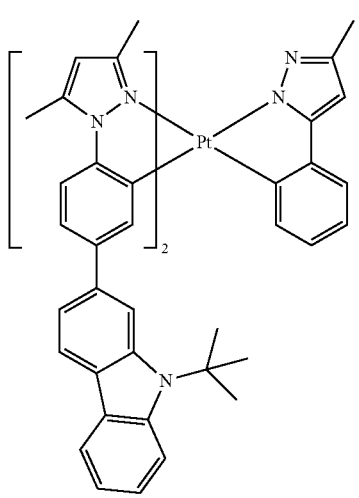
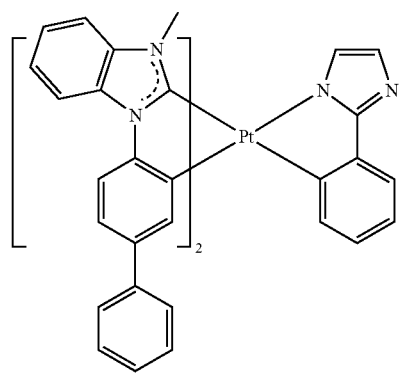

415
-continued
416
-continued
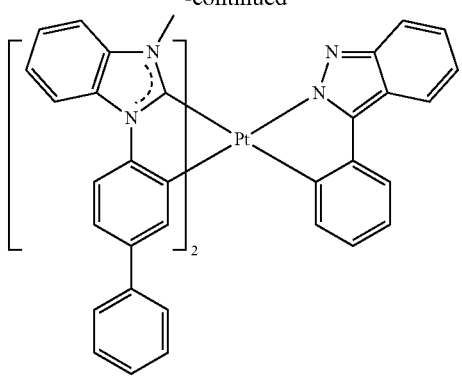
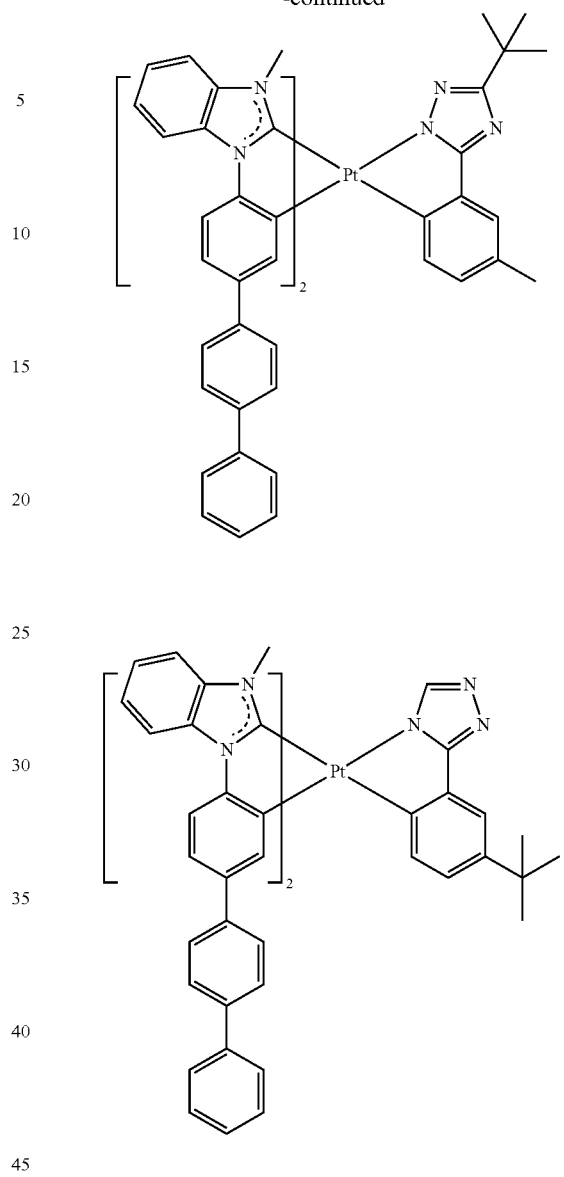
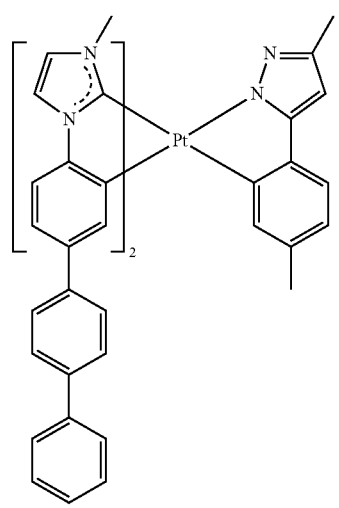
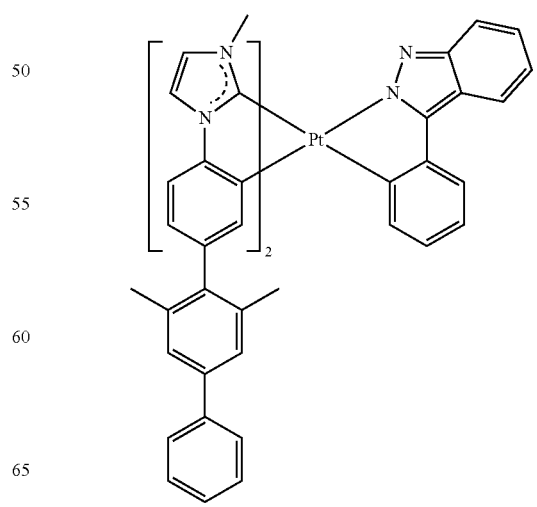

417
-continued
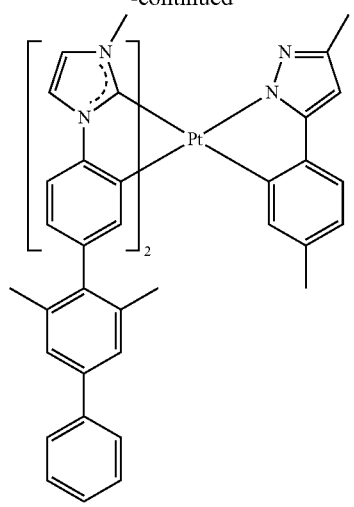
418
-continued
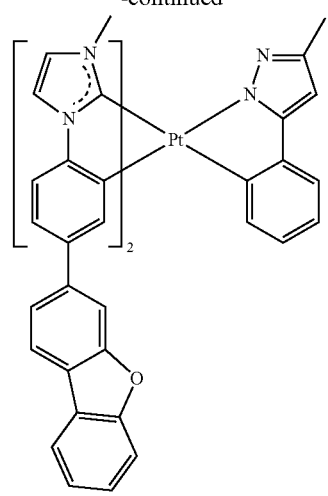
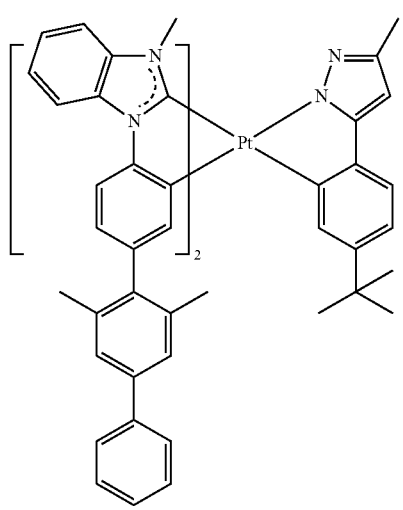
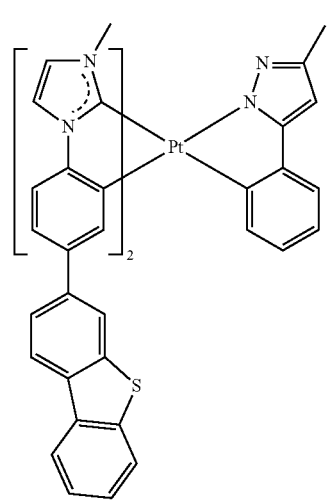
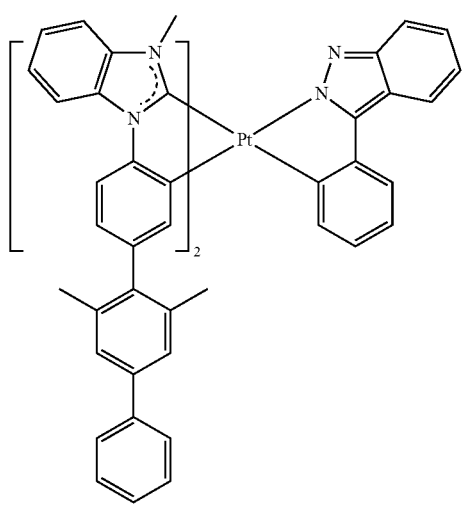

419
-continued
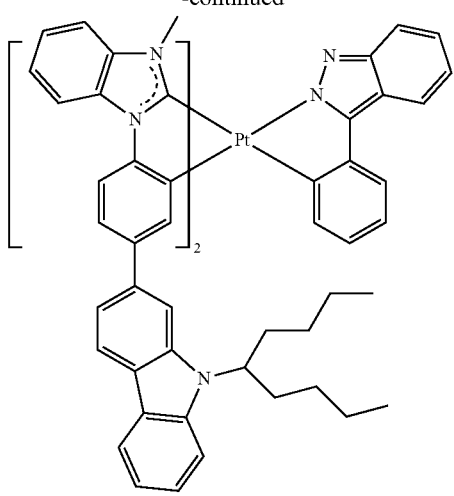
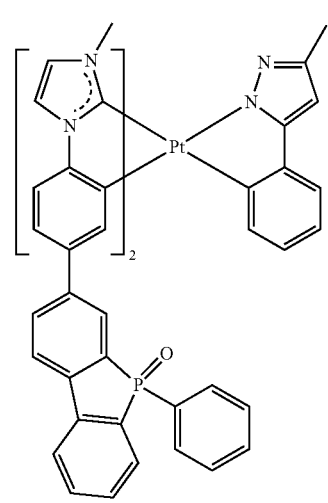
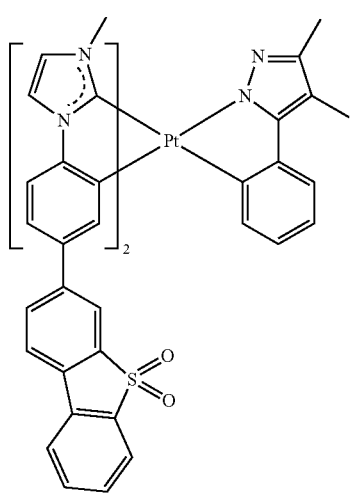
420
-continued
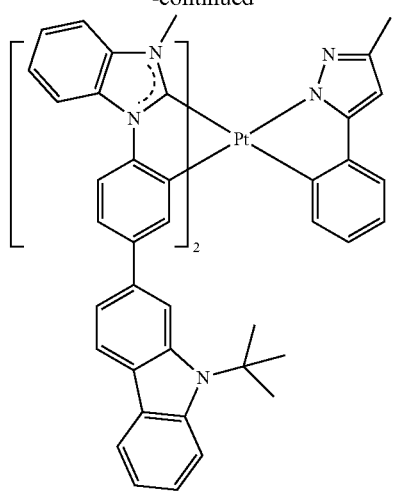
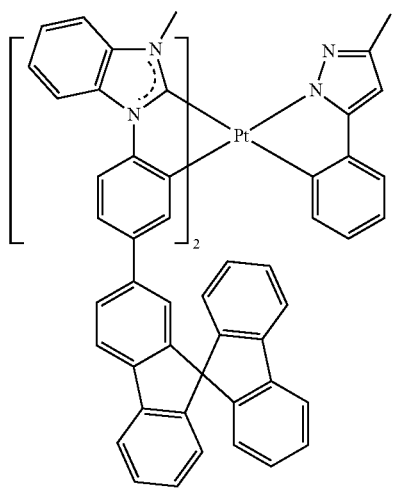
Structures Pt-10
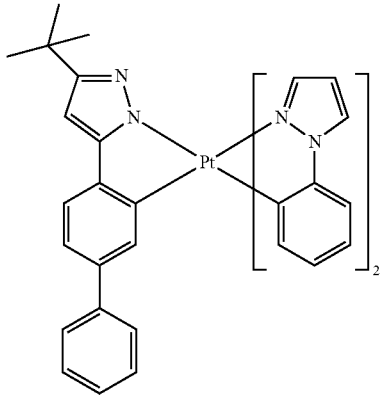

421
-continued
422
-continued
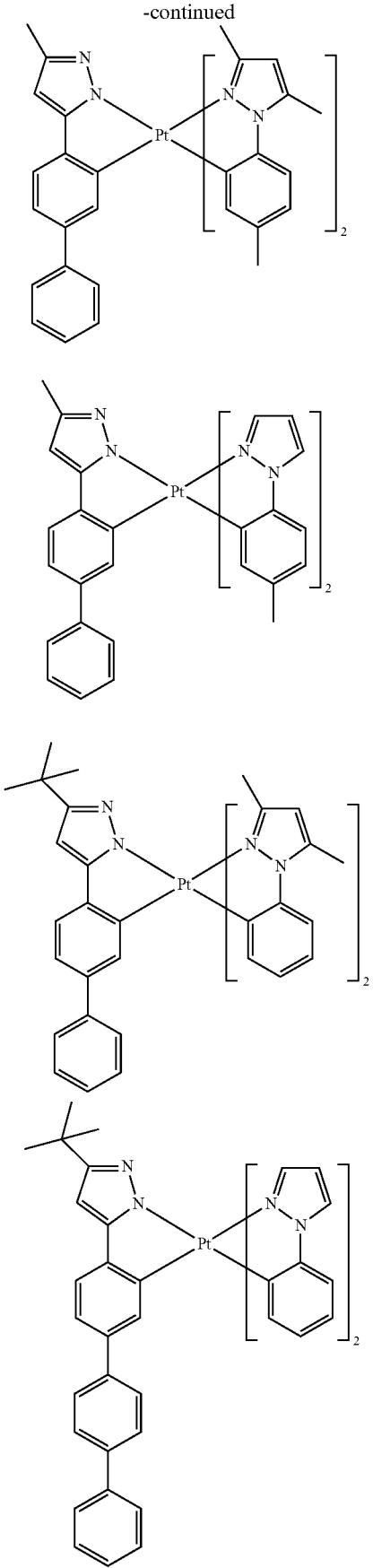

423
-continued
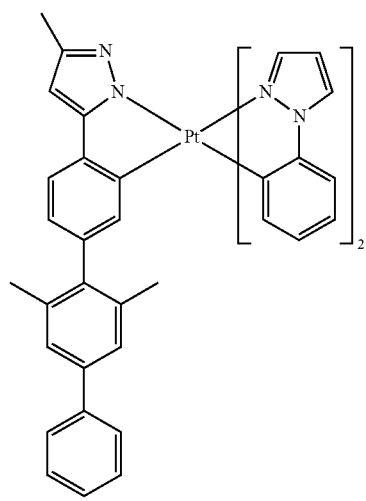
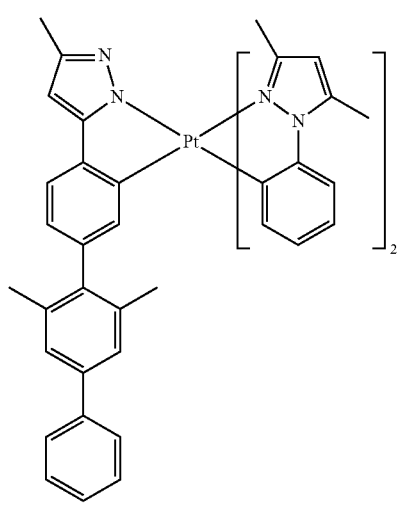
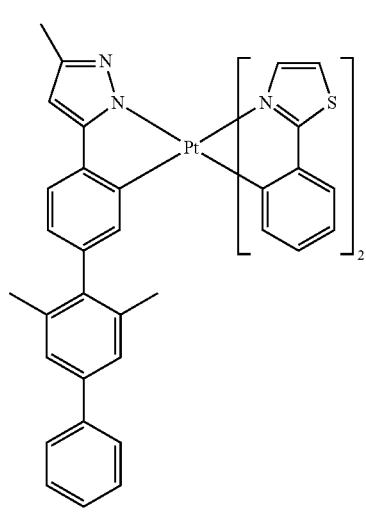
424
-continued
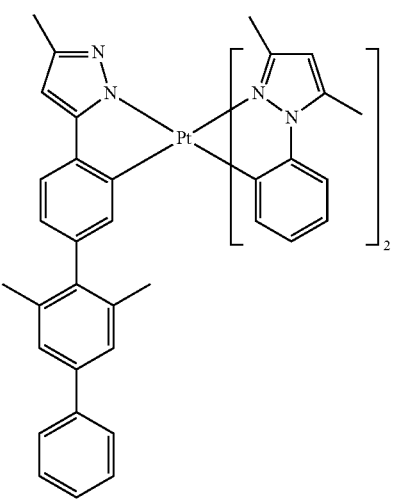
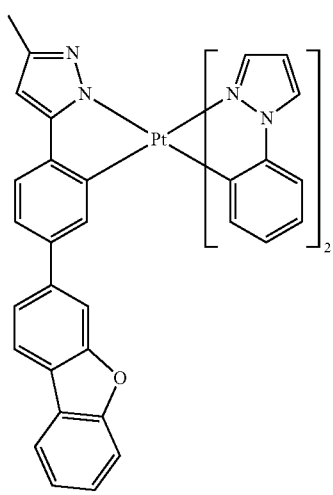
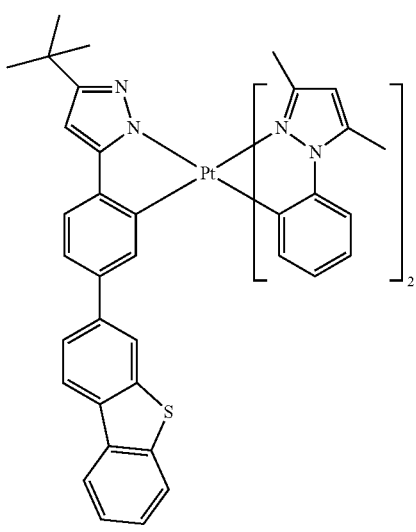

425
-continued
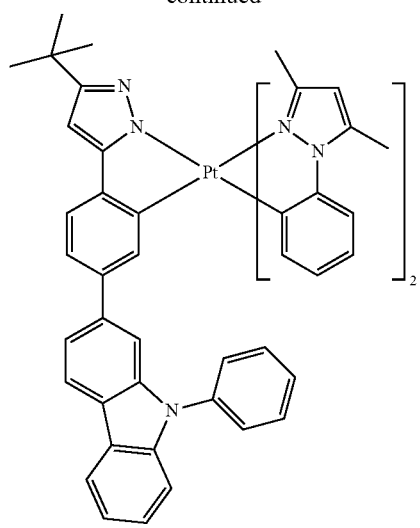
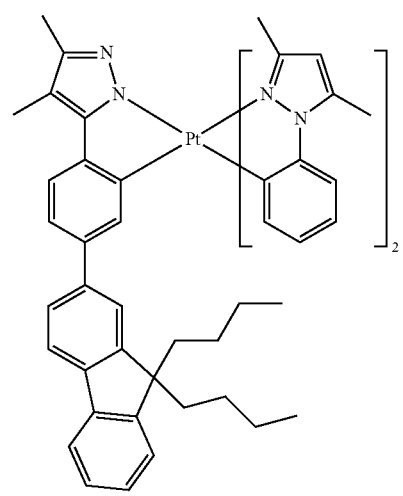
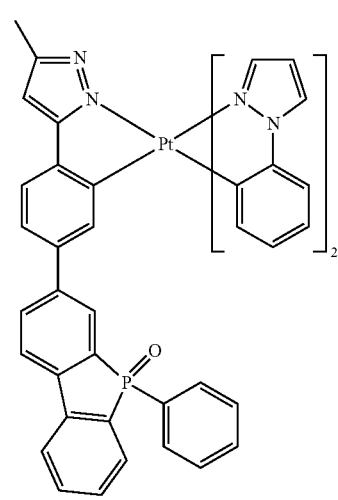
426
-continued
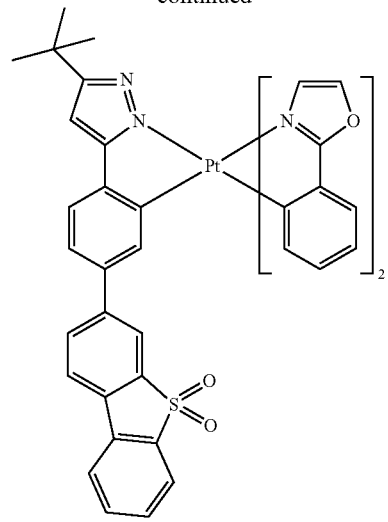
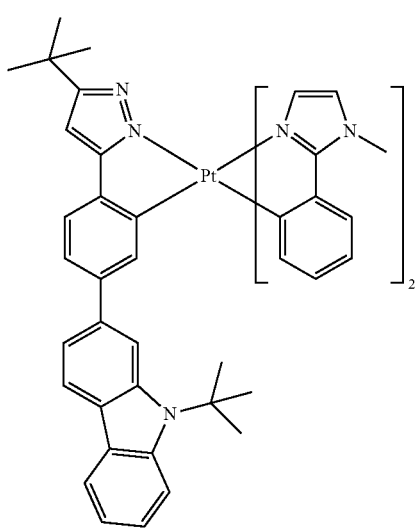
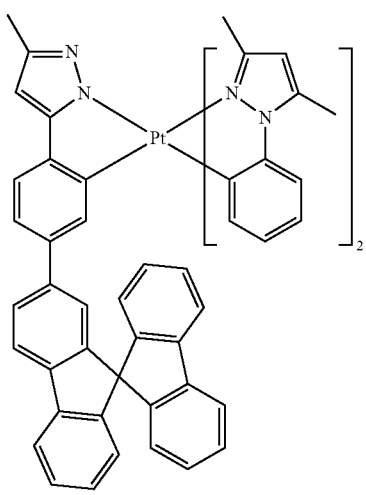

Structures Pt-11
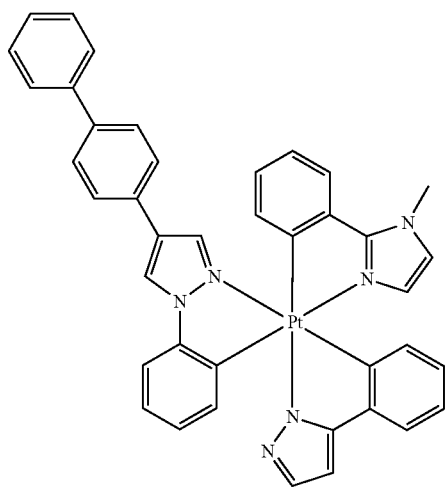
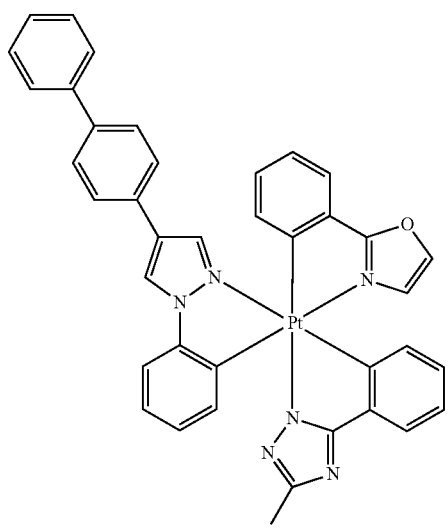
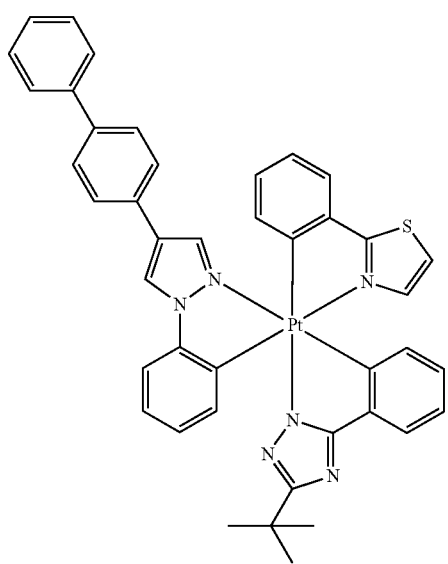
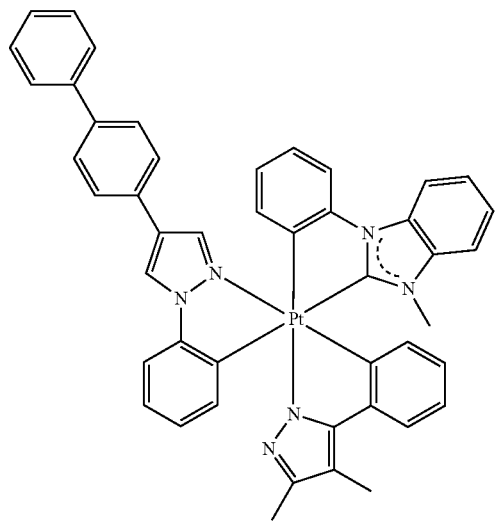
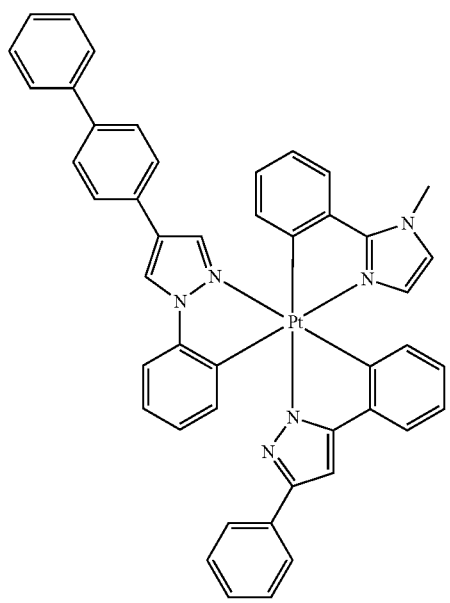
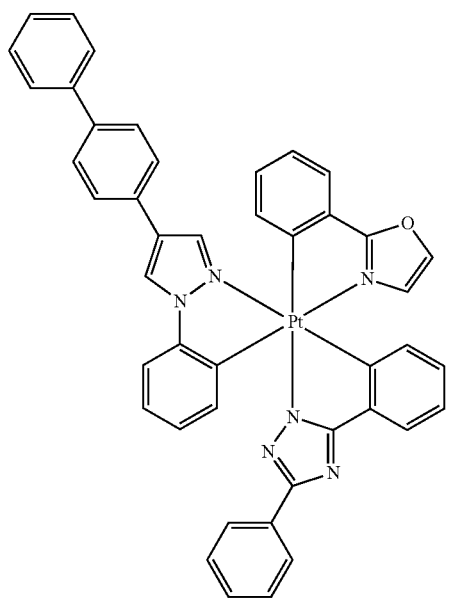

429
-continued
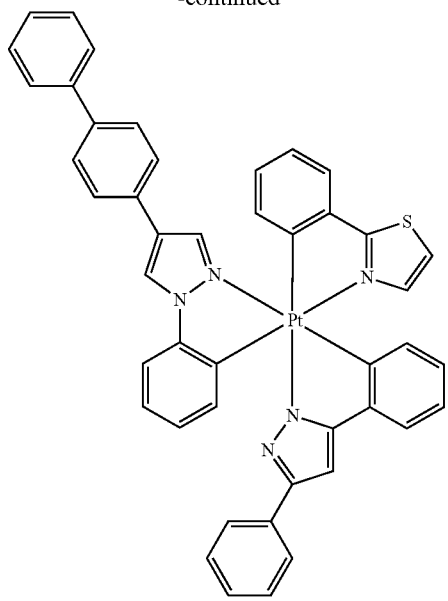
430
-continued
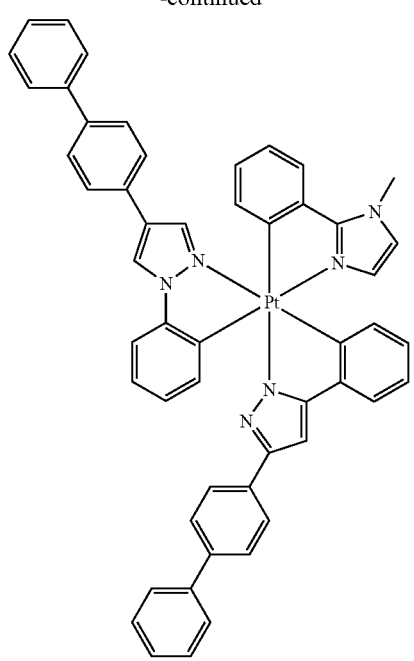
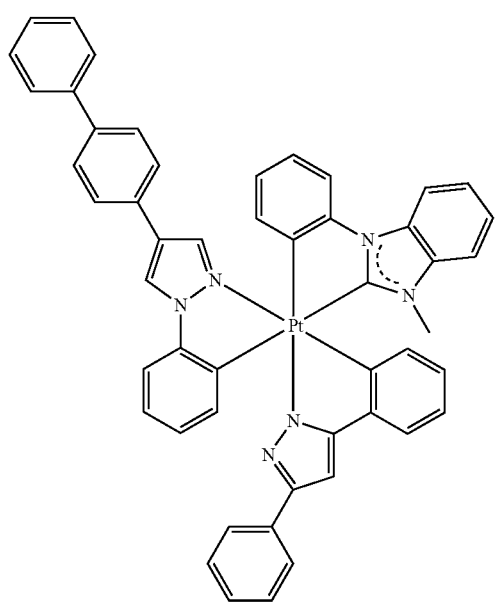
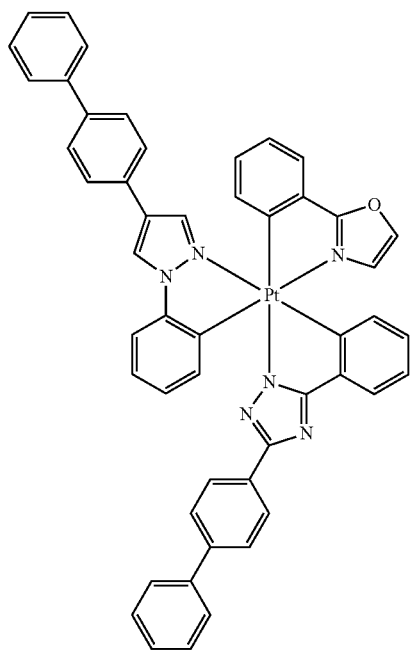

431
-continued
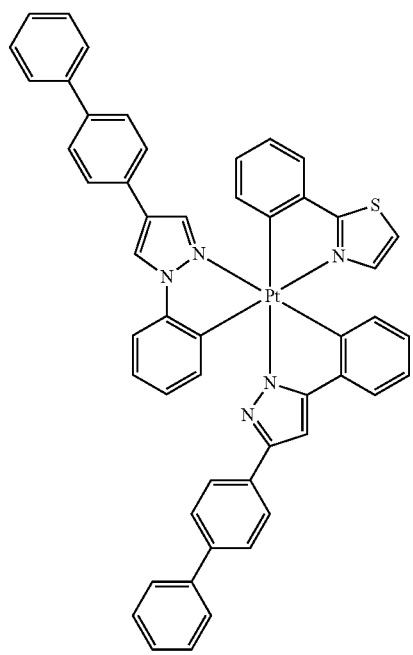
432
-continued
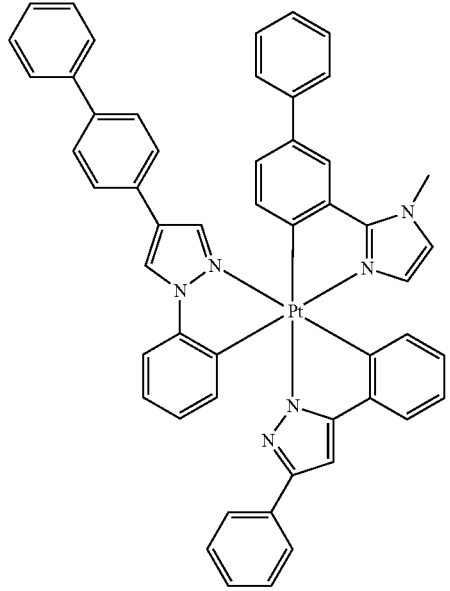
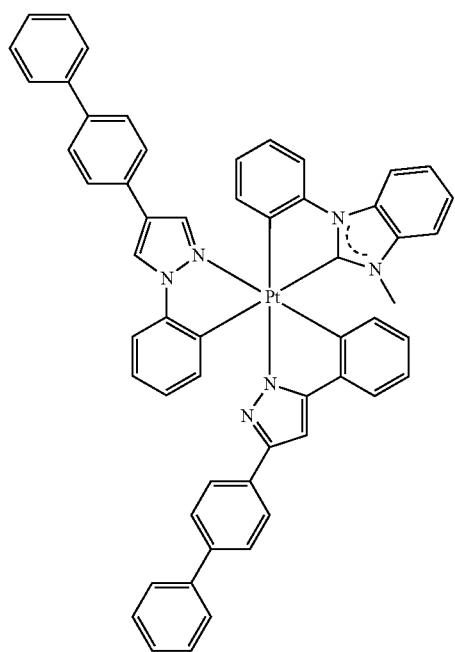
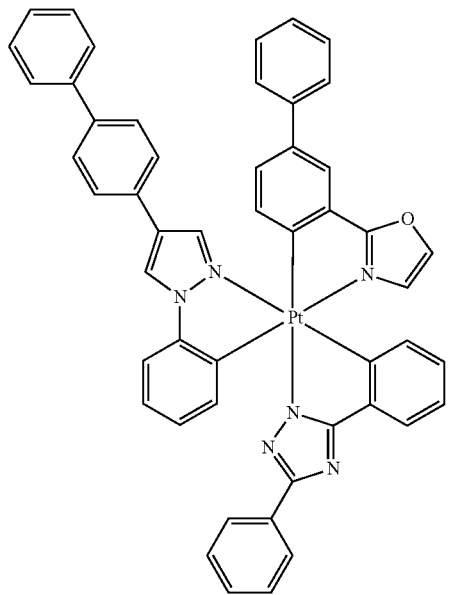

433
-continued
434
-continued
Structures Pt-12
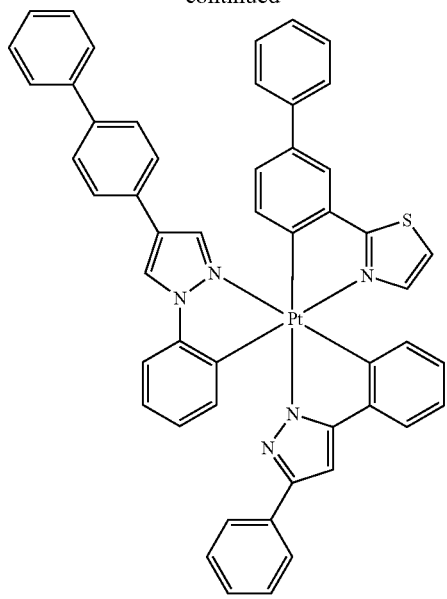
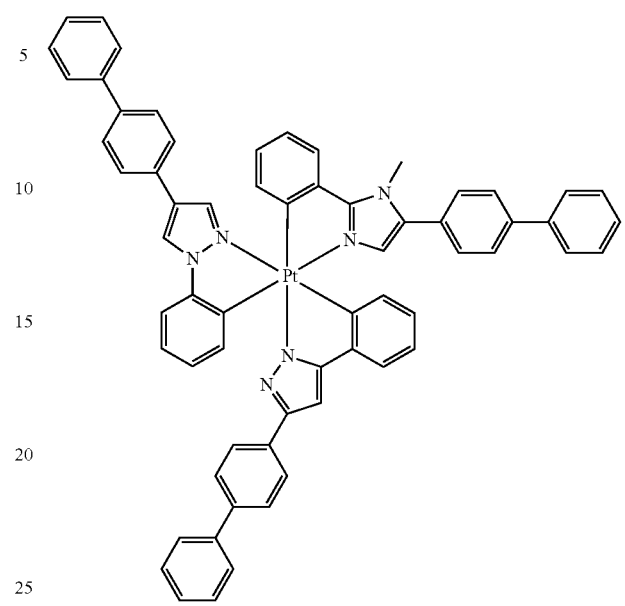
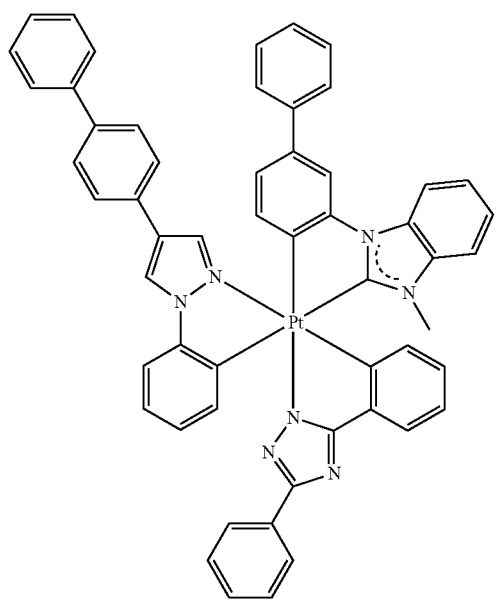
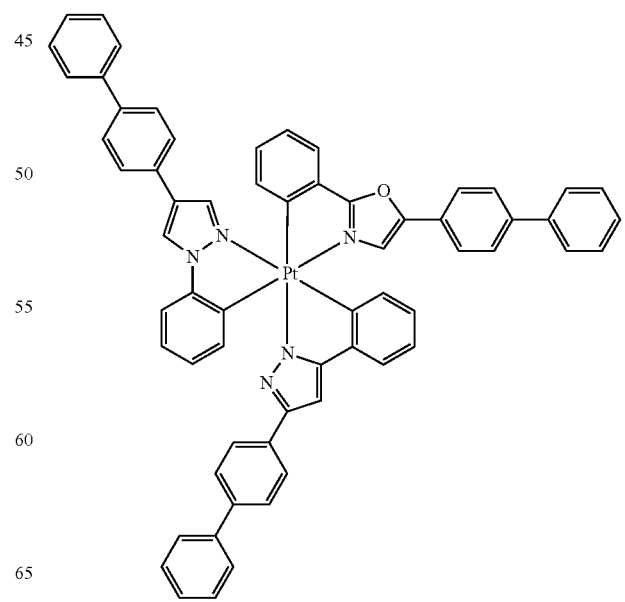

435
-continued
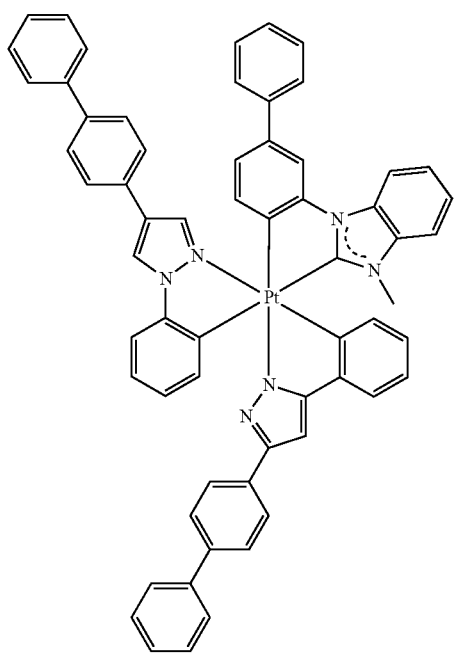
436
-continued
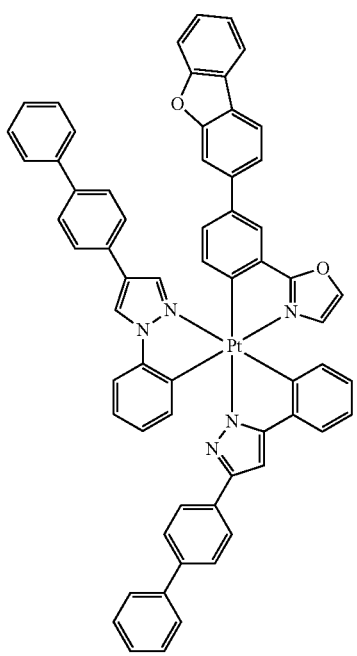
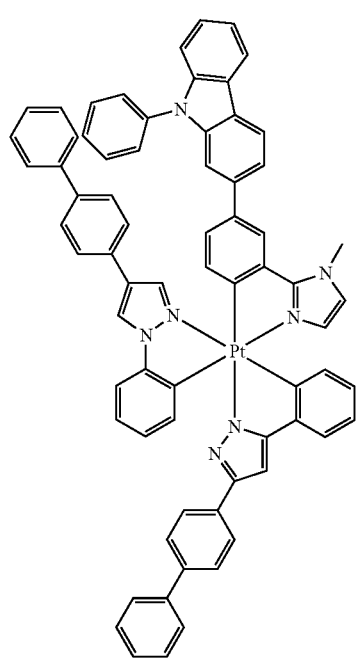
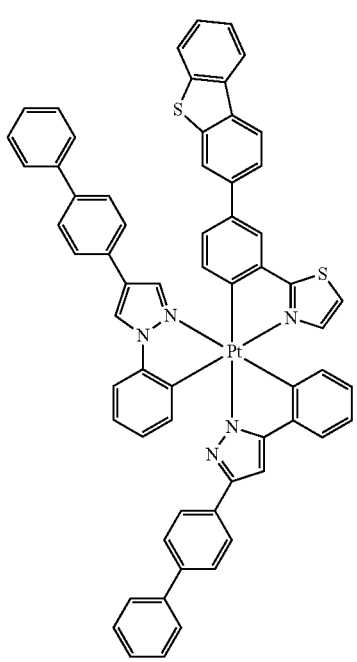

437
-continued
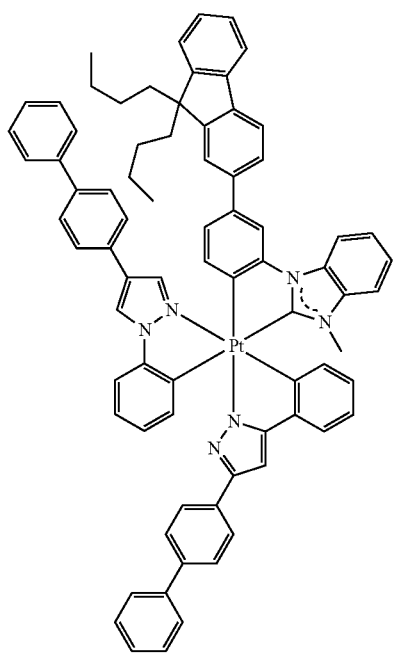
438
-continued
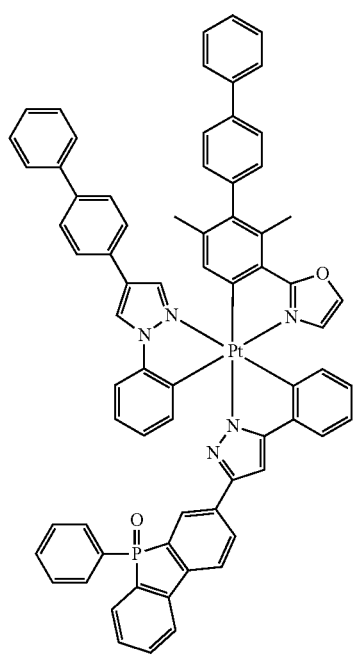
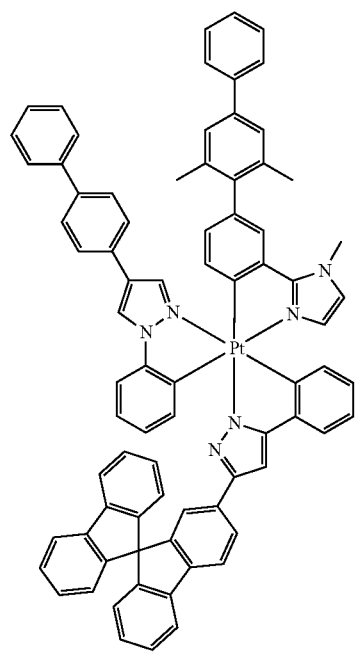
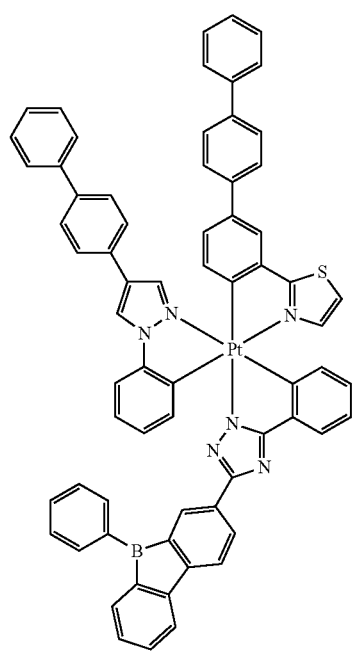

439
-continued
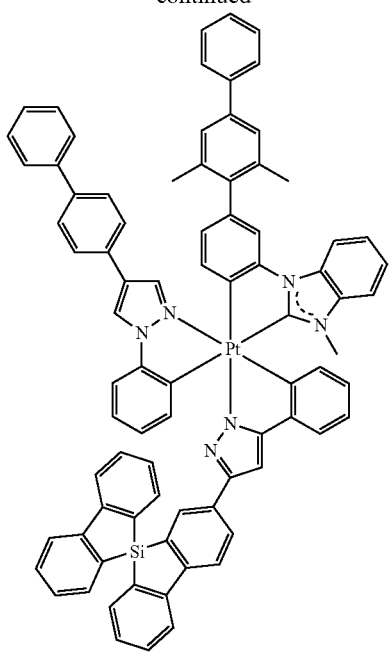
Structures Pt-13
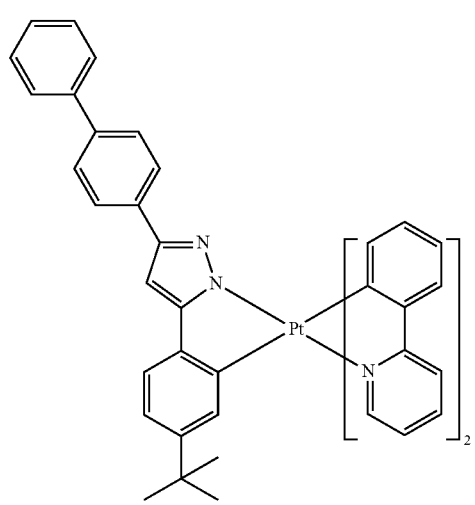
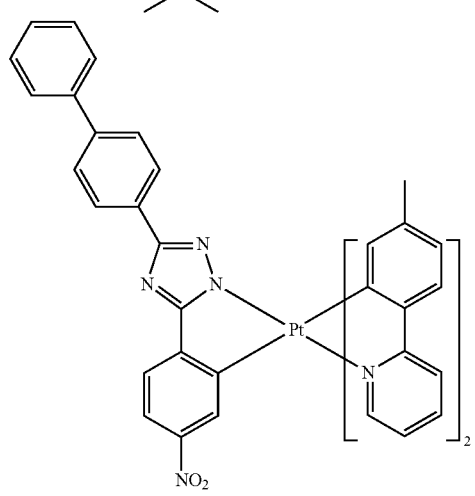
440
-continued
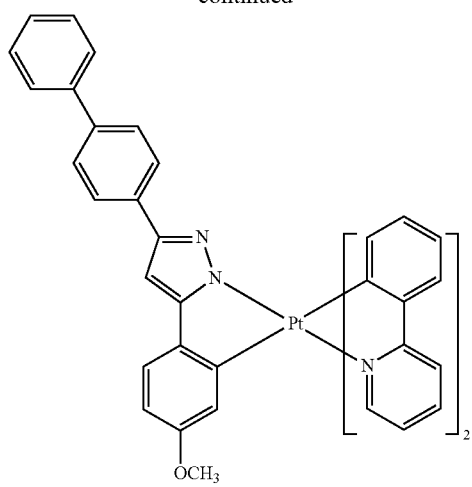
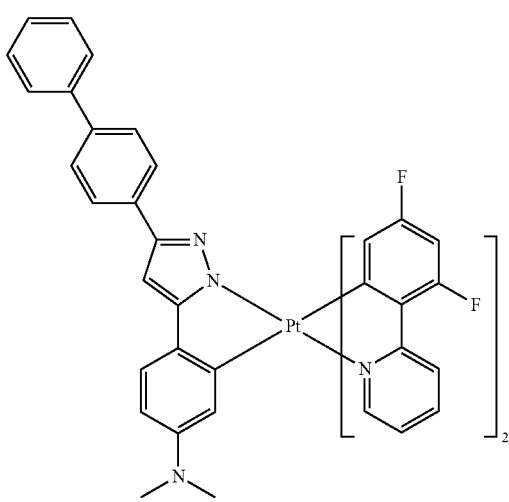
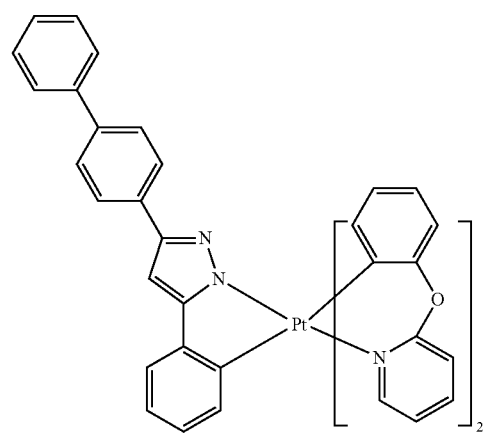

441
-continued
442
-continued
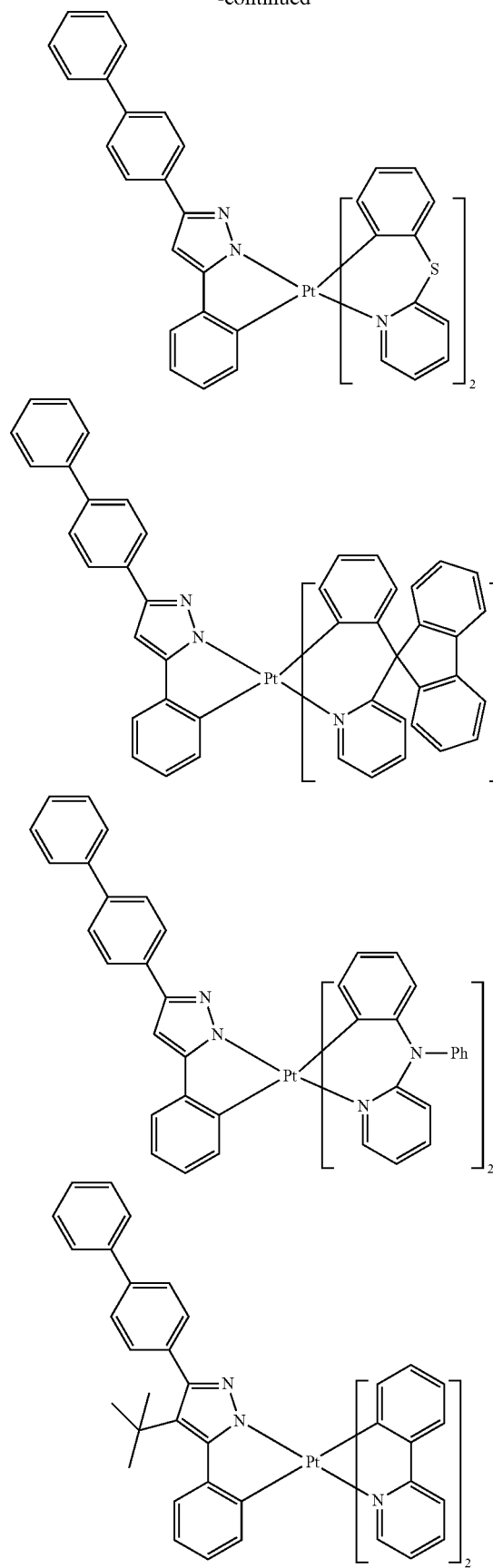
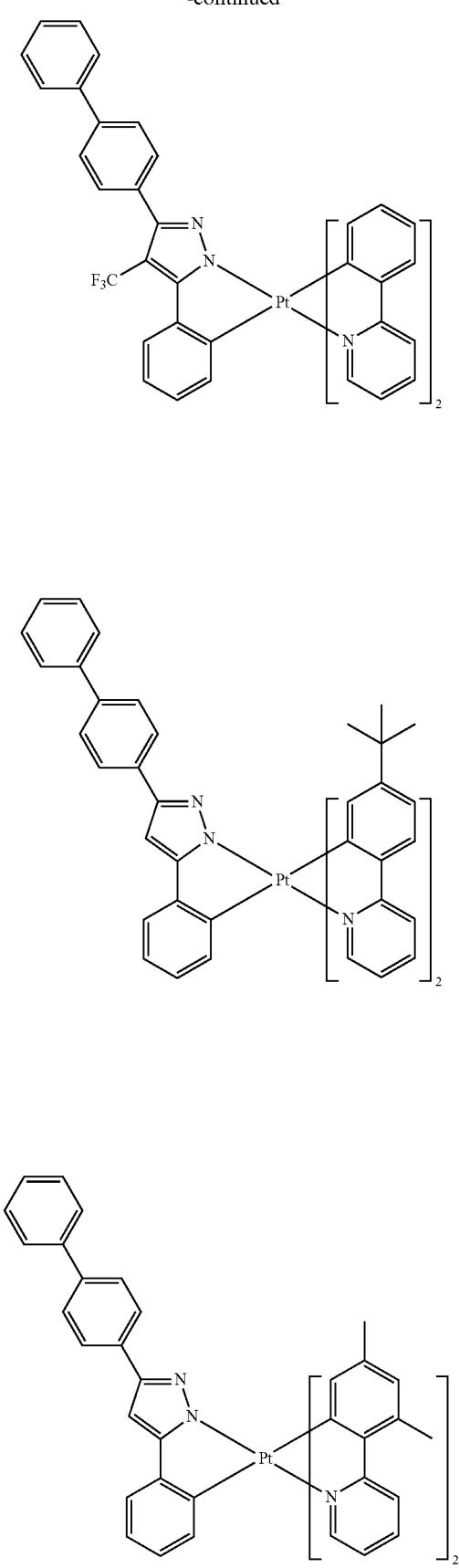

443
-continued
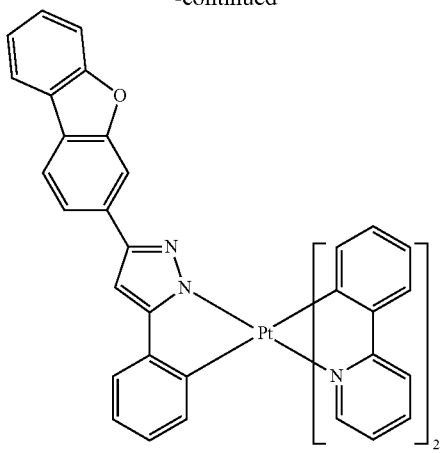
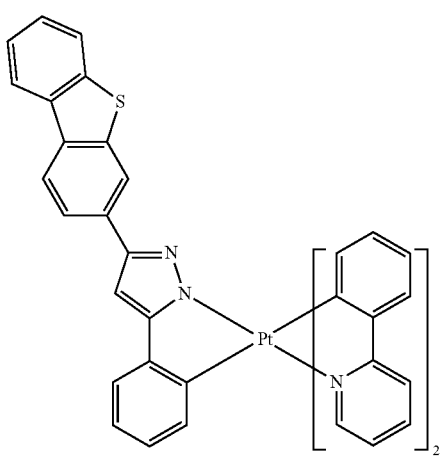
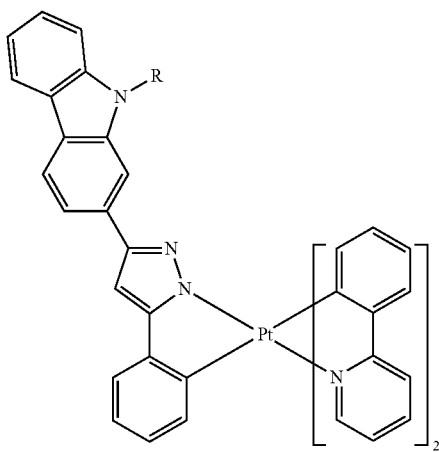
444
-continued
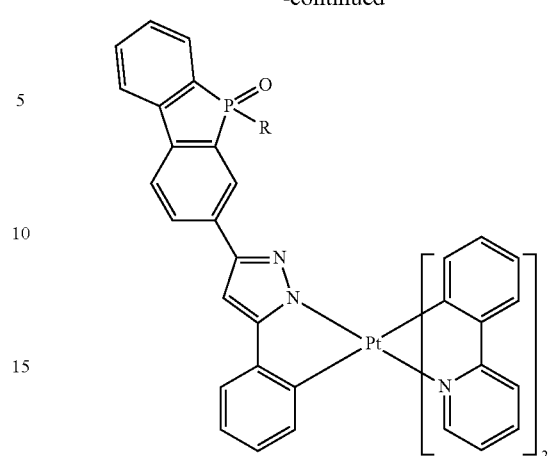
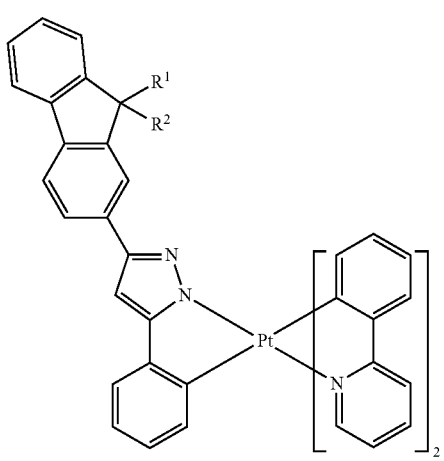
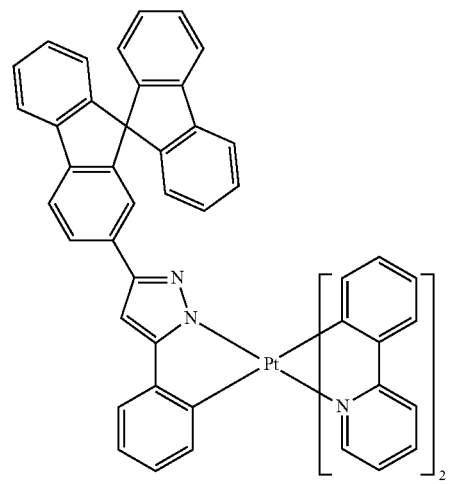

-continued

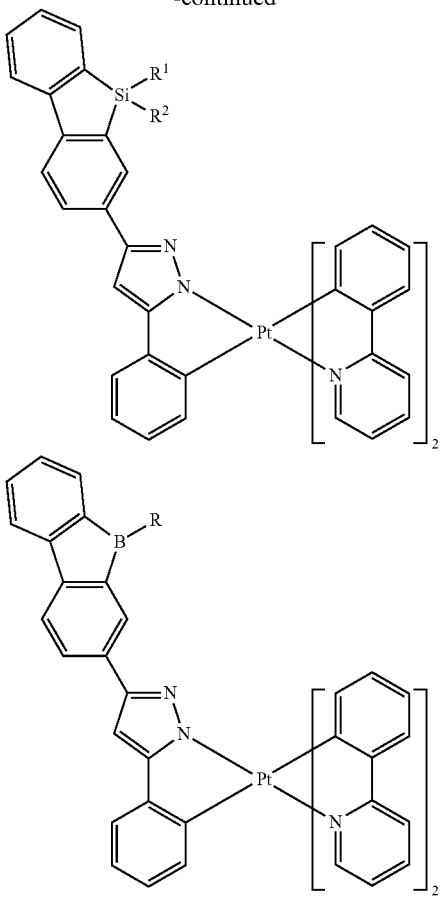

In the compounds shown in Structures Ir-1 to Ir-25, Rh-1 to Rh-25, and Pt-1 to Pt-13 above, each of R, $R^1$, $R^2$, $R^3$, and $R^4$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof. In another aspect, each of R, $R^1$, $R^2$, $R^3$ and $R^4$ is independently hydrogen, halogen, hydroxyl, thiol, nitro, cyano; or substituted or unsubstituted: aryl, cycloalkyl, cycloalkenyl, heterocyclyl, heteroaryl, alkyl, alkenyl, alkynyl, or amino. In another aspect, each of R, $R^1$, $R^2$, $R^3$ and $R^4$ is independently hydrogen; or substituted or unsubstituted: aryl, cycloalkyl, cycloalkenyl, heterocyclyl, heteroaryl, alkyl, alkenyl, or alkynyl.

2. Devices

Also disclosed herein are devices including one or more of the compounds disclosed herein.

The compounds disclosed herein are suited for use in a wide variety of devices, including, for example, optical and electro-optical devices, including, for example, photo-absorbing devices such as solar- and photo-sensitive devices, organic light emitting diodes (OLEDs), photo-emitting devices, or devices capable of both photo-absorption and emission and as markers for bio-applications.

Figure 2:
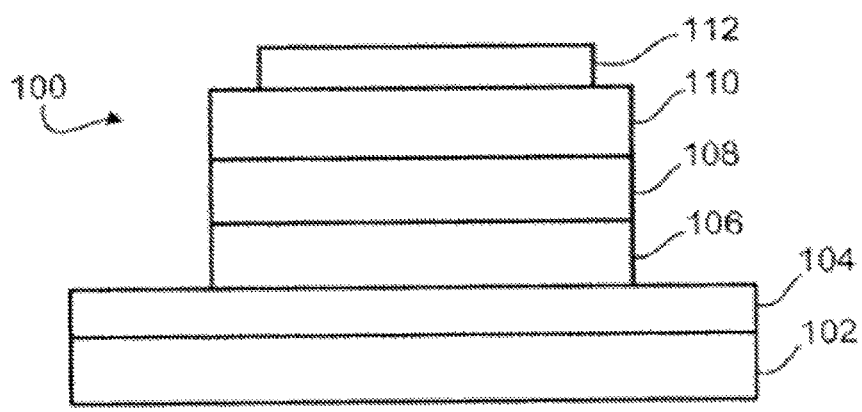
FIG. 2 depicts a device including a metal complex as disclosed herein.

Compounds described herein can be used in a light emitting device such as an OLED. FIG. 2 depicts a cross-sectional view of an OLED 100. OLED 100 includes substrate 102, anode 104, hole-transporting material(s) (HTL) 106, light processing material 108, electron-transporting material(s) (ETL) 110, and a metal cathode layer 112. Anode 104 is typically a transparent material, such as indium tin oxide. Light processing material 108 may be an emissive material (EML) including an emitter and a host.

In various aspects, any of the one or more layers depicted in FIG. 2 may include indium tin oxide (ITO), poly(3,4-ethylenedioxythiophene) (PEDOT), polystyrene sulfonate (PSS), N,N'-di-1-naphthyl-N,N-diphenyl-1,1'-biphenyl-4,4'diamine (NPD), 1,1-bis((di-4-tolylamino)phenyl)cyclohexane (TAPC), 2,6-Bis(N-carbazolyl)pyridine (mCpy), 2,8-bis(diphenylphosphoryl)dibenzothiophene (PO15), LiF, Al, or a combination thereof.

Light processing material 108 may include one or more compounds of the present disclosure optionally together with a host material. The host material can be any suitable host material known in the art. The emission color of an OLED is determined by the emission energy (optical energy gap) of the light processing material 108, which can be tuned by tuning the electronic structure of the emitting compounds, the host material, or both. Both the hole-transporting material in the HTL layer 106 and the electron-transporting material(s) in the ETL layer 110 may include any suitable hole-transporter known in the art.

Compounds described herein may exhibit phosphorescence. Phosphorescent OLEDs (i.e., OLEDs with phosphorescent emitters) typically have higher device efficiencies than other OLEDs, such as fluorescent OLEDs. Light emitting devices based on electrophosphorescent emitters are described in more detail in WO2000/070655 to Baldo et al., which is incorporated herein by this reference for its teaching of OLEDs, and in particular phosphorescent OLEDs.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to be limiting in scope. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Various methods for the preparation of the compounds described herein are recited in the examples. These methods are provided to illustrate various methods of preparation, but are not intended to limit any of the methods recited herein. Accordingly, one of skill in the art in possession of this disclosure could readily modify a recited method or utilize a different method to prepare one or more of the compounds described herein. The following aspects are only exemplary and are not intended to be limiting in scope. Temperatures, catalysts, concentrations, reactant compositions, and other process conditions can vary, and one of skill in the art, in possession of this disclosure, could readily select appropriate reactants and conditions for a desired complex.

$^1$H spectra were recorded at 400 MHz, $^{13}$C NMR spectra were recorded at 100 MHz on Varian Liquid-State NMR instruments in $CDCl_3$ or DMSO-$d_6$ solutions and chemical shifts were referenced to residual protiated solvent. If $CDCl_3$ was used as solvent, $^1$H NMR spectra were recorded with tetramethylsilane ($\delta$=0.00 ppm) as internal reference; $^{13}$C NMR spectra were recorded with CDCl$_3$ ($\delta$=77.00 ppm) as internal reference. If DMSO-d$_6$ was used as solvent, $^1$H NMR spectra were recorded with residual H$_2$O ($\delta$=3.33 ppm) as internal reference; $^{13}$C NMR spectra were recorded with DMSO-d$_6$ ($\delta$=39.52 ppm) as an internal reference. The following abbreviations (or combinations thereof) were used to explain $^1$H NMR multiplicities: s=singlet, d=doublet, t=triplet, q=quartet, p=quintet, m=multiplet, br=broad.

General Synthetic Routes

A general synthetic route for the compounds disclosed herein includes:

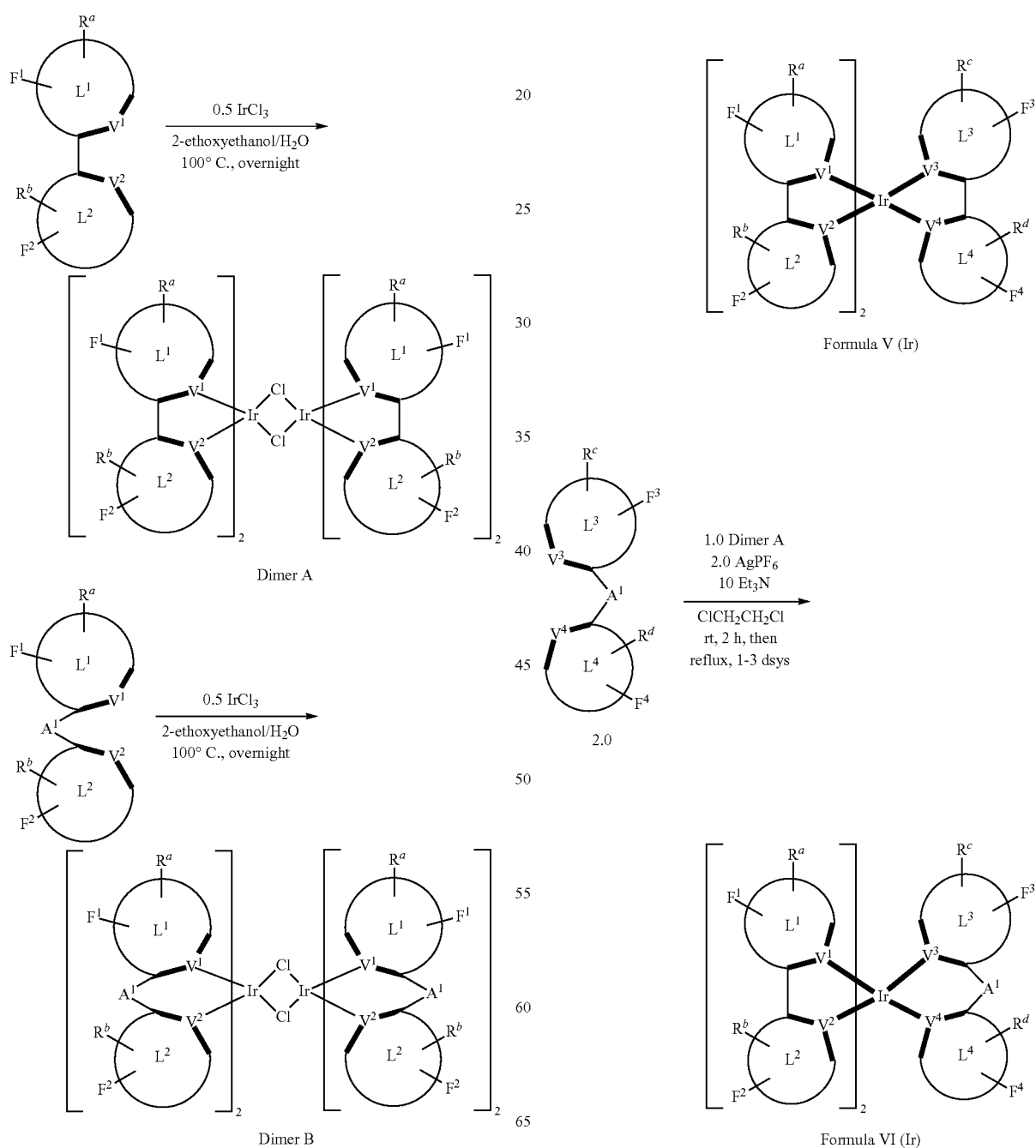

449
-continued

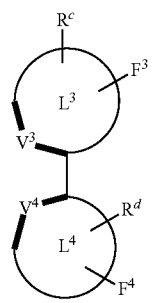

1.0 Dimer B
2.0 AgPF$_6$
10 Et$_3$N
$\xrightarrow{\text{ClCH}_2\text{CH}_2\text{Cl}}$
rt, 2 h, then
reflux, 1-3 dsys 2.0

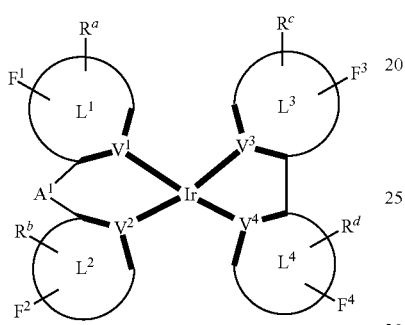

Formula VIII (Ir)

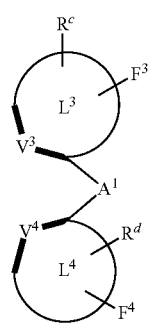

1.0 Dimer B
2.0 AgPF$_6$
10 Et$_3$N
$\xrightarrow{\text{ClCH}_2\text{CH}_2\text{Cl}}$
rt, 2 h, then
reflux, 1-3 dsys 2.0

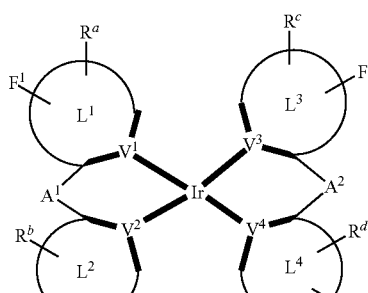

Formula IX (Ir)

450
-continued

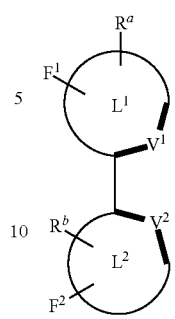

1.0 Dimer A
2.0 AgPF$_6$
10 Et$_3$N
$\xrightarrow{\text{ClCH}_2\text{CH}_2\text{Cl}}$
rt, 2 h, then
reflux, 1-3 dsys 2.0

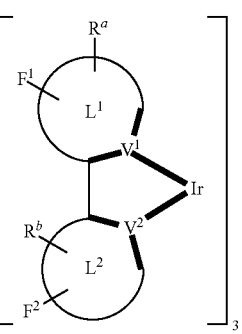

Formula VII (Ir)

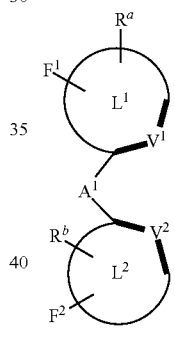

1.0 Dimer A
2.0 AgPF$_6$
10 Et$_3$N
$\xrightarrow{\text{ClCH}_2\text{CH}_2\text{Cl}}$
rt, 2 h, then
reflux, 1-3 dsys 2.0

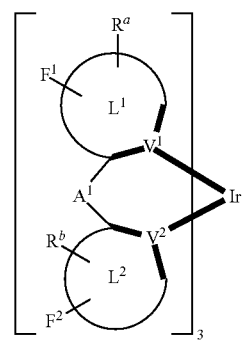

Formula X (Ir)

mer-Formula I-Formula X (Ir) $\xrightarrow[\text{solvent}]{h\nu}$ fac-Formula I-Formula X (Ir)

The rhodium complexes Formula I (Rh)-Formula X (Rh) can be synthesized through similar methods.

A synthetic route for the disclosed compounds herein also includes:

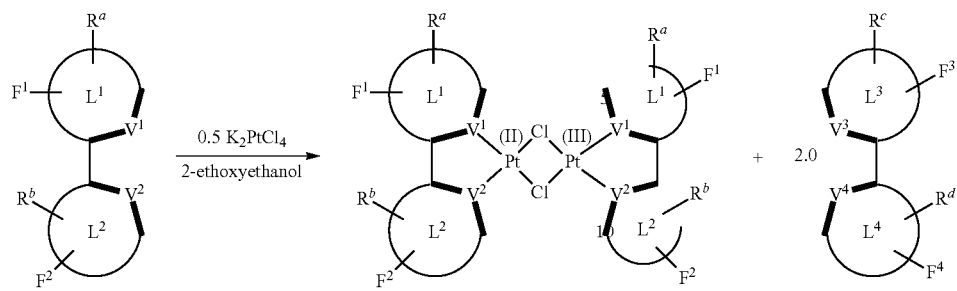
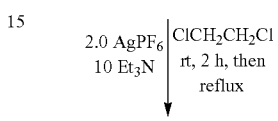
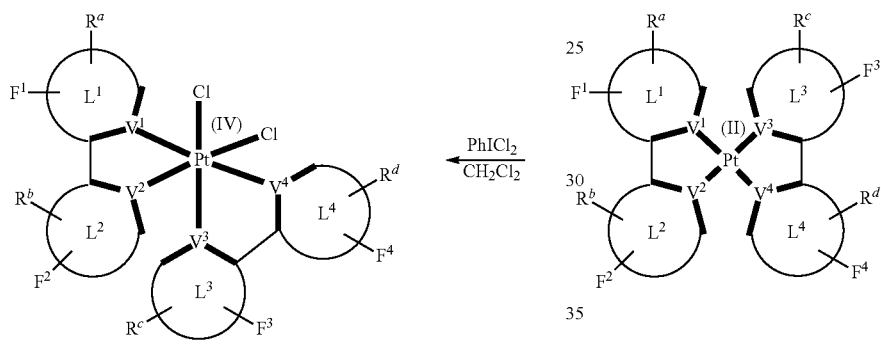
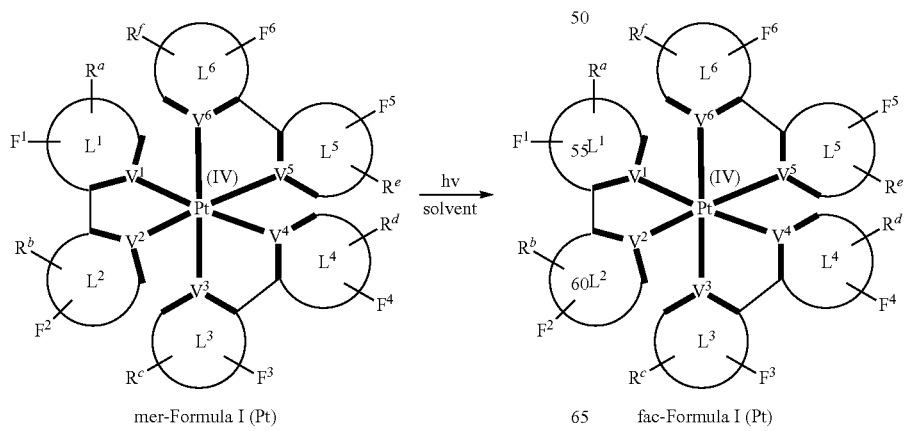
mer-Formula I (Pt)   fac-Formula I (Pt)

Other mer- or fac-Pt(IV) complexes Formula I (Pt)-Formula X (Pt) can be obtained through similar methods.

1. Example 1

The iridium complex mer-(fppy)₂Ir(1a) was prepared according to the following scheme:

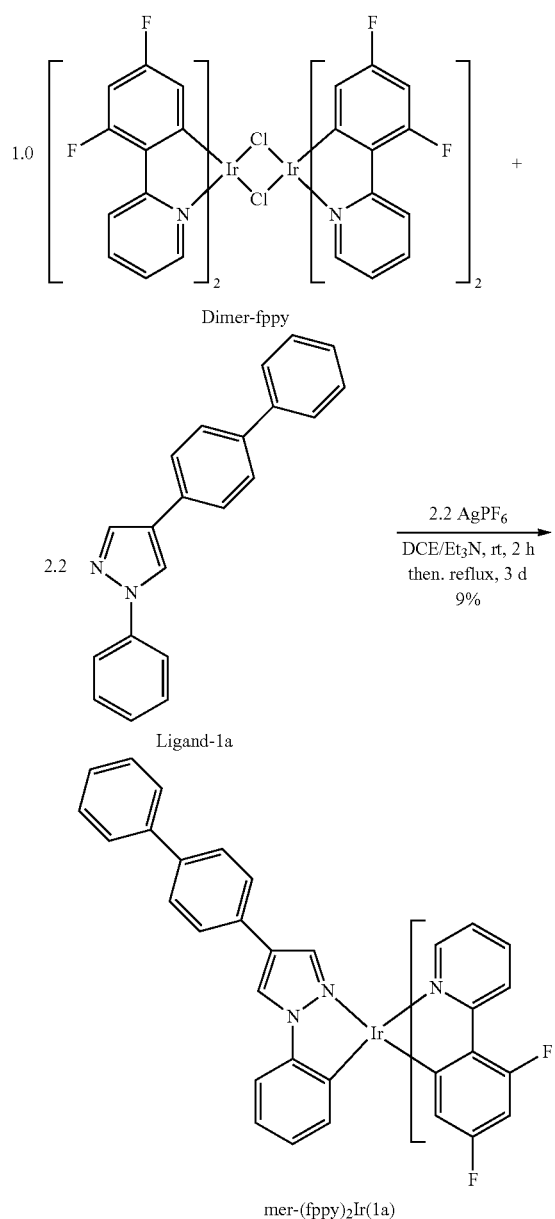

Figure 3:
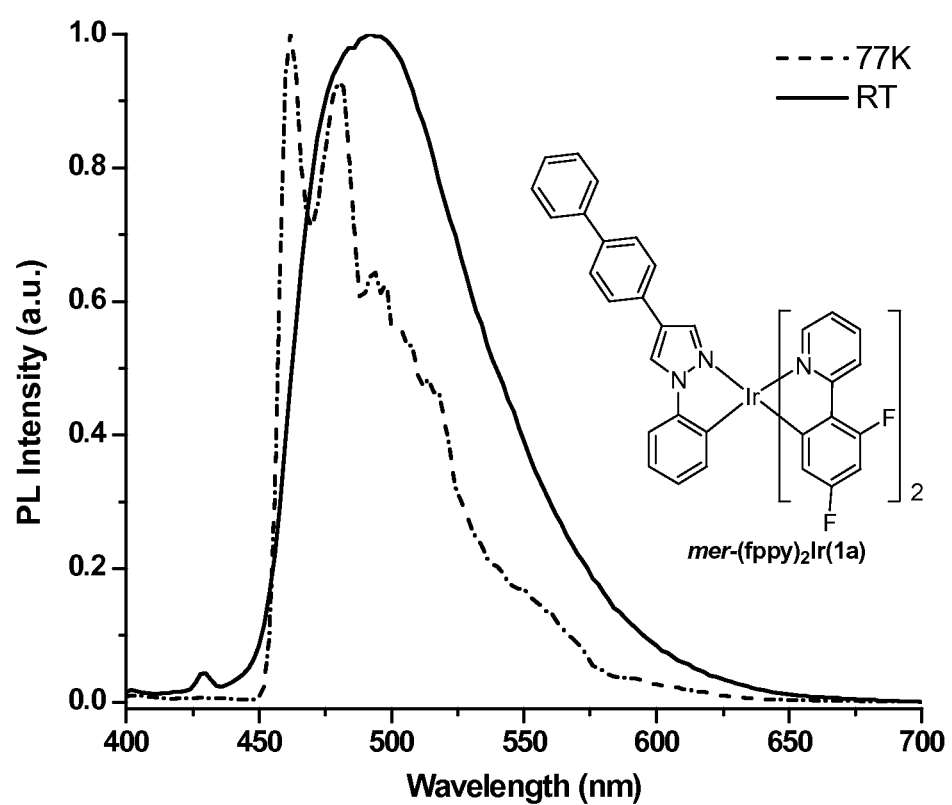
FIG. 3 shows emission spectra of mer-(fppy)$_2$Ir(1a) in CH$_2$Cl$_2$ at room temperature and in 2-methyltetrahydrofuran at 77K.

A mixture of Dimer-fppy (230 mg, 0.19 mmol, 1.0 eq), ligand Ligand-1a (124 mg, 0.42 mmol, 2.2 eq) and AgPF₆ (106 mg, 0.42 mmol, 2.2 eq) in ClCH₂CH₂Cl (20 mL) and Et₃N (1 mL) under an atmosphere of nitrogen was stirred at room temperature for 2 hours, then refluxed for 3 days and cooled to ambient temperature. The solvent was removed, and the residue was purified through column chromatography on silica gel using dichloromethane/hexane (1:1) as eluent to obtain the desired product mer-(fppy)₂Ir(1a) 30 mg as a yellow solid in 9% yield. ¹H NMR (DMSO-d₆, 400 MHz): δ 5.73 (d, J=7.2 Hz, 1H), 5.96 (d, J=7.6 Hz, 1H), 6.65-6.81 (m, 3H), 6.89 (t, J=2.0 Hz, 1H), 7.05 (t, J=2.0 Hz, 1H), 7.14-7.19 (m, 2H), 7.36-7.39 (m, 1H), 7.45-7.52 (m, 3H), 7.69-7.93 (m, 10H), 8.13 (d, J=5.6 Hz, 1H), 8.18 (d, J=8.0 Hz, 1H), 8.24 (d, J=8.0 Hz, 1H), 9.38 (s, 1H). Emission spectra of mer-(fppy)₂Ir(1a) at room temperature in CH₂Cl₂ and at 77K in 2-methyltetrahydrofuran are shown in FIG. 3.

2. Example 2

The iridium complex fac-(fppy)₂Ir(1a) was prepared according to the following scheme:

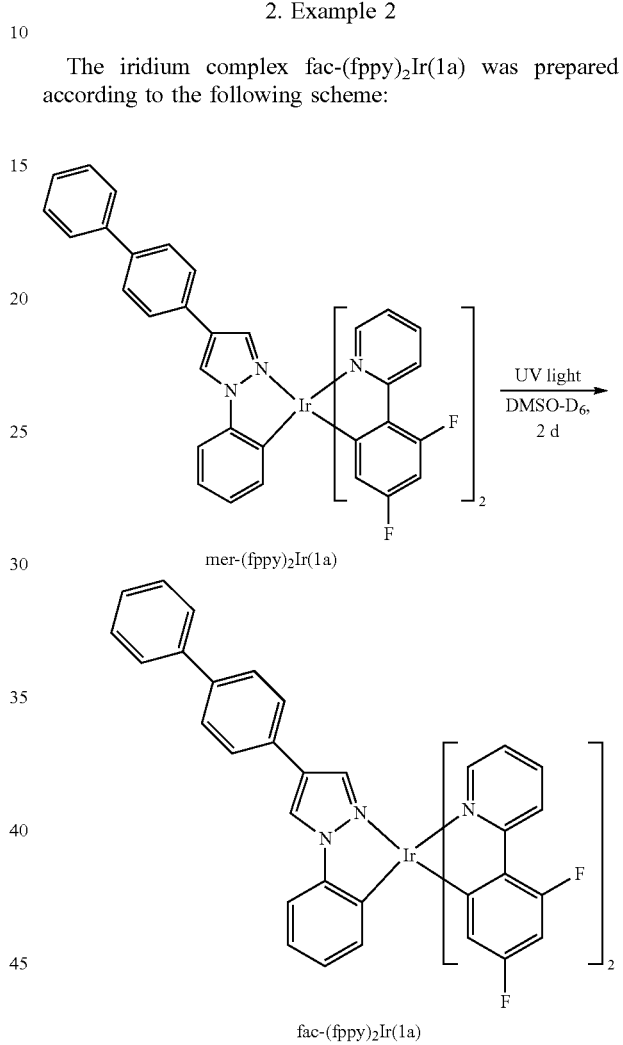

Figure 4:
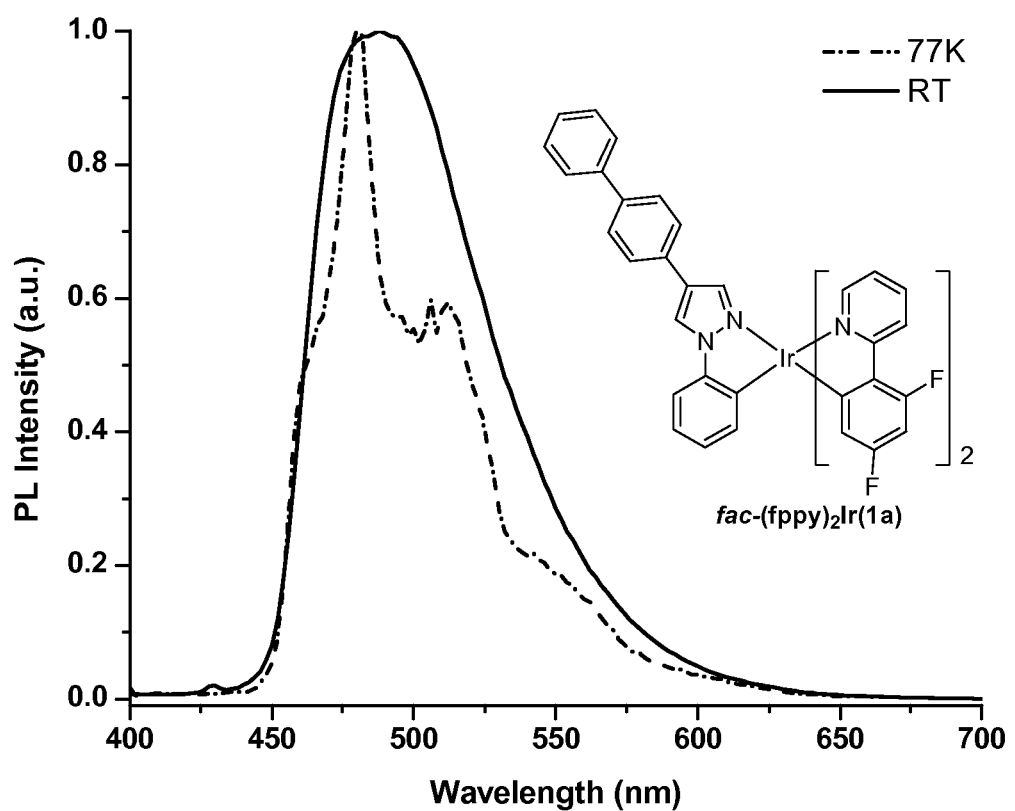
FIG. 4 shows emission spectra of fac-(fppy)$_2$Ir(1a) in CH$_2$Cl$_2$ at room temperature and in 2-methyltetrahydrofuran at 77K.

A solution of mer-(fppy)₂Ir(1a) in DMSO-d₆ was kept under UV light for 2 days, monitored by ¹H NMR until the mer-(fppy)₂Ir(1a) was consumed completely to give fac-(fppy)₂Ir(1a). ¹H NMR (DMSO-d₆, 400 MHz): δ 6.00 (dd, J=9.6, 2.4 Hz, 1H), 6.09 (dd, J=9.2, 2.4 Hz, 1H), 6.39 (dd, J=7.6, 0.8 Hz, 1H), 6.56-6.63 (m, 2H), 6.66 (t, J=8.0 Hz, 1H), 6.84-6.88 (m, 1H), 7.14 (t, J=7.6 Hz, 1H), 7.19 (t, J=7.2 Hz, 1H), 7.27 (t, J=7.2 Hz, 1H), 7.37 (t, J=7.6 Hz, 2H), 7.54-7.71 (m, 10H), 7.81-7.86 (m, 2H), 8.15 (t, J=7.2 Hz, 2H), 9.24 (s, 1H). Emission spectra of fac-(fppy)₂Ir(1a) at room temperature in CH₂Cl₂ and at 77K in 2-methyltetrahydrofuran are shown in FIG. 4.

3. Example 3

The iridium complex mer-(fppy)Ir(1a)₂ was prepared according to the following scheme:

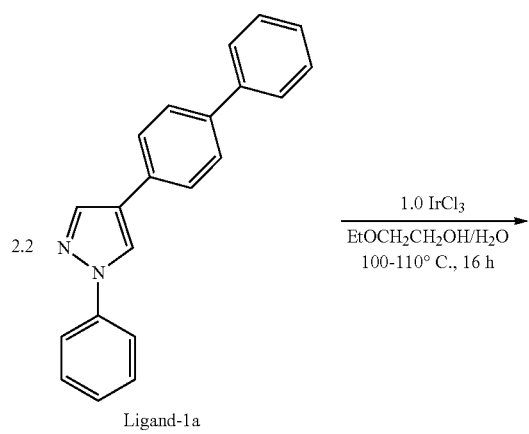

Ligand-1a

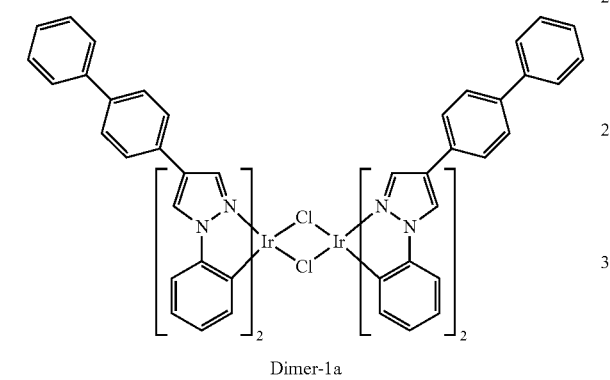

Dimer-1a

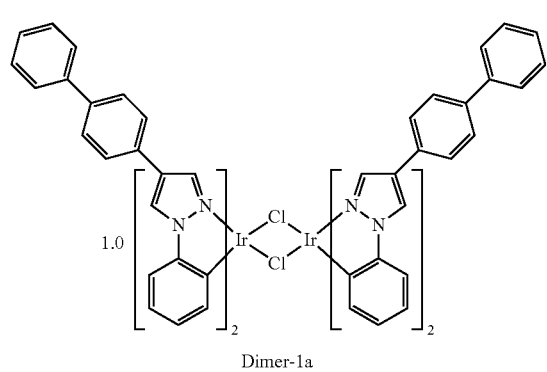

Dimer-1a

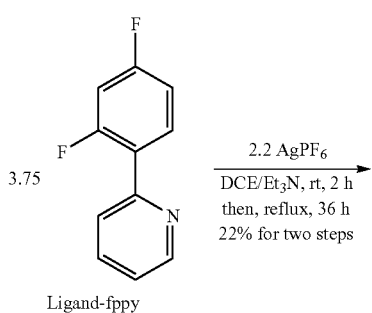

Ligand-fppy

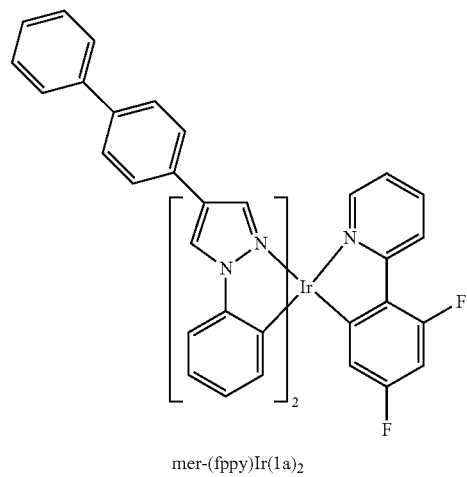

mer-(fppy)Ir(1a)₂

Synthesis of iridium complex Dimer-1a:

Dimer-1a

A mixture of Ligand-1a (575 mg, 1.94 mmol, 2.0 eq), IrCl₃ (289 mg, 0.97 mmol, 1.0 eq) in EtCH₂CH₂OH (10 mL) and H₂O (3.3 mL) under an atmosphere of nitrogen was stirred at 100-110° C. for 16 hours and cooled to ambient temperature. The precipitate was filtered off and washed with water, methanol, and Et₂O. Then the collected solid was dried in air to give the desired product Dimer-1a as a light yellow solid (565 mg), which was used directly for the next steps. ¹H NMR (DMSO-$d_6$, 400 MHz): δ 5.97 (d, J=7.2 Hz, 2H), 6.34 (d, J=7.6 Hz, 2H), 6.68-6.75 (m, 4H), 6.91-6.99 (m, 4H), 7.38 (t, J=7.6 Hz, 4H), 7.49 (t, J=7.6 Hz, 8H), 7.60 (d, J=8.0 Hz, 2H), 7.63 (d, J=8.0 Hz, 2H), 7.74-7.88 (m, 20H), 7.97 (d, J=7.56 Hz, 4H), 8.56 (s, 2H), 8.87 (s, 2H), 9.40 (s, 2H), 9.53 (s, 2H).

457
Synthesis of iridium complex mer-(fppy)Ir(1a)₂:

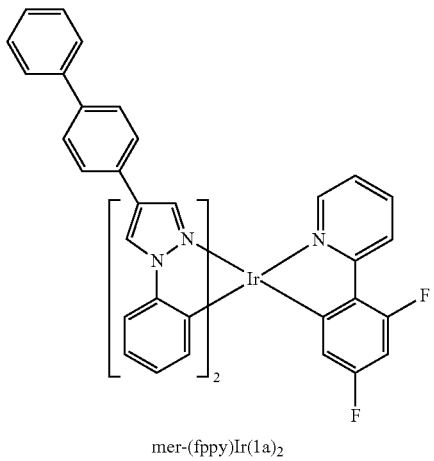

mer-(fppy)Ir(1a)₂

Figure 5:
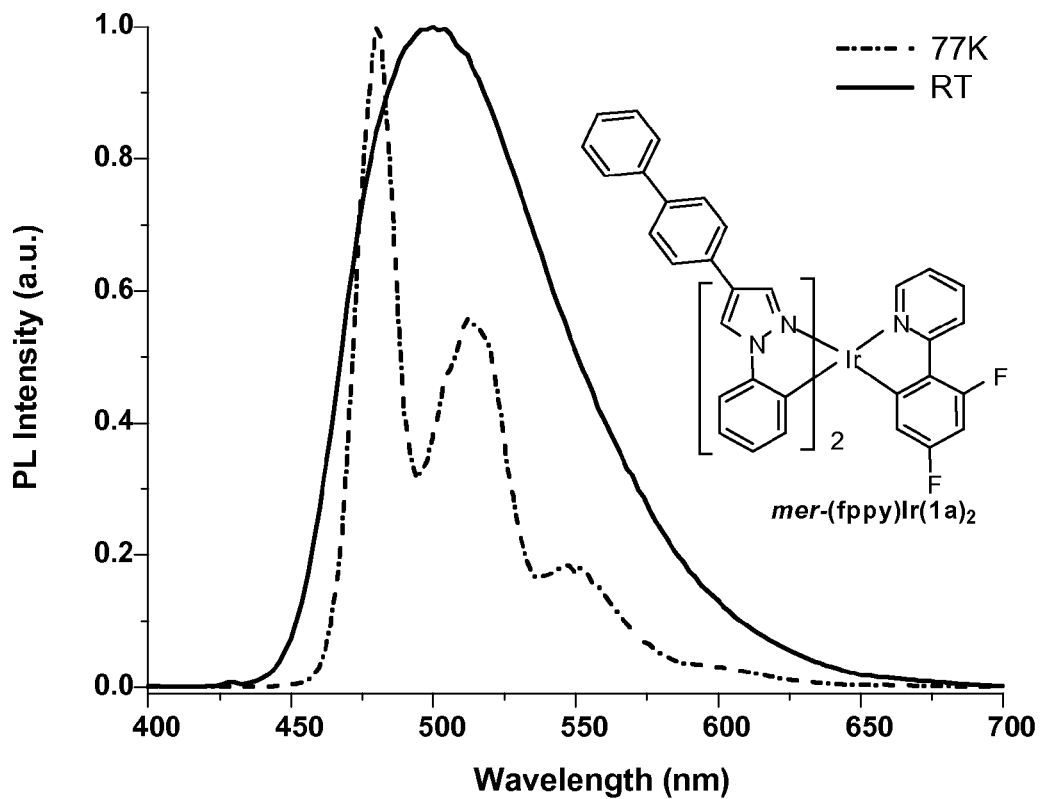
FIG. 5 shows emission spectra of mer-(fppy)Ir(1a)$_2$ in CH$_2$Cl$_2$ at room temperature and in 2-methyltetrahydrofuran at 77K.

A mixture of Dimer-1a (261 mg, 0.16 mmol, 1.0 eq), ligand Ligand-fppy (115 mg, 0.60 mmol, 3.75 eq) and AgPF₆ (126 mg, 0.50 mmol, 3.1 eq) in ClCH₂CH₂Cl (20 mL) and Et₃N (1 mL) under an atmosphere of nitrogen was stirred at room temperature for 2 hours, then refluxed for 36 hours and cooled to ambient temperature. The solvent was removed and the residue was purified through column chromatography on silica gel using dichloromethane/hexane (1:1) as eluent to obtain the desired product mer-(fppy)Ir(1a)₂ 94 mg as a yellow solid in 22% yield. ¹H NMR (DMSO-d₆, 400 MHz): δ 6.39 (d, J=8.0 Hz, 1H), 6.45 (dd, J=8.0, 3.2 Hz, 1H), 6.68-6.79 (m, 3H), 6.89-6.96 (m, 2H), 7.03 (t, J=8.0 Hz, 1H), 7.25 (t, J=7.2 Hz, 1H), 7.34-7.39 (m, 3H), 7.46-7.50 (m, 5H), 7.61 (d, J=7.6 Hz, 1H), 7.68-7.79 (m, 13H), 7.95 (t, J=8.0 Hz, 1H), 8.19 (d, J=5.6 Hz, 1H), 8.32 (d, J=9.6 Hz, 1H), 9.30 (d, J=8.4 Hz, 2H). Emission spectra of mer-(fppy)Ir(1a)₂ at room temperature in CH₂Cl₂ and at 77K in 2-methyltetrahydrofuran are shown in FIG. 5.

4. Example 4

The iridium complex fac-(fppy)Ir(1a)₂ was prepared according to the following scheme:

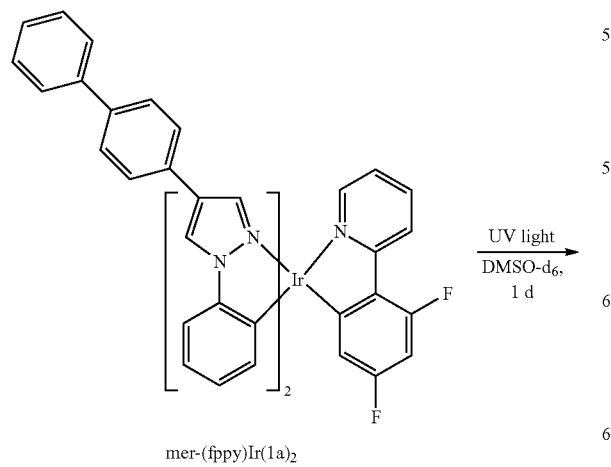

mer-(fppy)Ir(1a)₂

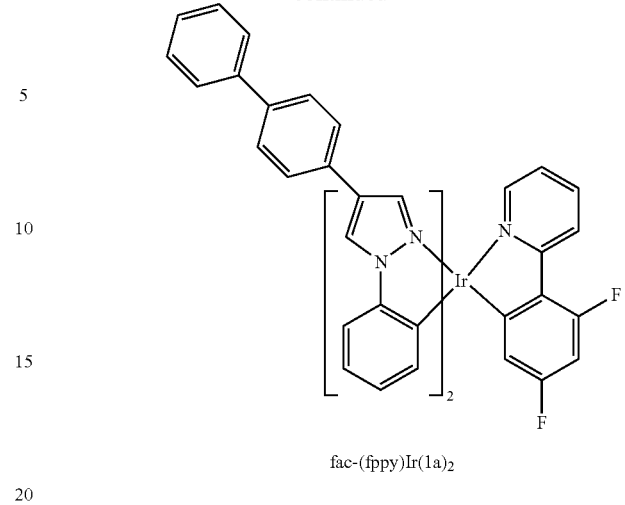

fac-(fppy)Ir(1a)₂

Figure 6:
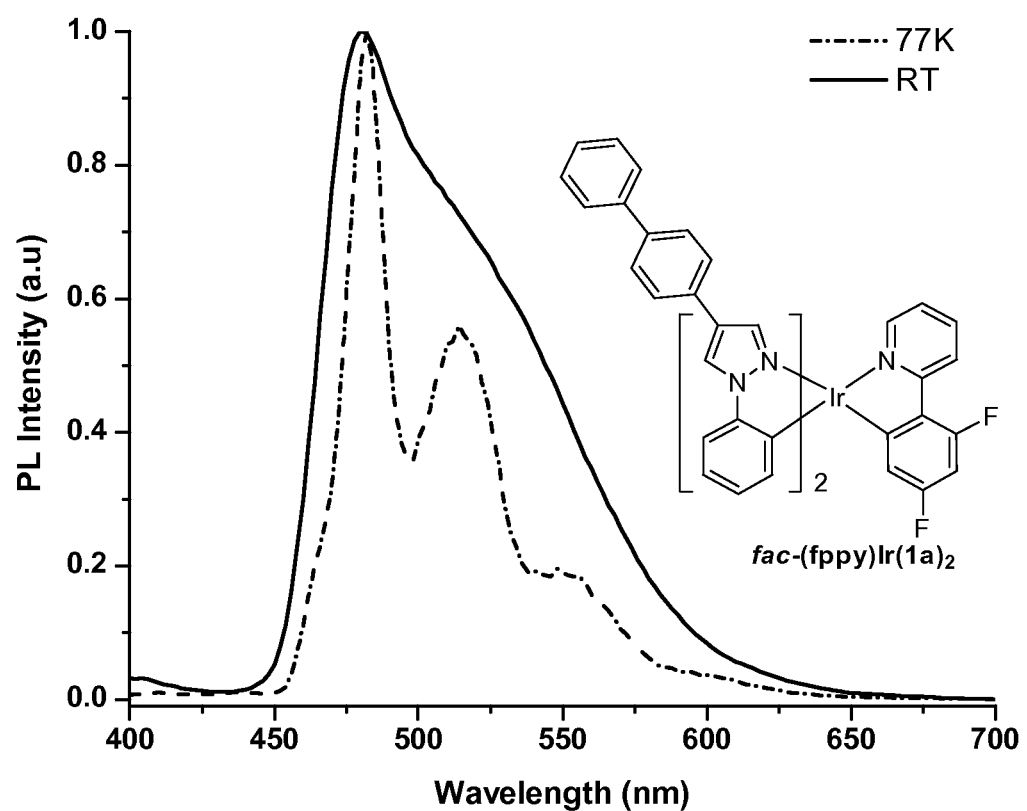
FIG. 6 shows emission spectra of fac-(fppy)Ir(1a)$_2$ in CH$_2$Cl$_2$ at room temperature and in 2-methyltetrahydrofuran at 77K.

A solution of mer-(fppy)Ir(1a)₂ in DMSO-d₆ was kept under UV light for 1 day, monitored by ¹H NMR until the mer-(fppy)Ir(1a)₂ was consumed completely to give fac-(fppy)Ir(1a)₂. ¹H NMR (DMSO-d₆, 400 MHz): δ 6.18 (dd, J=7.6, 2.0 Hz, 1H), 6.46 (d, J=5.6 Hz, 1H), 6.54 (d, J=6.0 Hz, 1H), 6.57-6.62 (m, 1H), 6.67 (t, J=5.6 Hz, 2H), 6.86-6.91 (m, 2H), 7.20 (t, J=5.6 Hz, 1H), 7.27-7.32 (m, 2H), 7.37-7.43 (m, 4H), 7.54-7.65 (m, 11H), 7.99 (s, 1H), 7.74-7.76 (m, 4H), 7.86 (t, J=6.0 Hz, 1H), 7.90 (d, J=4.4 Hz, 1H), 8.17 (t, J=6.4 Hz, 1H), 9.25 (s, 2H). Emission spectra of fac-(fppy)₂Ir(1a)₂ at room temperature in CH₂Cl₂ and at 77K in 2-methyltetrahydrofuran are shown in FIG. 6.

5. Example 5

The iridium complex mer-(fppy)Ir(1b)₂ was prepared according to the following scheme:

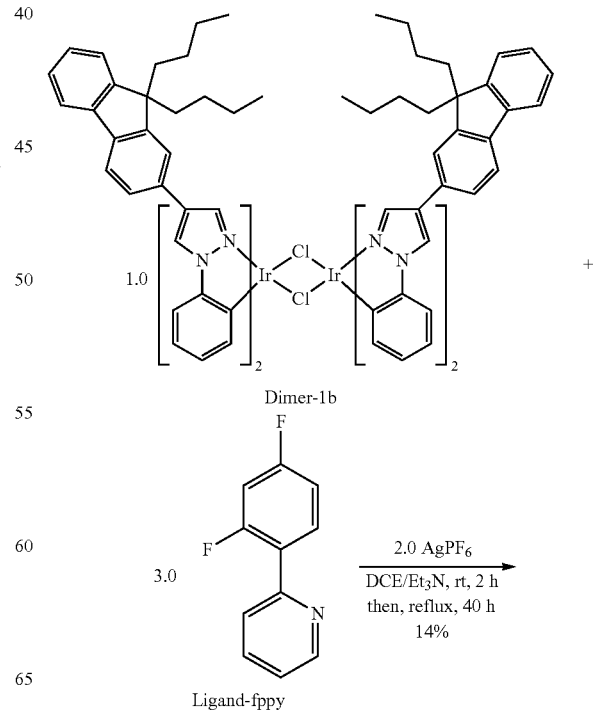

Ligand-fppy

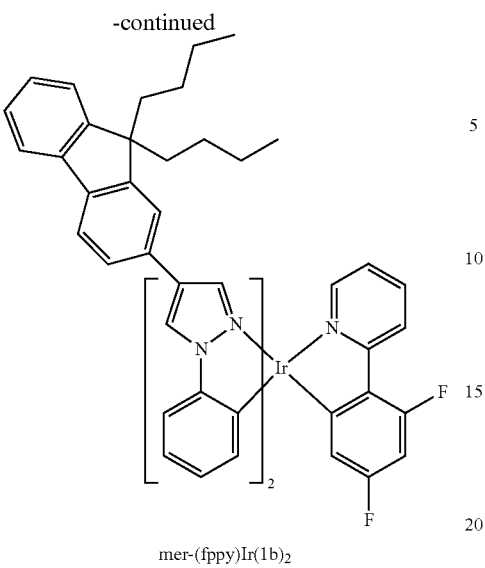

mer-(fppy)Ir(1b)₂

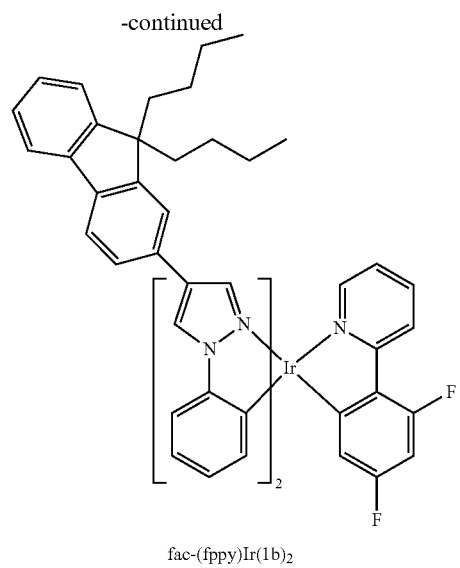

fac-(fppy)Ir(1b)₂

Figure 7:
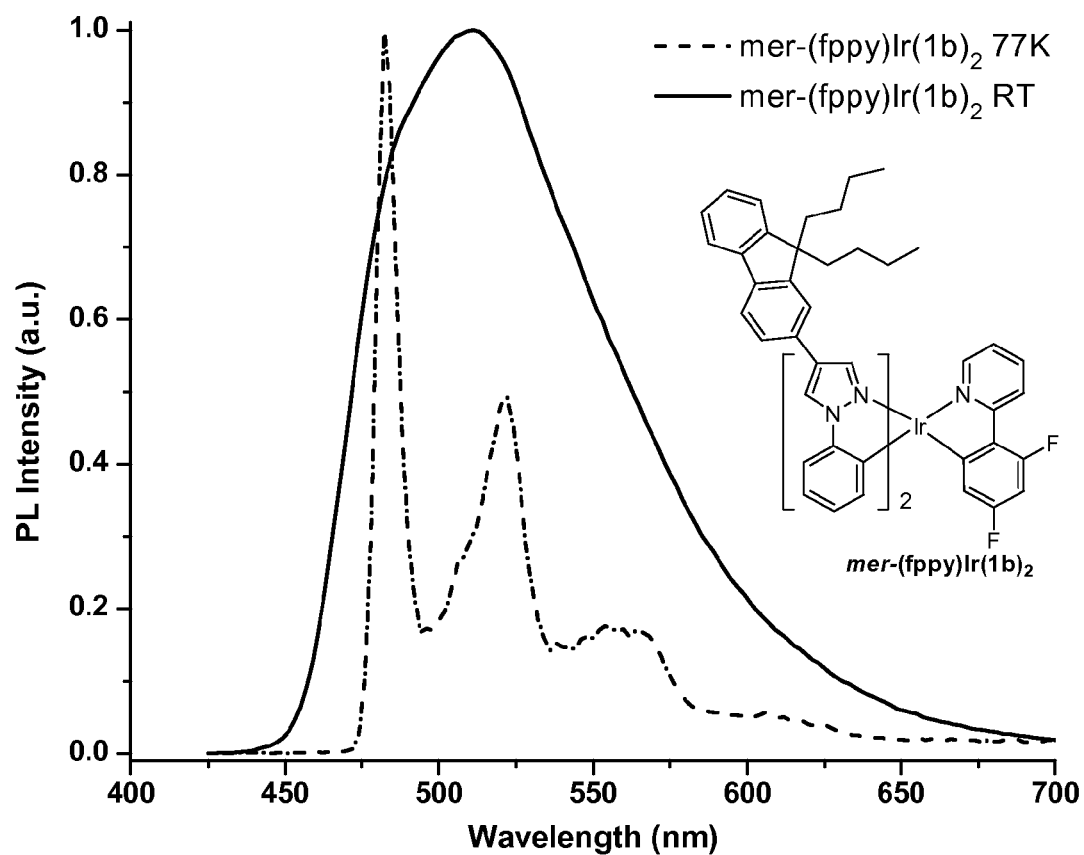
FIG. 7 shows emission spectra of mer-(fppy)Ir(1b)$_2$ in CH$_2$Cl$_2$ at room temperature and in 2-methyltetrahydrofuran at 77K.

A mixture of Dimer-1b (360 mg, 0.17 mmol, 1.0 eq), ligand Ligand-fppy (81 mg, 0.51 mmol, 3.0 eq) and AgPF₆ (86 mg, 0.34 mmol, 2.0 eq) in ClCH₂CH₂Cl (20 mL) and Et₃N (1 mL) under an atmosphere of nitrogen was stirred at room temperature for 2 hours, then refluxed for 40 hours and cooled to ambient temperature. The solvent was removed and the residue was purified through column chromatography on silica gel using dichloromethane/hexane (1:1) as eluent to obtain the desired product mer-(fppy)Ir(1b)₂ 52 mg as a yellow solid in 14% yield. ¹H NMR (DMSO-d₆, 400 MHz): δ 0.41-0.57 (m, 8H), 0.58-0.65 (m, 12H), 0.96-1.07 (m, 8H), 2.02-2.06 (m, 8H), 6.43-6.45 (m, 2H), 6.68-6.75 (m, 2H), 6.78 (t, J=7.6 Hz, 1H), 6.90-6.97 (m, 2H), 7.04 (td, J=7.6, 2.0 Hz, 1H), 7.25 (t, J=6.8 Hz, 1H), 7.30-7.34 (m, 5H), 7.42-7.44 (m, 2H), 7.47 (s, 1H), 7.55 (d, J=8.0 Hz, 1H), 7.61-7.65 (m, 2H), 7.70 (d, J=7.6 Hz, 1H), 7.74-7.80 (m, 6H), 7.93-7.97 (m, 1H), 8.19 (d, J=5.2 Hz, 1H), 8.31-8.34 (m, 1H), 9.33 (d, J=7.2 Hz, 2H). Emission spectra of mer-(fppy)Ir(1b)₂ at room temperature in CH₂Cl₂ and at 77K in 2-methyltetrahydrofuran are shown in FIG. 7.

6. Example 6

The iridium complex fac-(fppy)Ir(1b)₂ was prepared according to the following scheme:

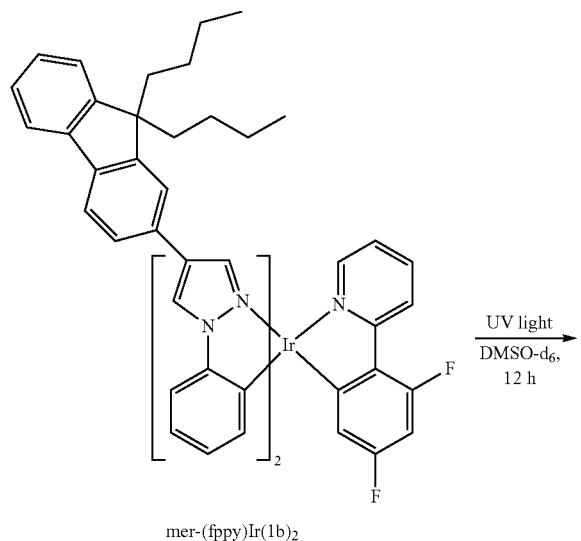

mer-(fppy)Ir(1b)₂

Figure 8:
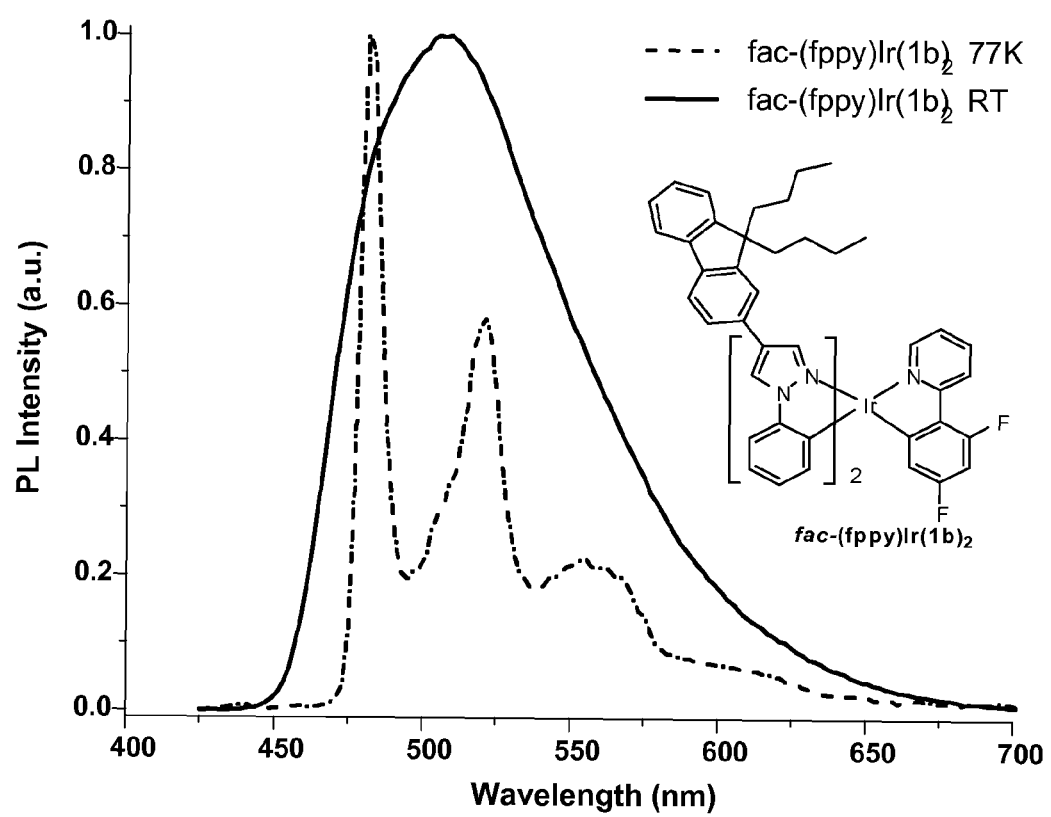
FIG. 8 shows emission spectra of fac-(fppy)Ir(1b)$_2$ in CH$_2$Cl$_2$ at room temperature and in 2-methyltetrahydrofuran at 77K.

A solution of mer-(fppy)Ir(1b)₂ in DMSO-d₆ was kept under UV light for 1 day, monitored by ¹H NMR until the mer-(fppy)Ir(1b)₂ was consumed completely to give fac-(fppy)Ir(1b)₂. Emission spectra of fac-(fppy)Ir(1b)₂ at room temperature in CH₂Cl₂ and at 77K in 2-methyltetrahydrofuran are shown in FIG. 8.

Further modifications and alternative embodiments of various aspects will be apparent to those skilled in the art in view of this description. Accordingly, this description is to be construed as illustrative only. It is to be understood that the forms shown and described herein are to be taken as examples of embodiments. Elements and materials may be substituted for those illustrated and described herein, parts and processes may be reversed, and certain features may be utilized independently, all as would be apparent to one skilled in the art after having the benefit of this description. Changes may be made in the elements described herein without departing from the spirit and scope as described in the following claims.

What is claimed is:
1. A compound of:

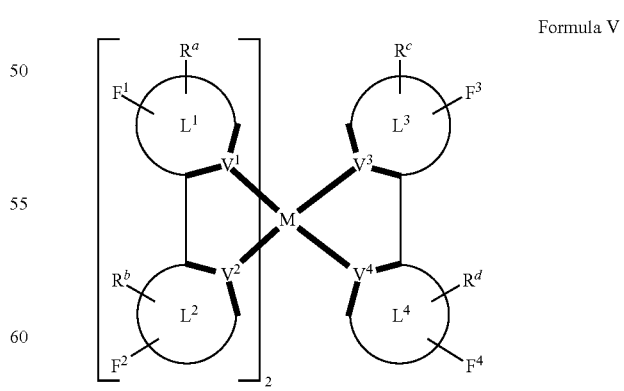

Formula V wherein:
M is Ir(III), Rh(III) or Pt(IV),
each $L^1$ and $L^3$ is independently substituted or unsubstituted: heteroaryl or N-heterocyclic carbene, each $L^2$ and $L^4$ is independently substituted or unsubstituted aryl, each of $V^1$ and $V^3$ is coordinated with M and is independently N or C, each of $V^2$ and $V^4$ is coordinated with M and is C, each of $F^1$, $F^2$, $F^3$, and $F^4$ is independently present or absent, wherein at least one of $F^1$, $F^2$, $F^3$, and $F^4$ is present, each of $R^a$, $R^b$, $R^c$, and $R^d$ is independently present or absent, and if present each $R^a$, $R^b$, $R^c$, and $R^d$ independently represents mono-, di-, or tri-substitutions, and wherein each $R^a$, $R^b$, $R^c$, and $R^d$ present is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, each of $R^1$, $R^2$, and $R^3$, if present, is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, each of $F^1$, $F^2$, $F^3$, and $F^4$ if present, is independently one of the following structures:

1 Aromatic Hydrocarbons and Their Derivatives

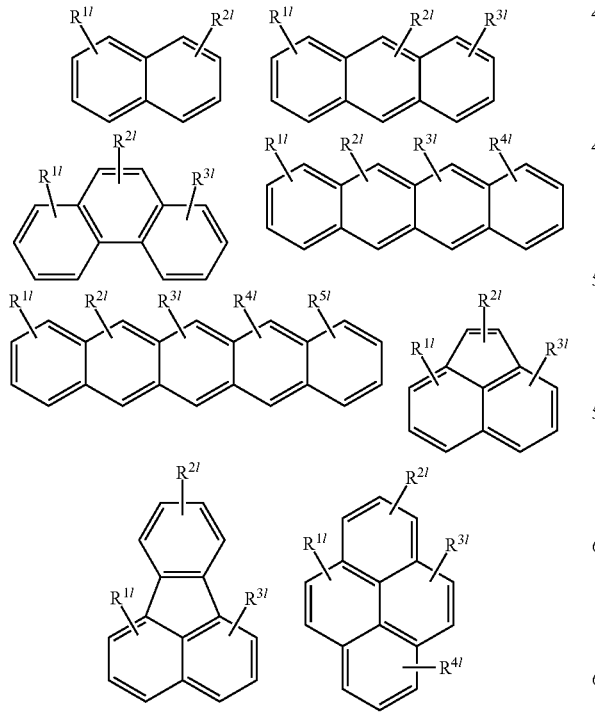

-continued

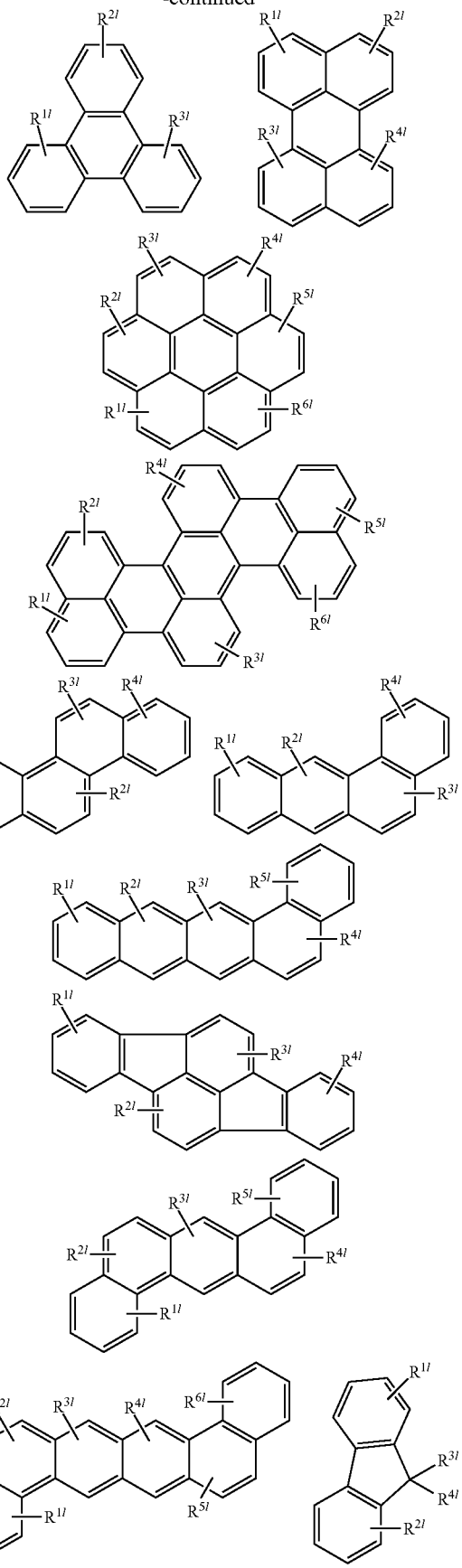

463
-continued
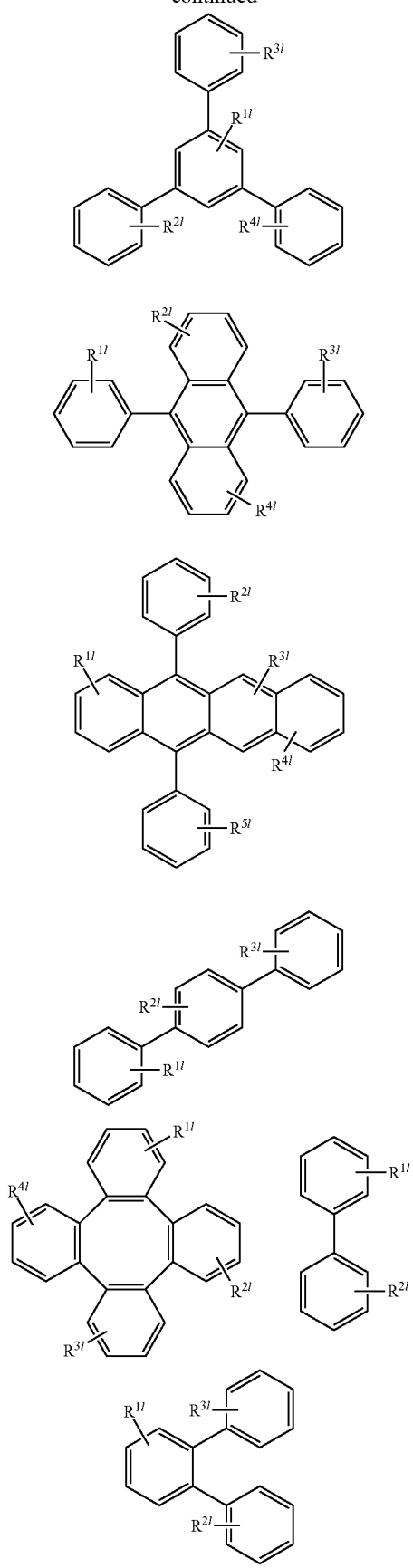
464
-continued
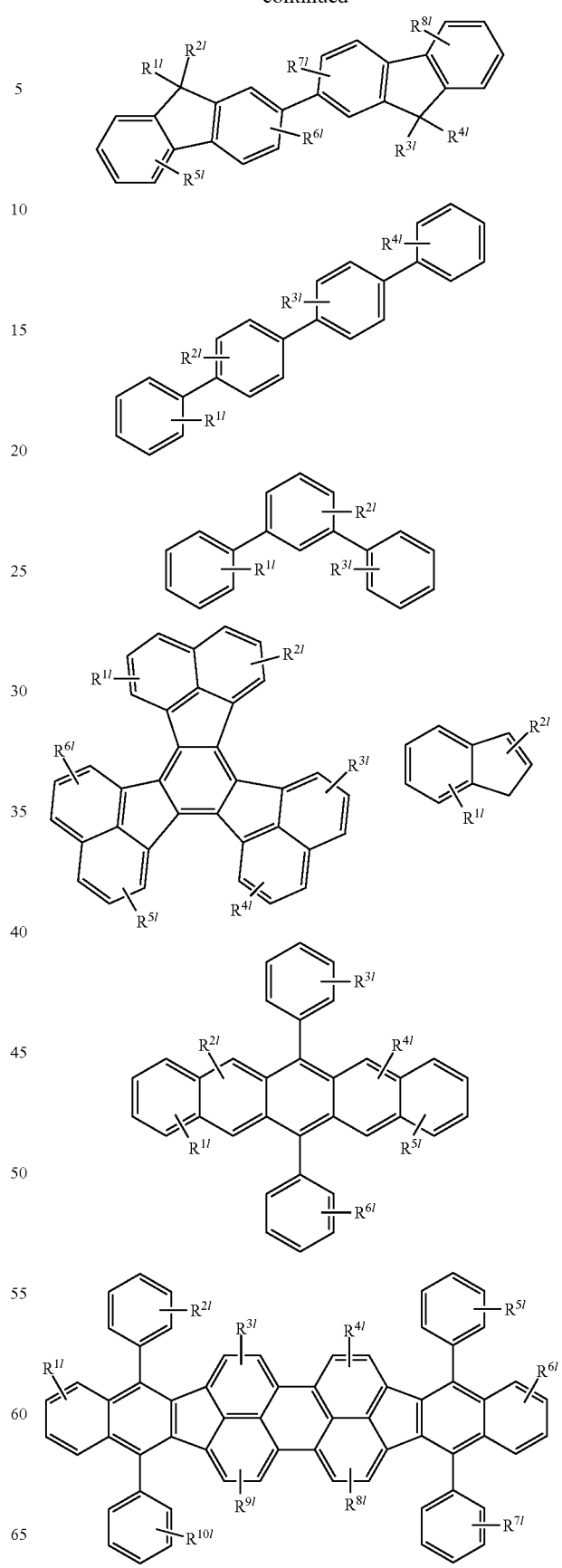

465
-continued
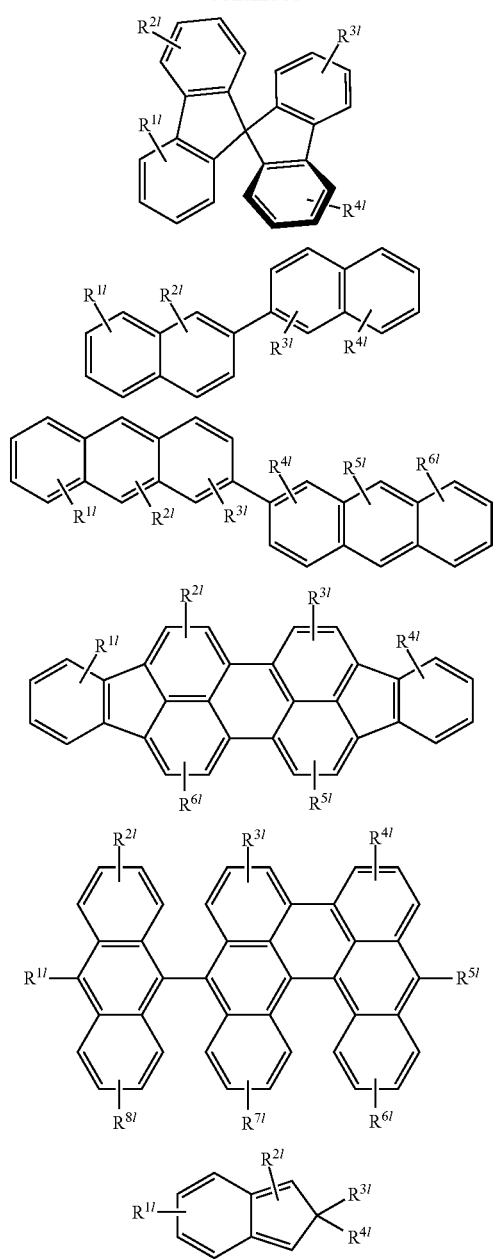
2. Arylethylene, Arylacetylene and Their Derivatives
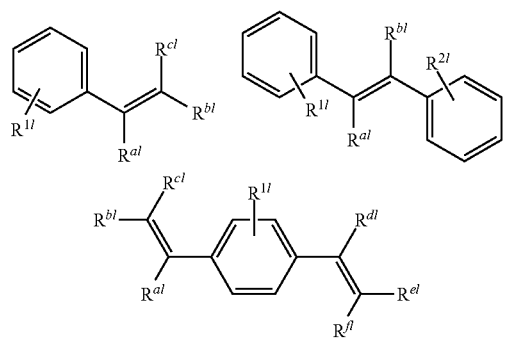
466
-continued
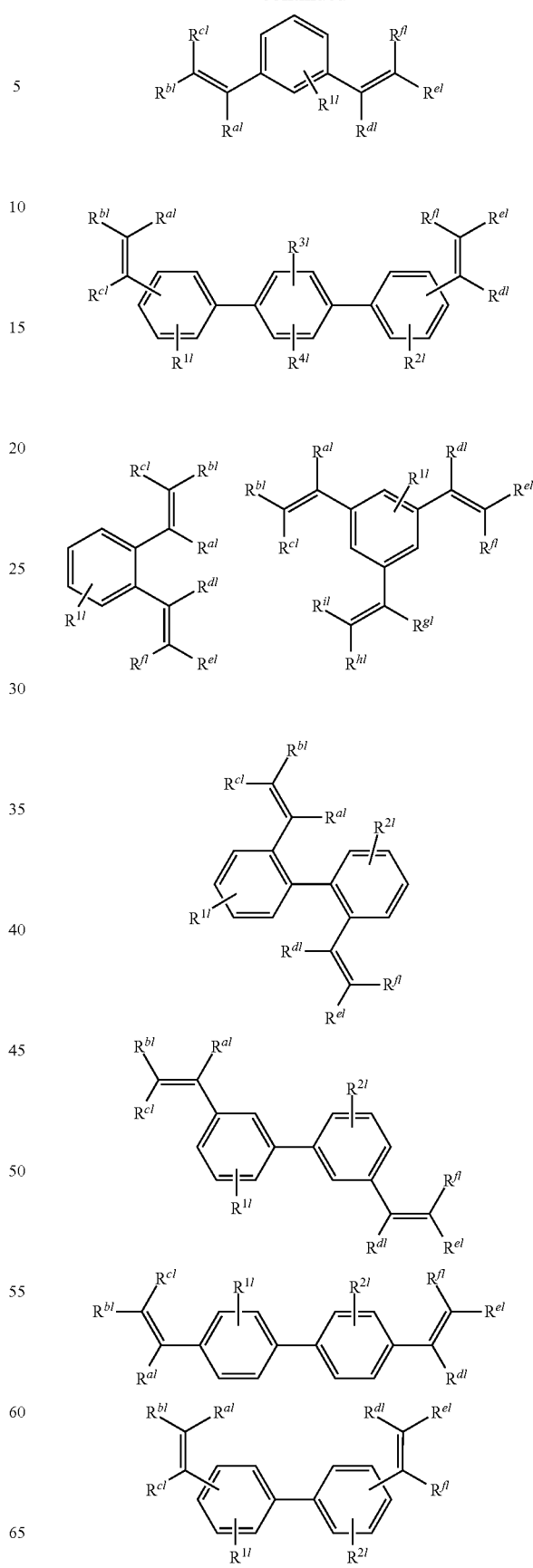

467
-continued
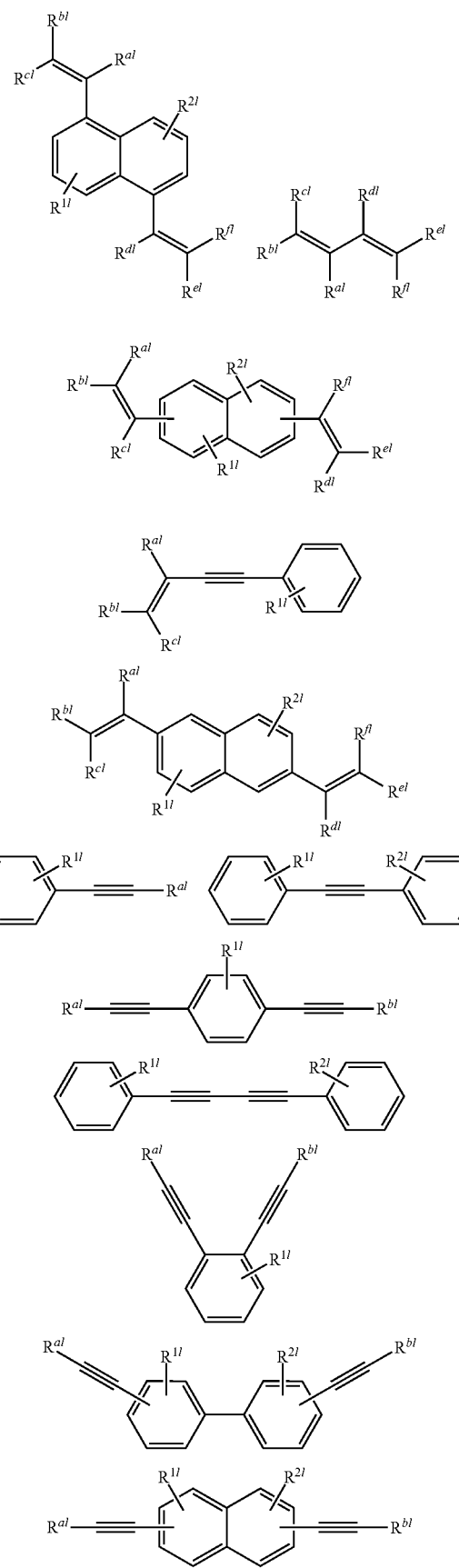
468
-continued
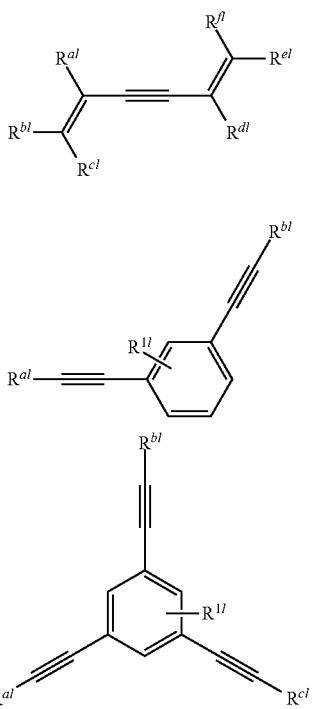
where each of $R^{al}$, $R^{bl}$, $R^{cl}$, $R^{dl}$, $R^{el}$, $R^{fl}$, $R^{gl}$, $R^{gl}$ and $R^{il}$ can be one of the following structure
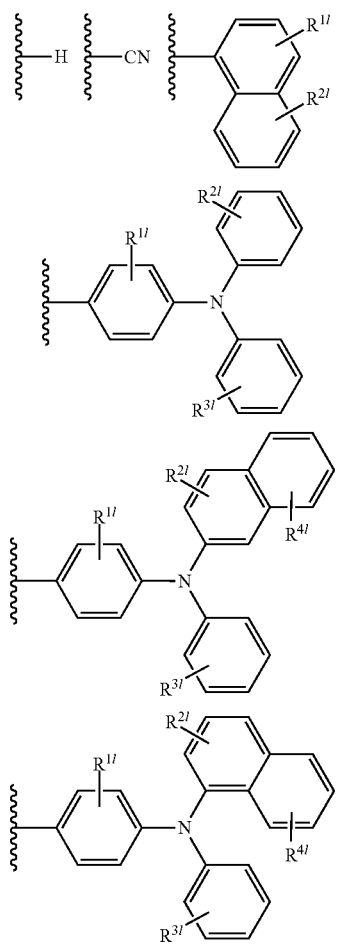

469
-continued
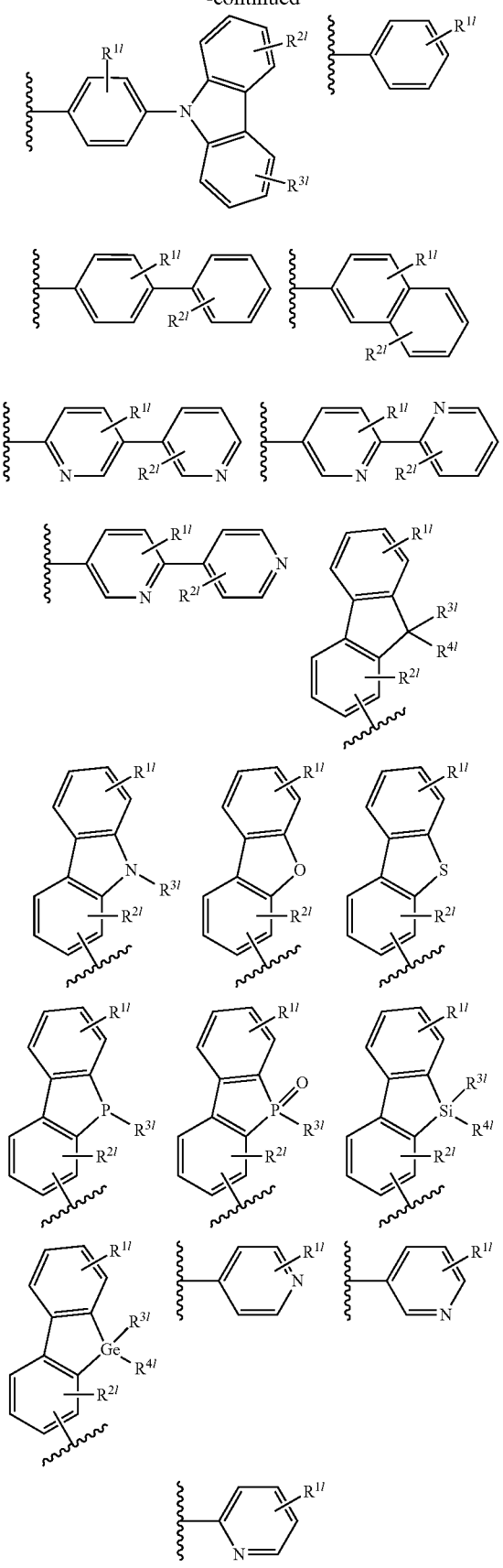
470
3. Heterocyclic Compounds and Their Derivatives
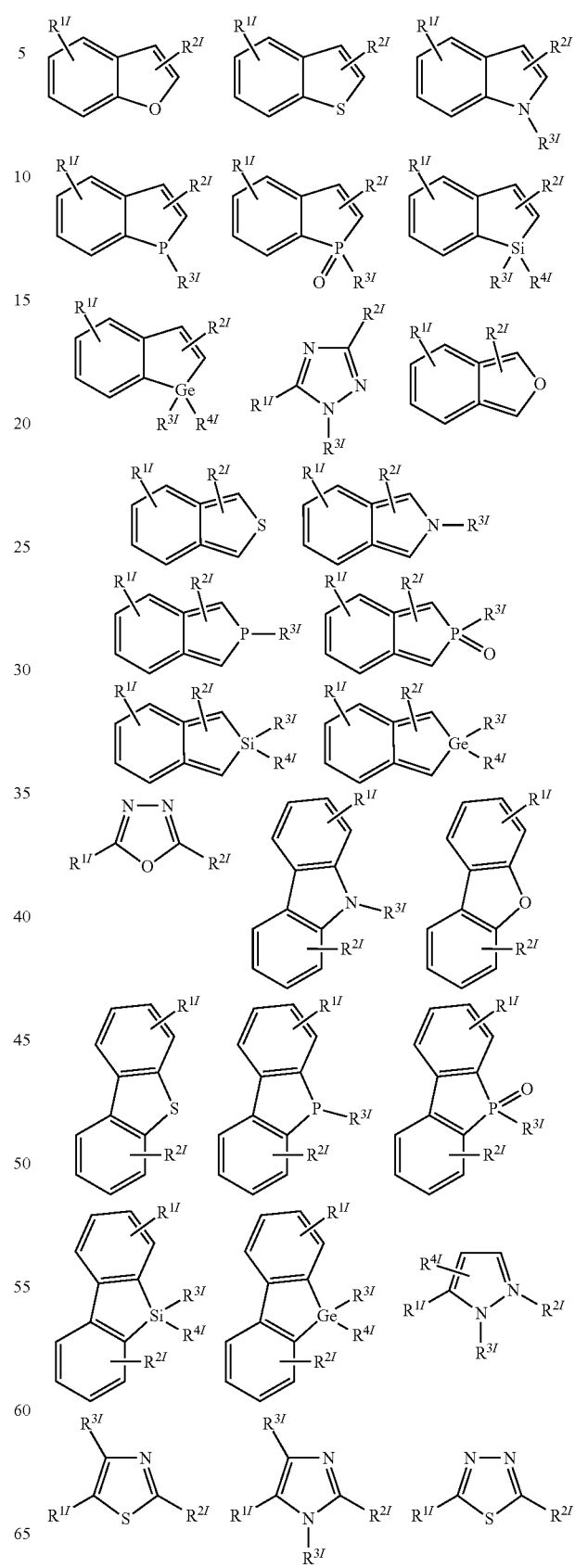

471
-continued
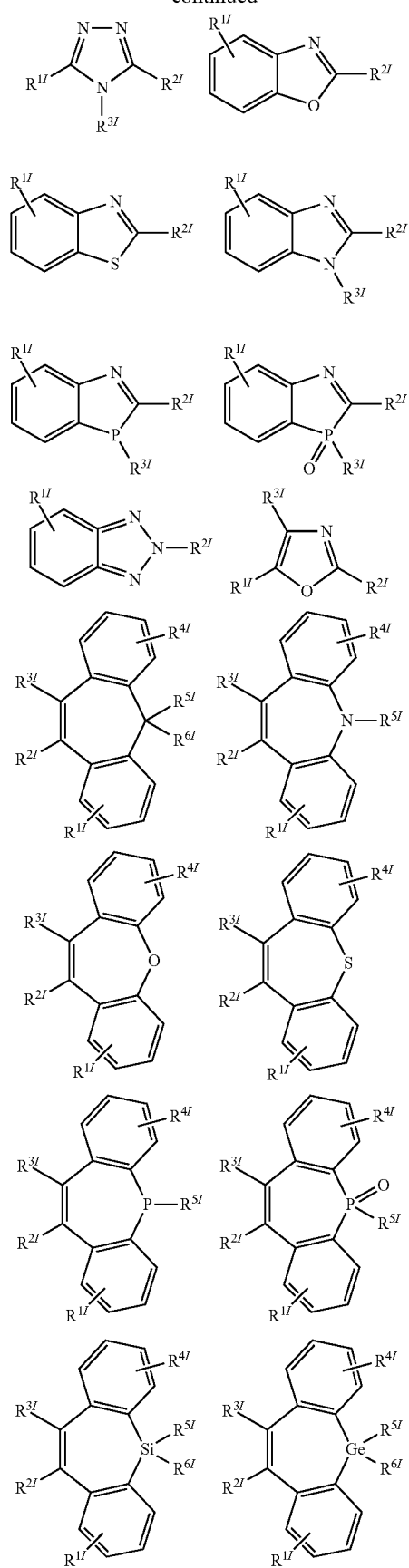
472
-continued
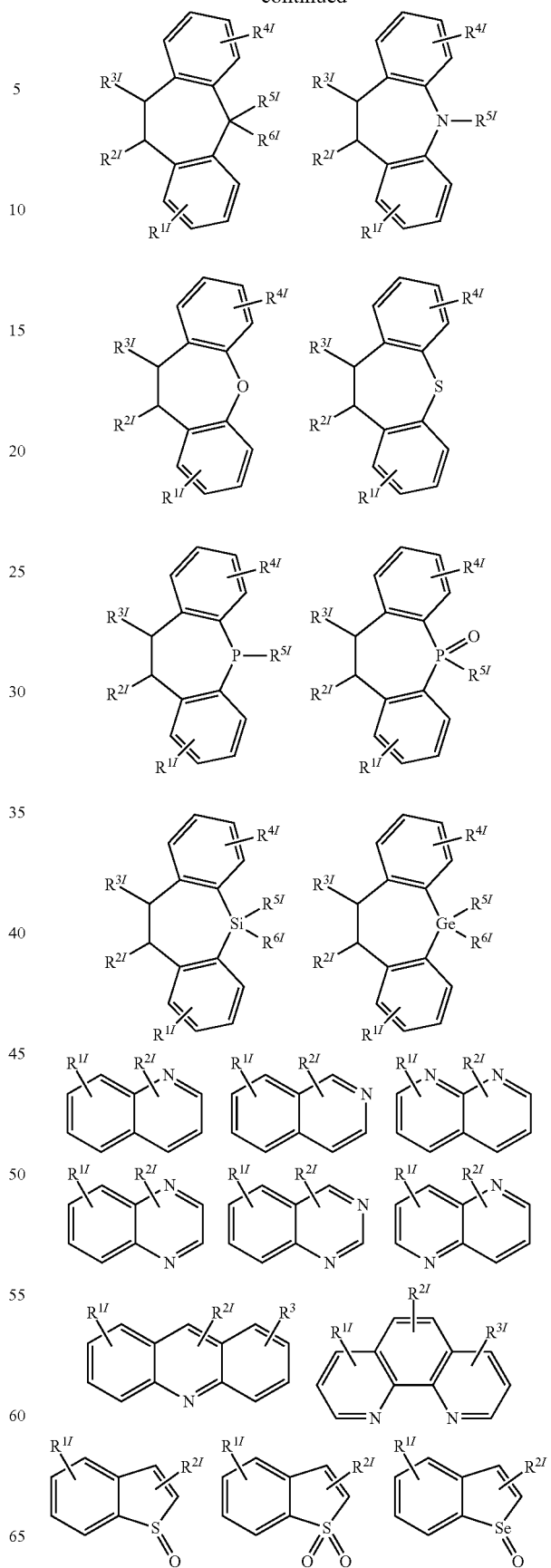

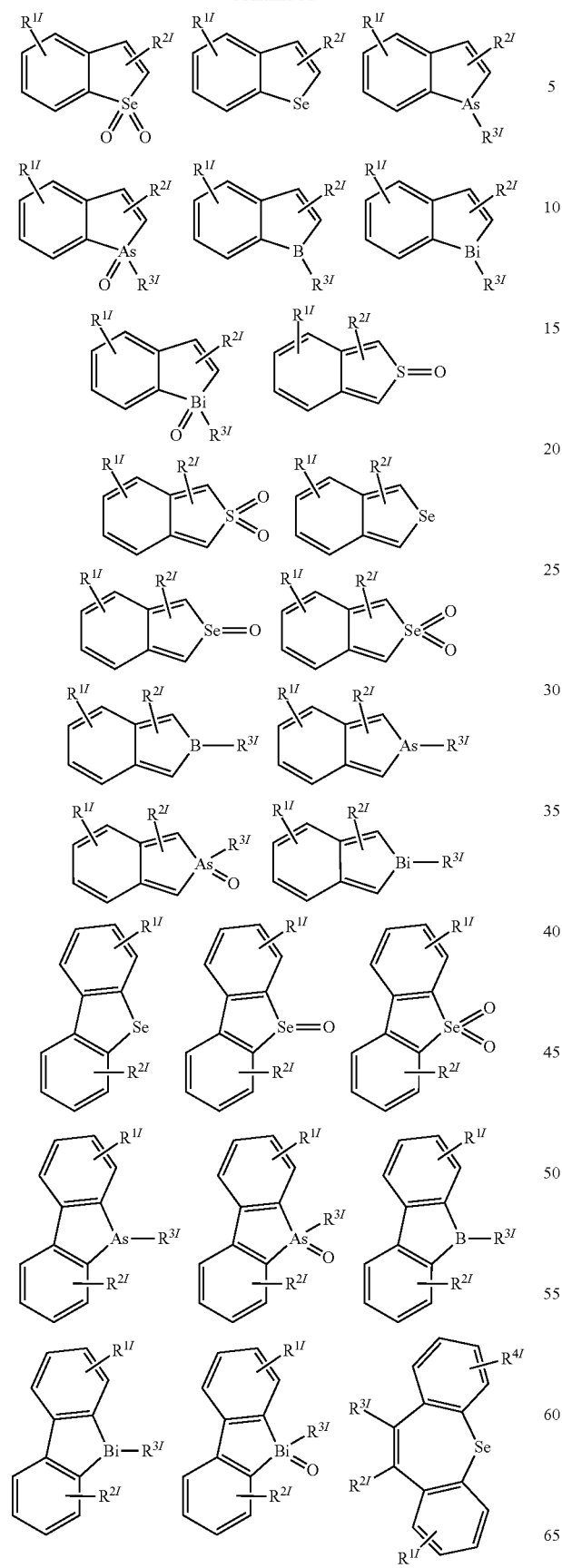
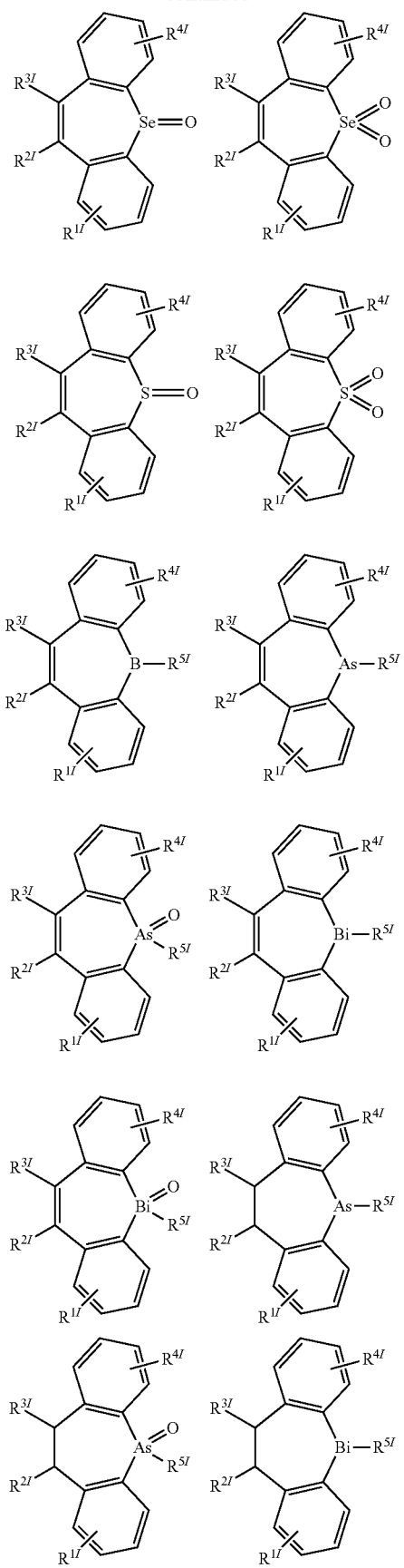

475
-continued
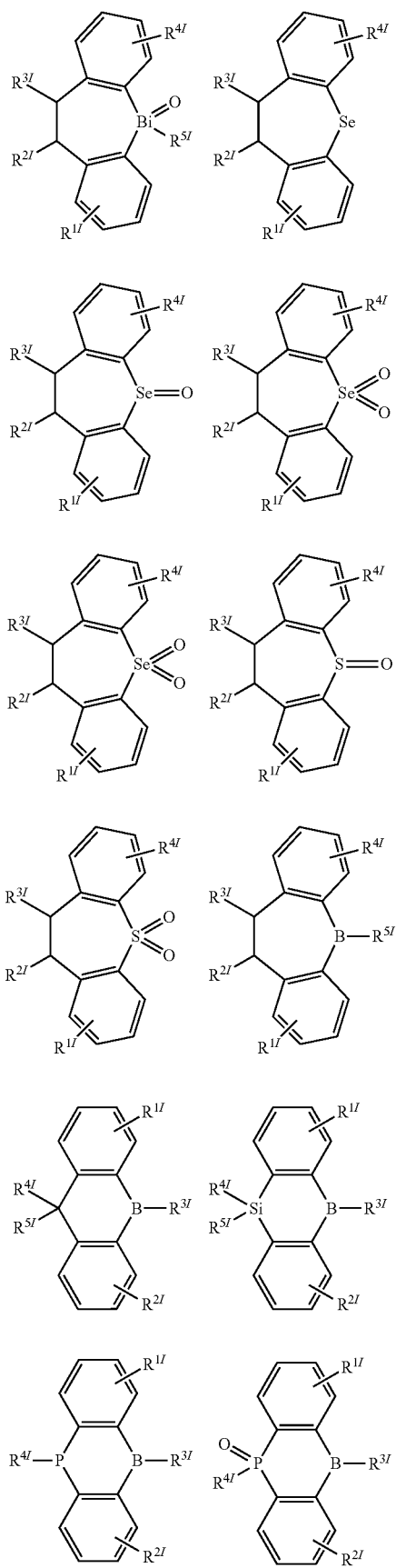
476
-continued
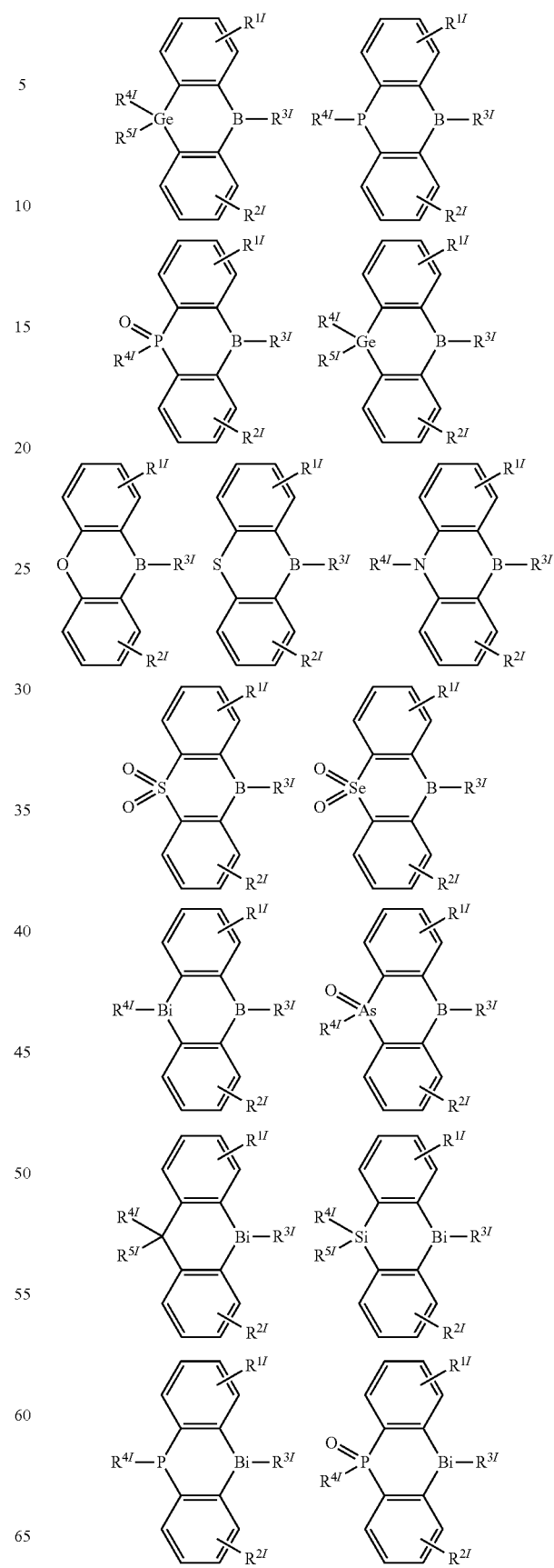

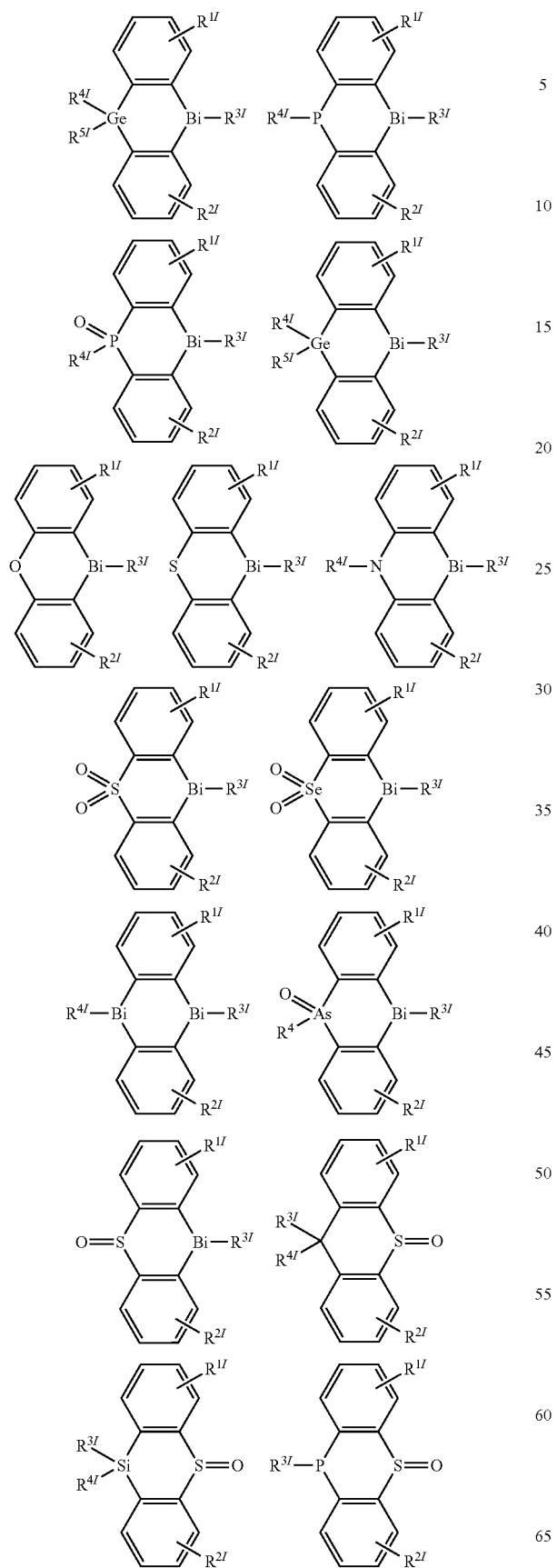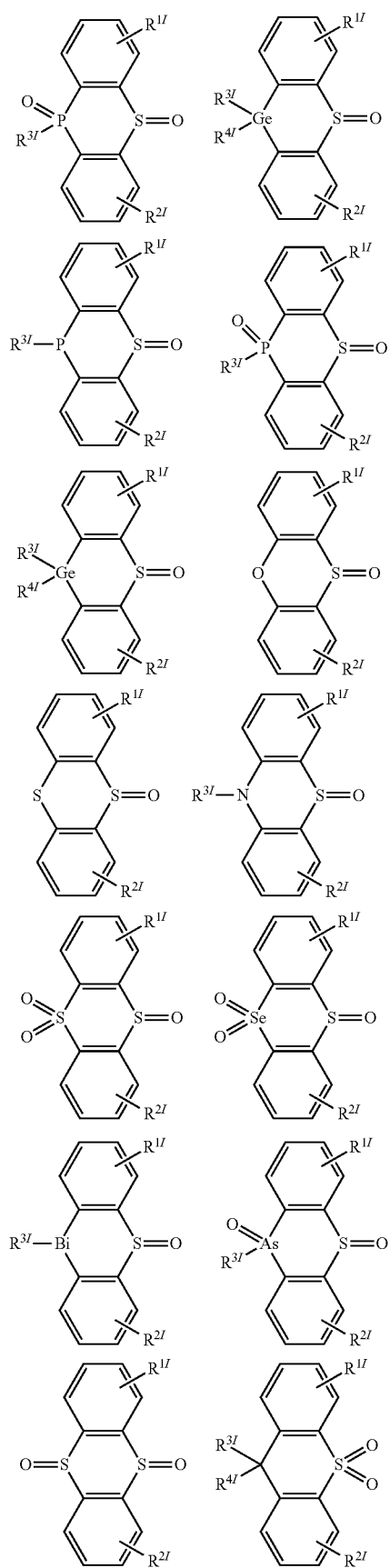

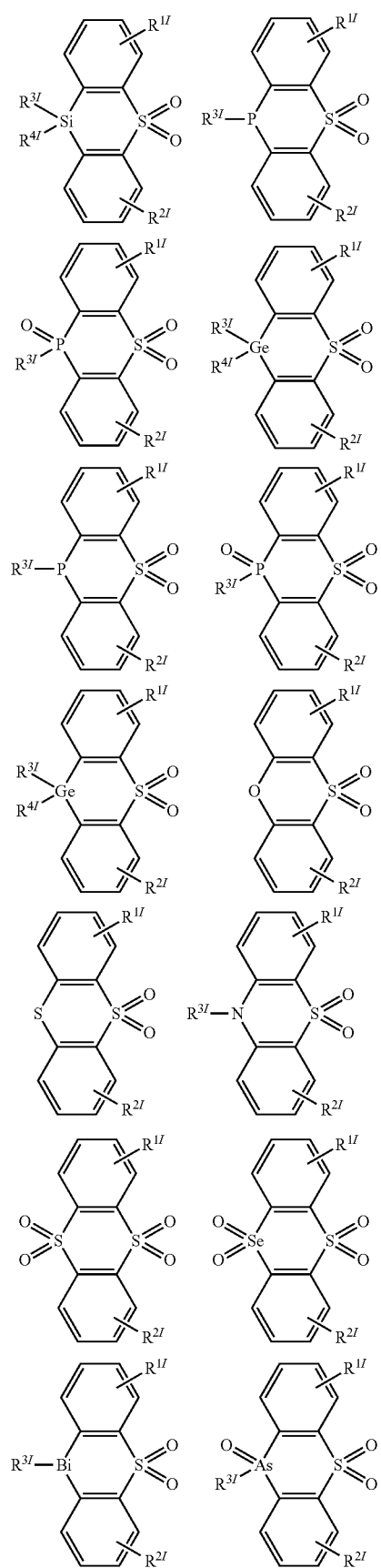
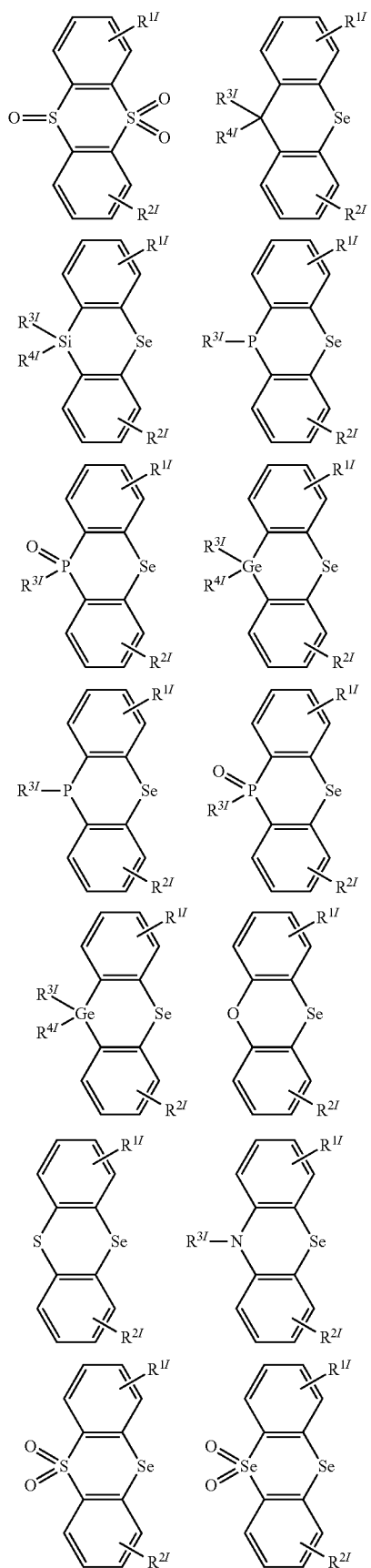

-continued
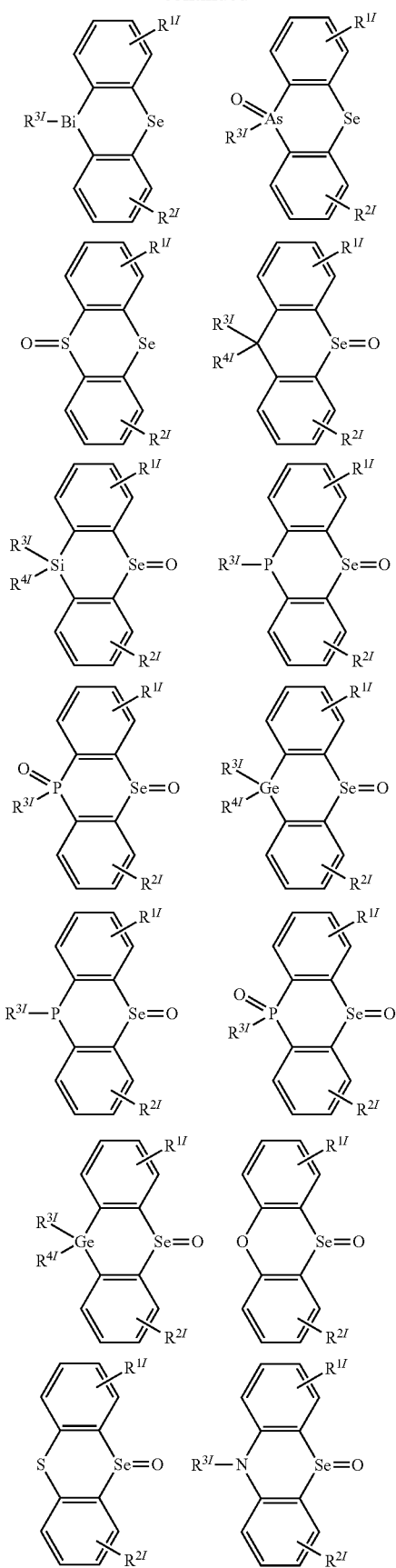
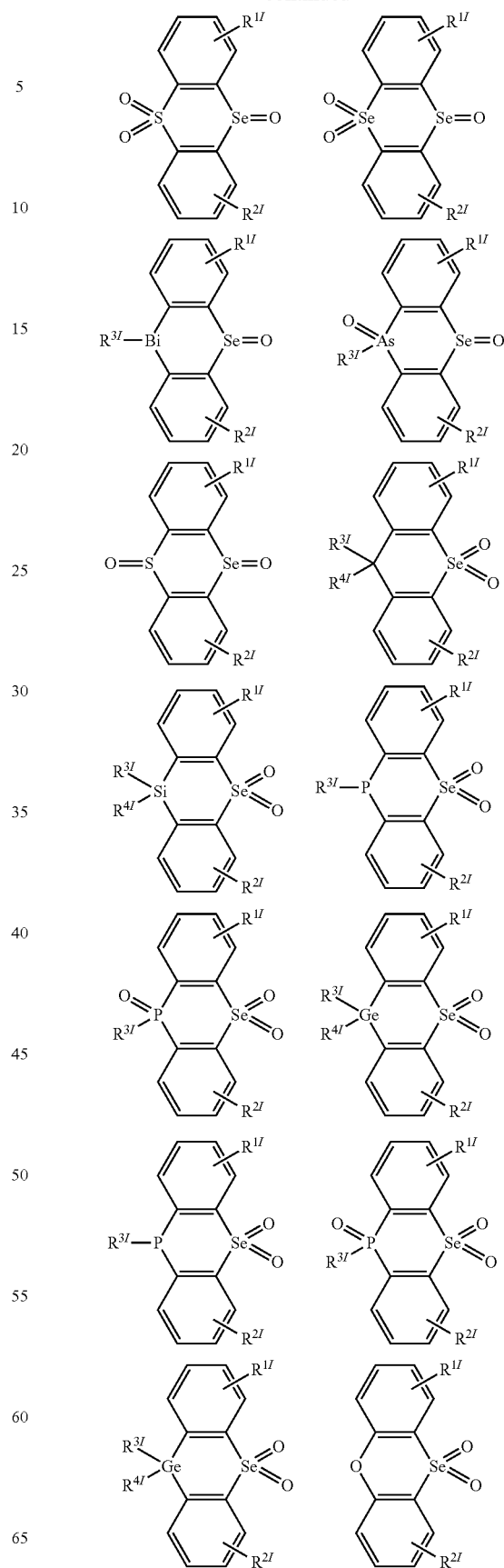

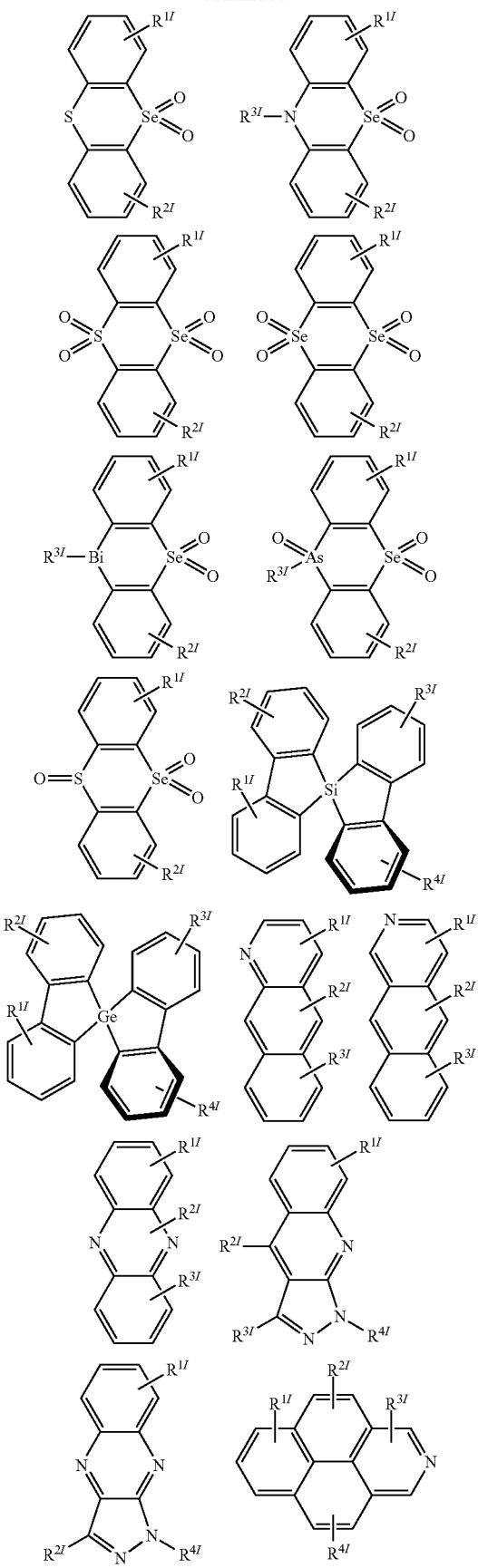
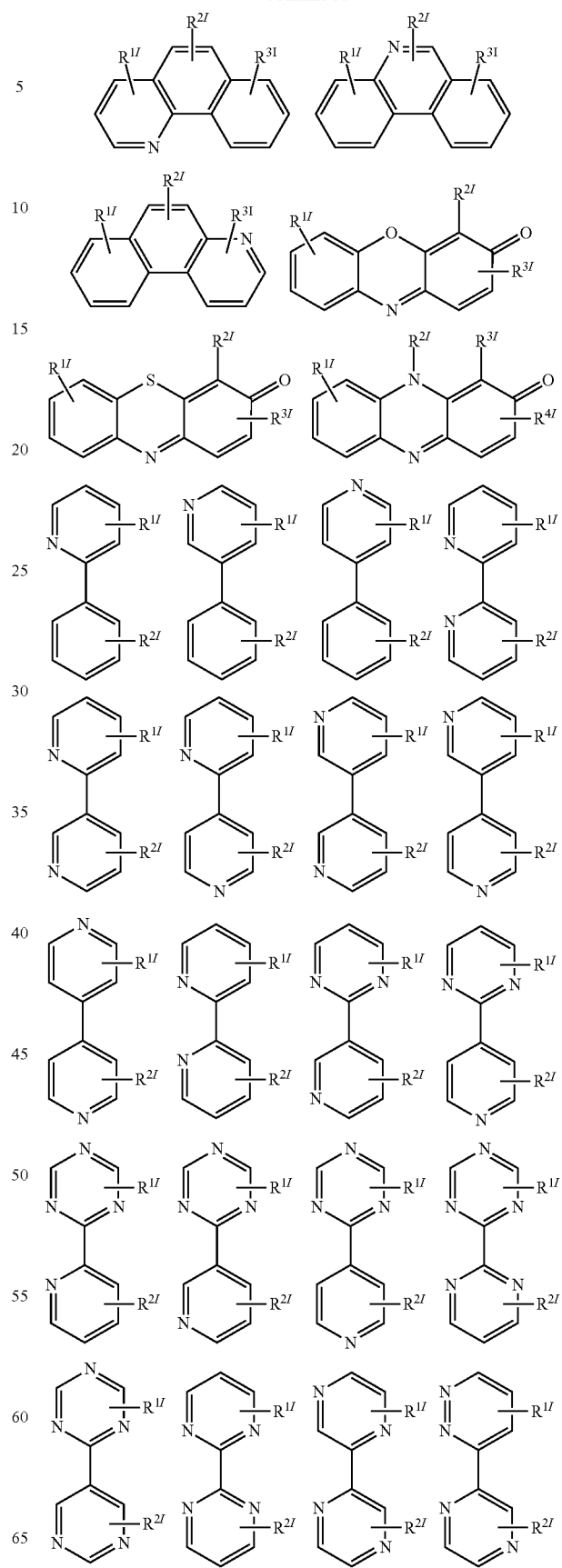

-continued
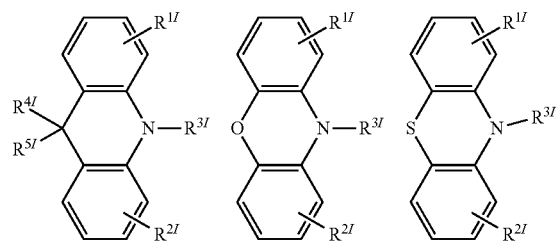
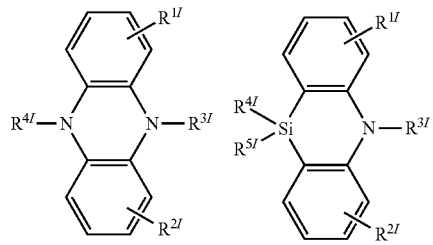
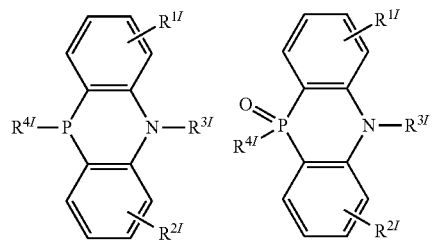
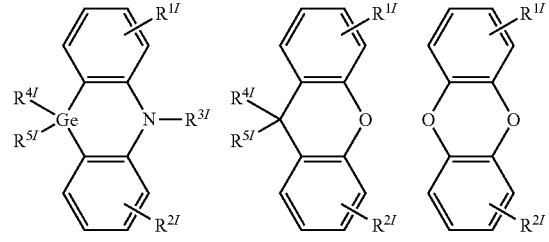
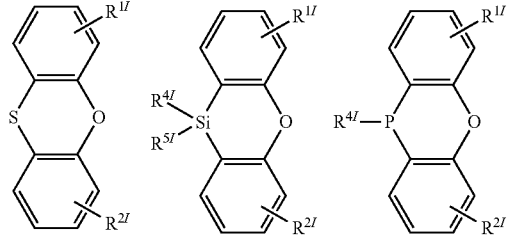
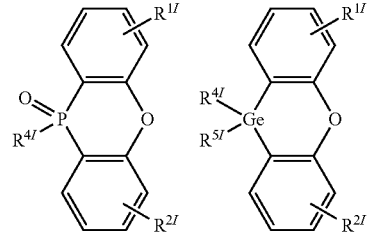
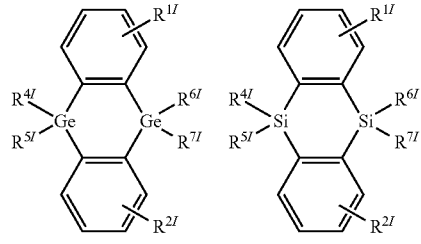
-continued
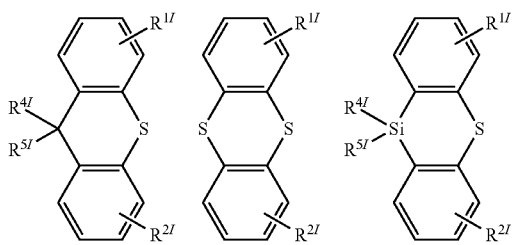
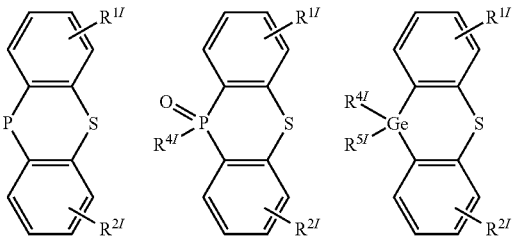
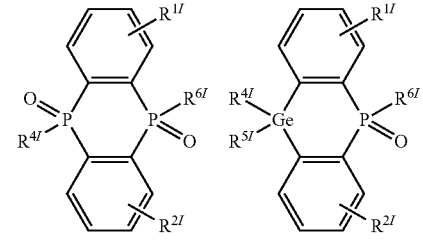
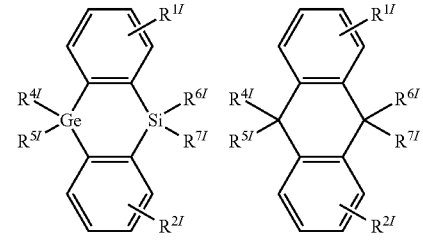
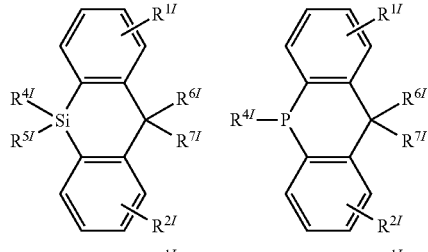
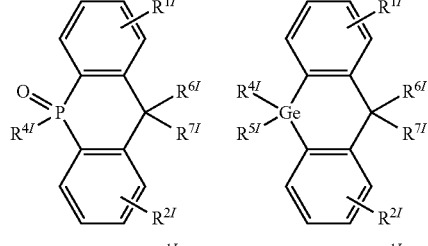
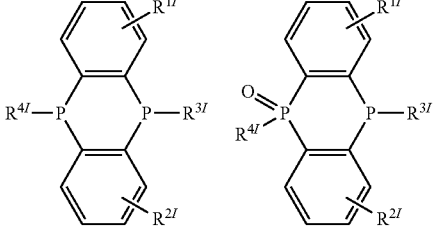

487
-continued
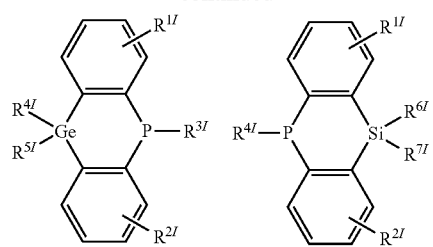
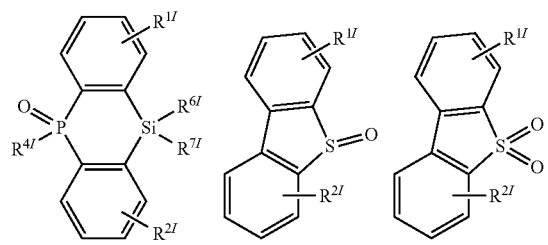
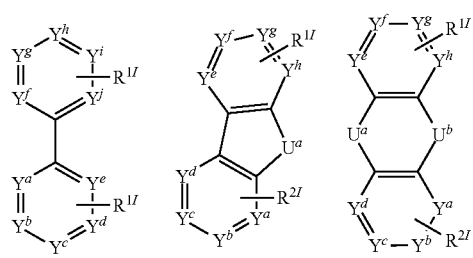
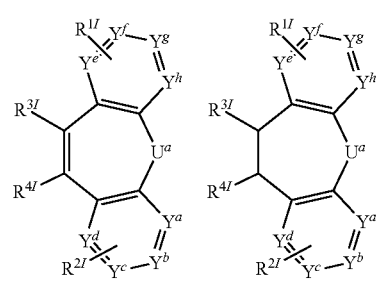
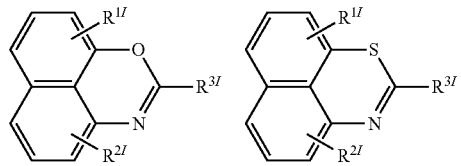
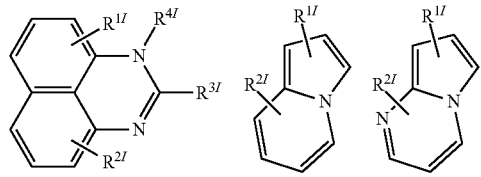
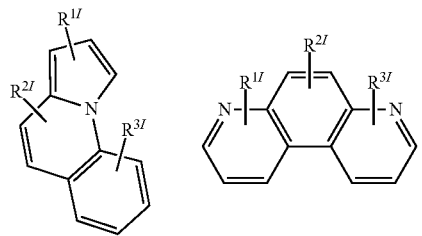
488
-continued
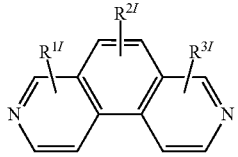
4. Other fluorescent luminophors
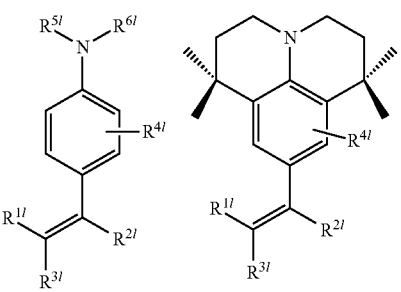
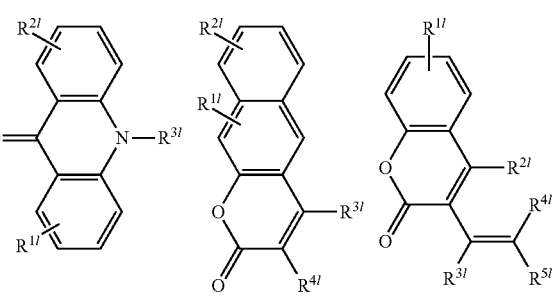
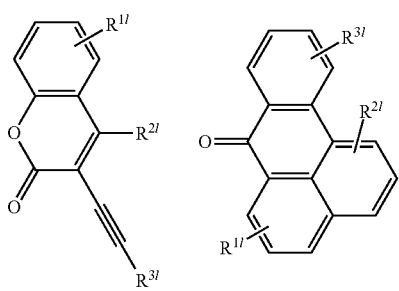
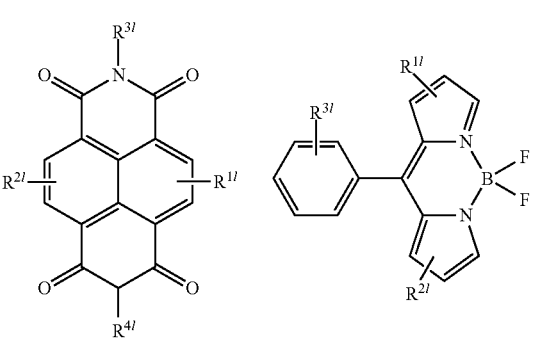

489
-continued
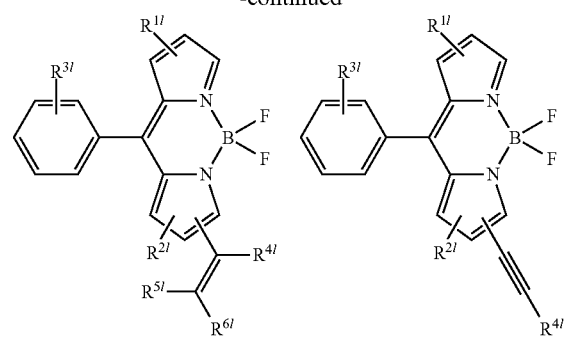
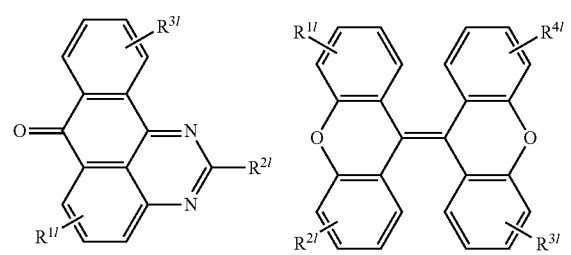
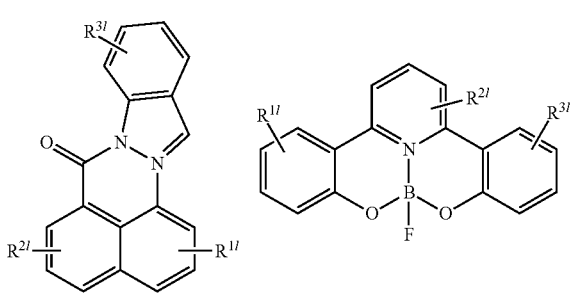
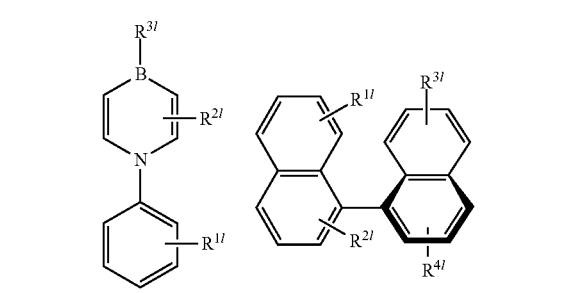
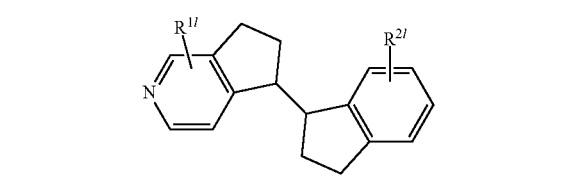
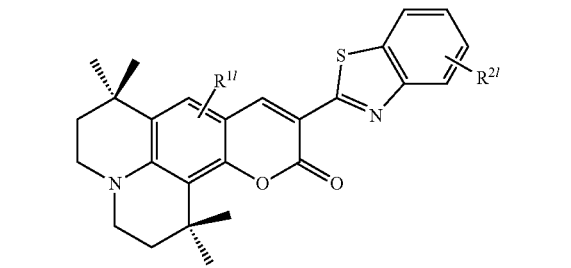
490
-continued
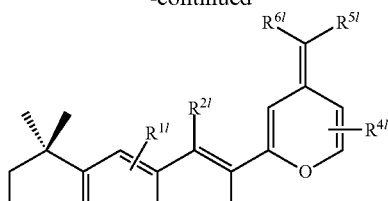
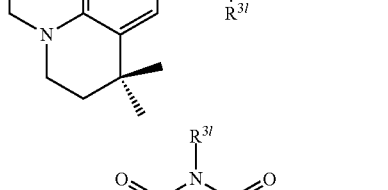
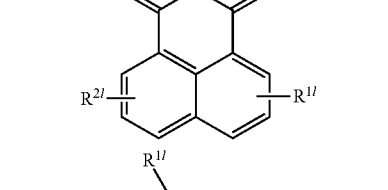
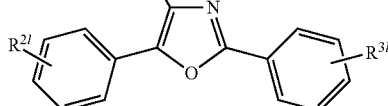
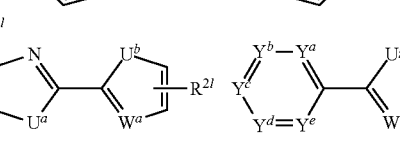
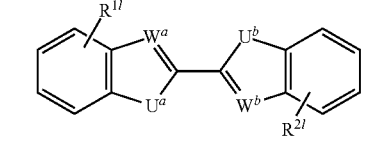
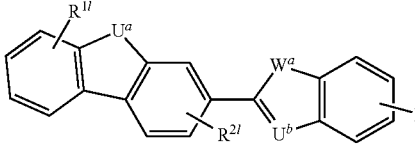
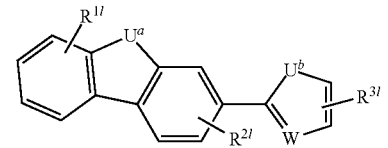
Coumarins
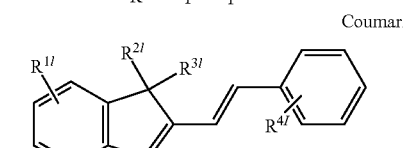
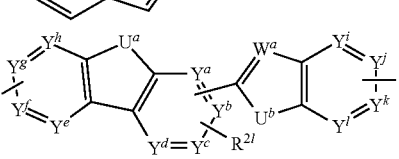

-continued

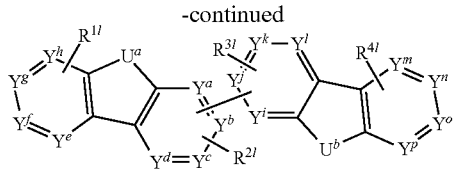

each of $R^{11}$, $R^{21}$, $R^{31}$, $R^{41}$, $R^{51}$, $R^{61}$, $R^{71}$, $R^{81}$, $R^{91}$, and $R^{101}$, if present, is a mono-, di-, tri-, or tetra-substitution, valency permitting, and each $R^{11}$, $R^{21}$, $R^{31}$, $R^{41}$, $R^{51}$, $R^{61}$, $R^{71}$, $R^{81}$, $R^{91}$, and $R^{101}$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, each of $Y^a$, $Y^b$, $Y^c$, $Y^d$, $Y^e$, $Y^f$, $Y^g$, $Y^h$, $Y^i$, $Y^k$, $Y^l$, $Y^m$, $Y^n$, $Y^o$, and $Y^p$, if present, is independently C, N or B, each of $U^a$ and $U^b$, if present, is independently $CH_2$, $CR^1R^2$, C=O, $CH_2$, $SiR^1R^2$, $GeH_2$, $GeR^1R^2$, NH, $NR^3$, PH, $PR^3$, $R^3P$=O, $AsR^3$, $R^3As$=O, O, S, S=O, $SO_2$, Se, Se=O, $SeO_2$, BH, $BR^3$, $R^3Bi$=O, BiH, or $BiR^3$, and each of W, $W^a$, and $W^b$, if present, is independently CH, $CR^1$, $SiR^1$, GeH, $GeR^1$, N, P, B, Bi, or Bi=O;

wherein heteroaryl is a 5- to 10-membered single or multi-cyclic aromatic ring that has 1 to 4 heteroatom selected from nitrogen, oxygen, sulfur and phosphorus incorporated with the ring, and heterocycyl is a 4- to 10-membered single or multi-cyclic non-aromatic group that has 1 to 4 heteroatom selected from nitrogen, oxygen, sulfur and phosphorus incorporated with the ring.

2. The compound of claim 1, wherein the compound has a neutral charge.

3. The compound of claim 1, wherein each of

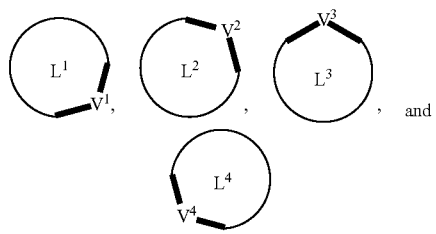

is independently one of the following structures:

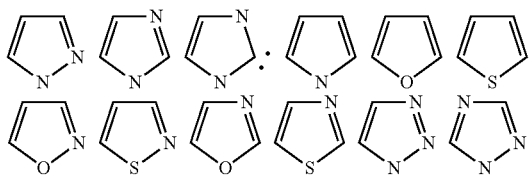

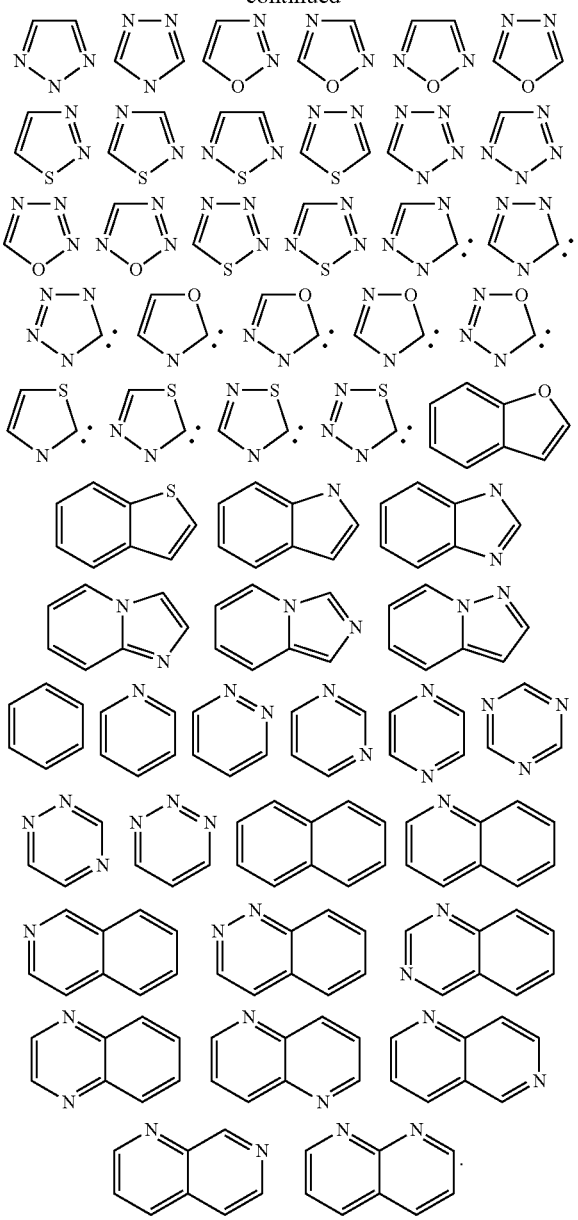

4. The compound of claim 1, wherein each of

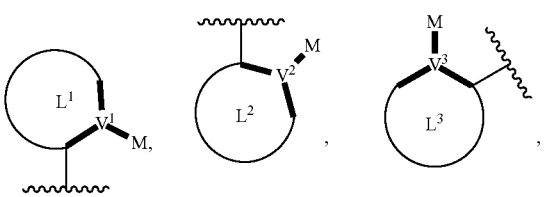

and

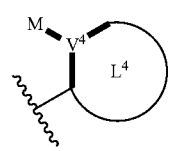

is independently one of the following structures:
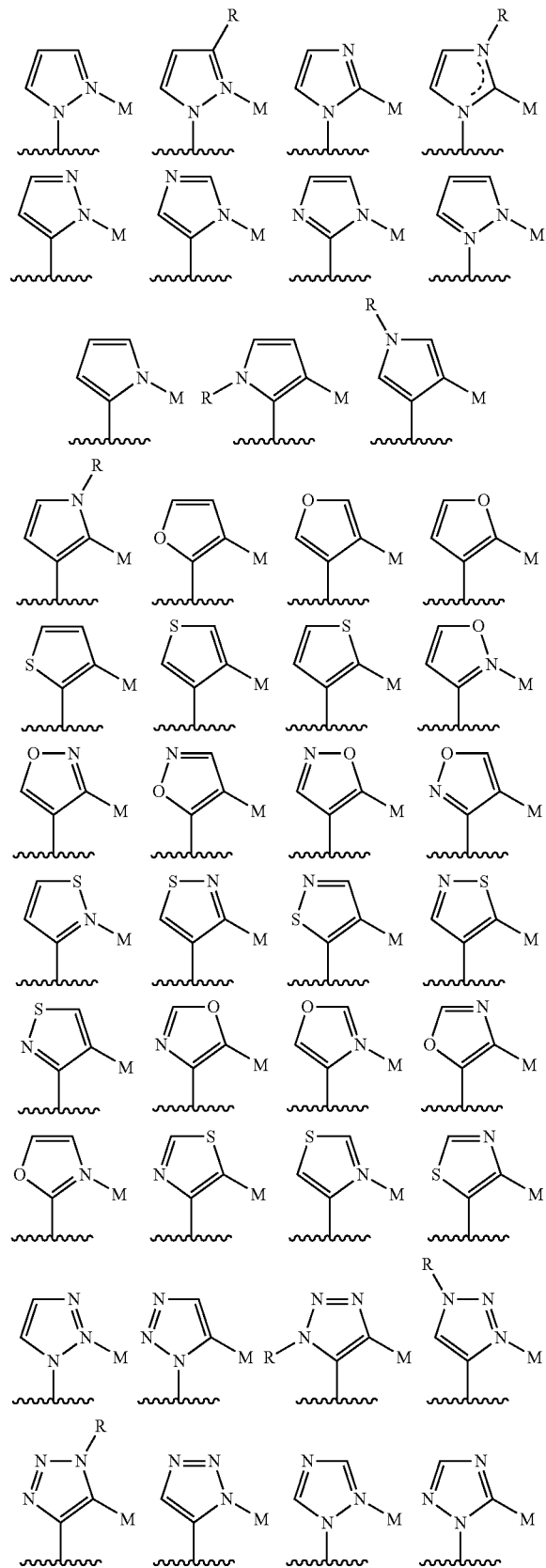
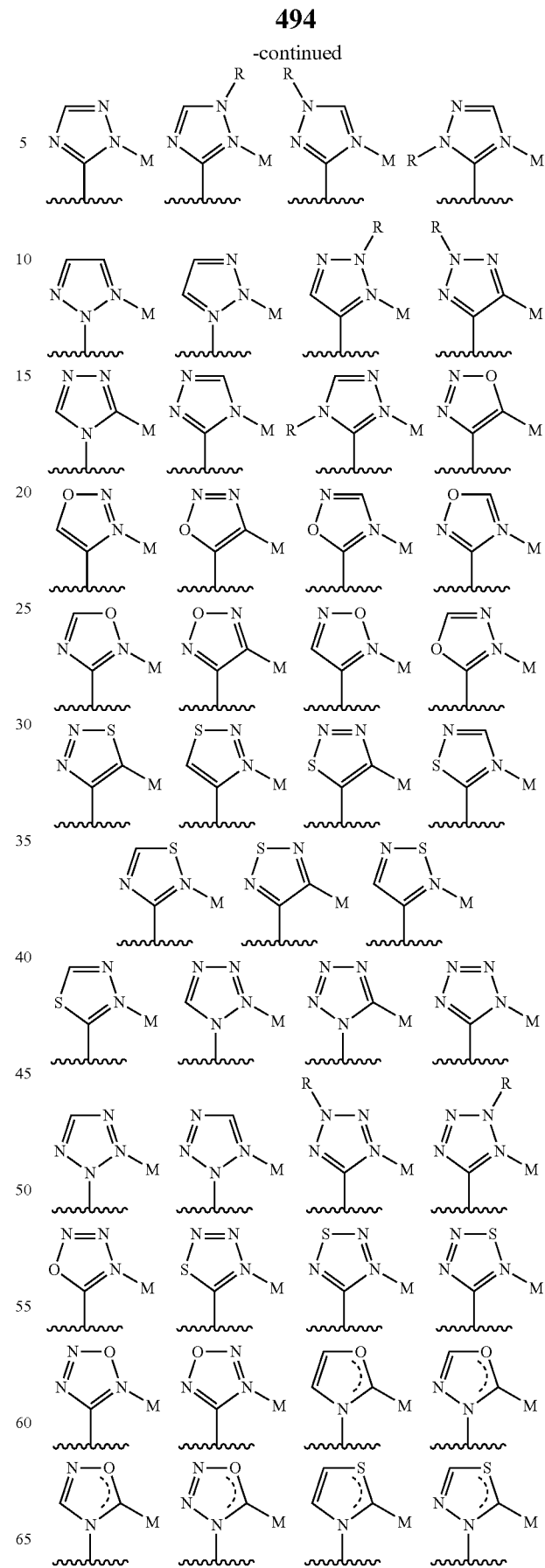

495
-continued

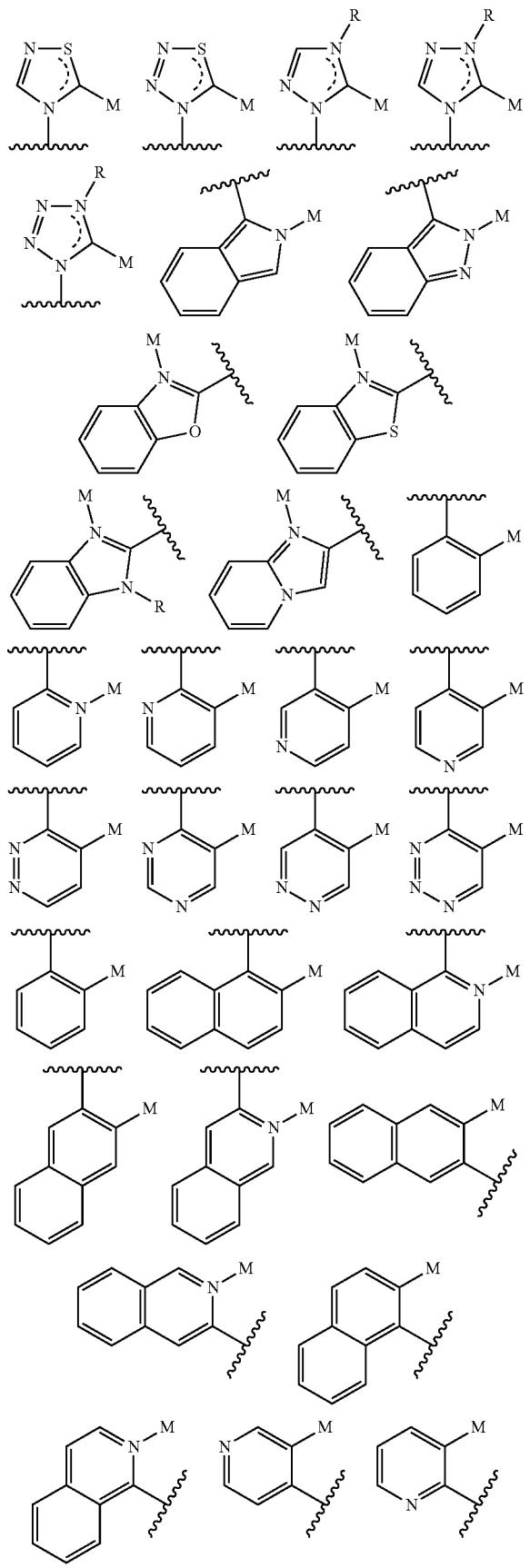

496
-continued

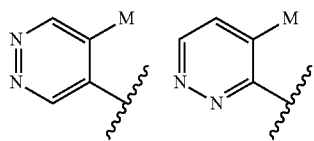

wherein R is deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

5. An emitter comprising the compound of claim 1, wherein the emitter is a delayed fluorescent and phosphorescent emitter.

6. An emitter comprising the compound of claim 1, wherein the emitter is a phosphorescent emitter.

7. An emitter comprising the compound of claim 1, wherein the emitter is a delayed fluorescent emitter.

8. A device comprising a compound of claim 1.

9. The device of claim 8, wherein the compound is selected to have 100% internal quantum efficiency in the device settings.

10. The device of claim 8, wherein the device is an organic light emitting diode.

11. The compound of claim 1, wherein polymeric comprises polyalkylene, polyester, or polyether.

12. The compound of claim 11, wherein polymeric comprises —(CH$_2$O)$_n$—CH$_3$, —(CH$_2$CH$_2$O)$_n$—CH$_3$, —[CH$_2$CH(CH$_3$)]$_n$—CH$_3$, —[CH$_2$CH(COOCH$_3$)]$_n$—CH$_3$, —[CH$_2$CH(COOCH$_2$CH$_3$)]$_n$—CH$_3$, or —[CH$_2$CH(COO$^t$Bu)]$_n$—CH$_3$, where n is an integer.

13. A compound selected from any of Structures Ir-1 to Ir-16 and Ir-19 to Ir-23:

Structures Ir-1

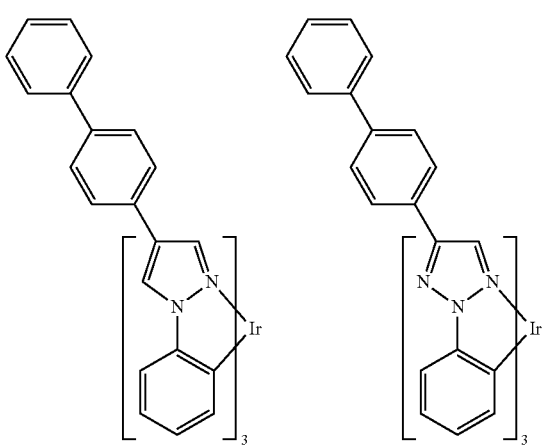

497
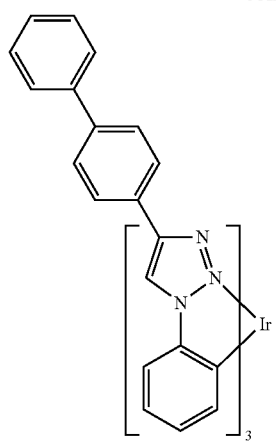 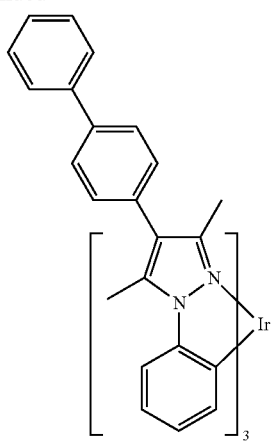
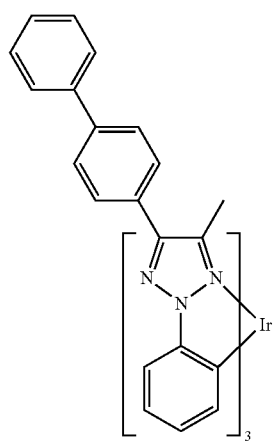 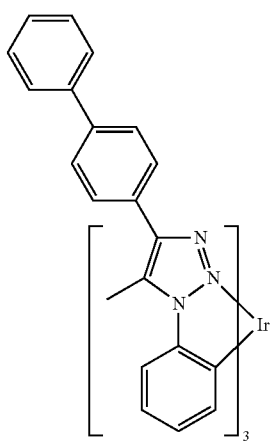
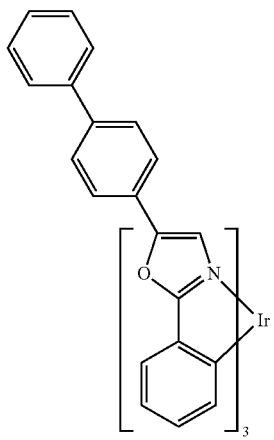 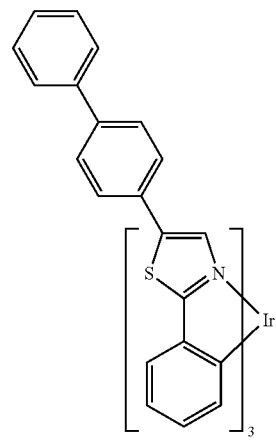
498
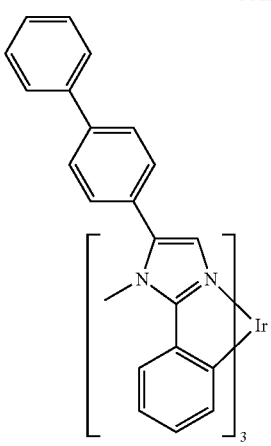 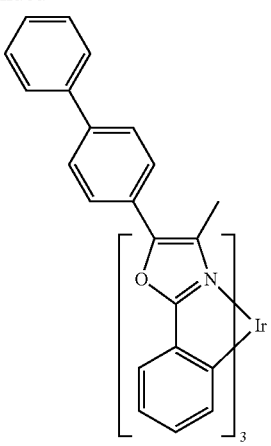
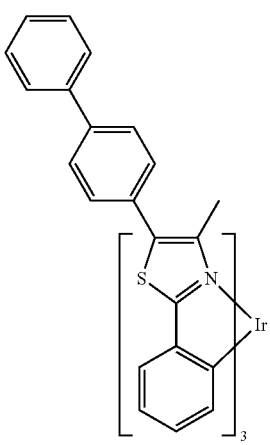 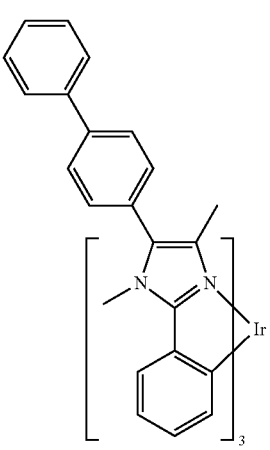
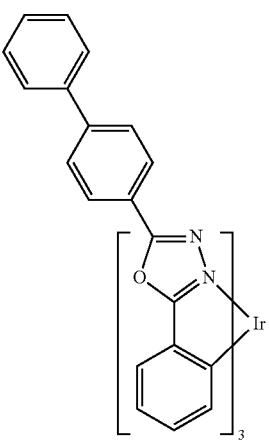 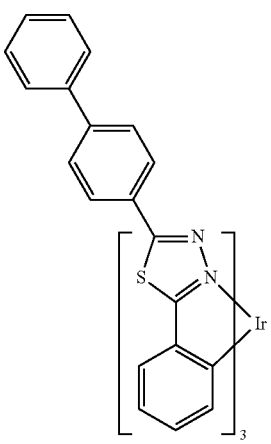

499
-continued
500
-continued
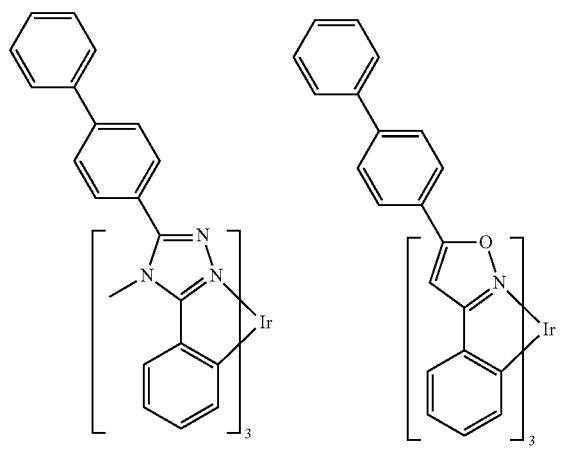
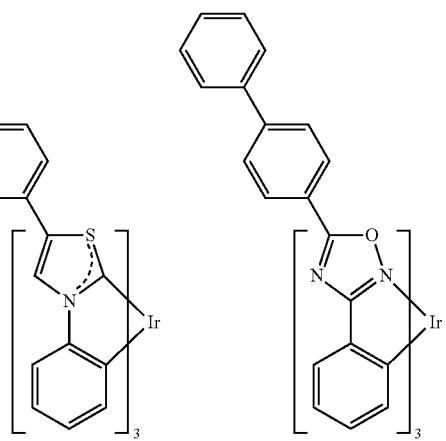
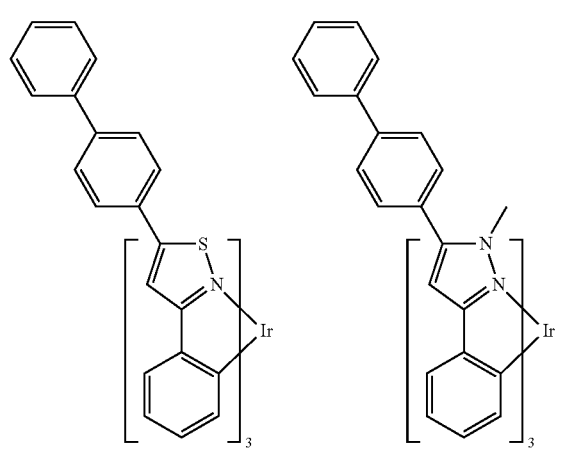
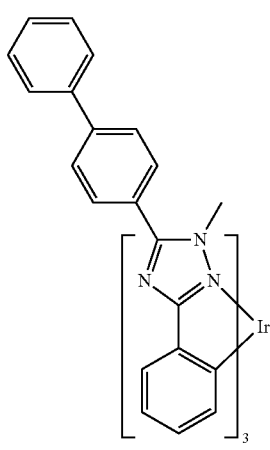
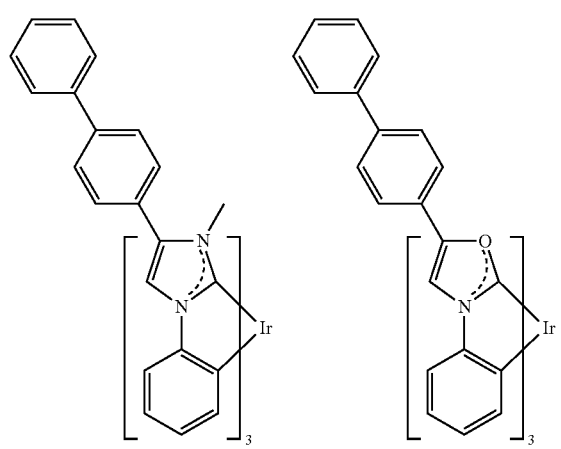
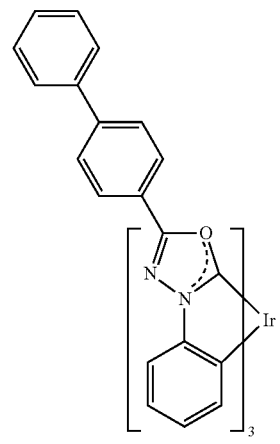

501
-continued
502
-continued
Structures Ir-2
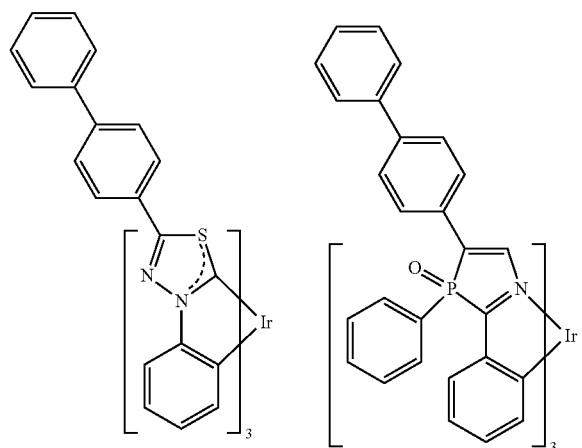
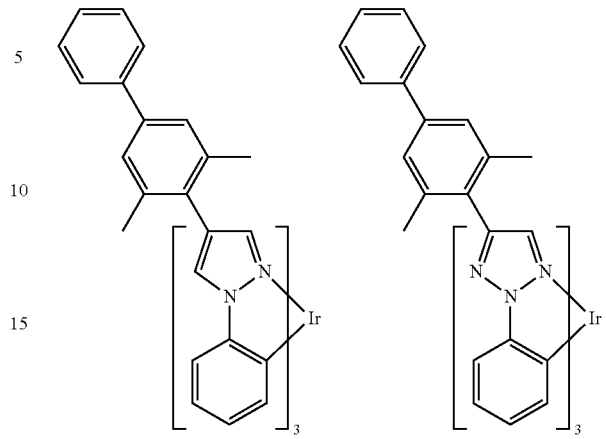
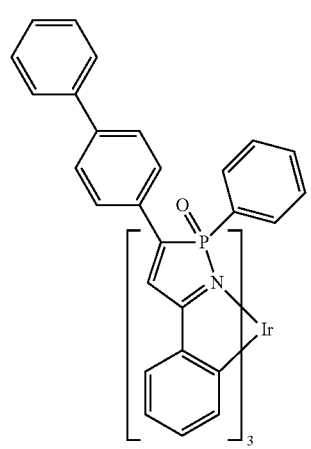
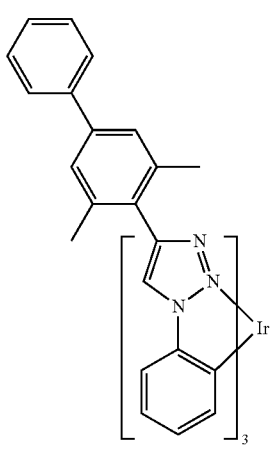
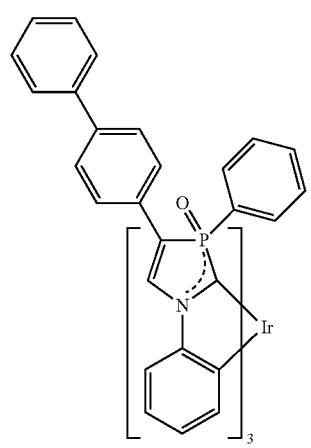
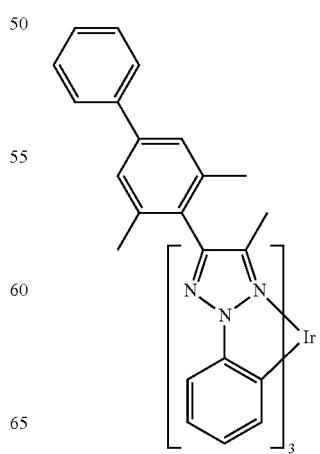

503
-continued
504
-continued
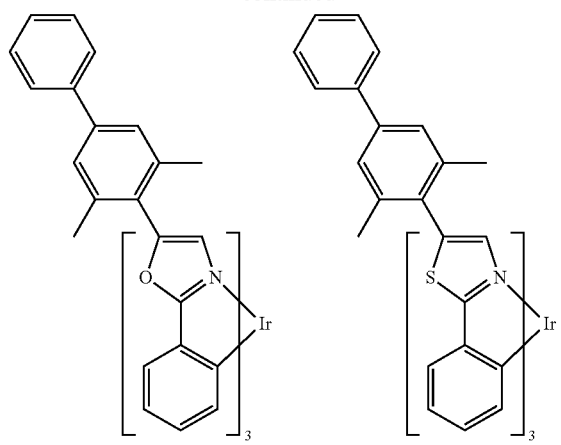
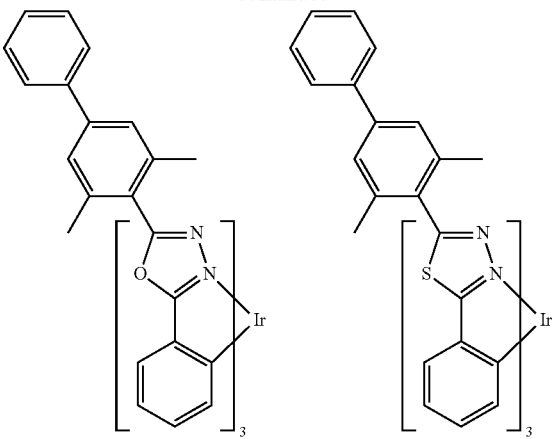
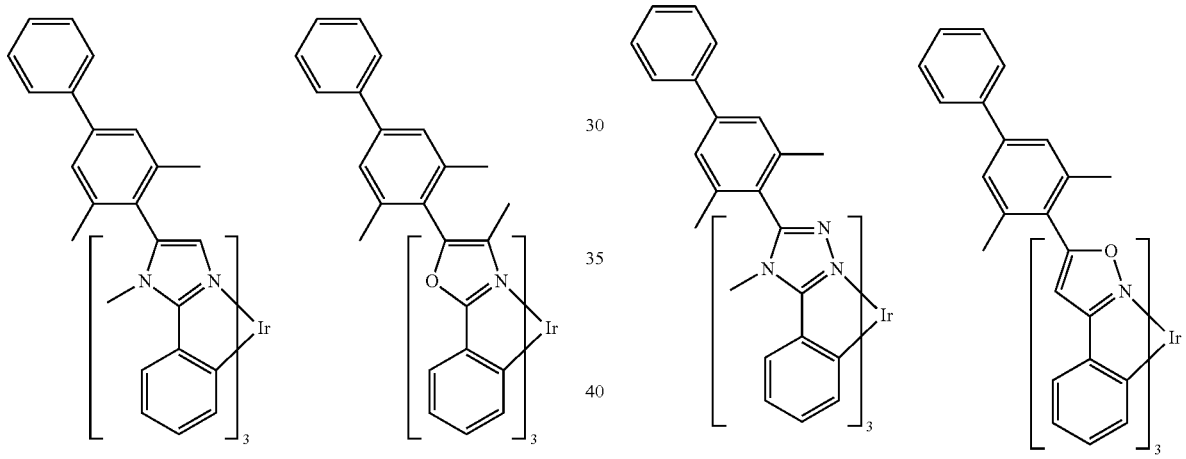
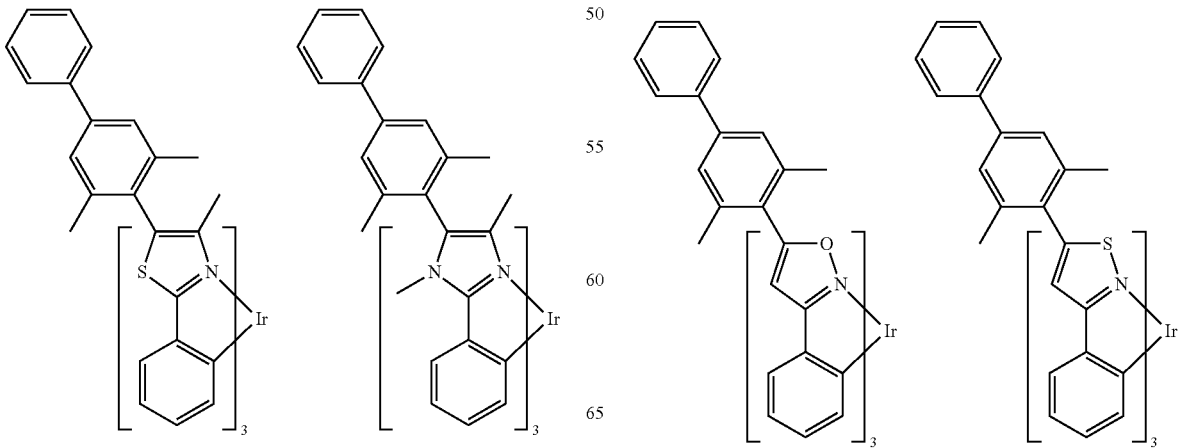

505
-continued
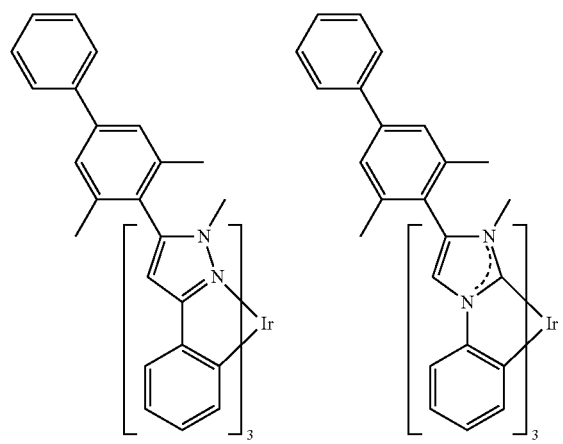
506
-continued
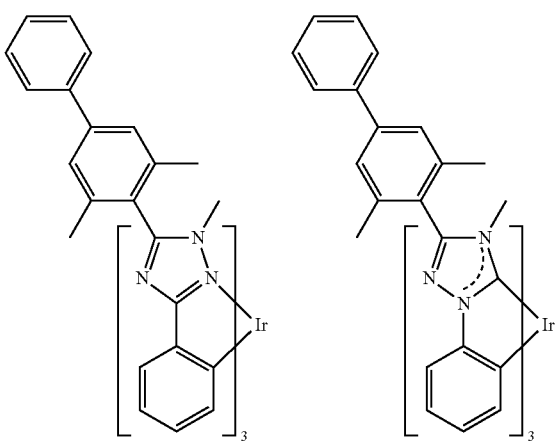
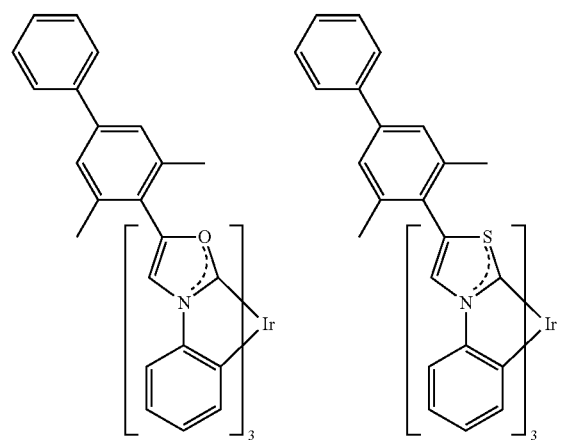
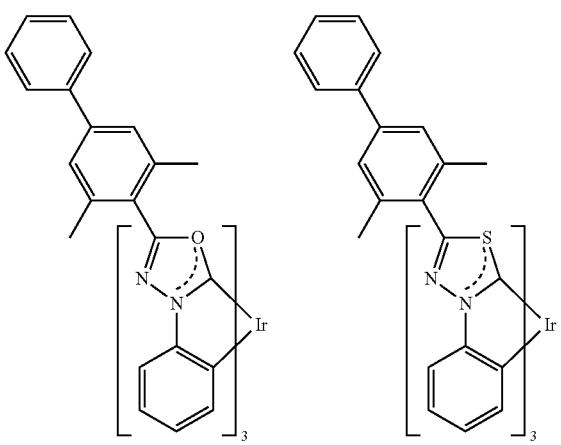
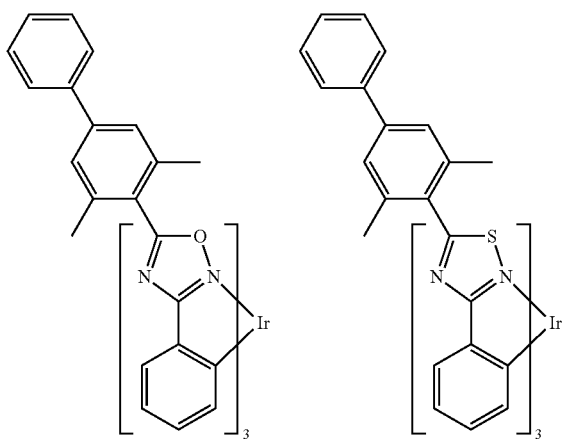
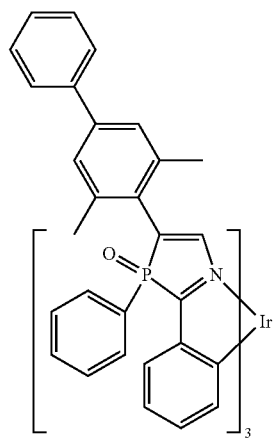

507
-continued
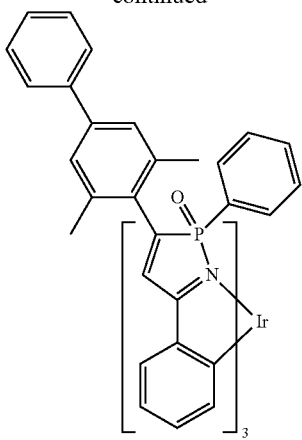
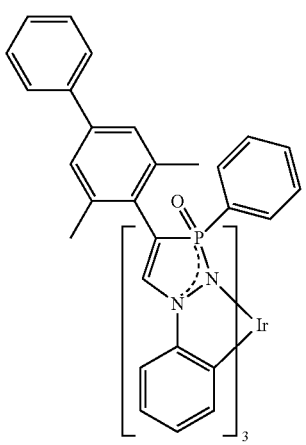
508
-continued
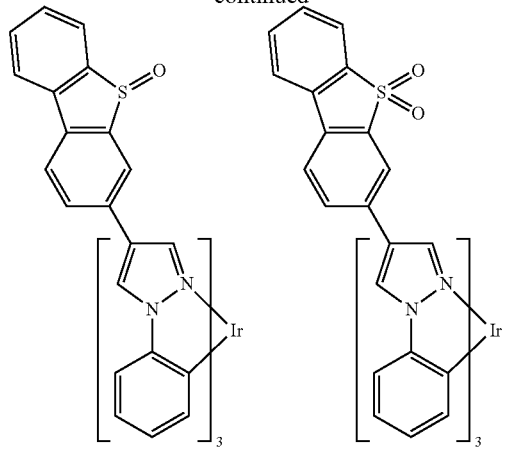
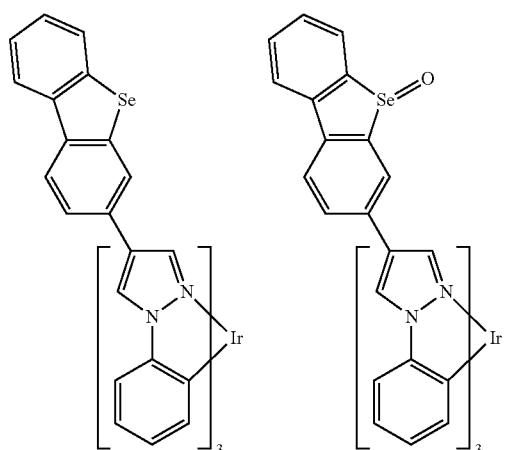
Structures Ir-3
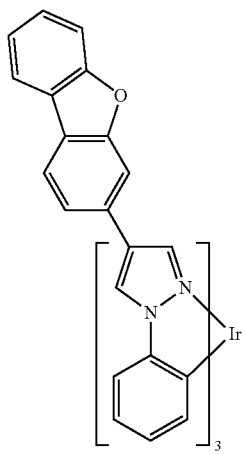 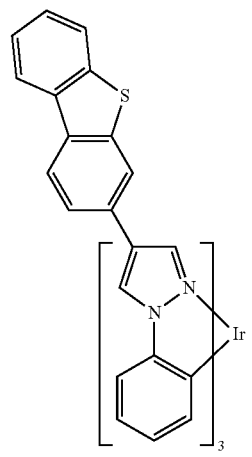 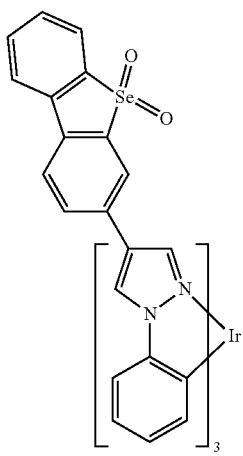 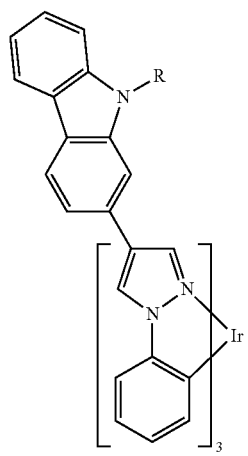

509
-continued
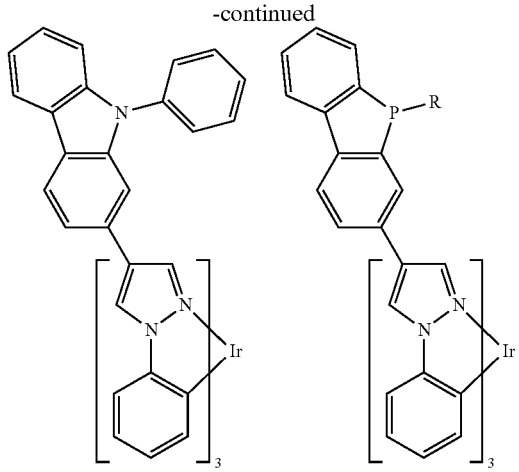
510
-continued
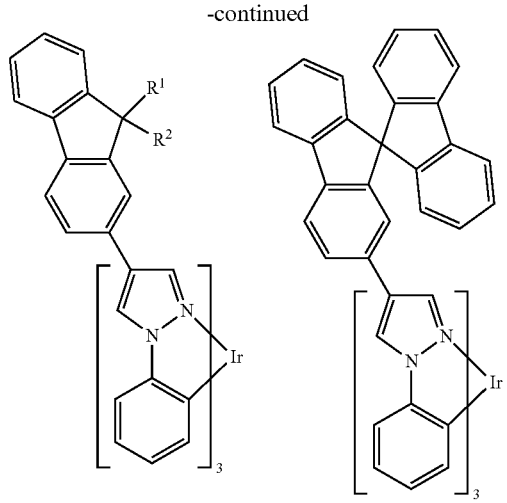
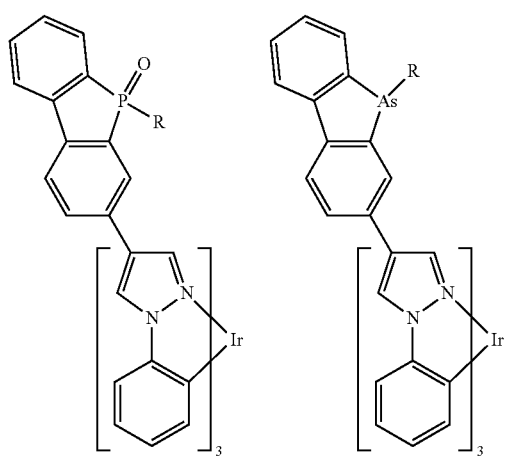
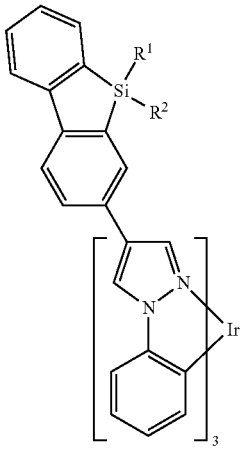
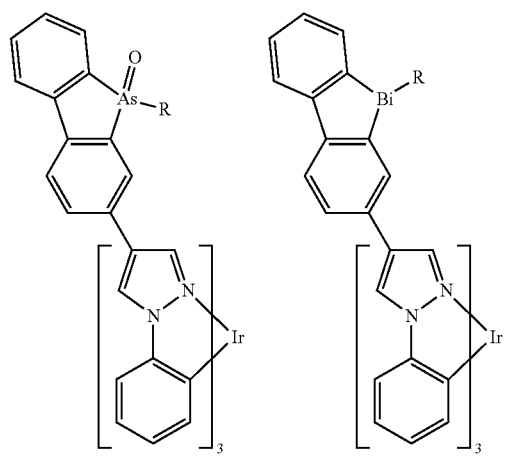
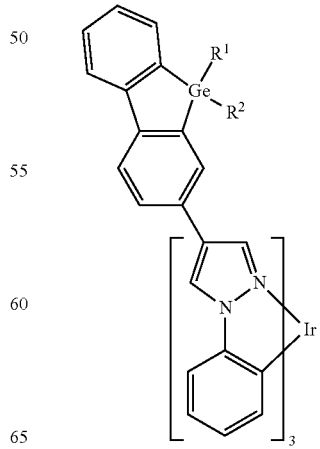

511
-continued
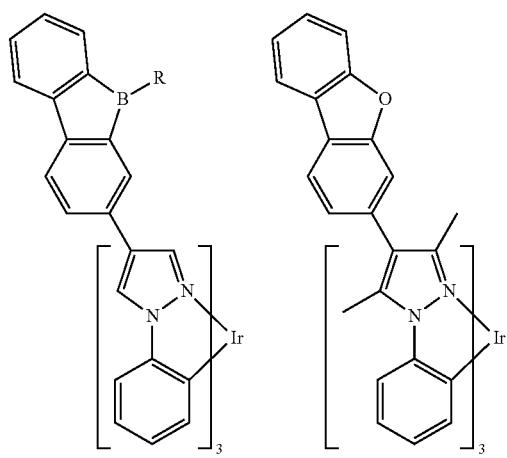
512
-continued
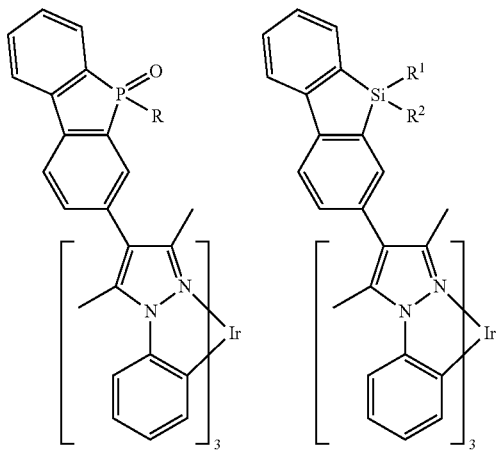
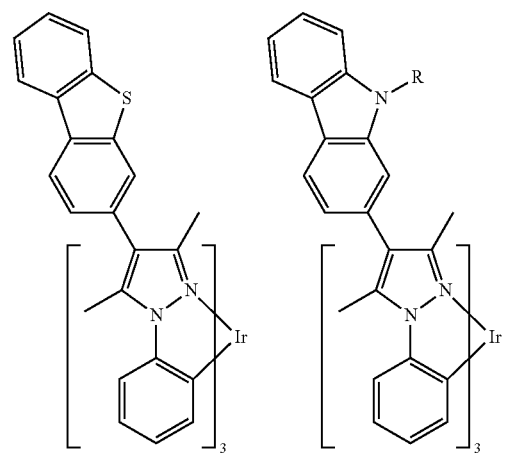
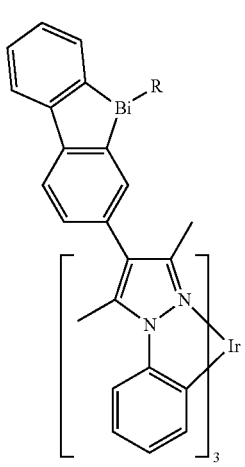 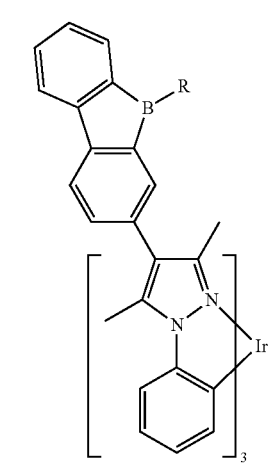
Structures Ir-4
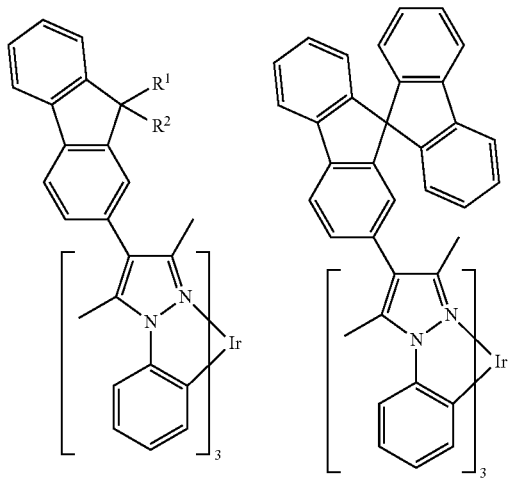
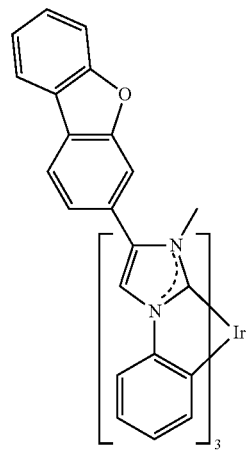 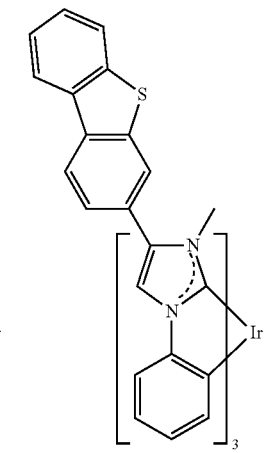

513
-continued
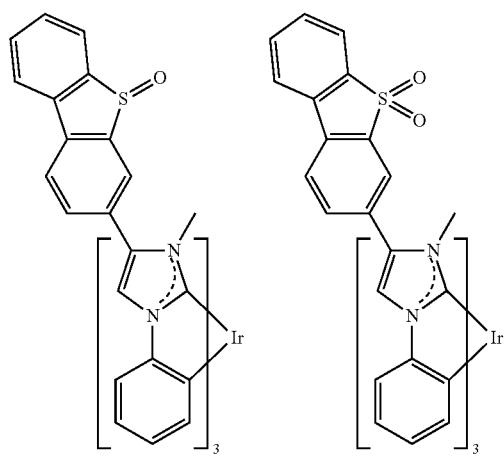
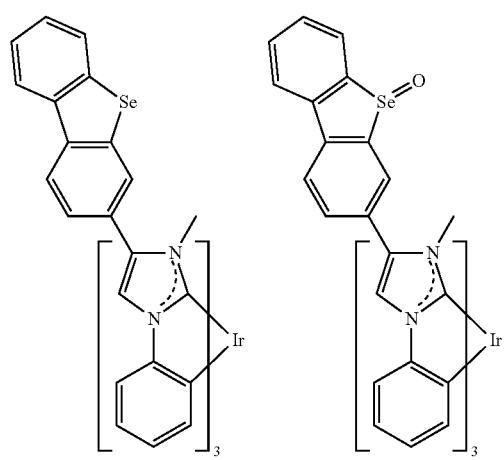
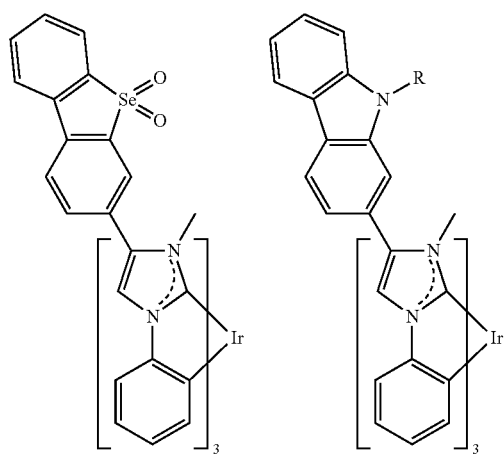
514
-continued
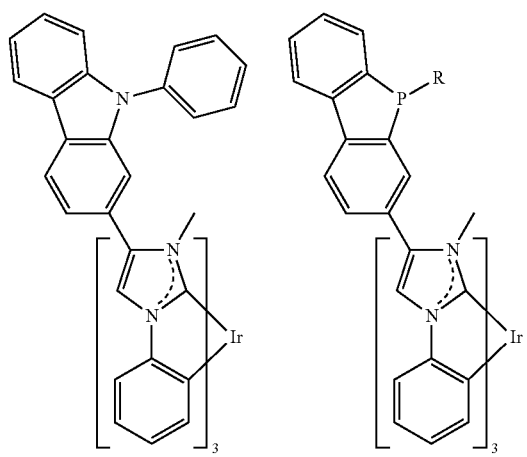
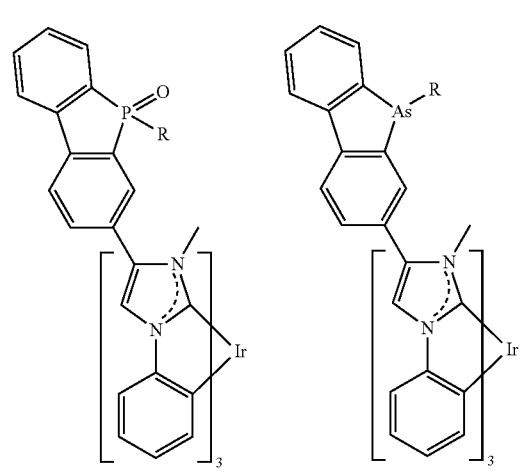
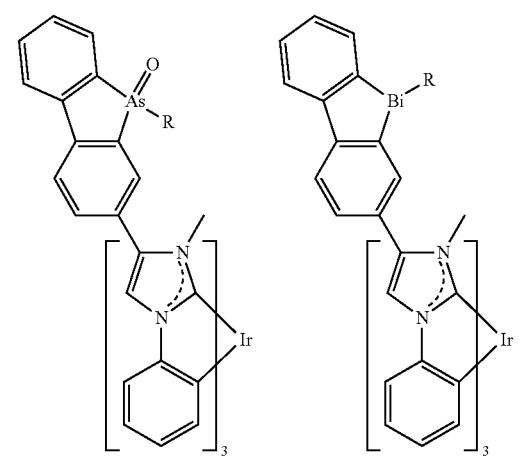

515
-continued
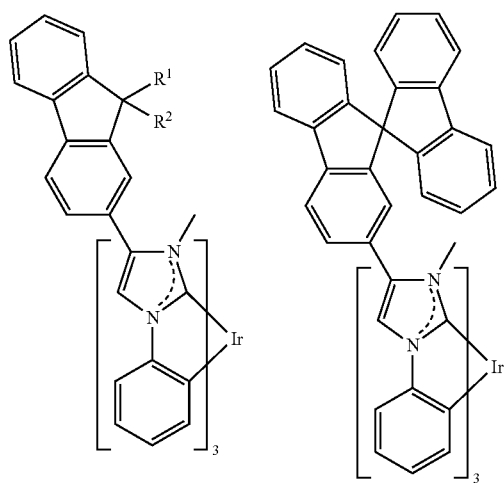
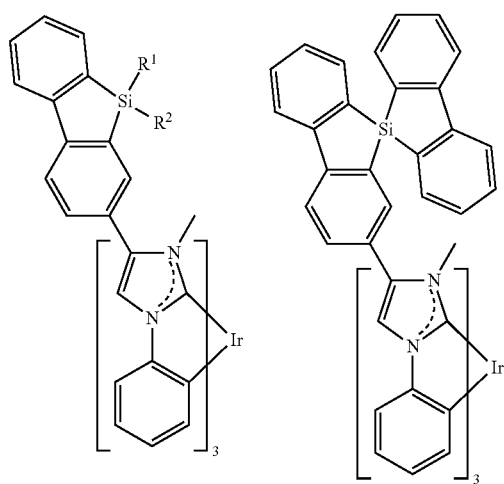
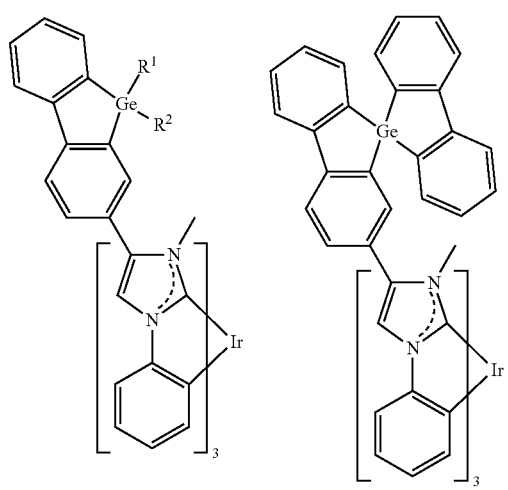
516
-continued
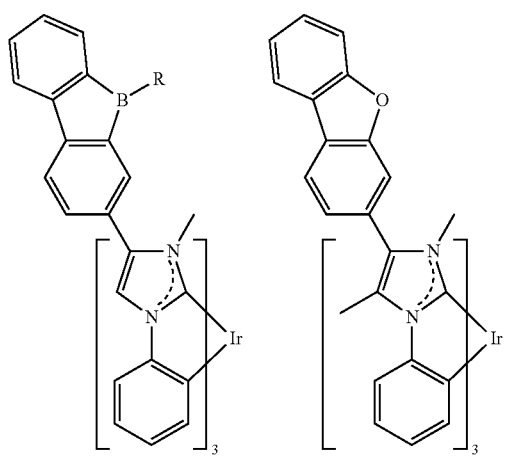
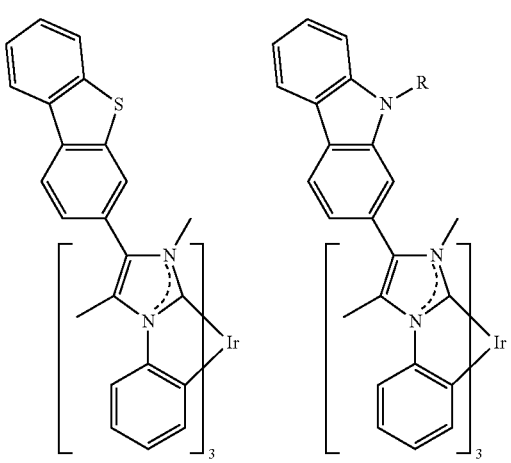
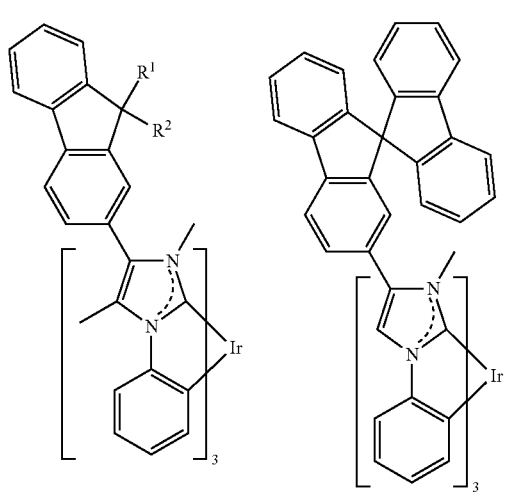

517
-continued
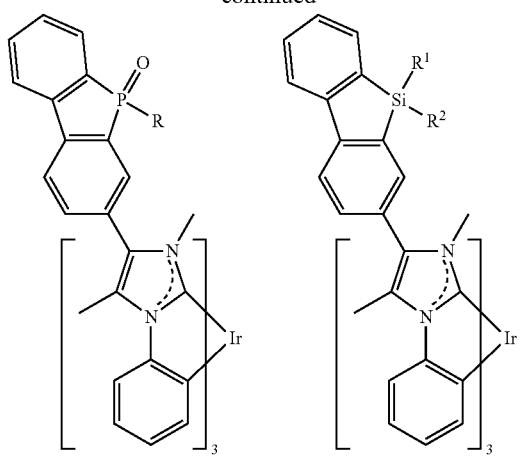
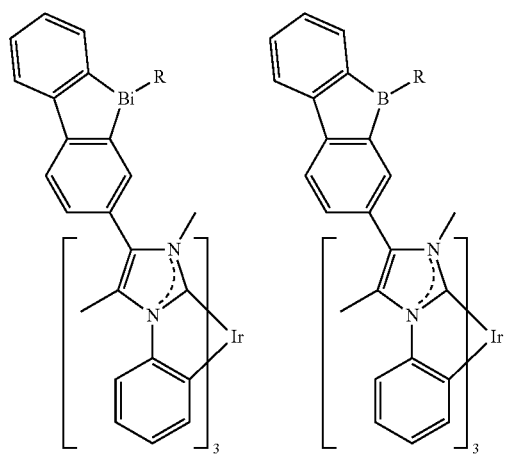
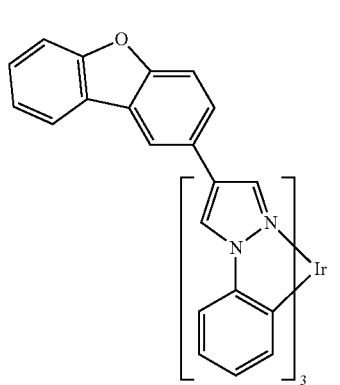
518
-continued
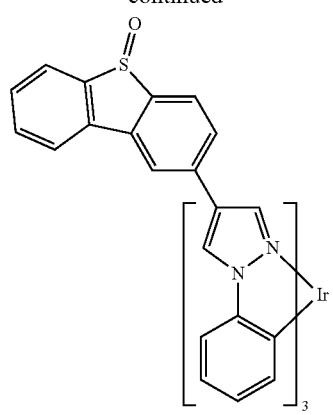
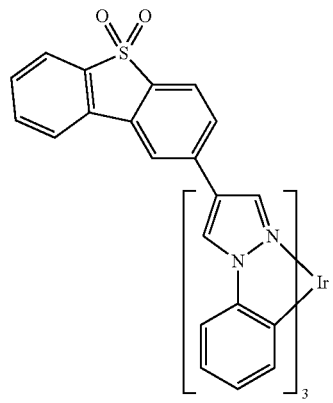
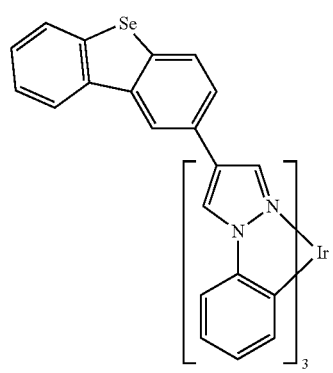
Structures Ir-5
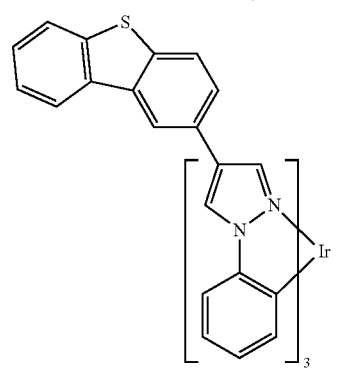
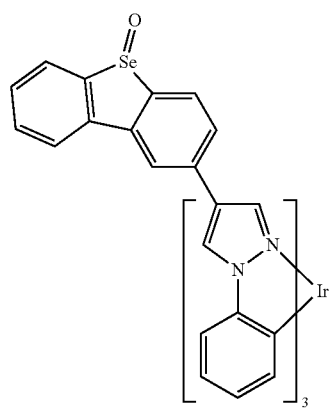

519
-continued

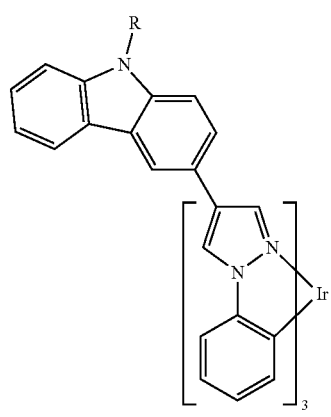
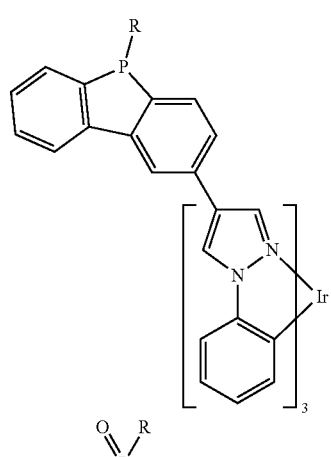
520
-continued
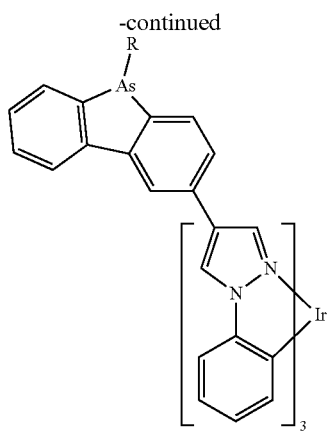
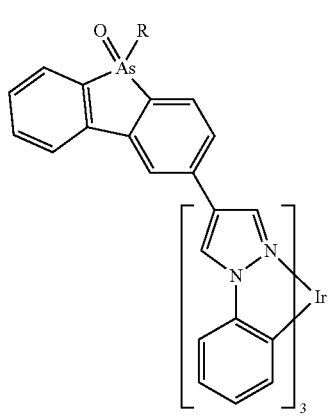
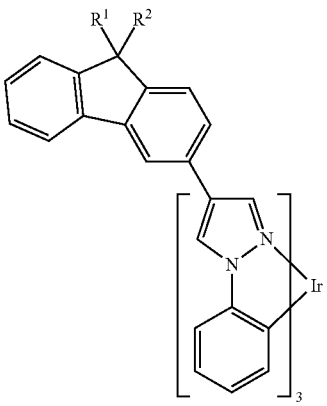
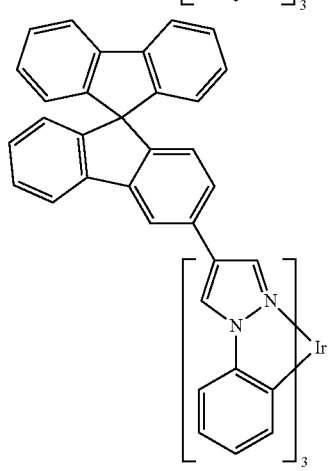

521
-continued
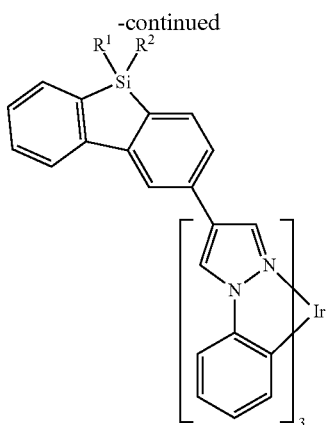
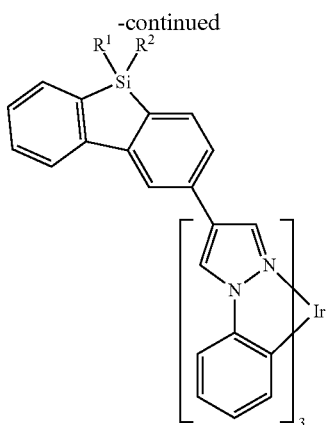
522
-continued
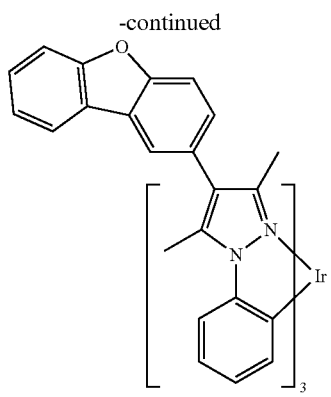
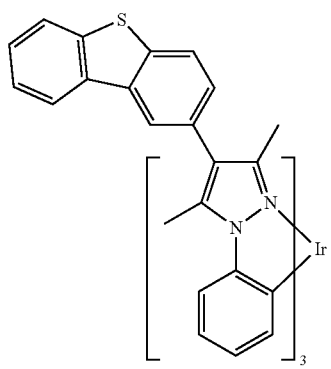
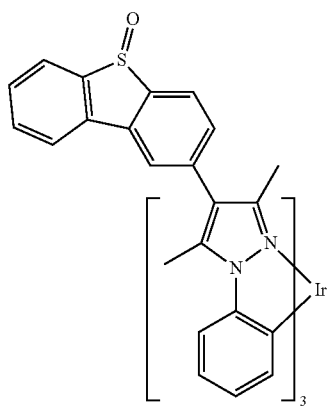
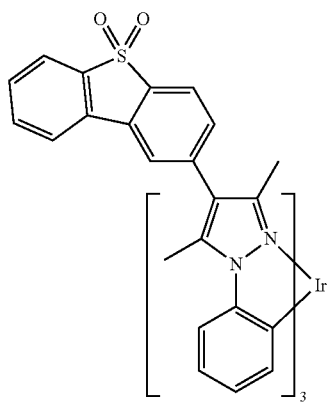

523
-continued
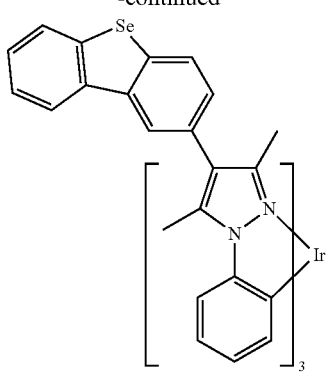
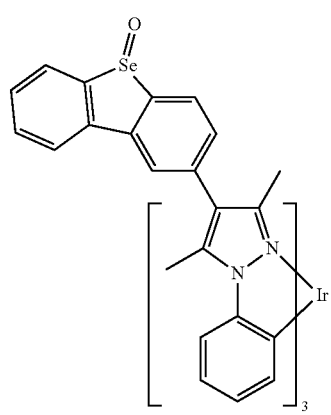
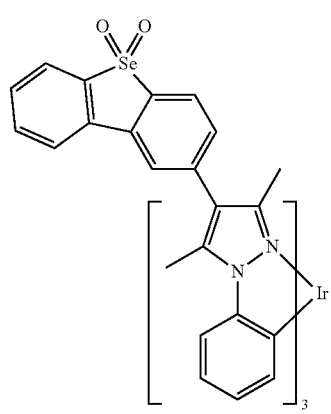
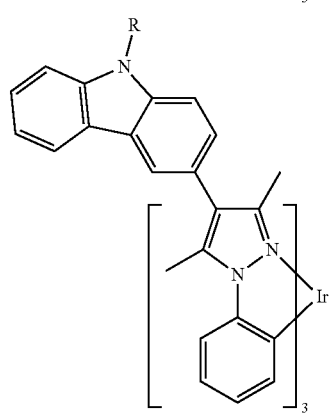
524
-continued
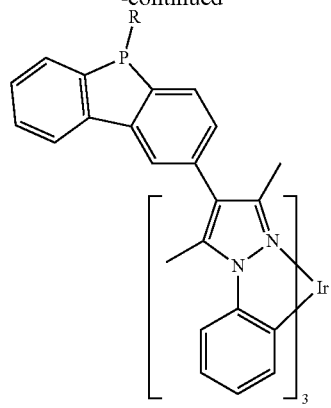
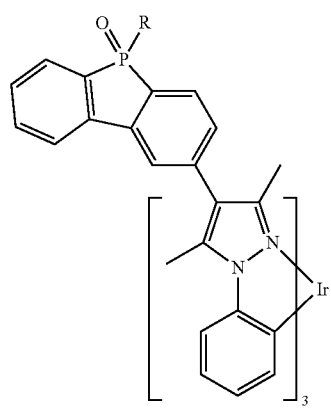
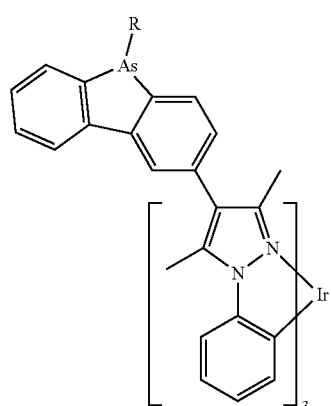
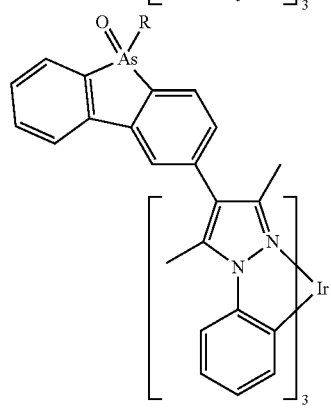

525
-continued
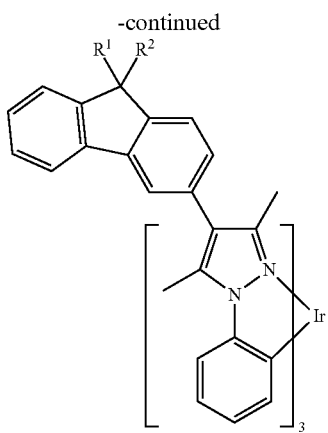
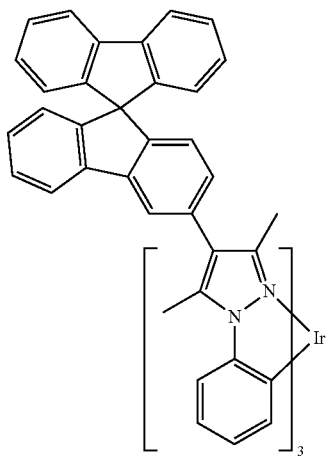
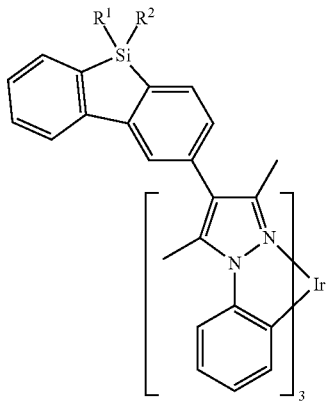
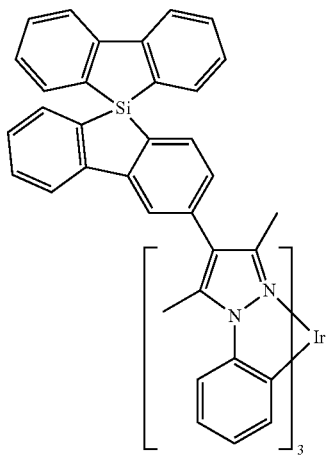
526
-continued
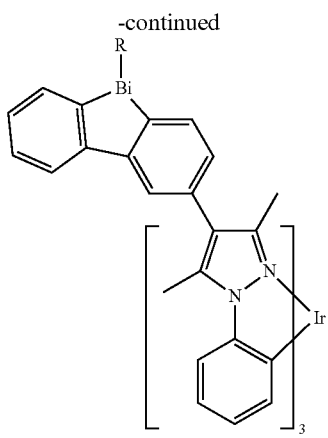
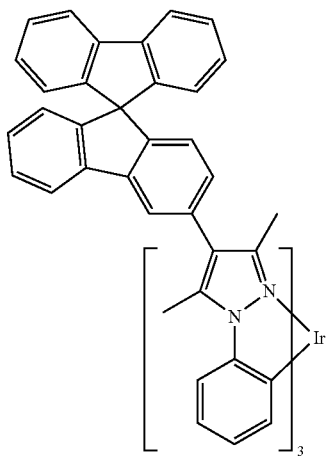
Structures Ir-6
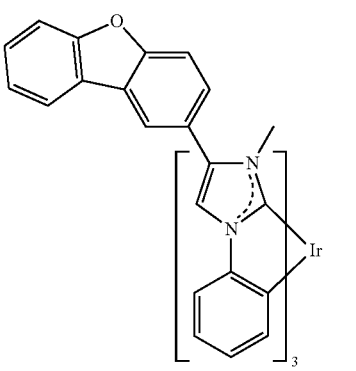
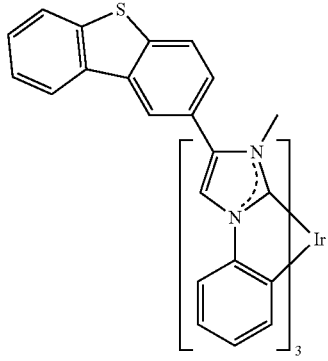

527
-continued
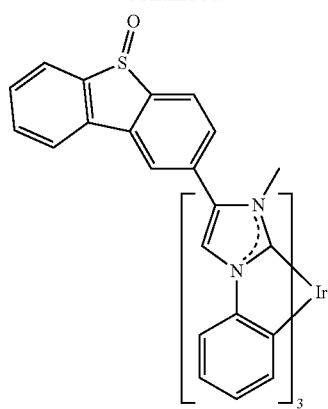
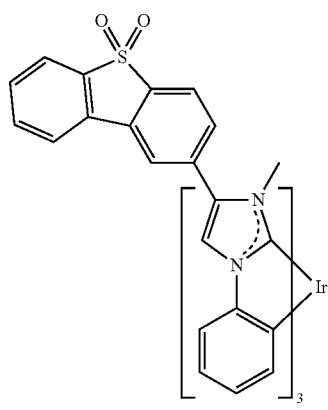
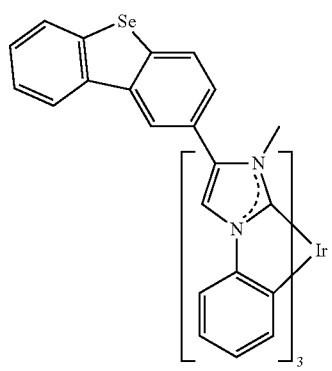
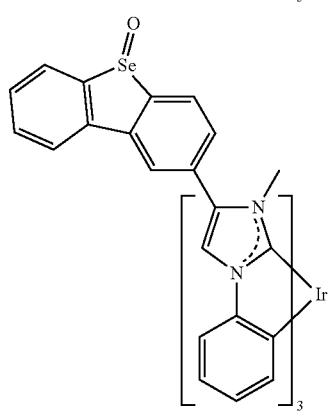
528
-continued
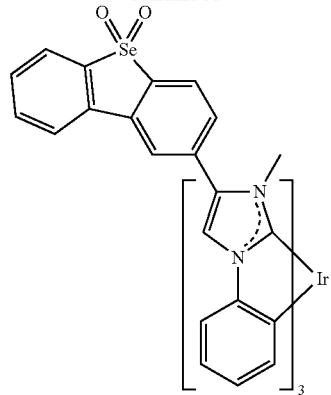
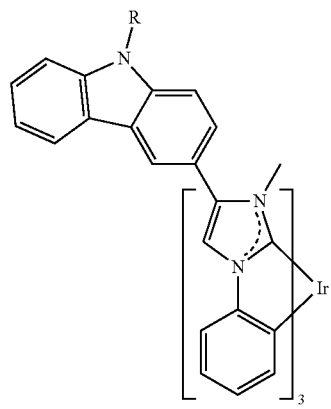
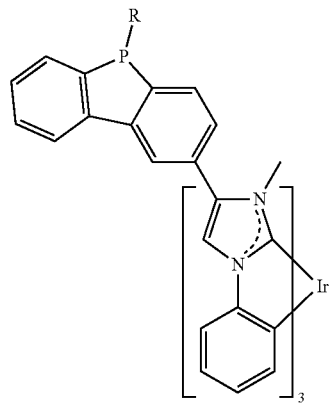
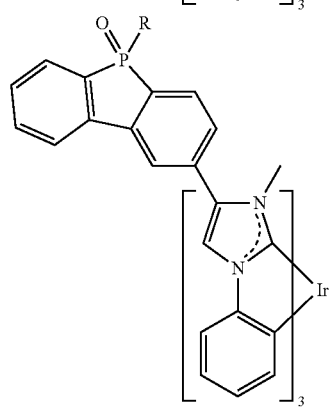

529
-continued
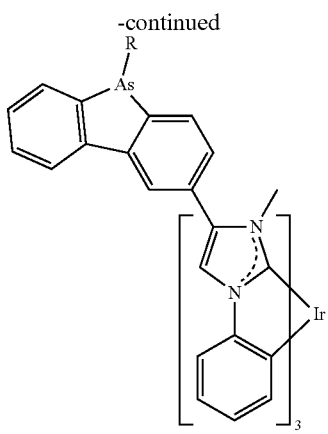
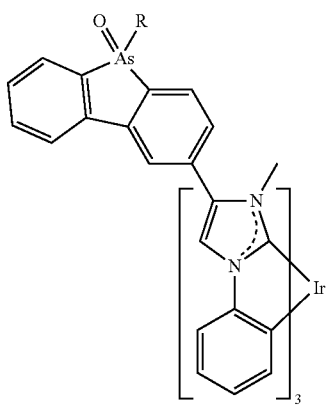
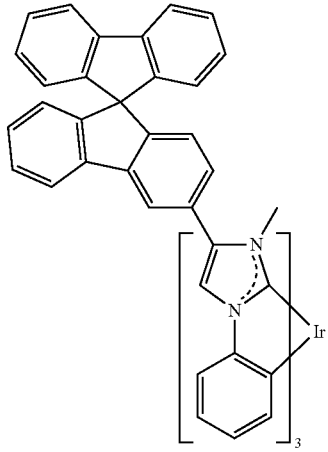
530
-continued
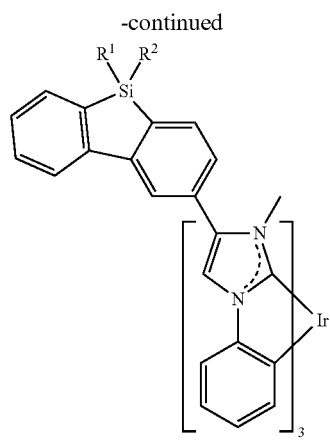
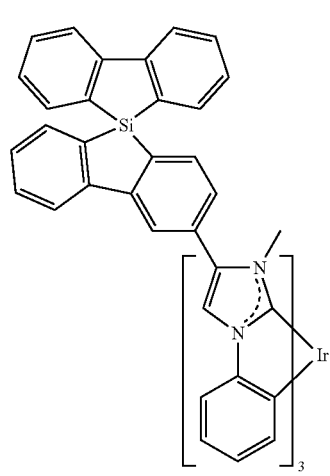
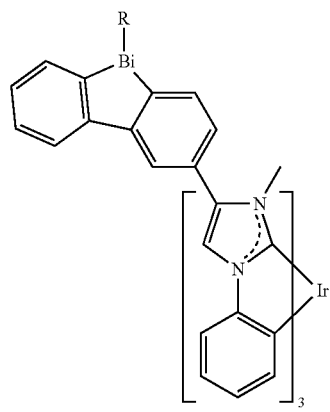
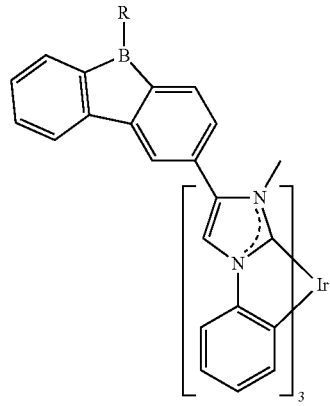

| 531 | 532 |
|---|---|
| -continued | -continued |
| 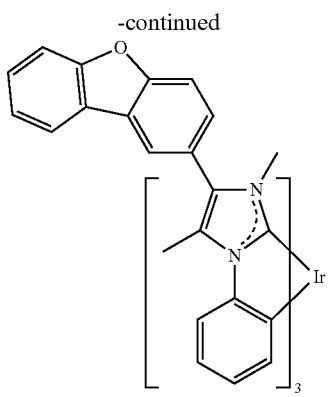 | 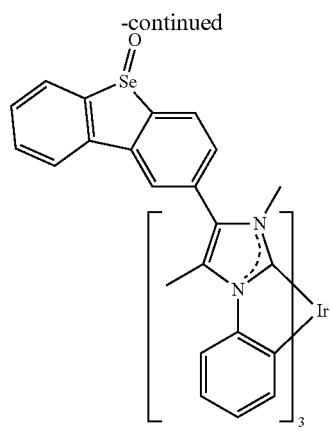 |
| 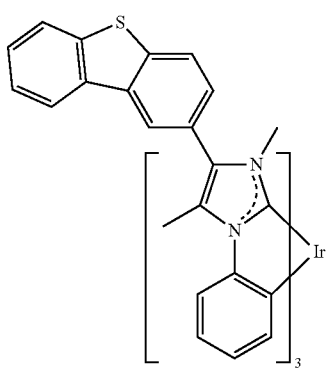 | 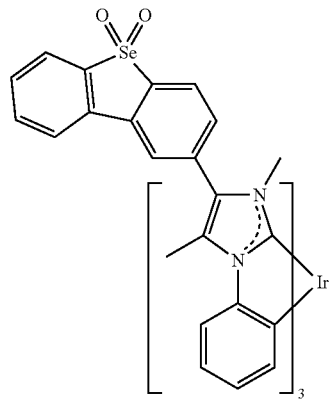 |
| 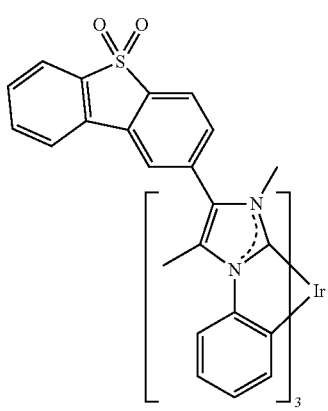 | 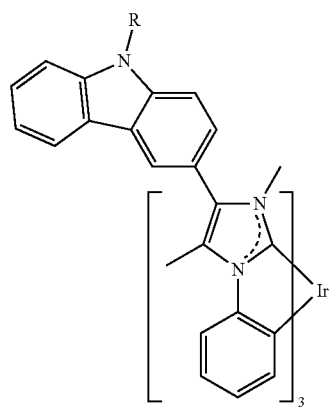 |
| 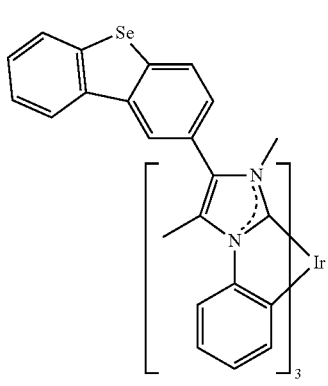 | 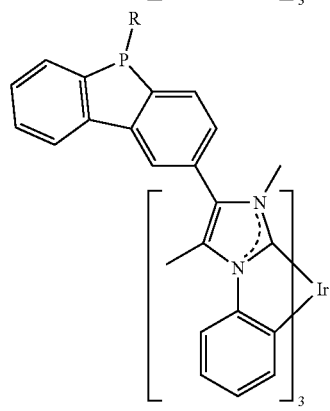 |

533                                   534
-continued                            -continued
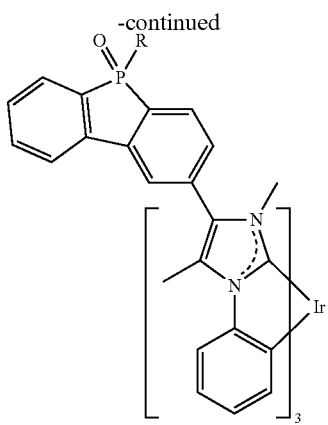
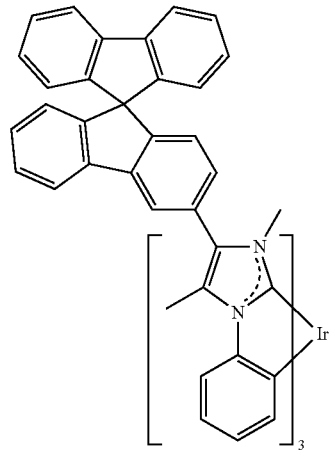
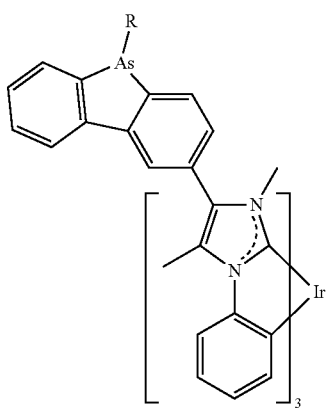
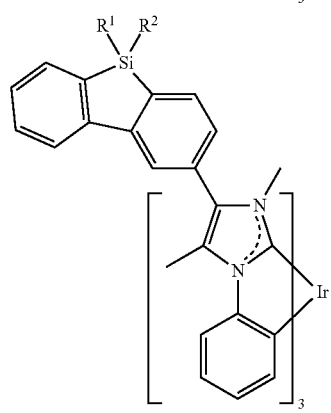
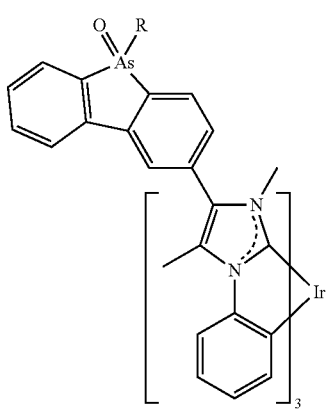
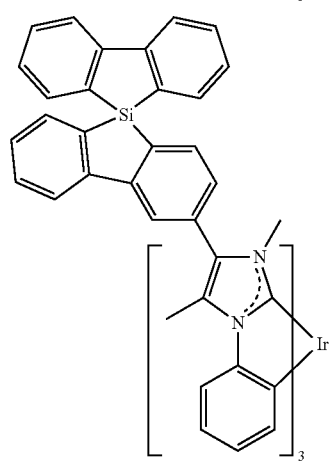
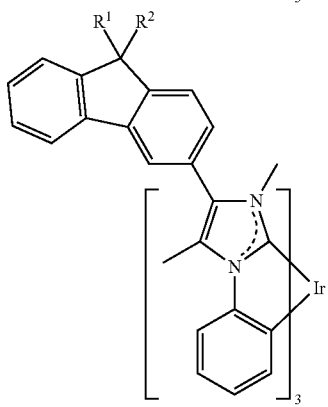
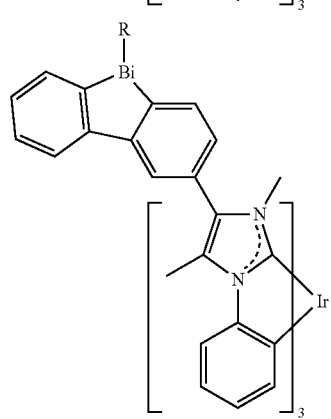

535
-continued
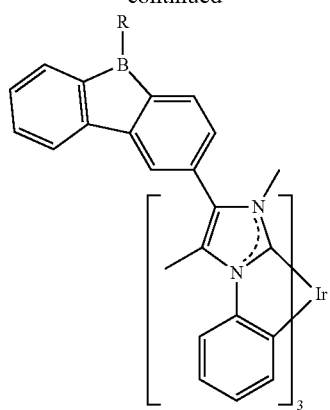
536
-continued
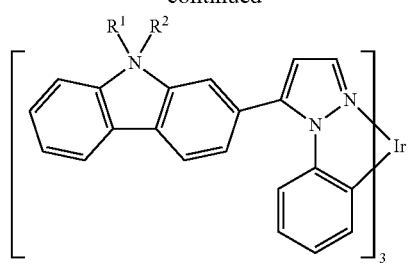
Structures Ir-7
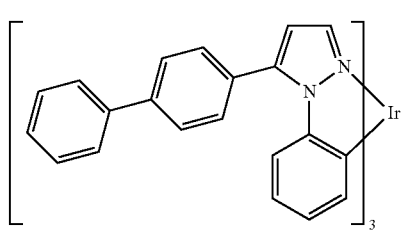
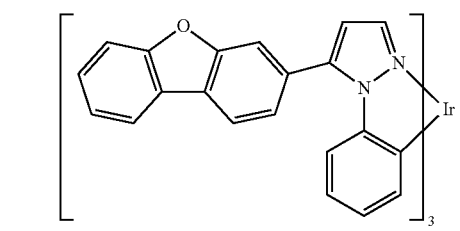
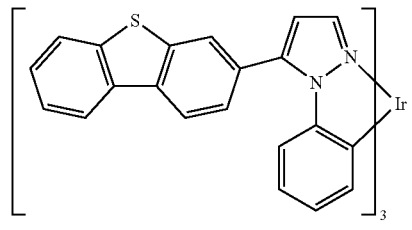
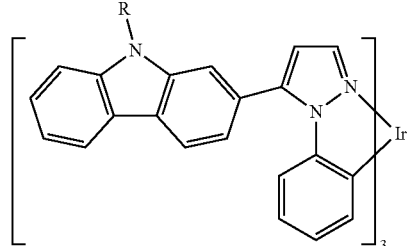
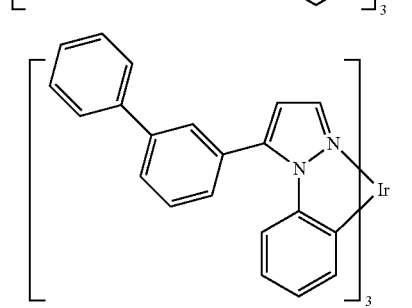
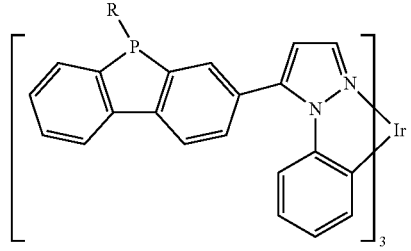
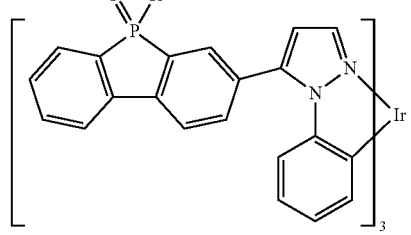
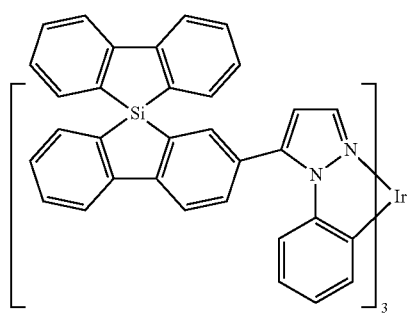

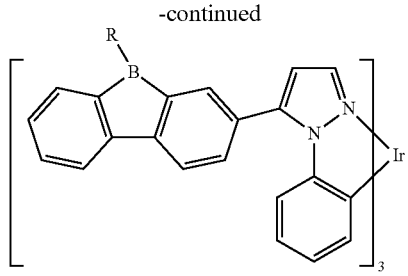
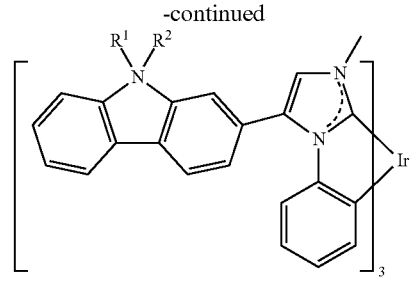
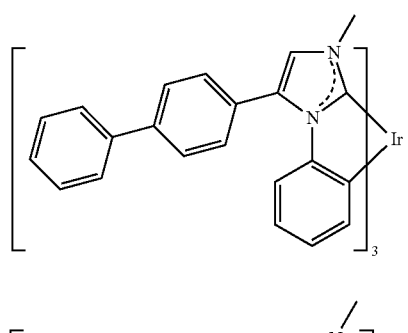
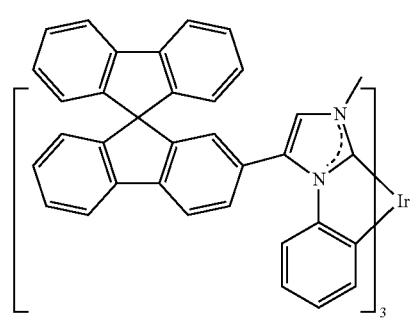
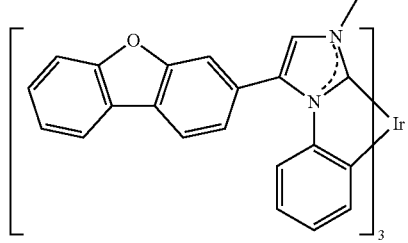
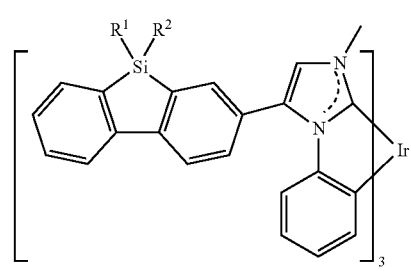
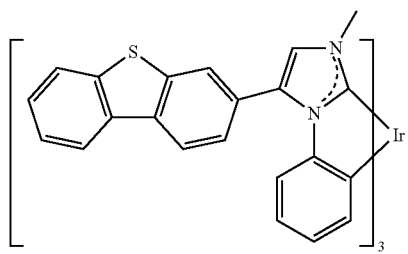
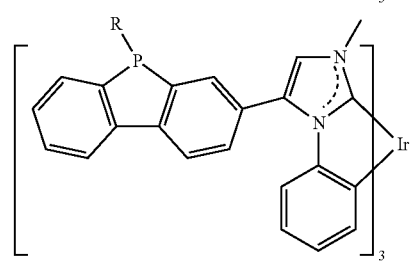
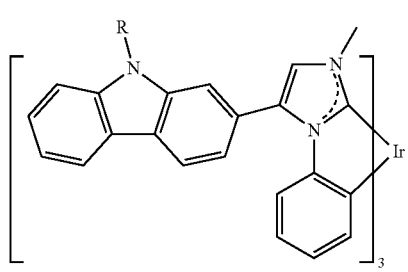
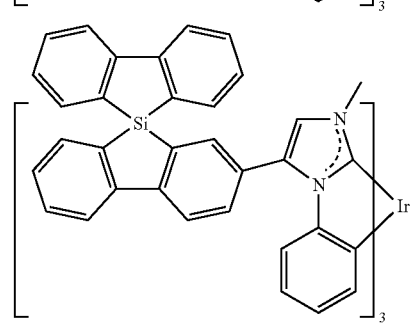

-continued
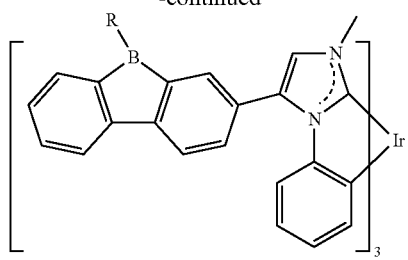
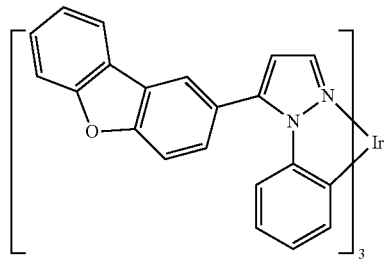
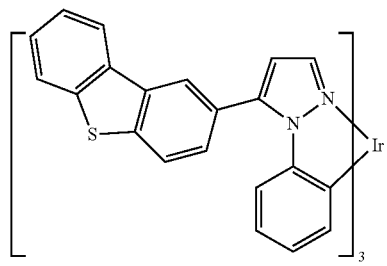
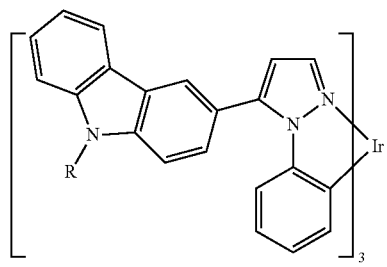
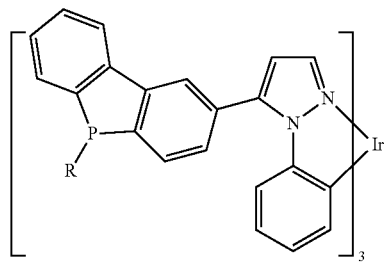
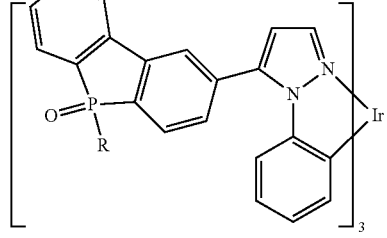
-continued
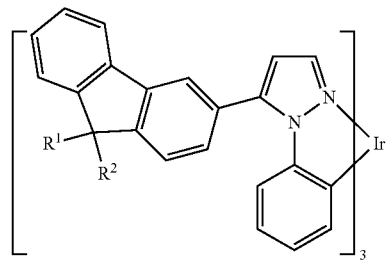
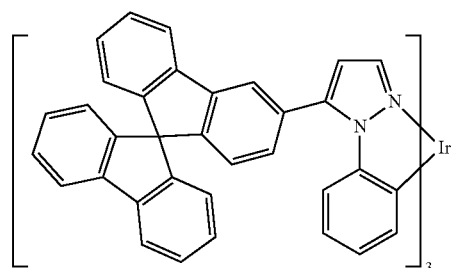
Structures Ir-8
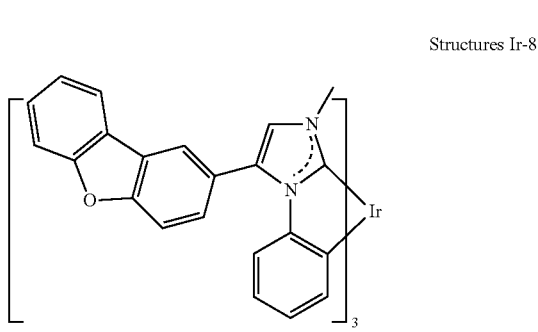
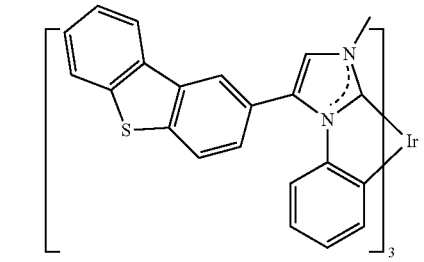
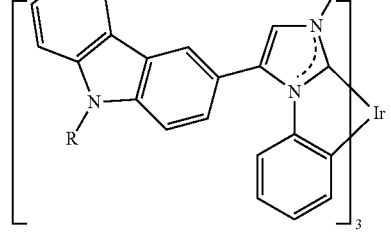
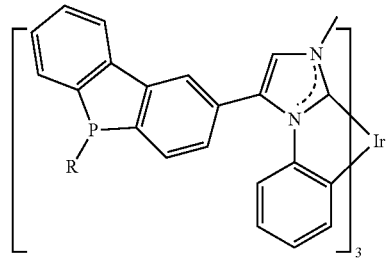

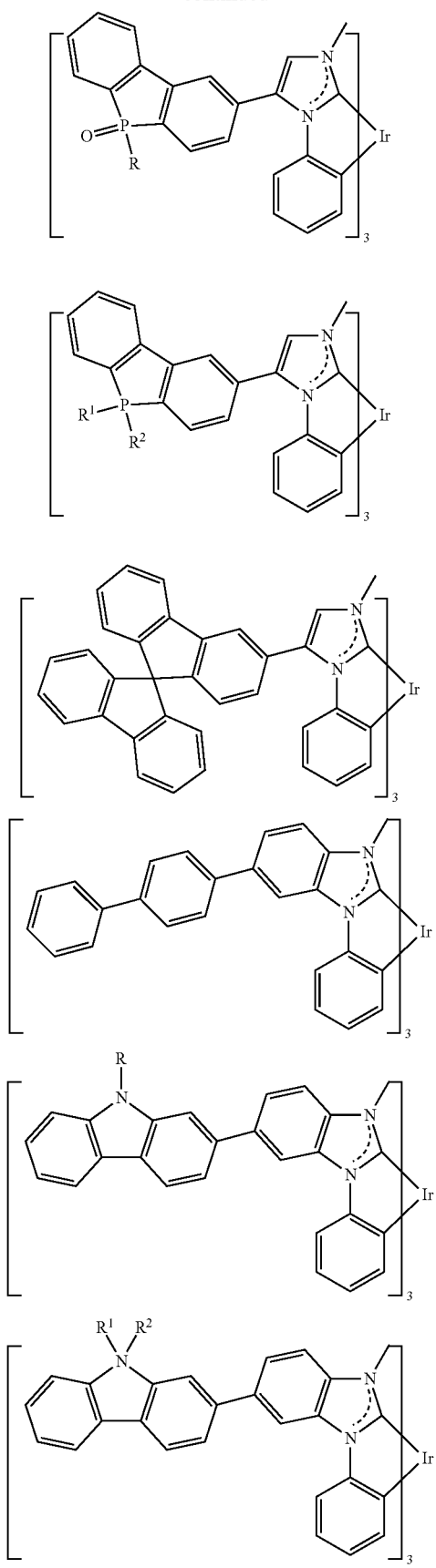
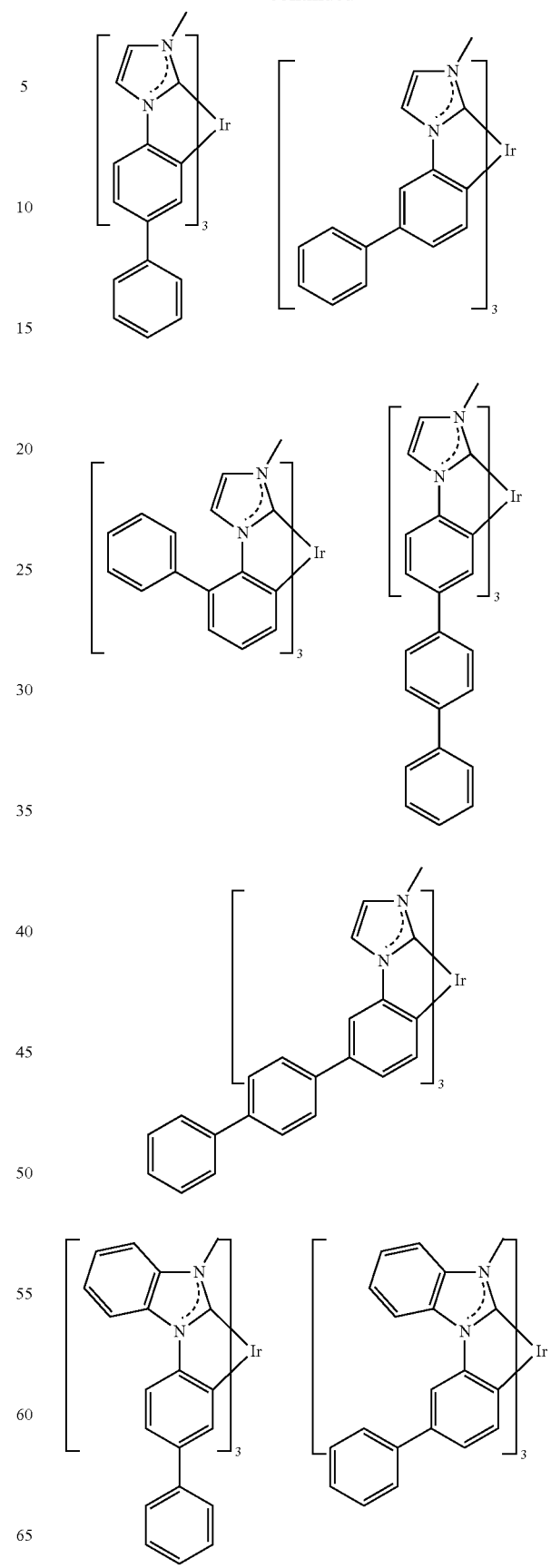

543
-continued
544
-continued
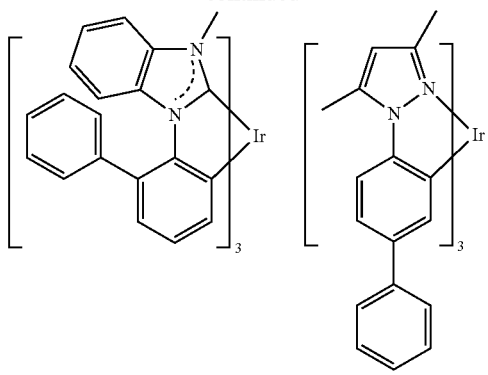
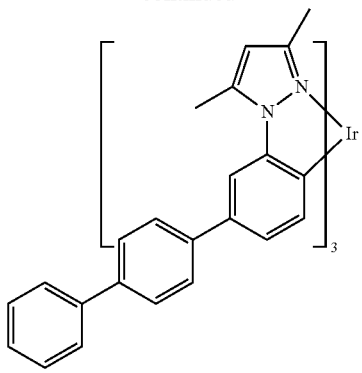
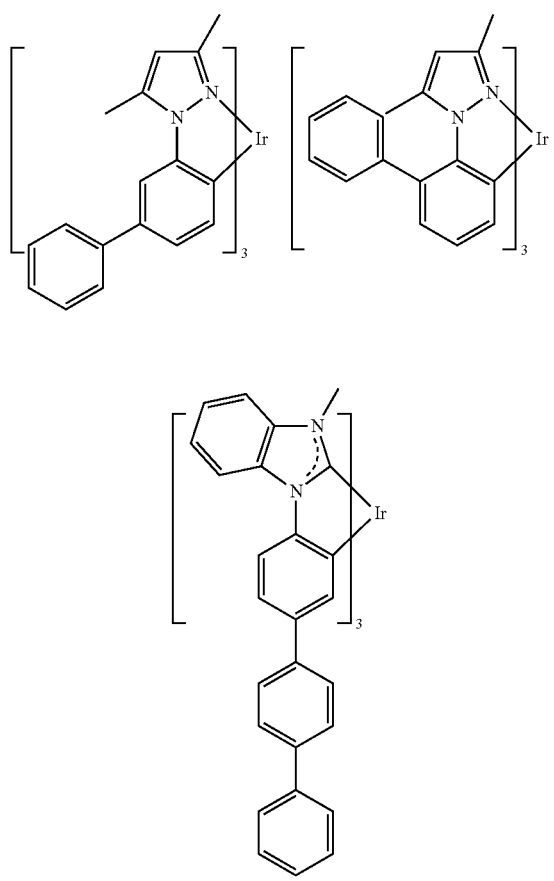
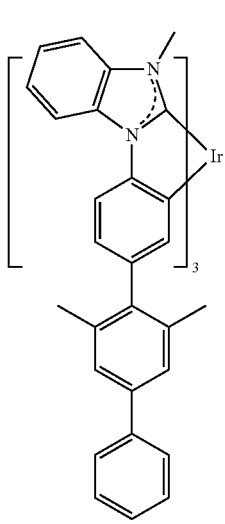
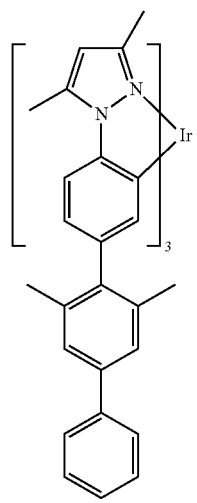
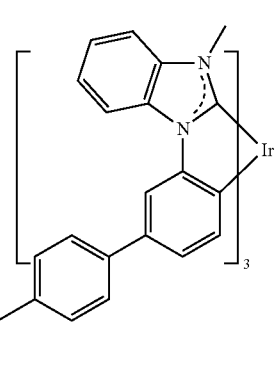
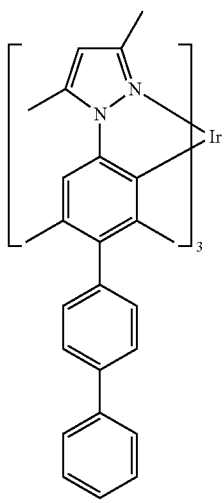
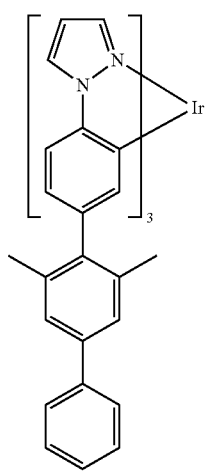

545
-continued
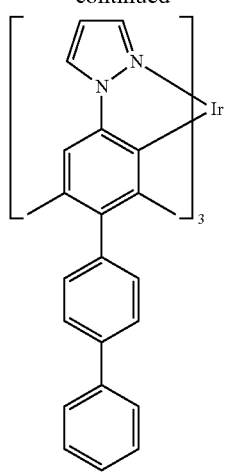
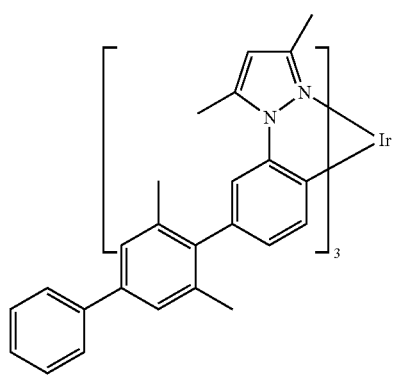
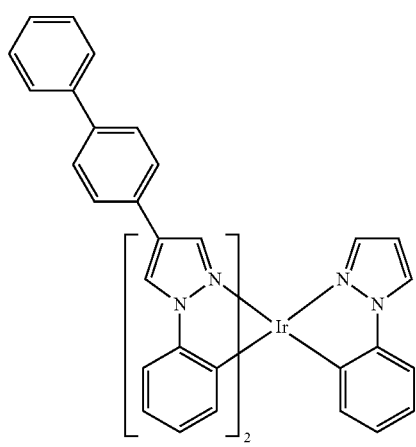
546
-continued
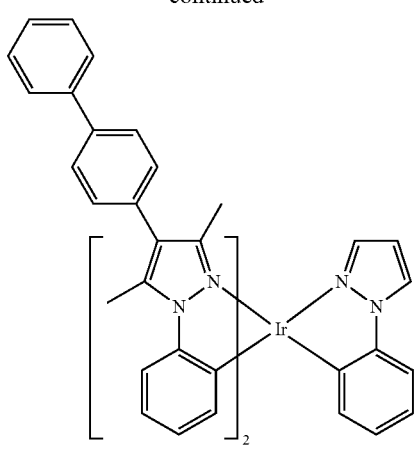
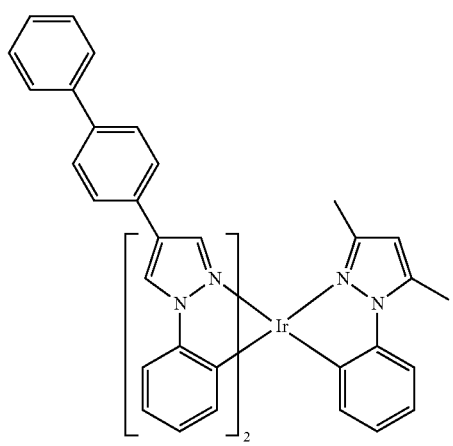
Structures Ir-9
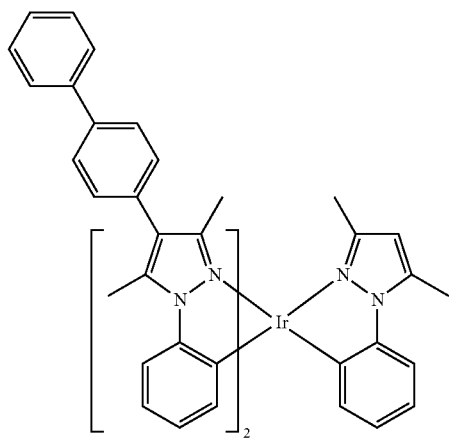

547
-continued
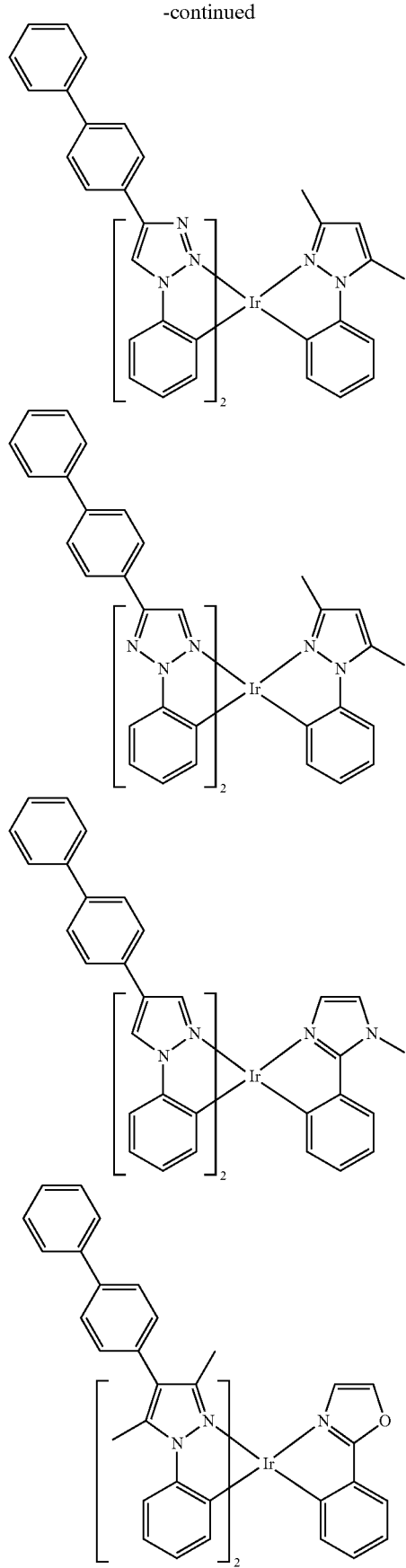
548
-continued
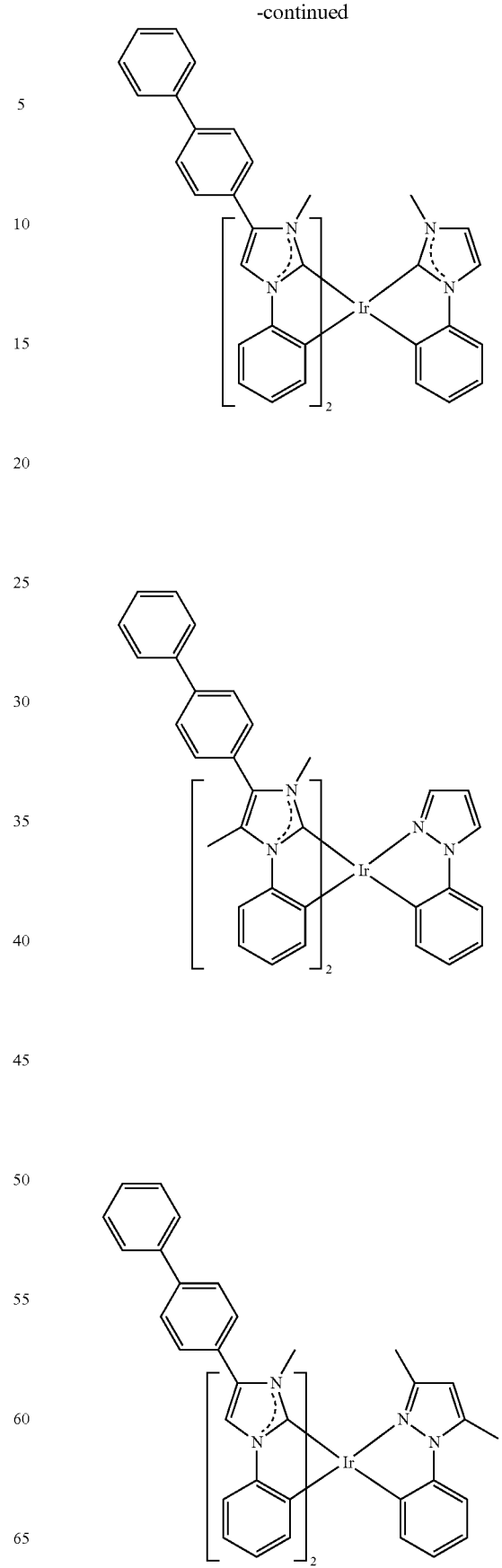

549
-continued
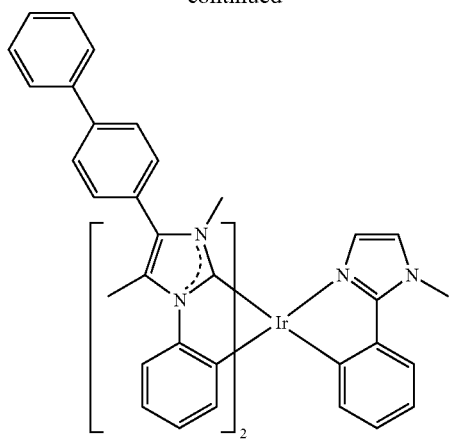
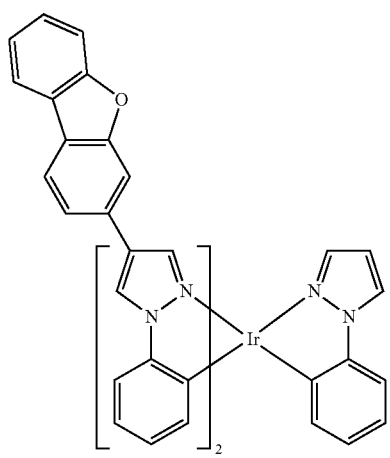
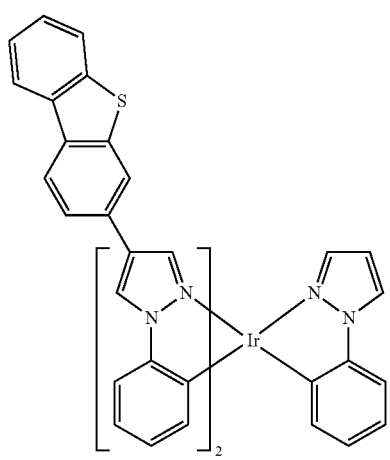
550
-continued
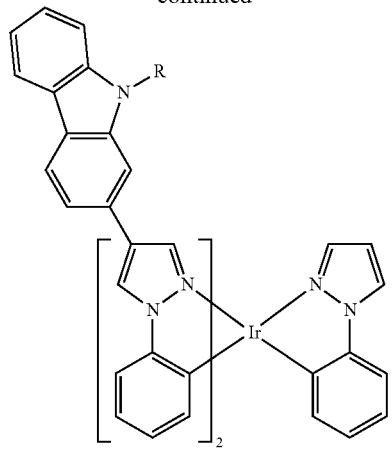
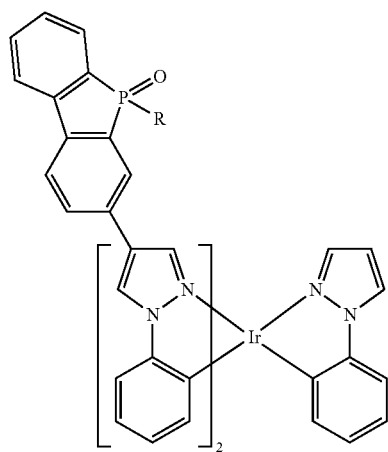
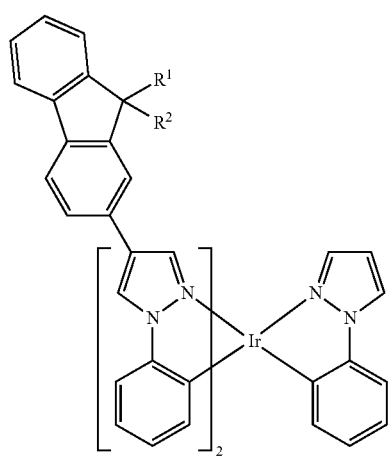

551
-continued
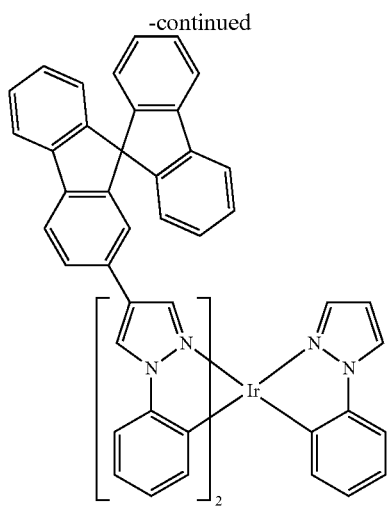
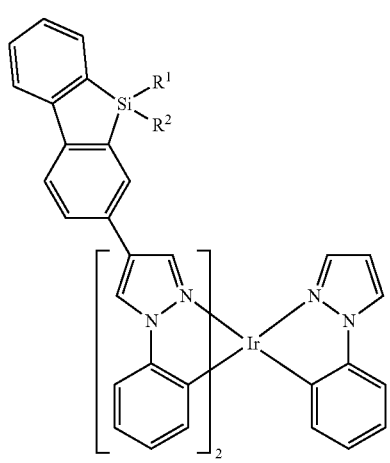
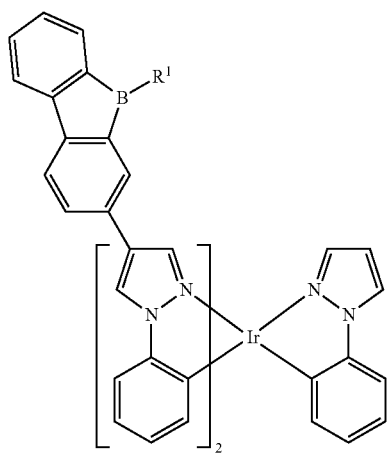
552
-continued
Structures Ir-10
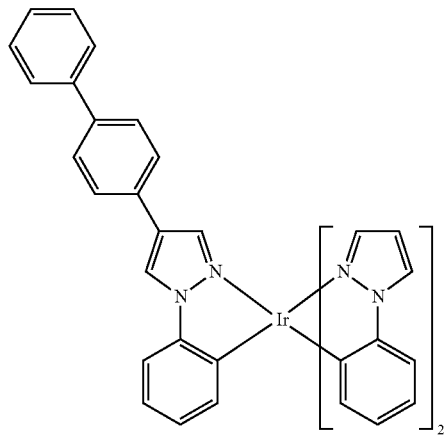
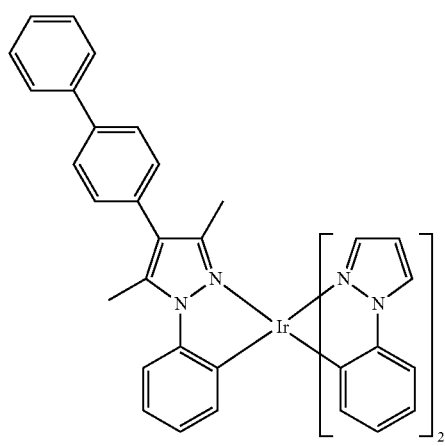
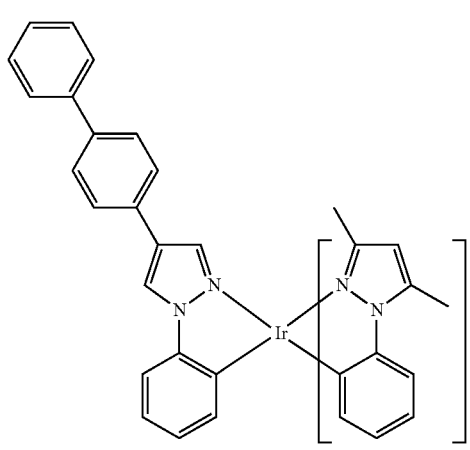

553
-continued
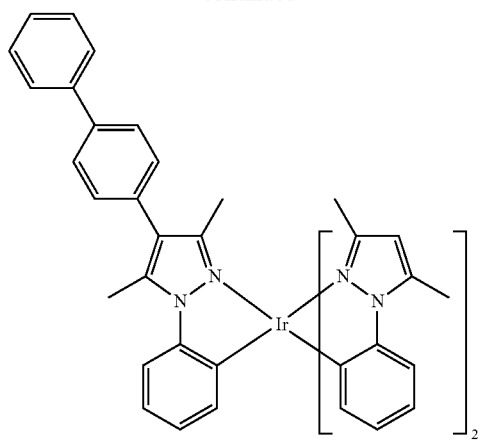
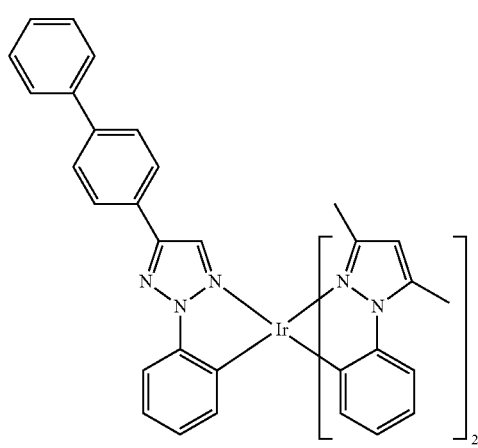
554
-continued
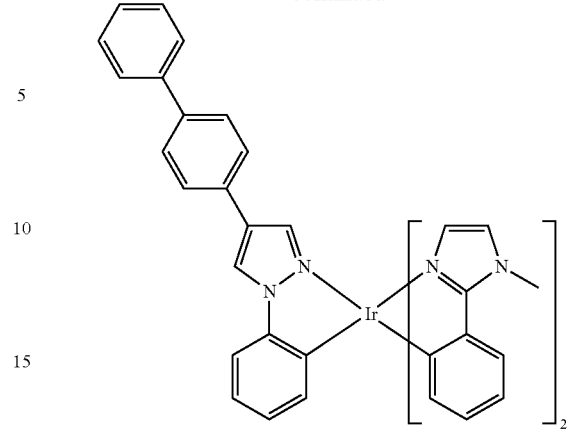
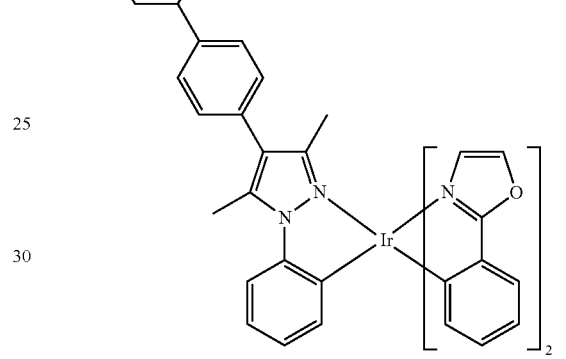
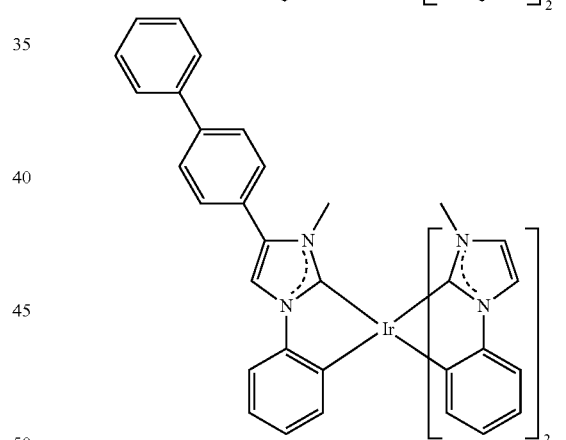

555
-continued
556
-continued
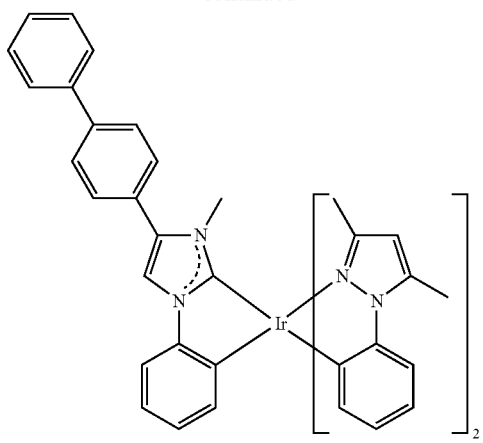
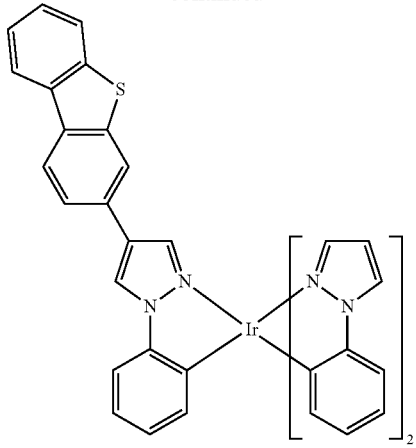
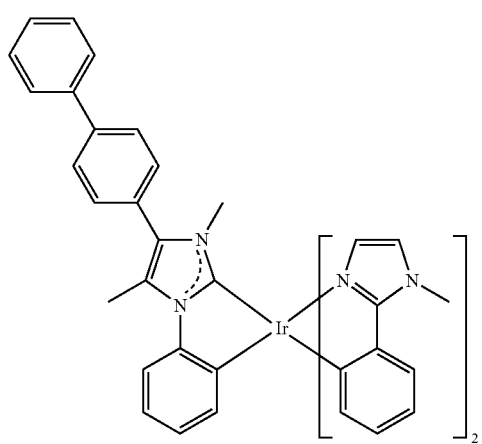
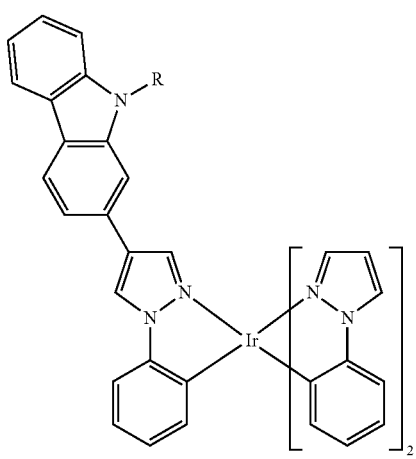
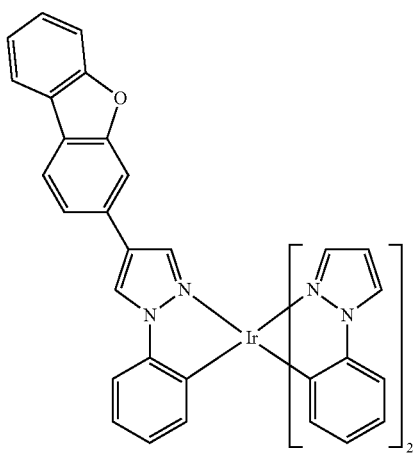
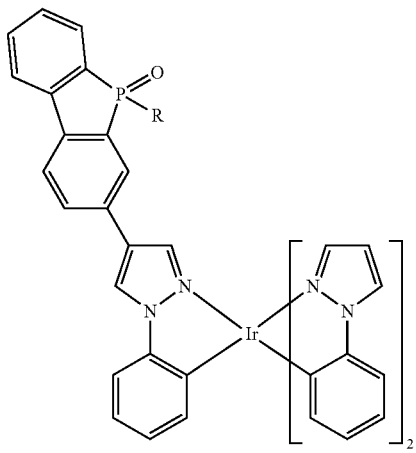

557
-continued
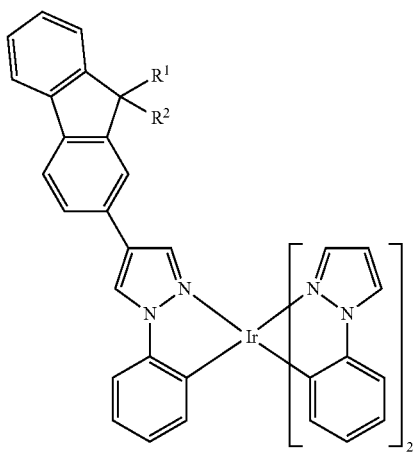
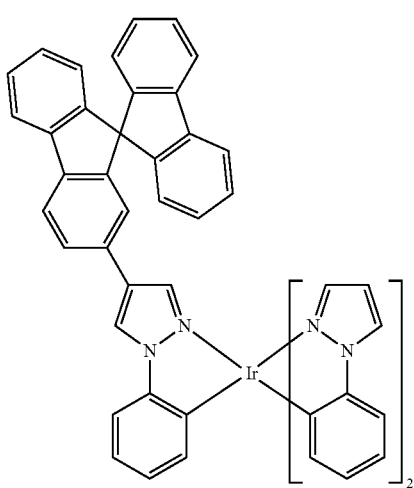
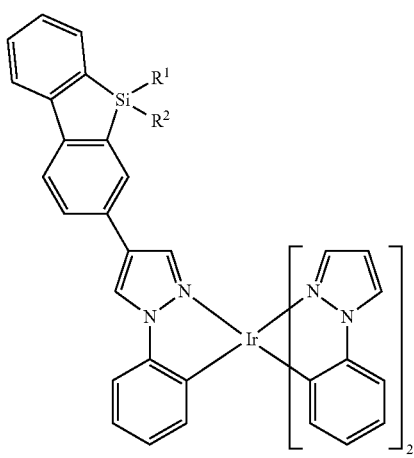
558
-continued
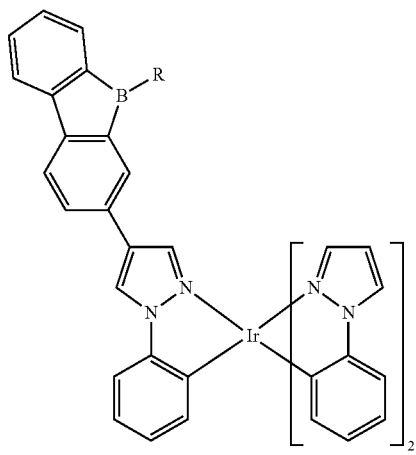
Structures Ir-11
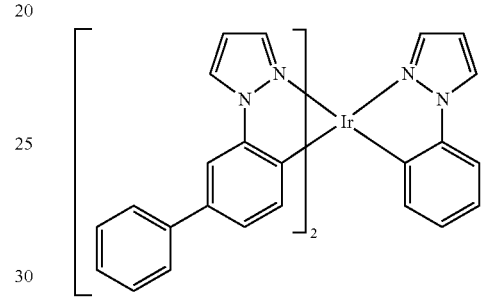
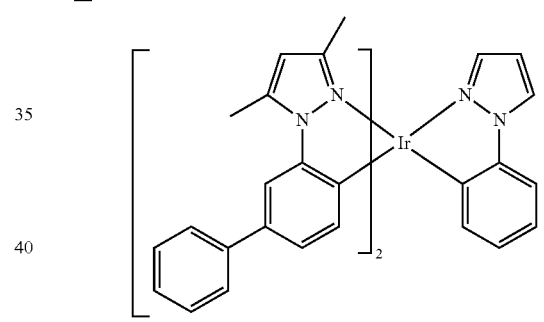
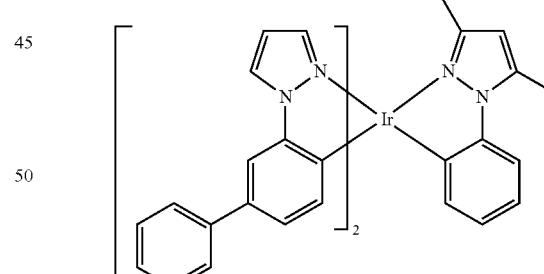
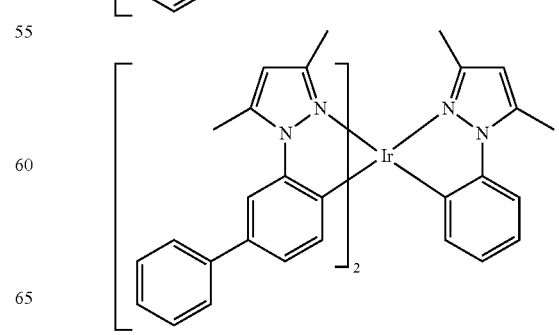

559
-continued
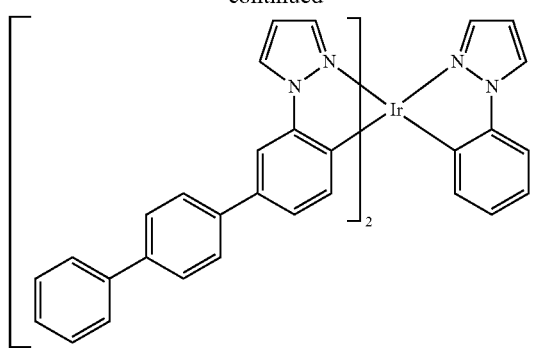
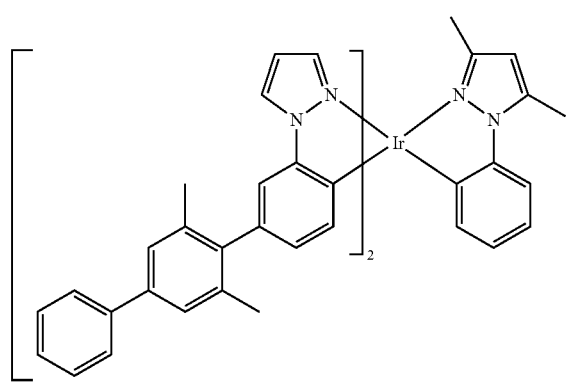
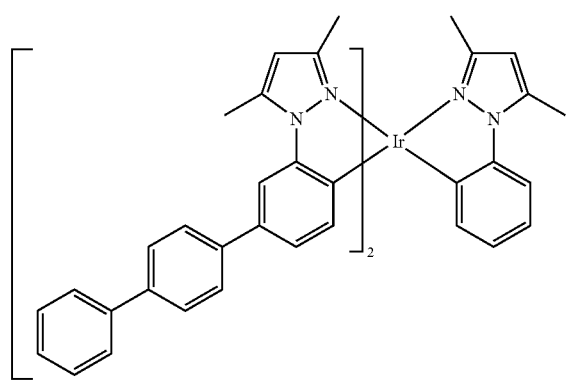
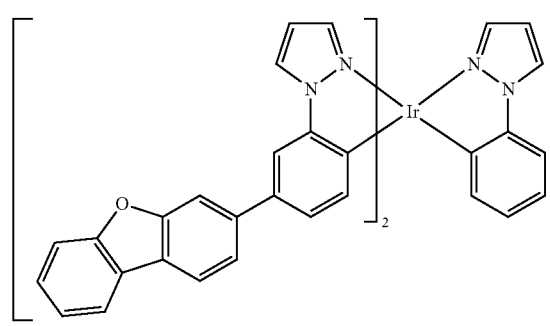
560
-continued
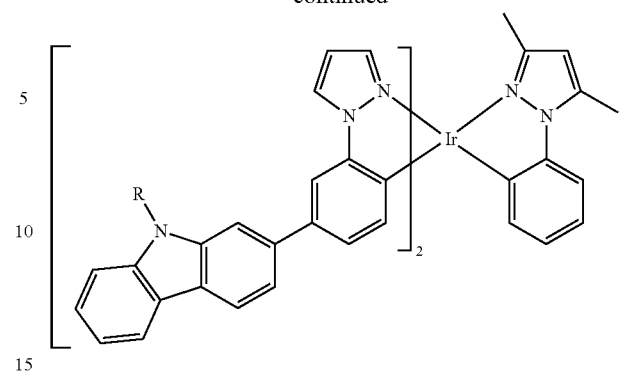
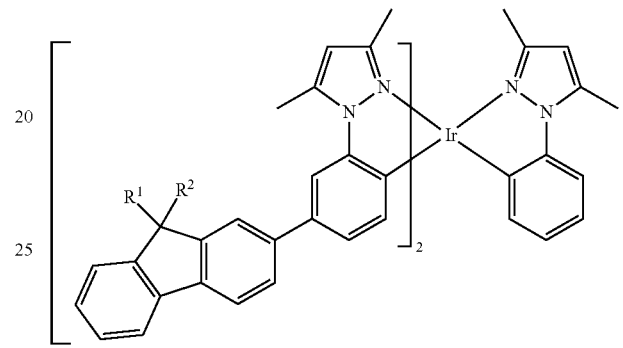
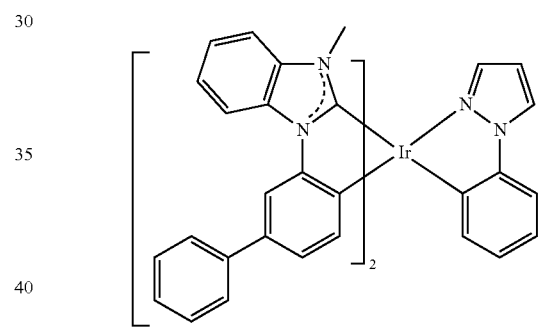
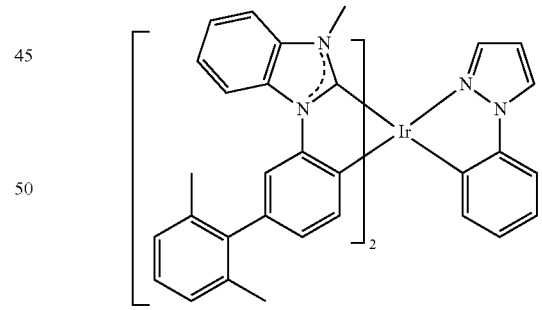
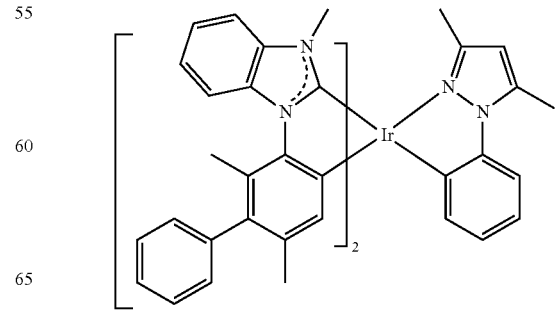

561
-continued
562
-continued
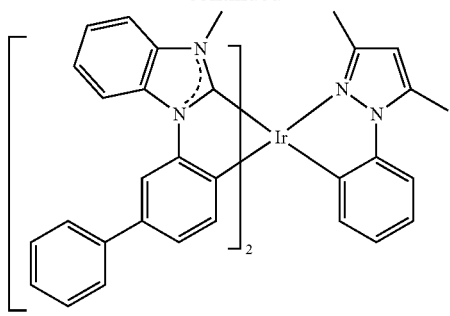
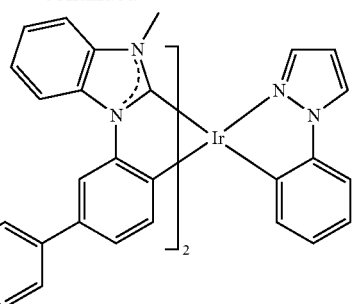
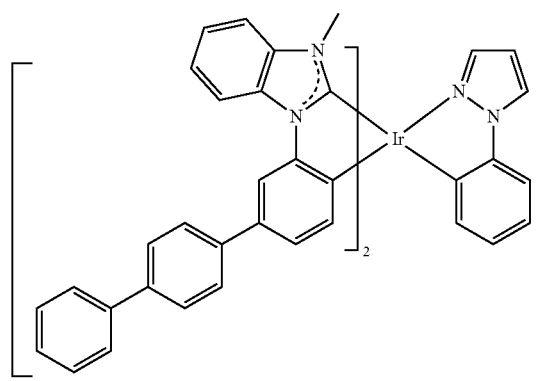
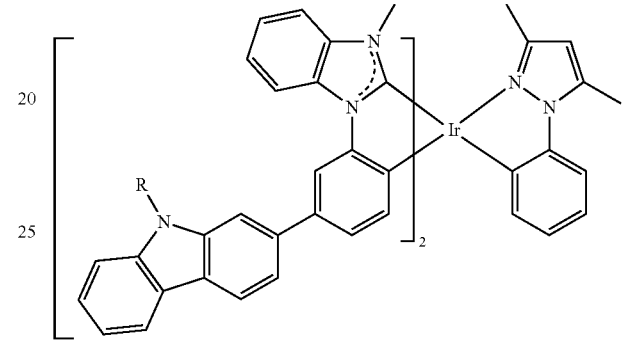
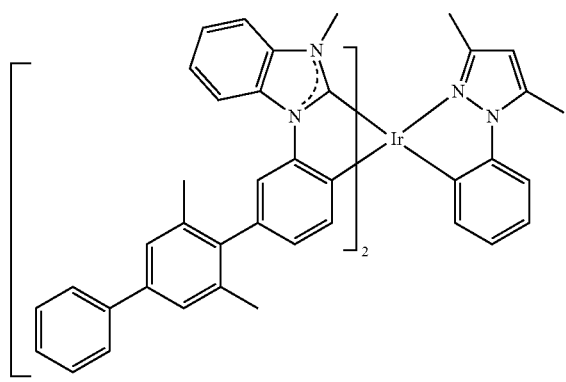
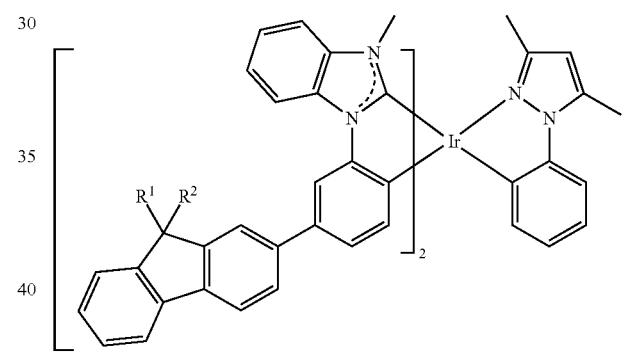
Structures Ir-12
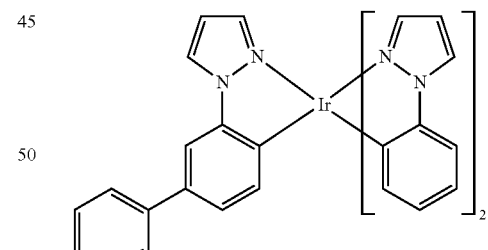
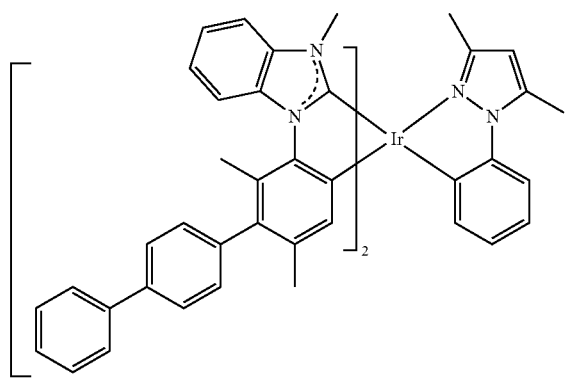
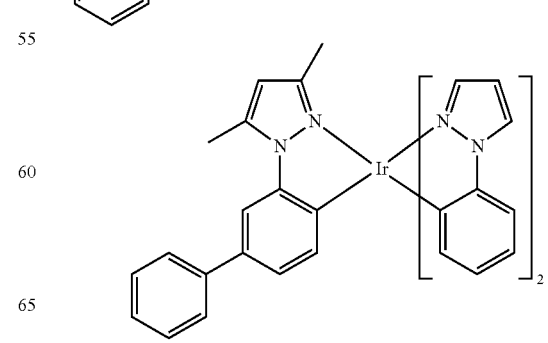

563
-continued
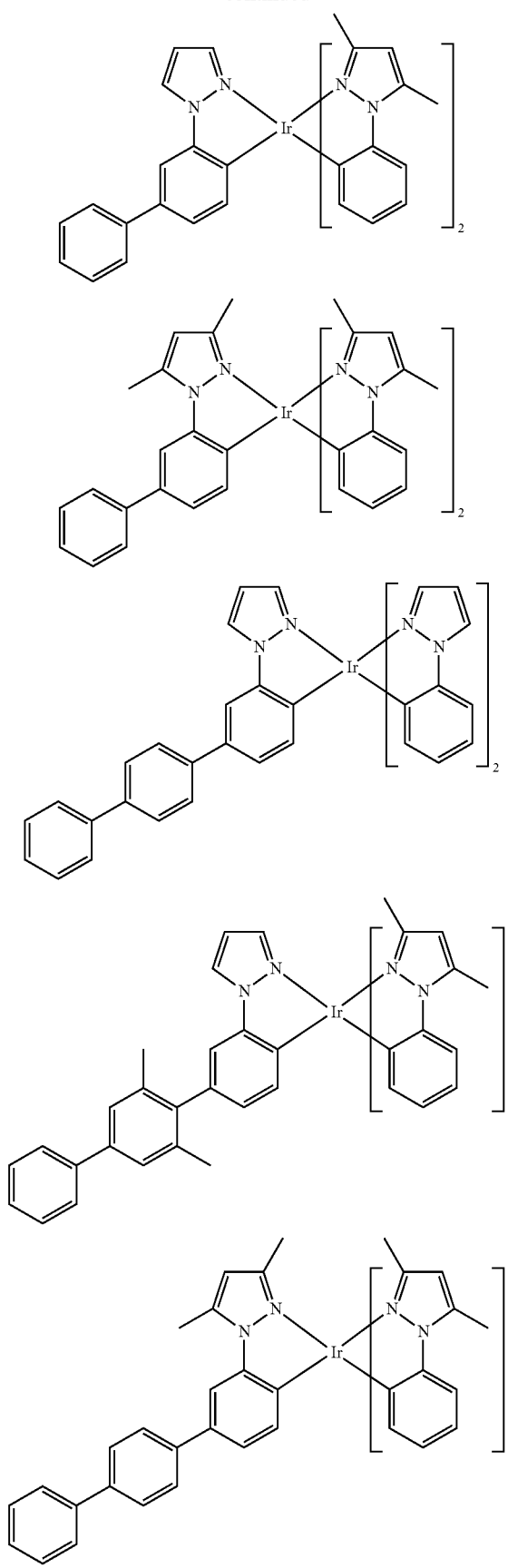
564
-continued
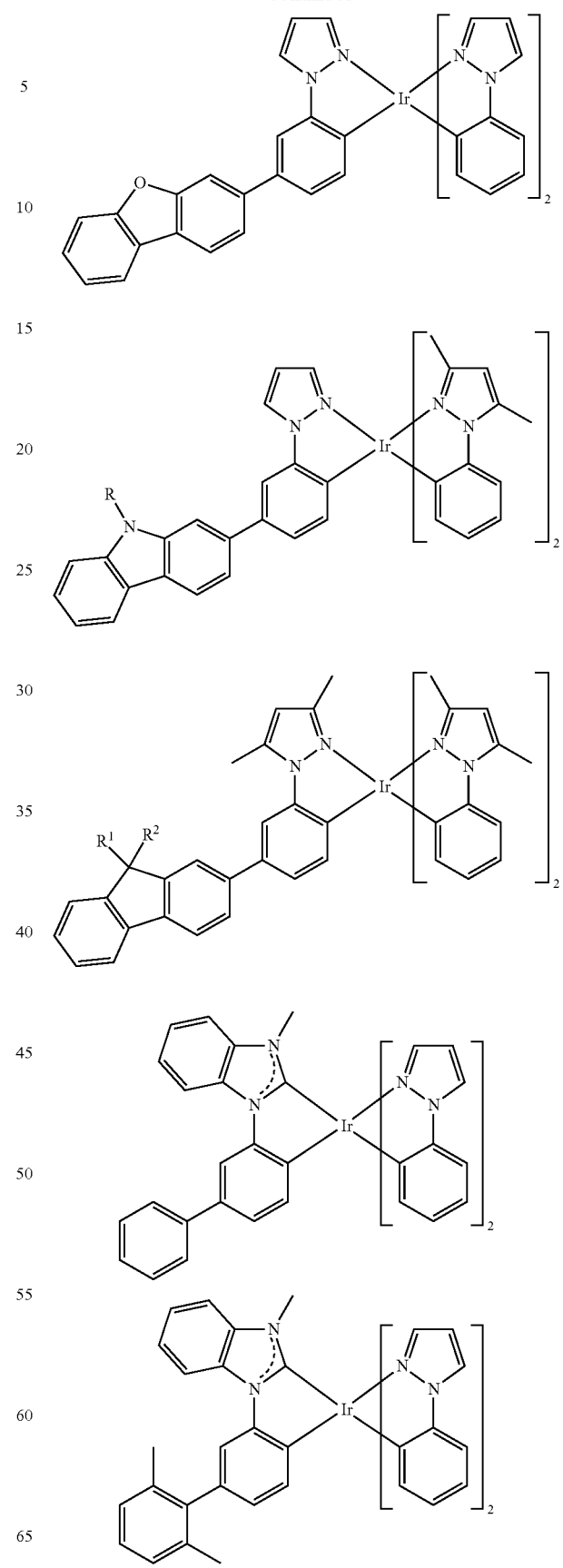

565
-continued
566
-continued
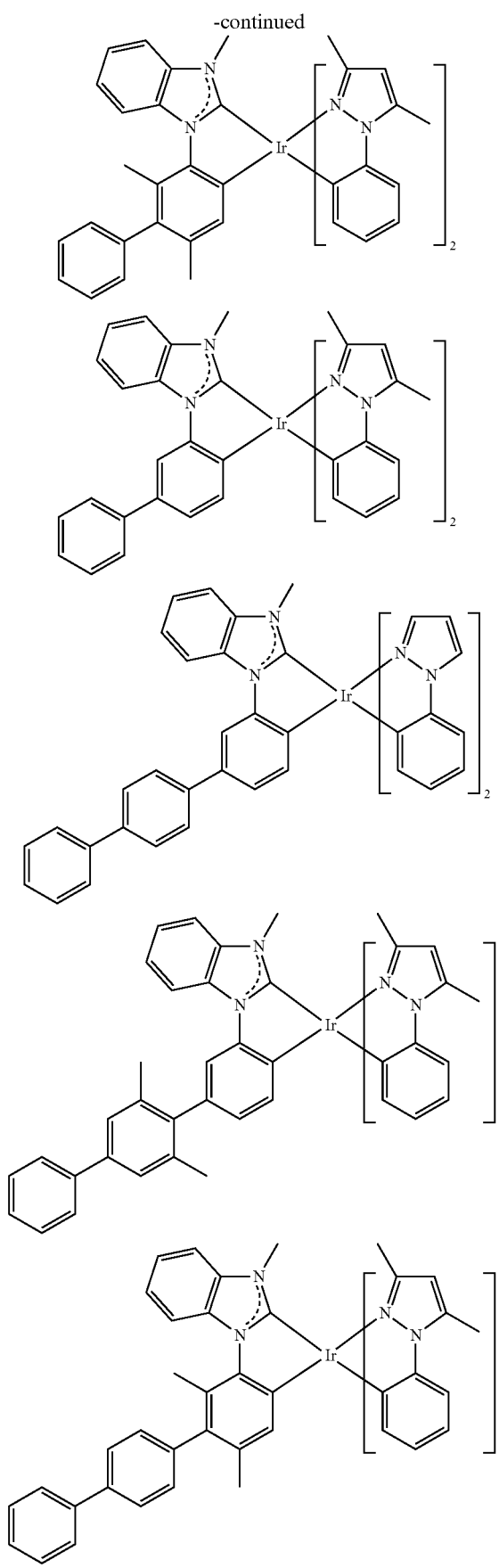
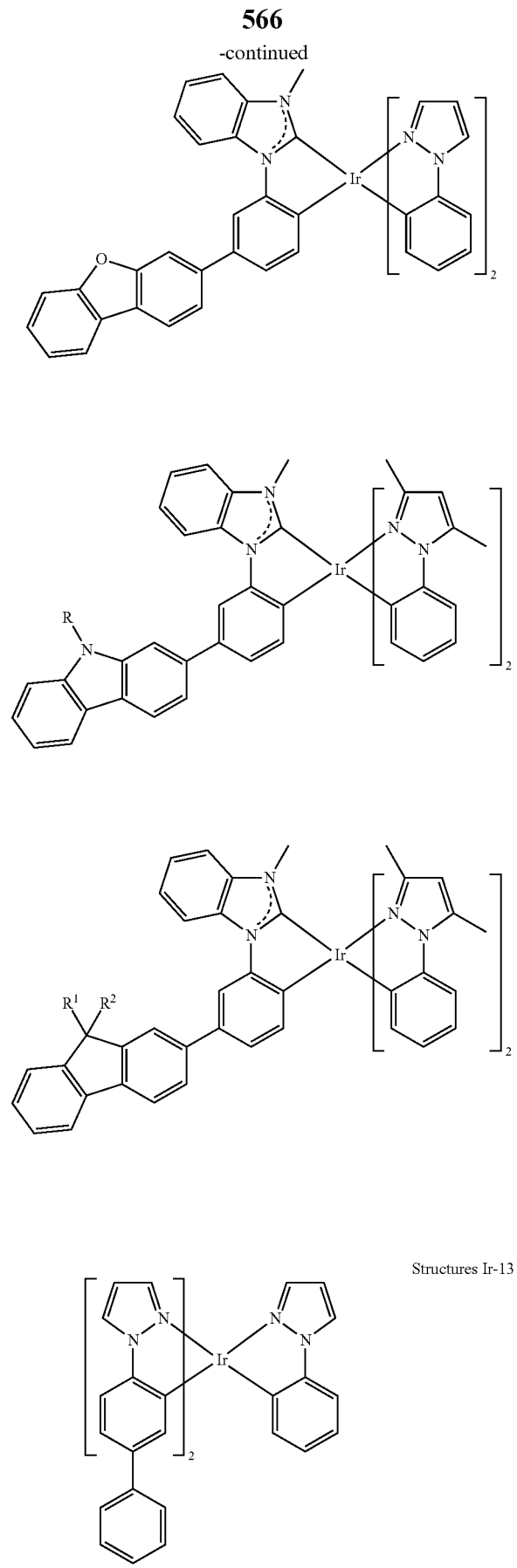
Structures Ir-13

567
-continued

568
-continued

569
-continued
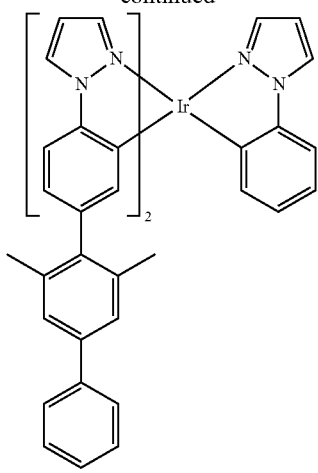
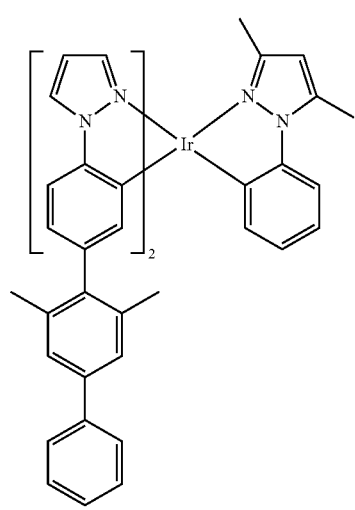
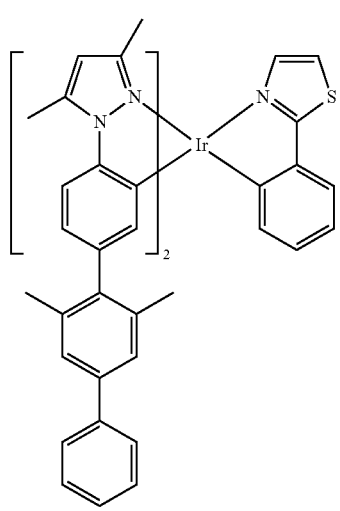
570
-continued
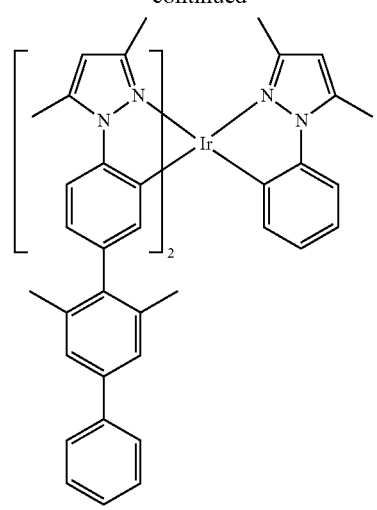
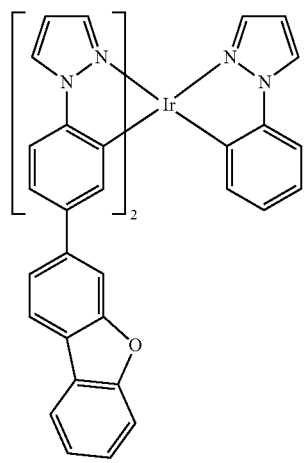
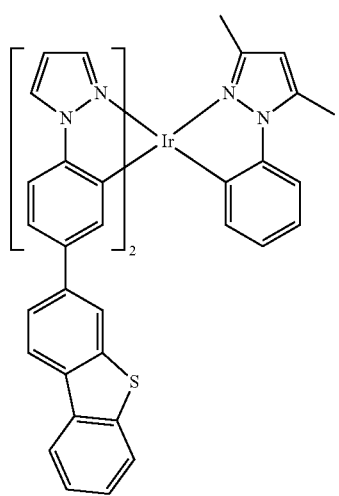

571
-continued
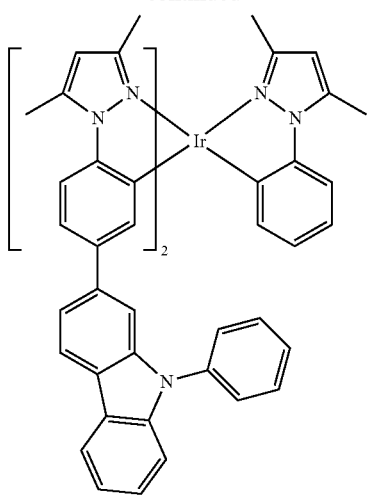
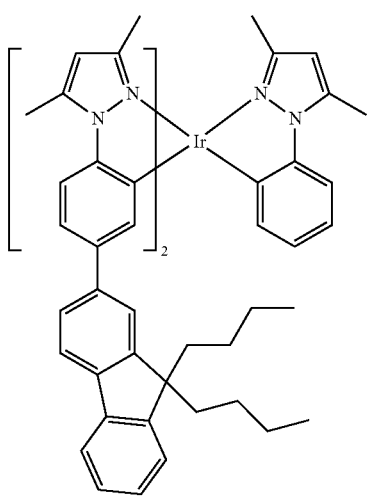
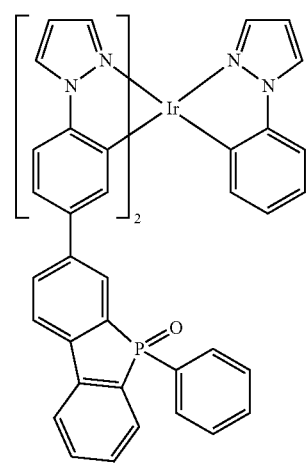
572
-continued
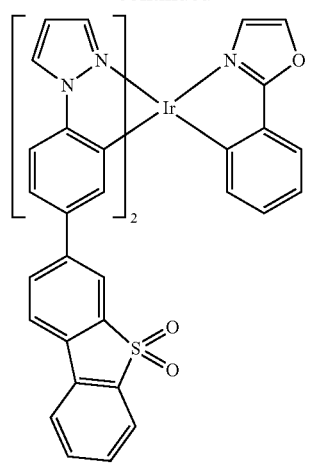
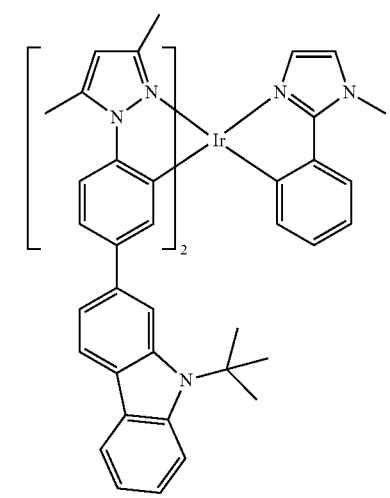
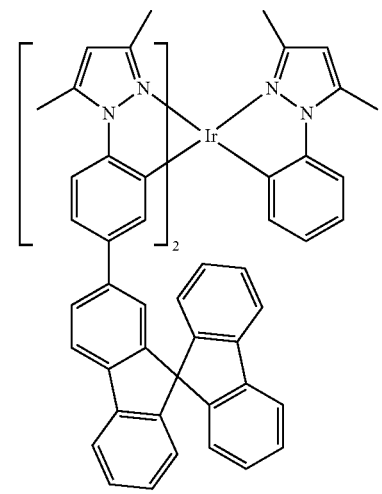

Structures Ir-14
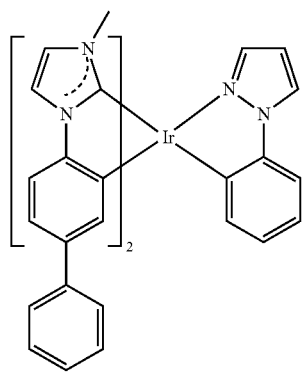
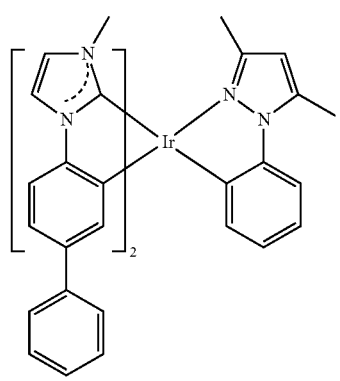
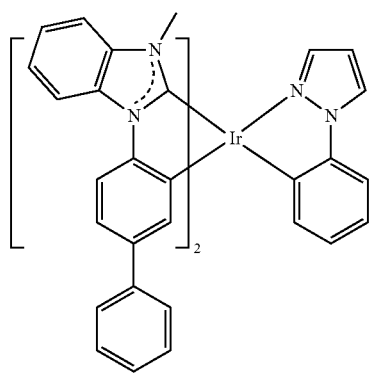
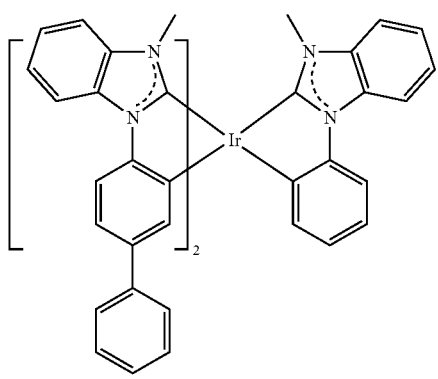
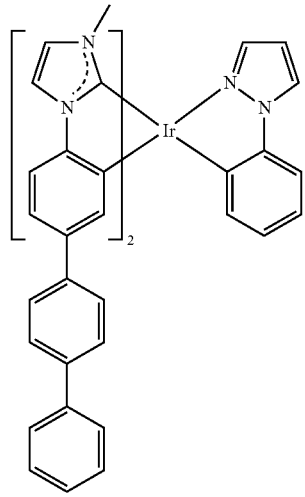
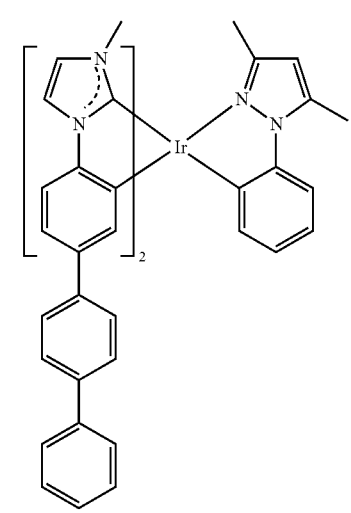
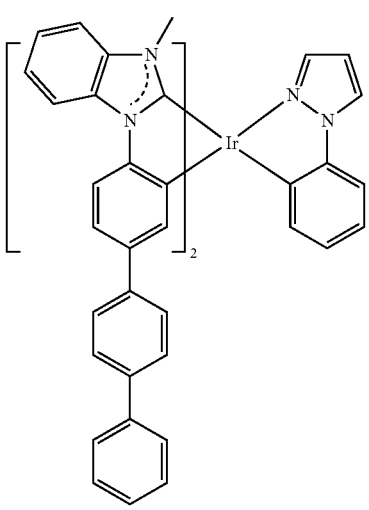

575 -continued
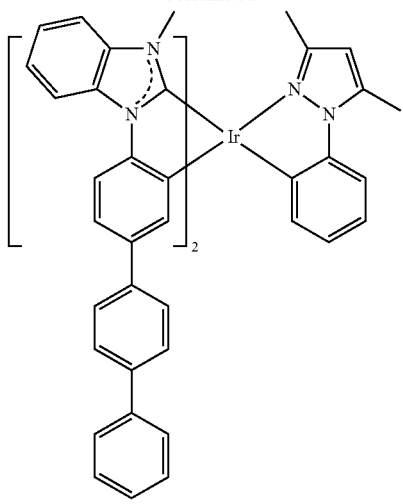
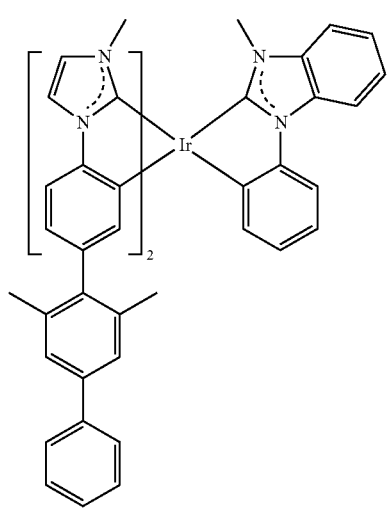
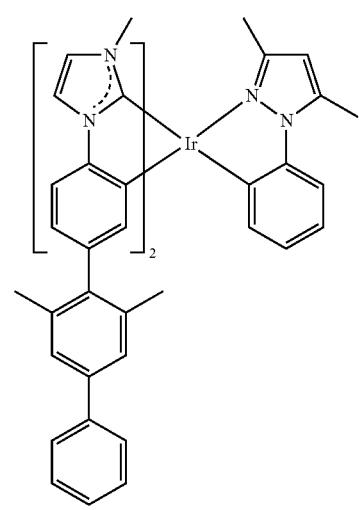
576 -continued
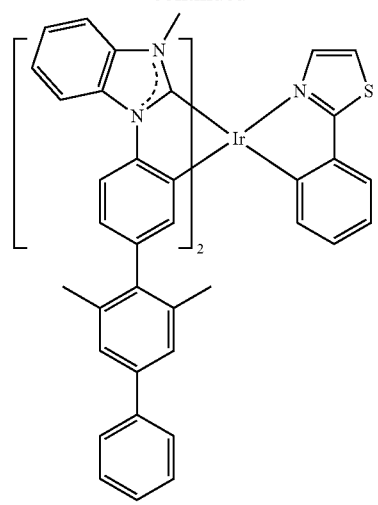
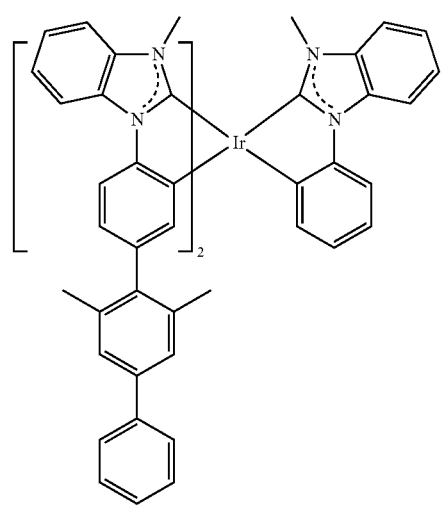
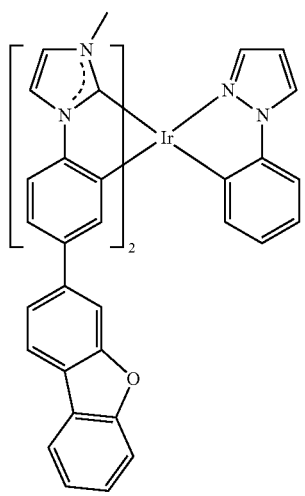

577
-continued
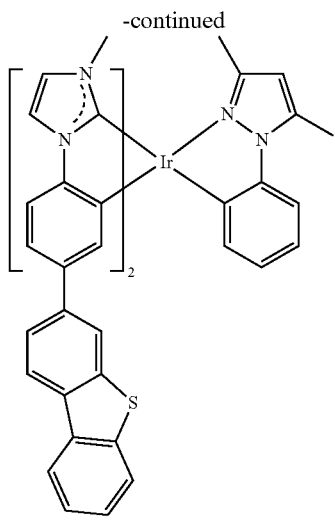
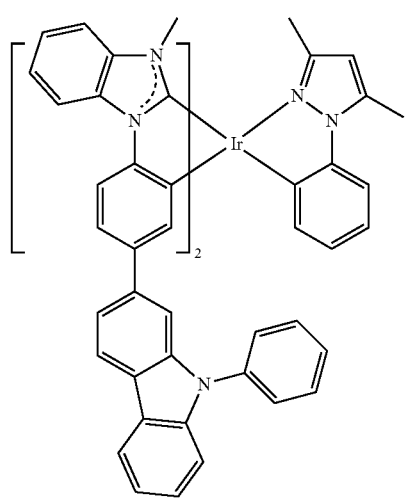
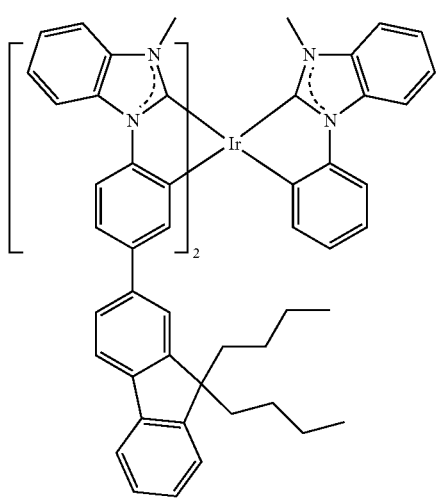
578
-continued
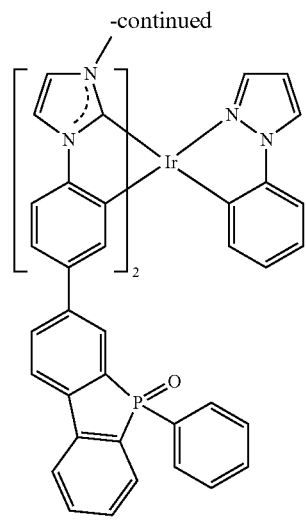
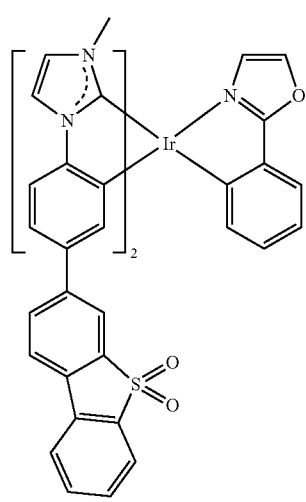
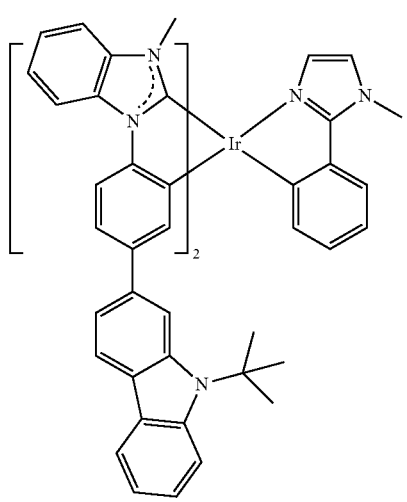

579
-continued
580
-continued
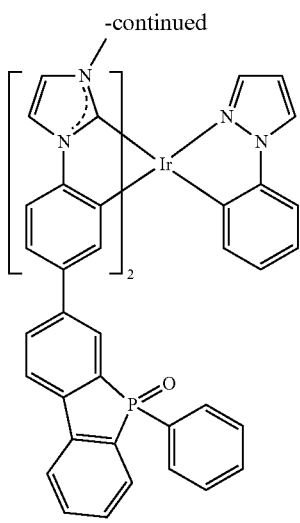
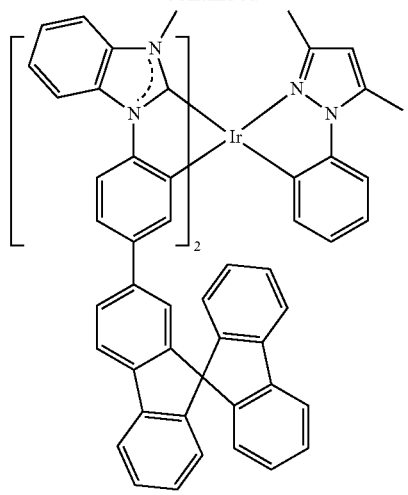
Structures Ir-15
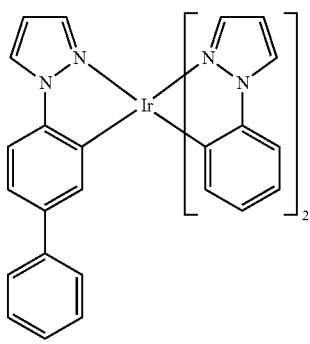
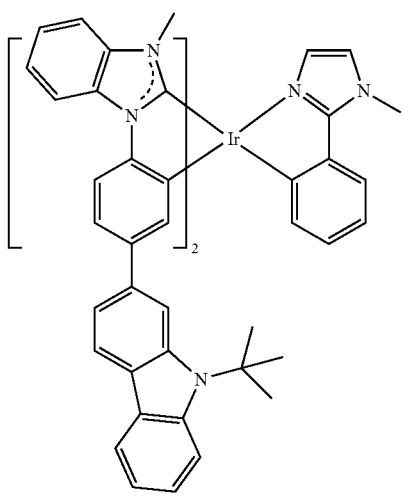
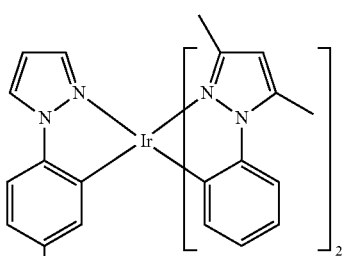
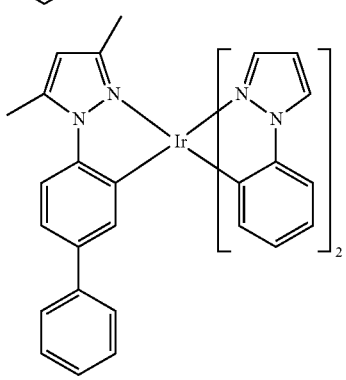

581
-continued
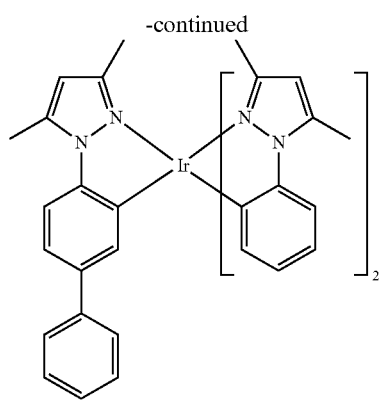
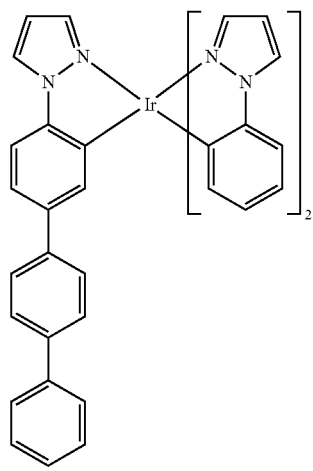
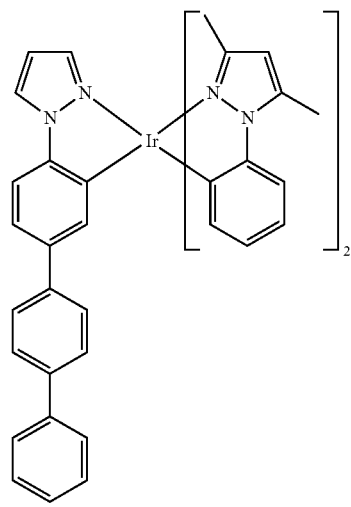
582
-continued
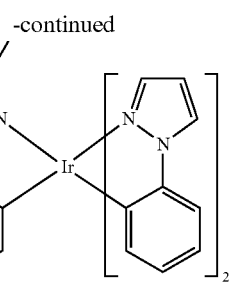
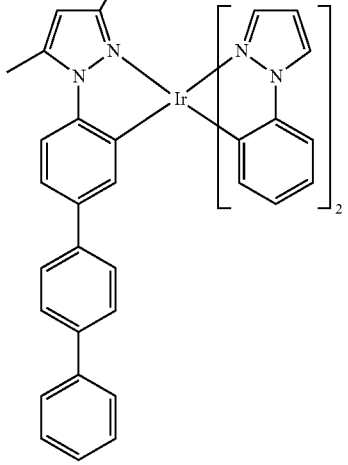
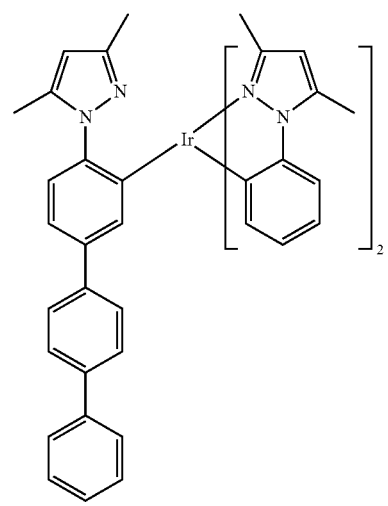
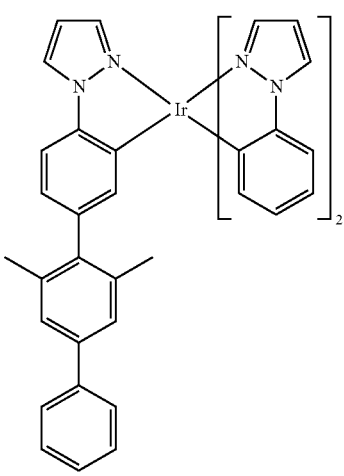

583
-continued
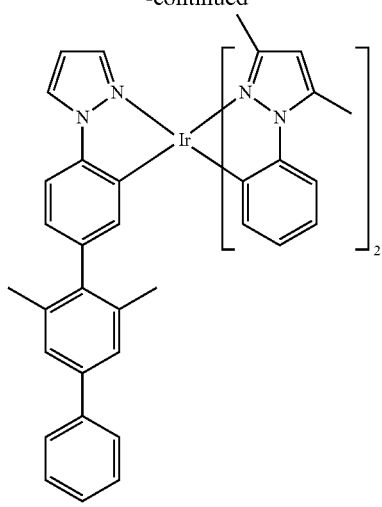
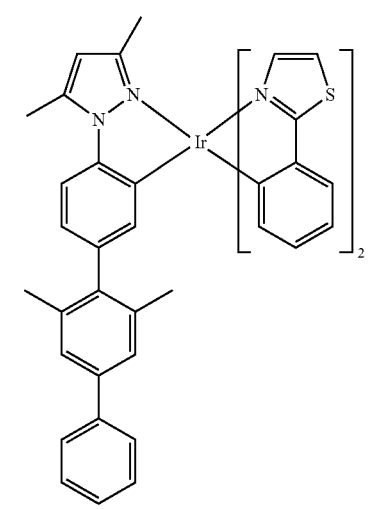
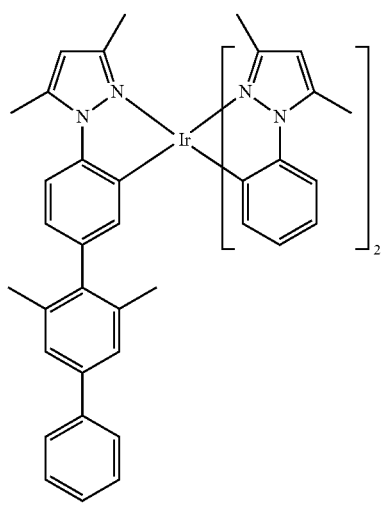
584
-continued

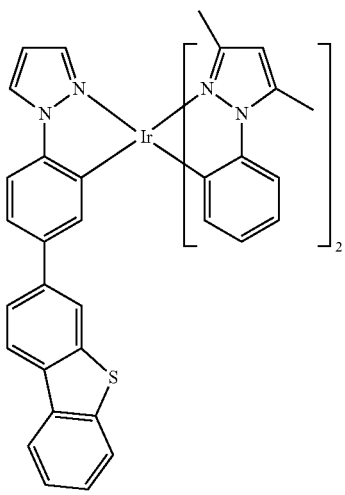
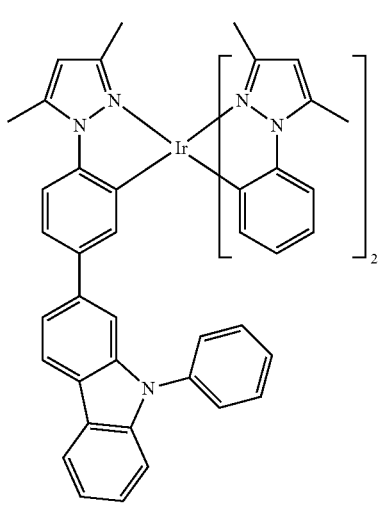

585
-continued
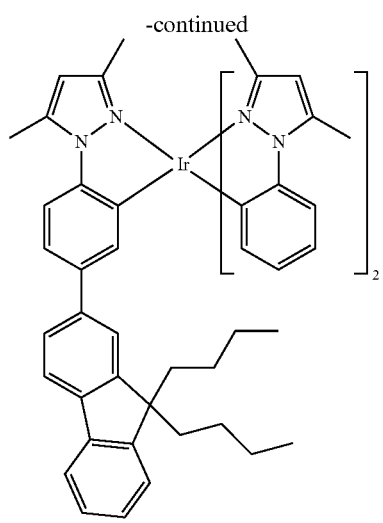
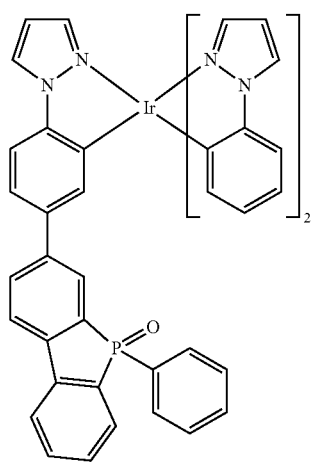
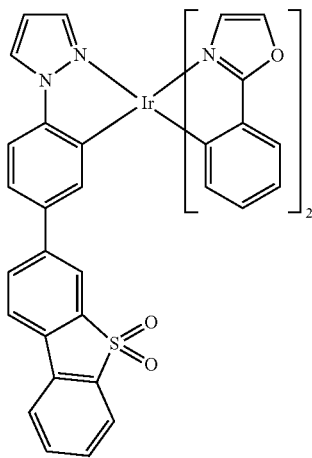
586
-continued
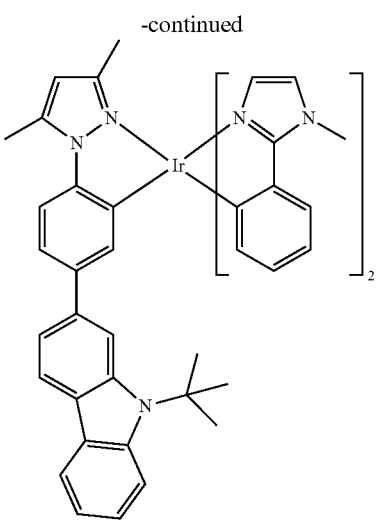
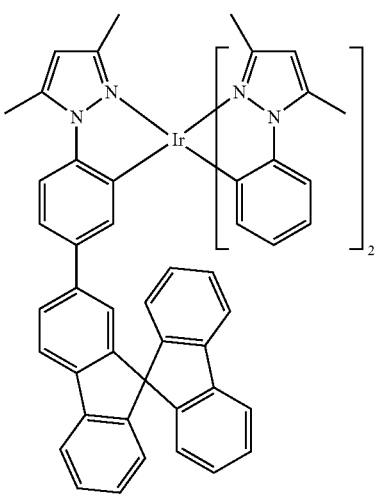
Structures Ir-16
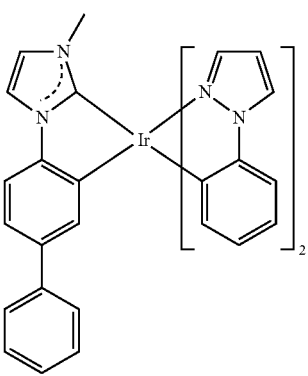

587
-continued
588
-continued
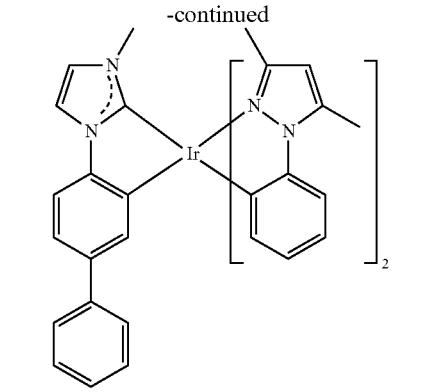
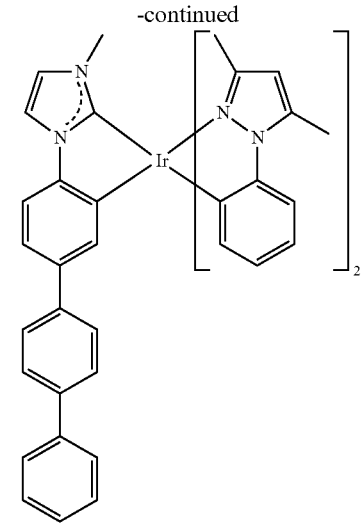
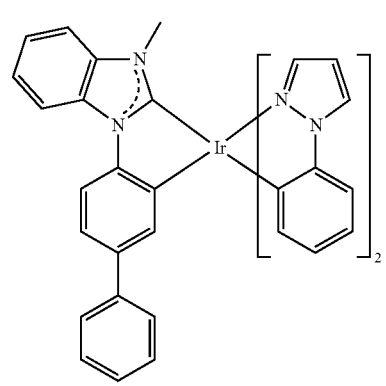
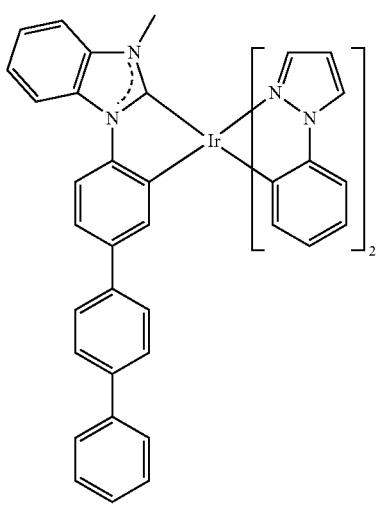
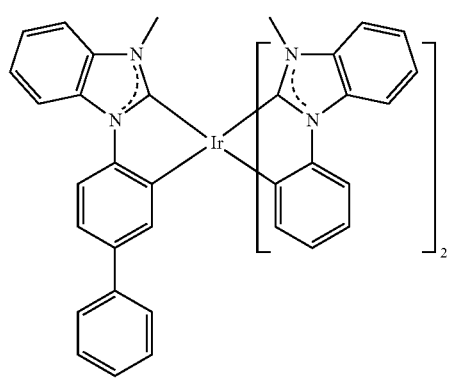
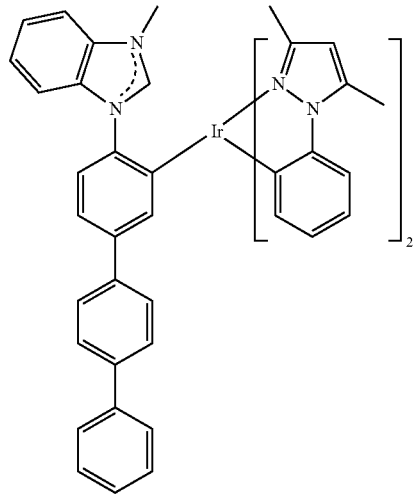
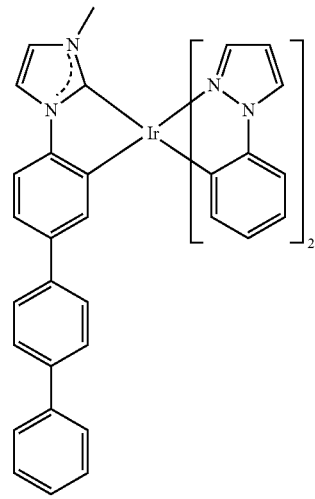

| 589 -continued | 590 -continued |
|---|---|
| 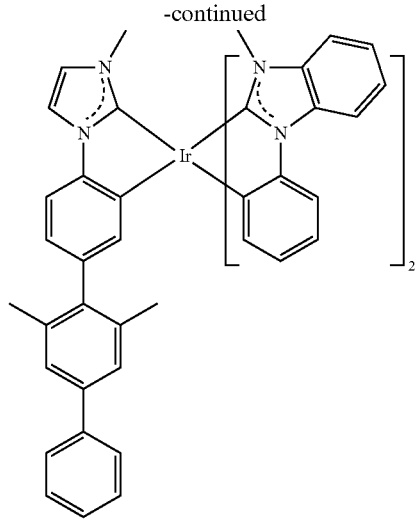 | 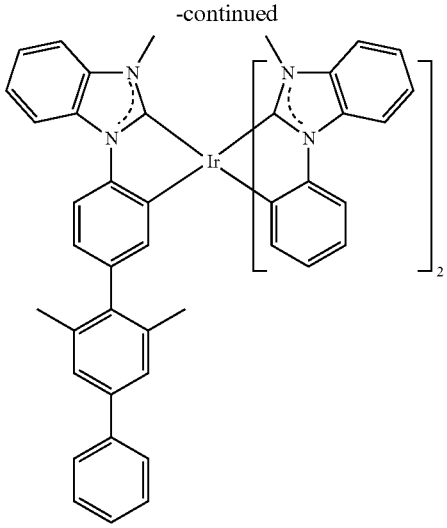 |
| 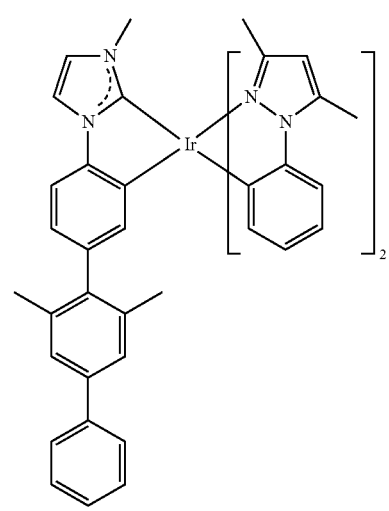 | 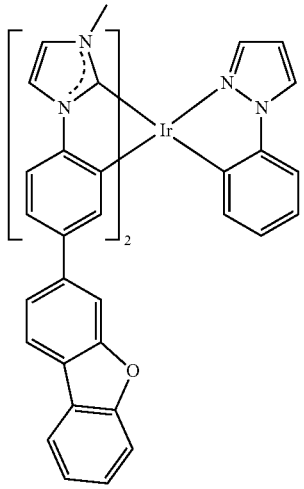 |
| 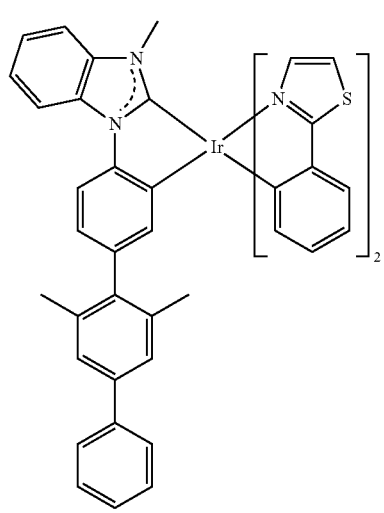 | 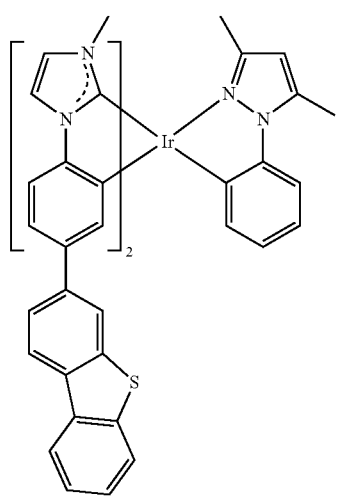 |

591
-continued
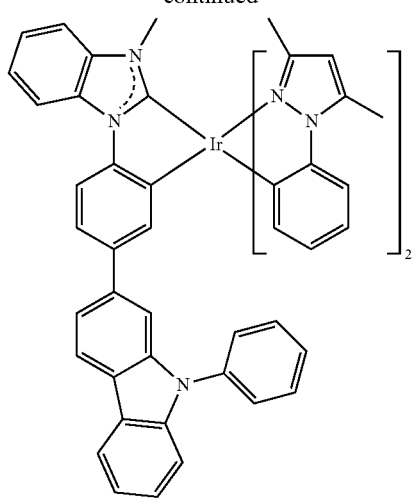
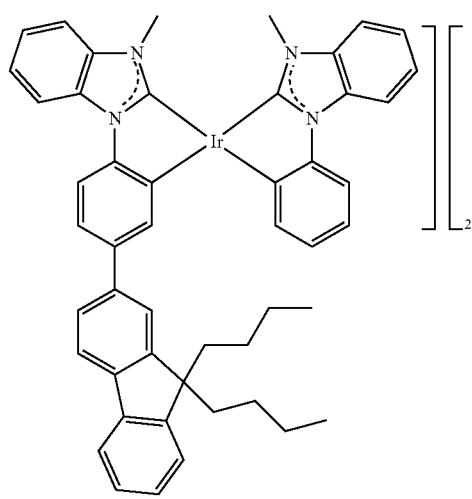
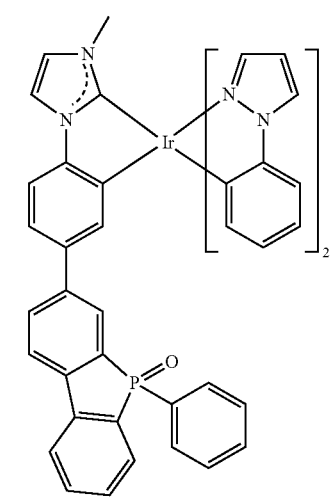
592
-continued
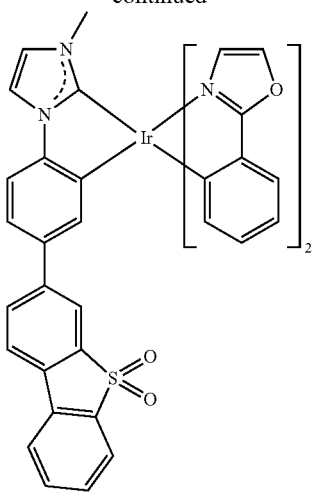
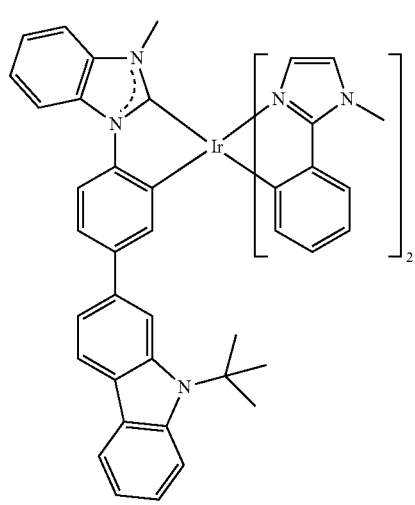
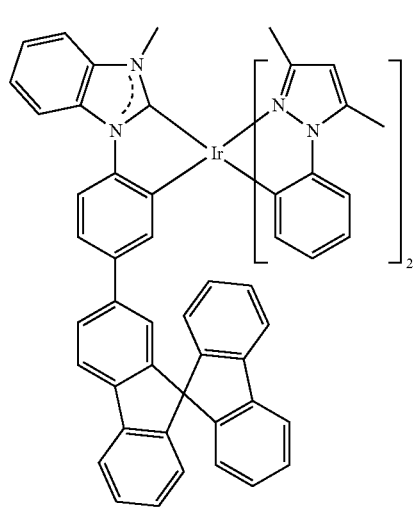

Structures Ir-20
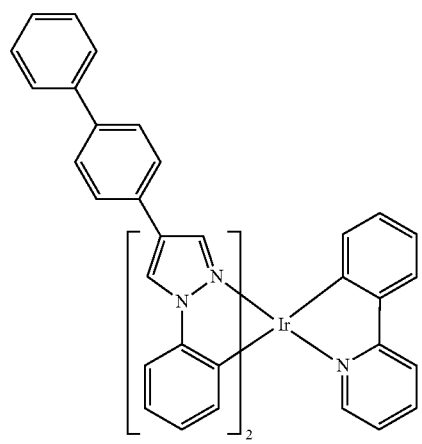
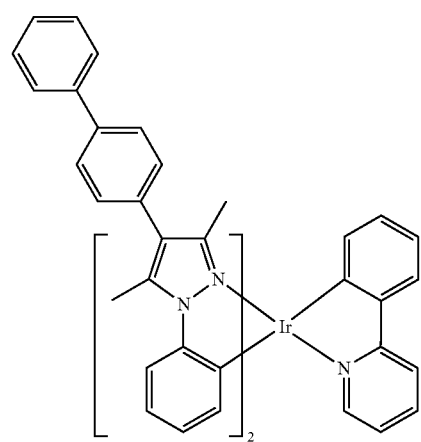
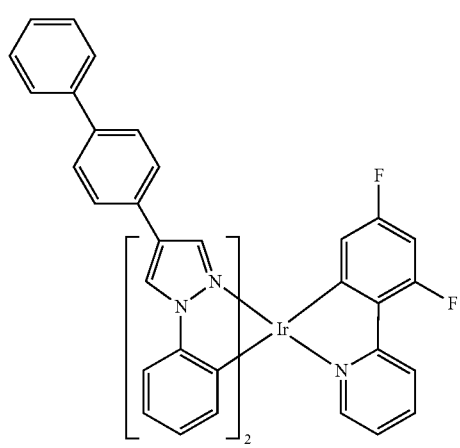
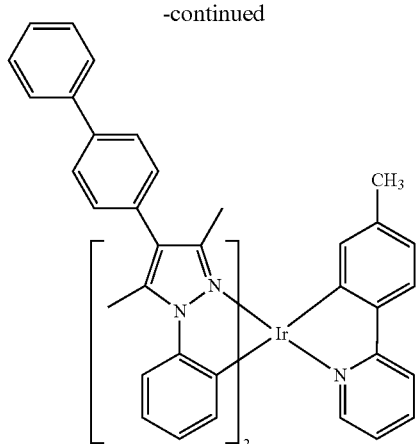
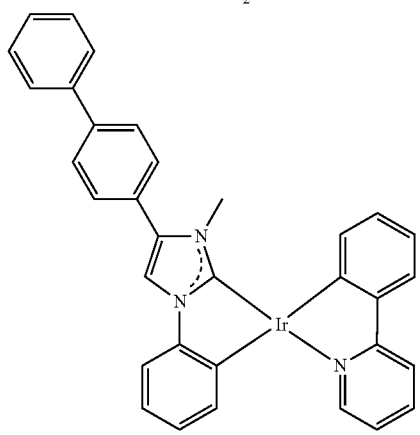
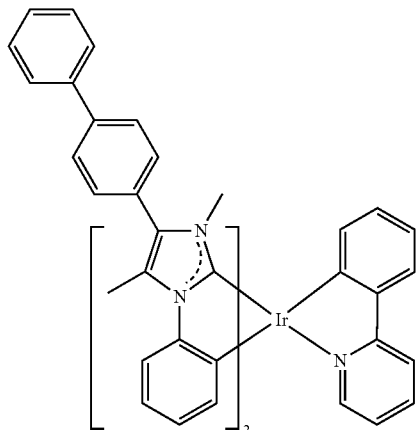
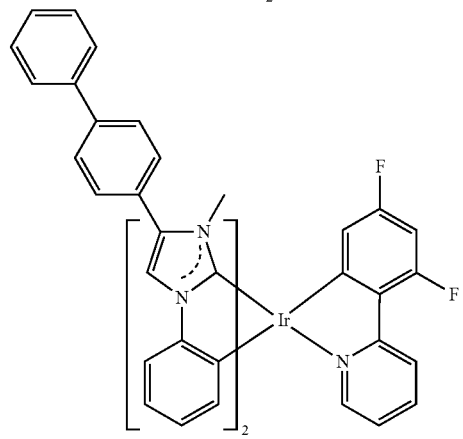

595
-continued
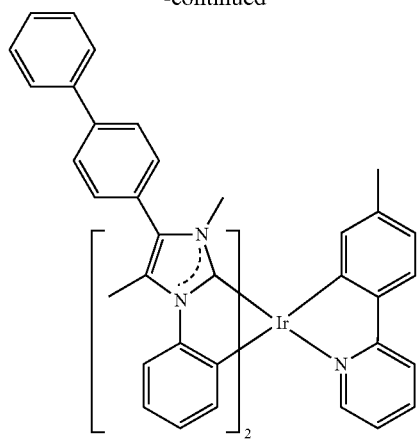
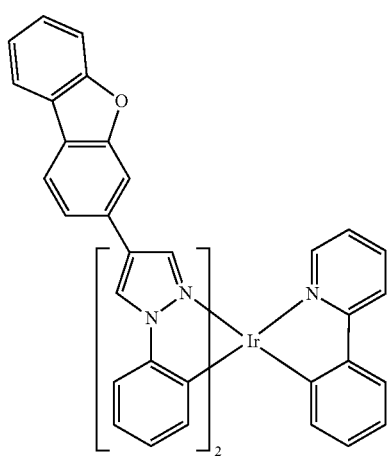
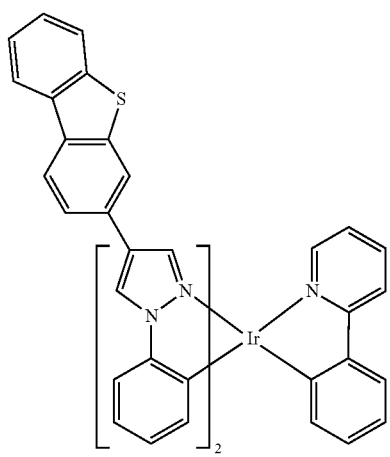
596
-continued
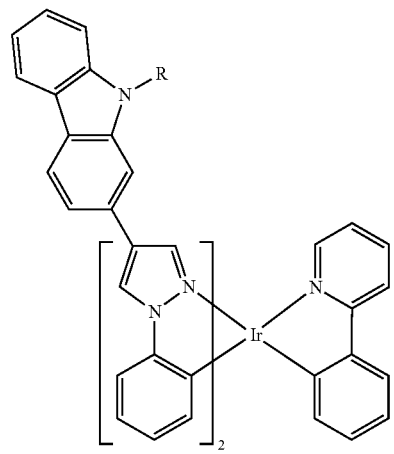
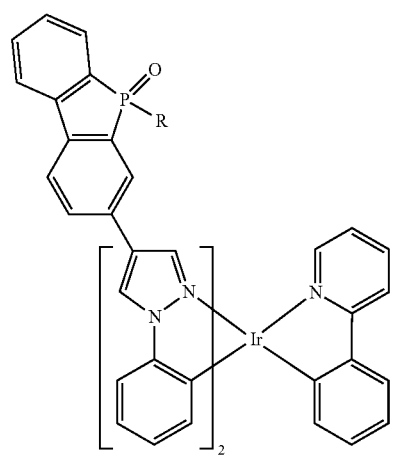
Structures Ir-21
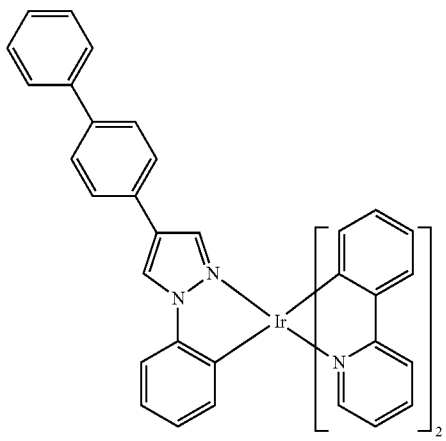

597
-continued
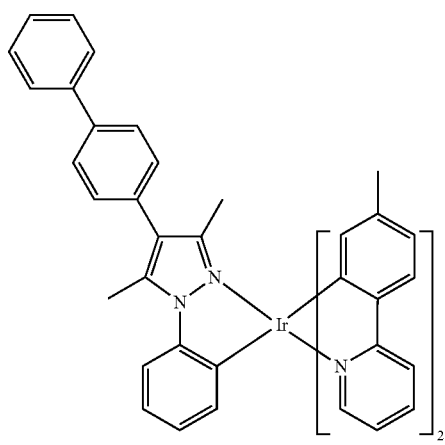
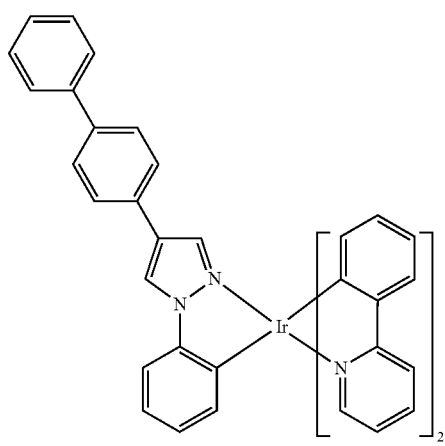
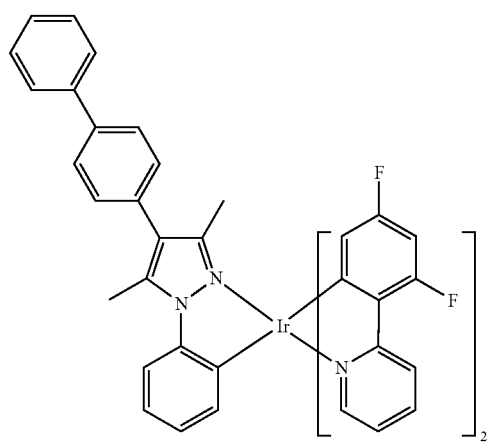
598
-continued
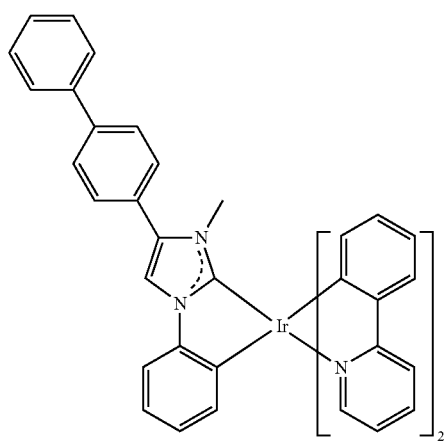
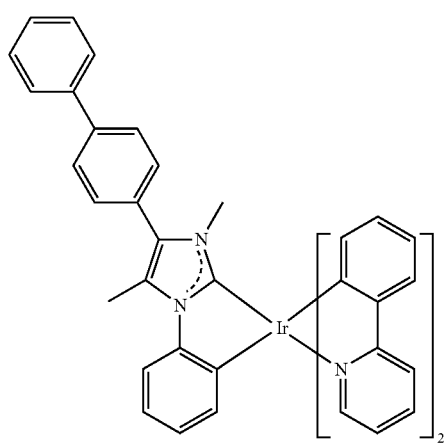
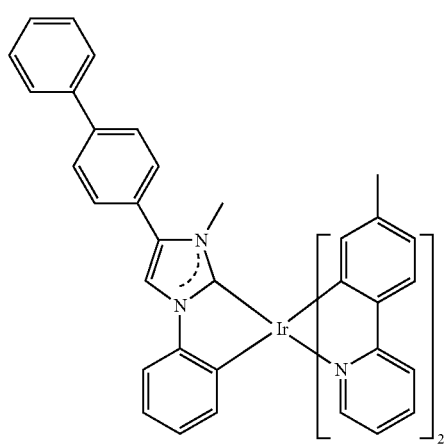

599
-continued
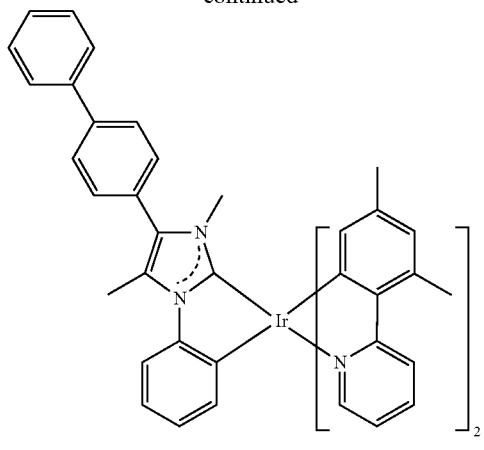
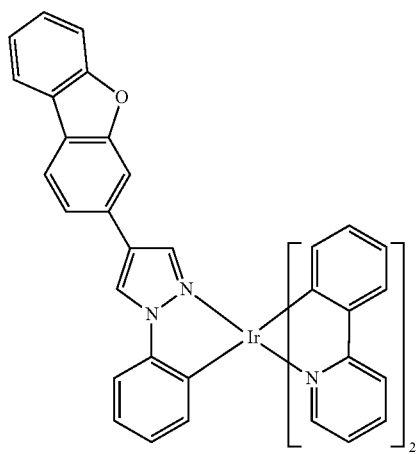
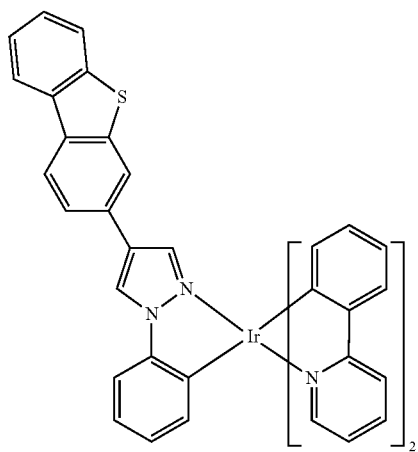
600
-continued
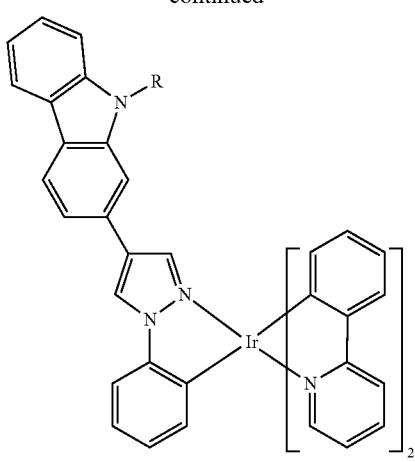
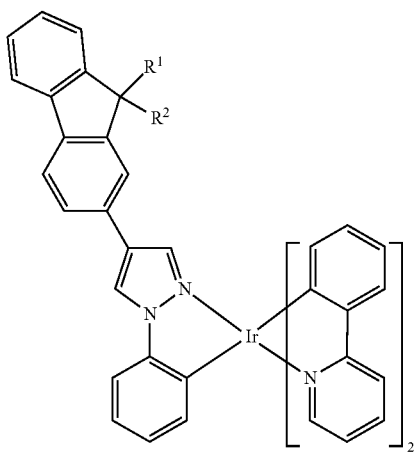

601
-continued
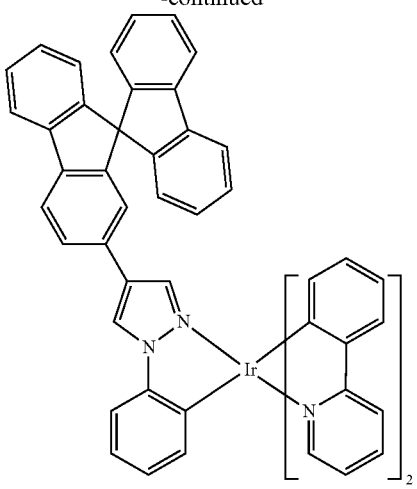
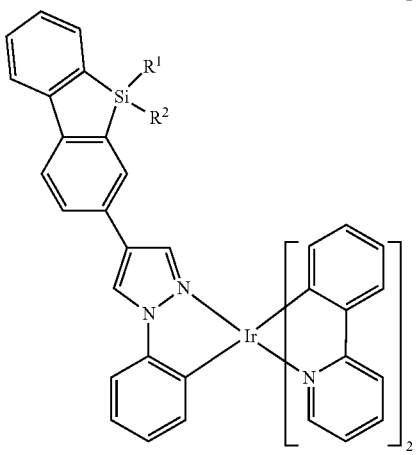
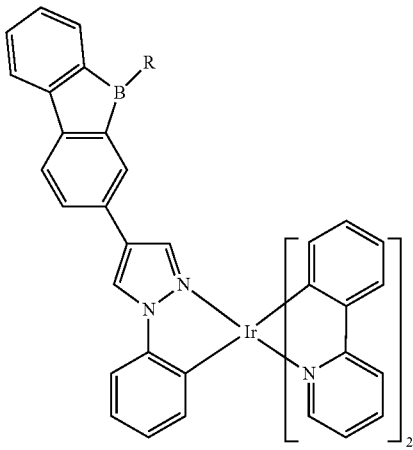
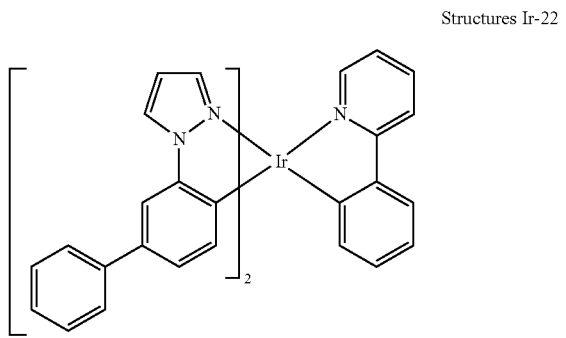
602
-continued
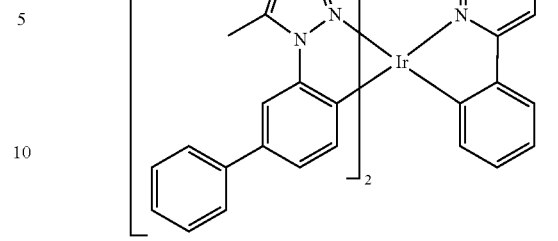
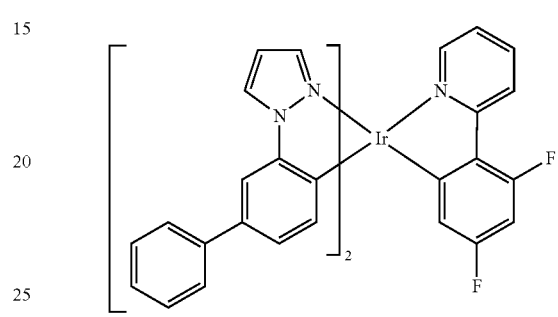
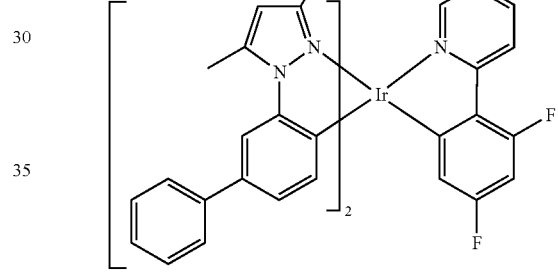
Structures Ir-22
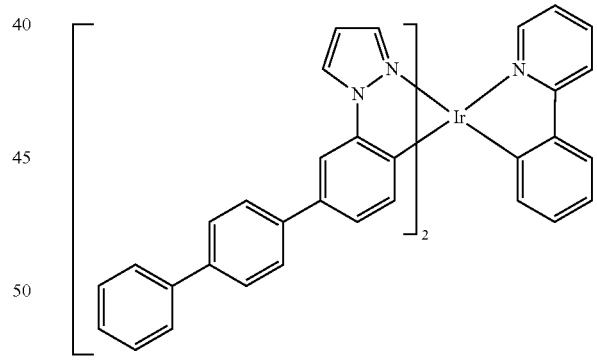
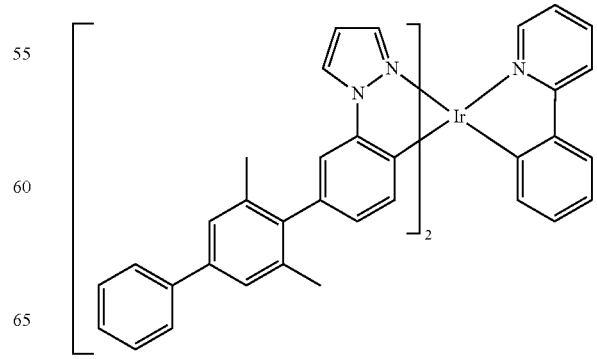

603
-continued
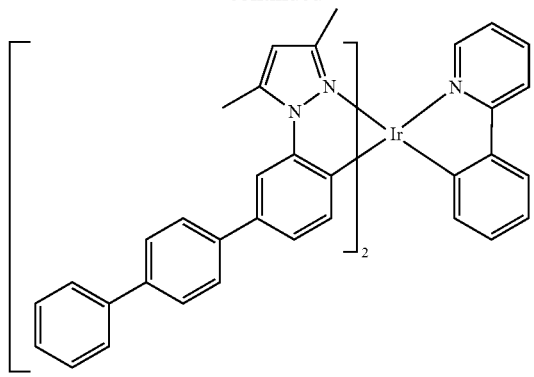
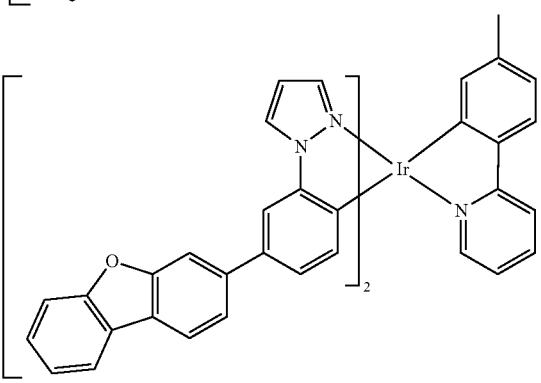
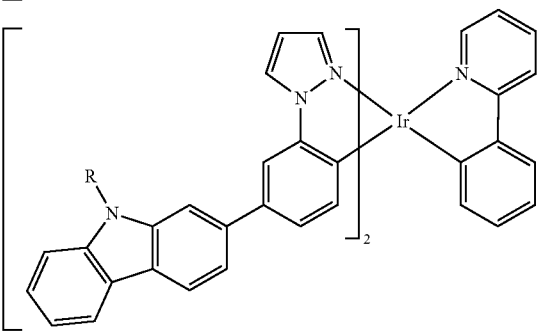
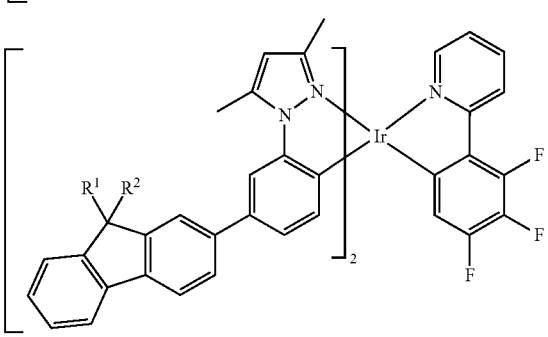
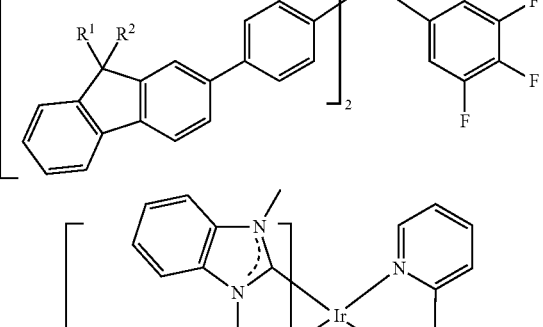
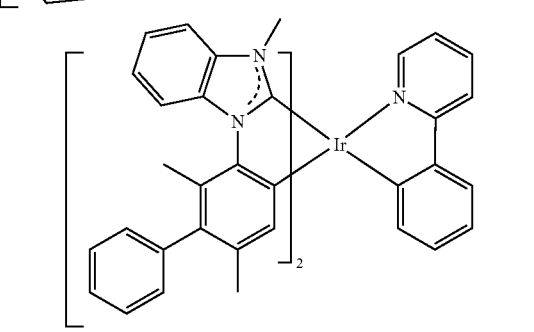
604
-continued
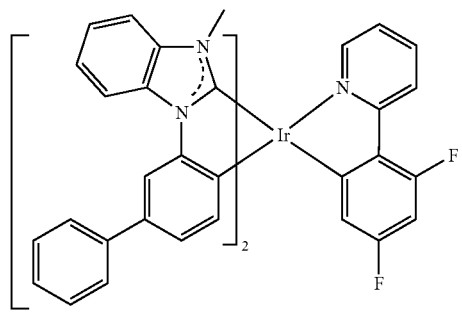
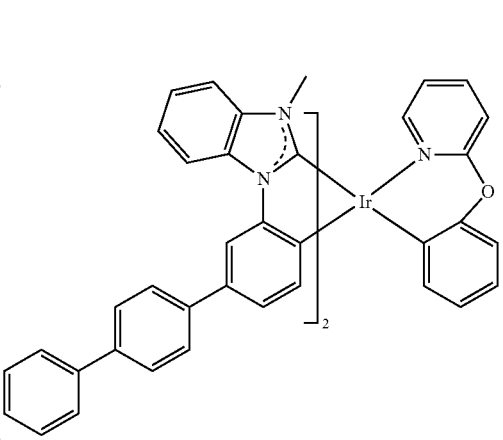
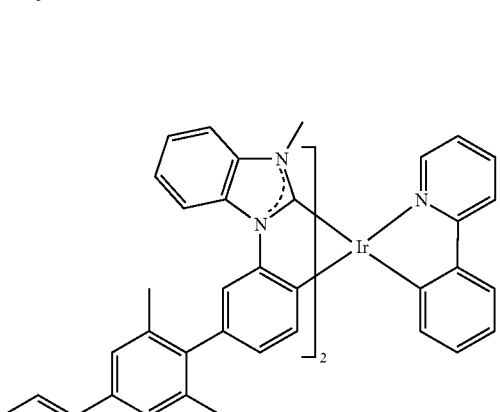
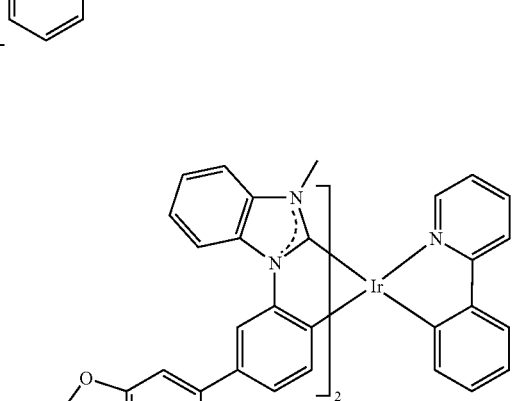

605
-continued
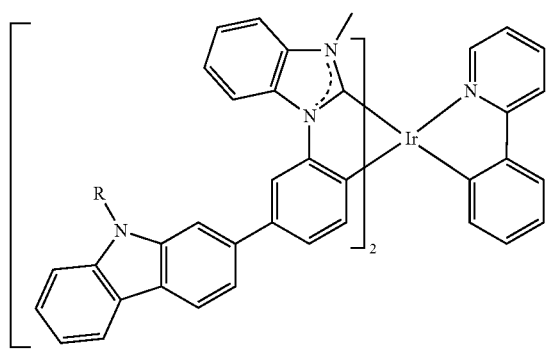
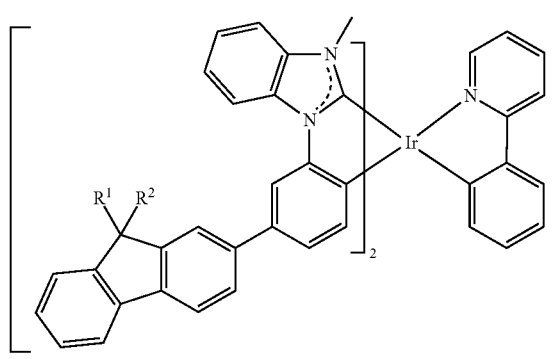
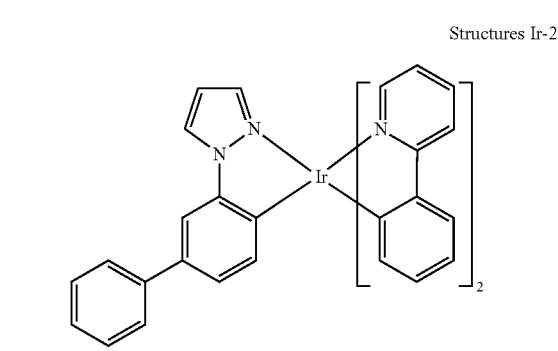
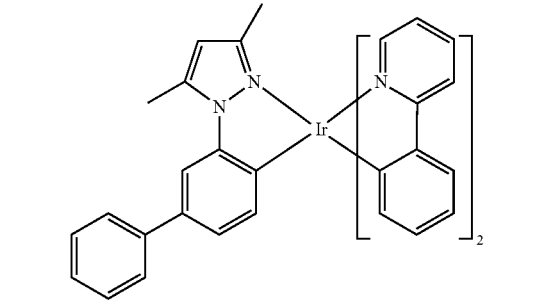
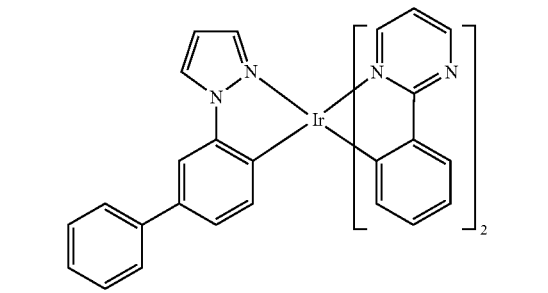
606
-continued
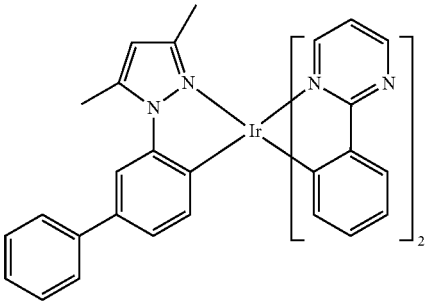
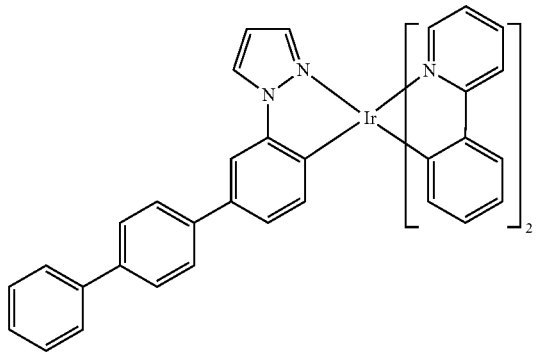
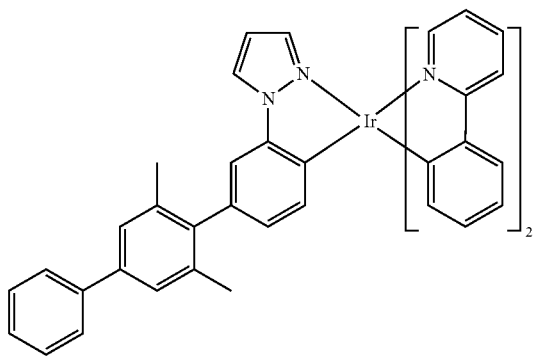
Structures Ir-23
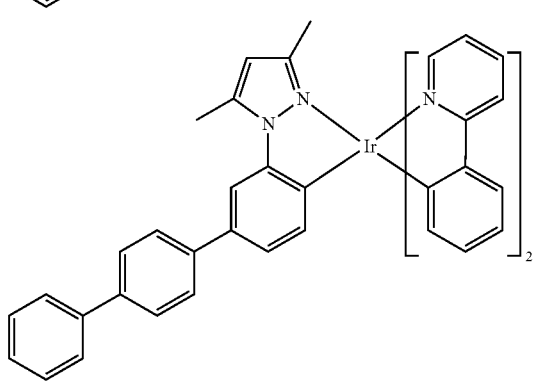
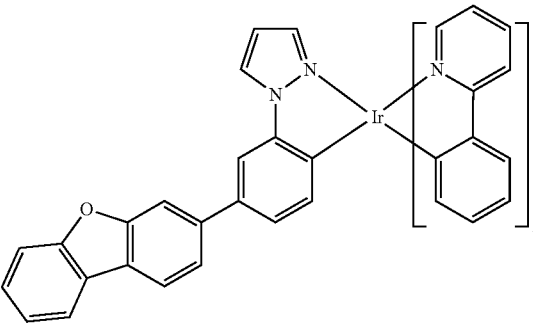

607
-continued
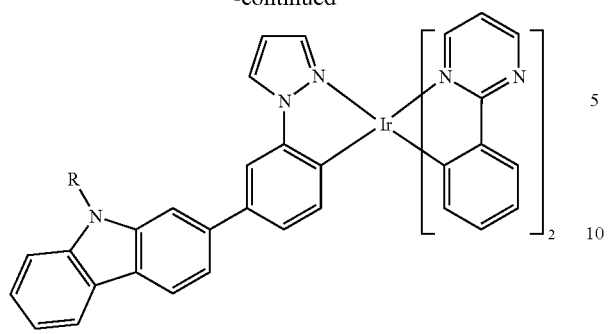
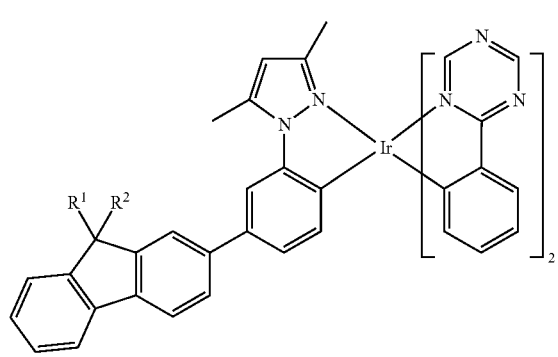
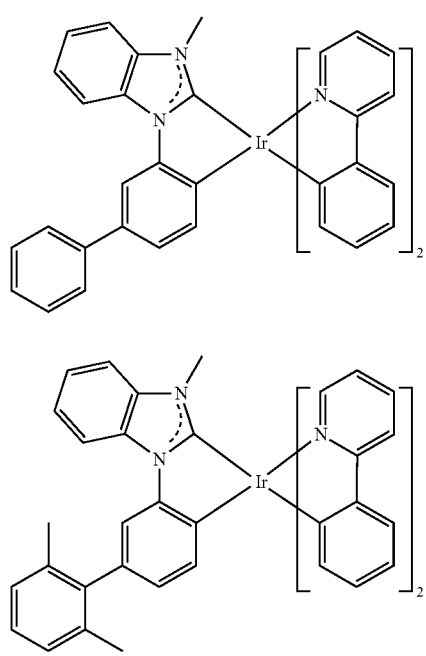
608
-continued
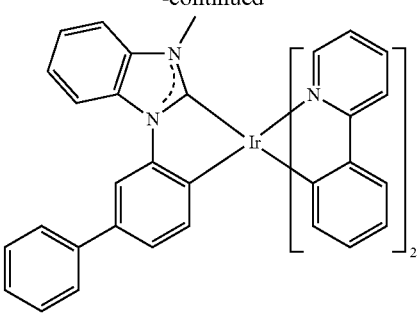
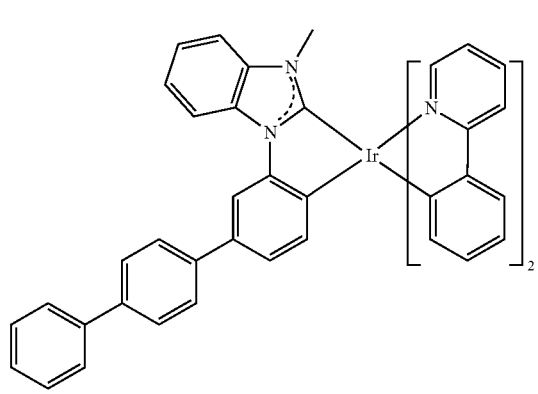
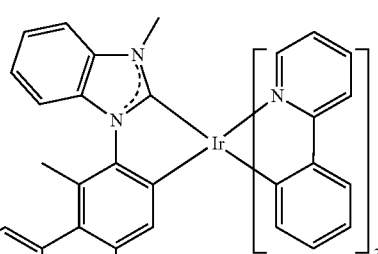

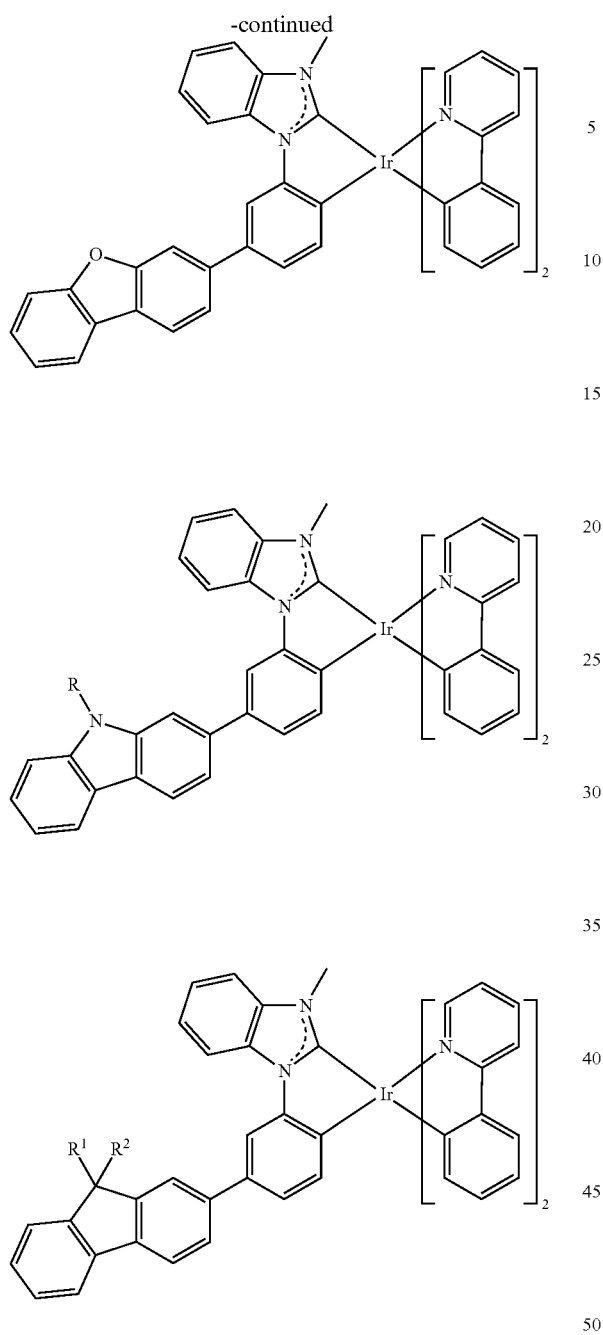

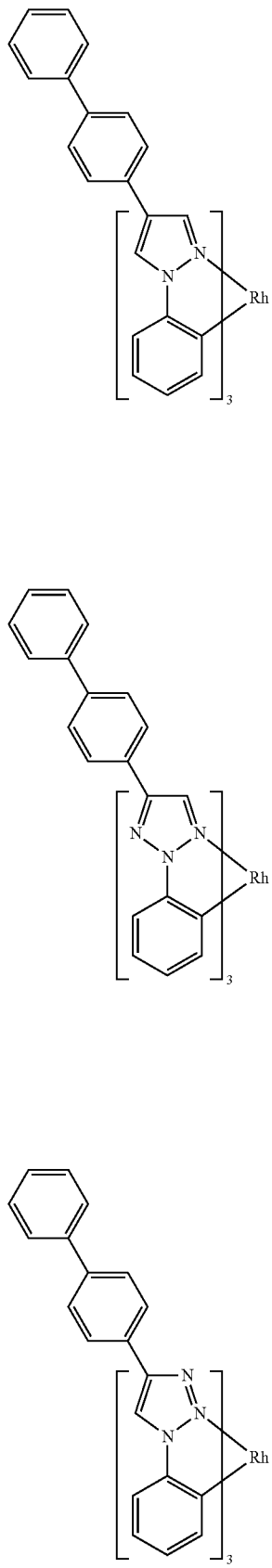

Structures Rh-1 wherein each of R, R¹, and R² is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

14. A compound selected from any of Structures Rh-1 to Rh-16 and Rh-19 to Rh-23:

611
-continued
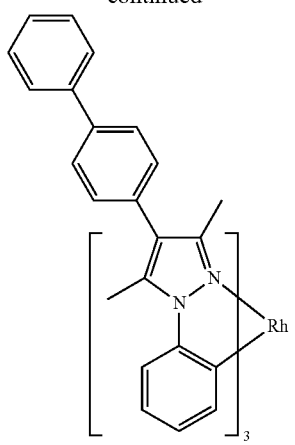
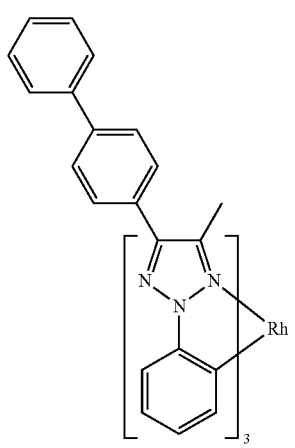
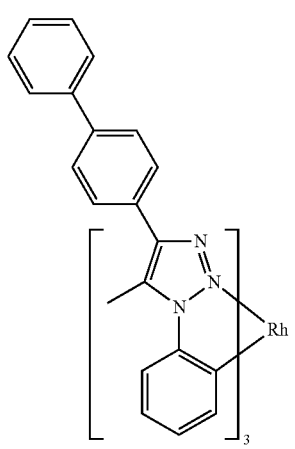
612
-continued
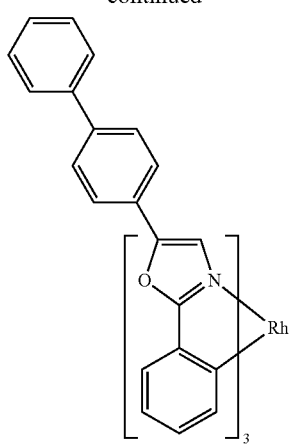
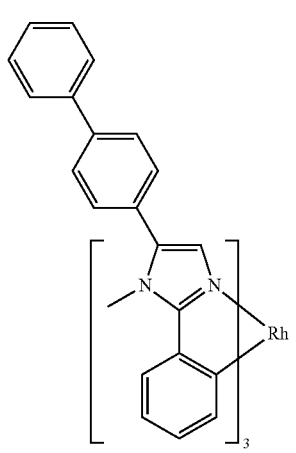

613
-continued
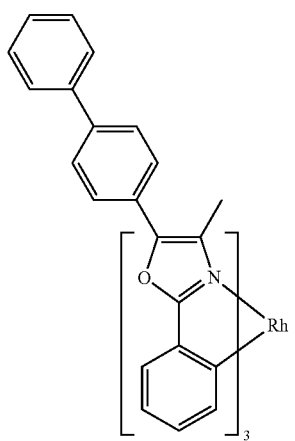
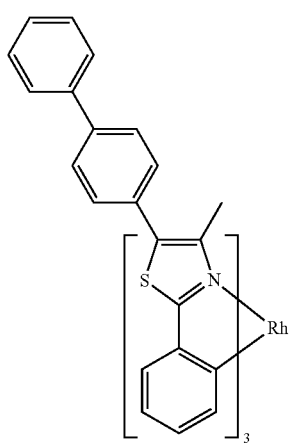
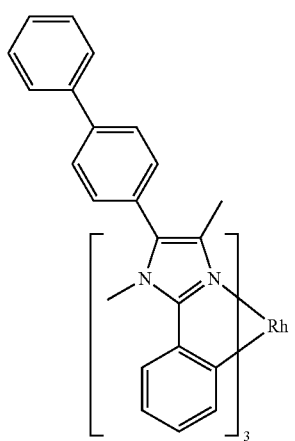
614
-continued
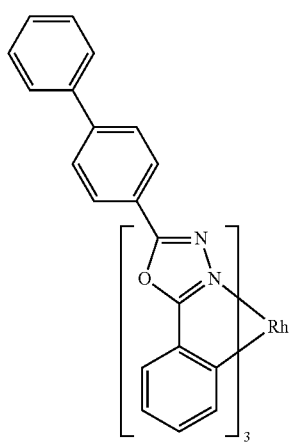
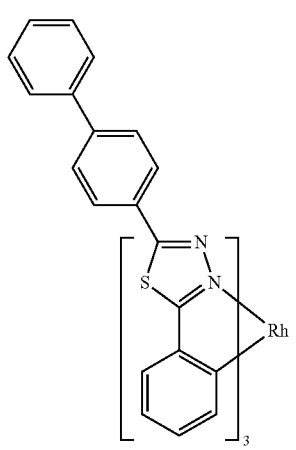
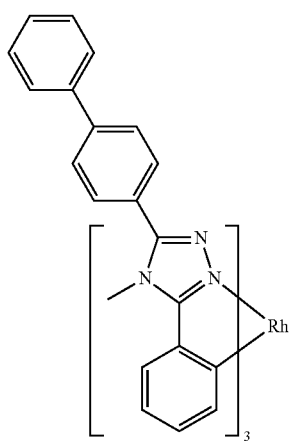

615
-continued
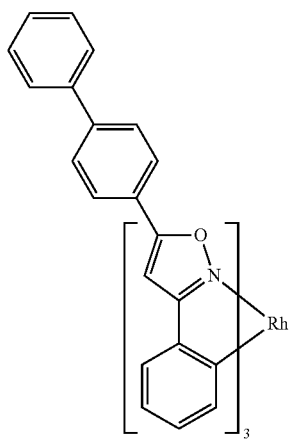
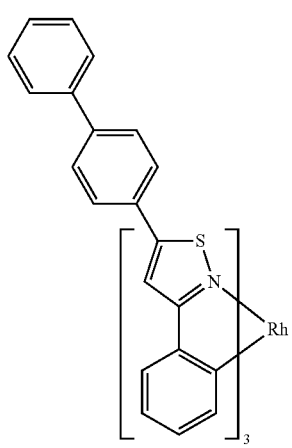
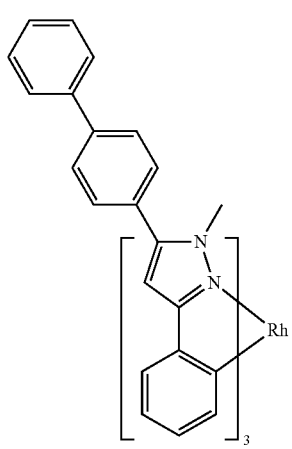
616
-continued
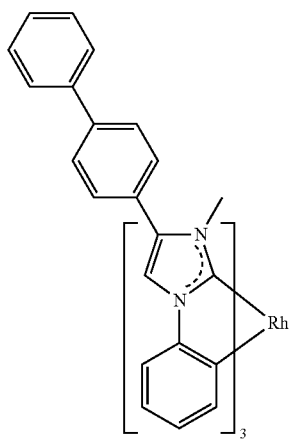
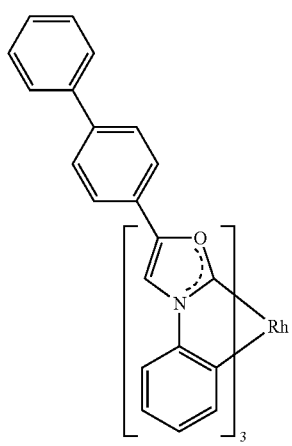
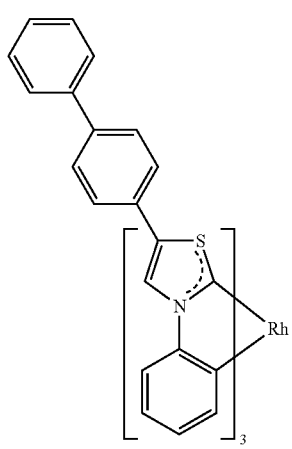

617
-continued
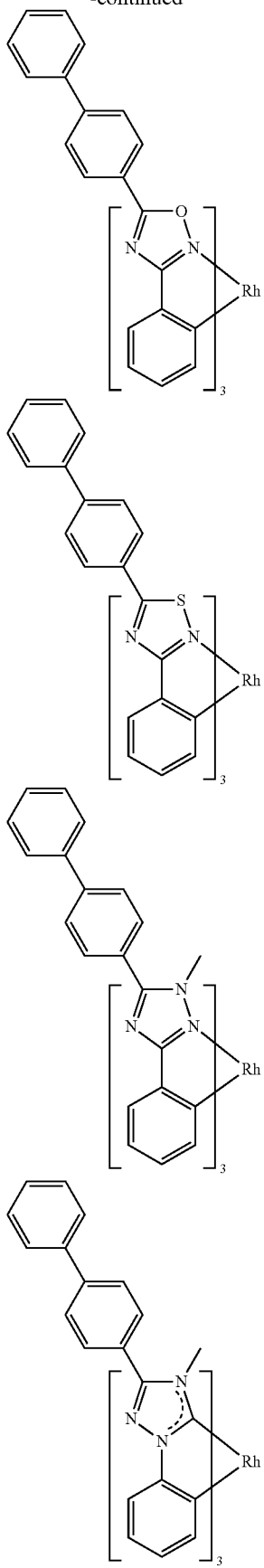
618
-continued
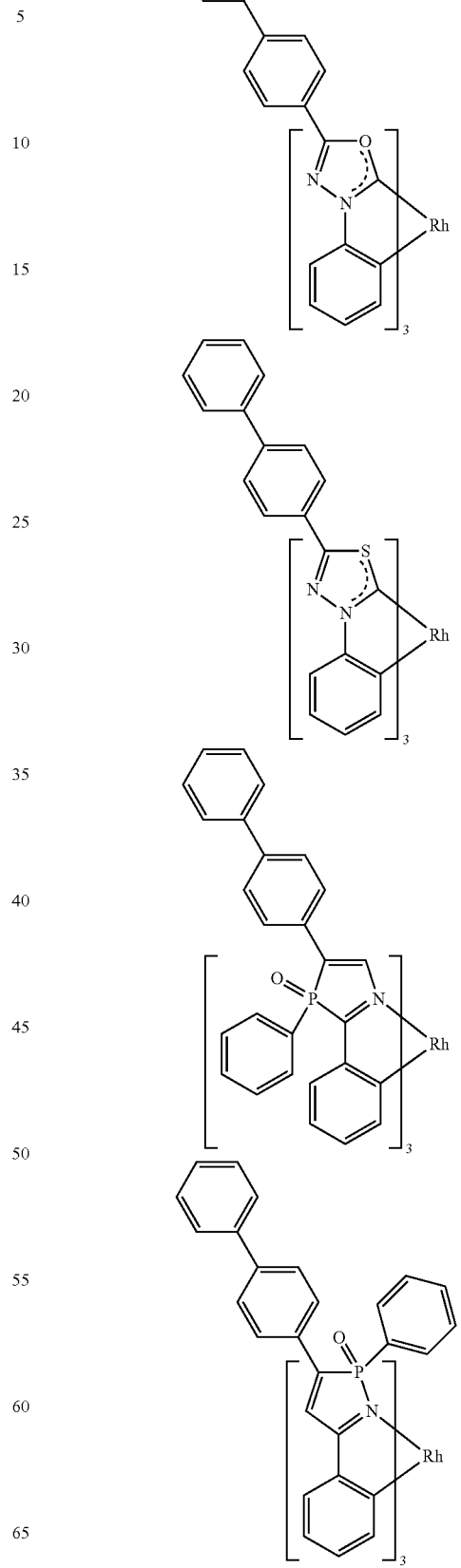

619
-continued
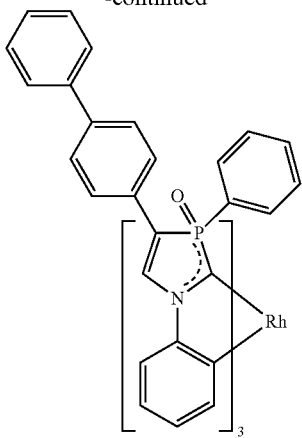
Structures Rh-2
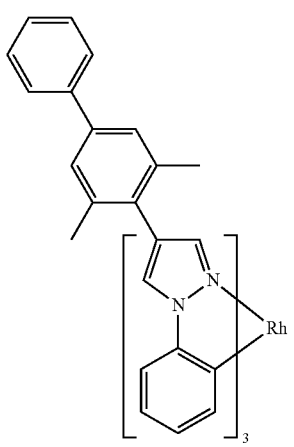
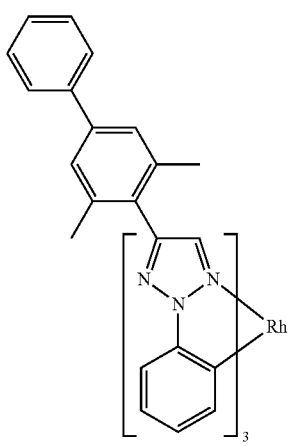
620
-continued
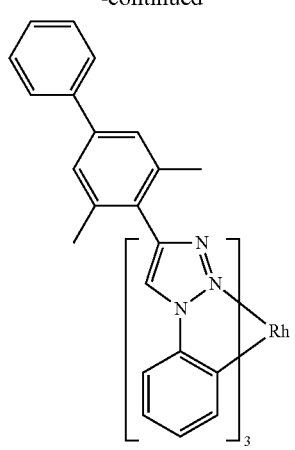
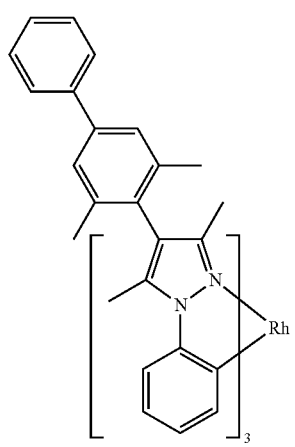
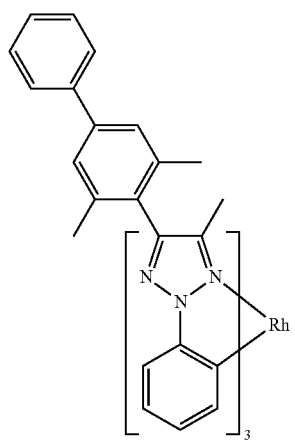

621
-continued
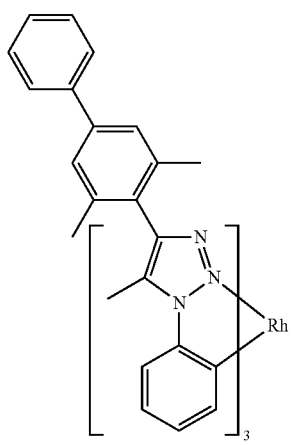
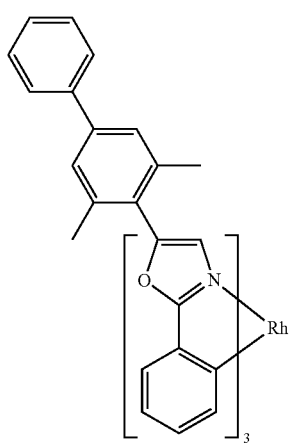
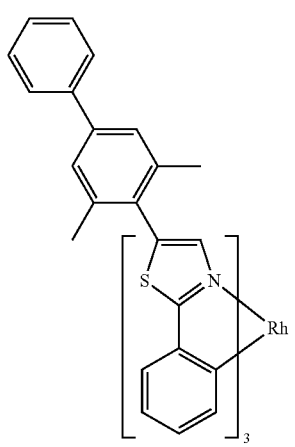
622
-continued
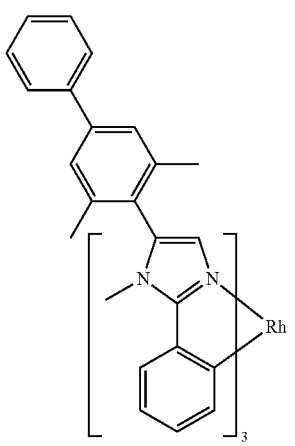
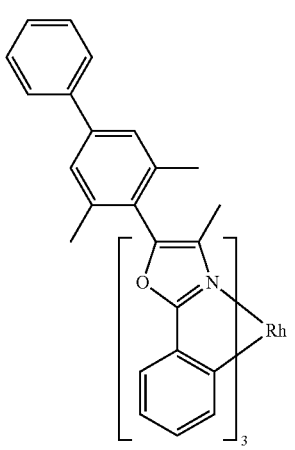
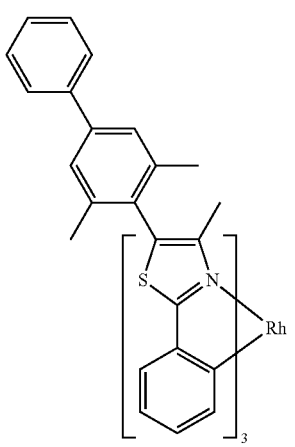

623
-continued
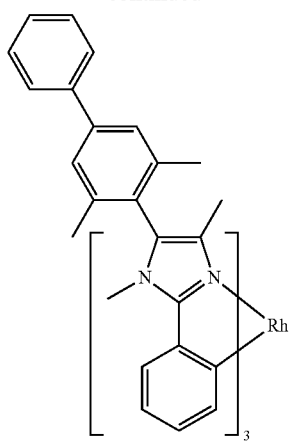
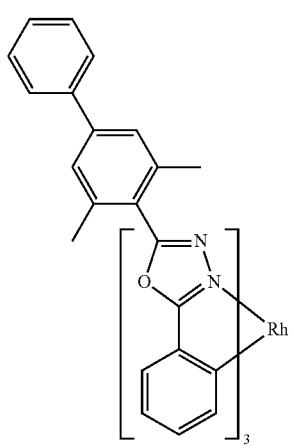
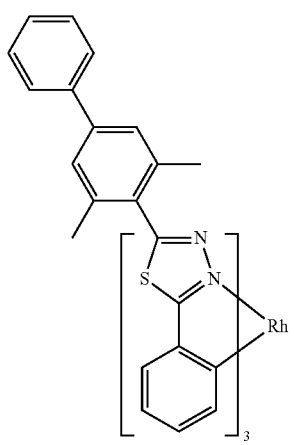
624
-continued
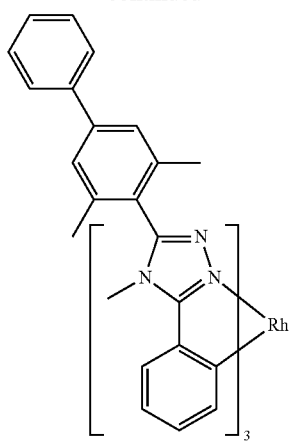
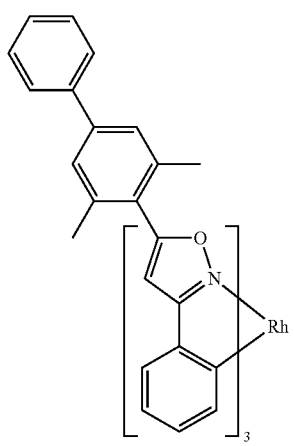
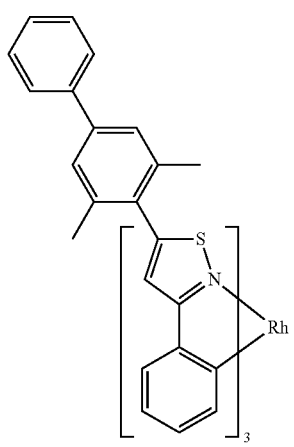

625
-continued
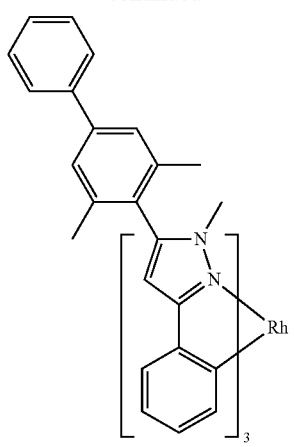
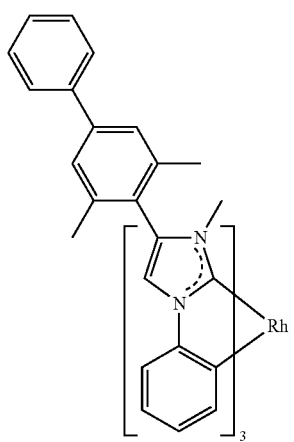
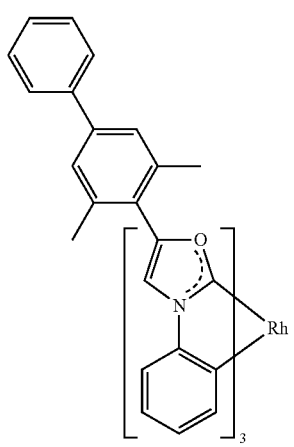
626
-continued
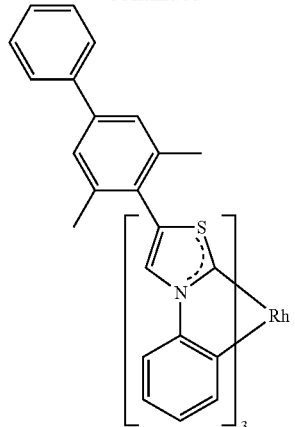
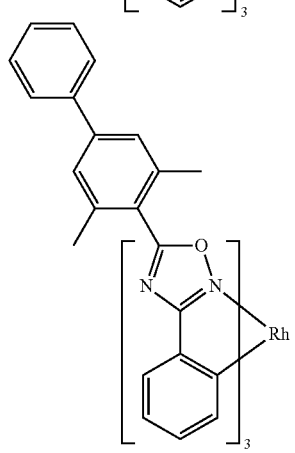
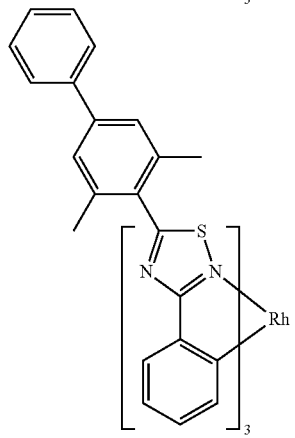
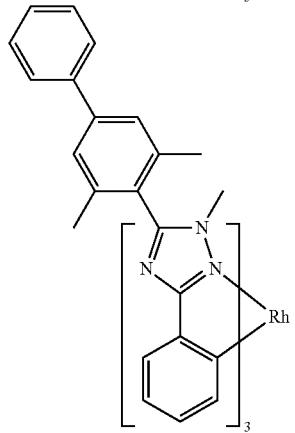

627
-continued
628
-continued
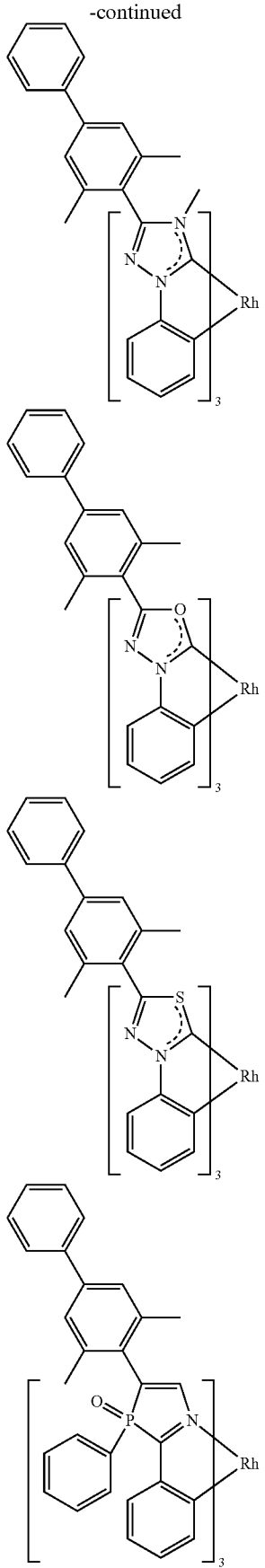
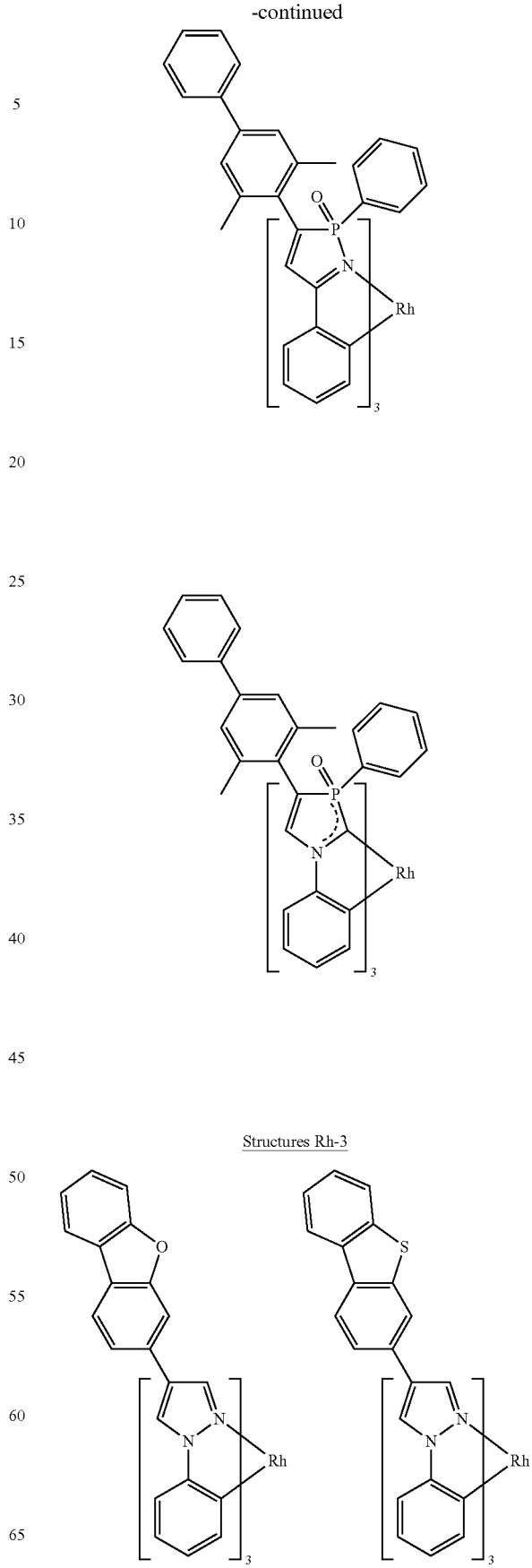
Structures Rh-3

629
-continued
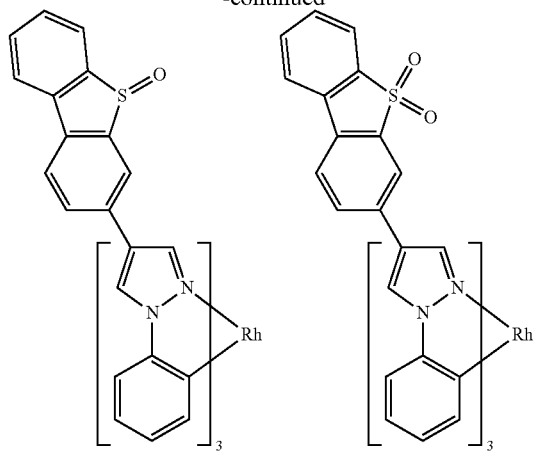
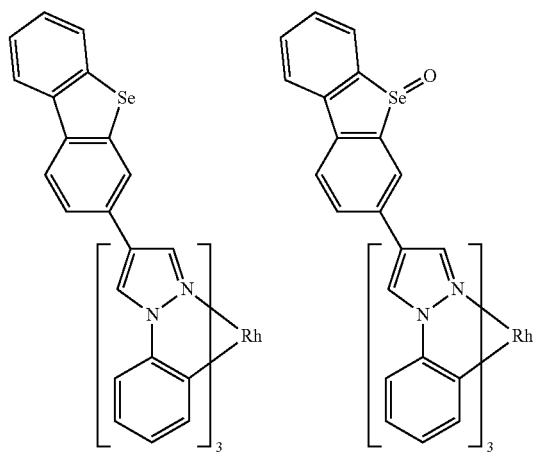
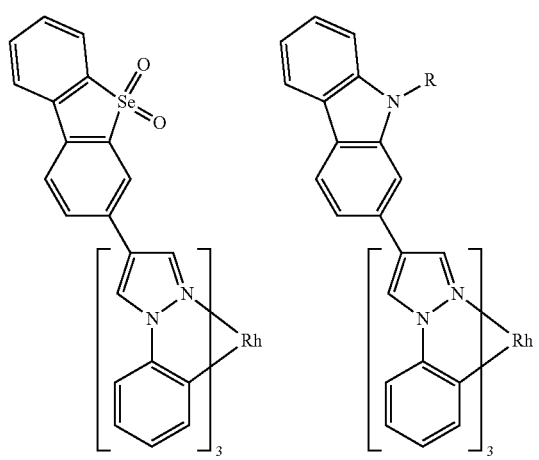
630
-continued
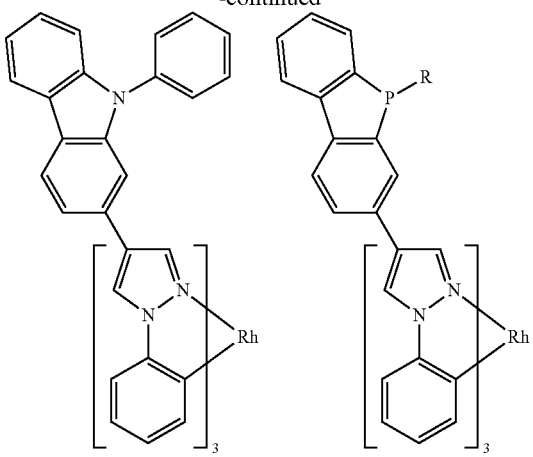
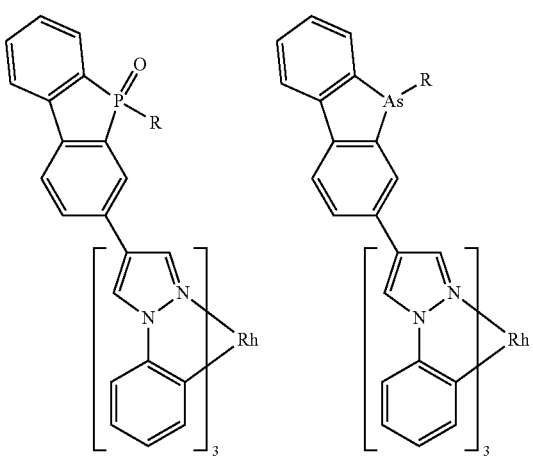
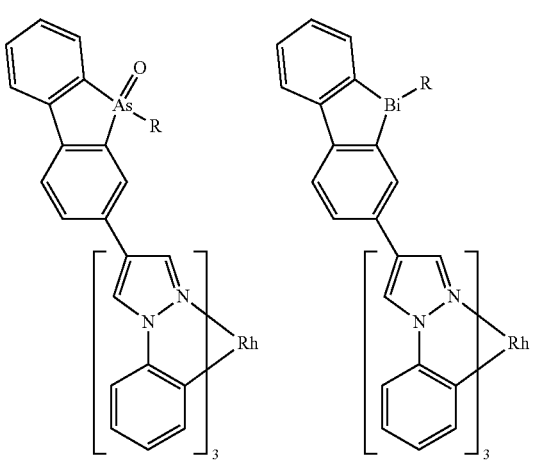

631
-continued
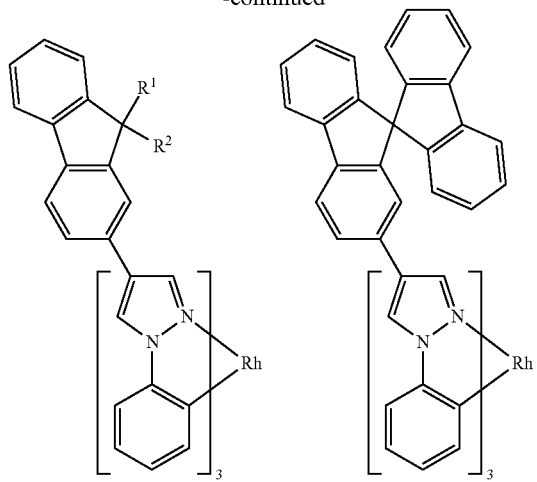
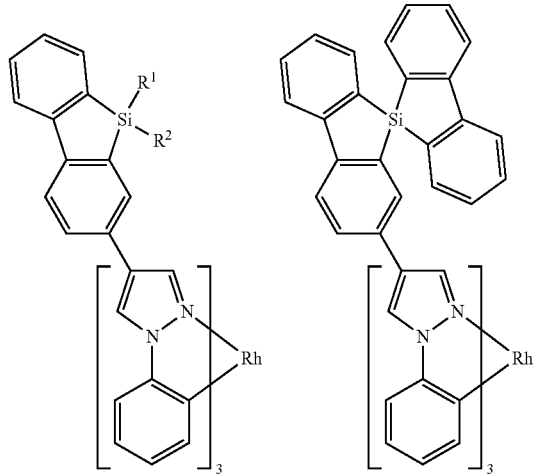
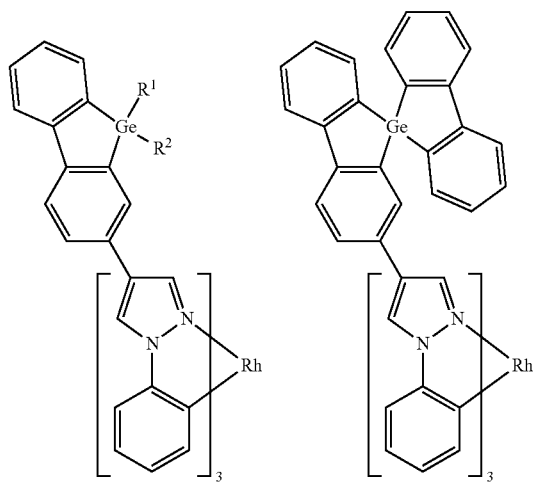
632
-continued
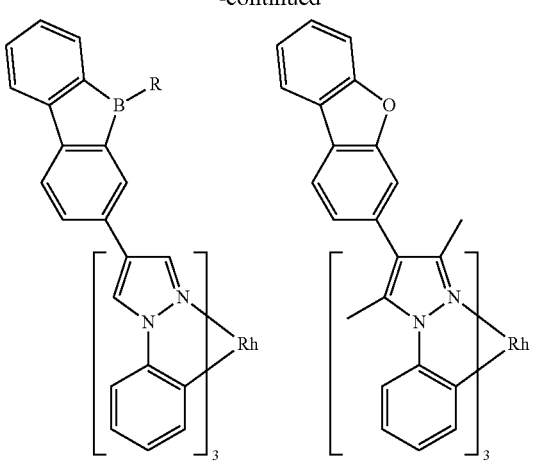
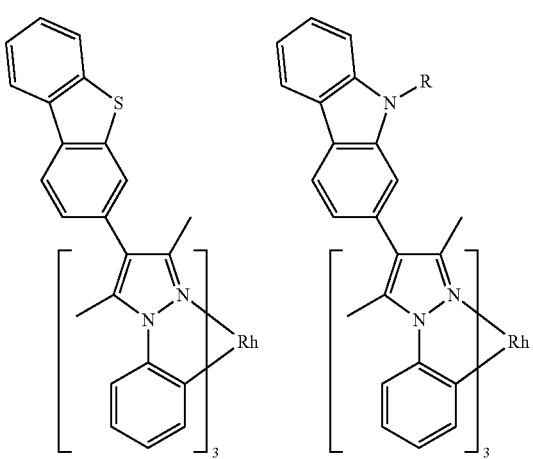
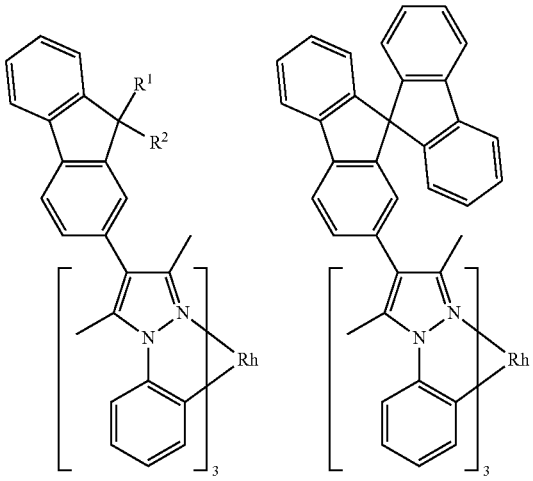

633
-continued
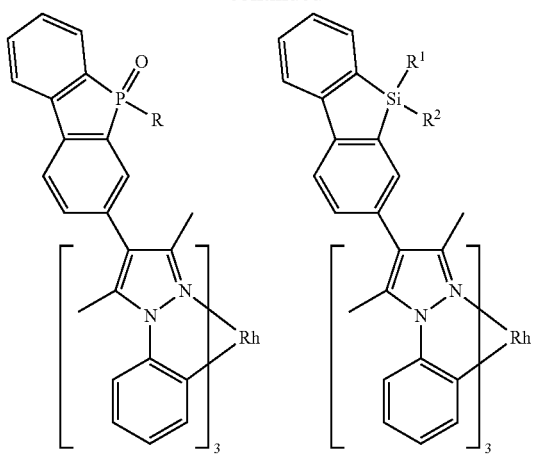
634
-continued
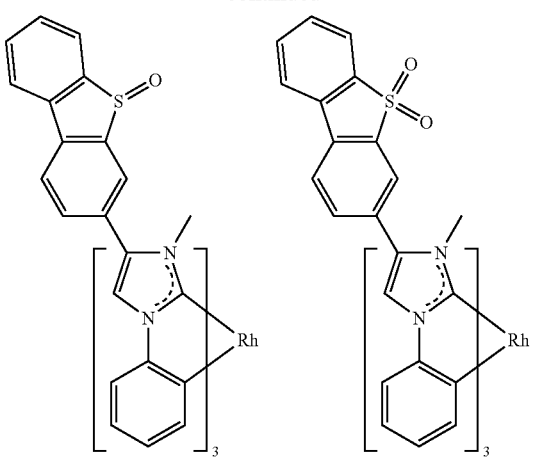
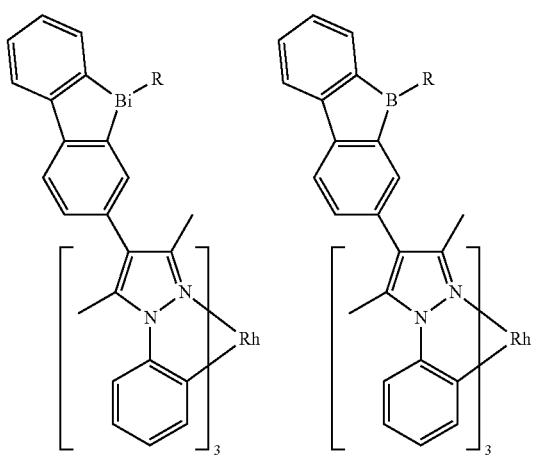
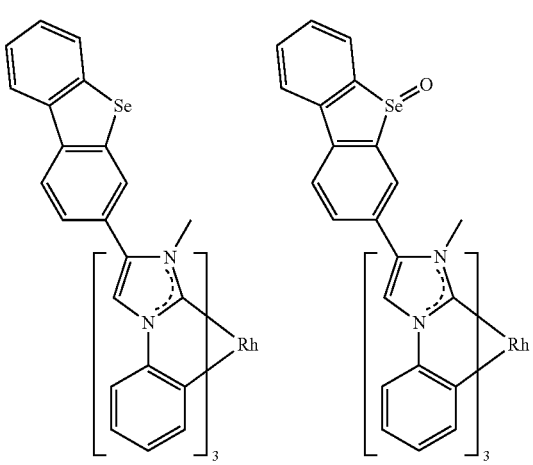
Structures Rh-4
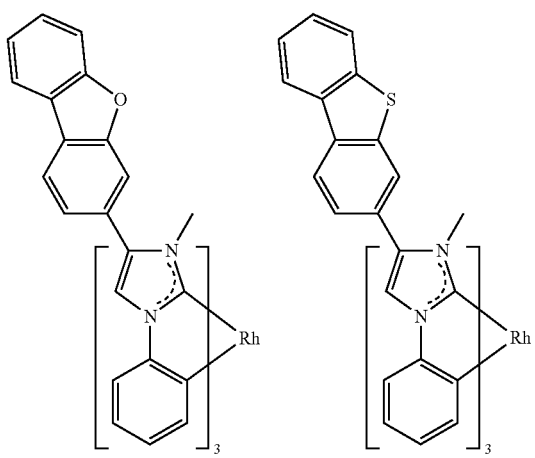
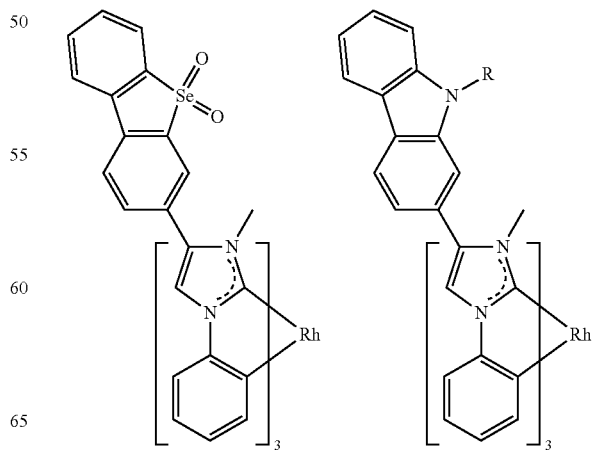

635
-continued
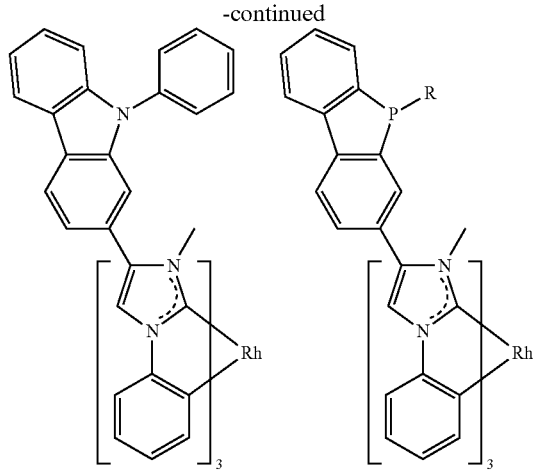
636
-continued
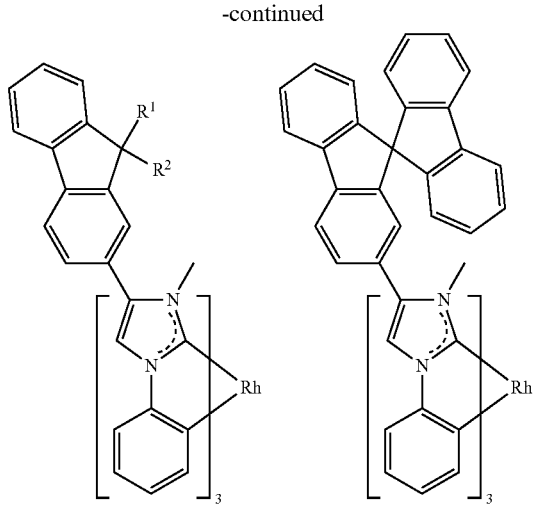
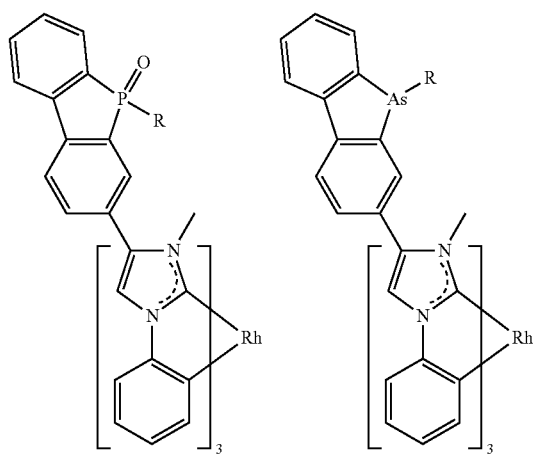
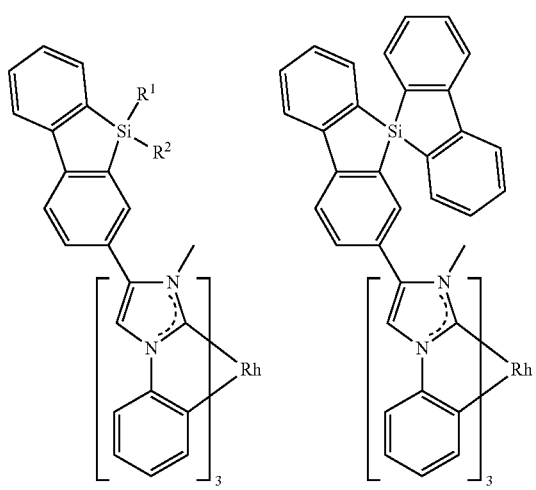
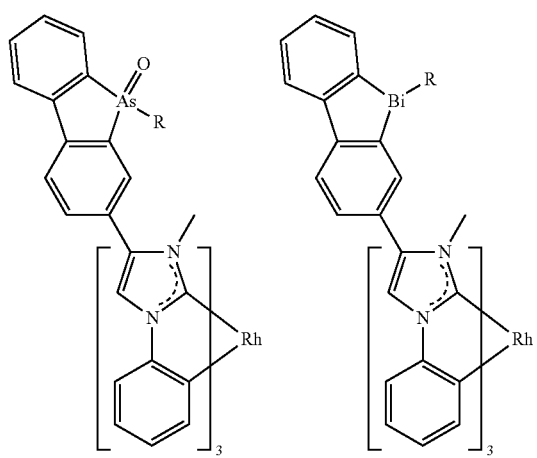
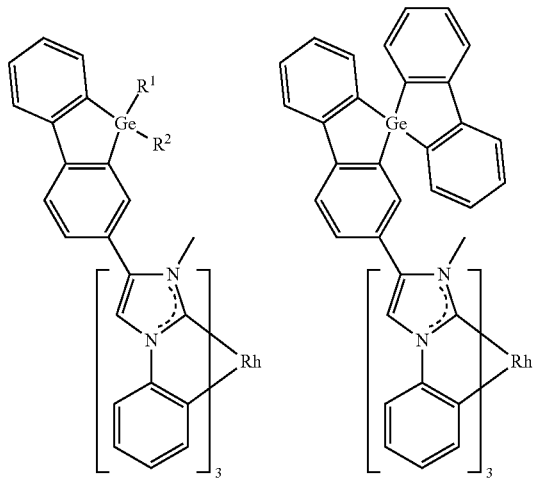

637
-continued
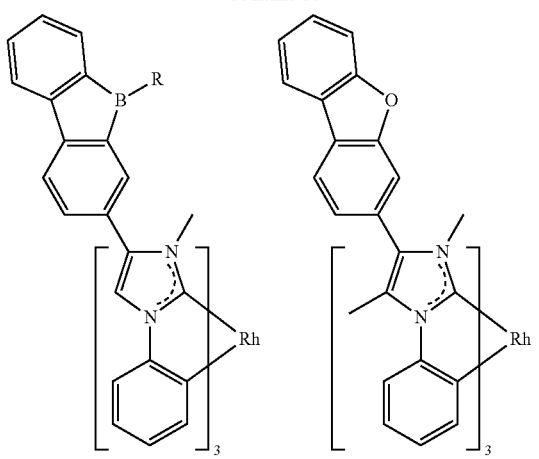
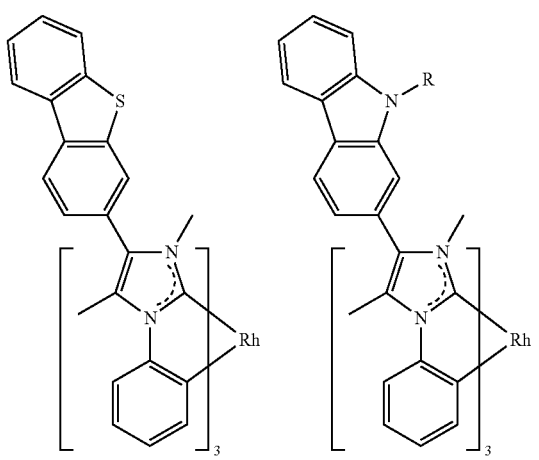
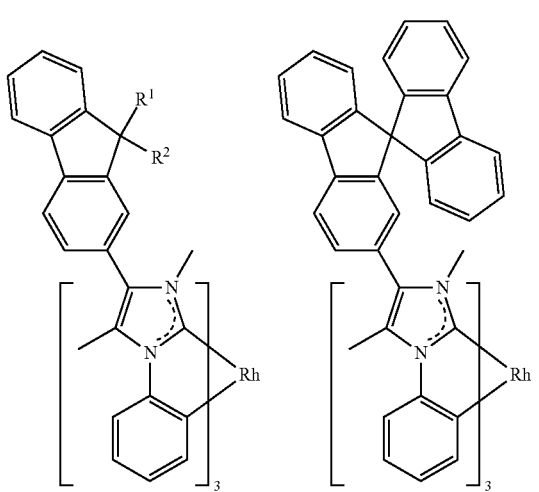
638
-continued
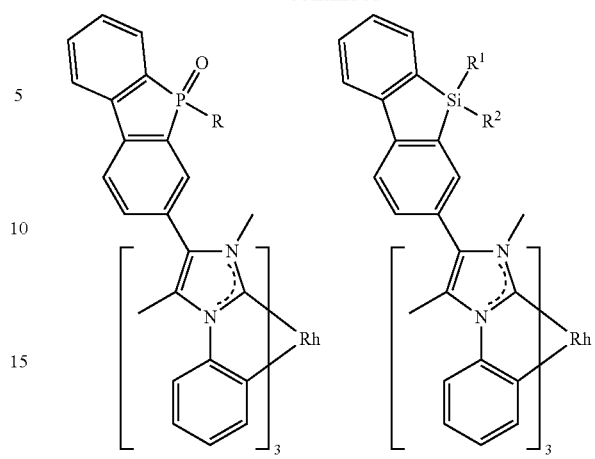
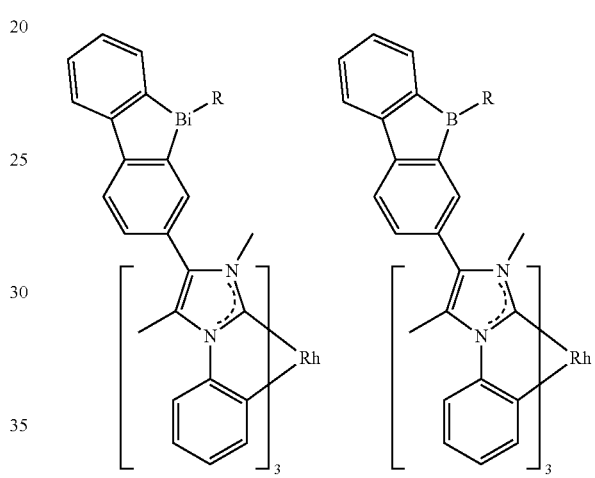
Structures Rh-5
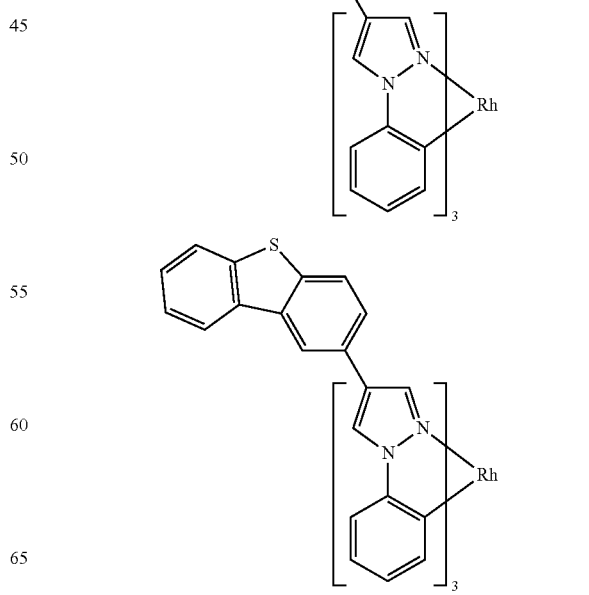

639 -continued

640 -continued

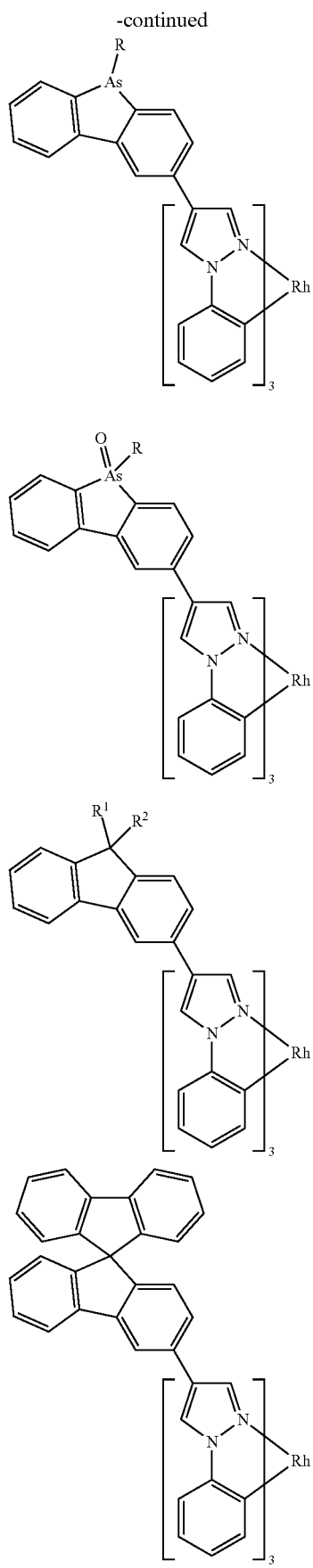

643
-continued
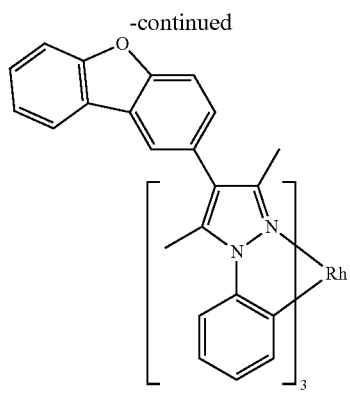
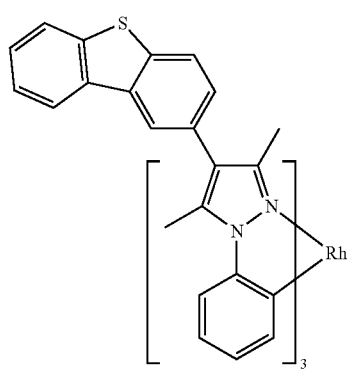
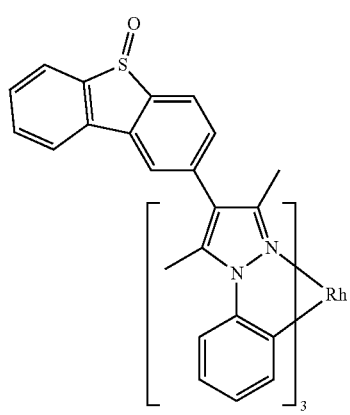
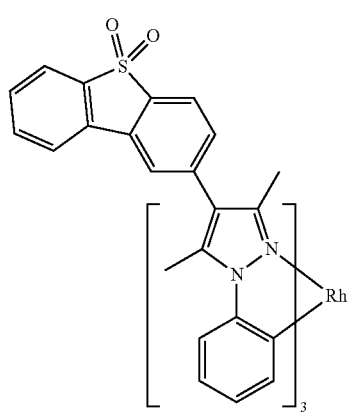
644
-continued
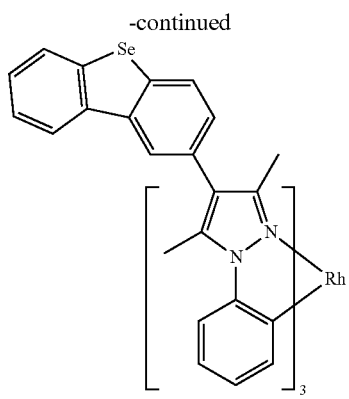
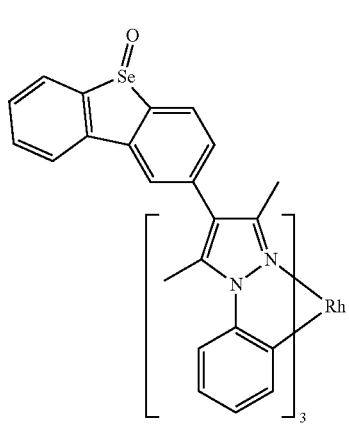
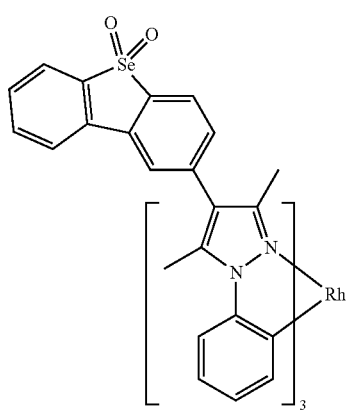
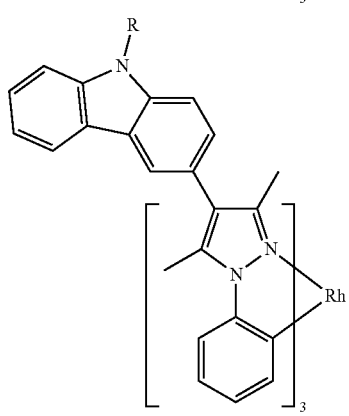

645
-continued
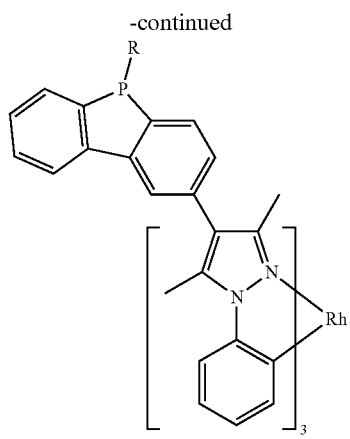
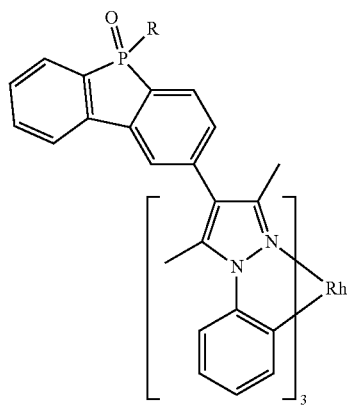
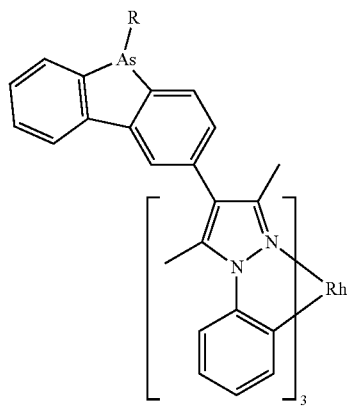
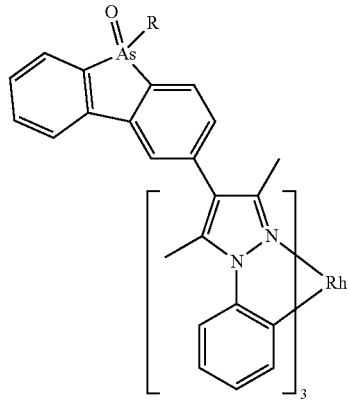
646
-continued
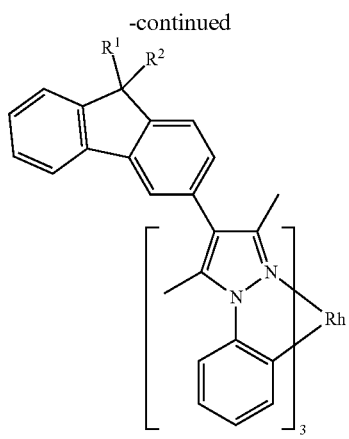
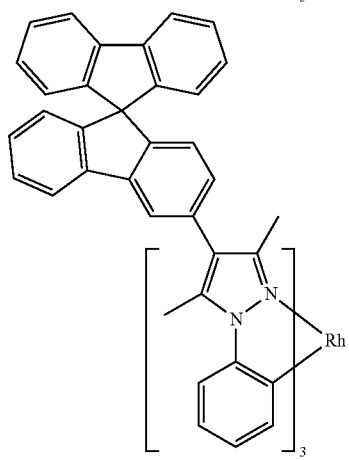
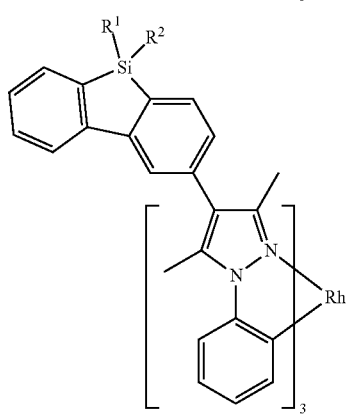
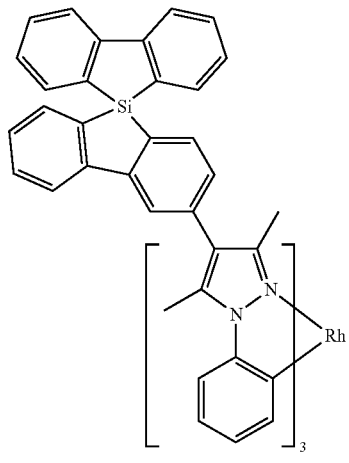

647
-continued
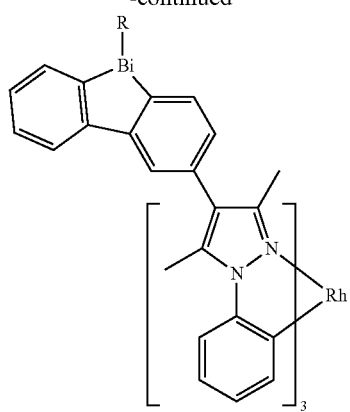
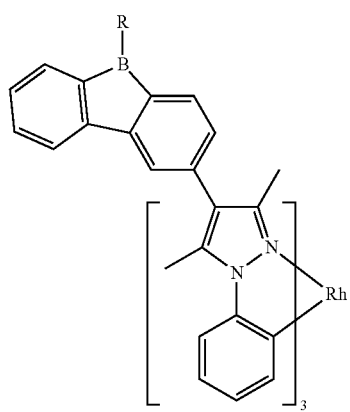
Structures Rh-6
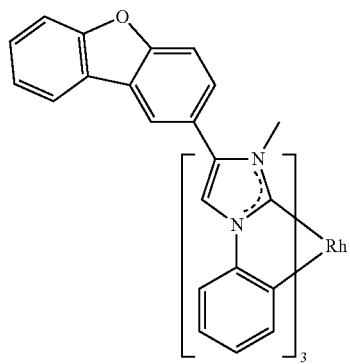
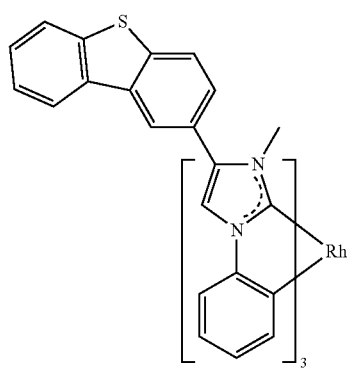
648
-continued
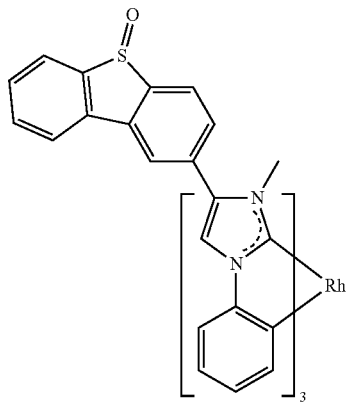
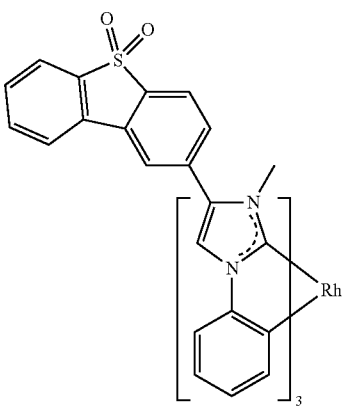
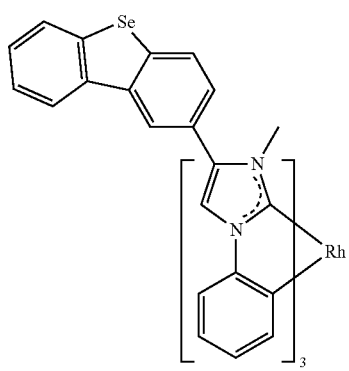
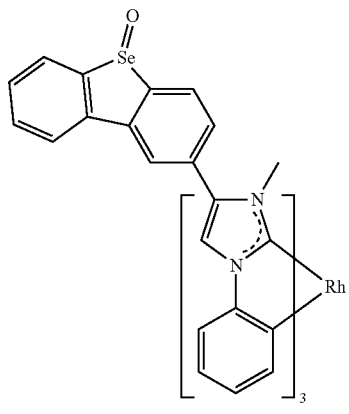

649
-continued
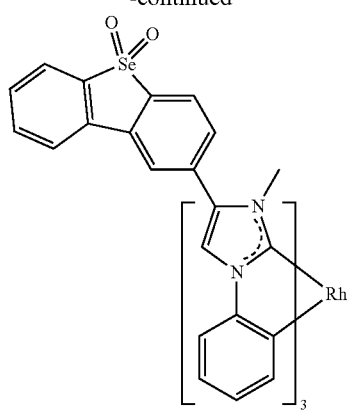
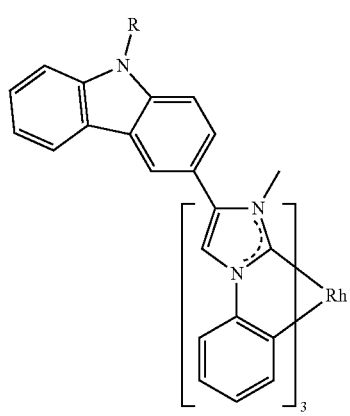
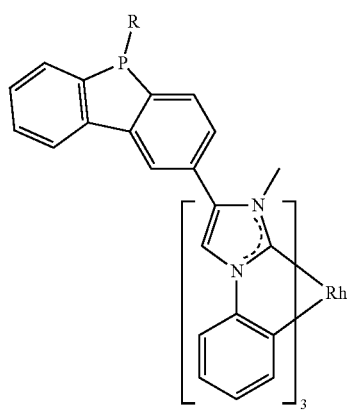
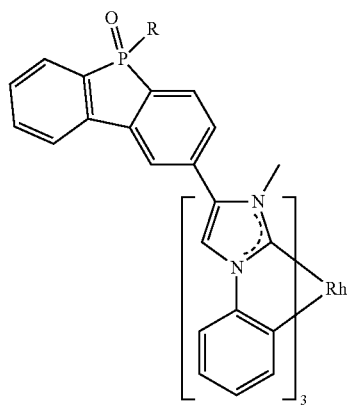
650
-continued
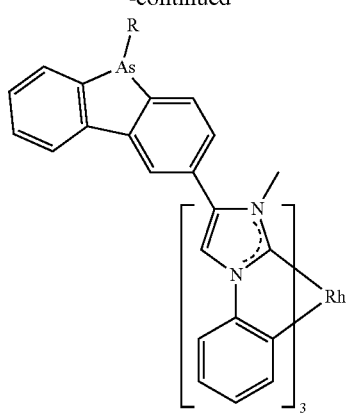
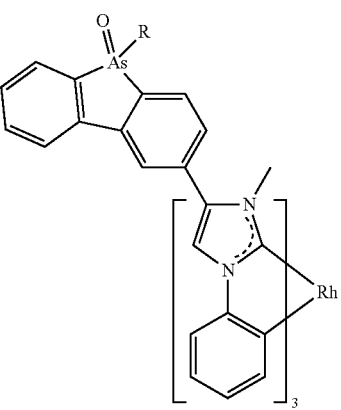
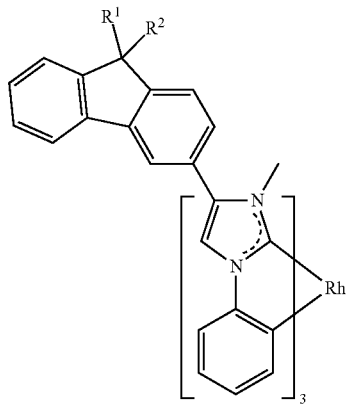
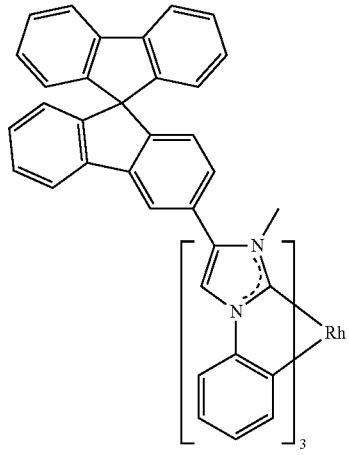

651
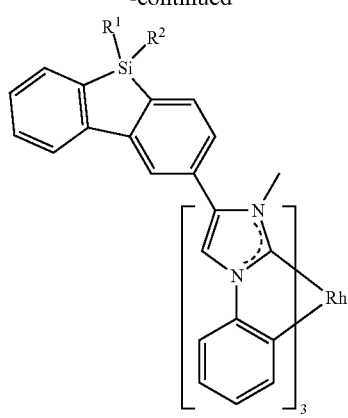
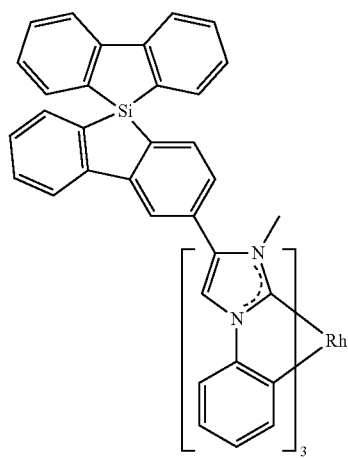
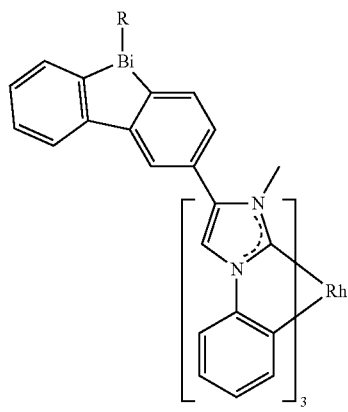
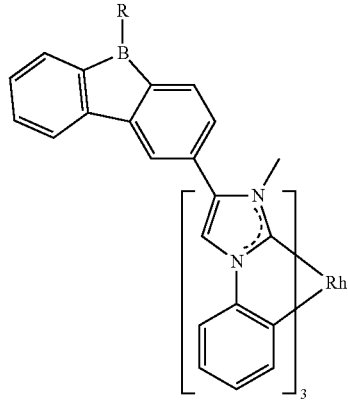
652
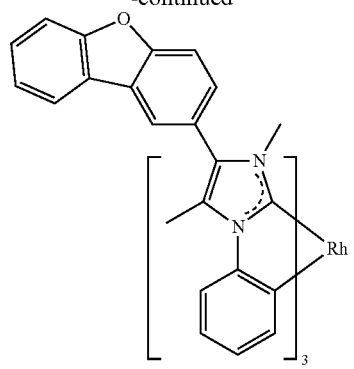
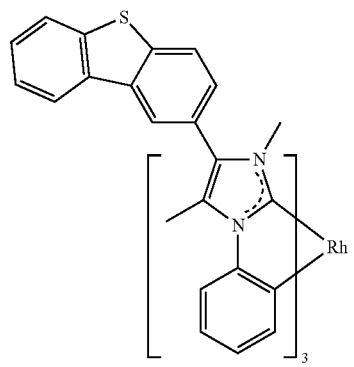
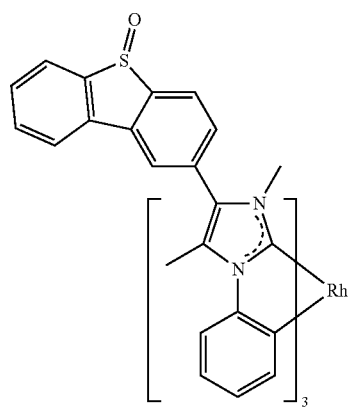
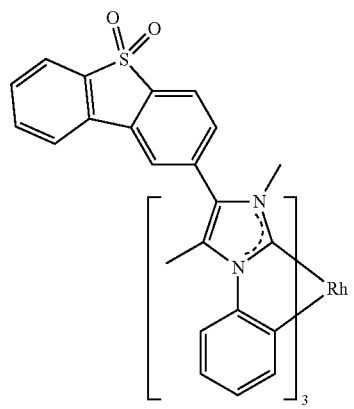

653
-continued
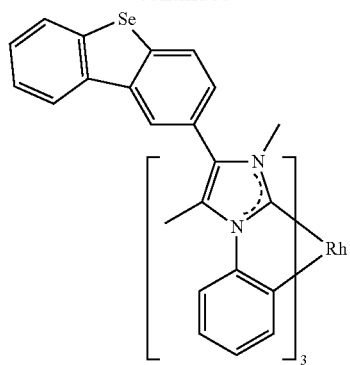
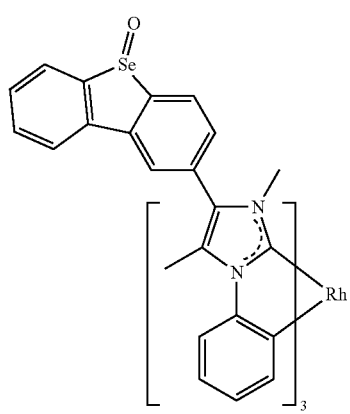
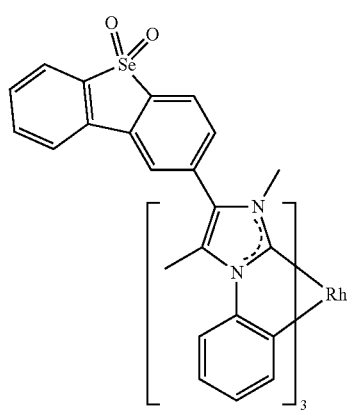
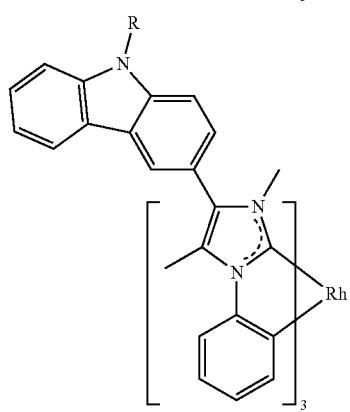
654
-continued
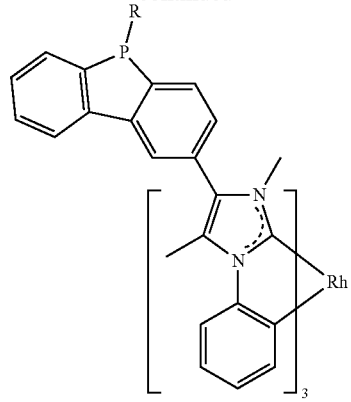
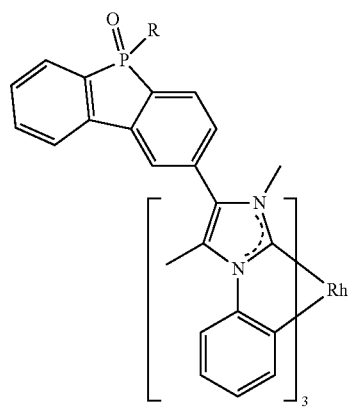
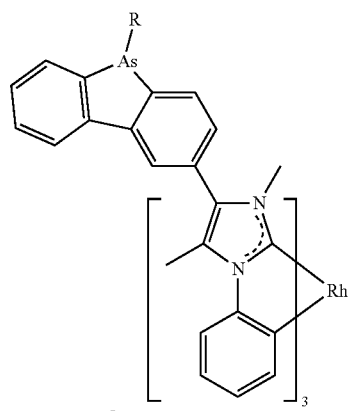
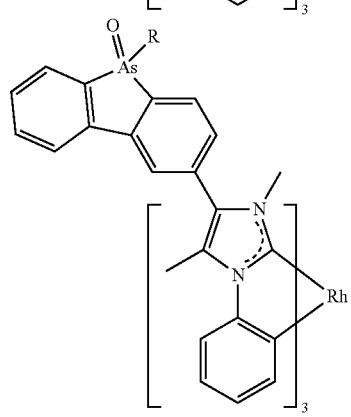

-continued
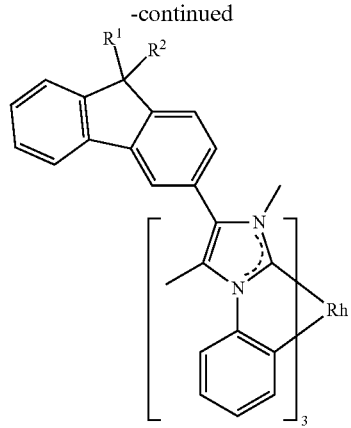
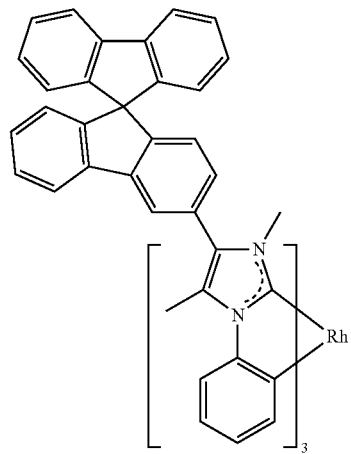
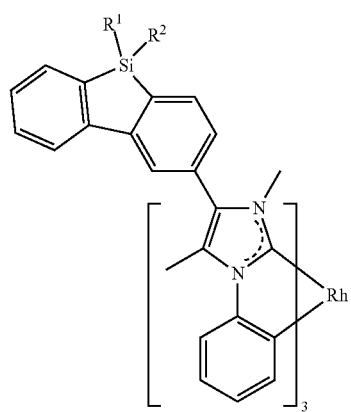
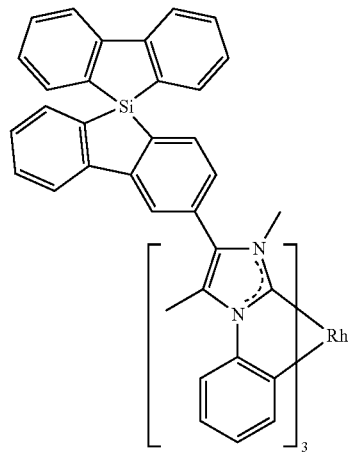
-continued
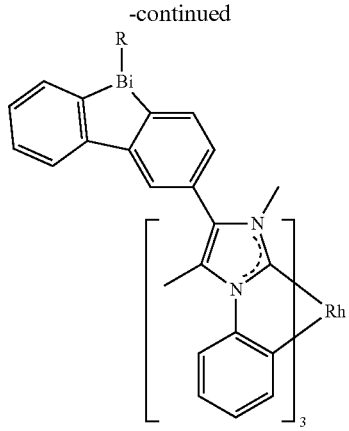
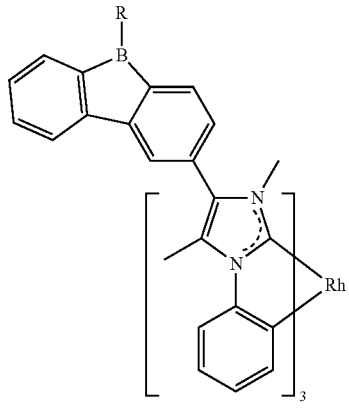
Structures Rh-7
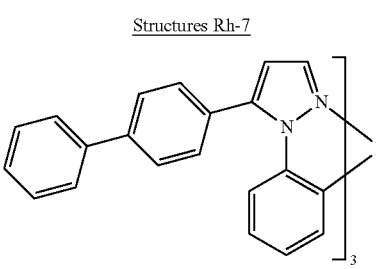
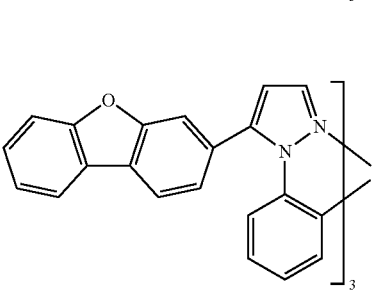
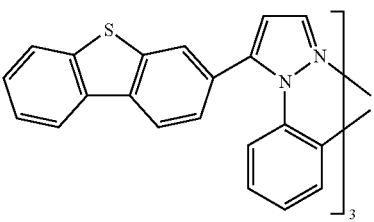

657
-continued
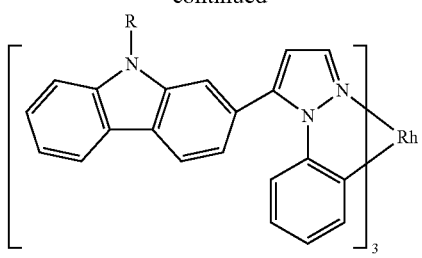
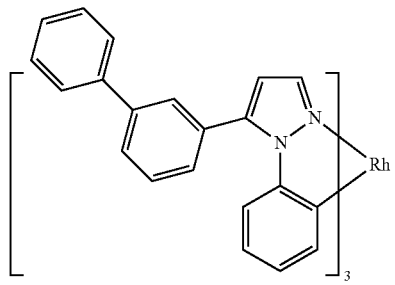
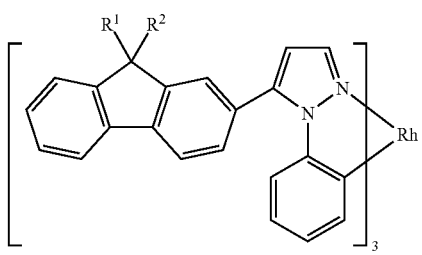
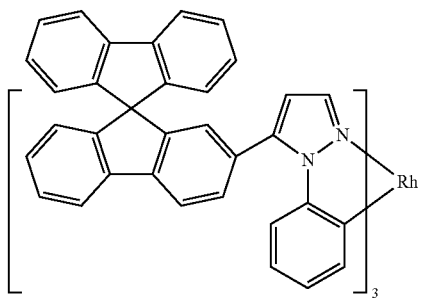
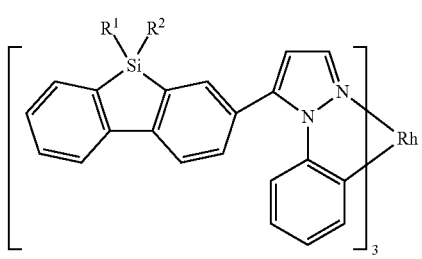
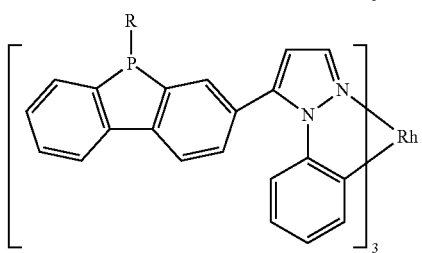
658
-continued
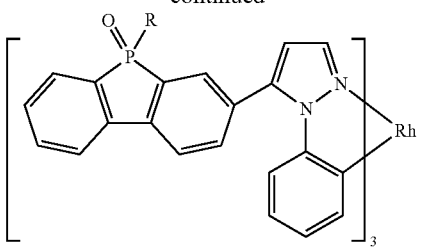
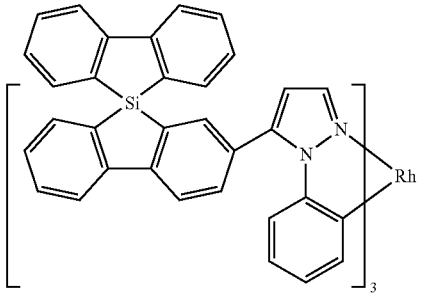
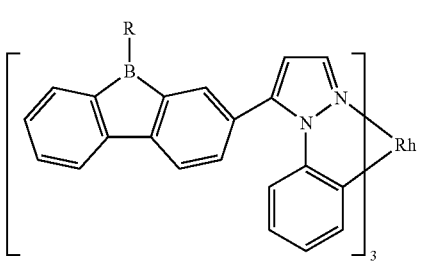
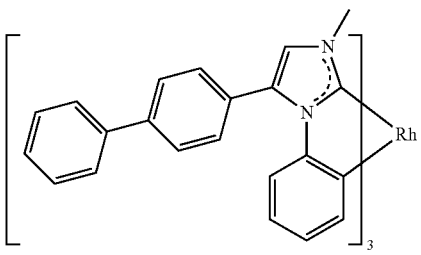
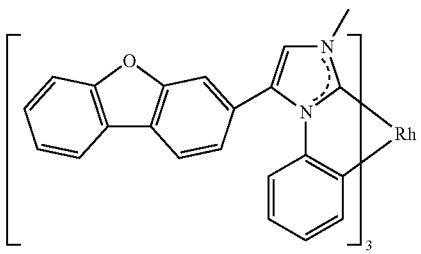
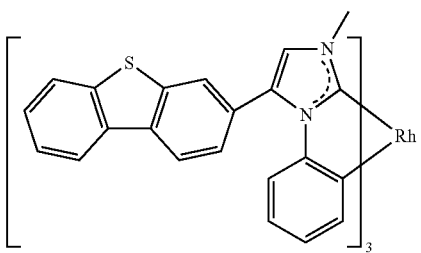

659
-continued
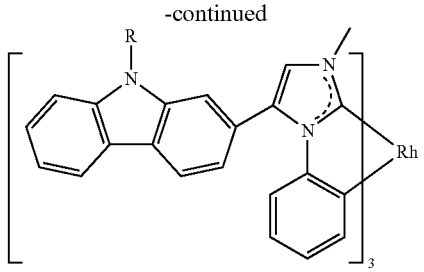
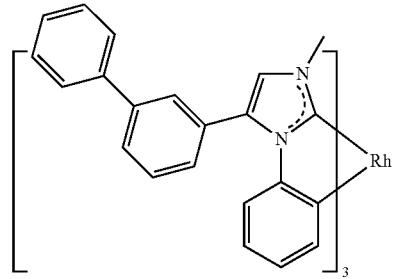
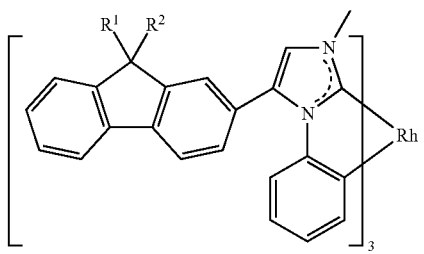
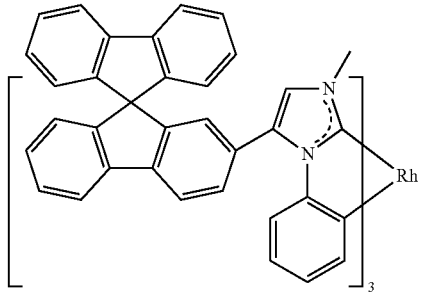
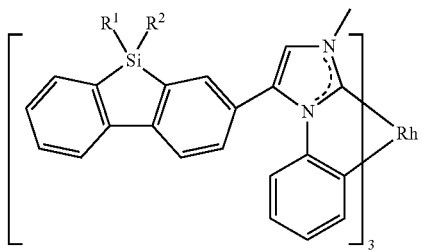
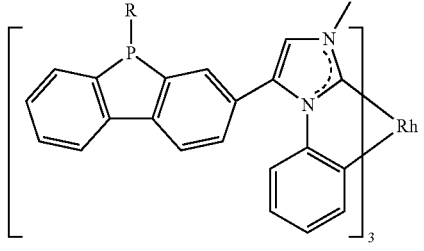
660
-continued
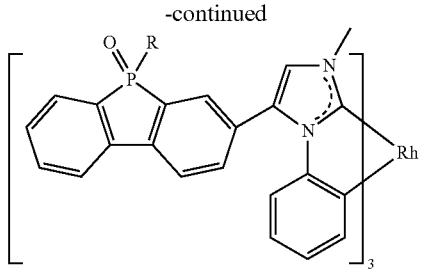
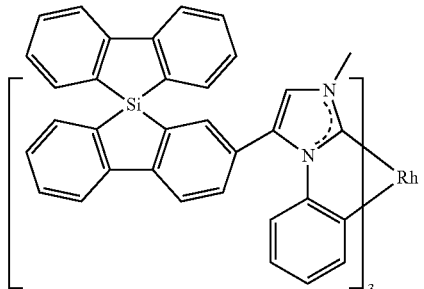
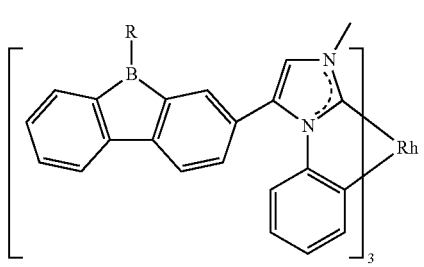
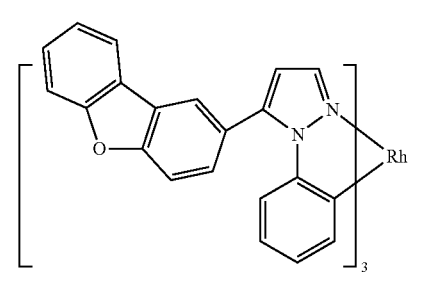
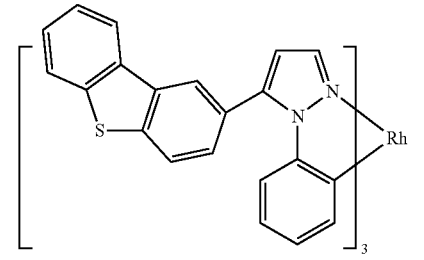
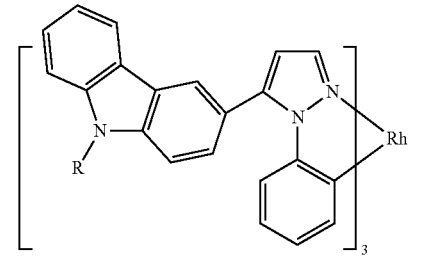

661
-continued
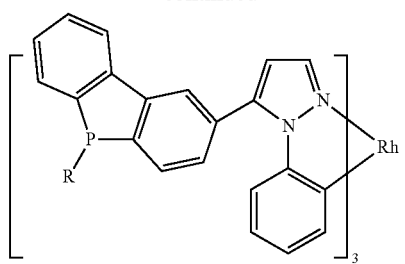
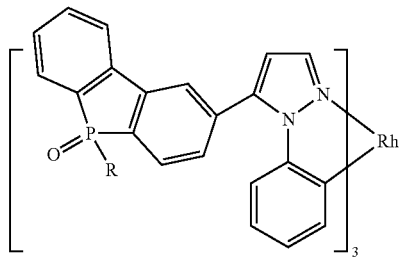
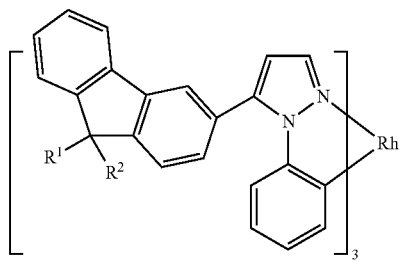
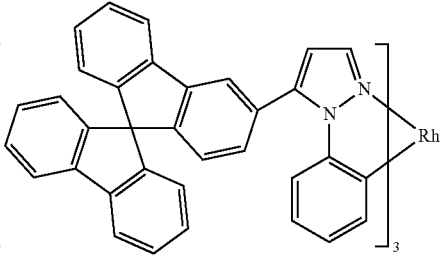
Structures Rh-8
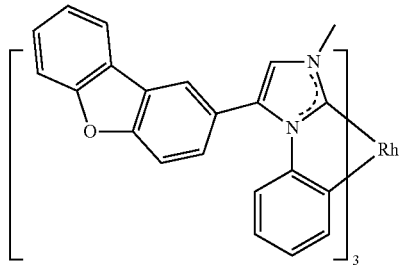
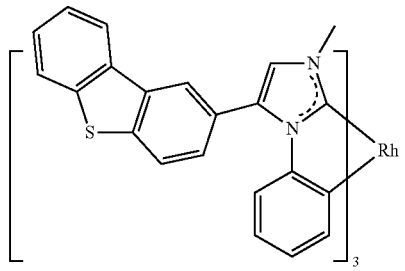
662
-continued
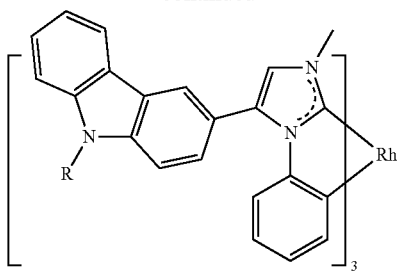
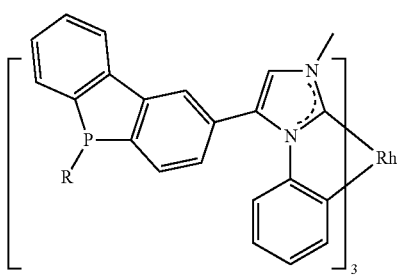
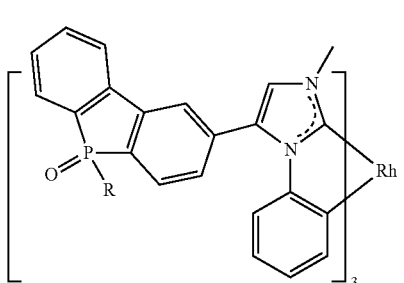
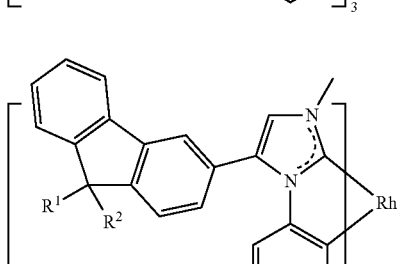
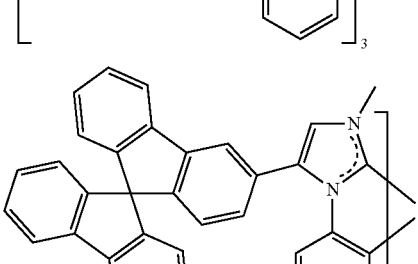
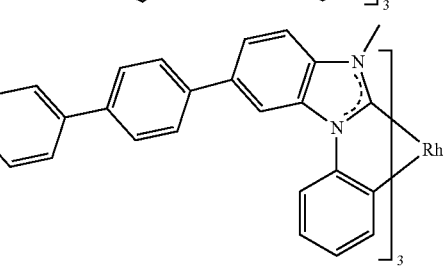

663
-continued
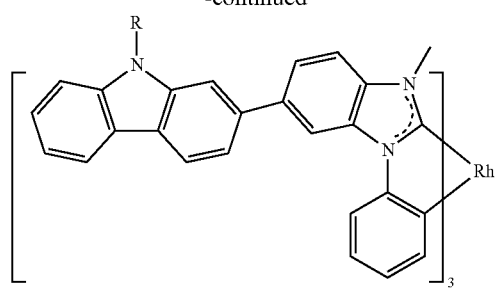
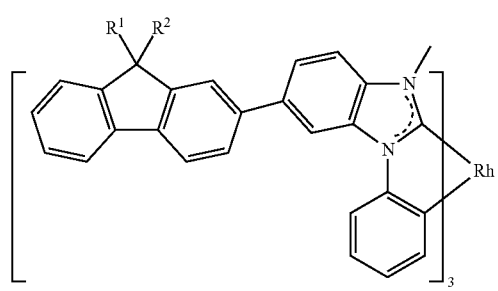
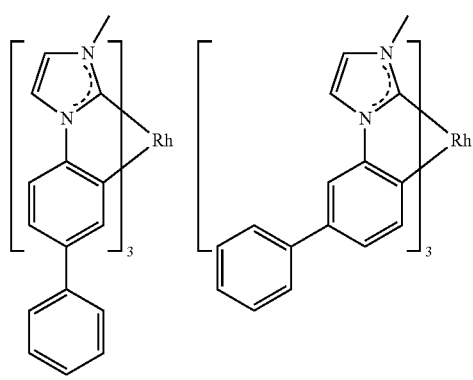
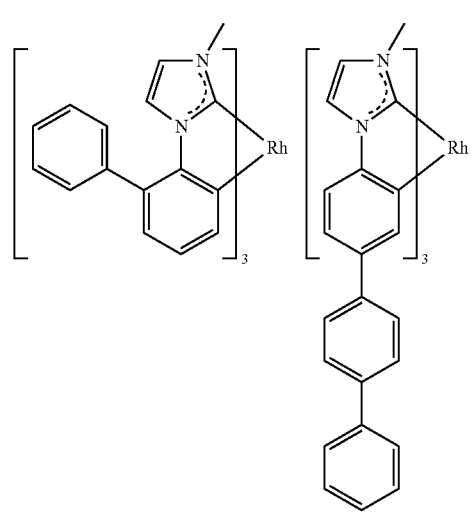
664
-continued
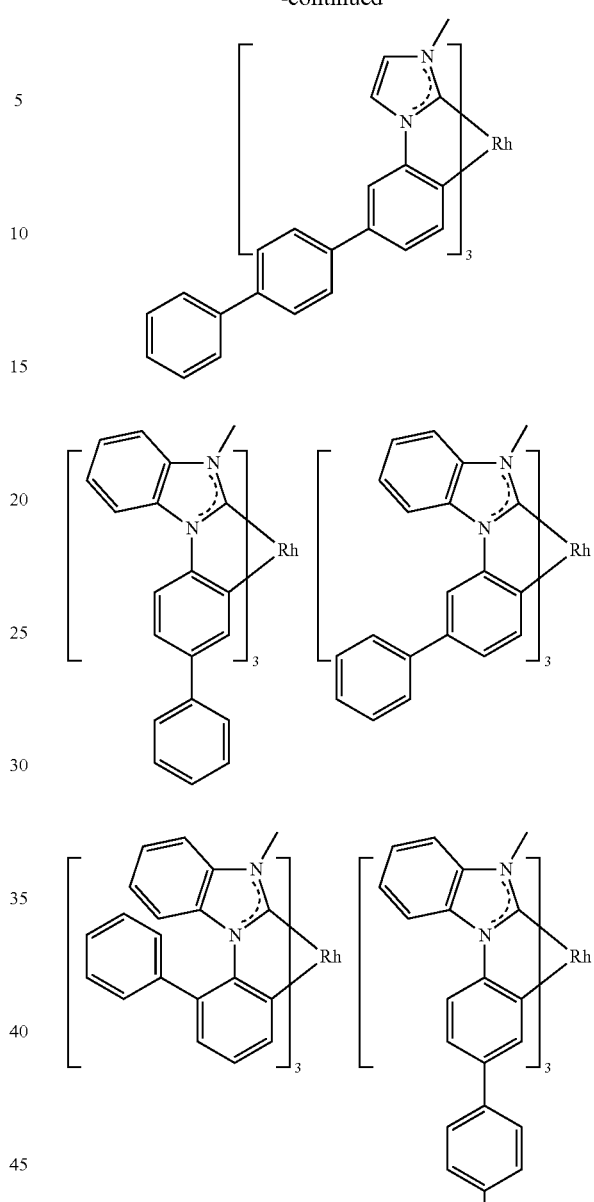
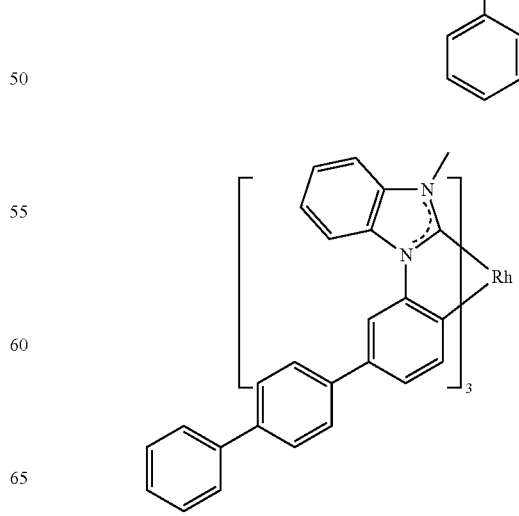

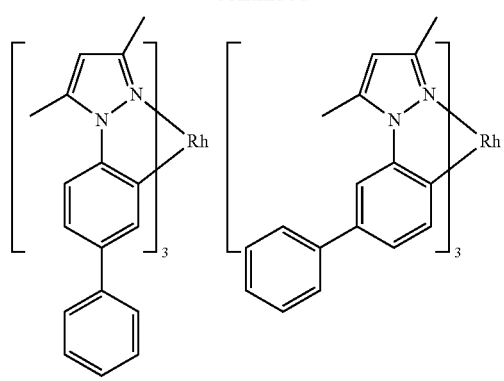
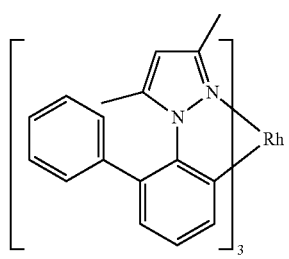
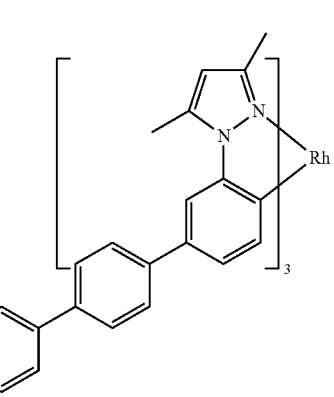
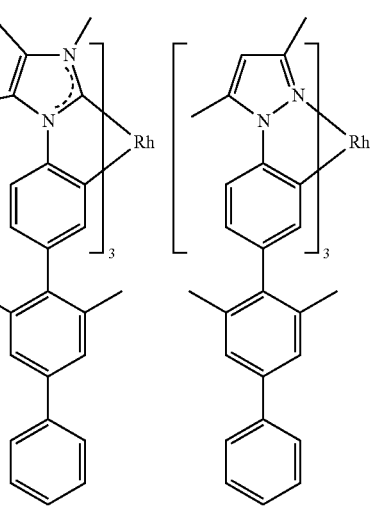
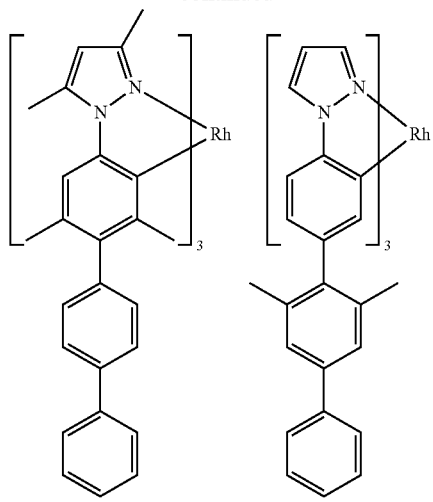
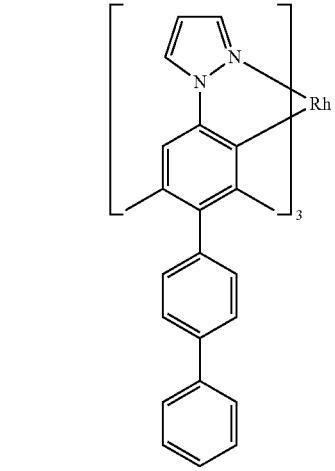
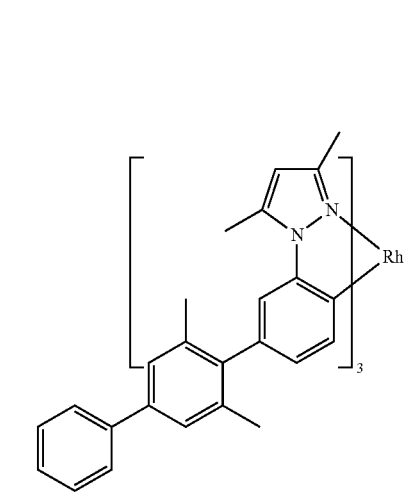

667
-continued
Structures Rh-9
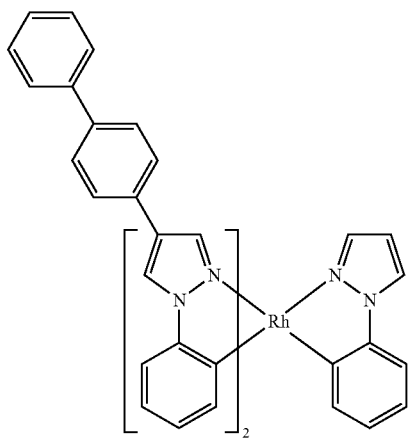
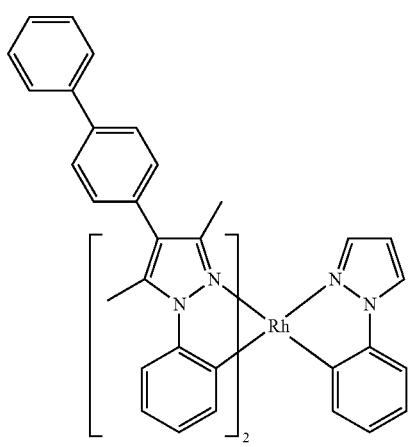
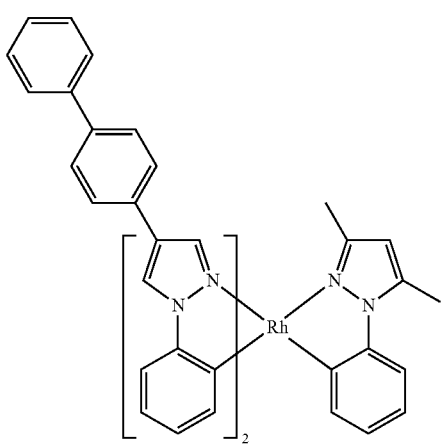
668
-continued
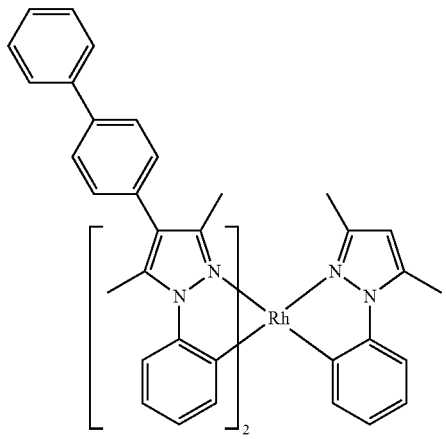
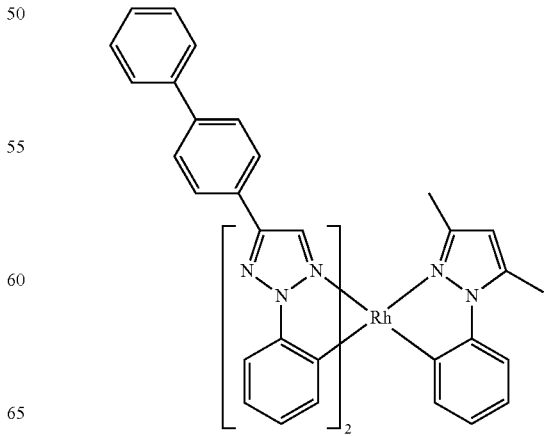

669
-continued
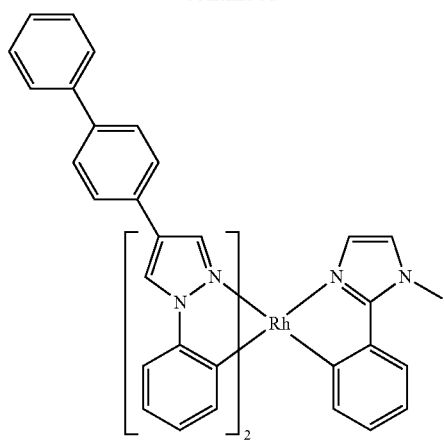
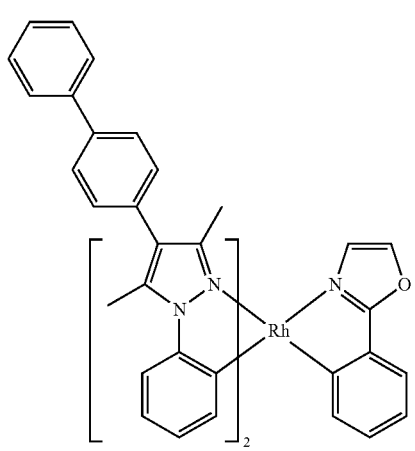
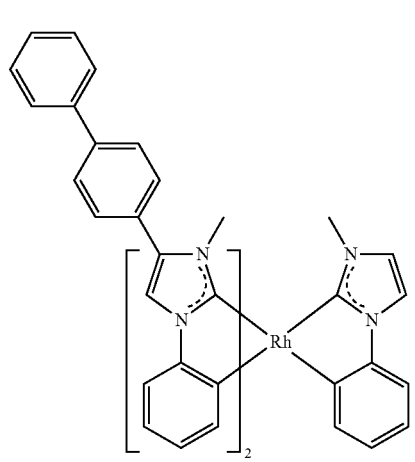
670
-continued
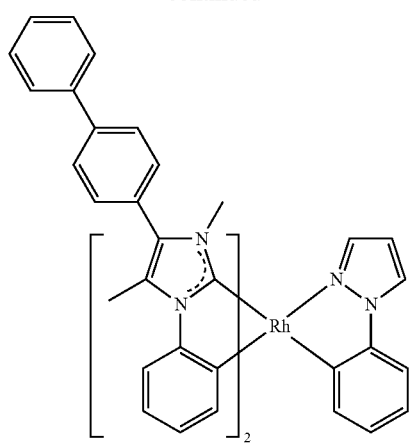
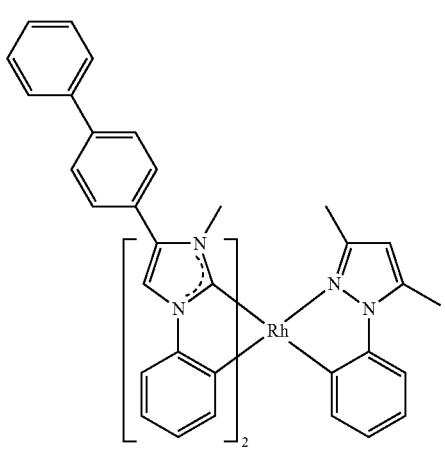
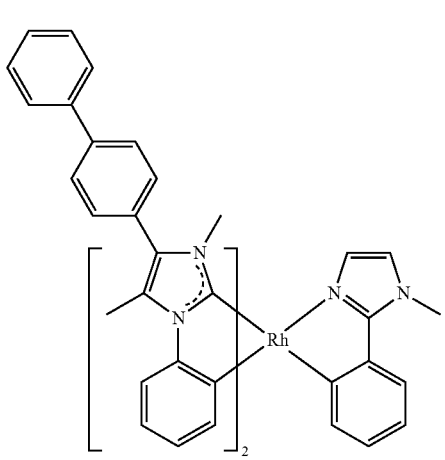

671
-continued
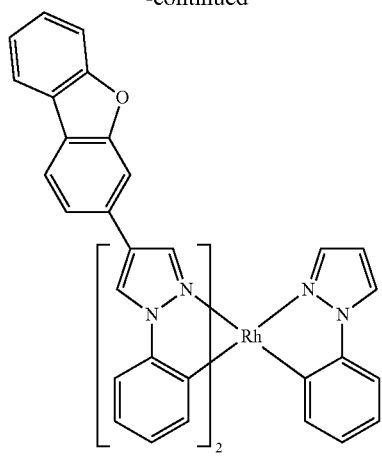
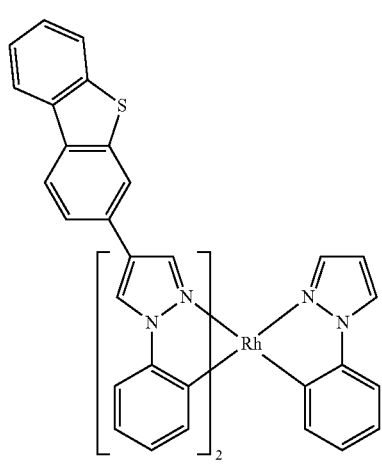
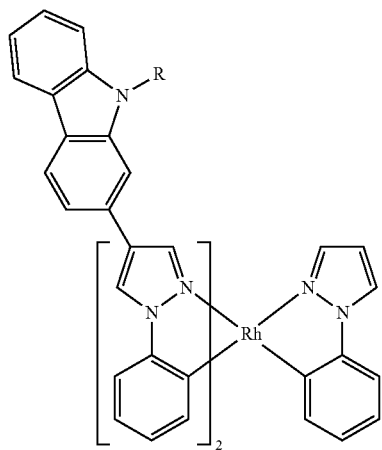
672
-continued
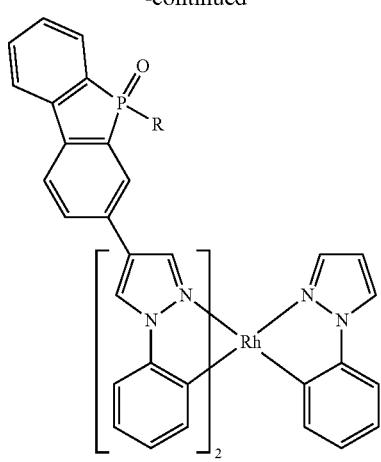
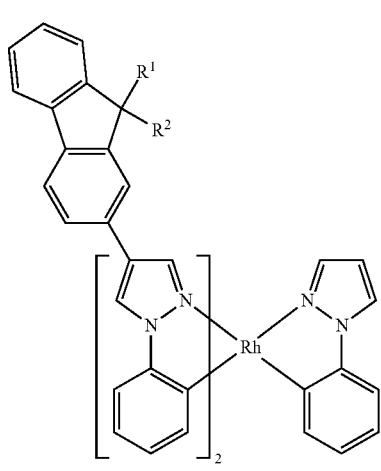
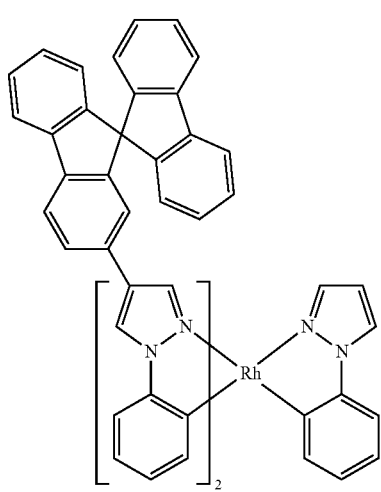

673
-continued
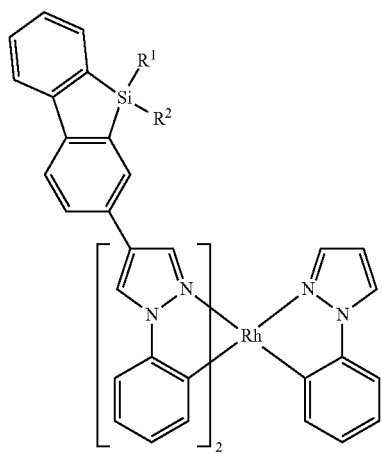
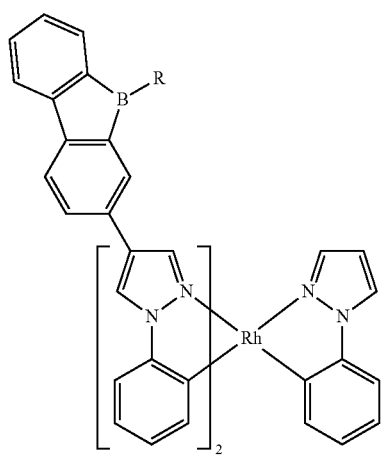
Structures Rh-10
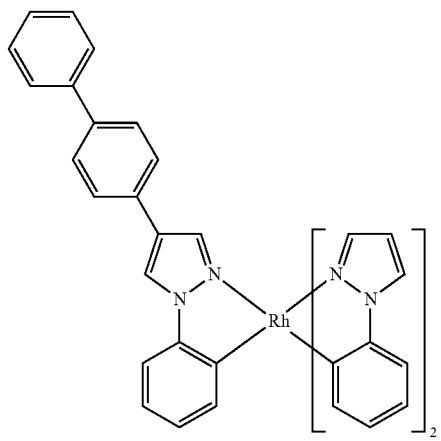
674
-continued
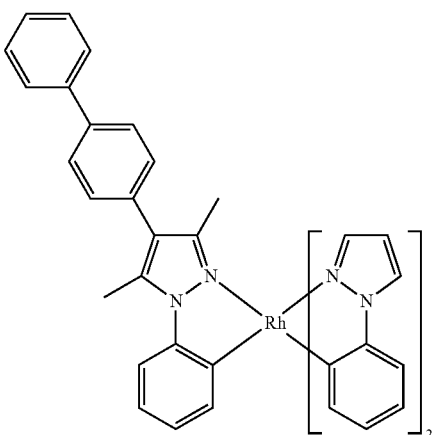
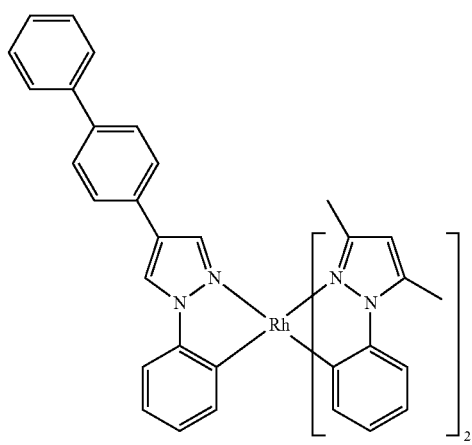
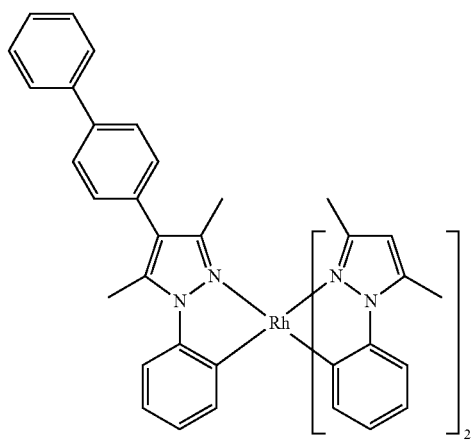

675
-continued
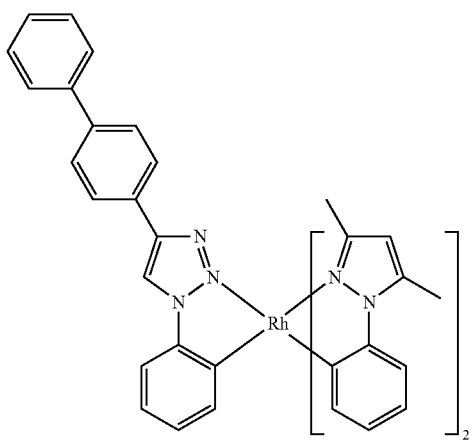
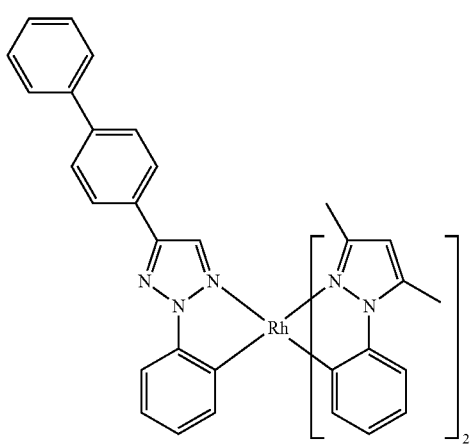
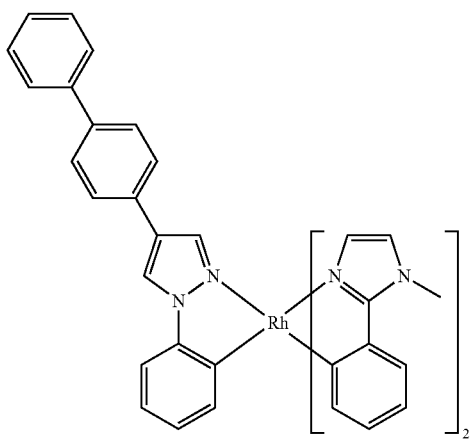
676
-continued
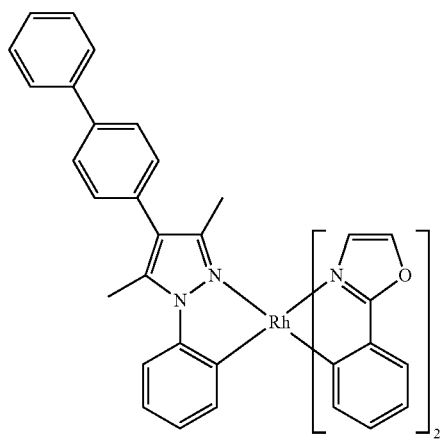
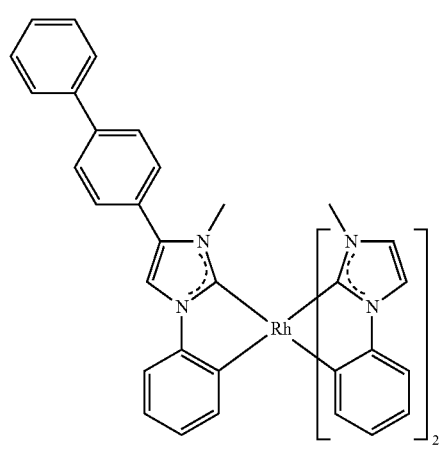
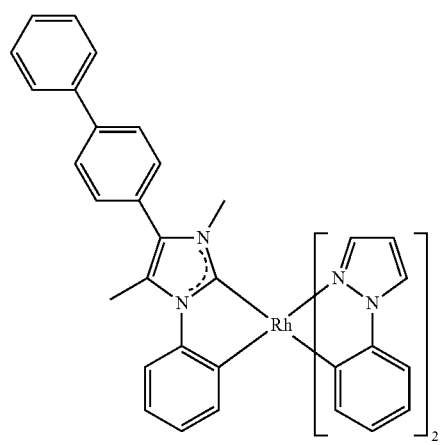

677
-continued
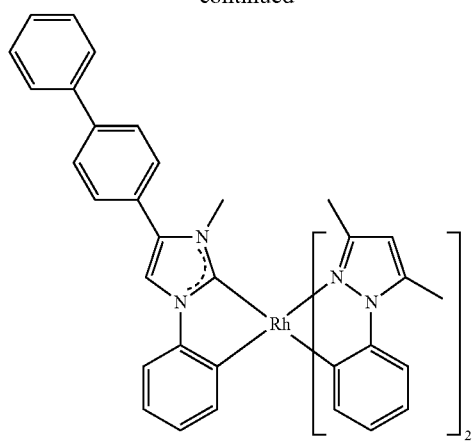
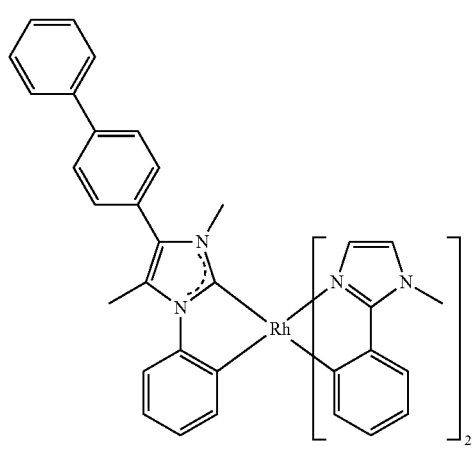
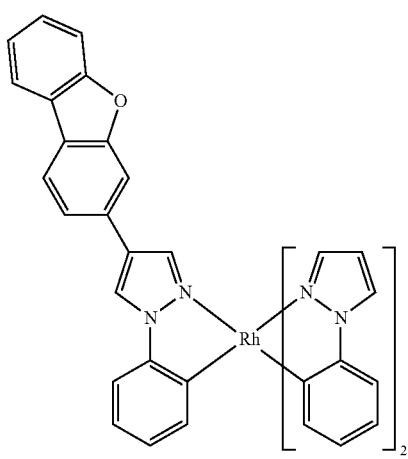
678
-continued
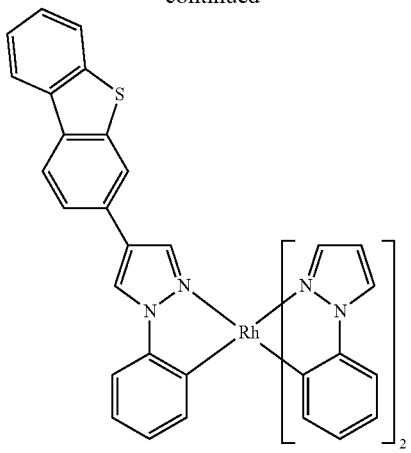
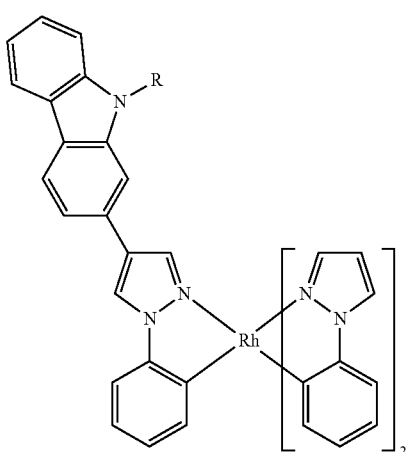
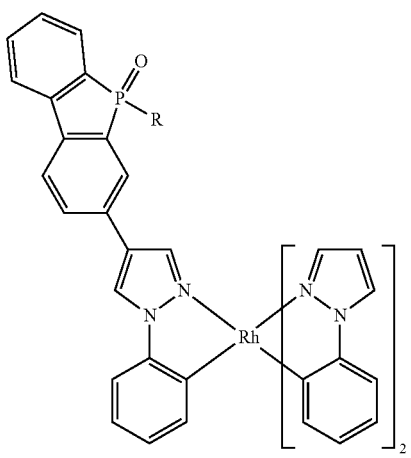

-continued
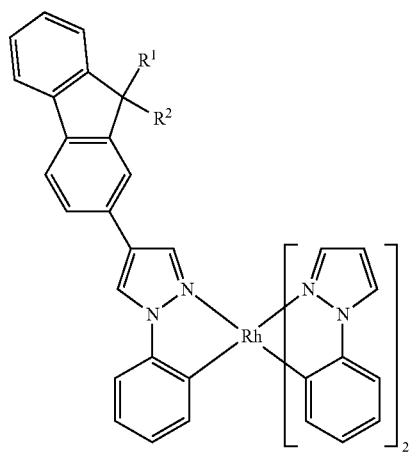
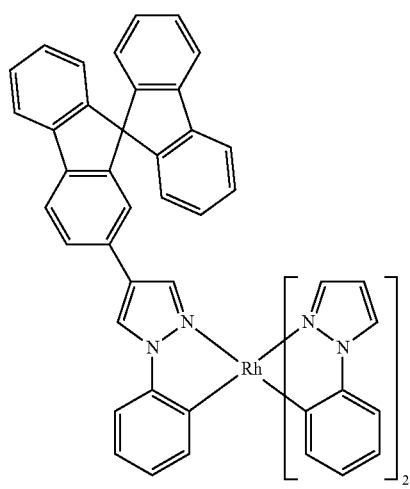
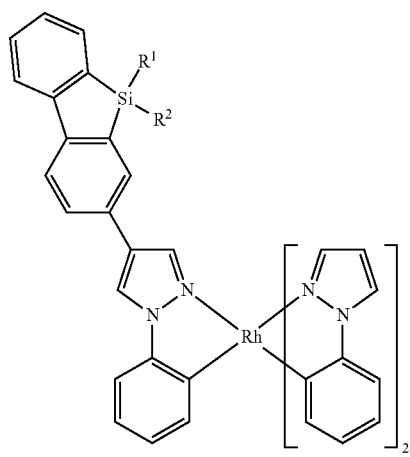
-continued
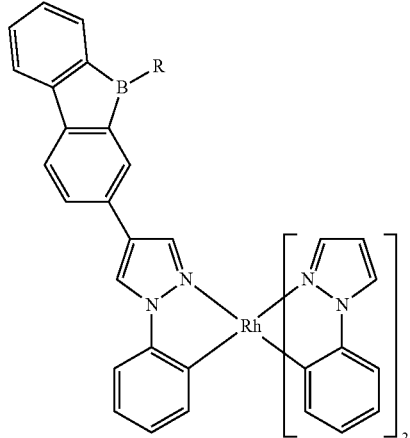
Structures Rh-11
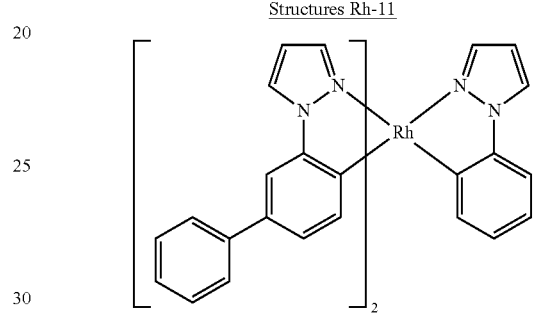
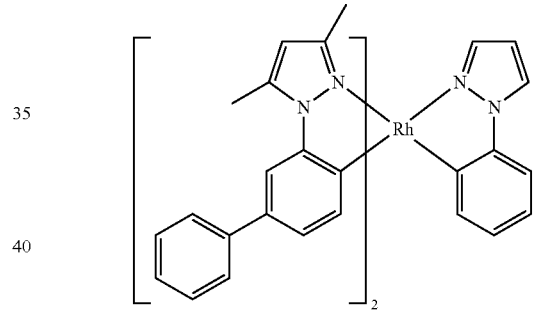
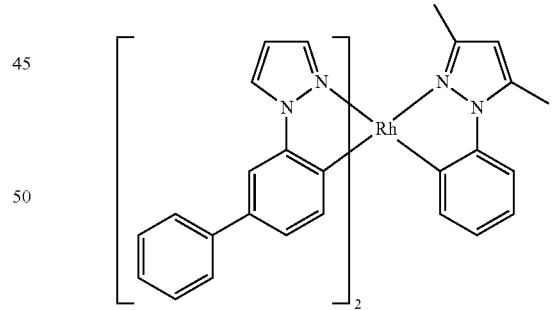
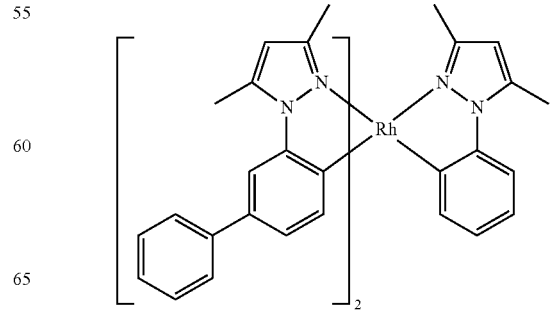

681
-continued
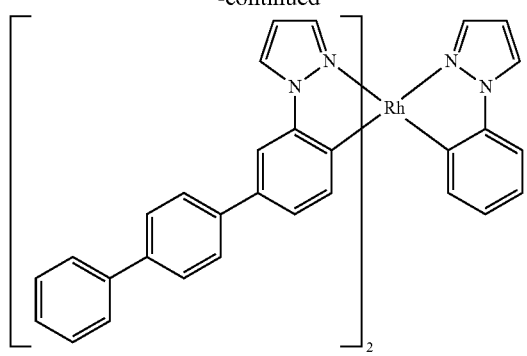
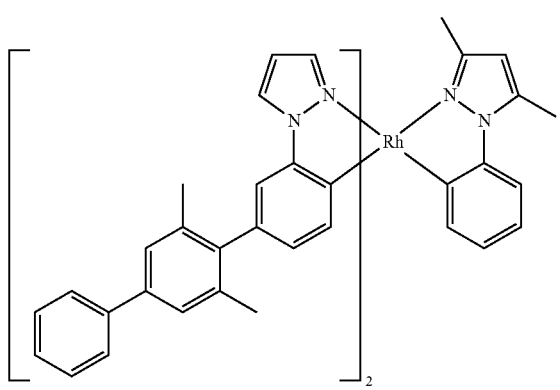
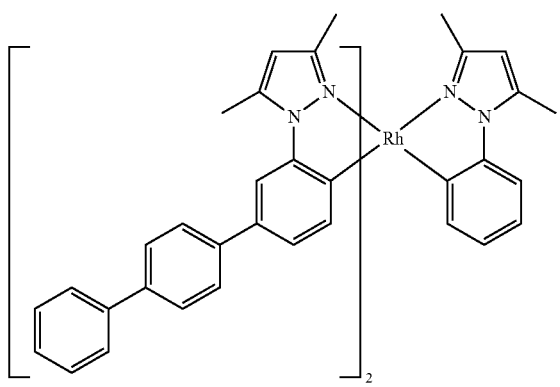
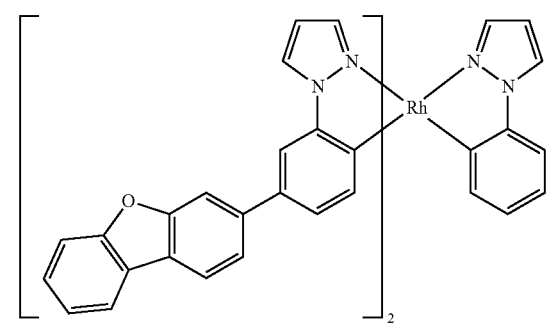
682
-continued
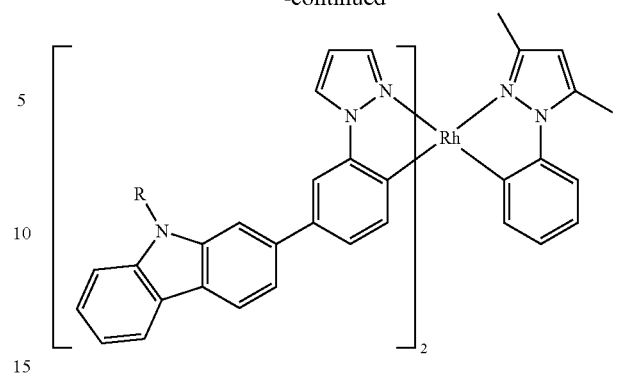
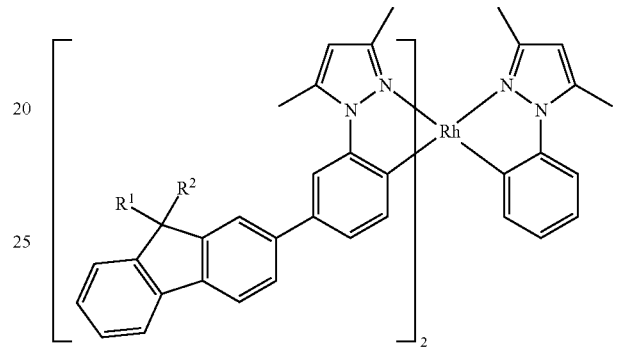
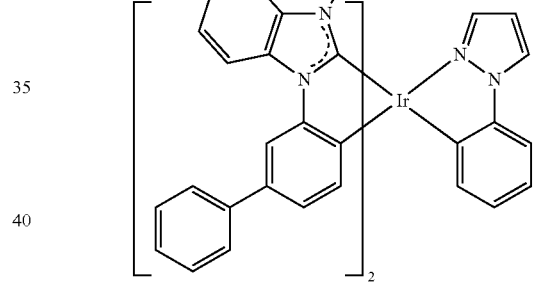
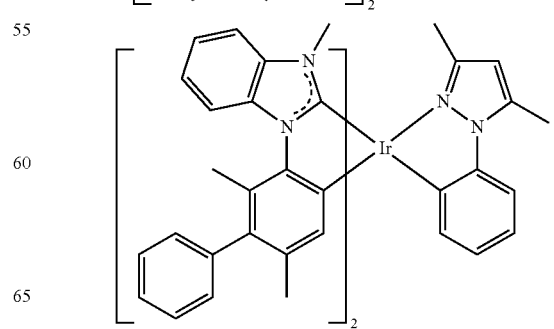

-continued
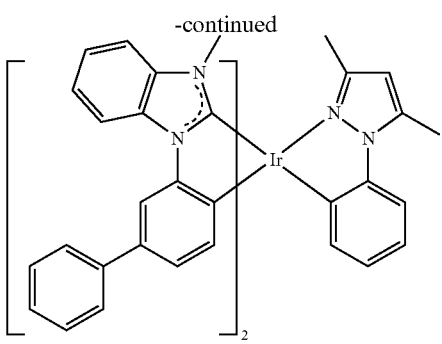
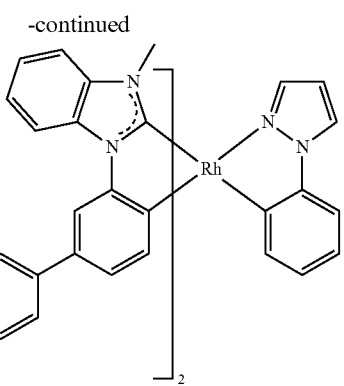
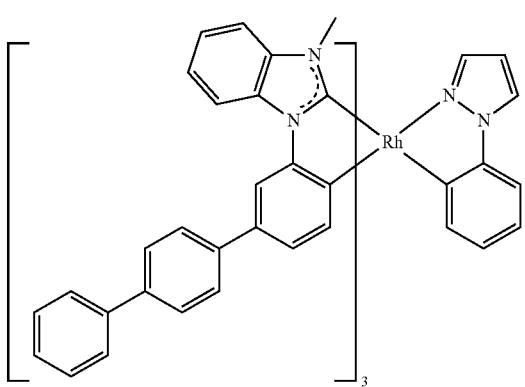
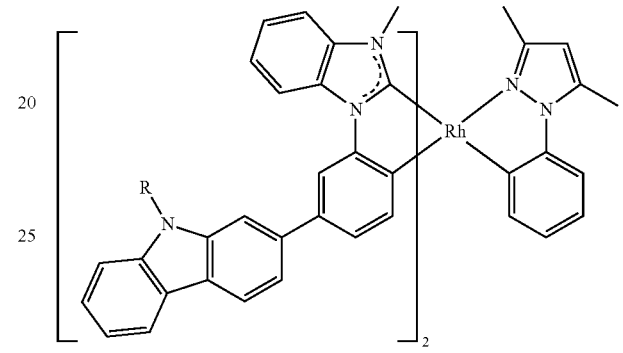
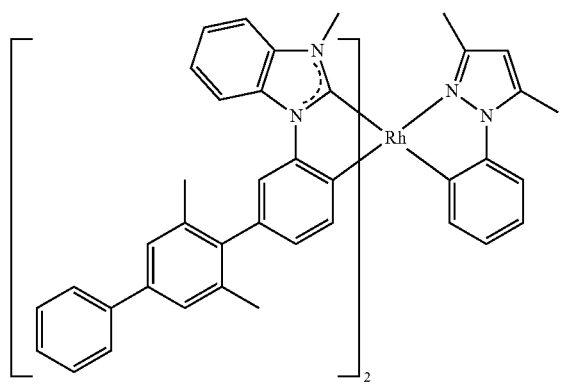
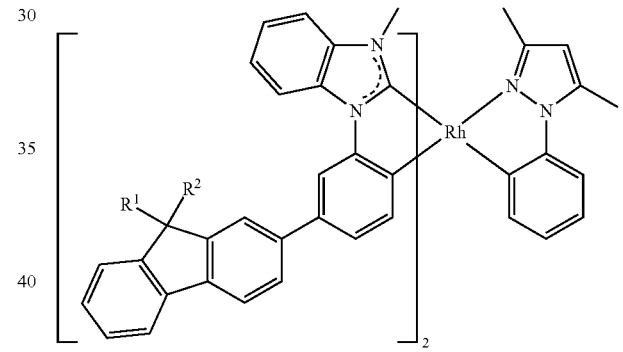
Structures Rh-12
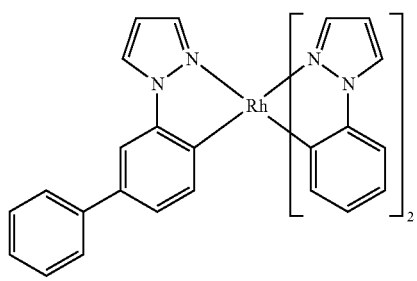
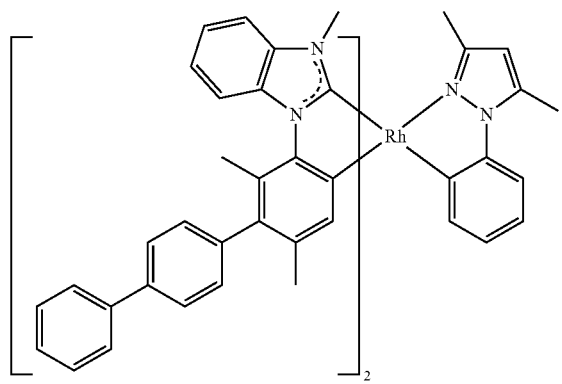
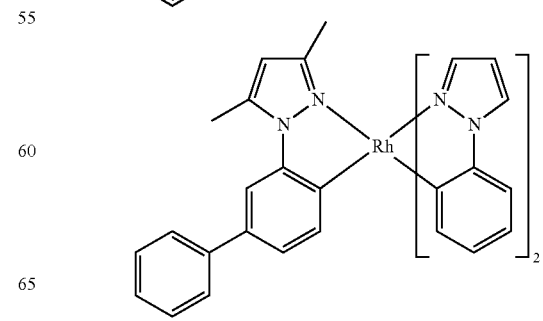

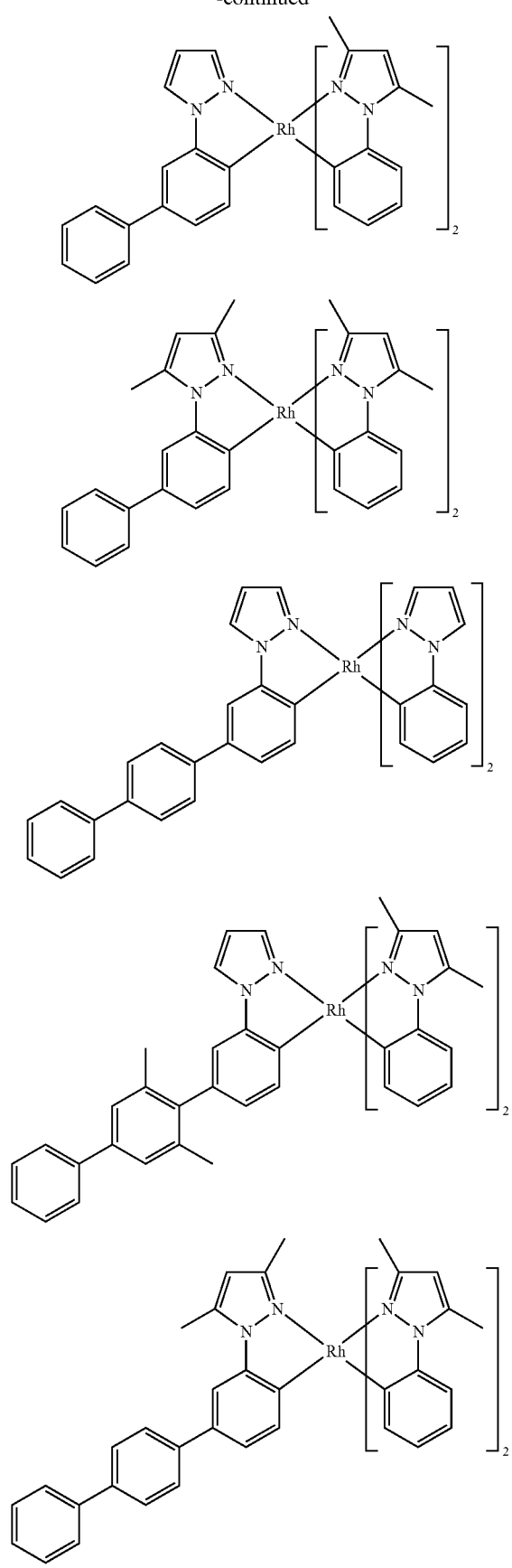
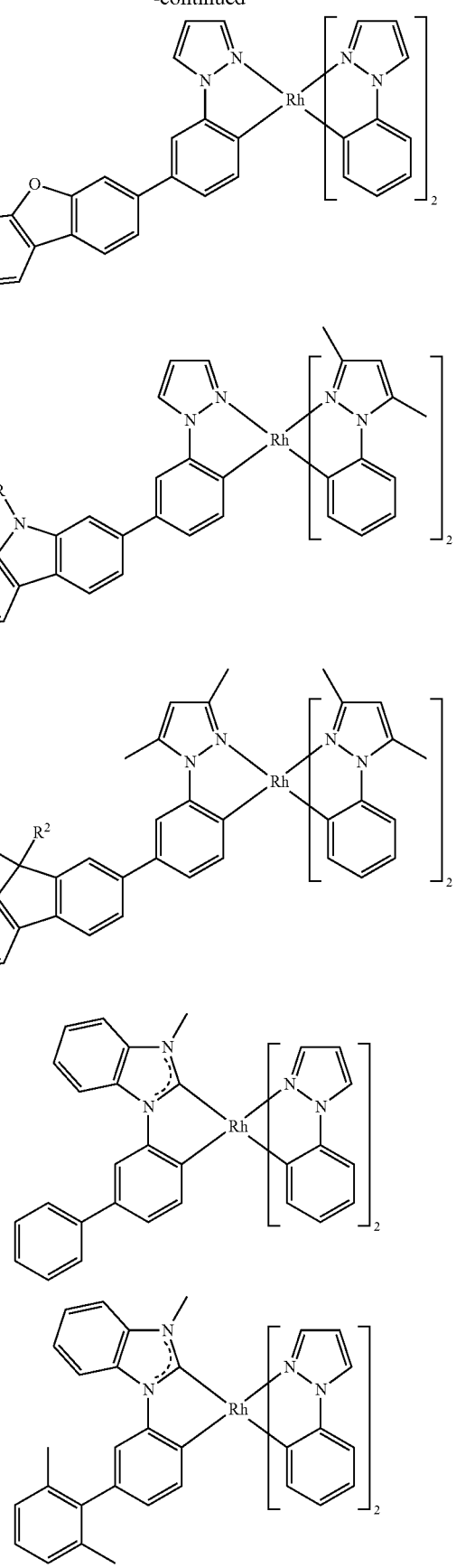

687
-continued
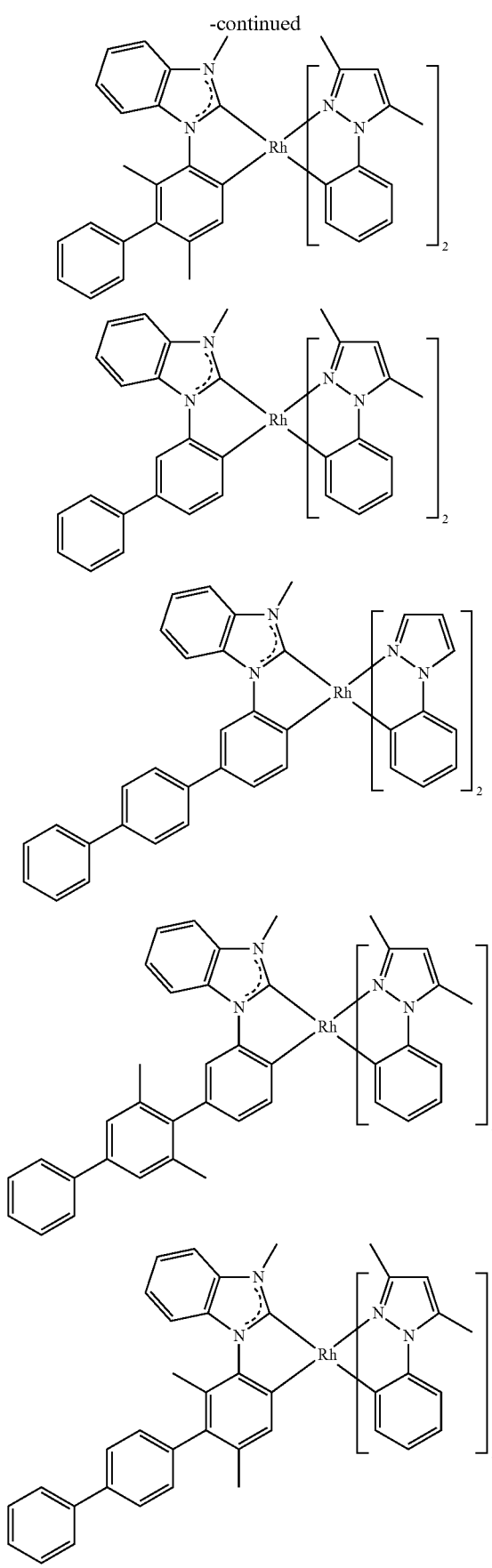
688
-continued
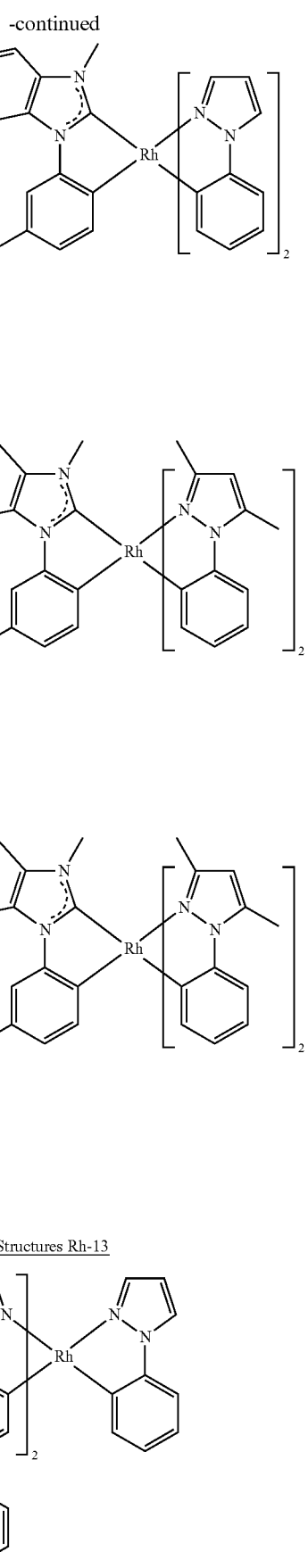
Structures Rh-13

689
-continued
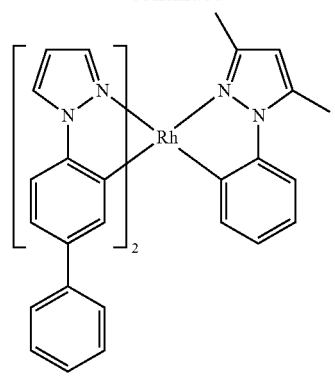
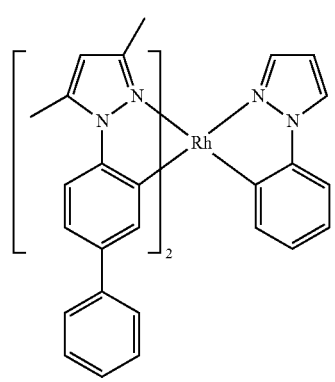
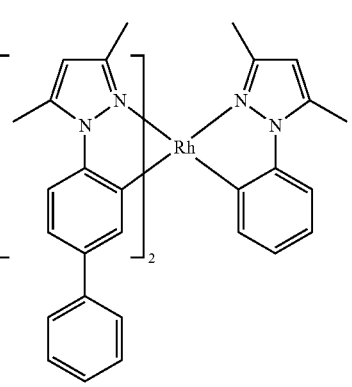
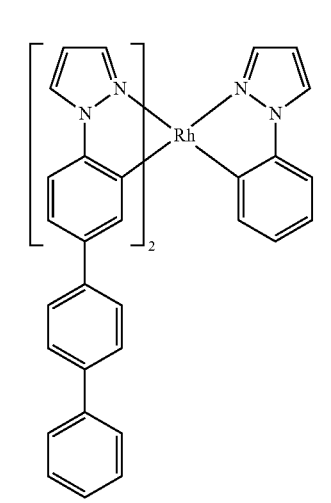
690
-continued
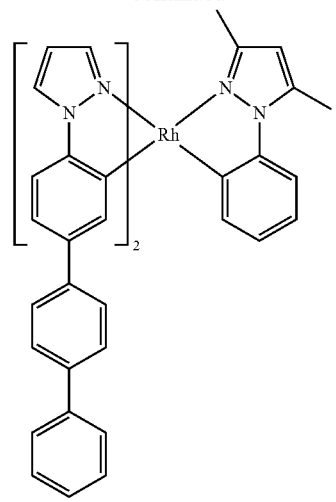
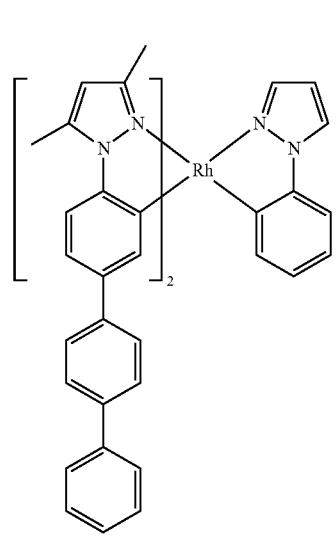
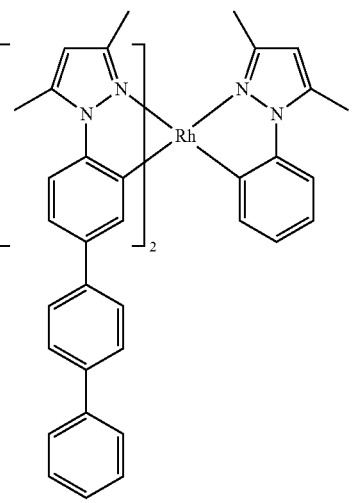

691
-continued
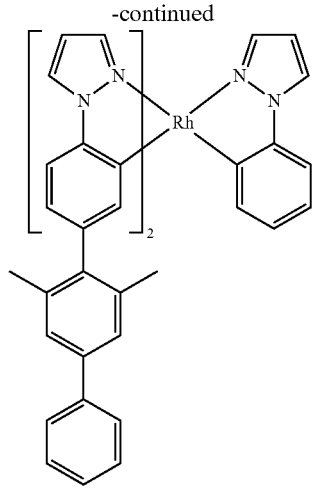
692
-continued
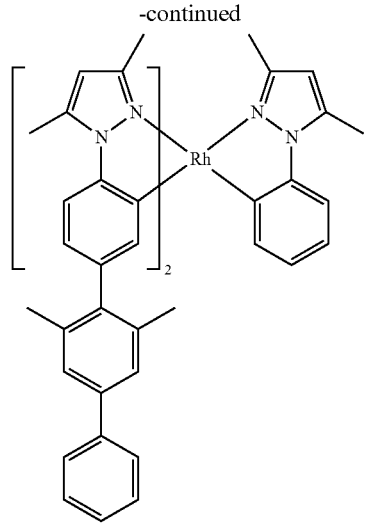
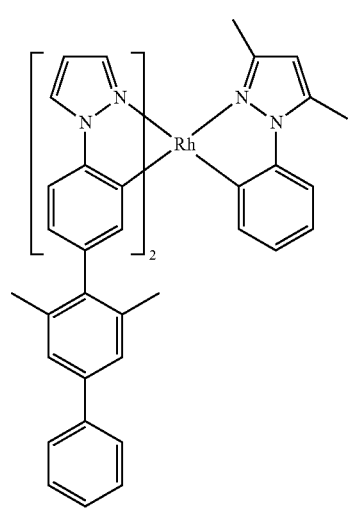
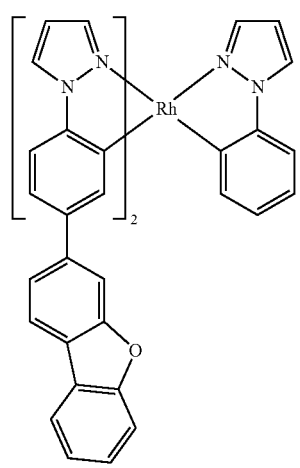
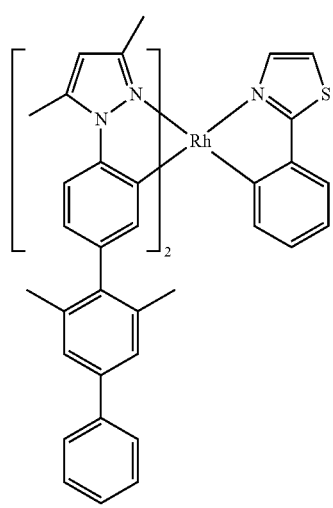
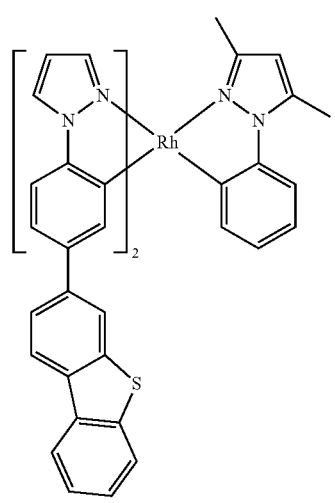

693
-continued
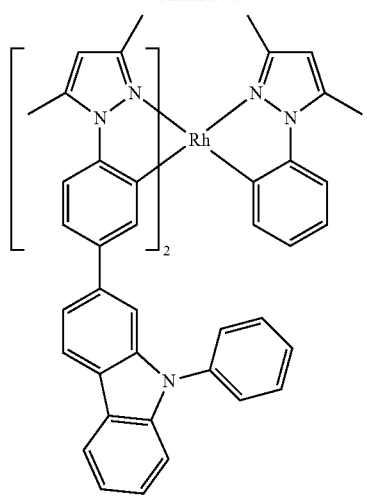
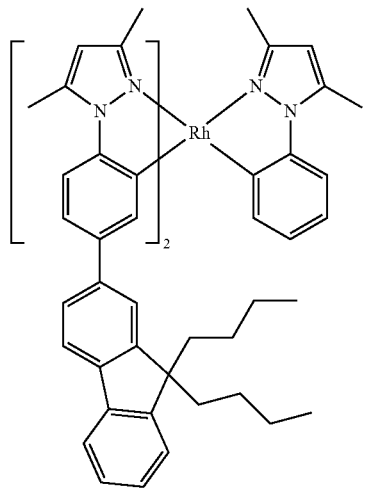
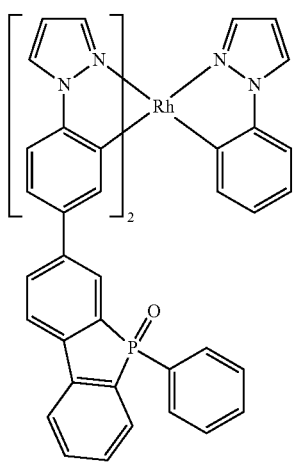
694
-continued
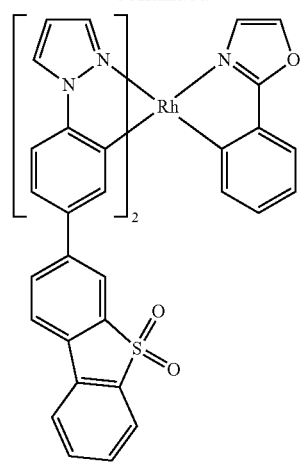
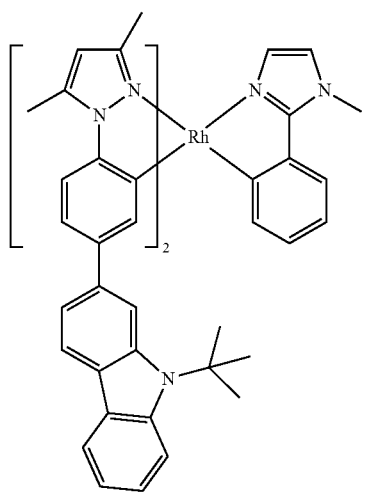
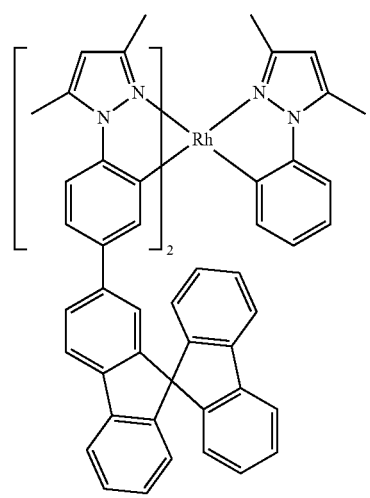

695
-continued
Structures Rh-14
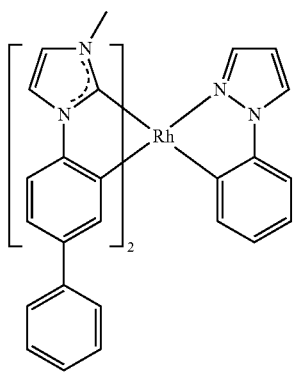
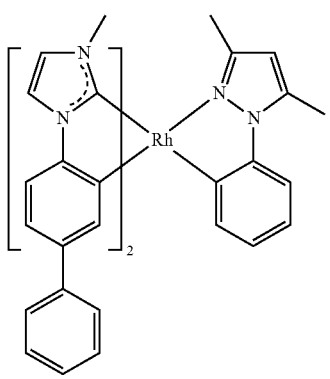
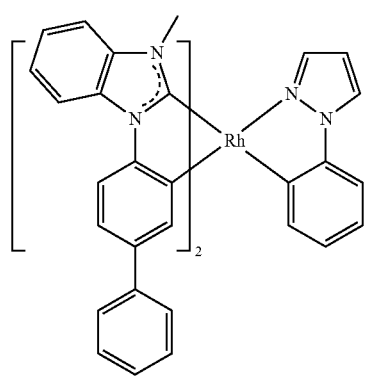
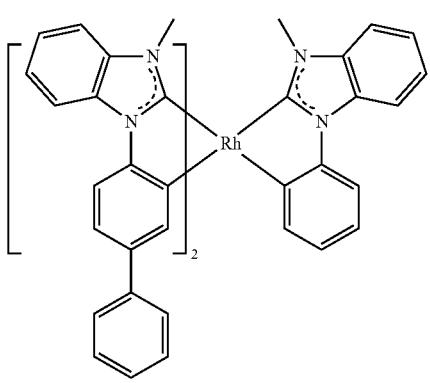
696
-continued
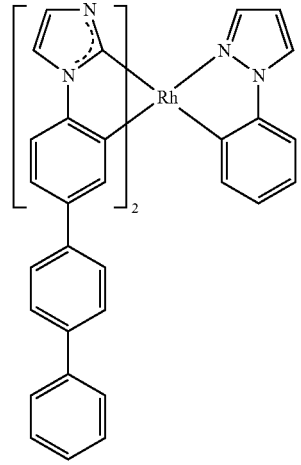
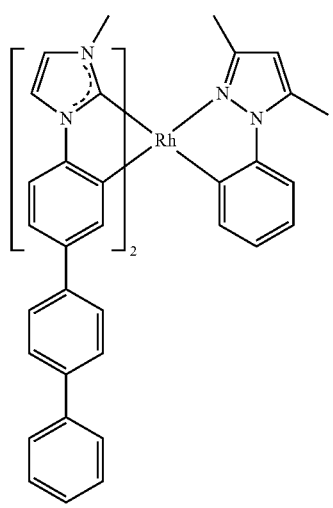
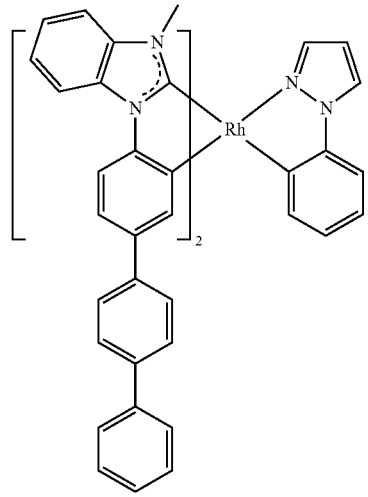

697
-continued
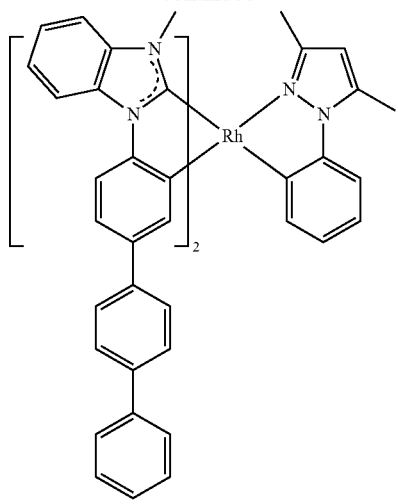
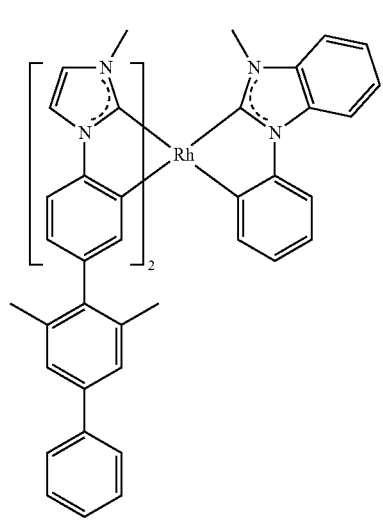
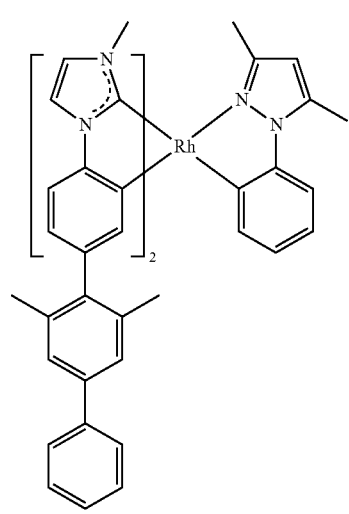
698
-continued
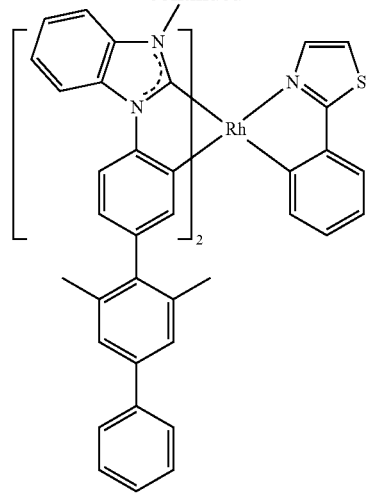
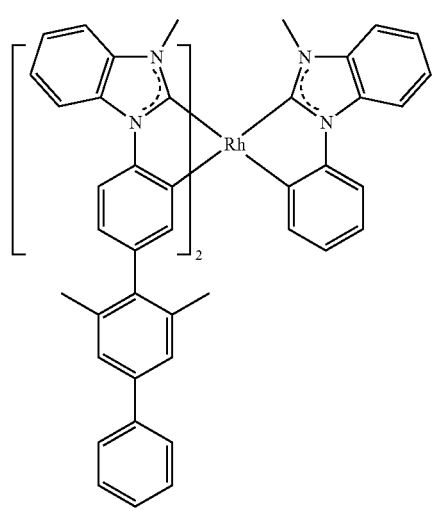
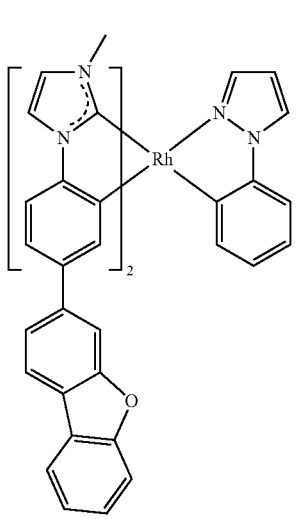

699
-continued
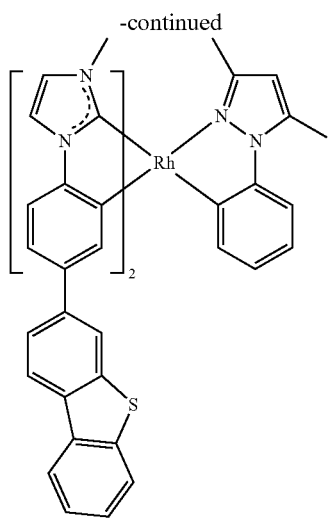
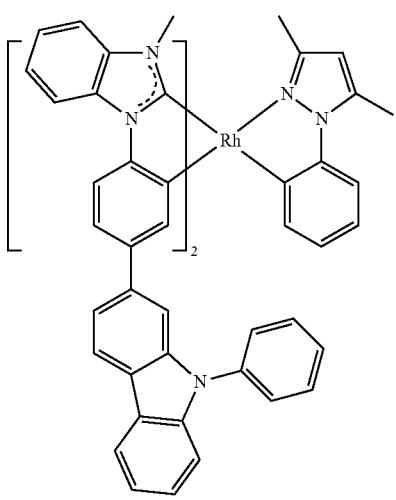
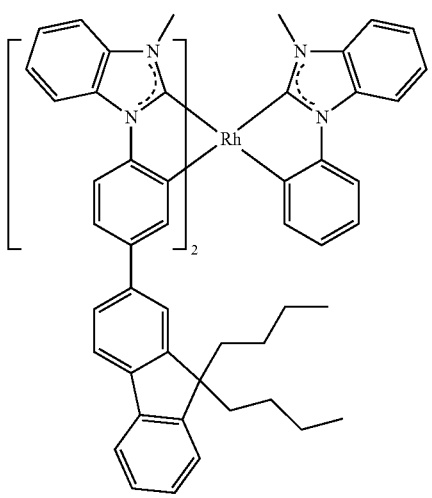
700
-continued
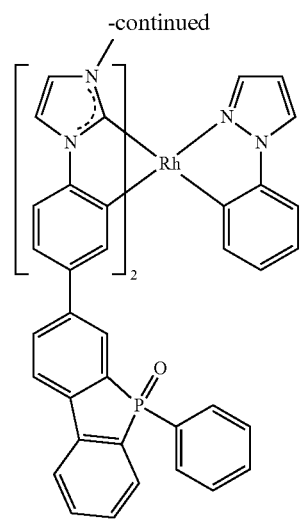
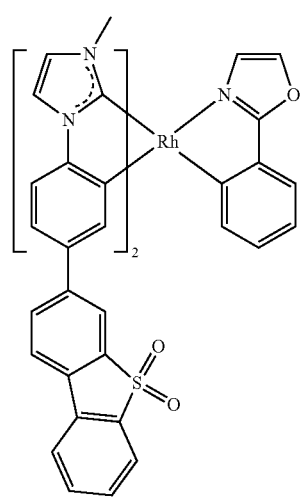
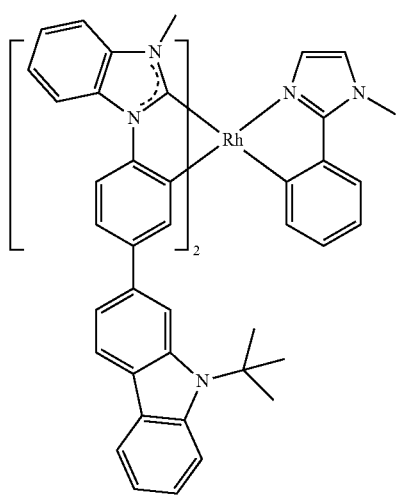

701
-continued
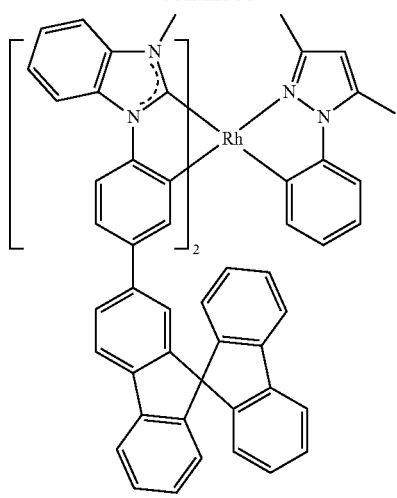
Structures Rh-15
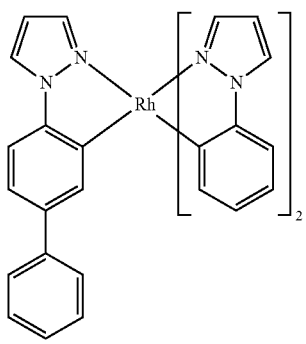
702
-continued
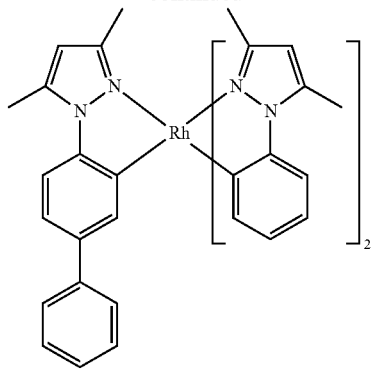
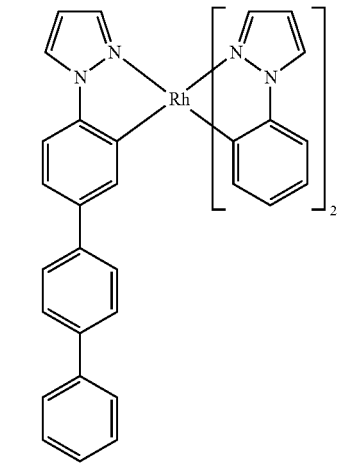
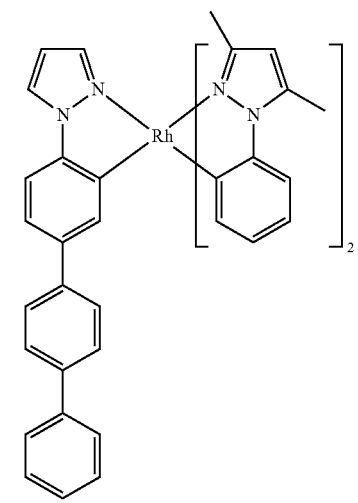

703
-continued
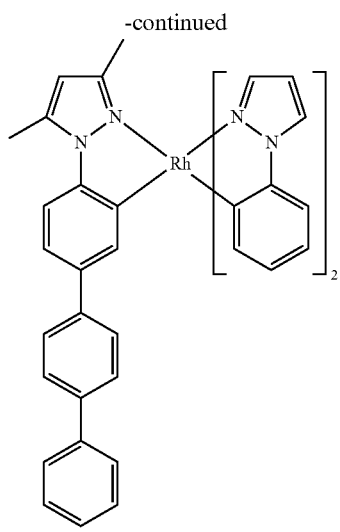
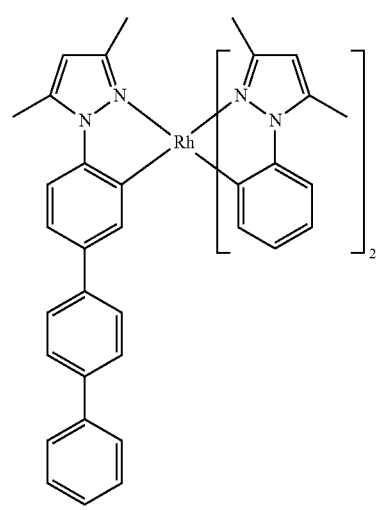
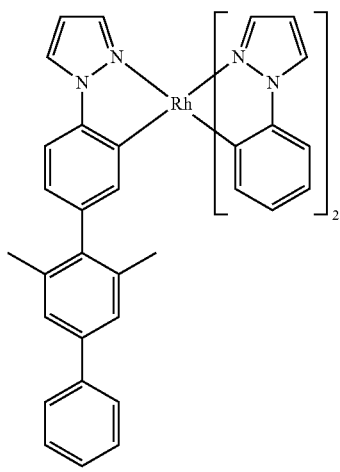
704
-continued
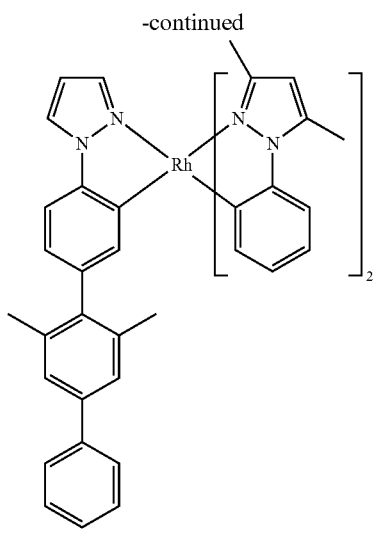
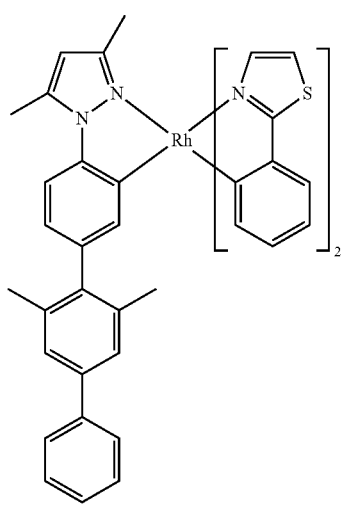
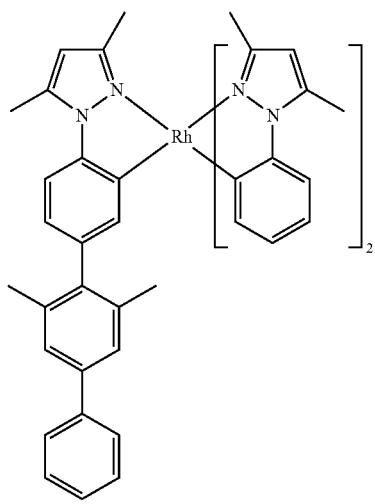

705
-continued
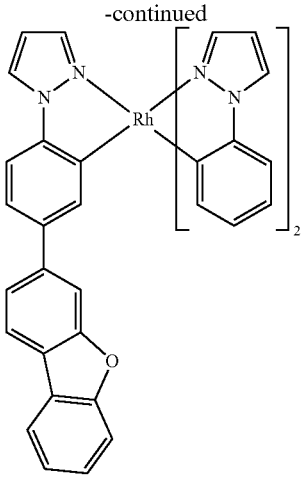
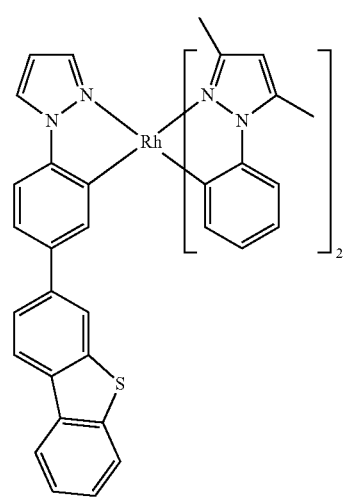
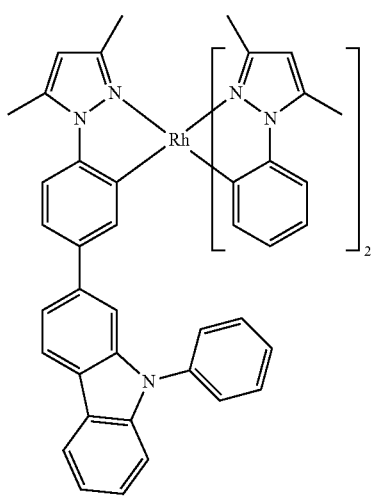
706
-continued
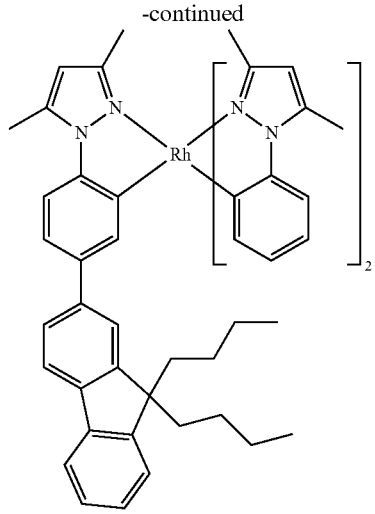
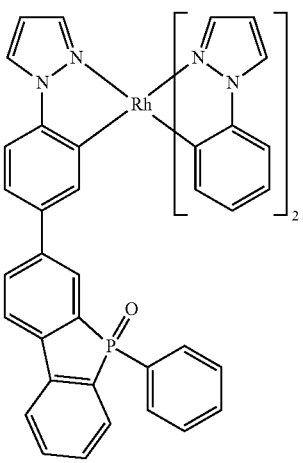
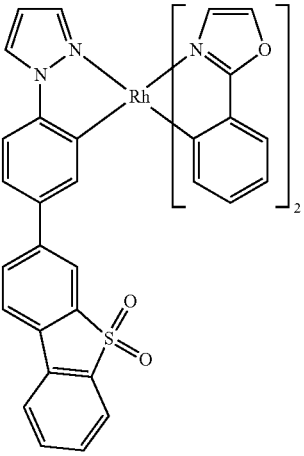

707
-continued
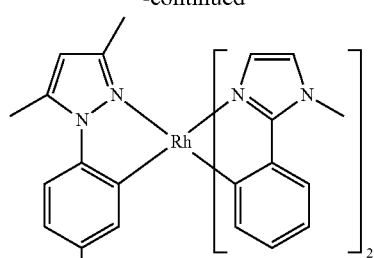
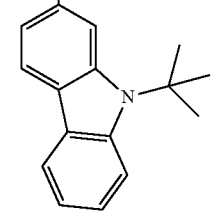
Structures Rh-16
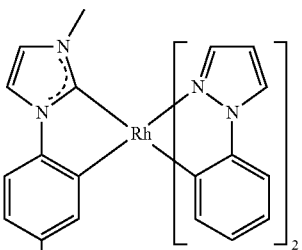
708
-continued
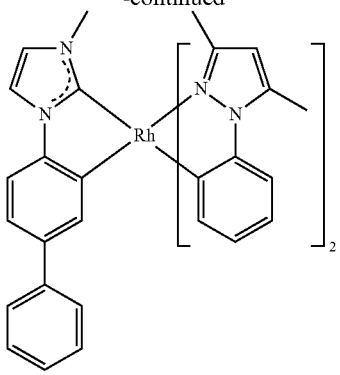
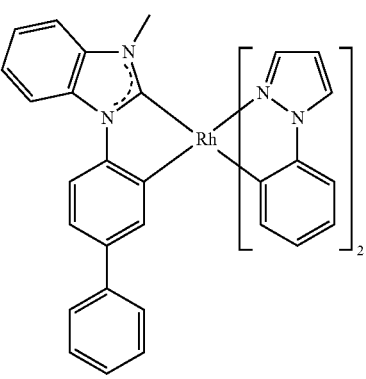
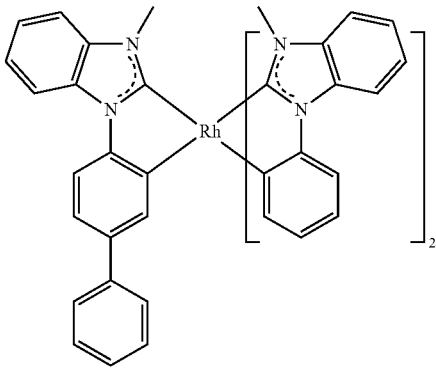
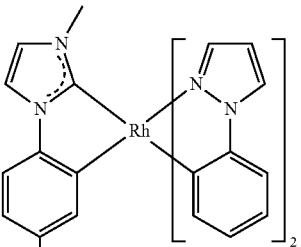

709
-continued
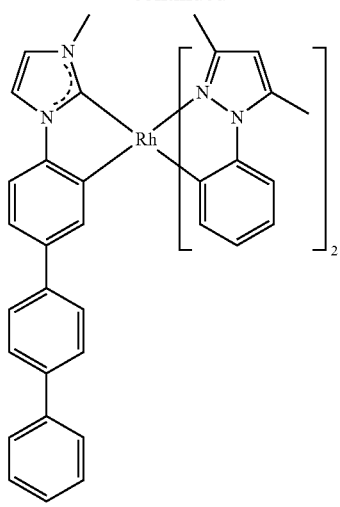
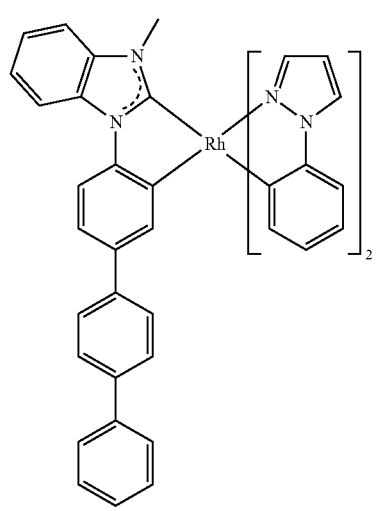
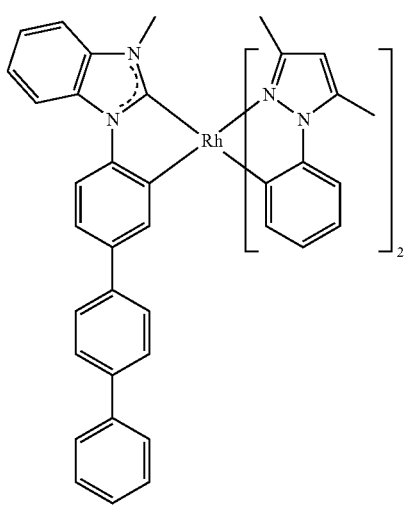
710
-continued
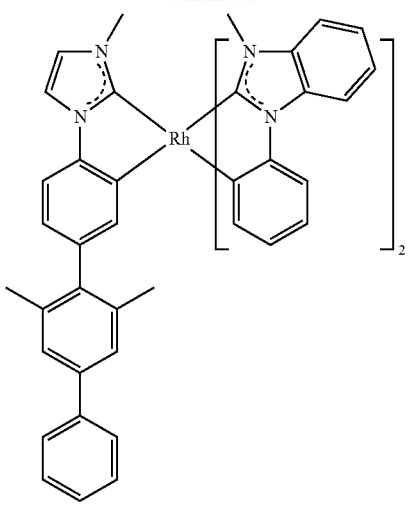
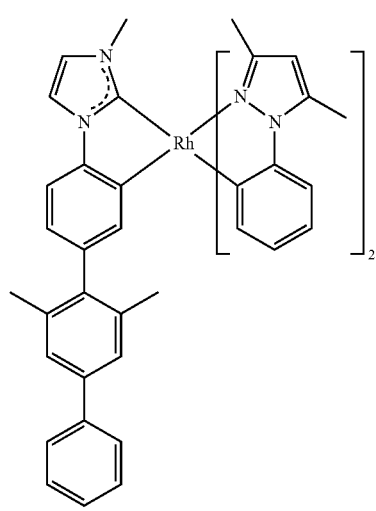
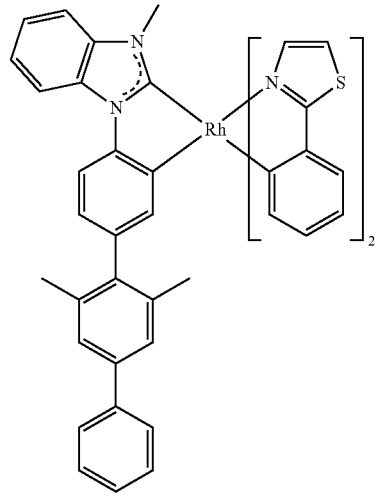

711
-continued
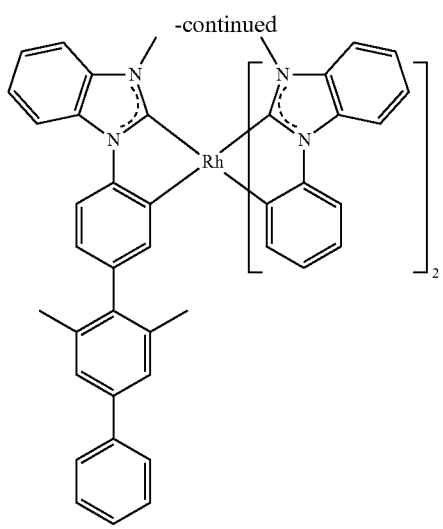
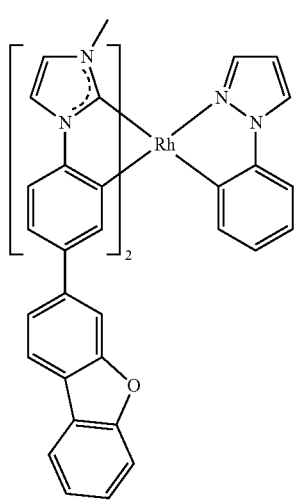
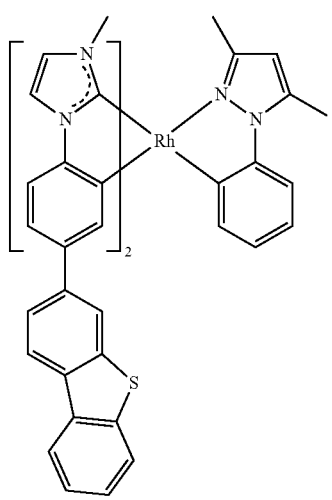
712
-continued
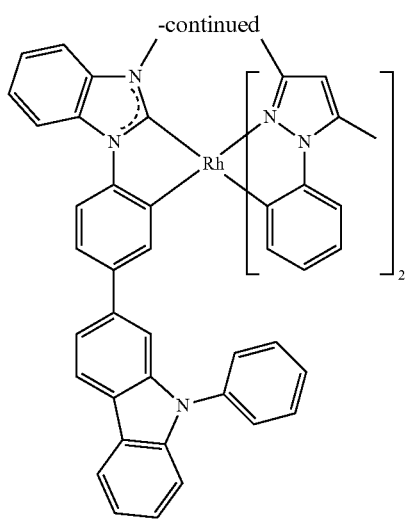
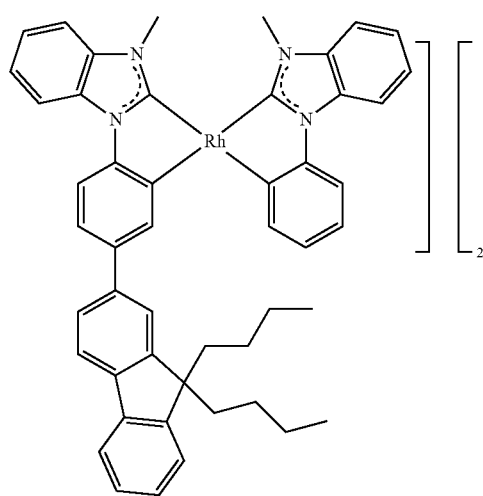
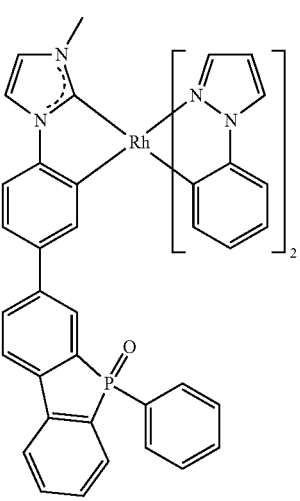

713
-continued
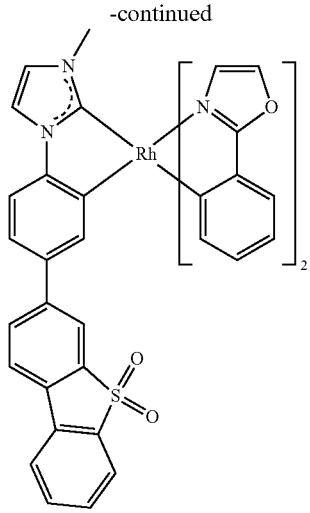
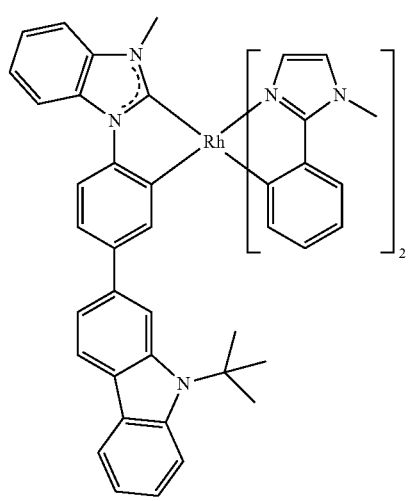
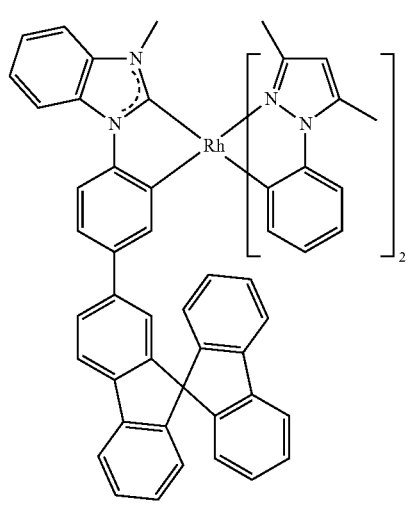
714
-continued
Structures Rh-19
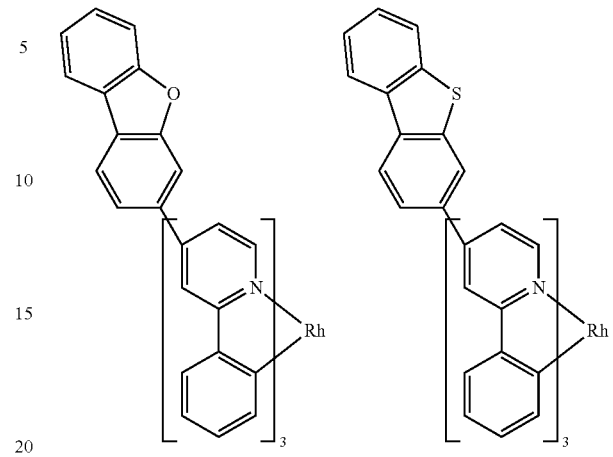
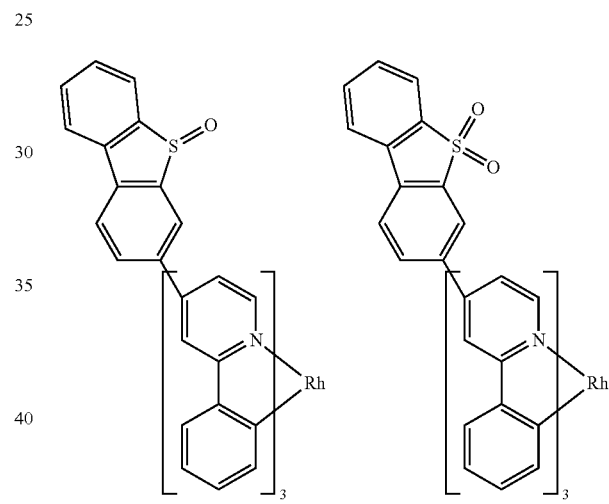
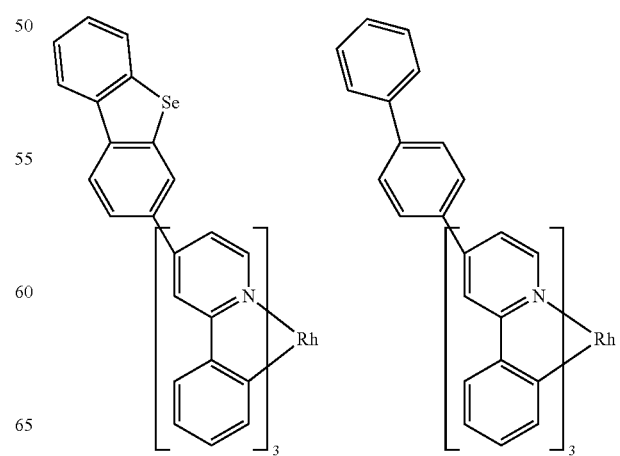

715
-continued
716
-continued
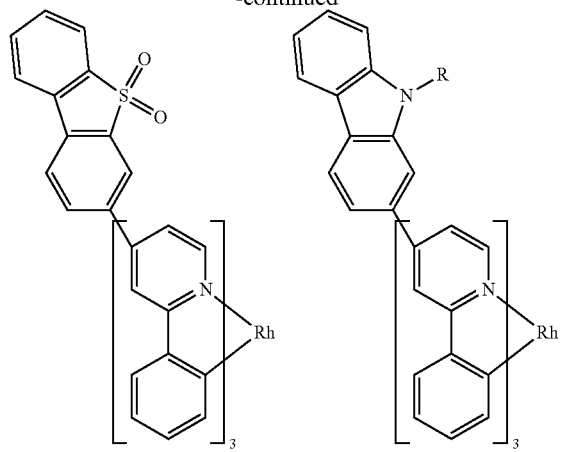
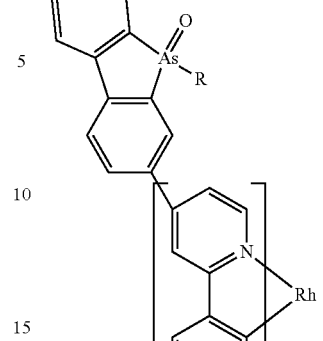
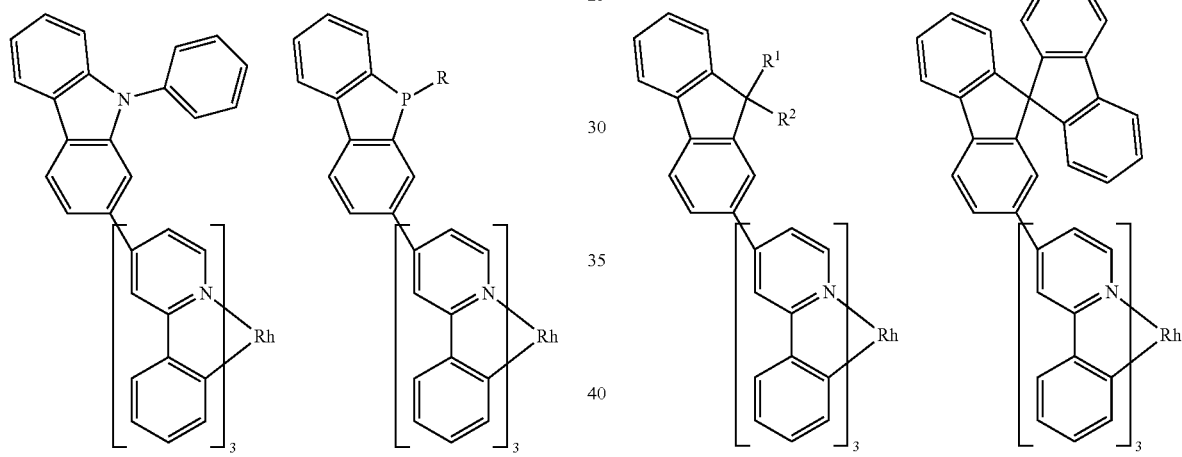
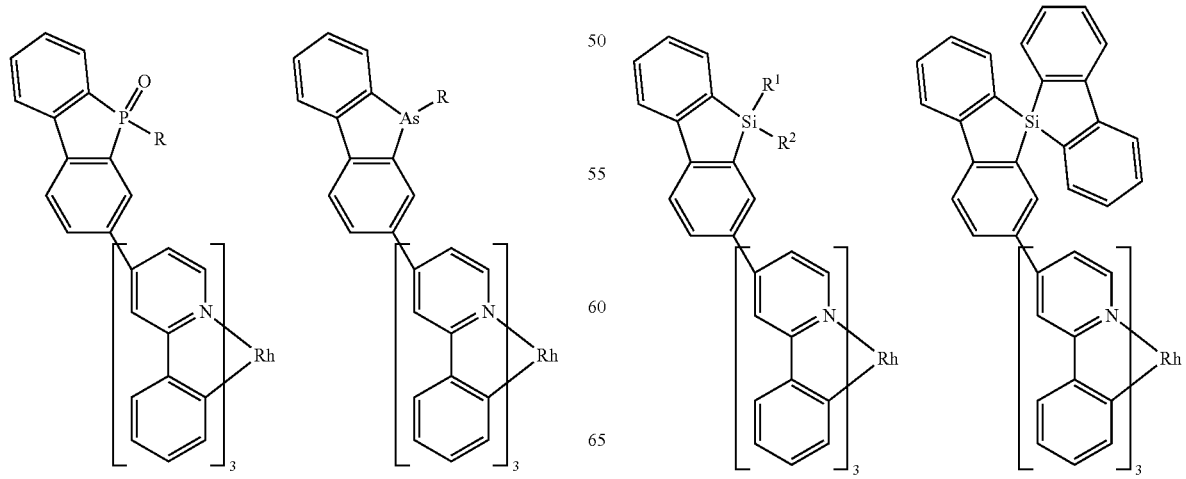

717
-continued
Structures Rh-20
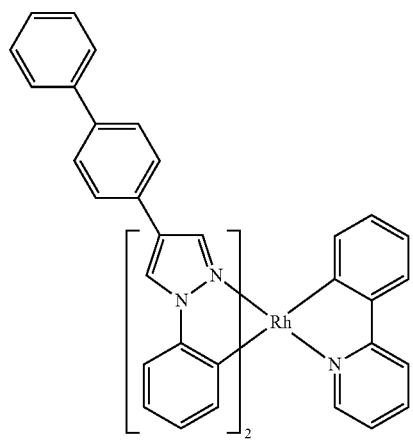
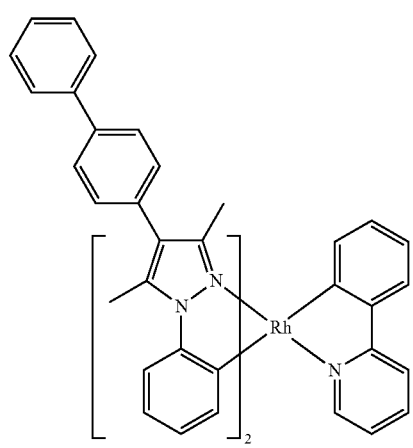
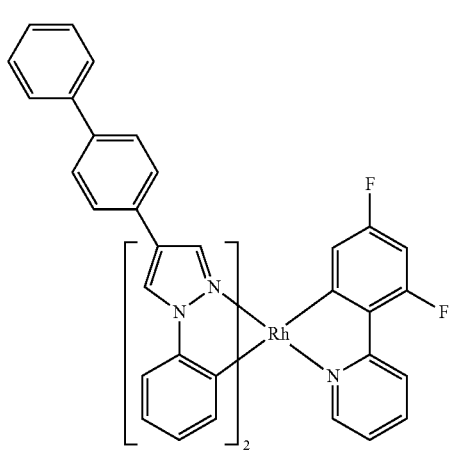
718
-continued
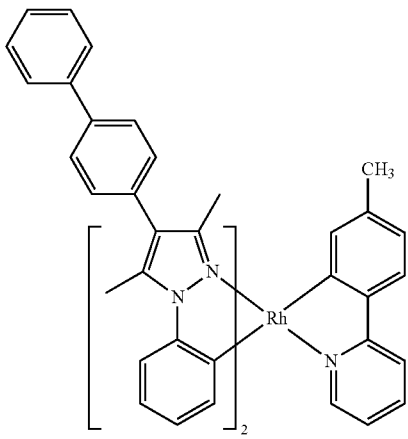
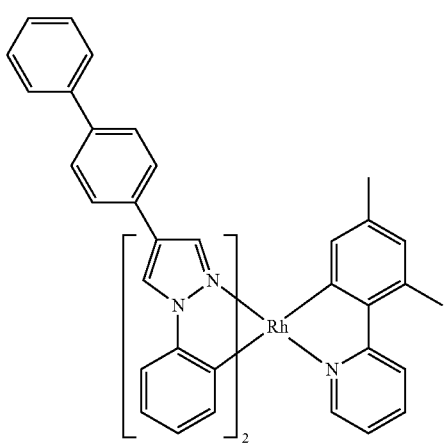
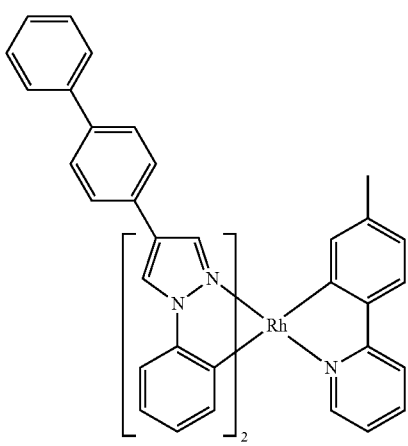

719
-continued
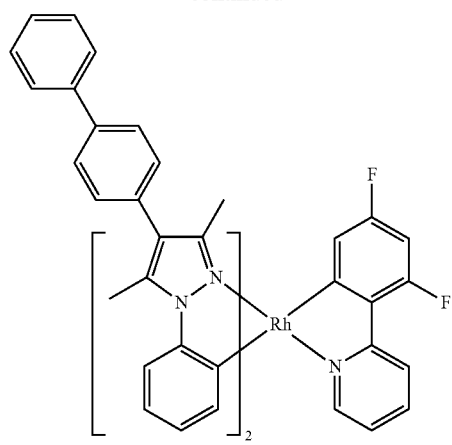
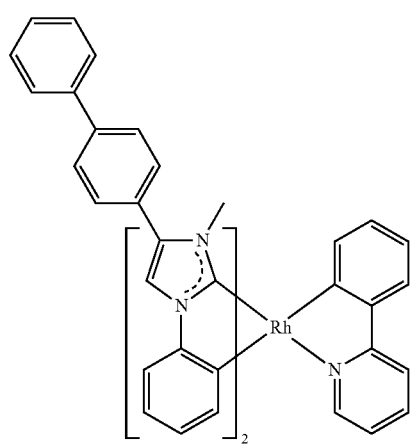
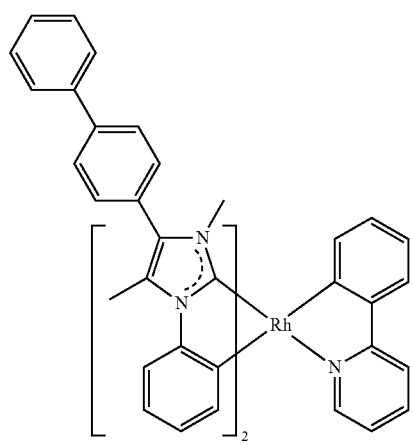
720
-continued
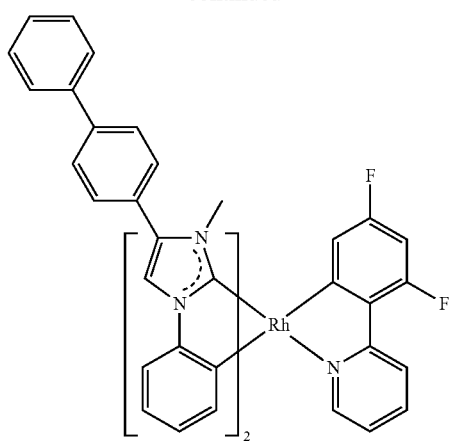
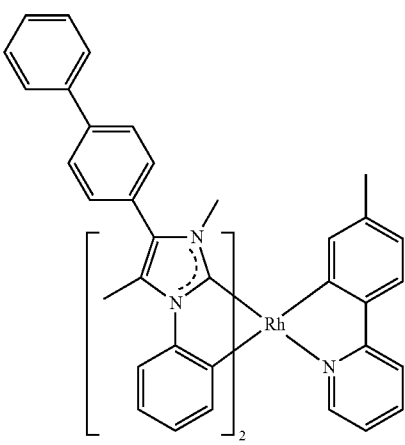
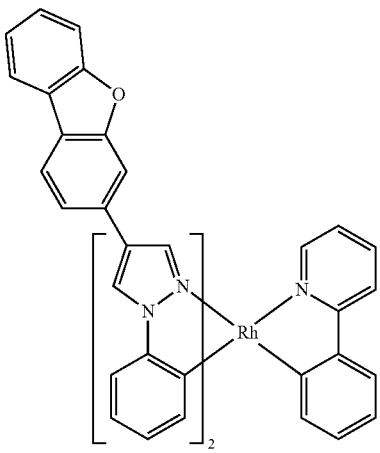

| 721 -continued | 722 -continued Structures Rh-21 |
|---|---|
| 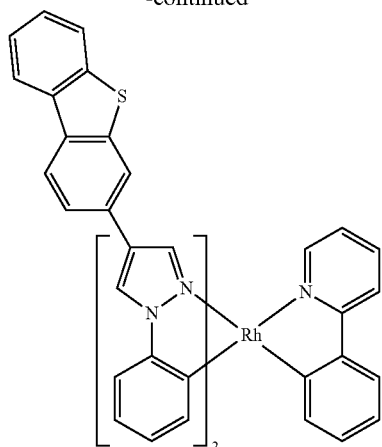 | 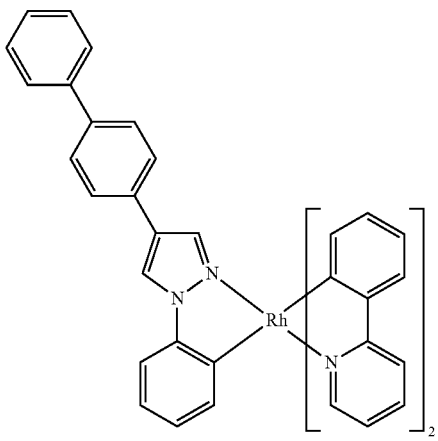 |
| 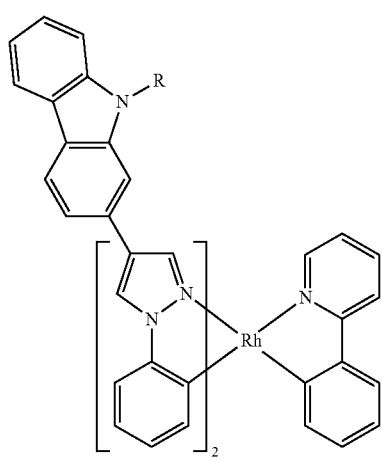 | 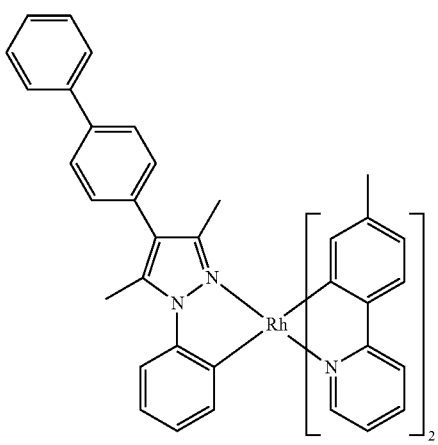 |
| 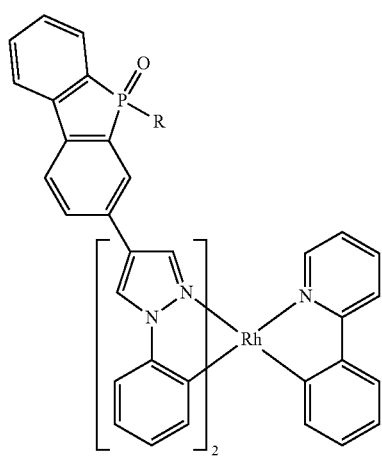 | 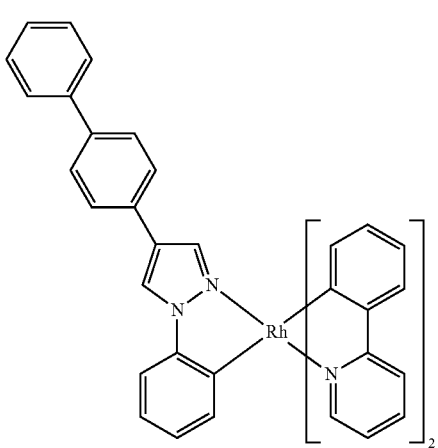 |

723
-continued
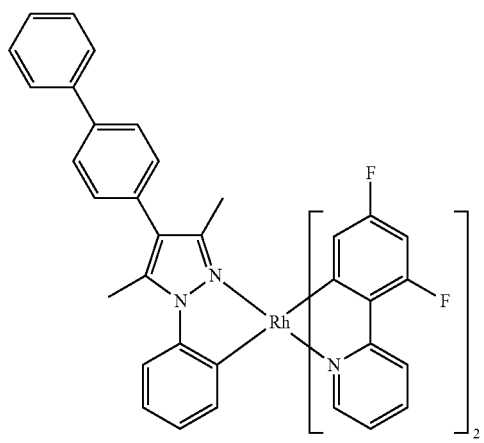
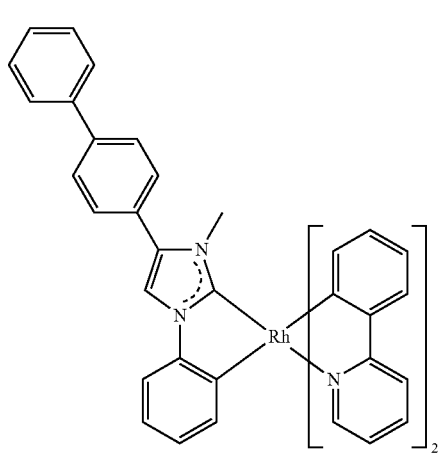
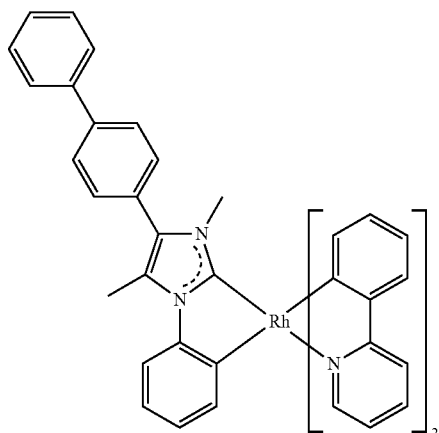
724
-continued
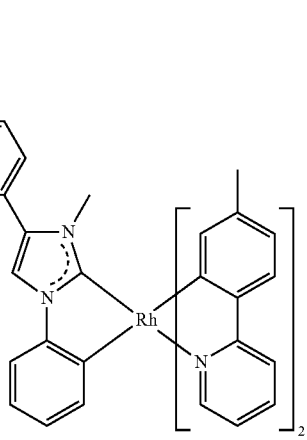
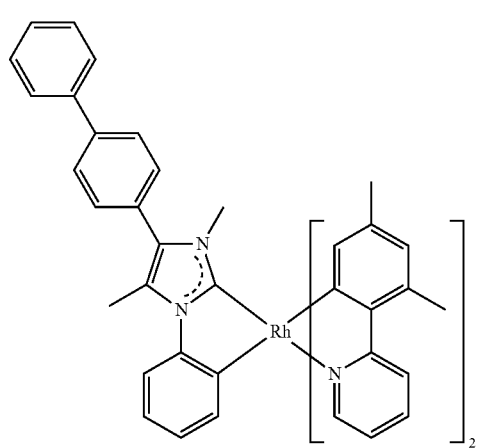
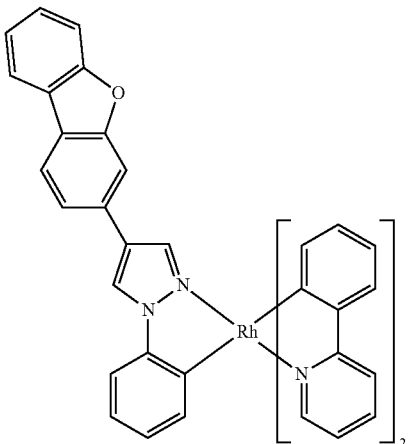

725
-continued
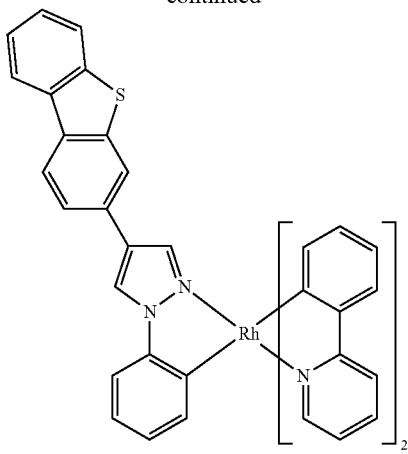
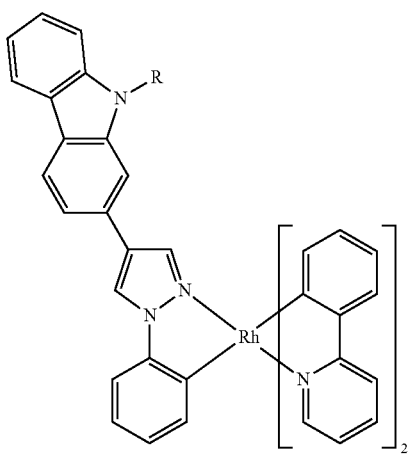
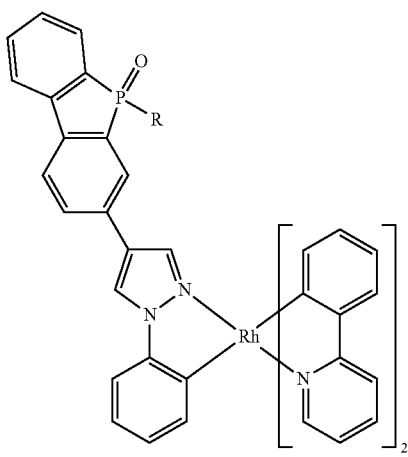
726
-continued
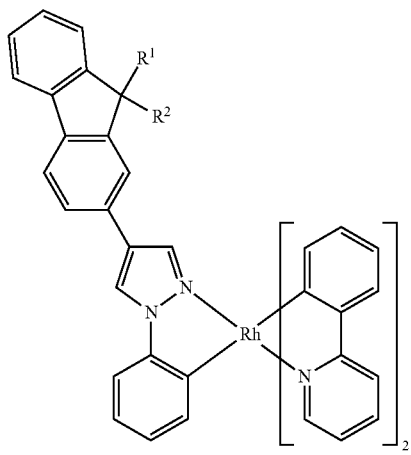
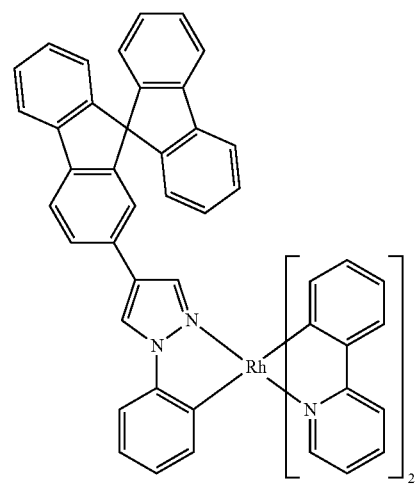
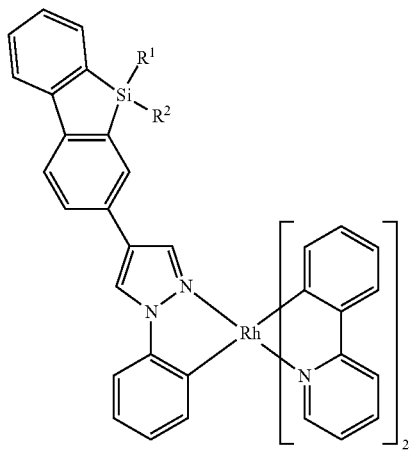

727
-continued
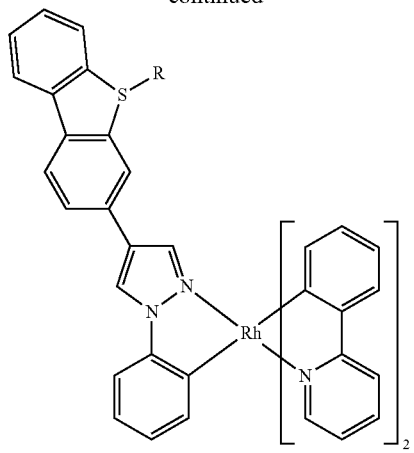
Structures Rh-22
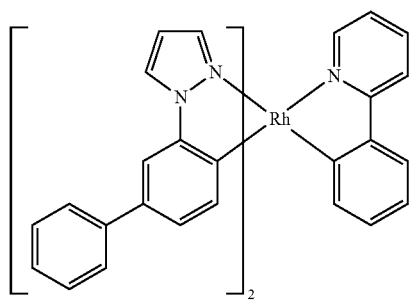
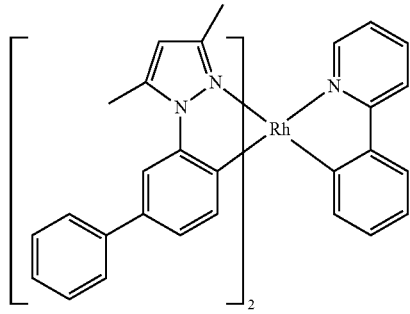
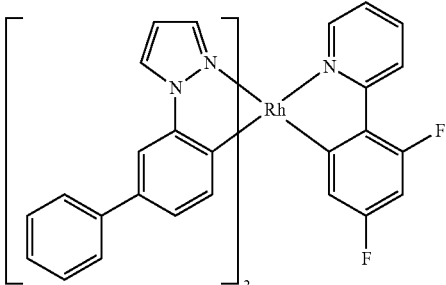
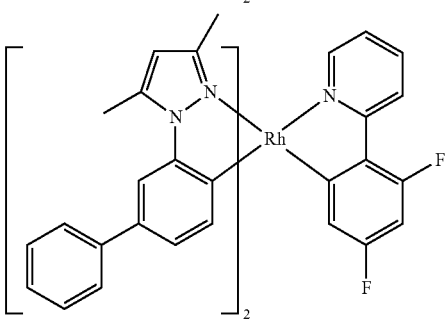
728
-continued
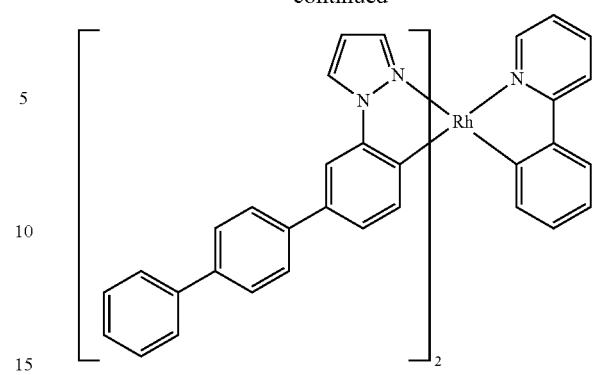
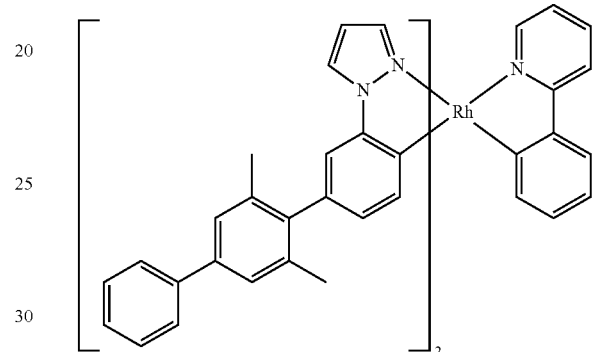
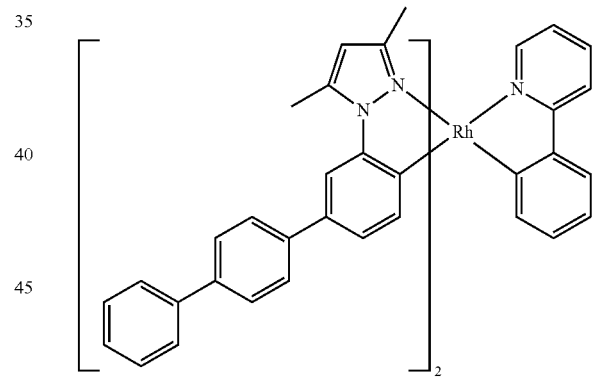
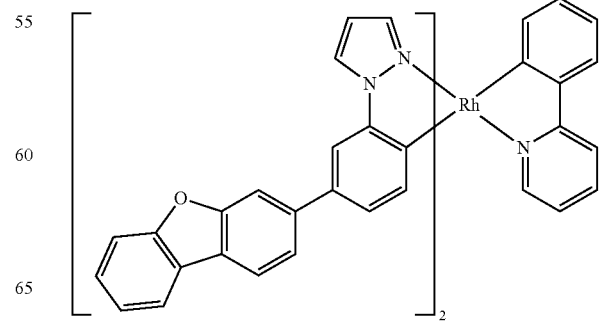

729
-continued
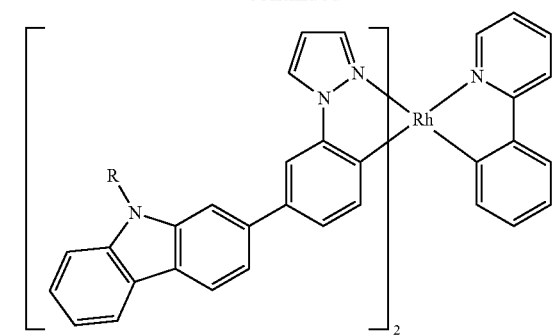
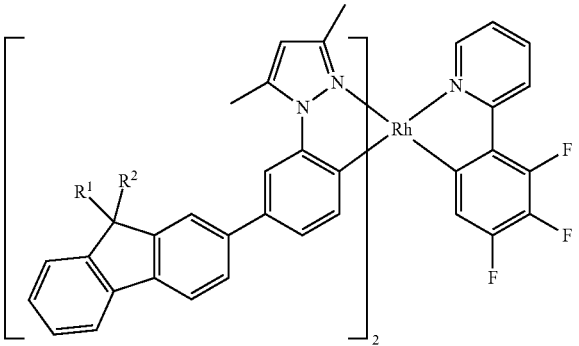
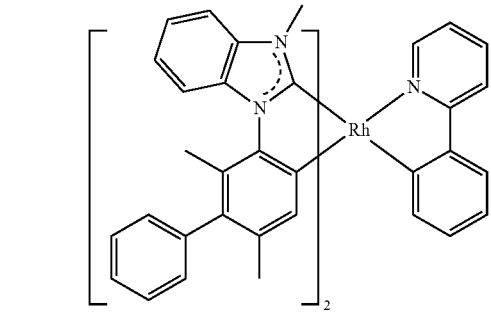
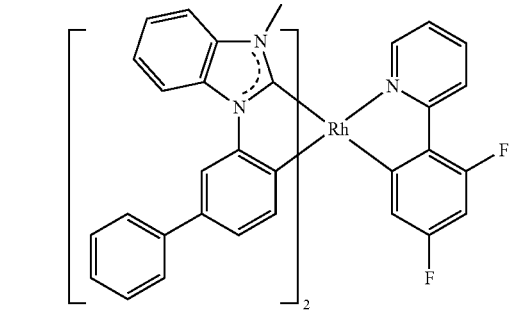
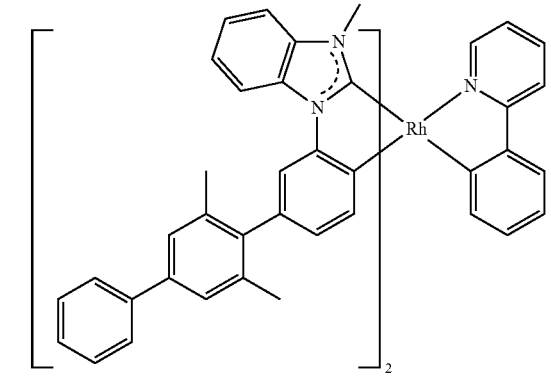
730
-continued
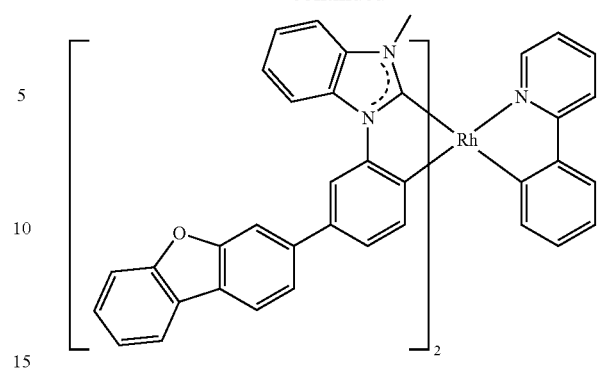
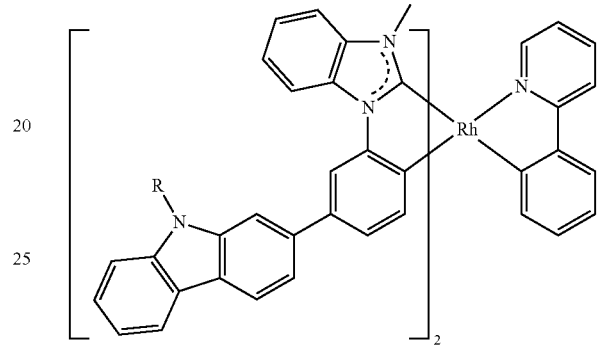
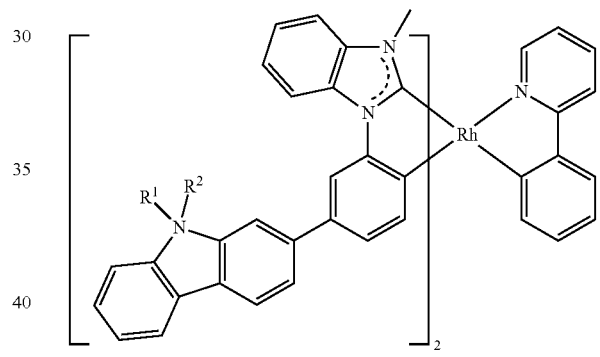
Structures Rh-23
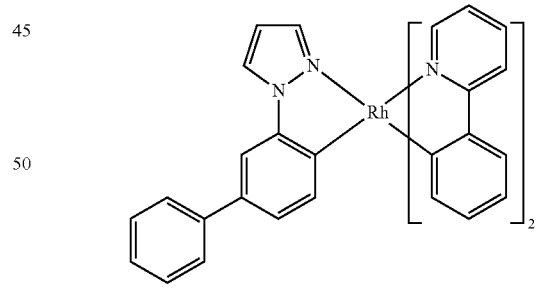
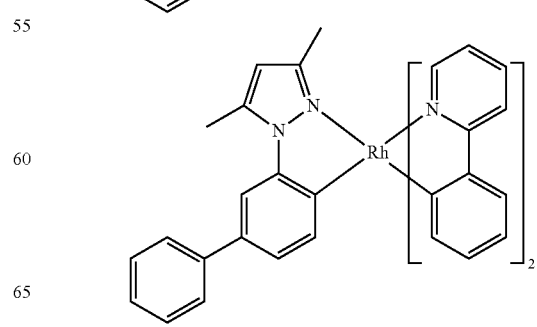

731
-continued
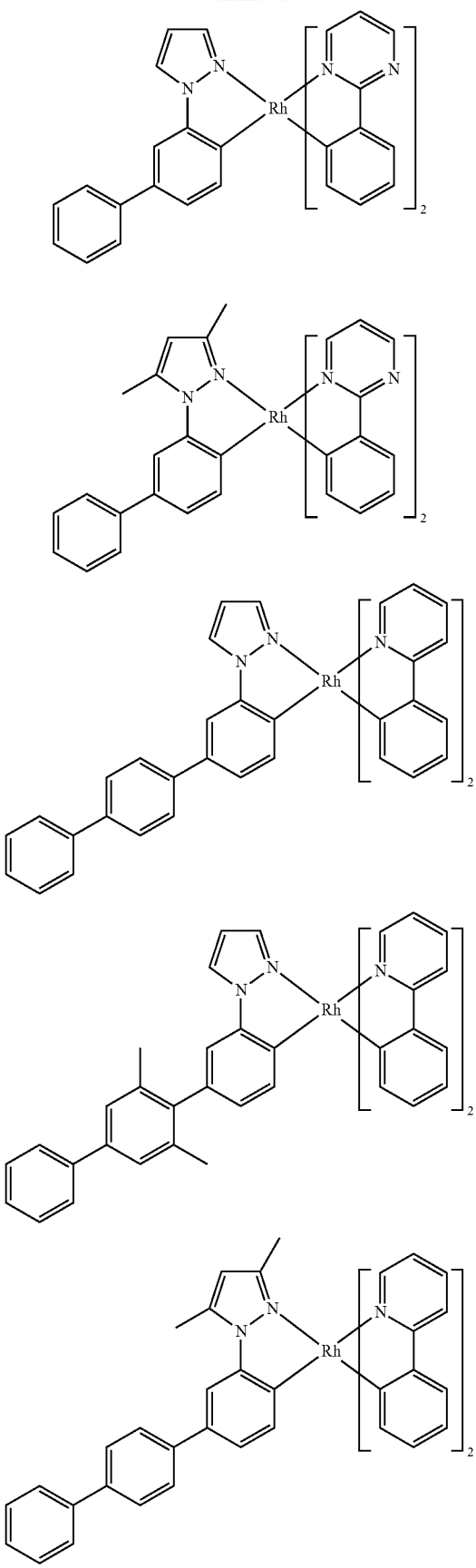
732
-continued
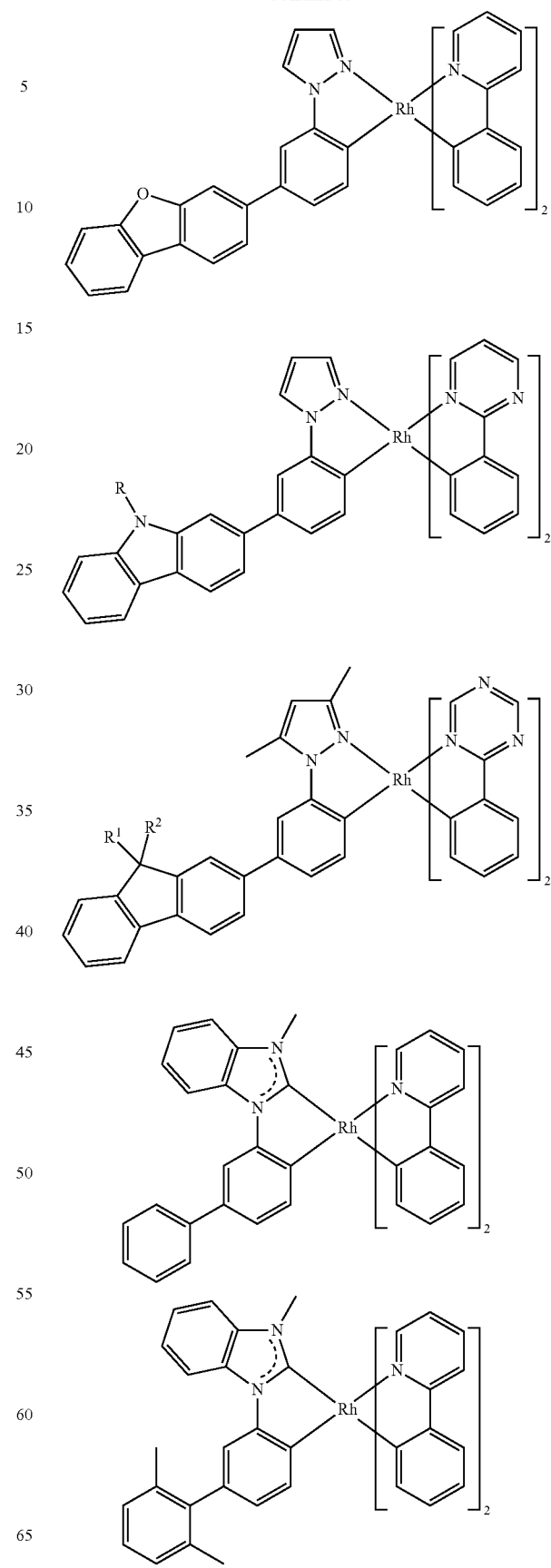

733
-continued

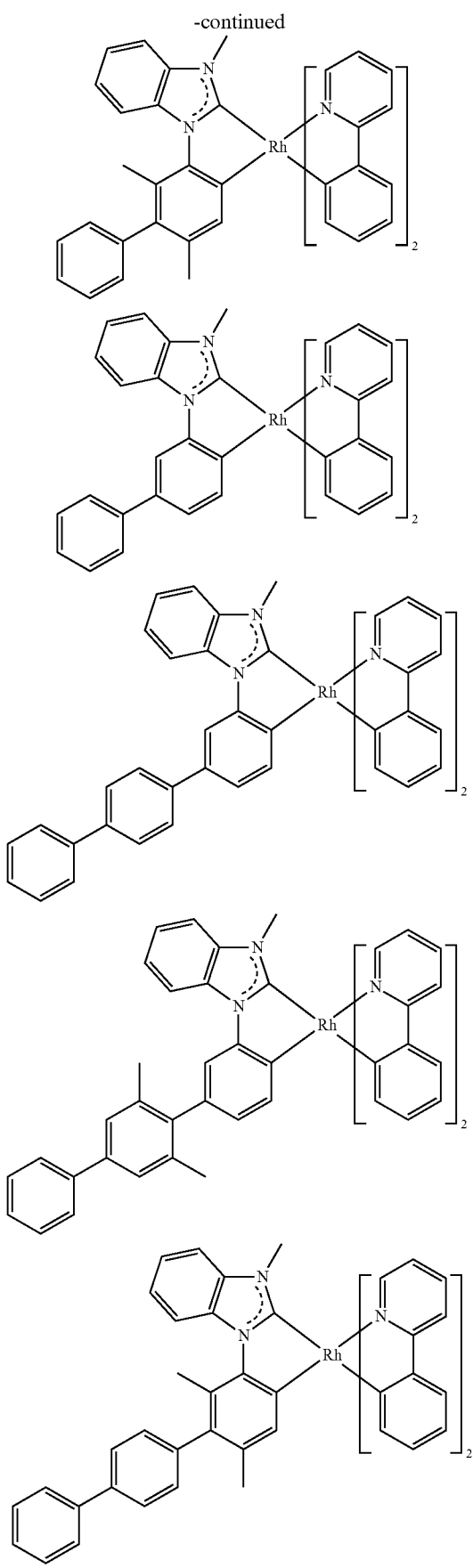

734
-continued

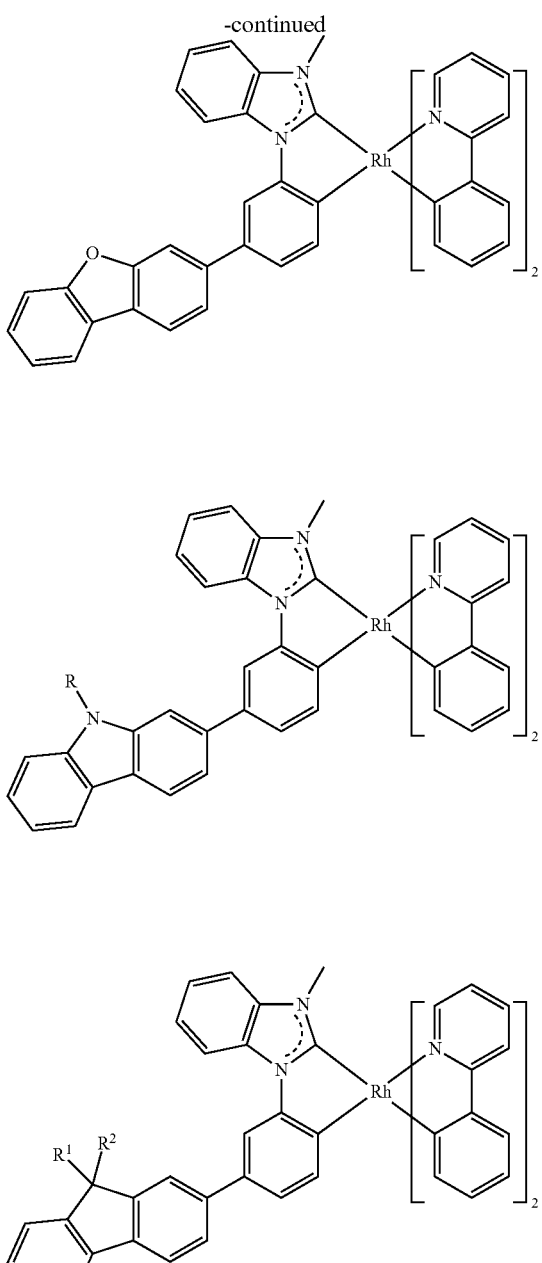

wherein each of R, R¹, and R² is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

15. A compound selected from any of Structures Pt-1 to Pt-10 and Pt-13:

Structures Pt-1
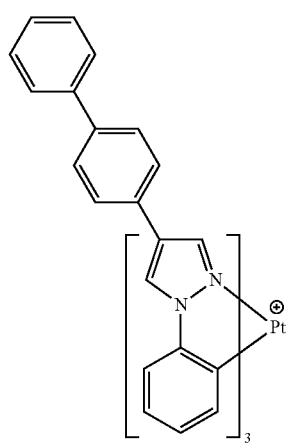
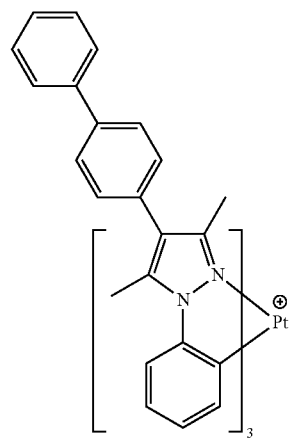
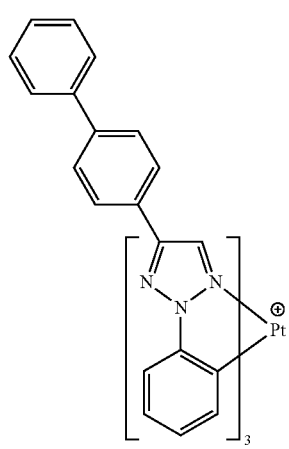
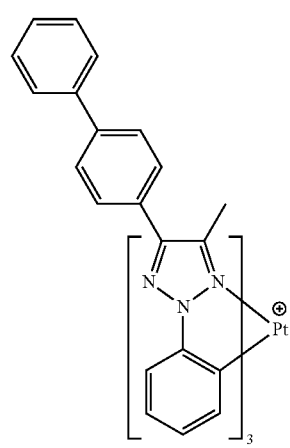
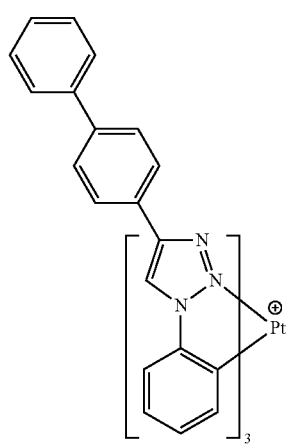
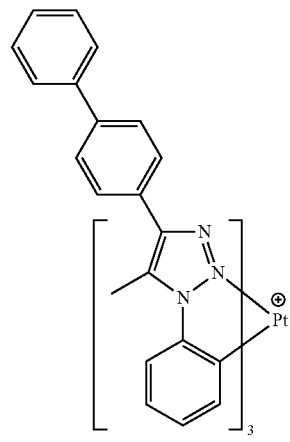

737
-continued
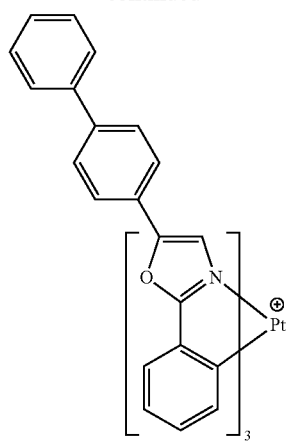
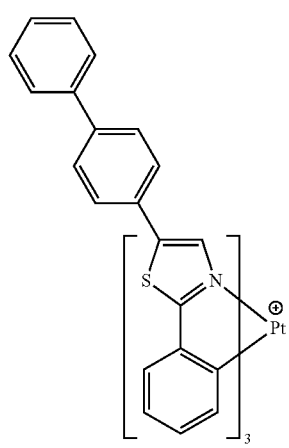
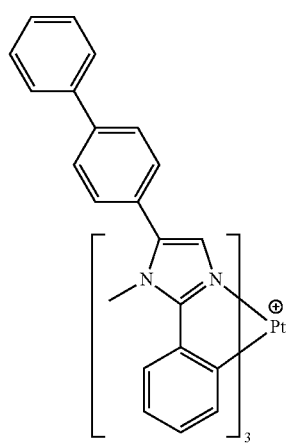
738
-continued
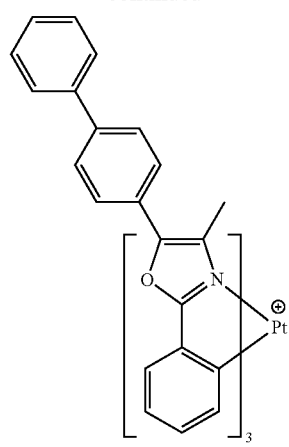
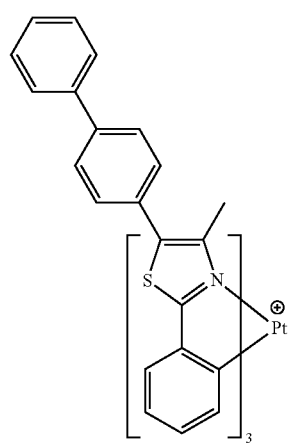
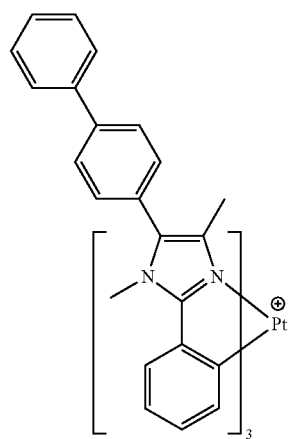

739
-continued
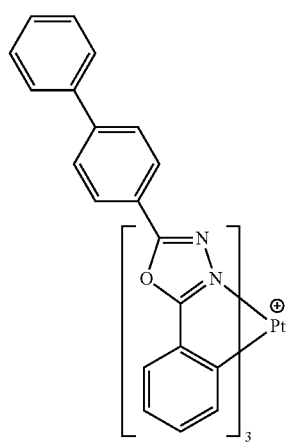
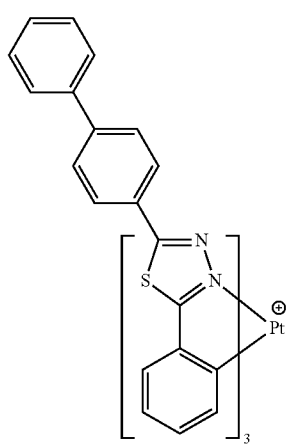
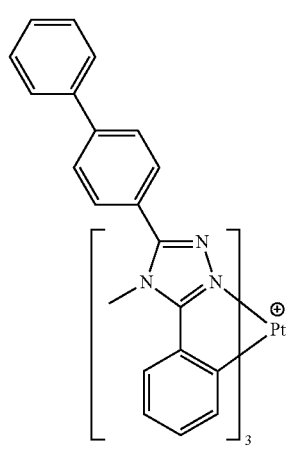
740
-continued
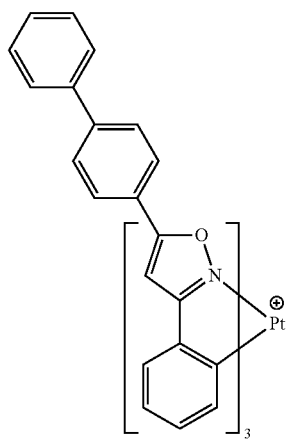
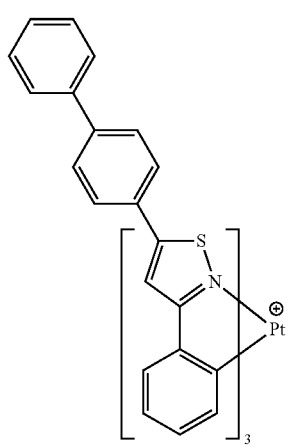
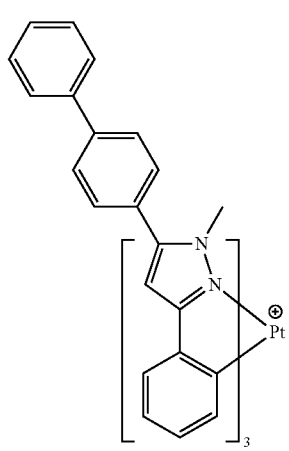

741
-continued
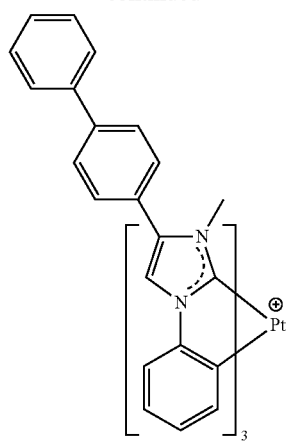
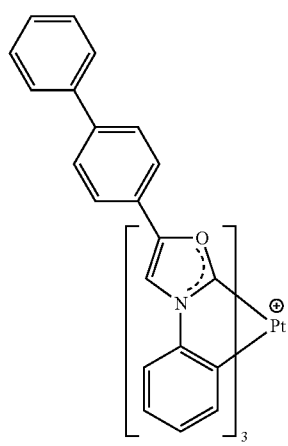
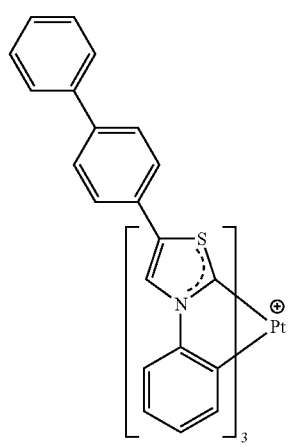
742
-continued
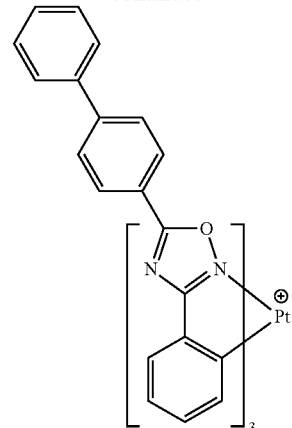
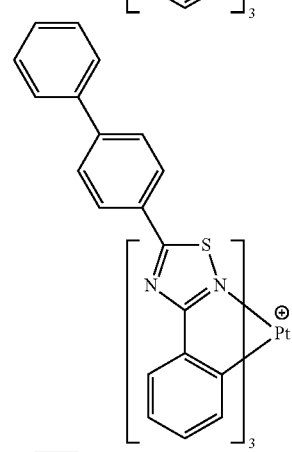
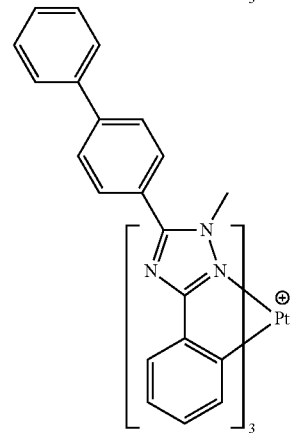
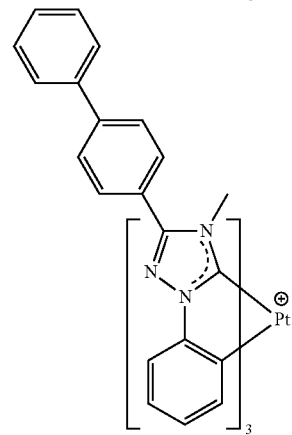

743
-continued
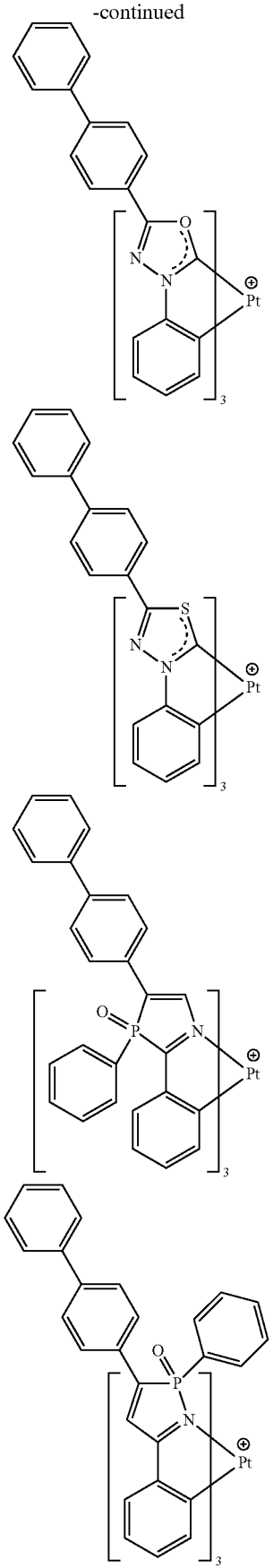
744
-continued
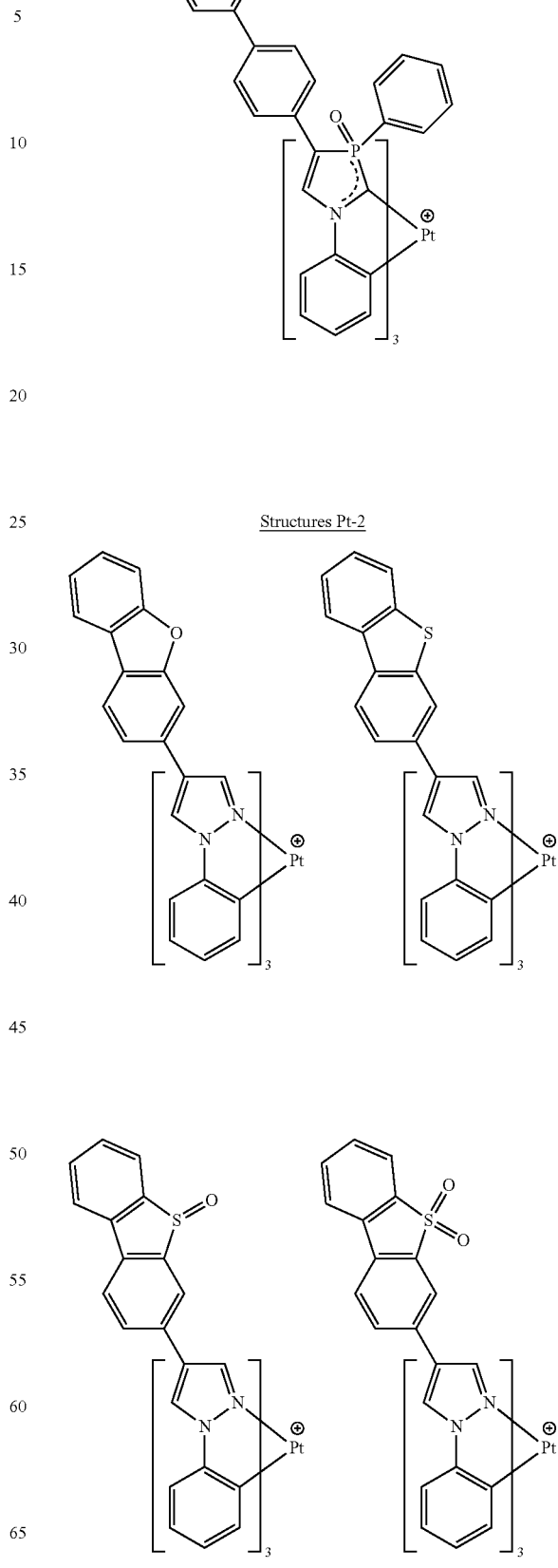
Structures Pt-2

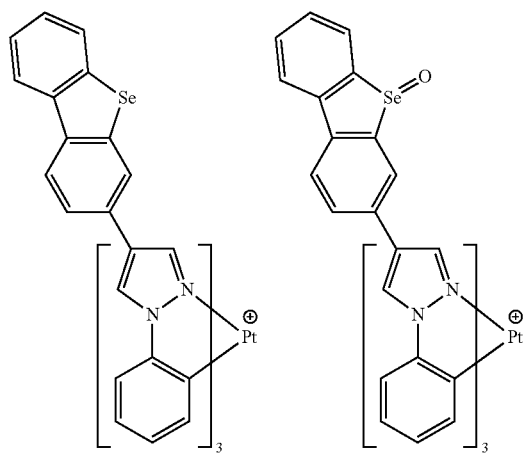
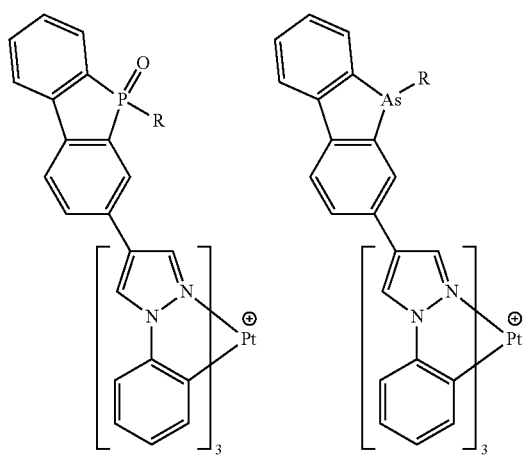
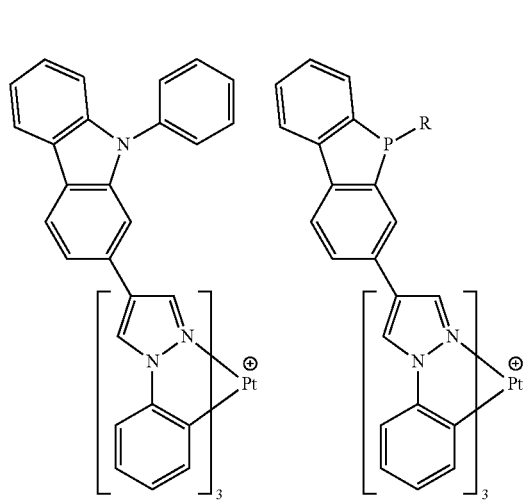

747
-continued
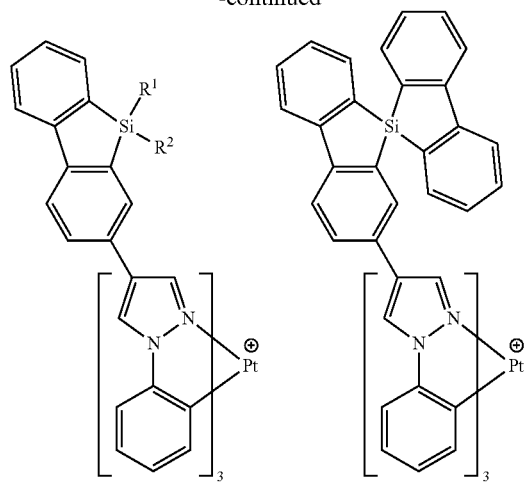
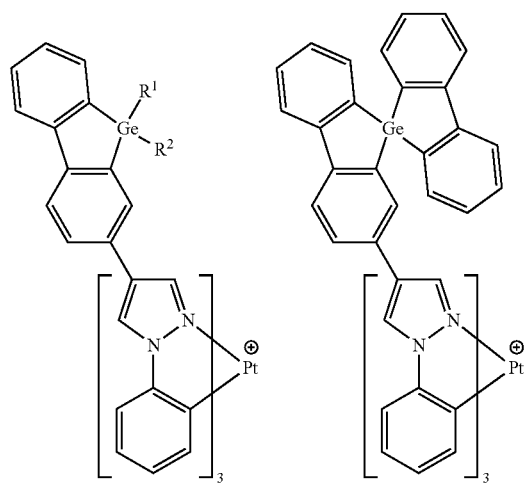
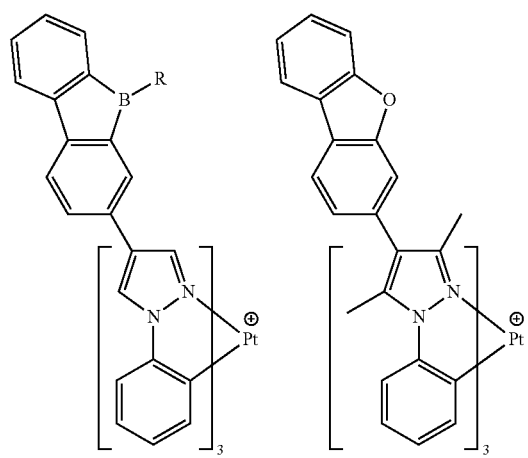
748
-continued
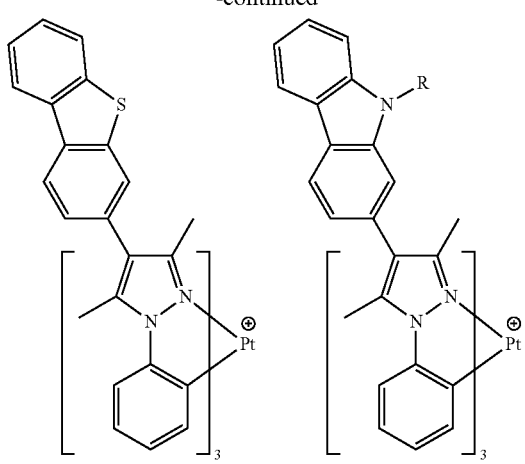
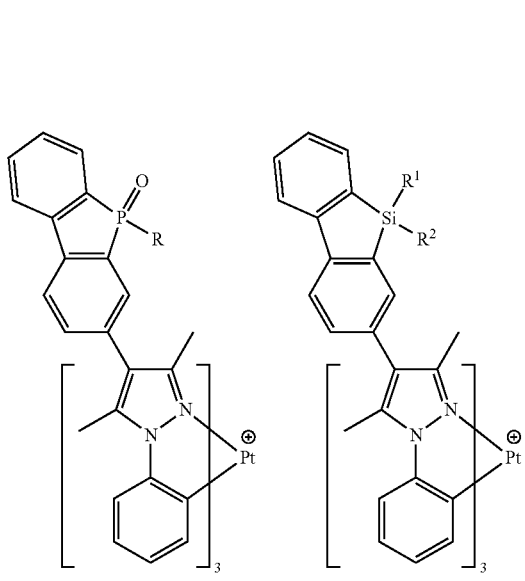

749
-continued
750
-continued
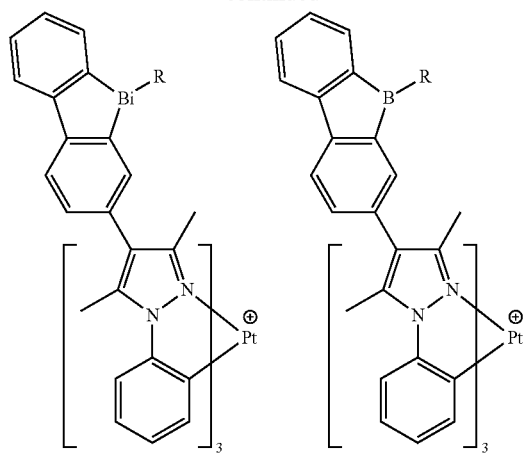
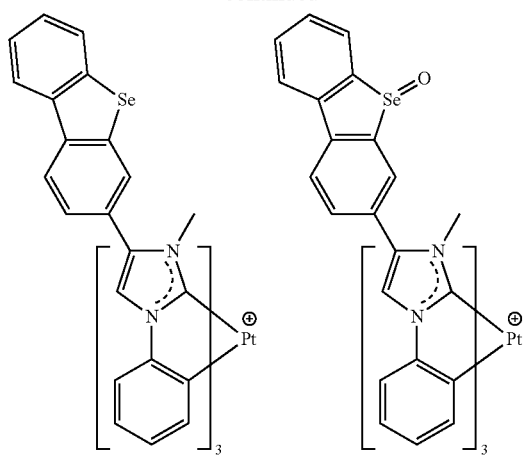
Structures Pt-3
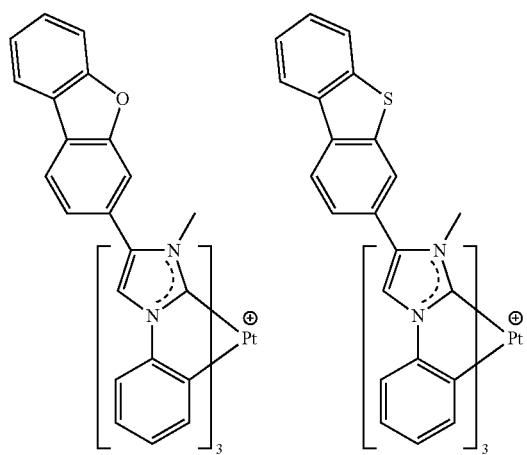
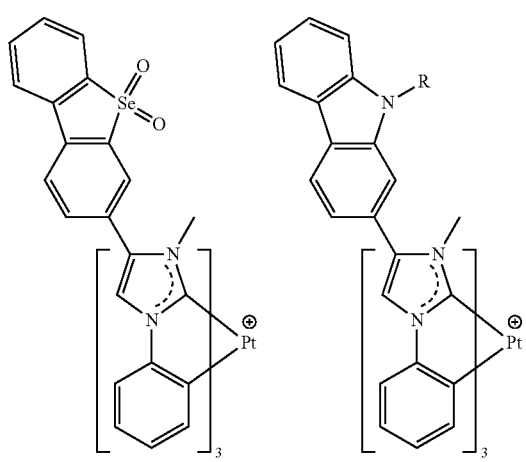
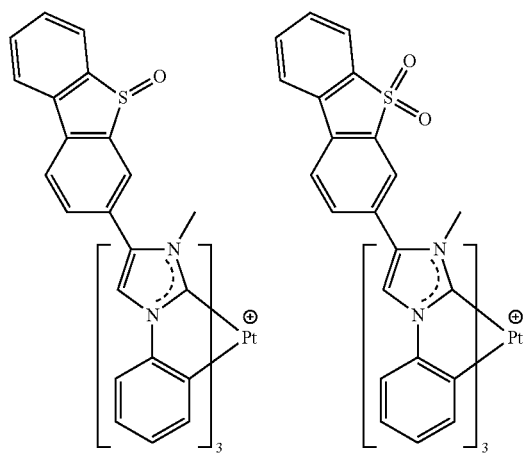
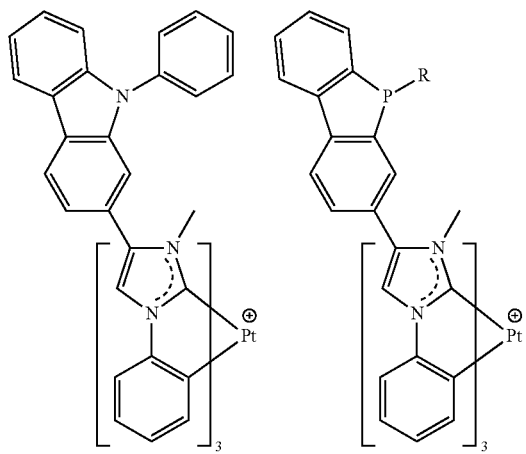

751
-continued
752
-continued
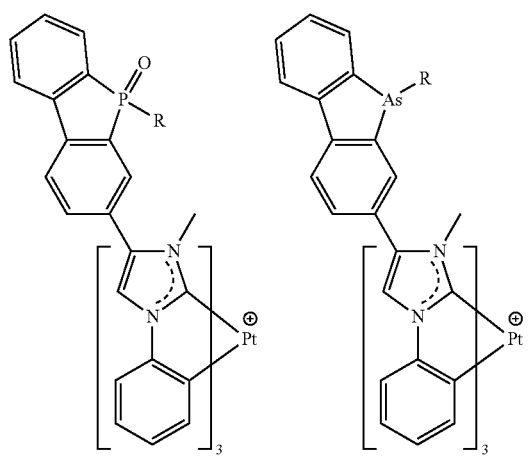
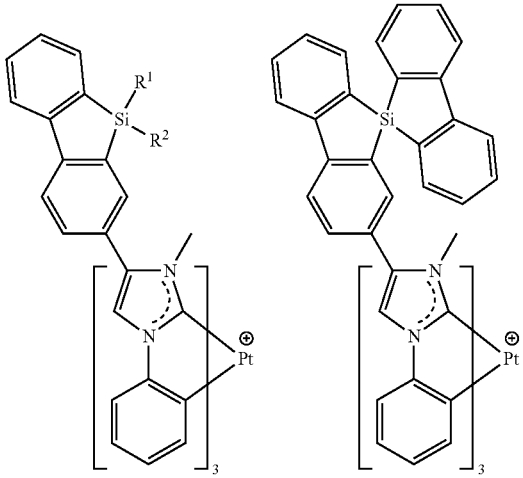
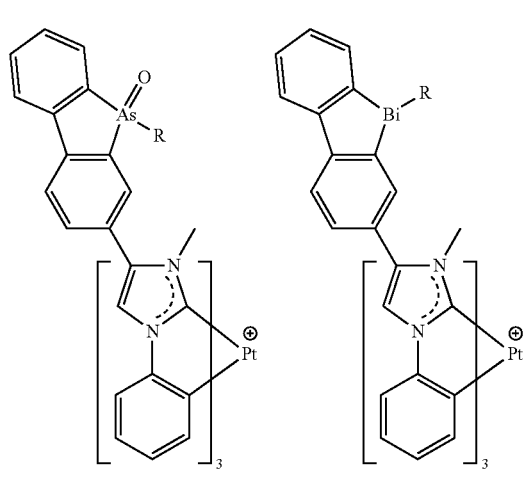
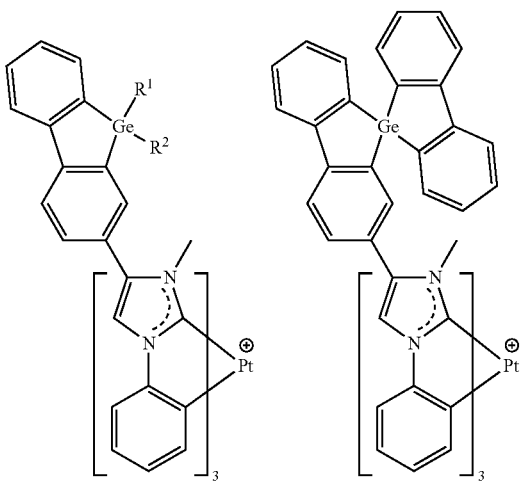
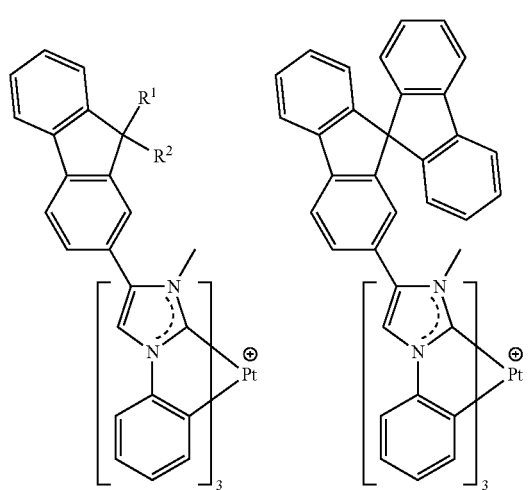
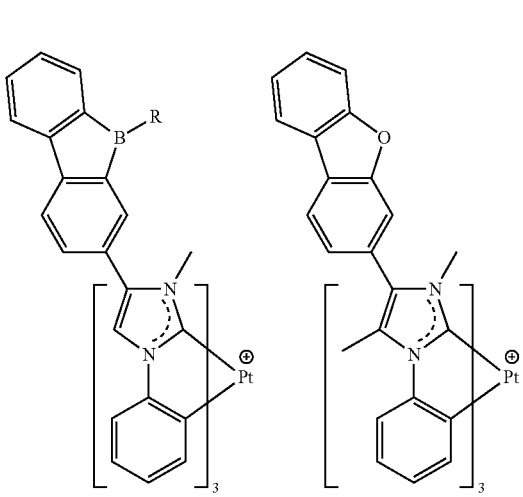

753
-continued
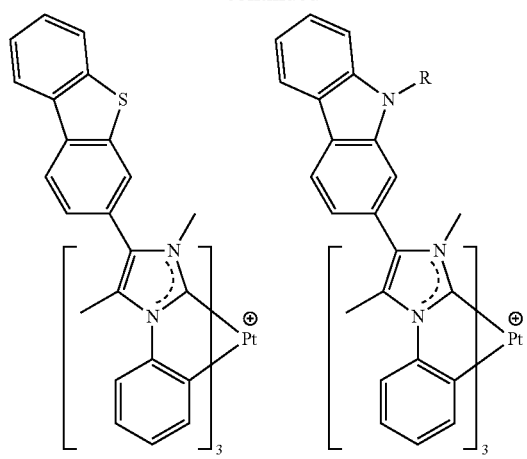
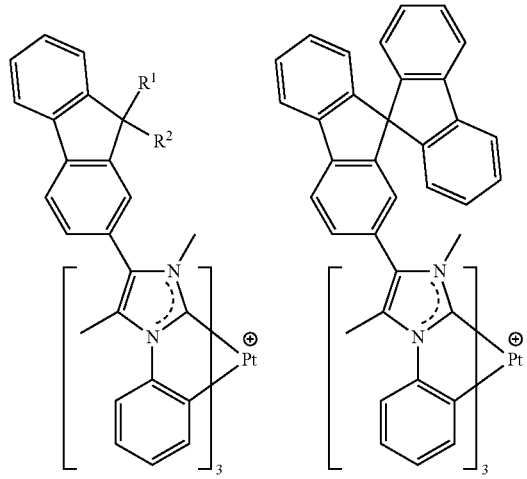
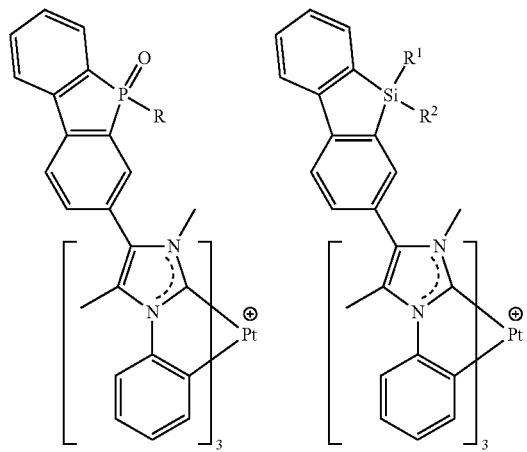
754
-continued
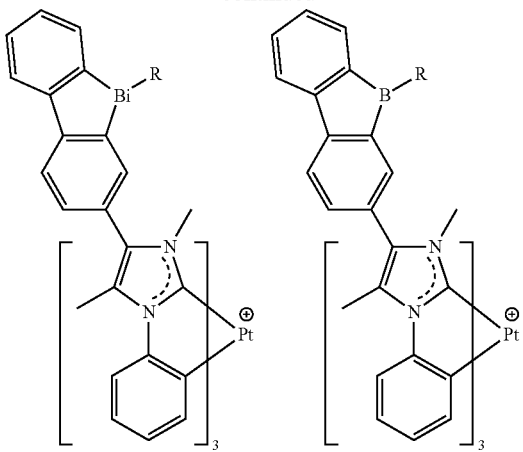
Structures Pt-4
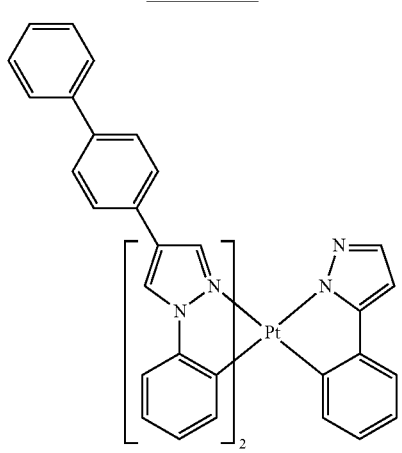
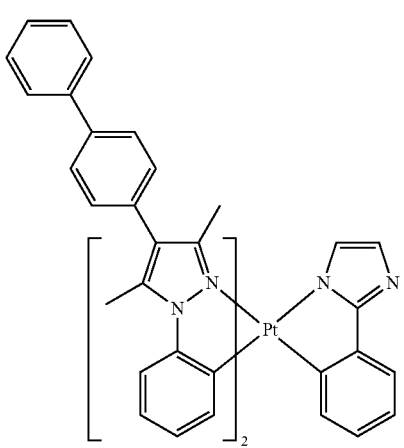

755
-continued
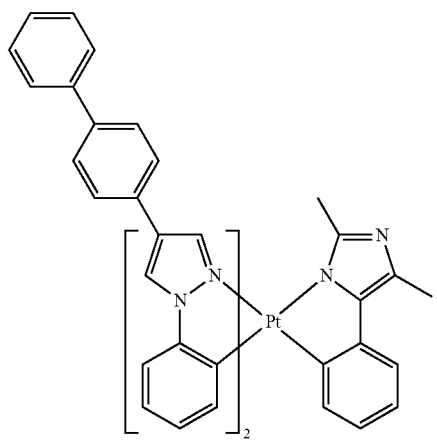
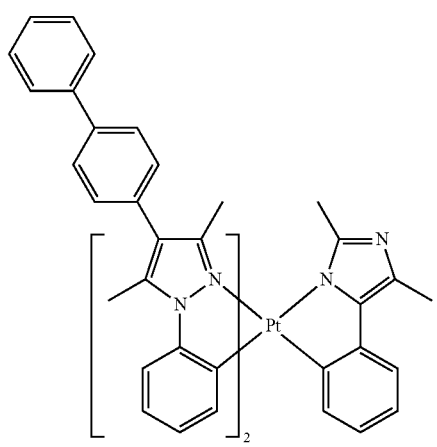
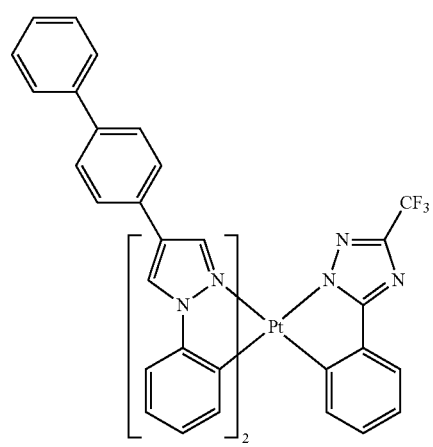
756
-continued
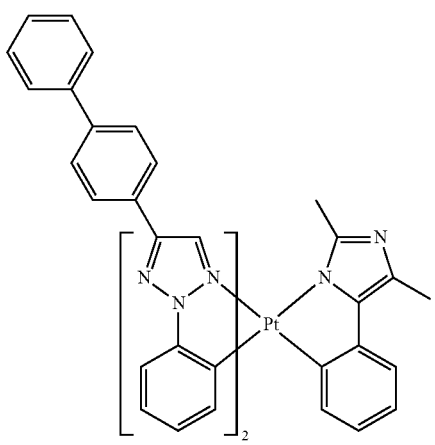
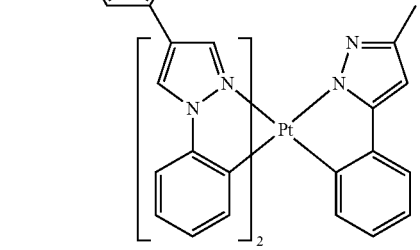
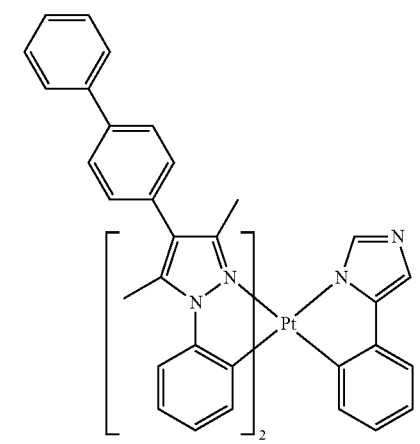

757
-continued
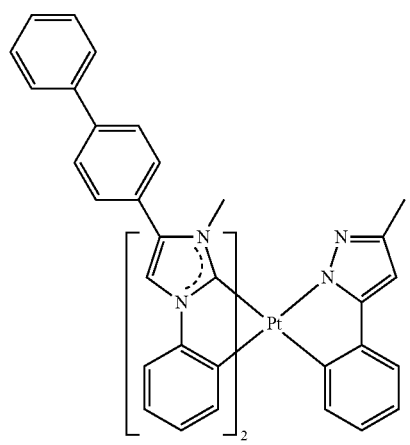
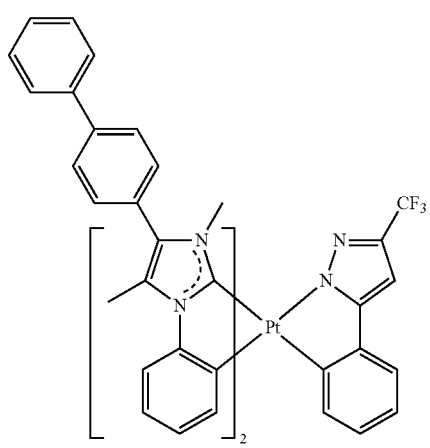
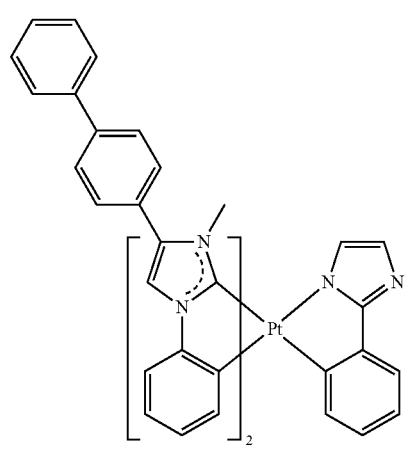
758
-continued
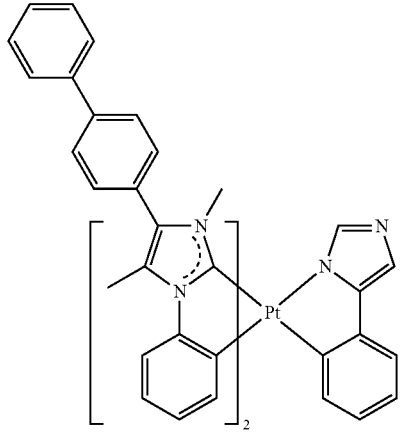
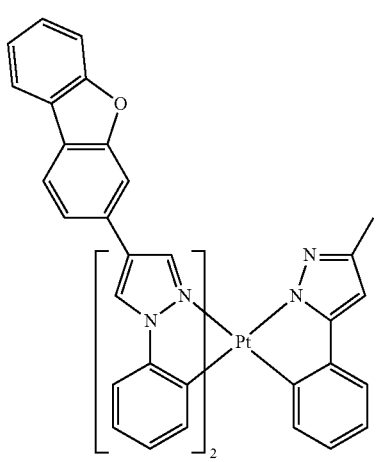
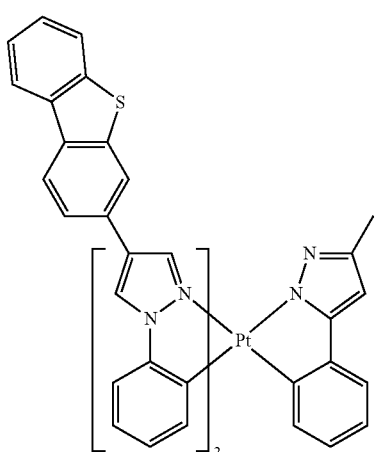

759
-continued
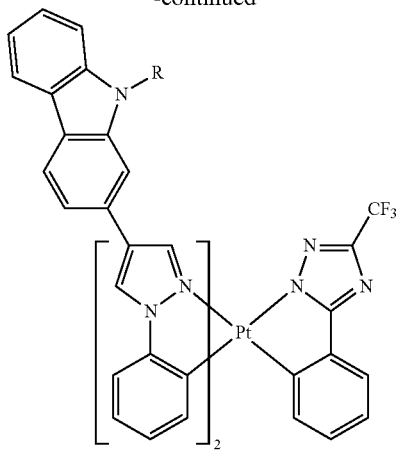
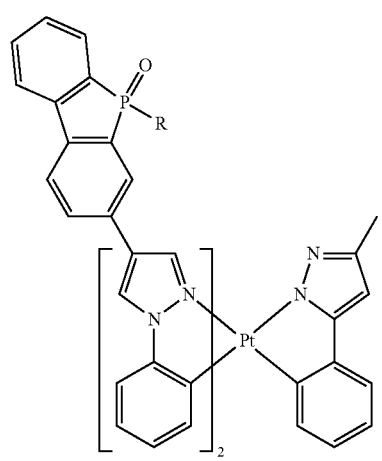
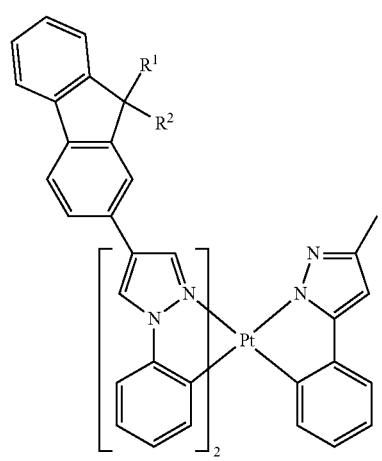
760
-continued
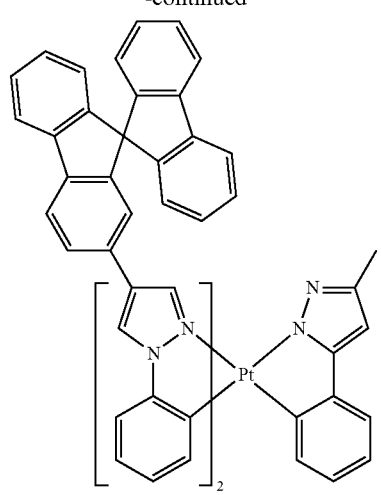
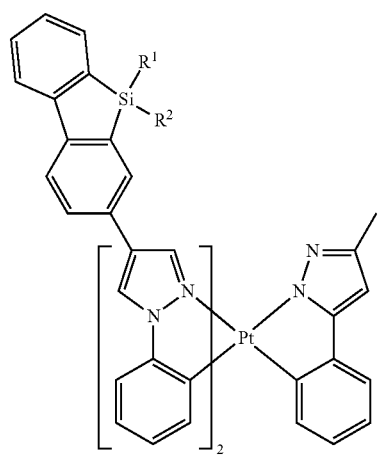
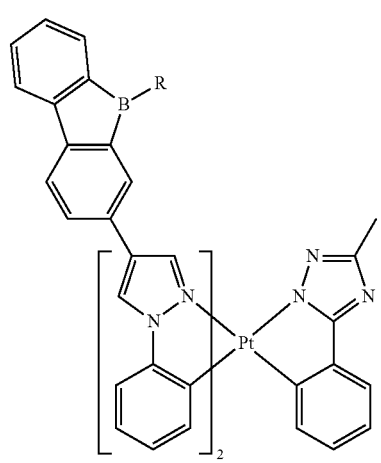

761
-continued
Structures Pt-5
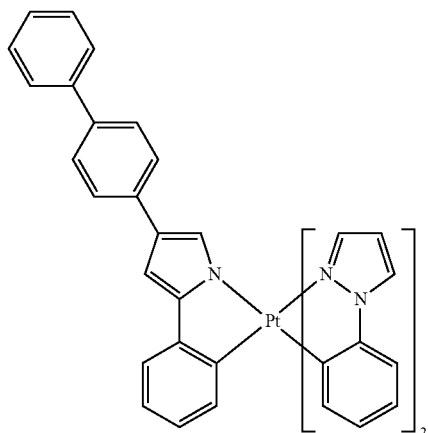
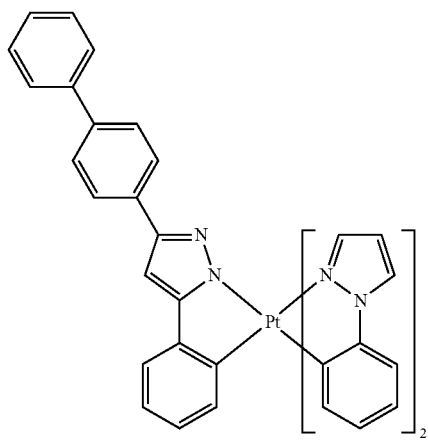
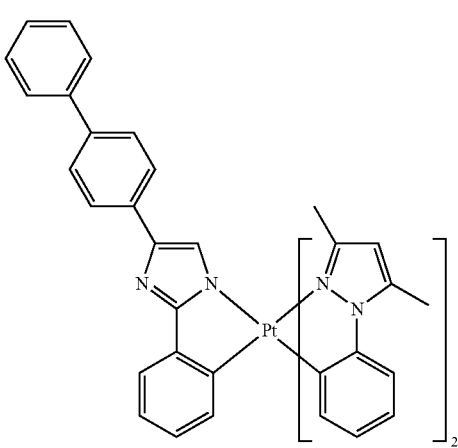
762
-continued
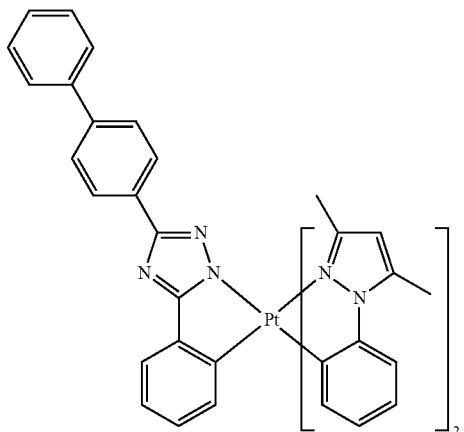
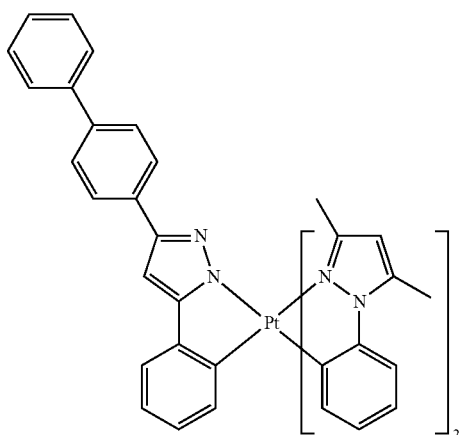
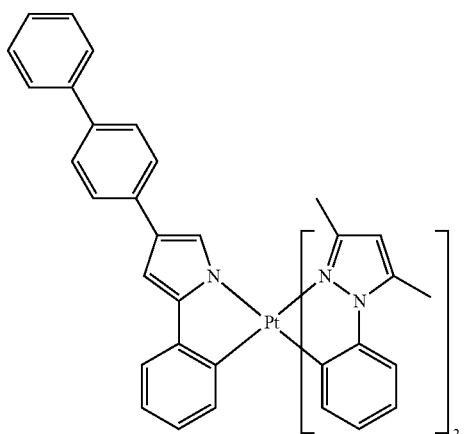

763
-continued
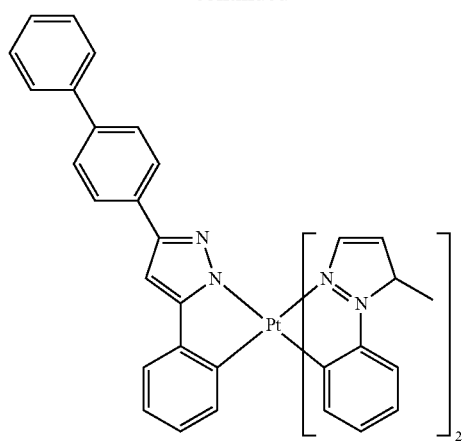
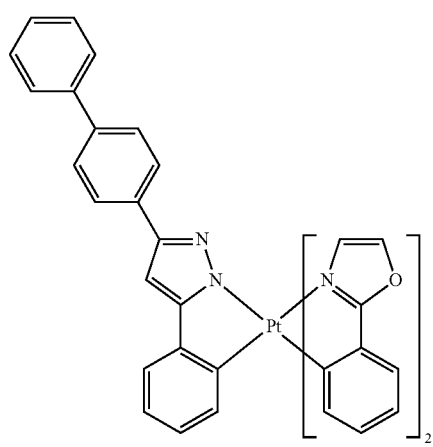
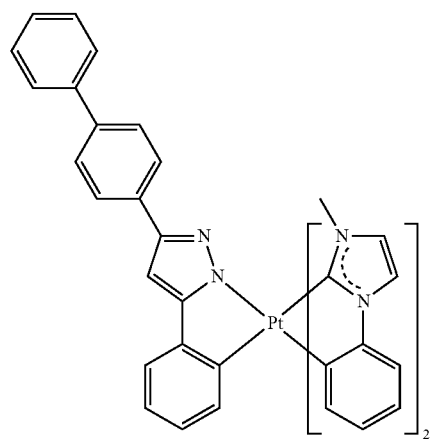
764
-continued
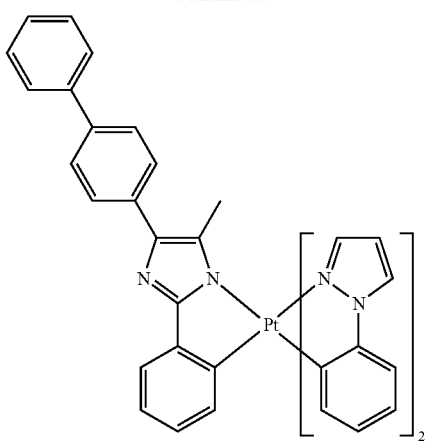
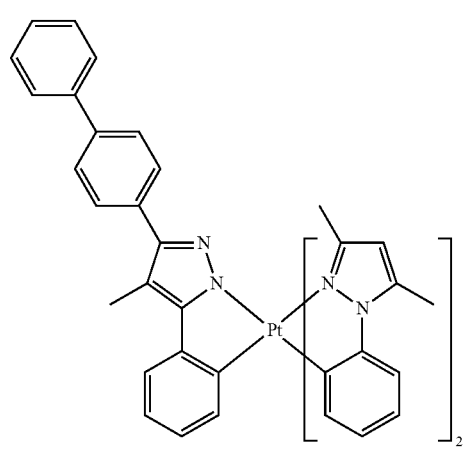
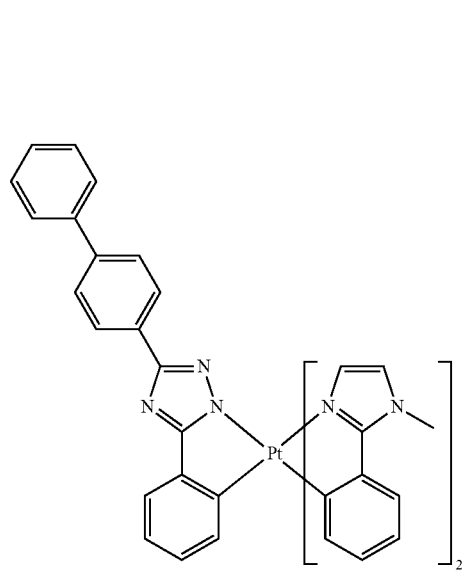

765
-continued
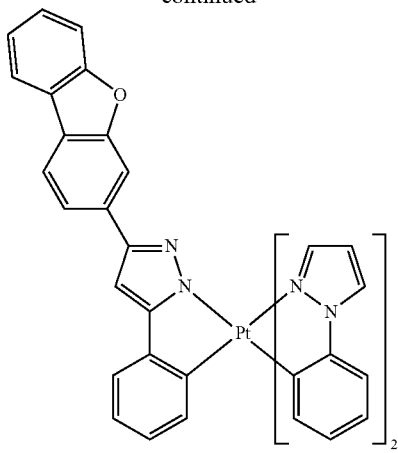
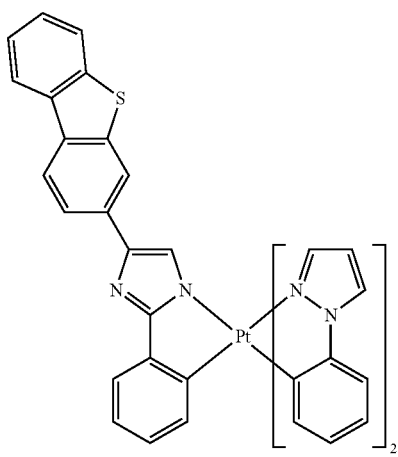
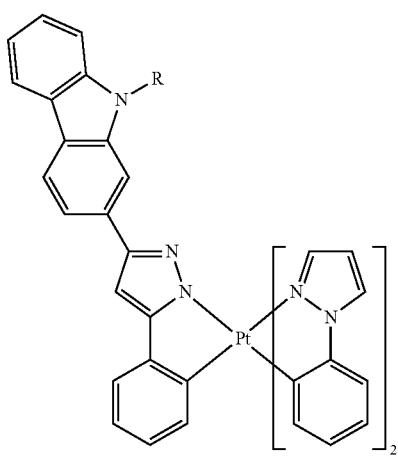
766
-continued
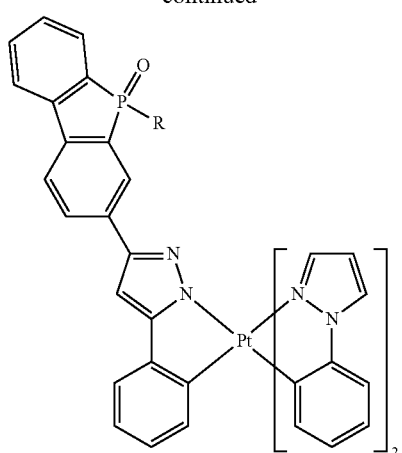
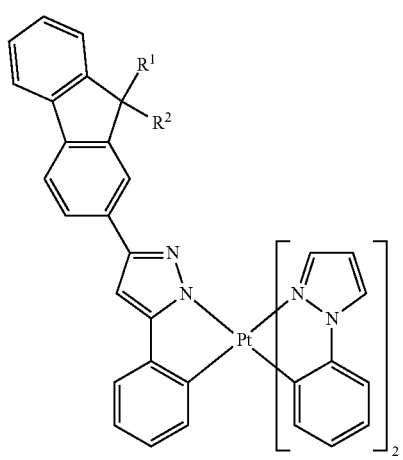
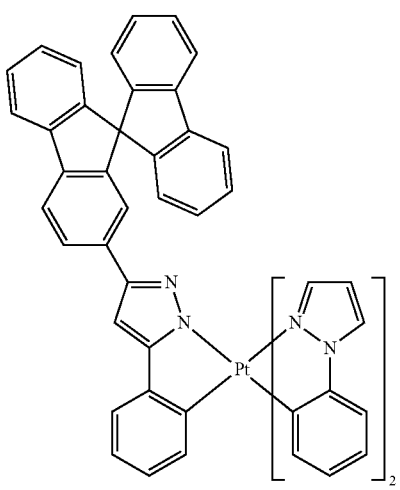

767
-continued
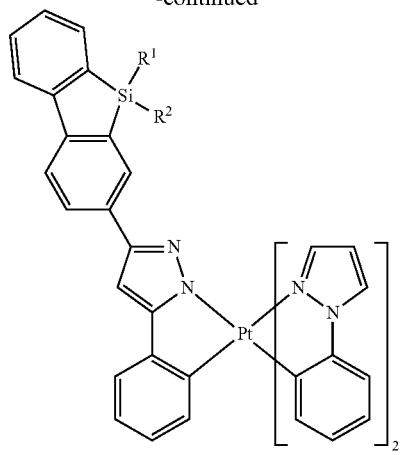
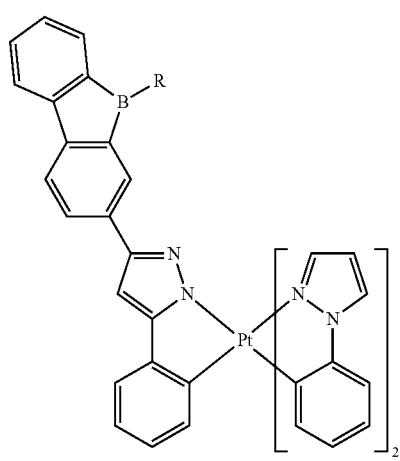
Structures Pt-6
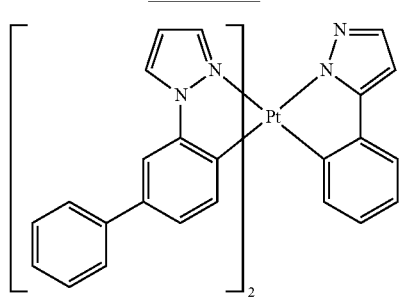
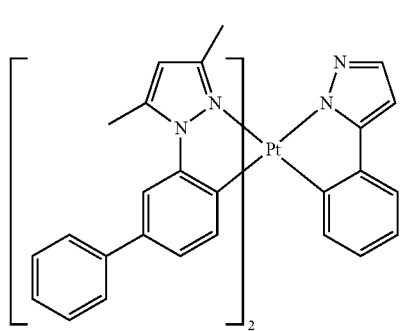
768
-continued
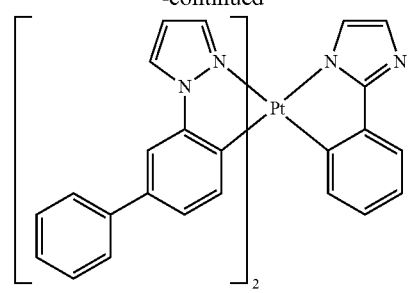
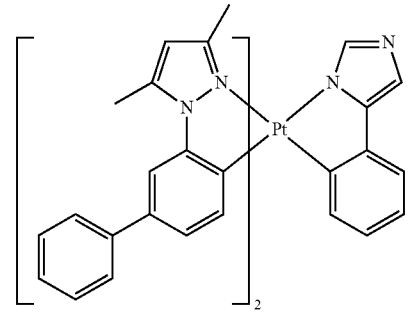
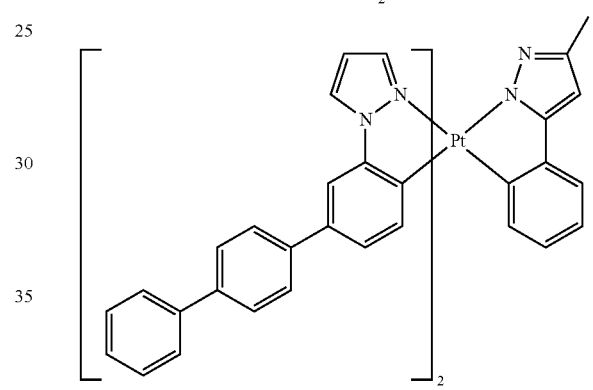
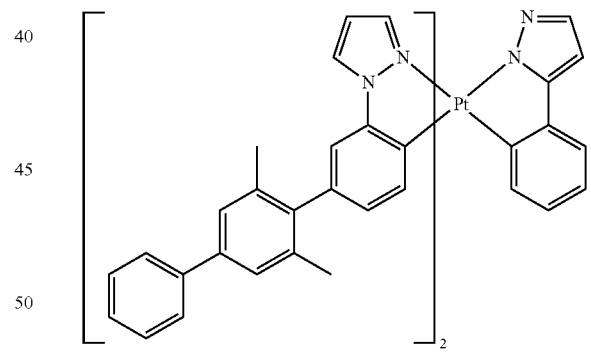
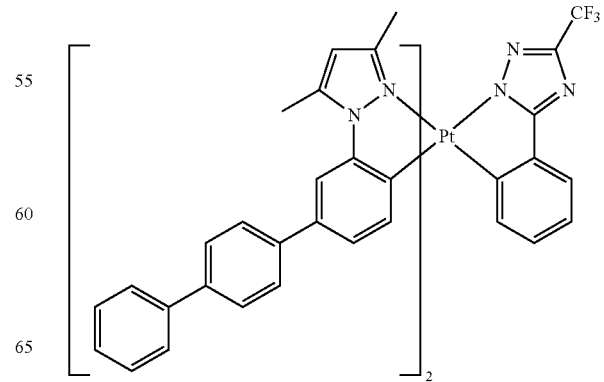

769
-continued
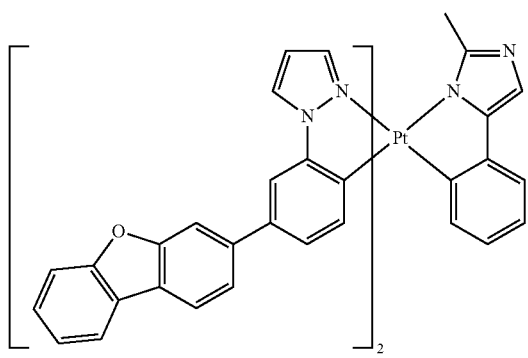
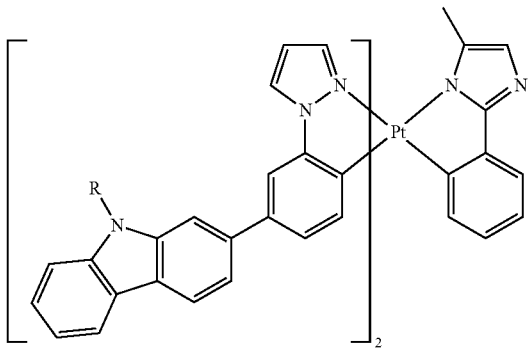
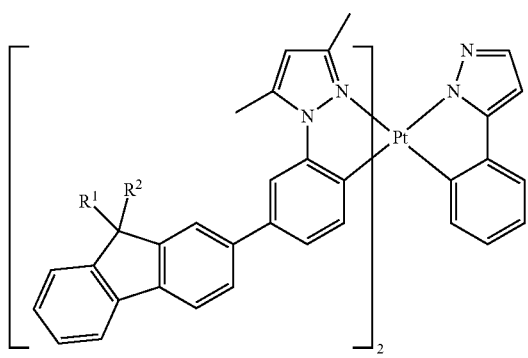
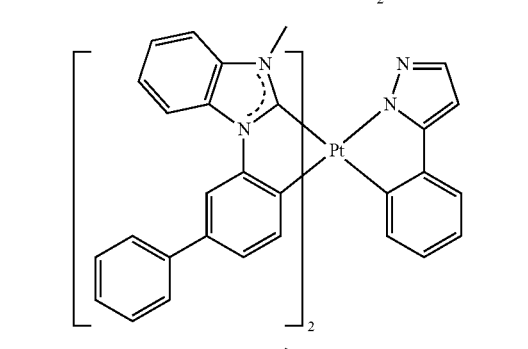
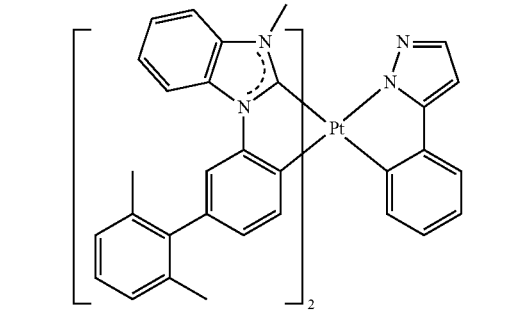
770
-continued
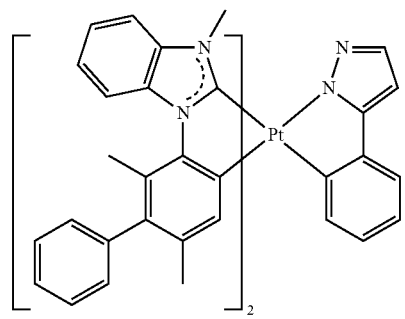
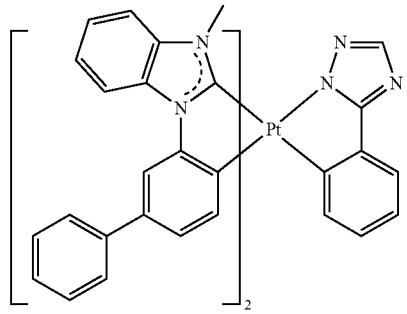
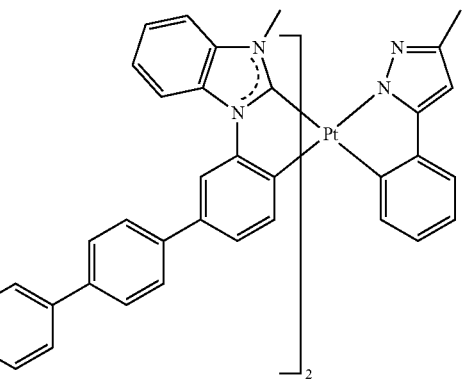
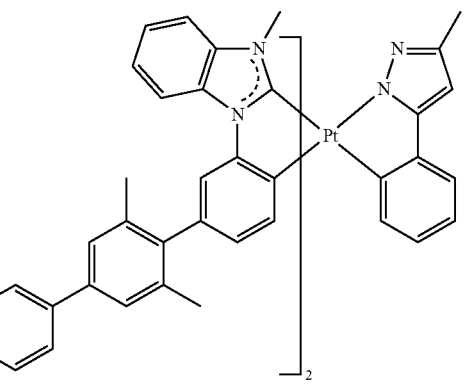

-continued
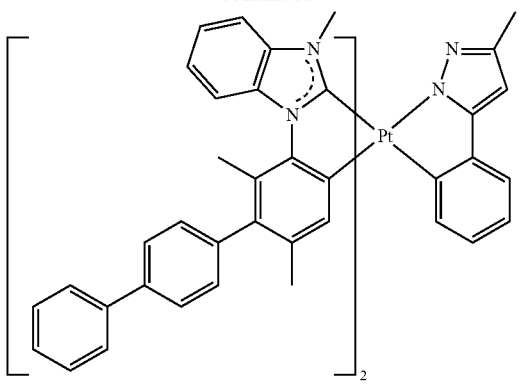
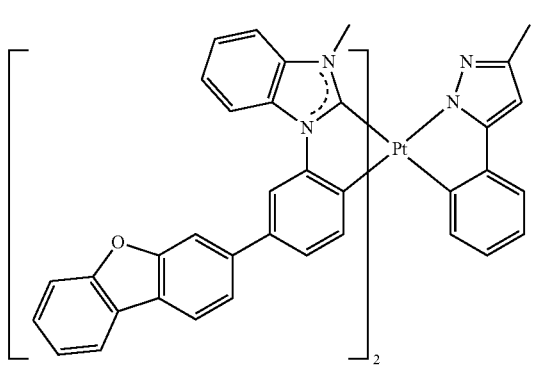
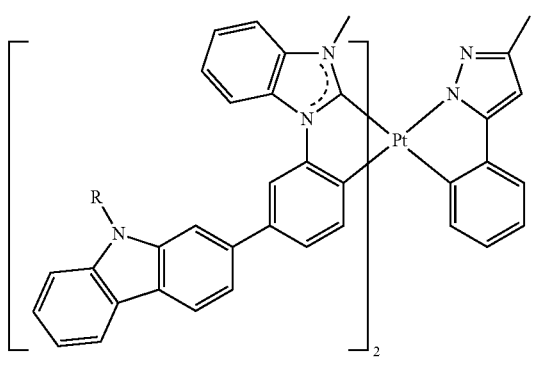
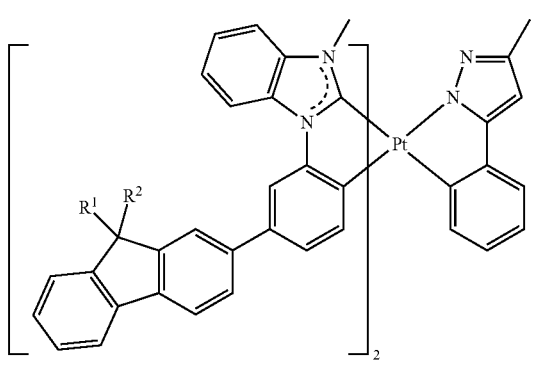
-continued
Structures Pt-7
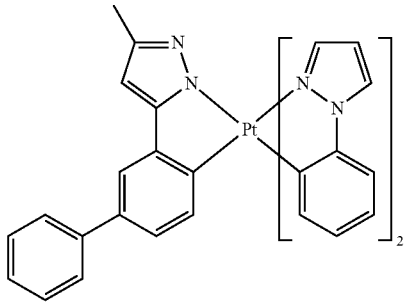
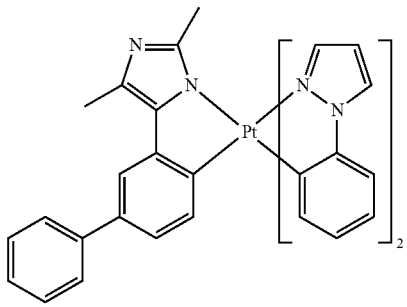
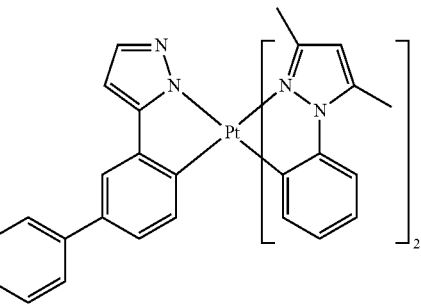
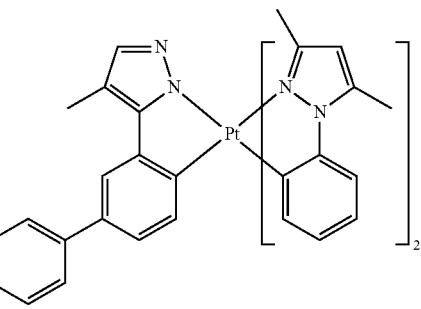
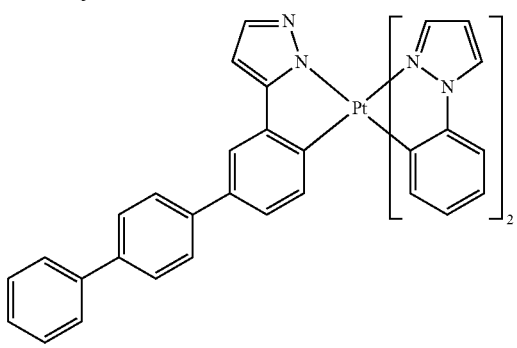

773
-continued
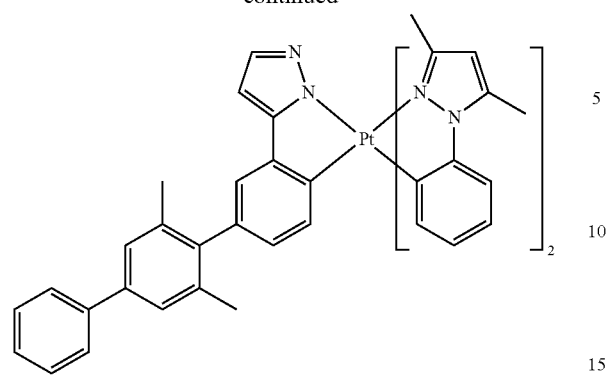
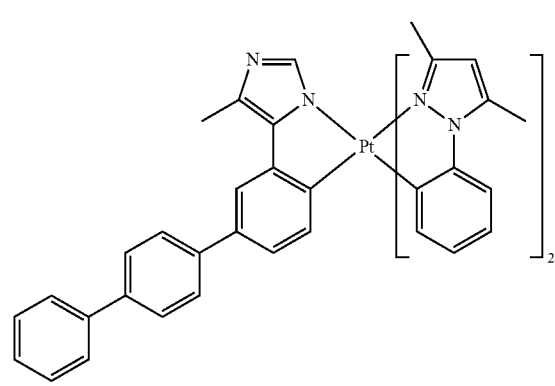
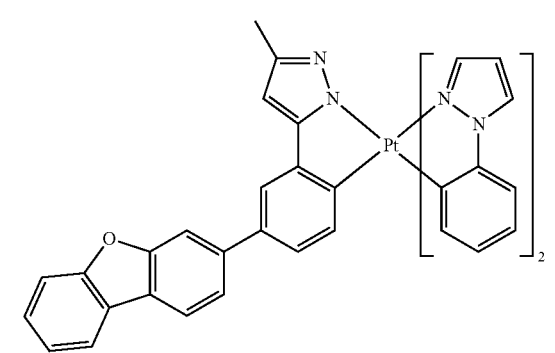
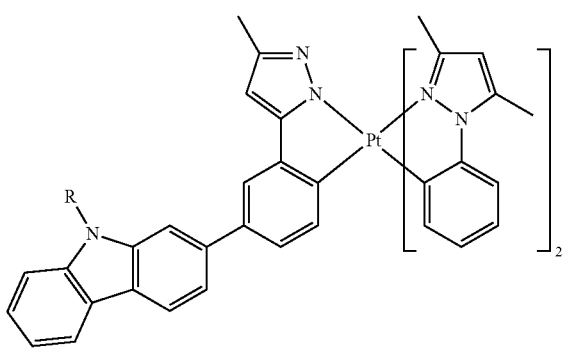
774
-continued
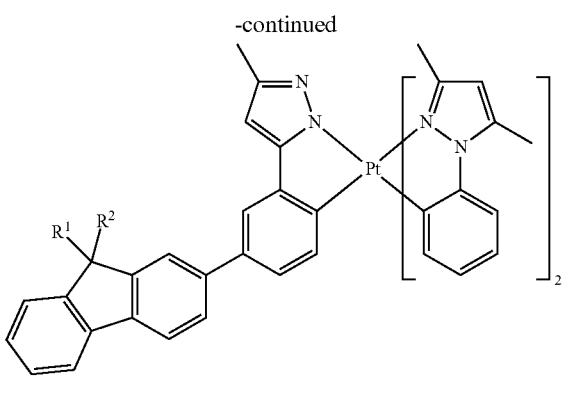
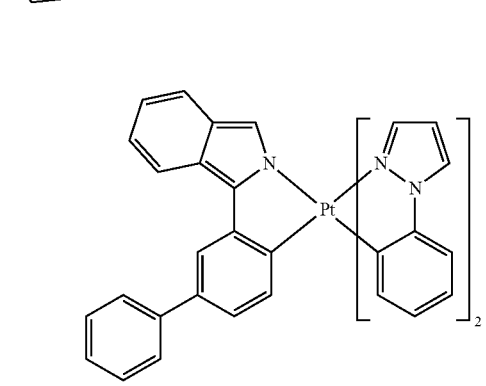
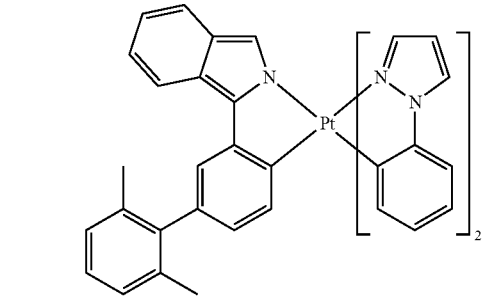
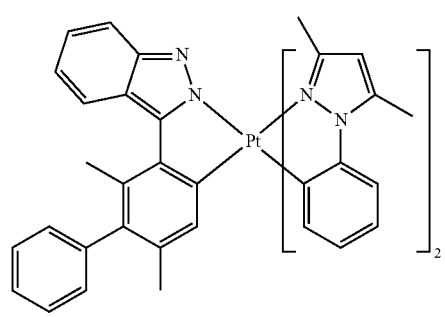
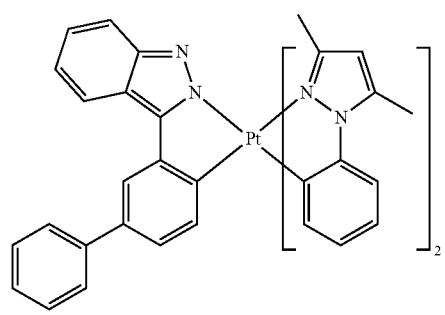

775
-continued
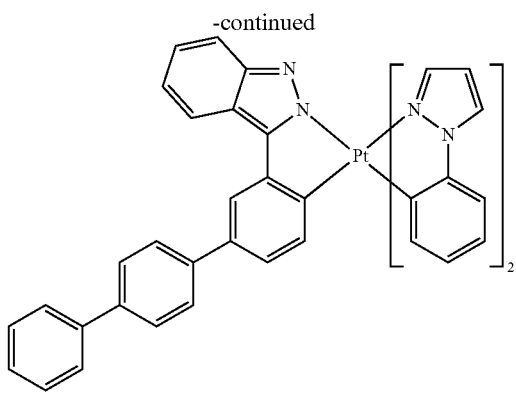
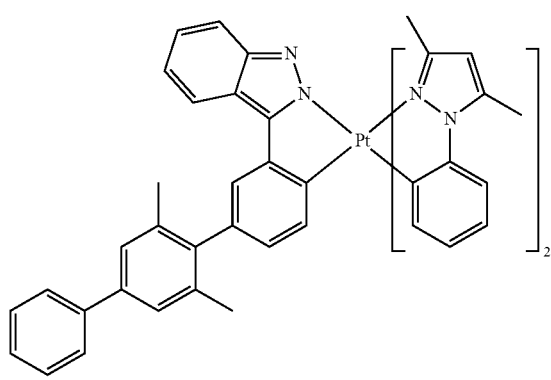
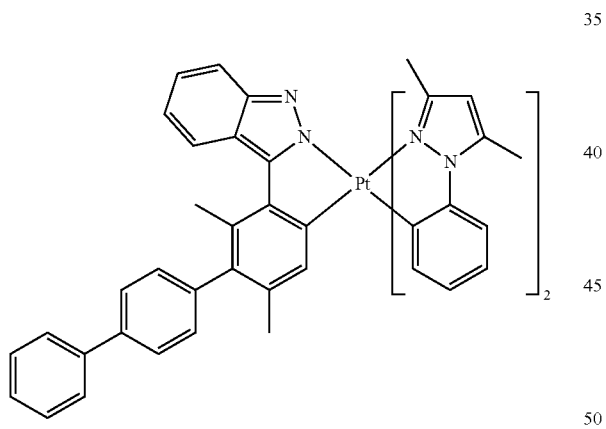
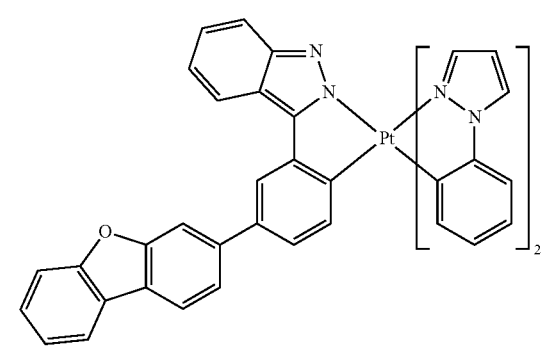
776
-continued
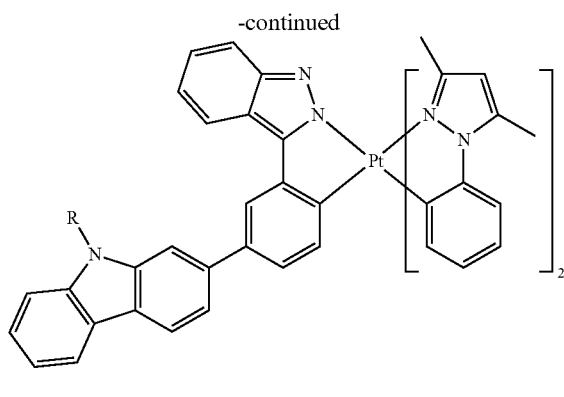
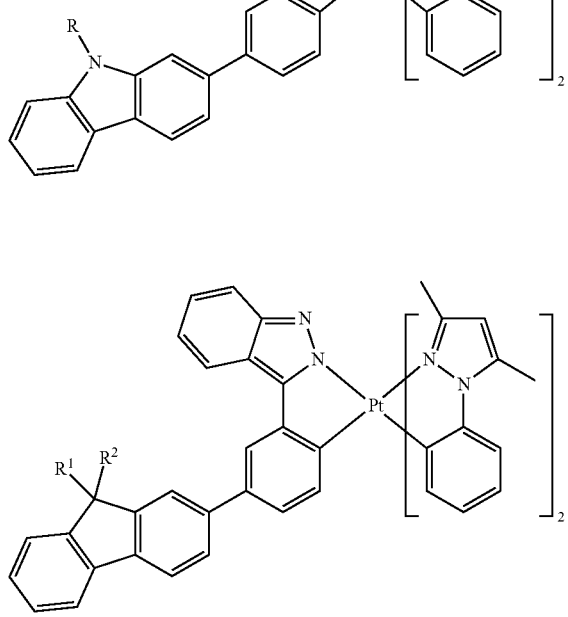
Structures Pt-8
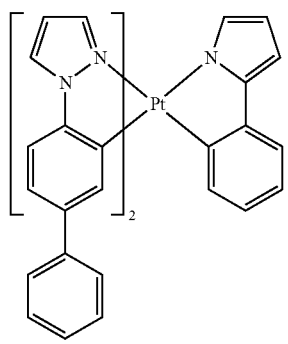
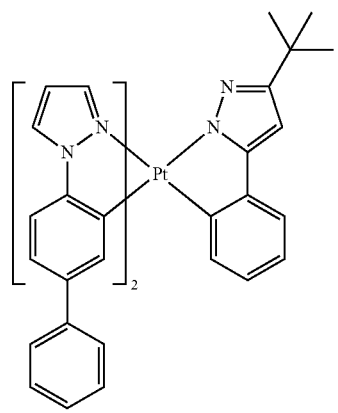

777
-continued
778
-continued
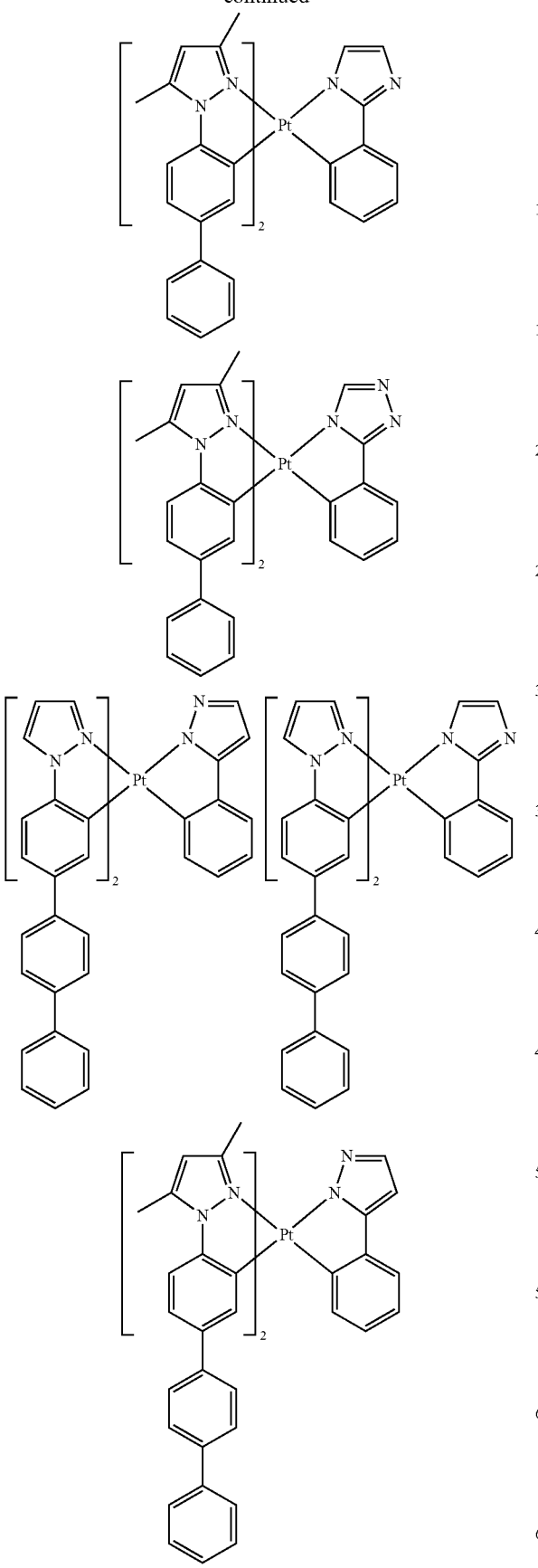
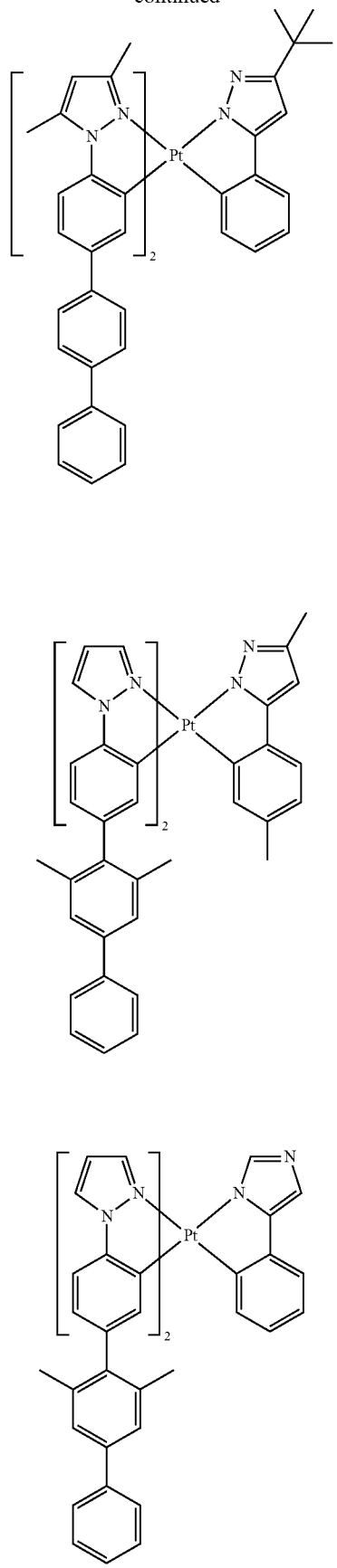

779
-continued
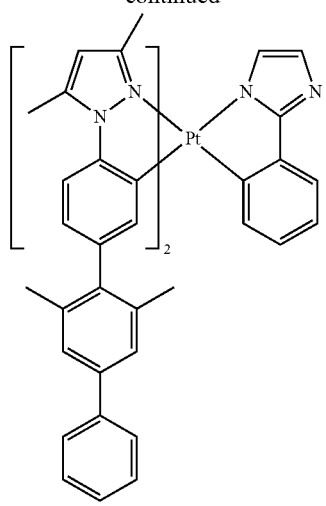
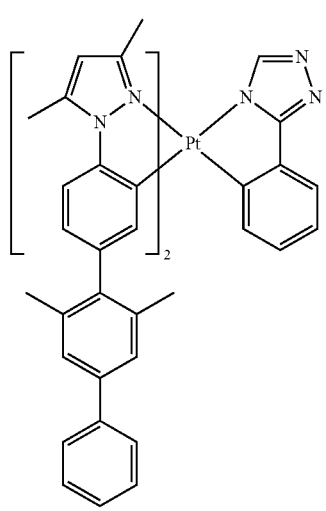
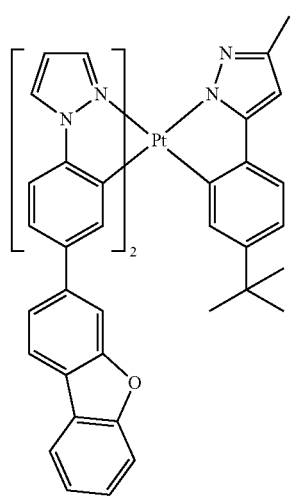
780
-continued
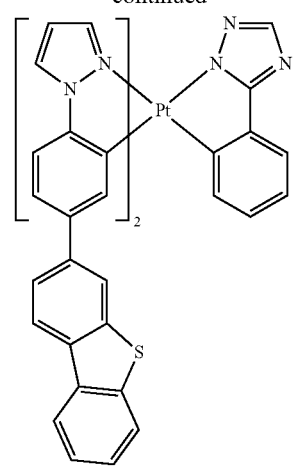
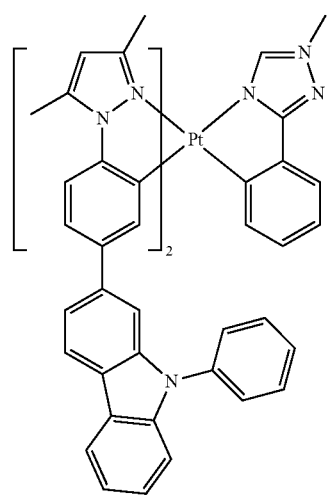
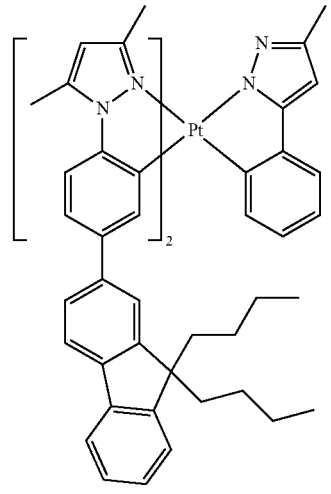

781
-continued
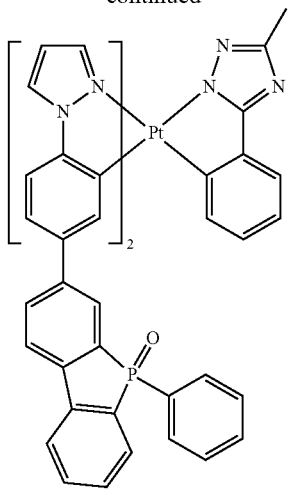
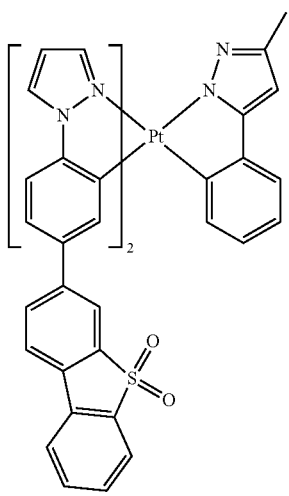
782
-continued
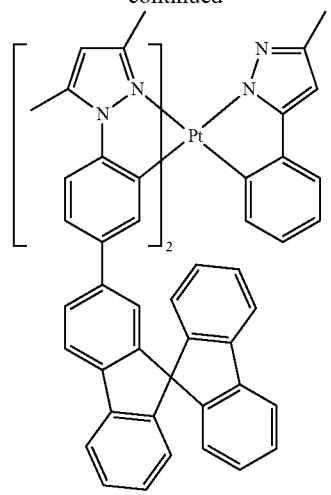
Structures Pt-9
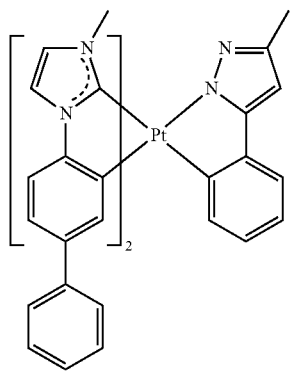
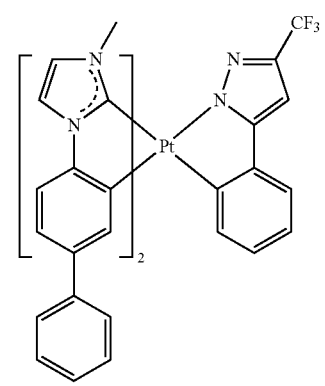
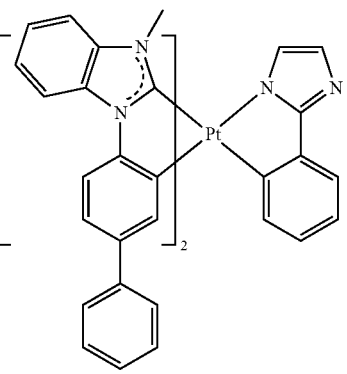

783
-continued
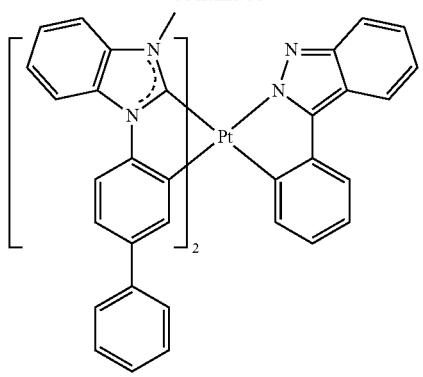
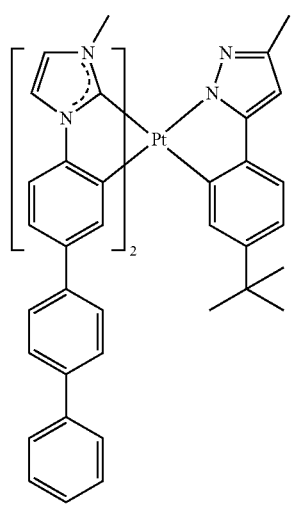
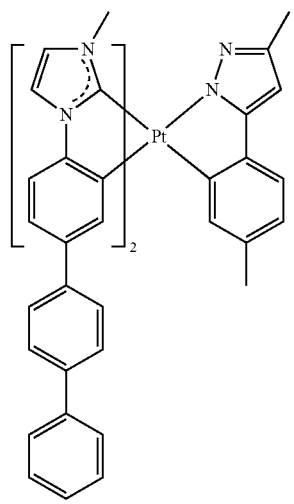
784
-continued
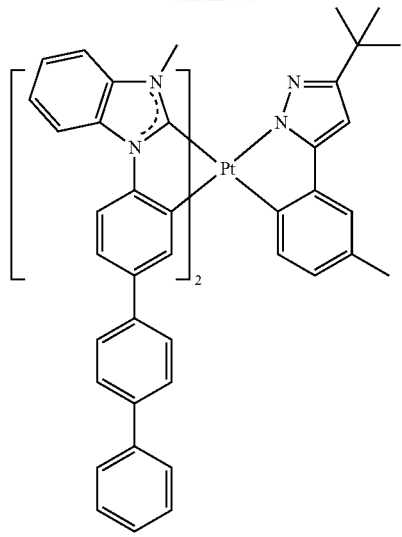
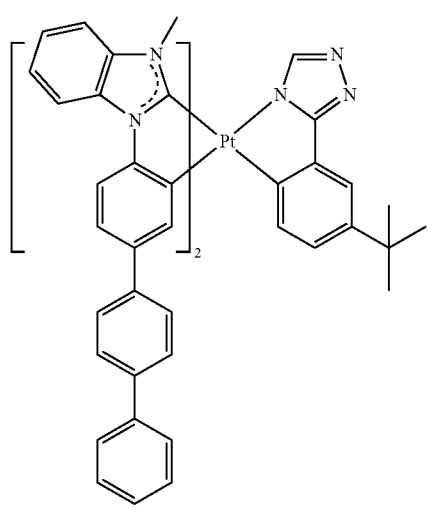
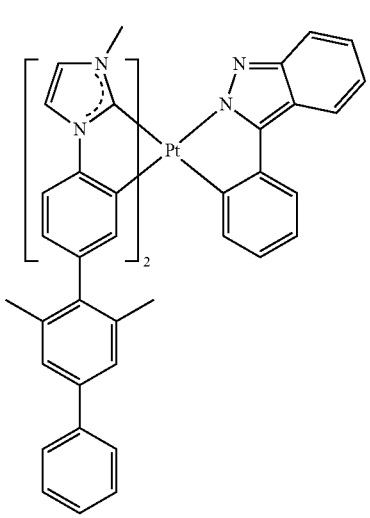

785
-continued
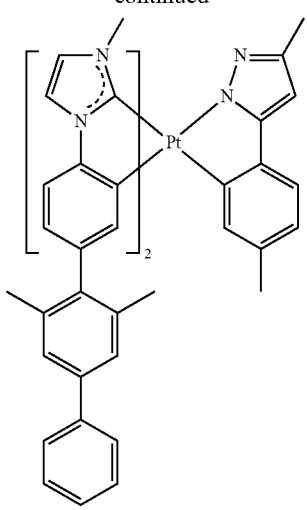
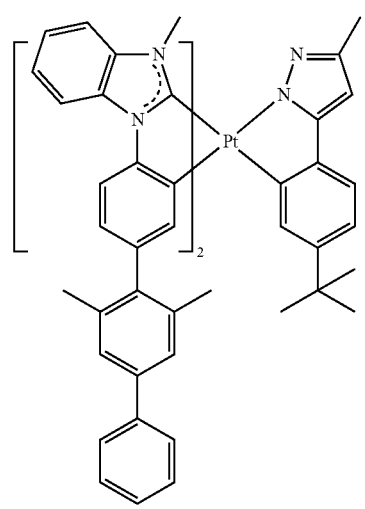
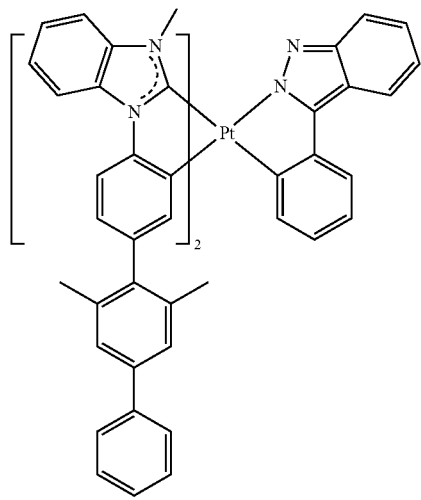
786
-continued
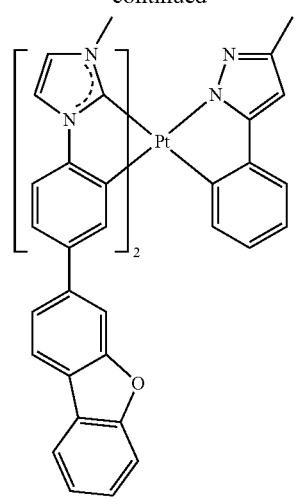
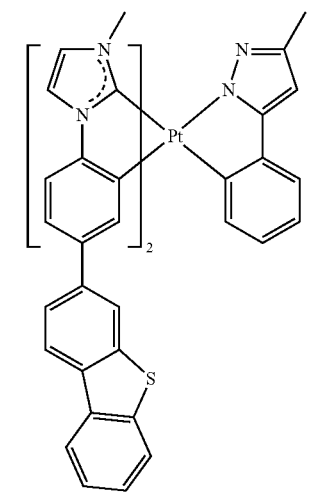
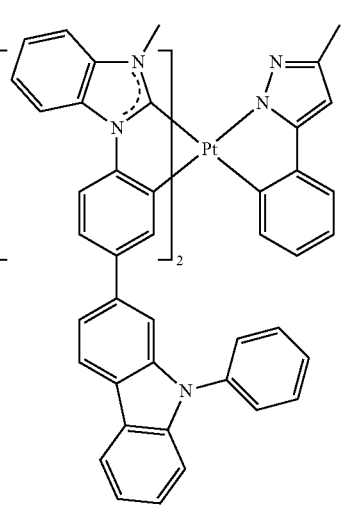

787
-continued
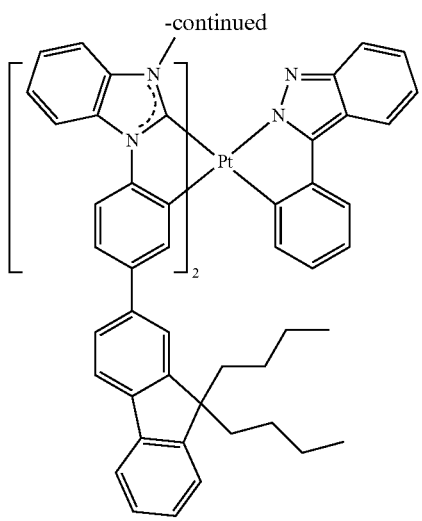
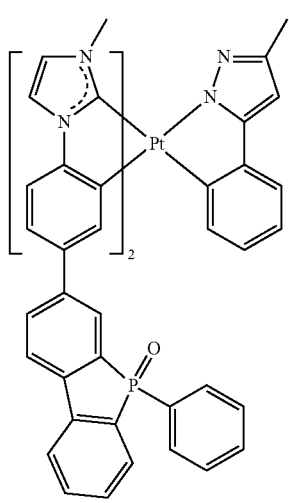
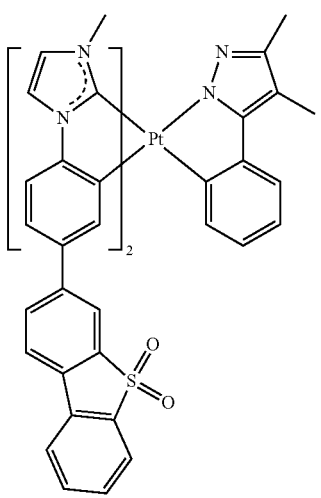
788
-continued
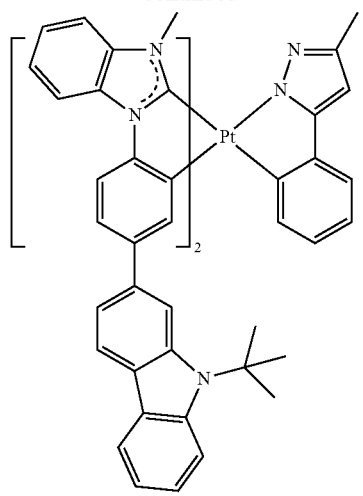
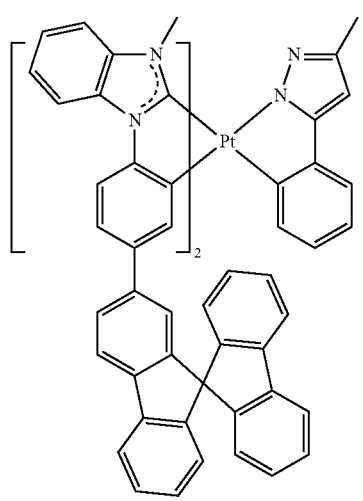
Structures Pt-10
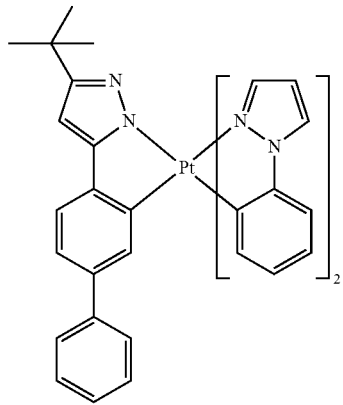

789
-continued
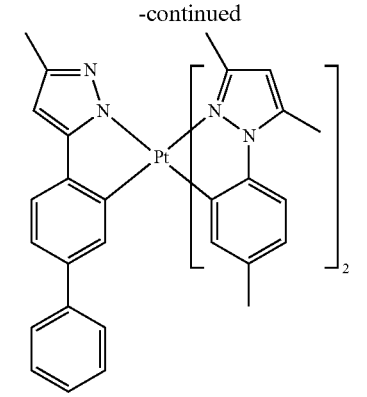
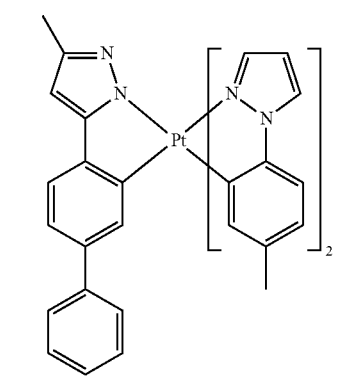
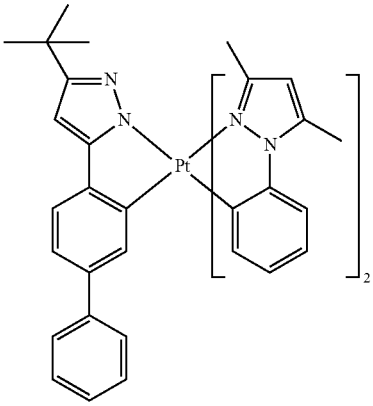
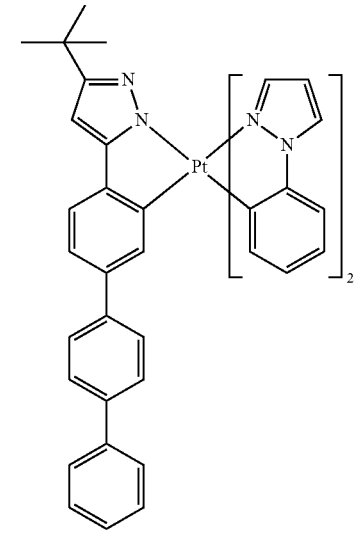
790
-continued
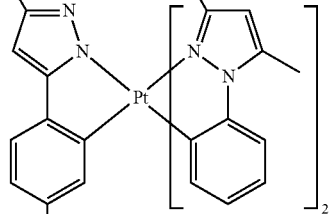
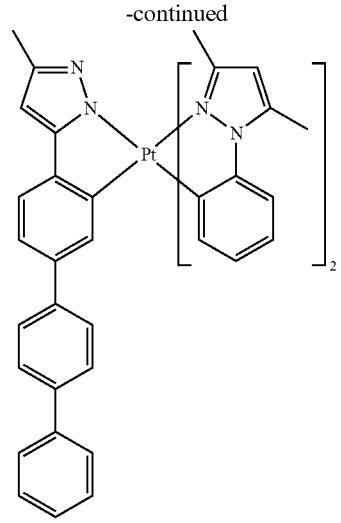
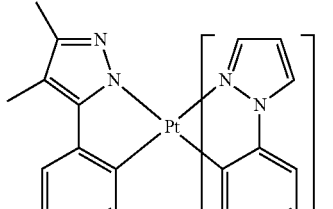
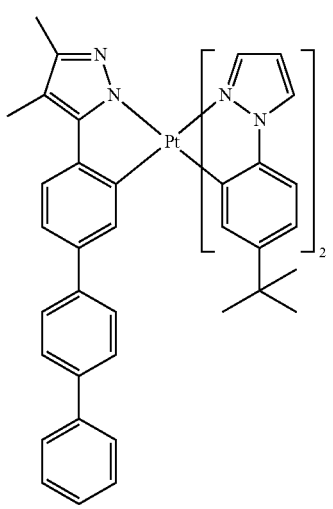
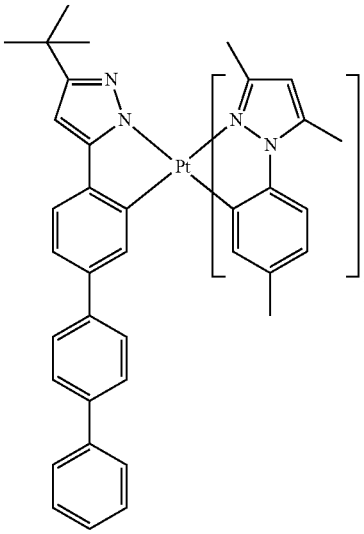

791
-continued
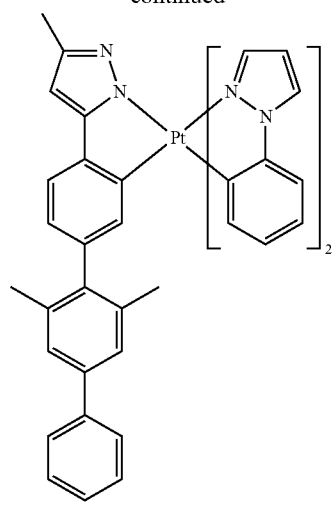
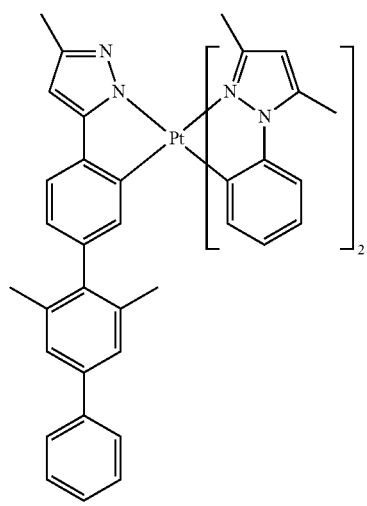
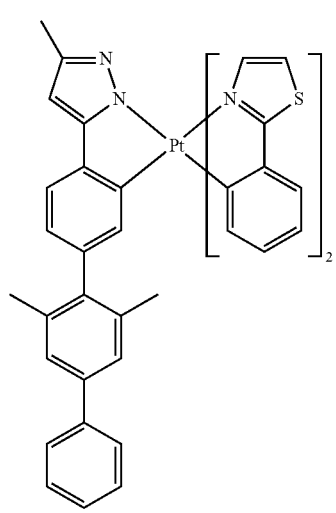
792
-continued
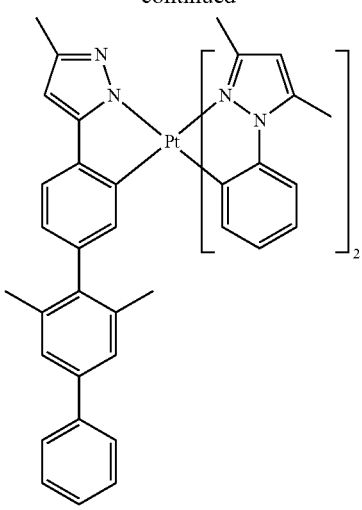
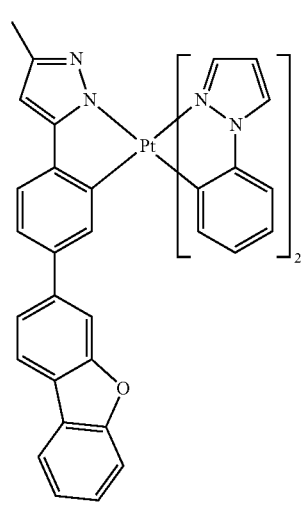
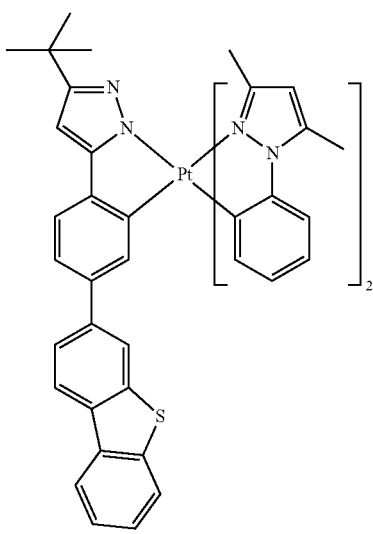

793
-continued
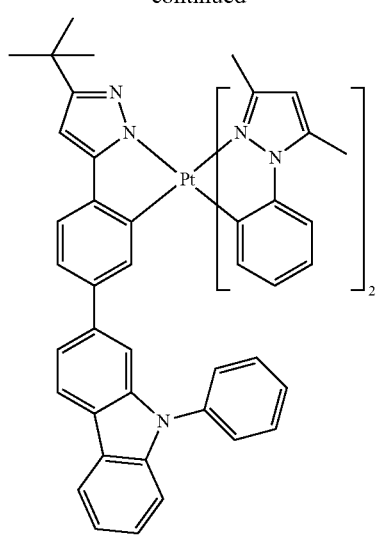
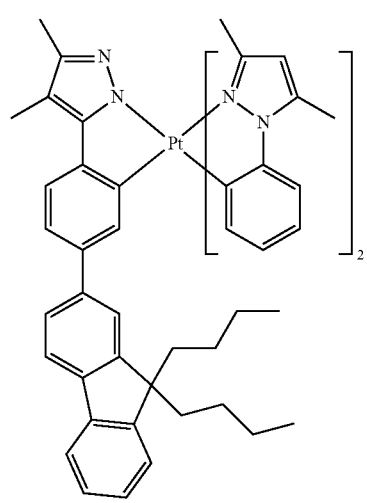
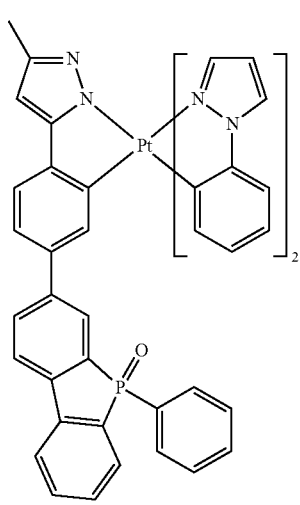
794
-continued
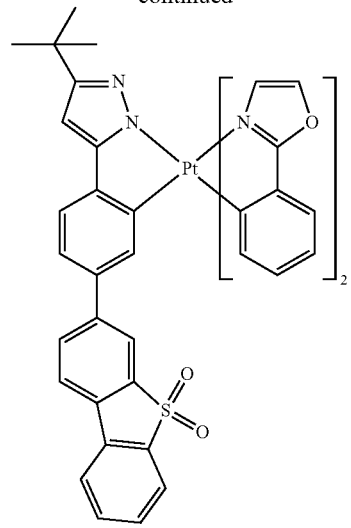
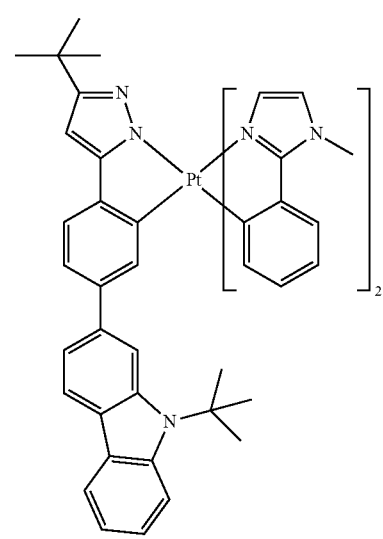
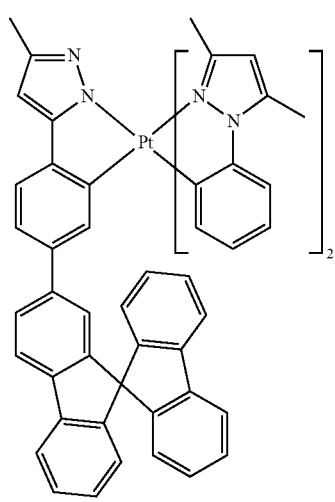

795
-continued
Structures Pt-13
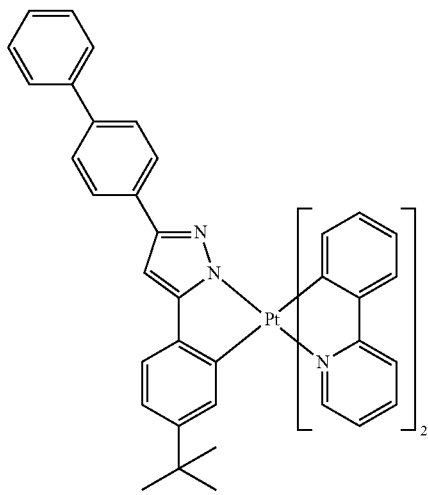
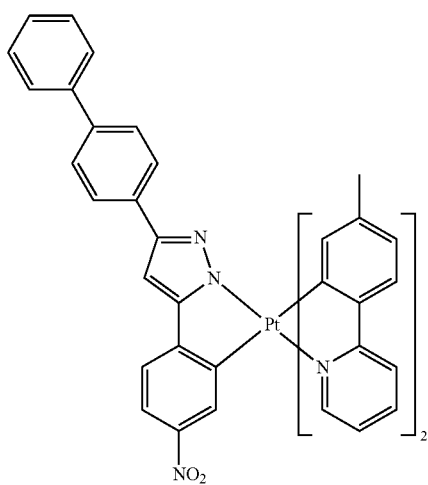
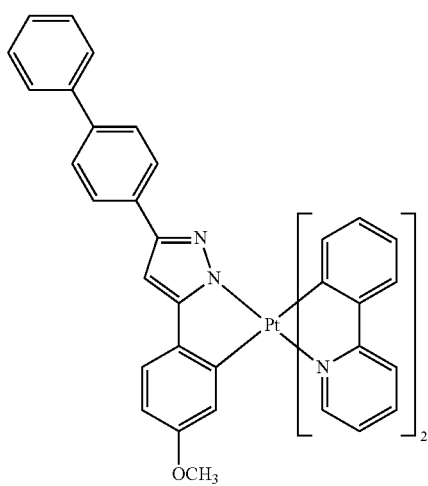
796
-continued
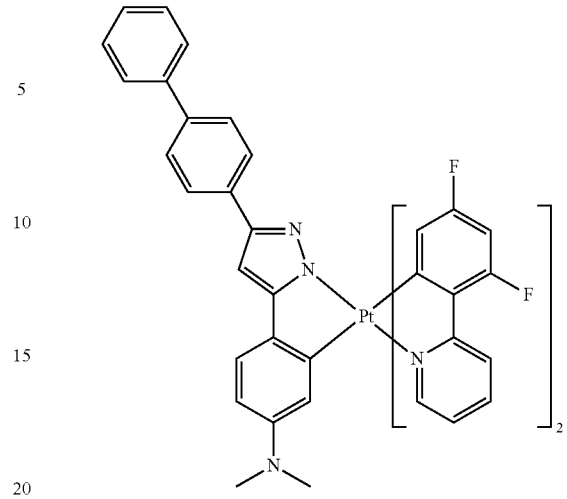
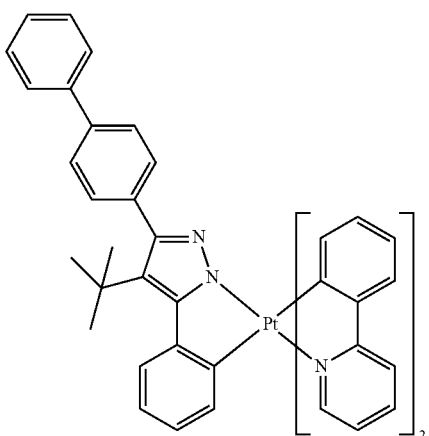
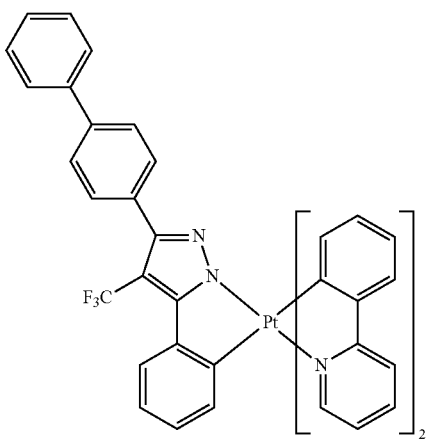

797
-continued
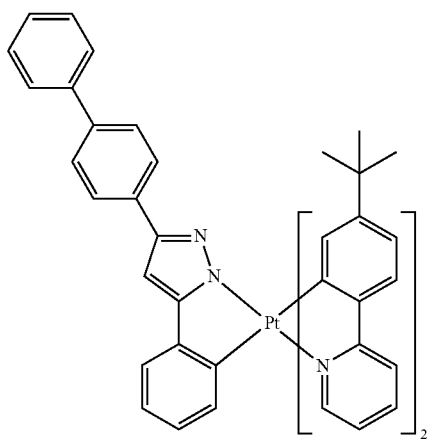
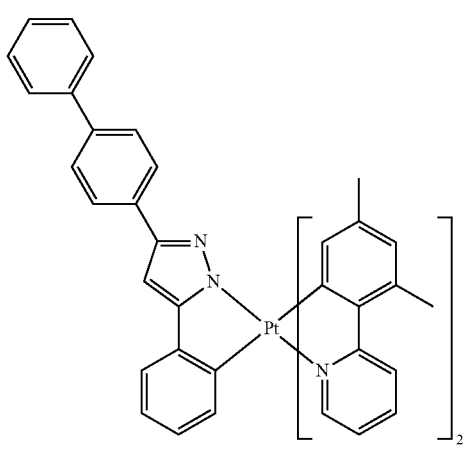
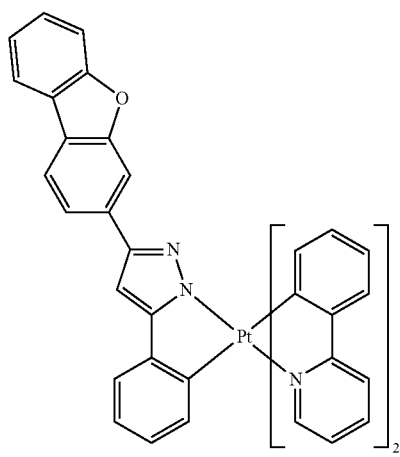
798
-continued
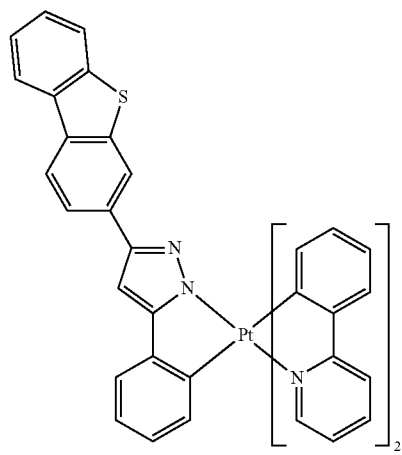
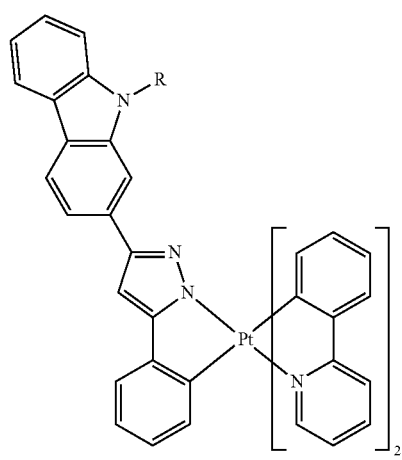
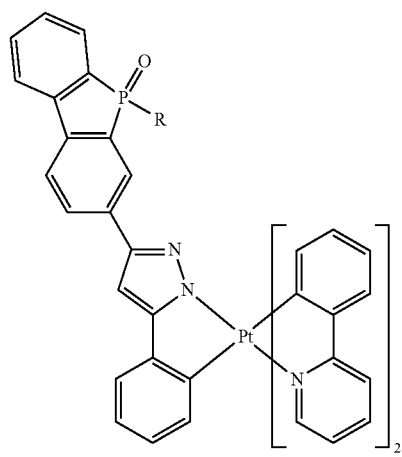

799
-continued

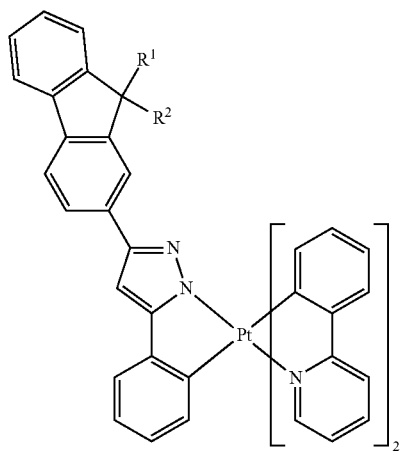

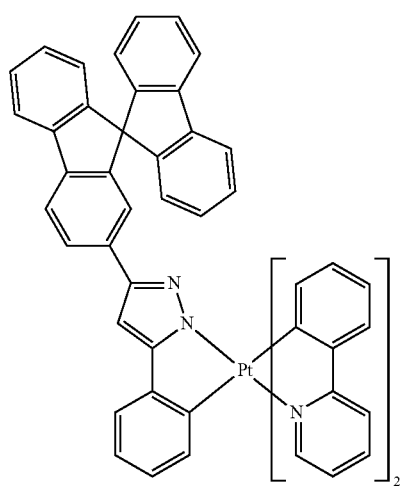

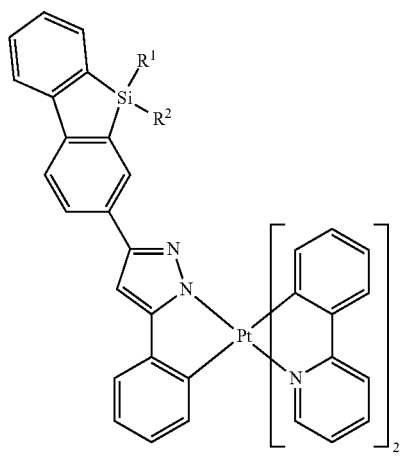

800
-continued

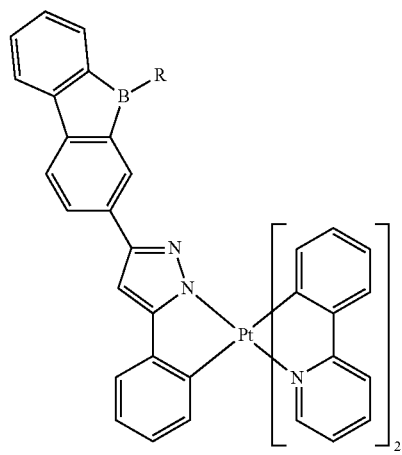

wherein each of R, $R^1$, and $R^2$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

16. A complex, which is:

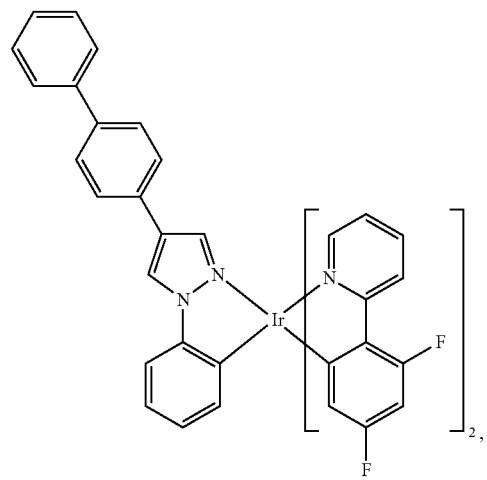

801
-continued
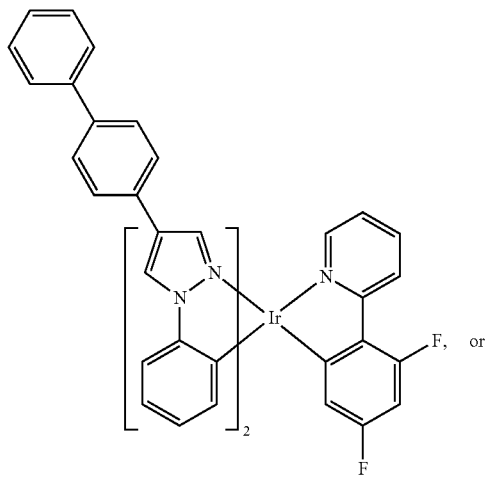
or
802
-continued
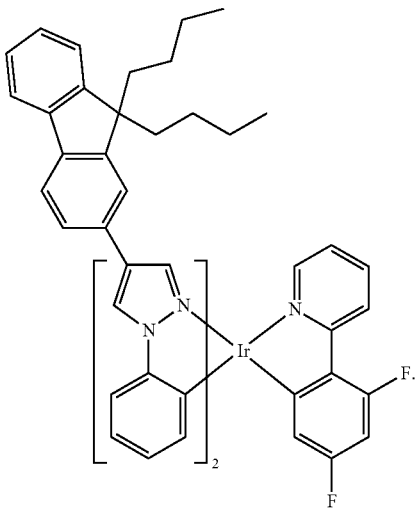
* * * * *

UNITED STATES PATENT AND TRADEMARK OFFICE
CERTIFICATE OF CORRECTION

PATENT NO. : 9,865,825 B2
APPLICATION NO. : 14/937136
DATED : January 9, 2018
INVENTOR(S) : Jian Li and Guijie Li It is certified that error appears in the above-identified patent and that said Letters Patent is hereby corrected as shown below:

In Claim 1, Column 462, Line 12-20 (Approx.)

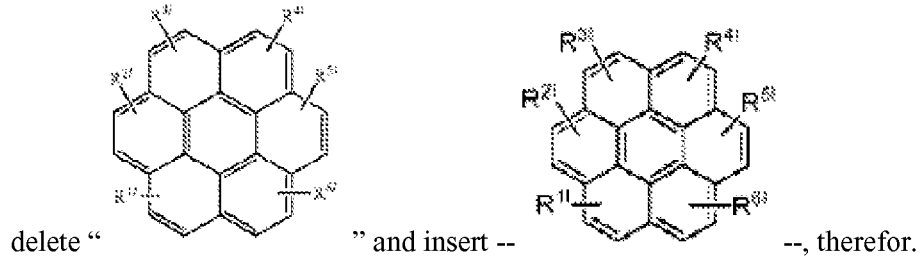

In Claim 1, Column 462, Line 30-35 (Second Structure)

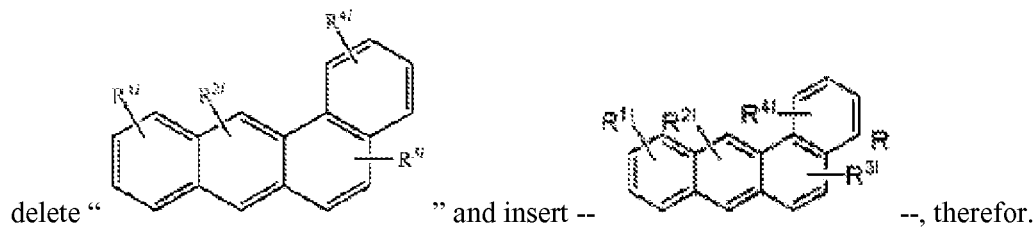

In Claim 1, Column 462, Line 36-44 (Approx.)

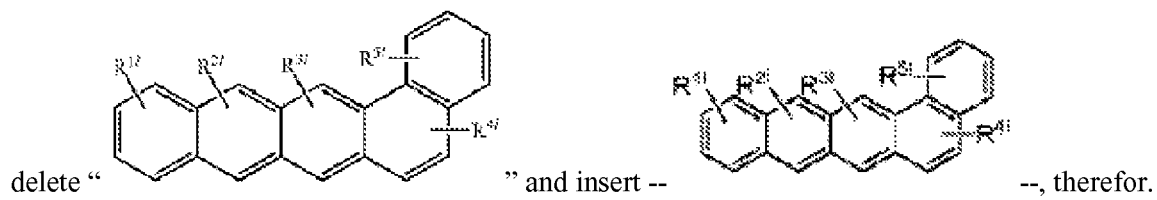

Signed and Sealed this
Third Day of July, 2018

Andrei Iancu
*Director of the United States Patent and Trademark Office*

CERTIFICATE OF CORRECTION (continued)
U.S. Pat. No. 9,865,825 B2

In Claim 1, Column 462, Line 50-57 (Approx.)

delete " 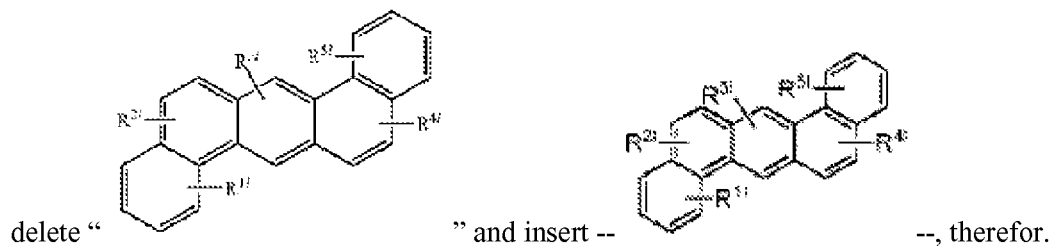 " and insert -- -- , therefor.

In Claim 1, Column 463, Line 47-56 (Approx.) (Structure 1)

delete " 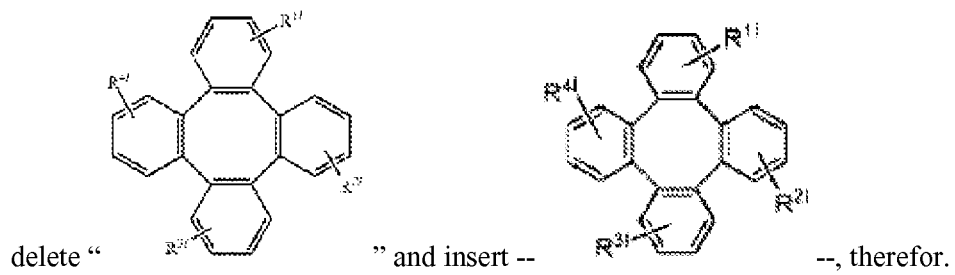 " and insert -- -- , therefor.

In Claim 1, Column 465, Line 31-44 (Approx.)

delete " 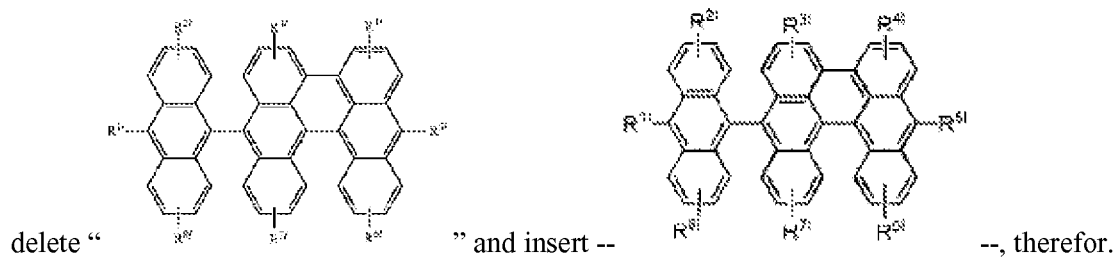 " and insert -- -- , therefor.

In Claim 1, Column 470, Line 15-20 (Approx.) (Structure 3)

delete " 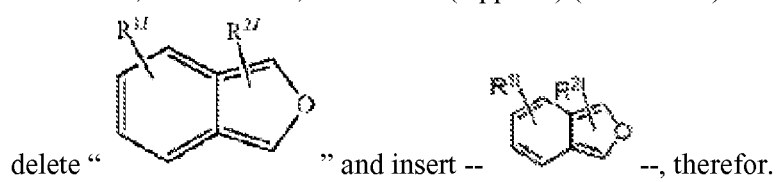 " and insert -- -- , therefor.

CERTIFICATE OF CORRECTION (continued)
U.S. Pat. No. 9,865,825 B2

In Claim 1, Column 470, Line 21-35 (Approx.)

delete " 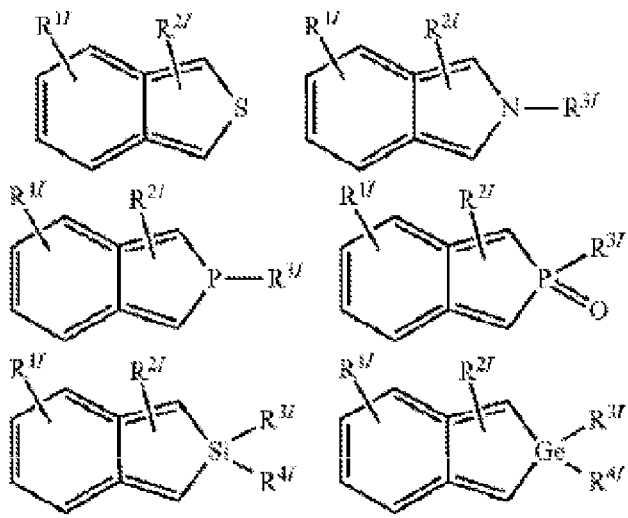 " and insert -- 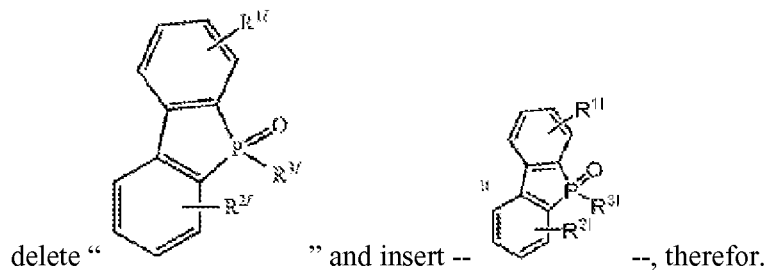 --, therefor.

In Claim 1, Column 470, Line 44-51 (Approx.) (Structure 3)

delete " " and insert -- --, therefor.

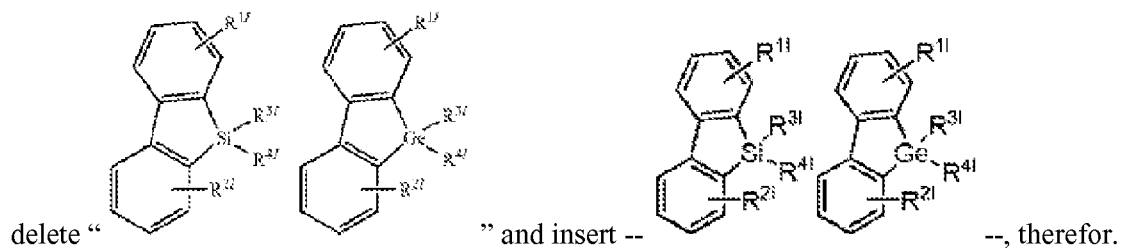

In Claim 1, Column 470, Line 52-60 (Approx.) (Structures 1 and 2)

delete " " and insert -- --, therefor.

In Claim 1, Column 470, Line 60-65 (Approx.) (Structure 2)

delete " 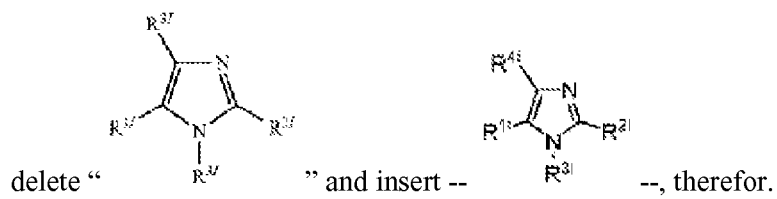 " and insert -- --, therefor.

In Claim 1, Column 471, Line 21-26 (Approx.) (Structure 1)
delete " 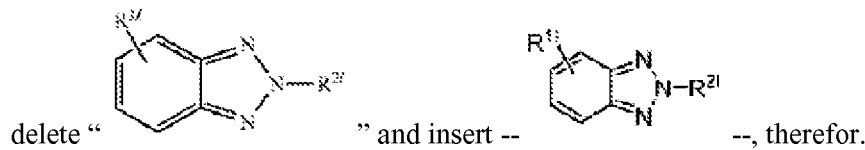 " and insert -- -- , therefor.
In Claim 1, Column 475, Line 25-34
before " 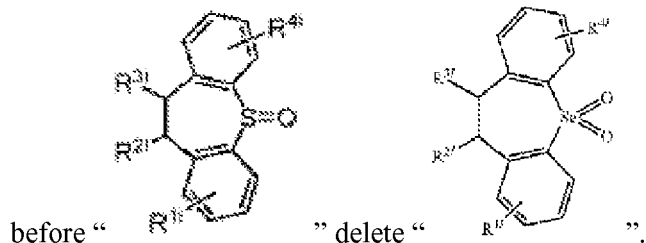 " delete " ".
In Claim 1, Column 476, Line 40-45
after " 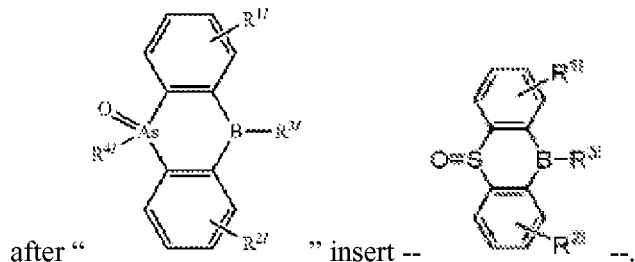 " insert -- --.
In Claim 1, Column 478, Line 11-20 (Approx.) (Structure 2)
delete " 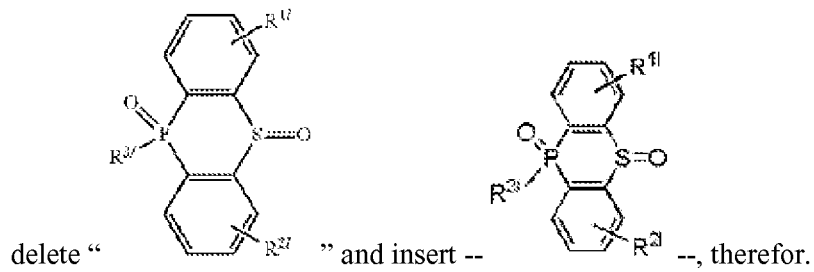 " and insert -- --, therefor.
In Claim 1, Column 478, Line 49-57 (Approx.) (Structure 2)
delete " 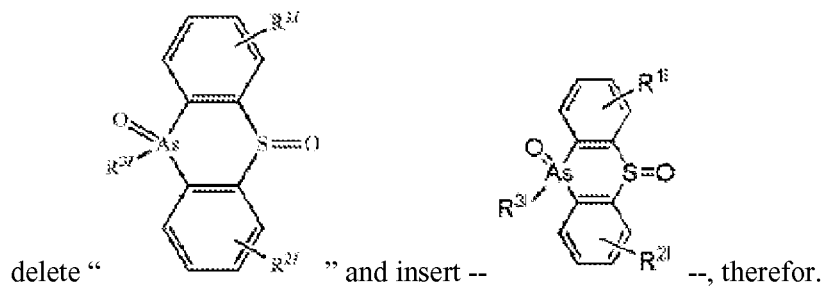 " and insert -- --, therefor.

CERTIFICATE OF CORRECTION (continued)
U.S. Pat. No. 9,865,825 B2

In Claim 1, Column 481, Line 39-47 (Approx.) (Structure 2)

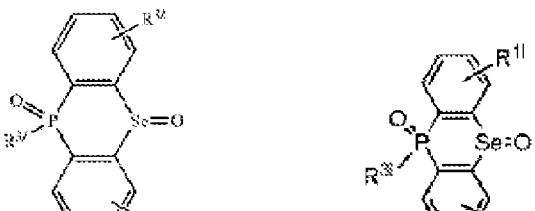

delete " " and insert -- --, therefor.

In Claim 1, Column 483, Line 59-65 (Approx.) (Structure 1)

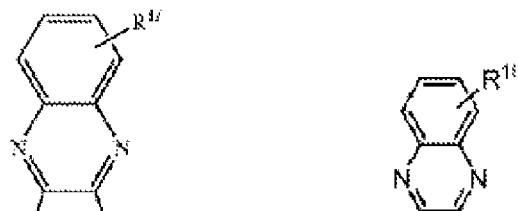

delete " " and insert -- --, therefor.

In Claim 1, Column 487, Line 24-32 (Approx.) (Structure 1)

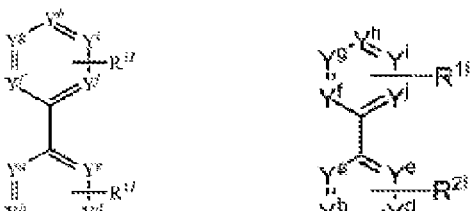

delete " " and insert -- --, therefor.

In Claim 1, Column 488, Line 55-65 (Approx.)

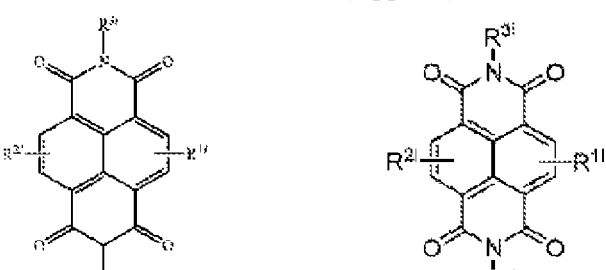

delete " " and insert -- --, therefor.

In Claim 1, Column 489, Line 50-55 (Approx.)

delete " " and insert -- --, therefor.

In Claim 1, Column 490, Line 55-60 (Approx.)
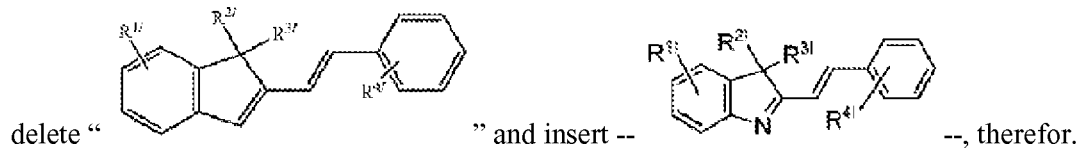
delete " " and insert -- --, therefor.
In Claim 1, Column 491, Line 38
delete "heterocycyl" and insert -- heterocyclyl --, therefor.
In Claim 13, Column 531, Line 34
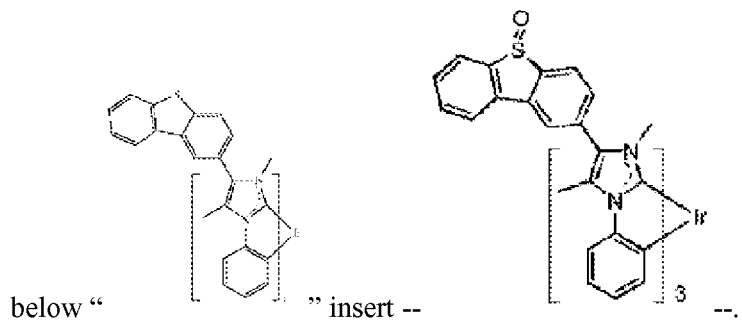
below " " insert -- --.
In Claim 13, Column 536, Line 2-11 (Approx.)
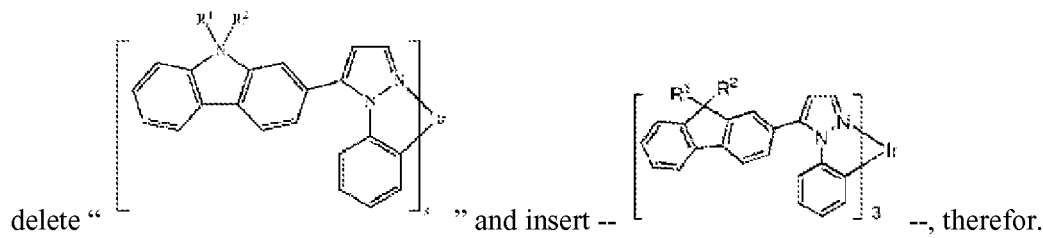
delete " " and insert -- --, therefor.
In Claim 13, Column 536, Line 45-54 (Approx.)
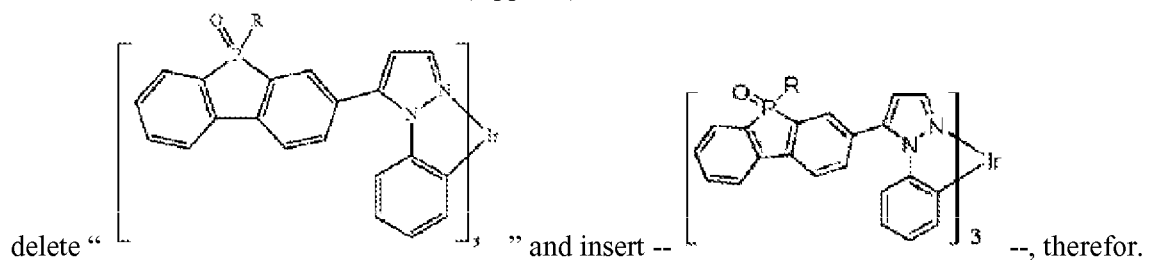
delete " " and insert -- --, therefor.
In Claim 13, Column 538, Line 2-11 (Approx.)
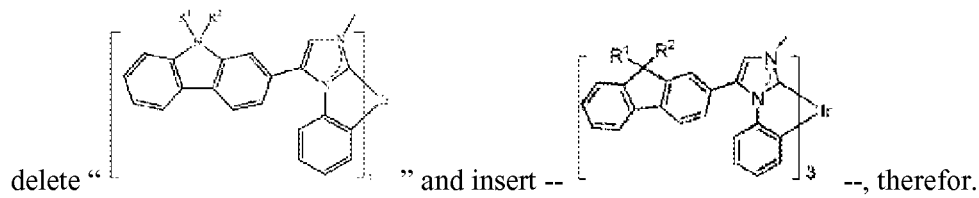
delete " " and insert -- --, therefor.

CERTIFICATE OF CORRECTION (continued)
U.S. Pat. No. 9,865,825 B2

In Claim 13, Column 541, Line 15-24 (Approx.)

delete " 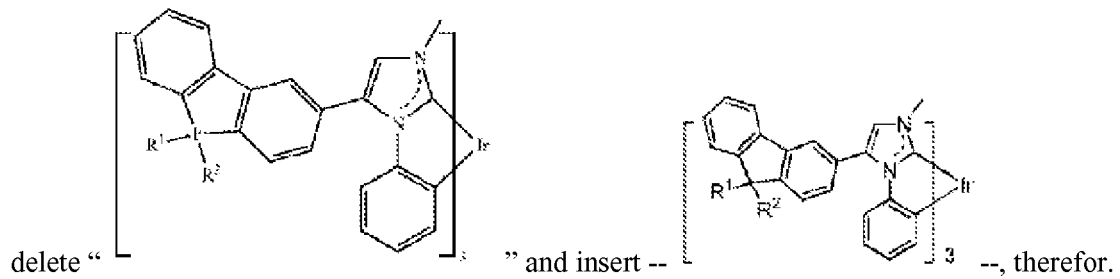 " and insert -- --, therefor.

In Claim 13, Column 551, Line 50-65 delete " 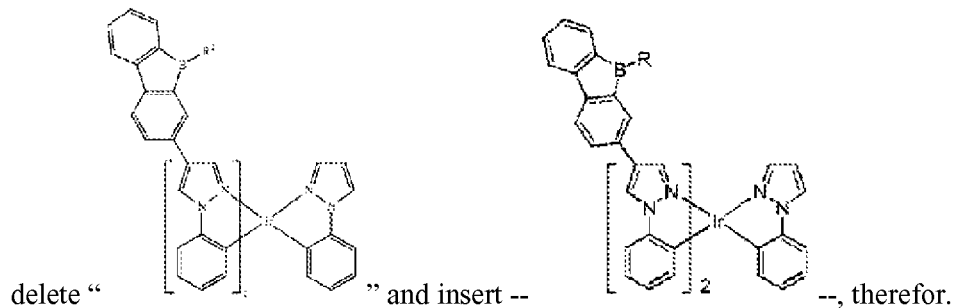 " and insert -- --, therefor.

In Claim 13, Column 556, Line 50-65 delete " 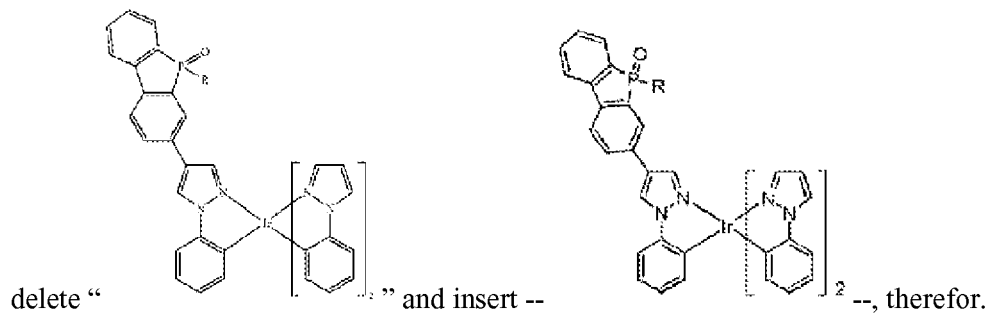 " and insert -- --, therefor.

In Claim 13, Column 579-580, Line 2-66 (Column 579) Line 2-21 (Column 580)
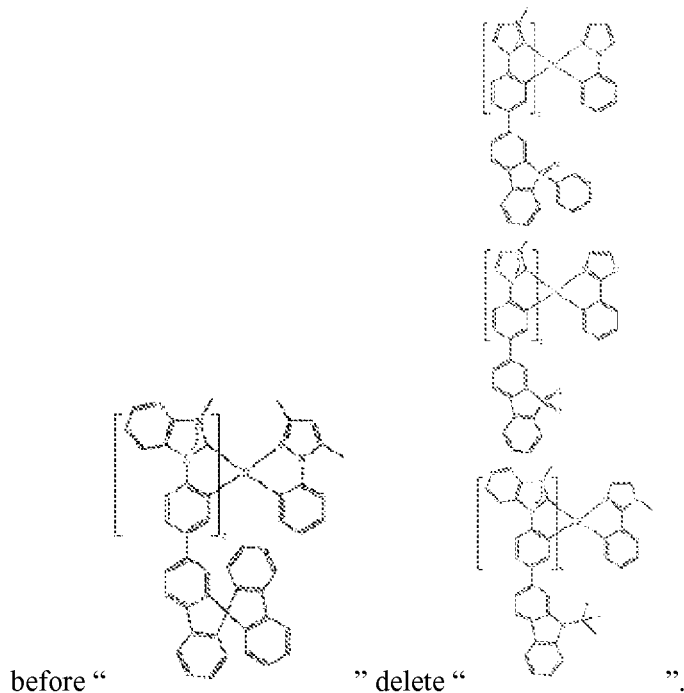
before " " delete " ".
In Claim 13, Column 591, Line 24-42
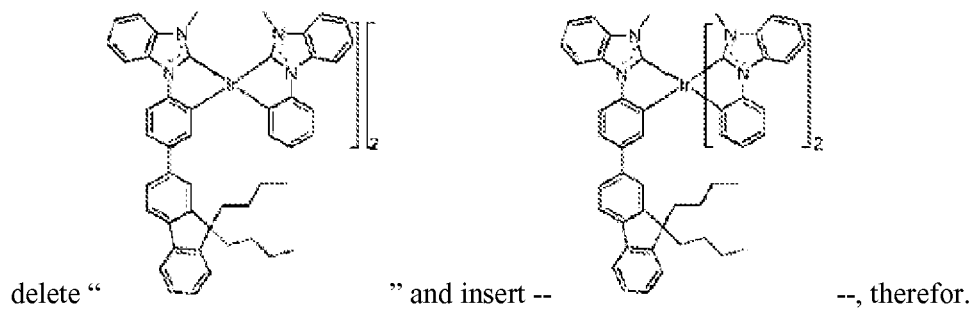
delete " " and insert -- --, therefor.
In Claim 13, Column 594, Line 18-33
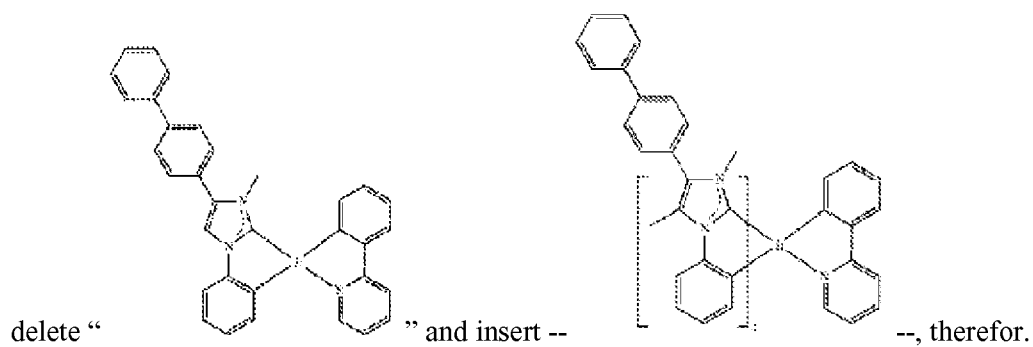
delete " " and insert -- --, therefor.

CERTIFICATE OF CORRECTION (continued)
U.S. Pat. No. 9,865,825 B2

Page 9 of 9

In Claim 14, Column 683, Line 16-31

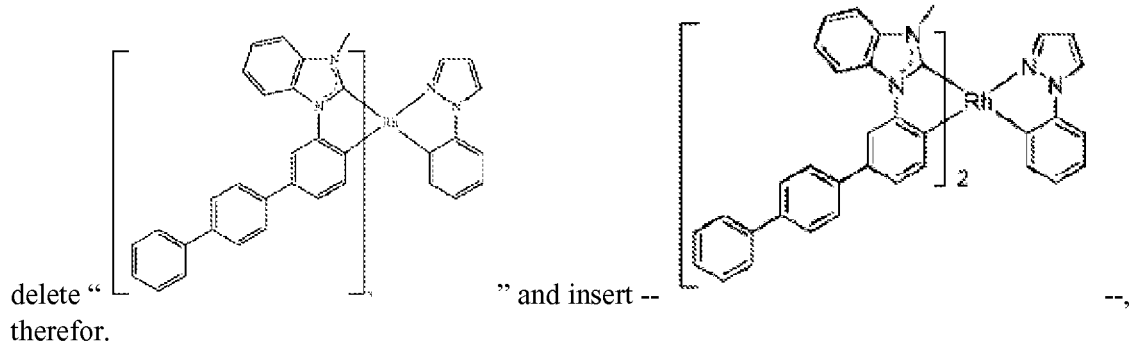

delete " " and insert -- --, therefor.

In Claim 14, Column 712, Line 25-45

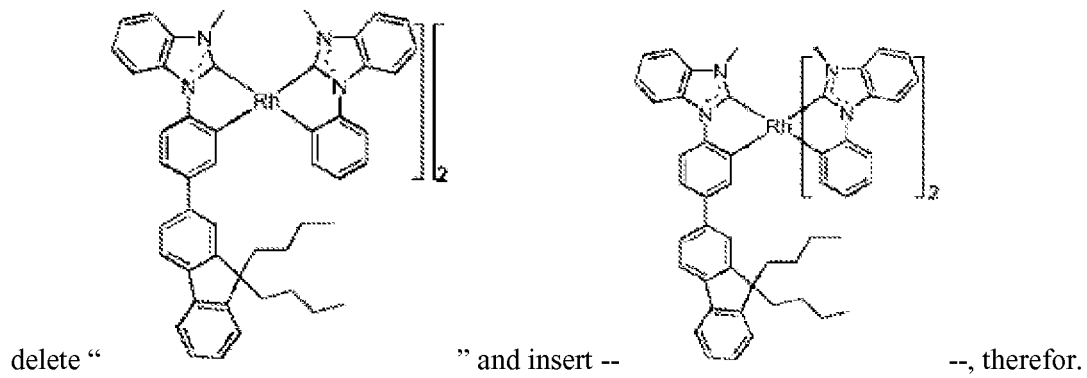

delete " " and insert -- --, therefor.